US006870033B1

(12) United States Patent
Hsei et al.

(10) Patent No.: US 6,870,033 B1
(45) Date of Patent: Mar. 22, 2005

(54) ANTIBODY FRAGMENT-POLYMER CONJUGATES AND HUMANIZED ANTI-IL-8 MONOCLONAL ANTIBODIES

(75) Inventors: Vanessa Hsei, San Jose, CA (US); Iphigenia Koumenis, Winston-Salem, NC (US); Steven R. Leong, Berkeley, CA (US); Leonard G. Presta, San Francisco, CA (US); Zahra Shahrokh, San Francisco, CA (US); Gerarado A. Zapata, Foster City, CA (US)

(73) Assignee: Genentech, Inc., South San Francisco, CA (US)

(*) Notice: Subject to any disclaimer, the term of this patent is extended or adjusted under 35 U.S.C. 154(b) by 0 days.

(21) Appl. No.: 09/355,014

(22) PCT Filed: Feb. 20, 1998

(86) PCT No.: PCT/US98/03337

§ 371 (c)(1),
(2), (4) Date: Sep. 13, 1999

(87) PCT Pub. No.: WO98/37200

PCT Pub. Date: Aug. 27, 1998

Related U.S. Application Data

(63) Continuation-in-part of application No. 09/012,116, filed on Jan. 22, 1998, now abandoned, and a continuation of application No. 08/804,444, filed on Feb. 21, 1997, now Pat. No. 6,117,980.

(51) Int. Cl.$^7$ ................................................ C07K 16/00

(52) U.S. Cl. ............................ 530/388.85; 530/391.1; 530/387.3; 424/133.1

(58) Field of Search .......................... 530/387.1, 387.3, 530/388.85, 391.5; 424/130.1, 133.1

(56) References Cited

U.S. PATENT DOCUMENTS

| | | |
|---|---|---|
| 4,002,531 A | 1/1977 | Royer |
| 4,179,337 A | 12/1979 | Davis et al. |
| 4,732,863 A | 3/1988 | Tomasi et al. |
| 5,147,537 A | 9/1992 | Sada et al. |
| 5,166,322 A | 11/1992 | Shaw et al. |
| 5,169,627 A | 12/1992 | Cunningham-Rundles |
| 5,527,528 A | 6/1996 | Allen et al. |
| 5,532,150 A | 7/1996 | Snow et al. |
| 5,595,732 A | 1/1997 | Hakini et al. |
| 5,620,689 A | 4/1997 | Allen et al. |
| 5,643,575 A | 7/1997 | Martinez et al. |
| 5,661,020 A | 8/1997 | Snow et al. |
| 5,670,132 A | 9/1997 | Griffiths et al. |
| 5,677,426 A | 10/1997 | Fong et al. |
| 5,679,532 A | 10/1997 | Repine |
| 5,686,070 A | 11/1997 | Doerschuk et al. |
| 5,695,760 A | 12/1997 | Faanes et al. |
| 5,698,196 A | 12/1997 | Matsushima et al. |
| 5,702,946 A | 12/1997 | Doerschuk et al. |
| 5,707,622 A | 1/1998 | Fong et al. |
| 5,766,897 A | 6/1998 | Braxton |
| 5,874,080 A | 2/1999 | Hebert et al. |

FOREIGN PATENT DOCUMENTS

| | | |
|---|---|---|
| EP | 770628 | 5/1997 |
| WO | WO 92/04372 | 3/1992 |
| WO | WO 94/12219 | 6/1994 |
| WO | WO 94/21235 | 9/1994 |
| WO | WO 95/11987 | 5/1995 |
| WO | WO 95/15769 | 6/1995 |
| WO | WO 95/23813 | 9/1995 |
| WO | WO 95/23865 | 9/1995 |
| WO | WO 95/32003 | 11/1995 |
| WO | WO 96/02576 | 2/1996 |
| WO | WO 96/09325 | 3/1996 |
| WO | WO 96/22785 | 8/1996 |
| WO | WO 96/34015 | 10/1996 |
| WO | WO 96/40733 | 12/1996 |
| WO | WO 97/01354 | 1/1997 |
| WO | WO 97/10847 | 3/1997 |
| WO | WO 97/40215 | 10/1997 |
| WO | WO 98/25971 | 6/1998 |
| WO | WO 98/37200 | 8/1998 |
| WO | WO 99/37779 | 7/1999 |

OTHER PUBLICATIONS

Wilchek et al., Methods in Enzymology 104:3–8, 10–11, 17–18, and 21–22, 1984.*

Rudikoff et al, PNAS 79:1979, 1982.*

Abuchowski and Davis, "Soluble Polymer–Enzyme Adducts" *Enzymes as Drugs,* Holcenberg, JS; Roberts. J eds. New York: Wiley, Chapter 13, pps. 367–383 (1981).

Adagen Label *Physicians' Desk Reference* (Product Information), 48 edition, Montvale, NJ:Medical Economics Data Production Company pps. 917–918 (1994).

Allen et al., "A new strategy for attachment of antibodies to sterically stabilized liposomes resulting in efficient targeting to cancer cells" *Biochimica et Biophysica Acta* 1237(2):99–108 (Jul. 26, 1995).

Anderson and Tomasi, "Polymer modification of antibody to eliminate immune complex and Fc binding" *Journal of Immunological Methods* 109(1):37–42 (Apr. 22, 1988).

(List continued on next page.)

*Primary Examiner*—Larry R. Helms
(74) *Attorney, Agent, or Firm*—Ginger R. Dreger; Heller Ehrman White & McAuliffe LLP

(57) ABSTRACT

Humanized anti-IL-8 monoclonal antibodies and variants thereof are described for use in diagnostic applications and in the treatment of inflammatory disorders. Also described is a conjugate formed by an antibody fragment covalently attached to a non-proteinaceous polymer, wherein the apparent size of the conjugate is at least about 500 kD. The conjugate exhibits substantially improved half-life, mean residence time, and/or clearance rate in circulation as compared to the underivatized parental antibody fragment.

10 Claims, 136 Drawing Sheets

OTHER PUBLICATIONS

Beauchamp et al., "A new procedure for the synthesis of polyethylene glycol–protein adducts; effects on function, receptor recognition, and clearance of superoxide dismutase, lactoferrin, and $\alpha_2$–macroglobulin" *Analytical Biochemistry* 131(1):25–33 (1983).

Bernard et al., "The American–European Consensus Conference on ARDS. Definitions, mechanisms, relevant outcomes, and clinical trial coordination" *American Journal of Respiratory & Critical Care Medicine* 149 (3 Pt 1):818–824 (Mar. 1994).

Brooks and Stocks, Use of polyacrylamide–derivatized antibody in dextran–poly(ethylene glycol) systems *Methods in Enzymology* 228:390–395 (1994).

Brumeanu et al., "Derivatization with monomethoxypolyethylene glycol of Igs expressing viral epitopes obviates adjuvant requirements" *Journal of Immunology* 154(7):3088–3095, (Apr. 1, 1995).

Carter et al., "Preparation and uses of Fab' fragments from *Escherichia coli*" *Antibody Engineering: a Practical Approach*, Hoogenboom, H., McCafferty, J., Chiswell. D. eds., Oxford, UK:IRL Press, Chapter 13 pps. 291–308 (1996).

Chamow et al., "Modification of CD4 immunoadhesin with monomethoxypoly(ethylene glycol) aldehyde via reductive alkylation" *Bioconjugate Chemistry* 5(2):133–140 (Mar.–Apr. 1994).

Chapman et al., "Therapeutic antibody fragments with prolonged in vivo half–lives" *Nature Biotechnology* 17(8):780–783 (Aug. 1999).

Clark et al., "Long–acting growth hormones produced by conjugation with polyethylene glycol" *Journal of Biological Chemistry* 271(36):21969–21977 (Sep. 6, 1996).

Cunningham–Rundles et al., "Biological activities of polyethylene–glycol immunoglobulin conjugates. Resistance to enzymatic degradation" *Journal of Immunological Methods* 152(2):177–190 (Aug. 10, 1992).

Davis et al., "Soluble. Nonantigenic Polyethylene Gylcol–Bound Enzymes" *Biomedical Polymers: Polymeric Materials and Pharmaceuticals for Biomedical Use*, Goldberg, E and Nakajima, A eds., New York:Academic Press pps. 441–452 (1980).

Delgado et al., "Analytical partitioning of poly(ethylene glycol)–modified proteins" *Journal of Chromatography B* 692(2):263–272 (May 9, 1997).

Delgado et al., "Distinct Influence of PEGylation on the Tumour Localisation of Transferrin and a Tumour–Specific Fab Fragment (F9)" *Journal of Cellular Biochemistry* (Abstr. A4–101, Keystone Symposium held at Hilton Head Island, SC, Jan 7–13 1995) Suppl. 19A:171 (1995).

Delgado et al., "Enhanced tumour specificity of an anti–carcinoembrionic antigen Fab' fragment by poly(ethylene glycol) (PEG) modification" *British Journal of Cancer* 73(2):175–182 (Jan. 1996).

Delgado et al., "The uses and properties of PEG–linked proteins" *Critical Reviews in Therapeutic Drug Carrier Systems* 9(3–4):249–304 (1992).

Deuel et al., "Amino acid sequence of human platelet factor 4" *Proc. Natl. Acad. Sci.* 74:2256–2258 (197.

Donnelly et al., "Interleukin–8 and development of adult respiratory distress syndrome in at–risk patient groups" *Lancet* 341(8846):643–647 (Mar. 13, 1993).

Elling and Kula, "Immunoaffinity partitioning: synthesis and use of polyethylene glycol–oxirane for coupling to bovine serum albumin and monoclonal antibodies" *Biotechnology and Applied Biochemistry* 13(3):354–362 (Jun. 1991).

Eno–Amooquaye et al., "Altered biodistribution of an antibody–enzyme conjugate modified with polyethylene glycol" *British Journal of Cancer* 73(11):1323–1327 (Jun. 1996).

Folkesson et al., "Acid aspiration–induced lung injury in rabbits is mediated by interleukin–8–dependen mechanisms" *Journal of Clinical Investigation* 96(1):107–116 (Jul. 1995).

Gonzalez et al., "Humanization of Murine 6G425:An Anti–IL8 Monoclonal Antibody Which Blocks Binding of 1L8 to Human Neutrophils" *1996 Keystone Symposia on Exploring and Exploiting Antibody and Ig Superfamil Combining Sites* (Poster) pps. 1–21 (Feb. 1996).

Harding et al., "Immunogenicity and pharmacokinetic attributes of poly(ethylene glycol)–grafted immunoliposomes" *Biochimica et Biophysica Acta* 1327(2):181–192 (Jul. 25, 1997).

Harris et al., "Synthesis and Characterization of Polyethylene Glycol) Derivatives" *J. Polym. Sci., Polym. Chem. Ed.* 22(2):341–352 (1984).

Haselgrubler et al., "Synthesis and applications of a new poly(ethylene glycol) derivative for the crosslinking of amines with thiols" *Bioconjugate Chemistry* 6(3):242–248 (May–Jun. 1995).

Hebert et al., "Endothelial and Leukocyte Forms of IL–8: Conversion by Thrombin and Interactions with Neutrophils" *J. Immunol.* 145 (9):3033–3040 (Nov. 1, 1990).

Hebert et al., "Interleukin–8: A Review" *Cancer Investigation* 11(6):743–750 (1993).

Herbert, C., "Humanized anti IL–8 antibodies: potential therapy for shock and ARDS?" (Summary of seminar presented at the 1997 Keystone Symposia on The Role of Chemokines in Leukocyte Trafficking and Disease held at the Copper Mountain Resort, CO on Mar. 31–Apr. 5, 1997) pps. 4.

Karr et al., "Use of poly(ethylene glycol)–modified antibody in cell extraction" *Methods in Enzymology* 228:377–390 (1994).

Katre N., "The Conjugation of Proteins with Polyethylene Glycol and other Polymers. Altering properties of proteins to enhance their therapeutic potential." *Advanced Drug Delivery Reviews* 10(1):91–114 (1993).

Kawamura et al., "Immune responses to polyethylene glycol modified L–asparaginase in mice" *Internationa Archives of Allergy & Applied Immunology* 76(4):324–330 (1985).

Kirportin et al., "Sterically stabilized anti–HER2 immunoliposomes: design and targeting to human breast cancer cells in vitro" *Biochemistry* 36(1):66–75 (Jan. 7, 1997).

Kitamura et al., "Chemical engineering of the monoclonal antibody A7 by polyethylene glycol for targeting cancer chemotherapy" *Cancer Research* 51(16):4310–4315 (Aug. 15, 1991).

Kitamura et al., "Polyethylene glycol modification of the monoclonal antibody A7 enhances its tumor localization" *Biochemical & Biophysical Research Communications* 171(3):1387–1394 (Sep. 28, 1990).

Knauf et al., "Relationship of Effective Molecular Size to Systemic Clearance in Rats of Recombinant Interleukin–2 Chemically Modified with Water Soluble Polymers" *The Journal of Biological Chemistry* 263(29):15064–15070 (Oct. 15, 1988).

Ko et al., "A sensitive enzyme–linked immunosorbent assay for human interleukin–8" *J. Immunol. Methods* 149:227–235 (1992).

Koumenis et al., "Tailoring antibody fragment with PEGylation without loss in biological activity" *Protein Science* (Abstract 109–M, presented at the Protein Society's Twelfth Symposium in San Diego, CA on Jul. 25–29, 1998) 7(Suppl. 1):73 (Jul. 1998).

Lang et al., "Suppression of antibody responses in rats to murine anti–CD4 monoclonal antibodies by conjugates with monomethoxypolyethylene glycol" *Immunology Letters* 32(3):247–252 (May 1992).

Lee and Sehon, "Suppression of reaginic antibodies with modified allergens. I. Reduction in allergenicity of protein allergens by conjugation to polyethylene glycol" *International Archives of Allergy & Applied Immunology* 56(2):159–170 (1978).

Mainolfi, E. et al., "Reduction of Immunogenicity of A Murine ANTI–ICAM–1 Antibody Through Pegylation Chemistry" *The 9th International Congress of Immunology* (*abstract book*) (abstract #5247) pps. 885 (1995.

Maiti et al., "Tolerogenic conjugates of xenogeneic monoclonal antibodies with monomethoxypolyethylene glycol. I. Induction of long–lasting tolerance to xenogeneic monoclonal antibodies" *International Journal of Cancer* Suppl. 3:17–22 (1988).

Maruyama et al., "Immunoliposomes bearing polyethyleneglycol–coupled Fab' fragment show prolonged circulation time and high extravasation into targeted solid tumors in vivo" *FEBS Letters* 413(1):177–180 (Aug. 11, 1997).

Maruyama et al., "Targeting efficiency of PEG–immunoliposome–conjugated antibodies at PEG terminals" *Advanced Drug Delivery Reviews* 24:235–242 (1997).

Matsumoto et al., "Prevention of cerebral edema and infarct in cerebral reperfusion injury by an antibody to interleukin–8" *Laboratory Investigation* 77(2):119–125 (Aug. 1997).

Mulligan et al., "Inbition of Lung Inflammatory Reactions in Rats by an Anti–Human IL–8 Antibody" *J. Immunol.* 150(12):5585–5595 (Jun. 15, 1993).

Nordvall et al., "IgG and IgE antibody patterns after immunotherapy with monomethoxy polyethyleneglycol modified honey bee venom" *Allergy: European Journal of Allergy & Clinical Immunology* 41(2):89–94 (Feb. 1986).

Pedley et al., "The potential for enhanced tumour localisation by poly(ethylene glycol) modification of anti–CEA antibody" *British Journal of Cancer* 70(6):1126–1130 (Dec. 1994).

Sekido et al., "Prevention of lung reperfusion injury in rabbits by a monoclonal antibody against interleukin–8" *Nature* 365:654–657 (Oct. 14, 1993).

Shahinian and Silvius, "A novel strategy affords high–yield coupling of antibody Fab' fragments to liposomes" *Biochimica et Biophysica Acta* 1239(2):157–167 (Nov. 1. 1995).

Sharp et al., "Synthesis and application of a poly(ethylene glycol)–antibody affinity ligand for cell separations in aqueous polymer two–phase systems" *Analytical Biochemistry* 154(1):110–117 (Apr. 1986).

(Shearwater Polymers, Inc.'s Jan. 1996 Catalog of Polyethylene Glycol Derivatives) pps. 1–50.

St. John et al., "Immunologic Therapy for ARDS. Septic Shock, and Multiple–Organ Failure" *Chest* 103:932–943 (1993).

Sticherling et al., "Immunohistochemical studies on NAP–17IL–8 in contact eczema and atopic dermatitis" *Arch. Dermatol. Res.* 284:82–85 (1992).

Sticherling et al., "Production and Characterization of Monoclonal Antibodies Against the Novel Neutrophil Activating Peptide NAP/IL–8" *J. Immunol.* 143(5):1629–1634 (Sep. 1, 1989).

Suzuki et al., "Physicochemical and biological properties of poly(ethylene glycol)–coupled immunoglobulin G. Part II. Effect of molecular weight of poly(ethylene glycol)" *Journal of Biomaterial:Science Polymer Edition* 1(2):71–84 (1989).

Suzuki et al., "Preparation and characteristics of magnetite–labelled antibody with the use of poly(ethylene glycol) derivatives" *Biotechnology & Applied Biochemistry* 21(Pt 3):335–345 (Jun. 1995).

Tanaka et al., "Synthesis and biological characterization of monocyte–derived neutrophil chemotactic factor" *FEBS letters* 236(2):467–470 (Aug. 1988).

Van Damme et al., "Purification of granulocyte chemotactic peptide/interleukin–8 reveals N–terminal sequence heterogeneity similar to that of β–thromboglobulin" *European Journal of Biochemistry* 181:337–344 (1989).

Veronese et al., "Improvement of pharmacokinetic, immunological and stability properties of asparaginal by conjugation to linear and branched monomethoxy poly(ethylene glycol)" *Journal of Controlled Release* 40:199–209 (1996).

Wie et al., "Suppression of reaginic antibodies with modified allergens. III, Preparation of tolerogen:conjugates of common allergens with monomethoxypolyethylene glycols of different molecular weights by the mixed anhydride method" *International Archives of Allergy & Applied Immunology* 64(1):84–99 (1981).

Yokoi et al., "Prevention of endotoxemia–induced acute respiratory distress syndrome–like lung injury : rabbits by a monoclonal antibody to IL–8" *Laboratory Investigation* 76(3):375–384 (Mar. 1997).

Yoshimoto et al., "Chemical modification of tryptophanase from *E. coli* with polyethylene glycol to reduce its immunoreactivity towards anti–tryptophanase antibodies" *Enzyme* 36(4):261–265 (1986).

Yoshimura et al., "Neutrophil attractant/activation protein–1 and monocyte chemoattractant protein–1 in rabbit. cDNA cloning and their expression in spleen cells" *J. Immunol.* 146:3483–3488 (1991).

Zapata et al., "Site–Specific Coupling of Monomethoxy-poly(ethylene glycol) to a Single–Sulfhydryl Humanized Fab'" (poster presented at the American Society for Biochemistry and Molecular Biology FASEB Meeting in San Francisco, CA on May 21–25 1995) pps. 1–27.

Zapata et al., "Site–Specific Coupling of Monomethoxy-poly(ethylene glycol) to a Single–Sulfhydryl Humanized Fab'" *FASEB Journal* (Abstract #1288, presented at the American Society for Biochemistry and Molecular Biology FASEB Meeting in San Francisco, CA on May 21–25, 1995) 9(6):A1479 (1995).

\* cited by examiner

Light Chain Primers:

MKLC-1, 22mer

5'    CAGTCCAACTGTTCAGGACGCC 3'

MKLC-2, 22mer

5'    GTGCTGCTCATGCTGTAGGTGC 3'

MKLC-3, 23mer

5'    GAAGTTGATGTCTTGTGAGTGGC    3'

Heavy Chain Primers:

IGG2AC-1, 24mer

5'    GCATCCTAGAGTCACCGAGGAGCC    3'

IGG2AC-2, 22mer

5'    CACTGGCTCAGGGAAATAACCC 3'

IGG2AC-3, 22mer

5'    GGAGAGCTGGGAAGGTGTGCAC 3'

FIG. 13

Light chain forward primer

SL001A-2  35 mer

```
5' ACAAACGCGTACGCT GACATCGTCATGACCCAGTC  3'
                    T T         T
                                A
```

Light chain reverse primer

SL001B  37 mer

```
5' GCTCTTCGAATG GTGGGAAGATGGATACAGTTGGTGC  3'
```

FIG. 14

Heavy chain forward primer

SL002B   39 mer

5' CGATGGGCCCGG ATAGACCGATGGGGCTGTTGTTTTGGC 3'
                  T                C
                  G
                  A

Heavy chain reverse primer

SL002B   39-MER

5' CGATGGGCCCGG ATAGACCGATGGGGCTGTTGTTTTGGC 3'
                  T
                  A
                  G

FIG. 15

```
  1 GACATTGTCA TGACACAGTC TCAAAAATTC ATGTCCACAT CAGTAGGAGA CAGGGTCAGC
    CTGTAACAGT ACTGTGTCAG AGTTTTAAG TACAGGTGTA GTCATCCTCT GTCCCAGTCG
  1 D  I  V  M  T  Q  S  Q  K  F  M  S  T  S  V  G  D  R  V  S

61 GTCACCTGCA AGGCCAGTCA GAATGTGGGT ACTAATGTAG CCTGGTATCA ACAGAAACCA
    CAGTGGACGT TCCGGTCAGT CTTACACCCA TGATTACATC GGACCATAGT TGTCTTTGGT
 21 V  T  C  K  A  S  Q  N  V  G  T  N  V  A  W  Y  Q  Q  K  P
                        *  *  *  *  *  *  *  *
                            CDR #1

121 GGGCAATCTC CTAAAGCACT GATTTACTCG TCATCCTACC GGTACAGTGG AGTCCCTGAT
    CCCGTTAGAG GATTTCGTGA CTAAATGAGC AGTAGGATGG CCATGTCACC TCAGGGACTA
 41 G  Q  S  P  K  A  L  I  Y  S  S  S  Y  R  Y  S  G  V  P  D
                            *  *  *  *  *  *  *
                                 CDR #2

181 CGCTTCACAG GCAGTGGATC TGGGACAGAT TTCACTCTCA CCATCAGCCA TGTGCAGTCT
    GCGAAGTGTC CGTCACCTAG ACCCTGTCTA AAGTGAGAGT GGTAGTCGGT ACACGTCAGA
 61 R  F  T  G  S  G  S  G  T  D  F  T  L  T  I  S  H  V  Q  S

241 GAAGACTTGG CAGACTATTT CTGTCAGCAA TATAACATCT ATCCTCTCAC GTTCGGTCCT
    CTTCTGAACC GTCTGATAAA GACAGTCGTT ATATTGTAGA TAGGAGAGTG CAAGCCAGGA
 81 E  D  L  A  D  Y  F  C  Q  Q  Y  N  I  Y  P  L  T  F  G  P
                            *  *  *  *  *  *  *  *
                                 CDR #3

301 GGGACCAAGC TGGAGTTGAA ACGGGCTGAT GCTGCACCAC CAACTGTATC CATCTTCCCA
    CCCTGGTTCG ACCTCAACTT TGCCCGACTA CGACGTGGTG GTTGACATAG GTAGAAGGGT
101 G  T  K  L  E  L  K  R  A  D  A  A  P  P  T  V  S  I  F  P

BstBI
361 CCATTCGAA
    GGTAAGCTT
121 P  F  E
```

FIG. 16

```
  1 TTCTATTGCT ACAAACGCGT ACGCTGAGGT GCAGCTGGTG GAGTCTGGGG GAGGCTTAGT
    AAGATAACGA TGTTTGCGCA TGCGACTCCA CGTCGACCAC CTCAGACCCC CTCCGAATCA
  1                                 E  V  Q  L  V  E  S  G  G   G  L  V

61 GCCGCCTGGA GGGTCCCTGA AACTCTCCTG TGCAGCCTCT GGATTCATAT TCAGTAGTTA
    CGGCGGACCT CCCAGGGACT TTGAGAGGAC ACGTCGGAGA CCTAAGTATA AGTCATCAAT
 13  P  P  G  G  S  L  K  L  S  C   A  A  S   G  F  I  F  S  S  Y
                                               ‾‾‾‾‾‾‾‾‾‾‾‾‾‾‾‾‾‾‾‾
                                                            CDR #1

121 TGGCATGTCT TGGGTTCGCC AGACTCCAGG CAAGAGCCTG GAGTTGGTCG CAACCATTAA
    ACCGTACAGA ACCCAAGCGG TCTGAGGTCC GTTCTCGGAC CTCAACCAGC GTTGGTAATT
 33  G  M  S   W  V  R  Q  T  P  G  K  S  L   E  L  V  A   T  I  N
    ‾‾‾‾‾‾‾‾                                               ‾‾‾‾‾‾‾‾

181 TAATAATGGT GATAGCACCT ATTATCCAGA CAGTGTGAAG GGCCGATTCA CCATCTCCCG
    ATTATTACCA CTATCGTGGA TAATAGGTCT GTCACACTTC CCGGCTAAGT GGTAGAGGGC
 53  N  N  G   D  S  T  Y   Y  P  D   S  V  K   G  R  F  T  I  S  R
    ‾‾‾‾‾‾‾‾‾‾‾‾‾‾‾‾‾‾‾‾‾‾‾‾‾‾‾‾‾‾‾‾‾‾‾‾‾‾‾‾
           CDR #2

241 AGACAATGCC AAGAACACCC TGTACCTGCA AATGAGCAGT CTGAAGTCTG AGGACACAGC
    TCTGTTACGG TTCTTGTGGG ACATGGACGT TTACTCGTCA GACTTCAGAC TCCTGTGTCG
 73  D  N  A  K  N  T  L  Y  L  Q  M  S  S   L  K  S  E   D  T  A

301 CATGTTTTAC TGTGCAAGAG CCCTCATTAG TTCGGCTACT TGGTTTGGTT ACTGGGGCCA
    GTACAAAATG ACACGTTCTC GGGAGTAATC AAGCCGATGA ACCAAACCAA TGACCCCGGT
 93  M  F  Y  C  A  R  A   L  I  S   S  A  T   W  F  G  Y  W  G  Q
                           ‾‾‾‾‾‾‾‾‾‾‾‾‾‾‾‾‾‾‾‾‾‾‾‾‾‾‾‾‾‾
                                     CDR #3

361 AGGGACTCTG GTCACTGTCT CTGCAGCCAA AACAACAGCC CCATCTGTCT
    TCCCTGAGAC CAGTGACAGA GACGTCGGTT TTGTTGTCGG GGTAGACAGA
113  G  T  L  V  T  V  S  A  A  K   T  T  A   P  S  V  Y

ApaI
411     ATCCGGG
        TAGGCCC
130       P
```

FIG. 17

VL.front       31-MER

5' ACAAACGCGTACGCTGATATCGTCATGACAG     3'

VL.rear 31-MER

5' GCAGCATCAGCTCTTCGAAGCTCCAGCTTGG     3'

VH.front.SPE    21-MER

5' CCACTAGTACGCAAGTTCACG               3'

VH.rear 33-MER

5' GATGGGCCCTTGGTGGAGGCTGCAGAGACAGTG        3'

FIG. 18

```
  1 ATGAAGAAGA ATATCGCATT TCTTCTTGCA TCTATGTTCG TTTTTTCTAT TGCTACAAAC
    TACTTCTTCT TATAGCGTAA AGAAGAACGT AGATACAAGC AAAAAAGATA ACGATGTTTG
-23 M   K   K   N   I   A   F   L   L   A   S   M   F   V   F   S   I   A   T   N

61 GCGTACGCTG ATATCGTCAT GACACAGTCT CAAAAATTCA TGTCCACATC AGTAGGAGAC
    CGCATGCGAC TATAGCAGTA CTGTGTCAGA GTTTTTAAGT ACAGGTGTAG TCATCCTCTG
 -3 A   Y   A   D   I   V   M   T   Q   S   Q   K   F   M   S   T   S   V   G   D

121 AGGGTCAGCG TCACCTGCAA GGCCAGTCAG AATGTGGGTA CTAATGTAGC CTGGTATCAA
    TCCCAGTCGC AGTGGACGTT CCGGTCAGTC TTACACCCAT GATTACATCG GACCATAGTT
 18 R   V   S   V   T   C   K   A   S   Q   N   V   G   T   N   V   A   W   Y   Q
                                        *   *   *   *   *   *   *   *   *   *
                                                    CDR #1

181 CAGAAACCAG GGCAATCTCC TAAAGCACTG ATTTACTCGT CATCCTACCG GTACAGTGGA
    GTCTTTGGTC CCGTTAGAGG ATTTCGTGAC TAAATGAGCA GTAGGATGGC CATGTCACCT
 38 Q   K   P   G   Q   S   P   K   A   L   I   Y   S   S   S   Y   R   Y   S   G
                                                    *   *   *   *   *   *   *
                                                        CDR #2

241 GTCCCTGATC GCTTCACAGG CAGTGGATCT GGGACAGATT TCACTCTCAC CATCAGCCAT
    CAGGGACTAG CGAAGTGTCC GTCACCTAGA CCCTGTCTAA AGTGAGAGTG GTAGTCGGTA
 58 V   P   D   R   F   T   G   S   G   S   G   T   D   F   T   L   T   I   S   H

301 GTGCAGTCTG AAGACTTGGC AGACTATTTC TGTCAGCAAT ATAACATCTA TCCTCTCACG
    CACGTCAGAC TTCTGAACCG TCTGATAAAG ACAGTCGTTA TATTGTAGAT AGGAGAGTGC
 78 V   Q   S   E   D   L   A   D   Y   F   C   Q   Q   Y   N   I   Y   P   L   T
                                                *   *   *   *   *   *   *   *
                                                        CDR #3
                    BstBI
361 TTCGGTCCTG GGACCAAGCT GGAGCTTCGA AGAGCTGTGG CTGCACCATC TGTCTTCATC
    AAGCCAGGAC CCTGGTTCGA CCTCGAAGCT TCTCGACACC GACGTGGTAG ACAGAAGTAG
 98 F   G   P   G   T   K   L   E   L   R   R   A   V   A   A   P   S   V   F   I

421 TTCCCGCCAT CTGATGAGCA GTTGAAATCT GGAACTGCTT CTGTTGTGTG CCTGCTGAAT
    AAGGGCGGTA GACTACTCGT CAACTTTAGA CCTTGACGAA GACAACACAC GGACGACTTA
118 F   P   P   S   D   E   Q   L   K   S   G   T   A   S   V   V   C   L   L   N

481 AACTTCTATC CCAGAGAGGC CAAAGTACAG TGGAAGGTGG ATAACGCCCT CCAATCGGGT
    TTGAAGATAG GGTCTCTCCG GTTTCATGTC ACCTTCCACC TATTGCGGGA GGTTAGCCCA
138 N   F   Y   P   R   E   A   K   V   Q   W   K   V   D   N   A   L   Q   S   G

541 AACTCCCAGG AGAGTGTCAC AGAGCAGGAC AGCAAGGACA GCACCTACAG CCTCAGCAGC
    TTGAGGGTCC TCTCACAGTG TCTCGTCCTG TCGTTCCTGT CGTGGATGTC GGAGTCGTCG
158 N   S   Q   E   S   V   T   E   Q   D   S   K   D   S   T   Y   S   L   S   S

601 ACCCTGACGC TGAGCAAAGC AGACTACGAG AAACACAAAG TCTACGCCTG CGAAGTCACC
    TGGGACTGCG ACTCGTTTCG TCTGATGCTC TTTGTGTTTC AGATGCGGAC GCTTCAGTGG
178 T   L   T   L   S   K   A   D   Y   E   K   H   K   V   Y   A   C   E   V   T

661 CATCAGGGCC TGAGCTCGCC CGTCACAAAG AGCTTCAACA GGGGAGAGTG
    GTAGTCCCGG ACTCGAGCGG GCAGTGTTTC TCGAAGTTGT CCCCTCTCAC
198 H   Q   G   L   S   S   P   V   T   K   S   F   N   R   G   E   C

711 TTAA
    AATT
216  O
```

FIG. 19

```
  1 ATGAAAAAGA ATATCGCATT TCTTCTTGCA TCTATGTTCG TTTTTTCTAT TGCTACAAAC
    TACTTTTTCT TATAGCGTAA AGAAGAACGT AGATACAAGC AAAAAAGATA ACGATGTTTG
-23 M   K   K    I   A   F   L   L   A   S   M   F   V   F   S   I   A   T   N

61 GCGTACGCTG AGGTGCAGCT GGTGGAGTCT GGGGGAGGCT TAGTGCCGCC TGGAGGGTCC
    CGCATGCGAC TCCACGTCGA CCACCTCAGA CCCCCTCCGA ATCACGGCGG ACCTCCCAGG
 -3 A   Y   A    E   V   Q   L   V   E   S   G   G   G   L   V   P   P   G   G   S

121 CTGAAACTCT CCTGTGCAGC CTCTGGATTC ATATTCAGTA GTTATGGCAT GTCTTGGGTT
    GACTTTGAGA GGACACGTCG GAGACCTAAG TATAAGTCAT CAATACCGTA CAGAACCCAA
 18 L   K   L    S   C   A   A   S   G   F   I   F   S   S   Y   G   M   S   W   V
                               ̲   ̲   ̲   ̲   ̲   ̲   ̲
                                       *   *   *   *   *
                                CDR #1

181 CGCCAGACTC CAGGCAAGAG CCTGGAGTTG GTCGCAACCA TTAATAATAA TGGTGATAGC
    GCGGTCTGAG GTCCGTTCTC GGACCTCAAC CAGCGTTGGT AATTATTATT ACCACTATCG
 38 R   Q   T    P   G   K   S   L   E   L   V   A   T   I   N   N   N   G   D   S
                                                          *   *   *   *   *   *   *   *

241 ACCTATTATC CAGACAGTGT GAAGGGCCGA TTCACCATCT CCCGAGACAA TGCCAAGAAC
    TGGATAATAG GTCTGTCACA CTTCCCGGCT AAGTGGTAGA GGGCTCTGTT ACGGTTCTTG
 58 T   Y   Y    P   D   S   V   K   G   R   F   T   I   S   R   D   N   A   K   N
    *   *   *    *   *   *   *   *
         CDR #2

301 ACCCTGTACC TGCAAATGAG CAGTCTGAAG TCTGAGGACA CAGCCATGTT TTACTGTGCA
    TGGGACATGG ACGTTTACTC GTCAGACTTC AGACTCCTGT GTCGGTACAA AATGACACGT
 78 T   L   Y    L   Q   M   S   S   L   K   S   E   D   T   A   M   F   Y   C   A

361 AGAGCCCTCA TTAGTTCGGC TACTTGGTTT GGTTACTGGG GCCAAGGGAC TCTGGTCACT
    TCTCGGGAGT AATCAAGCCG ATGAACCAAA CCAATGACCC CGGTTCCCTG AGACCAGTGA
 98 R   A   L    I   S   S   A   T   W   F   G   Y   W   G   Q   G   T   L   V   T
                ̲   ̲   ̲   ̲   ̲   ̲   ̲   ̲   ̲   ̲
                *   *   *   *   *   *   *   *   *   *
                        CDR #3
                        ApaI
421 GTCTCTGCAG CCTCCACCAA GGGCCCATCG GTCTTCCCCC TGGCACCCTC CTCCAAGAGC
    CAGAGACGTC GGAGGTGGTT CCCGGGTAGC CAGAAGGGGG ACCGTGGGAG GAGGTTCTCG
118 V   S   A    A   S   T   K   G   P   S   V   F   P   L   A   P   S   S   K   S

481 ACCTCTGGGG GCACAGCGGC CCTGGGCTGC CTGGTCAAGG ACTACTTCCC CGAACCGGTG
    TGGAGACCCC CGTGTCGCCG GGACCCGACG GACCAGTTCC TGATGAAGGG GCTTGGCCAC
138 T   S   G    G   T   A   A   L   G   C   L   V   K   D   Y   F   P   E   P   V

541 ACGGTGTCGT GGAACTCAGG CGCCCTGACC AGCGGCGTGC ACACCTTCCC GGCTGTCCTA
    TGCCACAGCA CCTTGAGTCC GCGGGACTGG TCGCCGCACG TGTGGAAGGG CCGACAGGAT
158 T   V   S    W   N   S   G   A   L   T   S   G   V   H   T   F   P   A   V   L

601 CAGTCCTCAG GACTCTACTC CCTCAGCAGC GTGGTGACCG TGCCCTCCAG CAGCTTGGGC
    GTCAGGAGTC CTGAGATGAG GGAGTCGTCG CACCACTGGC ACGGGAGGTC GTCGAACCCG
178 Q   S   S    G   L   Y   S   L   S   S   V   V   T   V   P   S   S   S   L   G
```

FIG. 20A

```
661 ACCCAGACCT ACATCTGCAA CGTGAATCAC AAGCCCAGCA ACACCAAGGT GGACAAGAAA
    TGGGTCTGGA TGTAGACGTT GCACTTAGTG TTCGGGTCGT TGTGGTTCCA CCTGTTCTTT
198  T  Q  T   Y  I  C   N  V  N   H  K  P   S  N  T   K  V  D   K  K

721 GTTGAGCCCA AATCTTGTGA CAAAACTCAC ACATGA
    CAACTCGGGT TTAGAACACT GTTTTGAGTG TGTACT
218  V  E  P   K  S  C   D  K  T   H  T  O
```

FIG. 20B

Light Chain Primers:

MKLC-1, 22mer

5'      CAGTCCAACTGTTCAGGACGCC 3'

MKLC-2, 22mer

5'      GTGCTGCTCATGCTGTAGGTGC 3'

MKLC-3, 23mer

5'      GAAGTTGATGTCTTGTGAGTGGC      3'

Heavy Chain Primers:

IGG2AC-1, 24mer

5'      GCATCCTAGAGTCACCGAGGAGCC      3'

IGG2AC-2, 22mer

5'      CACTGGCTCAGGGAAATAACCC 3'

IGG2AC-3, 22mer

5'      GGAGAGCTGGGAAGGTGTGCAC 3'

FIG. 21

Light chain forward primer

6G4.light.Nsi   36-MER

```
5' CCAATGCATACGCT GAC ATC GTG ATG ACC CAG ACC CC 3'
                  T   T       T       T
                                  A       A
```

Light chain reverse primer

6G4.light.Mun   35-MER

5' AGA TGT CAA TTG CTC ACT GGA TGG TGG GAA GAT GG 3'

FIG. 22

Heavy chain forward primer

6G4.heavy.Mlu 32-MER

5' CAAACGCGTACGCT GAG ATC CAG CTG CAG CAG 3'
                            T           C

Heavy chain reverse primer

SL002B 39-MER

5' CGATGGGCCCGG ATAGACCGATGGGGCTGTTGTTTTGGC 3'
                 T
                 A
                 G

FIG. 23

```
 70 G ATATCGTGAT GACACAGACA CCACTCTCCC TGCCTGTCAG TCTTGGAGAT
    C TATAGCACTA CTGTGTCTGT GGTGAGAGGG ACGGACAGTC AGAACCTCTA
  1   D   I   V   M   T   Q   T   P   L   S   L   P   V   S   L   G   D

121 CAGGCCTCCA TCTCTTGCAG ATCTAGTCAG AGCCTTGTAC ACGGTATTGG AAACACCTAT
    GTCCGGAGGT AGAGAACGTC TAGATCAGTC TCGGAACATG TGCCATAACC TTTGTGGATA
 18   Q   A   S   I   S   C   R   S   S   Q   S   L   V   H   G   I   G   N   T   Y
                                              *   *   *   *   *   *   *   *   *   *   *   *   *   *   *
                                                          CDR #1

181 TTACATTGGT ACCTGCAGAA GCCAGGCCAG TCTCCAAAGC TCCTGATCTA CAAAGTTTCC
    AATGTAACCA TGGACGTCTT CGGTCCGGTC AGAGGTTTCG AGGACTAGAT GTTTCAAAGG
 38   L   H   W   Y   L   Q   K   P   G   Q   S   P   K   L   L   I   Y   K   V   S
      *   *                                                              *   *   *
                                                                        CDR #2

241 AACCGATTTT CTGGGGTCCC AGACAGGTTC AGTGGCAGTG GATCAGGGAC AGATTTCACA
    TTGGCTAAAA GACCCCAGGG TCTGTCCAAG TCACCGTCAC CTAGTCCCTG TCTAAAGTGT
 58   N   R   F   S   G   V   P   D   R   F   S   G   S   G   S   G   T   D   F   T
      *   *   *   *

301 CTCAGGATCA GCAGAGTGGA GGCTGAGGAT CTGGGACTTT ATTTCTGCTC TCAAAGTACA
    GAGTCCTAGT CGTCTCACCT CCGACTCCTA GACCCTGAAA TAAAGACGAG AGTTTCATGT
 78   L   R   I   S   R   V   E   A   E   D   L   G   L   Y   F   C   S   Q   S   T
                                                                          *   *   *
                                                                        CDR #3

361 CATGTTCCGC TCACGTTCGG TGCTGGGACC AAGCTGGAGC TGAAACGGGC TGATGCTGCA
    GTACAAGGCG AGTGCAAGCC ACGACCCTGG TTCGACCTCG ACTTTGCCCG ACTACGACGT
 98   H   V   P   L   T   F   G   A   G   T   K   L   E   L   K   R   A   D   A   A
      *   *   *   *   *
                                                          MunI
421 CCAACTGTAT CCATCTTCCC ACCATCCAGT GAGCAATTGA
    GGTTGACATA GGTAGAAGGG TGGTAGGTCA CTCGTTAACT
118  P   T   V   S   I   F   P   P   S   S   E   Q   L   K
```

FIG. 24

```
 70 G AGATTCAGCT GCAGCAGTCT GGACCTGAGC TGATGAAGCC TGGGGCTTCA
    C TCTAAGTCGA CGTCGTCAGA CCTGGACTCG ACTACTTCGG ACCCCGAAGT
  1 E    I  Q  L    Q  Q  S    G  P  E  L    M  K  P    G  A  S

121 GTGAAGATAT CCTGCAAGGC TTCTGGTTAT TCATTCAGTA GCCACTACAT GCACTGGGTG
    CACTTCTATA GGACGTTCCG AAGACCAATA AGTAAGTCAT CGGTGATGTA CGTGACCCAC
 18 V  K  I  S    C  K  A    S  G  Y    S  F  S  S    H  Y  M    H  W  V
                                  *  *  *  *  *    *  *  *  *
                                      CDR #1

181 AAGCAGAGCC ATGGAAAGAG CCTTGAGTGG ATTGGCTACA TTGATCCTTC CAATGGTGAA
    TTCGTCTCGG TACCTTTCTC GGAACTCACC TAACCGATGT AACTAGGAAG GTTACCACTT
 38 K  Q  S    H  G  K  S    L  E  W    I  G  Y  I    D  P  S    N  G  E
                                                        *  *  *  *  *  *  *
                                                           CDR #2

241 ACTACTTACA ACCAGAAATT CAAGGGCAAG GCCACATTGA CTGTAGACAC ATCTTCCAGC
    TGATGAATGT TGGTCTTTAA GTTCCCGTTC CGGTGTAACT GACATCTGTG TAGAAGGTCG
 58 T  T  Y  N    Q  K  F    K  G  K    A  T  L  T    V  D  T    S  S  S
    *  *  *  *    *  *  *    *  *

301 ACAGCCAACG TGCATCTCAG CAGCCTGACA TCTGATGACT CTGCAGTCTA TTTCTGTGCA
    TGTCGGTTGC ACGTAGAGTC GTCGGACTGT AGACTACTGA GACGTCAGAT AAAGACACGT
 78 T  A  N  V    H  L  S    S  L  T    S  D  D  S    A  V  Y    F  C  A

361 AGAGGGGACT ATAGATACAA CGGCGACTGG TTTTTCGATG TCTGGGGCGC AGGGACCACG
    TCTCCCCTGA TATCTATGTT GCCGCTGACC AAAAAGCTAC AGACCCCGCG TCCCTGGTGC
 98 R  G  D  Y    R  Y  N    G  D  W    F  F  D  V    W  G  A    G  T  T
       *  *  *  *    *  *  *    *  *  *    *  *  *
                        CDR #3
    BstEII                                              ApaI
421 GTCACCGTCT CCTCCGCCAA AACCGACAGC CCCATCGGTC TATCCGGGCC
    CAGTGGCAGA GGAGGCGGTT TTGGCTGTCG GGGTAGCCAG ATAGGCCCGG
118 V  T  V  S    S  A  K    T  D  S    P  I  G    L  S  G  P

471 CATC
    GTAG
135 I
```

FIG. 25

5' CTTGGTGGAGGCGGAGGAGACG 3'

Mutagenesis Primer for 6G425VL

DS/VF  38MER

5' GAAACGGGCTGTTGCTGCACCAACTGTATTCATCTTCC 3'

SYN.BstEII  31 MER

5' GTCACCGTCT CCTCCGCCTC CACCAAGGGC C 3'

SYN.Apa  22 MER

5' CTTGGTGGAGGCGGAGGAGACG   3'

FIG. 26

```
  1 ATGAAGAAGA ATATCGCATT TCTTCTTGCA TCTATGTTCG TTTTTTCTAT TGCTACAAAT
    TACTTCTTCT TATAGCGTAA AGAAGAACGT AGATACAAGC AAAAAAGATA ACGATGTTTA
-23 M   K   K    I   A   F   L   L   A   S   M   F   V   F   S   I   A   T   N

61 GCATACGCTG ATATCGTGAT GACACAGACA CCACTCTCCC TGCCTGTCAG TCTTGGAGAT
    CGTATGCGAC TATAGCACTA CTGTGTCTGT GGTGAGAGGG ACGGACAGTC AGAACCTCTA
 -3 A   Y   A   D   I   V   M   T   Q   T   P   L   S   L   P   V   S   L   G   D

121 CAGGCCTCCA TCTCTTGCAG ATCTAGTCAG AGCCTTGTAC ACGGTATTGG AAACACCTAT
    GTCCGGAGGT AGAGAACGTC TAGATCAGTC TCGGAACATG TGCCATAACC TTTGTGGATA
 18 Q   A   S   I   S   C   R   S   S   Q   S   L   V   H   G   I   G   N   T   Y
                                        *   *   *   *   *   *   *   *   *   *   *   *   *
                                                    CDR #1

181 TTACATTGGT ACCTGCAGAA GCCAGGCCAG TCTCCAAAGC TCCTGATCTA CAAAGTTTCC
    AATGTAACCA TGGACGTCTT CGGTCCGGTC AGAGGTTTCG AGGACTAGAT GTTTCAAAGG
 38 L   H   W   Y   L   Q   K   P   G   Q   S   P   K   L   L   I   Y   K   V   S
    *   *                                                                   *   *   *
                                                                              CDR #2

241 AACCGATTTT CTGGGGTCCC AGACAGGTTC AGTGGCAGTG GATCAGGGAC AGATTTCACA
    TTGGCTAAAA GACCCCAGGG TCTGTCCAAG TCACCGTCAC CTAGTCCCTG TCTAAAGTGT
 58 N   R   F   S   G   V   P   D   R   F   S   G   S   G   S   G   T   D   F   T
    *   *   *   *

301 CTCAGGATCA GCAGAGTGGA GGCTGAGGAT CTGGGACTTT ATTTCTGCTC TCAAAGTACA
    GAGTCCTAGT CGTCTCACCT CCGACTCCTA GACCCTGAAA TAAAGACGAG AGTTTCATGT
 78 L   R   I   S   R   V   E   A   E   D   L   G   L   Y   F   C   S   Q   S   T
                                                                            *   *   *
                                                                              CDR #3

361 CATGTTCCGC TCACGTTCGG TGCTGGGACC AAGCTGGAGC TGAAACGGGC TGTTGCTGCA
    GTACAAGGCG AGTGCAAGCC ACGACCCTGG TTCGACCTCG ACTTTGCCCG ACAACGACGT
 98 H   V   P   L   T   F   G   A   G   T   K   L   E   L   K   R   A   V   A   A
    *   *   *   *   *

421 CCAACTGTAT TCATCTTCCC ACCATCCAGT GAGCAATTGA AATCTGGAAC TGCCTCTGTT
    GGTTGACATA AGTAGAAGGG TGGTAGGTCA CTCGTTAACT TTAGACCTTG ACGGAGACAA
118 P   T   V   F   I   F   P   P   S   S   E   Q   L   K   S   G   T   A   S   V

481 GTGTGCCTGC TGAATAACTT CTATCCCAGA GAGGCCAAAG TACAGTGGAA GGTGGATAAC
    CACACGGACG ACTTATTGAA GATAGGGTCT CTCCGGTTTC ATGTCACCTT CCACCTATTG
138 V   C   L   L   N   N   F   Y   P   R   E   A   K   V   Q   W   K   V   D   N

541 GCCCTCCAAT CGGGTAACTC CCAGGAGAGT GTCACAGAGC AGGACAGCAA GGACAGCACC
    CGGGAGGTTA GCCCATTGAG GGTCCTCTCA CAGTGTCTCG TCCTGTCGTT CCTGTCGTGG
158 A   L   Q   S   G   N   S   Q   E   S   V   T   E   Q   D   S   K   D   S   T

601 TACAGCCTCA GCAGCACCCT GACGCTGAGC AAAGCAGACT ACGAGAAACA CAAAGTCTAC
    ATGTCGGAGT CGTCGTGGGA CTGCGACTCG TTTCGTCTGA TGCTCTTTGT GTTTCAGATG
178 Y   S   L   S   S   T   L   T   L   S   K   A   D   Y   E   K   H   K   V   Y
```

FIG. 27A

661 GCCTGGCGAAG TCACCCATCA GGGCCTGAGC TCGCCCGTCA CAAAGAGCTT CAACAGGGGA
    CGGACGCTTC AGTGGGTAGT CCCGGACTCG AGCGGGCAGT GTTTCTCGAA GTTGTCCCCT
198  A   C   E   V    T   H   Q    G   L   S    S   P   V   T    K   S   F    N   R   G

721 GAGTGTTAA
    CTCACAATT
218  E   C   O

FIG. 27B

```
  1 ATGAAAAAGA ATATCGCATT TCTTCTTGCA TCTATGTTCG TTTTTTCTAT TGCTACAAAC
    TACTTTTTCT TATAGCGTAA AGAAGAACGT AGATACAAGC AAAAAAGATA ACGATGTTTG
-23 M  K  K   N  I  A  F   L  L  A   S  M  F   V  F  S   I  A  T  N

61 GCGTACGCTG AGATTCAGCT GCAGCAGTCT GGACCTGAGC TGATGAAGCC TGGGGCTTCA
    CGCATGCGAC TCTAAGTCGA CGTCGTCAGA CCTGGACTCG ACTACTTCGG ACCCCGAAGT
 -3 A  Y  A   E  I  Q  L   Q  Q  S   G  P  E   L  M  K  P   G  A  S

121 GTGAAGATAT CCTGCAAGGC TTCTGGTTAT TCATTCAGTA GCCACTACAT GCACTGGGTG
    CACTTCTATA GGACGTTCCG AAGACCAATA AGTAAGTCAT CGGTGATGTA CGTGACCCAC
 18 V  K  I  S   C  K  A   S  G  Y   S  F  S  S   H  Y  M   H  W  V
                                    ─ ─ ─ ─ ─ ─ ─ ─
                                     *  *  *  *  *
                                        CDR #1

181 AAGCAGAGCC ATGGAAAGAG CCTTGAGTGG ATTGGCTACA TTGATCCTTC CAATGGTGAA
    TTCGTCTCGG TACCTTTCTC GGAACTCACC TAACCGATGT AACTAGGAAG GTTACCACTT
 38 K  Q  S  H   G  K  S   L  E  W   I  G  Y   I  D  P  S   N  G  E
                                           *  *  * * *  *  *  *
                                                    CDR #2

241 ACTACTTACA ACCAGAAATT CAAGGGCAAG GCCACATTGA CTGTAGACAC ATCTTCCAGC
    TGATGAATGT TGGTCTTTAA GTTCCCGTTC CGGTGTAACT GACATCTGTG TAGAAGGTCG
 58 T  T  Y   N  Q  K  F   K  G  K   A  T  L   T  V  D  T   S  S  S
    *  *  *   *  *  *  *   *  *

301 ACAGCCAACG TGCATCTCAG CAGCCTGACA TCTGATGACT CTGCAGTCTA TTTCTGTGCA
    TGTCGGTTGC ACGTAGAGTC GTCGGACTGT AGACTACTGA GACGTCAGAT AAAGACACGT
 78 T  A  N  V   H  L  S   S  L  T   S  D  D  S   A  V  Y   F  C  A

361 AGAGGGGACT ATAGATACAA CGGCGACTGG TTTTTCGATG TCTGGGGCGC AGGGACCACG
    TCTCCCCTGA TATCTATGTT GCCGCTGACC AAAAAGCTAC AGACCCCGCG TCCCTGGTGC
 98 R  G  D   Y  R  Y  N   G  D  W   F  F  D   V  W  G  A   G  T  T
         ─ ─ ─ ─ ─ ─ ─ ─ ─ ─ ─ ─ ─ ─
         *  *  *  *  *  *  *  *  *  *
                   CDR #3

421 GTCACCGTCT CCTCCGCCTC CACCAAGGGC CCATCGGTCT TCCCCCTGGC ACCCTCCTCC
    CAGTGGCAGA GGAGGCGGAG GTGGTTCCCG GGTAGCCAGA AGGGGGACCG TGGGAGGAGG
118 V  T  V  S   S  A  S   T  K  G   P  S  V   F  P  L  A   P  S  S

481 AAGAGCACCT CTGGGGGCAC AGCGGCCCTG GGCTGCCTGG TCAAGGACTA CTTCCCCGAA
    TTCTCGTGGA GACCCCCGTG TCGCCGGGAC CCGACGGACC AGTTCCTGAT GAAGGGGCTT
138 K  S  T  S   G  G  T   A  A  L   G  C  L   V  K  D  Y   F  P  E

541 CCGGTGACGG TGTCGTGGAA CTCAGGCGCC CTGACCAGCG GCGTGCACAC CTTCCCGGCT
    GGCCACTGCC ACAGCACCTT GAGTCCGCGG GACTGGTCGC CGCACGTGTG GAAGGGCCGA
158 P  V  T  V   S  W  N   S  G  A   L  T  S   G  V  H  T   F  P  A

601 GTCCTACAGT CCTCAGGACT CTACTCCCTC AGCAGCGTGG TGACCGTGCC CTCCAGCAGC
    CAGGATGTCA GGAGTCCTGA GATGAGGGAG TCGTCGCACC ACTGGCACGG GAGGTCGTCG
178 V  L  Q  S   S  G  L   Y  S  L   S  S  V   V  T  V  P   S  S  S
```

FIG. 28A

```
661  TTGGGCACCC AGACCTACAT CTGCAACGTG AATCACAAGC CCAGCAACAC CAAGGTGGAC
     AACCCGTGGG TCTGGATGTA GACGTTGCAC TTAGTGTTCG GGTCGTTGTG GTTCCACCTG
198   L  G  T  Q   T  Y  I   C  N  V   N  H  K  P   S  N  T   K  V  D

721  AAGAAAGTTG AGCCCAAATC TTGTGACAAA ACTCACACAT GA
     TTCTTTCAAC TCGGGTTTAG AACACTGTTT TGAGTGTGTA CT
218   K  K  V  E   P  K  S   C  D  K   T  H  T  O

FIG. 28B
```

Variable Light Chain Domain

```
              10         20     abcde 30         40
6G425    DIVMTQTPLSLPVSLGDQASISCRSSQSLVHGIGNTYLHWYLQKPGQSPKLLIY
          #   # #  ## #  ### #                 #   ##
F(ab)-1  DIQMTQSPSSLSASVGDRVTITCRSSQSLVHGIGNTYLHWYQQKPGKAPKLLIY
                              # ##########
humkI    DIQMTQSPSSLSASVGDRVTITCRASKTI-----SKYLAWYQQKPGKAPKLLIY
                                 ===========
                         +++++++++++++++++
                                 L1

50         60         70         80         90         100
6G425    YKVSNRPSGVPDRFSDSGSGTDFTLRISRVEAEDLGLYFCSQSTHVPLTFGAGTKLELKR
          #  #          #    ##### ### #            #  # #
F(ab)-1  YKVSNRFSGVPSRFSGSGSGTDFTLTISSLQPEDFATYYCSQSTHVPLTFGQGTKVEIKR
          ## ###                             # ####
humkI    YSGSTLESGVPSRFSGSGSGTDFTLTISSLQPEDFATYYCQQHNEYPLTFGQGTKVEIKR
          ===                                  ======
          +++++++                              ++++++++
           L2                                    L3
```

Variable Heavy Chain Domain

```
              10         20         30         40
6G425    EIQLQQSGPELMKPGASVKISCKASGYSFSSHYMHWVKQSHGKSLEWI
          #  ## ## ##   # ###  #           # ## #  #
F(ab)-1  EVQLVESGGGLVQPGGSLRLSCAASGYSFSSHYMHWVRQAPGKGLEWV
                                  # ## # #
humIII   EVQLVESGGGLVQPGGSLRLSCAASGFSFTGHWMNWVRQAPGKGLEWV
                                  =======
                                   +++++
                                    H1

50  a             70         80  abc      90         100        110
6G425    GYIDPSNGETTYNQKPKGKATLTVDTSSSTANVHLSSLTSDDSAVYFCAARGDYRYNGDWFFDVWGAGT
                           ## ### # ## ###### ### # #                          #
F(ab)-1  GYIDPSNGETTYNQKFKGRFTISRDNSKNTLYLQMNSLRAEDTAVYYCAARGDYRYNGDWFFDVWGQGT
          # # ## # ####                                  # # # ### #
humIII   GMIHPSDSETRYADSVKGRFTISRDNSKNTLYLQMNSLRAEDTAVYYCAARGIYFY-GTTYFDYWGQGT
           ====                                          ============
          +++++++++++++++++                              ++++++++++++
                H2                                            H3
```

Amino Acid Sequence of the humanized anti-IL-8 6G4.2.5V11 Light Chain

MKKNIAFLLASMFVFSIATNAYADIQMTQSPSSLSASVGDRVTITCRSSQSLVHGIGNTY
LHWYQQKPGKAPKLLIYKVSNRFSGVPSRFSGSGSGTDFTLTISSLQPEDFATYCSQST
HVPLTFGQGTKVEIKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRG
EC

Amino Acid Sequence of the humanized anti-IL-8 6G4.2.5V11 Heavy Chain

MKKNIAFLLASMFVFSIATNAYAEVQLVQSGGGLVQPGGSLRLSCAASGYSFSSHYMH
WVRQAPGKGLEWVGYIDPSNGETTYNQKFKGRFTLSRDNSKNTAYLQMNSLRAEDTAVYY
CARGDYRYNGDWFFDVWGQGTLVTVSSASTKGPSVFPLAPSSKSTSGGTAALGCLVKDYF
PEPVTVSWNSGALTSGVHTFPAVLQSSGLYSLSSVVTVPSSSLGTQTYICNVNHKPSNTK
VDKKVEPKSCDKTHT

Amino Acid Sequence of the peptide linker and M13 Phage Coat (gene-III)

SGGGSGSGDFDYEKMANANKGAMTENADENALQSDAKGKLDSVATDYGAAIDGFIGDVS
GLANGNGATGDFAGSSNSQMAQVGDGDNSPLMNNFRQYLPSLPQSVECRPFVFSAGKPY
EFSIDCDKINLFRGVFAFLLYVATFMYVFSTFANILRNKES

FIG. 31A

```
  1 ATGAAAAAGA ATATCGCATT TCTTCTTGCA TCTATGTTCG TTTTTTCTAT TGCTACAAAC
    TACTTTTTCT TATAGCGTAA AGAAGAACGT AGATACAAGC AAAAAAGATA ACGATGTTTG
-23 M   K   K    I   A   F    L   L   A    S   M   F   V    F   S   I    A   T   N

61 GCATACGCTG ATATCCAGAT GACCCAGTCC CCGAGCTCCC TGTCCGCCTC TGTGGGCGAT
    CGTATGCGAC TATAGGTCTA CTGGGTCAGG GGCTCGAGGG ACAGGCGGAG ACACCCGCTA
 -3 A   Y   A   D    I   Q   M    T   Q   S    P   S   S    L   S   A   S    V   G   D

121 AGGGTCACCA TCACCTGCAG GTCAAGTCAA AGCTTAGTAC ATGGTATAGG TAACACGTAT
    TCCCAGTGGT AGTGGACGTC CAGTTCAGTT TCGAATCATG TACCATATCC ACGATGCATA
 18 R   V   T   I    T   C   R    S   S   Q    S   L   V   H    G   I   G    N   T   Y

181 TTACACTGGT ATCAACAGAA ACCAGGAAAA GCTCCGAAAC TACTGATTTA CAAAGTATCC
    AATGTGACCA TAGTTGTCTT TGGTCCTTTT CGAGGCTTTG ATGACTAAAT GTTTCATAGG
 38 L   H   W   Y    Q   Q   K    P   G   K    A   P   K    L   L   I   Y    K   V   S

241 AATCGATTCT CTGGAGTCCC TTCTCGCTTC TCTGGATCCG GTTCTGGGAC GGATTTCACT
    TTAGCTAAGA GACCTCAGGG AAGAGCGAAG AGACCTAGGC CAAGACCCTG CCTAAAGTGA
 58 N   R   F   S    G   V   P    S   R   F    S   G   S    G   S   G    T    D   F   T

301 CTGACCATCA GCAGTCTGCA GCCAGAAGAC TTCGCAACTT ATTACTGTTC ACAGAGTACT
    GACTGGTAGT CGTCAGACGT CGGTCTTCTG AAGCGTTGAA TAATGACAAG TGTCTCATGA
 78 L   T   I   S    S   L   Q    P   E   D    F   A   T    Y   Y   C    S   Q   S   T

361 CATGTCCCGC TCACGTTTGG ACAGGGTACC AAGGTGGAGA TCAAACGAAC TGTGGCTGCA
    GTACAGGGCG AGTGCAAACC TGTCCCATGG TTCCACCTCT AGTTTGCTTG ACACCGACGT
 98 H   V   P   L    T   F   G    Q   G   T    K   V   E    I   K   R    T   V   A   A

421 CCATCTGTCT TCATCTTCCC GCCATCTGAT GAGCAGTTGA AATCTGGAAC TGCTTCTGTT
    GGTAGACAGA AGTAGAAGGG CGGTAGACTA CTCGTCAACT TTAGACCTTG ACGAAGACAA
118 P   S   V   F    I   F   P    P   S   D    E   Q   L    K   S   G    T   A   S   V

481 GTGTGCCTGC TGAATAACTT CTATCCCAGA GAGGCCAAAG TACAGTGGAA GGTGGATAAC
    CACACGGACG ACTTATTGAA GATAGGGTCT CTCCGGTTTC ATGTCACCTT CCACCTATTG
138 V   C   L   L    N   N   F    Y   P   R    E   A   K    V   Q   W    K   V   D   N

541 GCCCTCCAAT CGGGTAACTC CCAGGAGAGT GTCACAGAGC AGGACAGCAA GGACAGCACC
    CGGGAGGTTA GCCCATTGAG GGTCCTCTCA CAGTGTCTCG TCCTGTCGTT CCTGTCGTGG
158 A   L   Q   S    G   N   S    Q   E   S    V   T   E    Q   D   S    K   D   S   T

601 TACAGCCTCA GCAGCACCCT GACGCTGAGC AAAGCAGACT ACGAGAAACA CAAAGTCTAC
    ATGTCGGAGT CGTCGTGGGA CTGCGACTCG TTTCGTCTGA TGCTCTTTGT GTTTCAGATG
178 Y   S   L   S    S   T   L    T   L   S    K   A   D    Y   E   K   H    K   V   Y

661 GCCTGCGAAG TCACCCATCA GGGCCTGAGC TCGCCCGTCA CAAAGAGCTT CAACAGGGGA
    CGGACGCTTC AGTGGGTAGT CCCGGACTCG AGCGGGCAGT GTTTCTCGAA GTTGTCCCCT
198 A   C   E   V    T   H   Q    G   L   S    S   P   V    T   K   S    F   N   R   G

721 GAGTGTTAAG CTGATCCTCT ACGCCGGACG CATCGTGGCC CTAGTACGCA ACTAGTCGTA
    CTCACAATTC GACTAGGAGA TGCGGCCTGC GTAGCACCGG GATCATGCGT TGATCAGCAT
218 E   C   O
```

FIG. 31B

Amino Acid Sequence of the humanized anti-IL-8 6G4.2.5V19 Light Chain

MKKNIAFLLASMFVFSIATNAYADIQMTQSPSSLSASVGDRVTITCRSSQSLVHGIGNTY
LHWYQQKPGKAPKLLIYKVSNRFSGVPSRFSGSGSGTDFTLTISSLQPEDFATYYCSQST
HVPLTFGQGTKVEIKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRG
EC

Amino Acid Sequence of the humanized anti-IL-8 6G4.2.5V19 Heavy Chain

MKKNIAFLLASMFVFSIATNAYAEVQLVESGGGLVQPGGSLRLSCAASGYSFSSHYMH
WVKQAPGKGLEWVGYIDPSNGETTYNQKFKGRFTLSRDNSKNTAYLQMNSLRAEDTAVYY
CARGDYRYNGDMFFDVWGQGTLVTVSSASTKGPSVFPLAPSSKSTSGGTAALGCLVKDYF
PEPVTVSWNSGALTSGVHTFPAVLQSSGLYSLSSVVTVPSSSLGTQTYICNVNHKPSNTK
VDKKVEPKSCDKTHT

FIG. 31C

Amino Acid Sequence of the humanized anti-IL-8 6G4.2.5V11N35A Light Chain

MKKNIAFLLASMFVFSIATNAYADIQMTQSPSSLSASVGDRVTITCRSSQSLVHGIGATY
LHWYQQKPGKAPKLLIYKVSNRFSGVPSRFSGSGSGTDFTLTISSLQPEDFATYCSQST
HVPLTFGQGTKVEIKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRG
EC

Amino Acid Sequence of the humanized anti-IL-8 6G4.2.5V11N35A Heavy Chain

MKKNIAFLLASMFVFSIATNAYAEVQLVQSGGGLVQPGGSLRLSCAASGYSFSSHYMH
WVRQAPGKGLEWVGYIDPSNGETTYNQKFKGRFTLSRDNSKNTAYLQMNSLRAEDTAVYY
CARGDYRYNGDWFFDVWGQGTLVTVSSASTKGPSVFPLAPSSKSTSGGTAALGCLVKDYF
PEPVTVSWNSGALTSGVHTFPAVLQSSGLYSLSSVVTVPSSSLGTQTYICNVNHKPSNTK
VDKKVEPKSCDKTHT

Amino Acid Sequence of the putative Pepsin Cleavage Site and GCN4 Leucine Zipper

CPPCPAPELLGGRMKQLEDKVEELLSKNYHLENEVARLKKLVGER

FIG. 35

```
  1 ATGAAAAAGA ATATCGCATT TCTTCTTGCA TCTATGTTCG TTTTTTCTAT TGCTACAAAC
    TACTTTTTCT TATAGCGTAA AGAAGAACGT AGATACAAGC AAAAAAGATA ACGATGTTTG
-23 M  K  K   N  I  A  F  L  L  A   S  M  F  V  P  S  I  A   T  N

61 GCATACGCTG ATATCCAGAT GACCCAGTCC CCGAGCTCCC TGTCCGCCTC TGTGGGCGAT
    CGTATGCGAC TATAGGTCTA CTGGGTCAGG GGCTCGAGGG ACAGGCGGAG ACACCCGCTA
 -3 A  Y  A   D  I  Q  M  T  Q  S   P  S  S  L  S  A  S   V  G  D

121 AGGGTCACCA TCACCTGCAG GTCAAGTCAA AGCTTAGTAC ATGGTATAGG TGCTACGTAT
    TCCCAGTGGT AGTGGACGTC CAGTTCAGTT TCGAATCATG TACCATATCC ACGATGCATA
 18 R  V  T   I  T  C  R  S  S  Q   S  L  V  H  G  I  G   A  T  Y

181 TTACACTGGT ATCAACAGAA ACCAGGAAAA GCTCCGAAAC TACTGATTTA CAAAGTATCC
    AATGTGACCA TAGTTGTCTT TGGTCCTTTT CGAGGCTTTG ATGACTAAAT GTTTCATAGG
 38 L  H  W   Y  Q  Q  K  P  G  K   A  P  K  L  L  I  Y   K  V  S

241 AATCGATTCT CTGGAGTCCC TTCTCGCTTC TCTGGATCCG GTTCTGGGAC GGATTTCACT
    TTAGCTAAGA GACCTCAGGG AAGAGCGAAG AGACCTAGGC CAAGACCCTG CCTAAAGTGA
 58 N  R  F   S  G  V  P  S  R  F   S  G  S  G  S  G  T   D  F  T

301 CTGACCATCA GCAGTCTGCA GCCAGAAGAC TTCGCAACTT ATTACTGTTC ACAGAGTACT
    GACTGGTAGT CGTCAGACGT CGGTCTTCTG AAGCGTTGAA TAATGACAAG TGTCTCATGA
 78 L  T  I   S  S  L  Q  P  E  D   F  A  T  Y  Y  C  S   Q  S  T

361 CATGTCCCGC TCACGTTTGG ACAGGGTACC AAGGTGGAGA TCAAACGAAC TGTGGCTGCA
    GTACAGGGCG AGTGCAAACC TGTCCCATGG TTCCACCTCT AGTTTGCTTG ACACCGACGT
 98 H  V  P   L  T  F  G  Q  G  T   K  V  E  I  K  R  T   V  A  A

421 CCATCTGTCT TCATCTTCCC GCCATCTGAT GAGCAGTTGA AATCTGGAAC TGCTTCTGTT
    GGTAGACAGA AGTAGAAGGG CGGTAGACTA CTCGTCAACT TTAGACCTTG ACGAAGACAA
118 P  S  V   F  I  F  P  P  S  D   E  Q  L  K  S  G  T   A  S  V

481 GTGTGCCTGC TGAATAACTT CTATCCCAGA GAGGCCAAAG TACAGTGGAA GGTGGATAAC
    CACACGGACG ACTTATTGAA GATAGGGTCT CTCCGGTTTC ATGTCACCTT CCACCTATTG
138 V  C  L   L  N  N  F  Y  P  R   E  A  K  V  Q  W  K   V  D  N

541 GCCCTCCAAT CGGGTAACTC CCAGGAGAGT GTCACAGAGC AGGACAGCAA GGACAGCACC
    CGGGAGGTTA GCCCATTGAG GGTCCTCTCA CAGTGTCTCG TCCTGTCGTT CCTGTCGTGG
158 A  L  Q   S  G  N  S  Q  E  S   V  T  E  Q  D  S  K   D  S  T

601 TACAGCCTCA GCAGCACCCT GACGCTGAGC AAAGCAGACT ACGAGAAACA CAAAGTCTAC
    ATGTCGGAGT CGTCGTGGGA CTGCGACTCG TTTCGTCTGA TGCTCTTTGT GTTTCAGATG
178 Y  S  L   S  S  T  L  T  L  S   K  A  D  Y  E  K  H   K  V  Y

661 GCCTGCGAAG TCACCCATCA GGGCCTGAGC TCGCCCGTCA CAAAGAGCTT CAACAGGGGA
    CGGACGCTTC AGTGGGTAGT CCCGGACTCG AGCGGGCAGT GTTTCTCGAA GTTGTCCCCT
198 A  C  E   V  T  H  Q  G  L  S   S  P  V  T  K  S  F   N  R  G

721 GAGTGTTAAG CTGATCCTCT ACGCCGGACG CATCGTGGCC CTAGTACGCA ACTAGTCGTA
    CTCACAATTC GACTAGGAGA TGCGGCCTGC GTAGCACCGG GATCATGCGT TGATCAGCAT
218 E  C  O
```

FIG. 36

```
781  AAAAGGGTAT CTAGAGGTTG AGGTGATTTT ATGAAAAAGA ATATCGCATT TCTTCTTGCA
     TTTTCCCATA GATCTCCAAC TCCACTAAAA TACTTTTTCT TATAGCGTAA AGAAGAACGT
 -1                                    M  K  K  N  I  A  F  L  L  A

841  TCTATGTTCG TTTTTTCTAT TGCTACAAAC GCGTACGCTG AGGTTCAGCT AGTGCAGTCT
     AGATACAAGC AAAAAAGATA ACGATGTTTG CGCATGCGAC TCCAAGTCGA TCACGTCAGA
-11  S  M  F  V  F  S  I  A  T  N  A  Y  A  E  V  Q  L  V  Q  S

901  GGCGGTGGCC TGGTGCAGCC AGGGGGCTCA CTCCGTTTGT CCTGTGCAGC TTCTGGCTAC
     CCGCCACCGG ACCACGTCGG TCCCCCGAGT GAGGCAAACA GGACACGTCG AAGACCGATG
  8  G  G  G  L  V  Q  P  G  G  S  L  R  L  S  C  A  A  S  G  Y

961  TCCTTCTCGA GTCACTATAT GCACTGGGTC CGTCAGGCCC CGGGTAAGGG CCTGGAATGG
     AGGAAGAGCT CAGTGATATA CGTGACCCAG GCAGTCCGGG GCCCATTCCC GGACCTTACC
 28  S  F  S  S  H  Y  M  H  W  V  R  Q  A  P  G  K  G  L  E  W

1021 GTTGGATATA TTGATCCTTC CAATGGTGAA ACTACGTATA ATCAAAAGTT CAAGGGCCGT
     CAACCTATAT AACTAGGAAG GTTACCACTT TGATGCATAT TAGTTTTCAA GTTCCCGGCA
 48  V  G  Y  I  D  P  S  N  G  E  T  T  Y  N  Q  K  F  K  G  R

1081 TTCACTTTAT CTCGCGACAA CTCCAAAAAC ACAGCATACC TGCAGATGAA CAGCCTGCGT
     AAGTGAAATA GAGCGCTGTT GAGGTTTTTG TGTCGTATGG ACGTCTACTT GTCGGACGCA
 68  F  T  L  S  R  D  N  S  K  N  T  A  Y  L  Q  M  N  S  L  R

1141 GCTGAGGACA CTGCCGTCTA TTACTGTGCA AGAGGGGATT ATCGCTACAA TGGTGACTGG
     CGACTCCTGT GACGGCAGAT AATGACACGT TCTCCCCTAA TAGCGATGTT ACCACTGACC
 88  A  E  D  T  A  V  Y  Y  C  A  R  G  D  Y  R  Y  N  G  D  W

1201 TTCTTCGACG TCTGGGGTCA AGGAACCCTG GTCACCGTCT CCTCGGCCTC CACCAAGGGC
     AAGAAGCTGC AGACCCCAGT TCCTTGGGAC CAGTGGCAGA GGAGCCGGAG GTGGTTCCCG
108  F  F  D  V  W  G  Q  G  T  L  V  T  V  S  S  A  S  T  K  G

1261 CCATCGGTCT TCCCCCTGGC ACCCTCCTCC AAGAGCACCT CTGGGGGCAC AGCGGCCCTG
     GGTAGCCAGA AGGGGGACCG TGGGAGGAGG TTCTCGTGGA GACCCCCGTG TCGCCGGGAC
128  P  S  V  F  P  L  A  P  S  S  K  S  T  S  G  G  T  A  A  L

1321 GGCTGCCTGG TCAAGGACTA CTTCCCCGAA CCGGTGACGG TGTCGTGGAA CTCAGGCGCC
     CCGACGGACC AGTTCCTGAT GAAGGGGCTT GGCCACTGCC ACAGCACCTT GAGTCCGCGG
148  G  C  L  V  K  D  Y  F  P  E  P  V  T  V  S  W  N  S  G  A

1381 CTGACCAGCG GCGTGCACAC CTTCCCGGCT GTCCTACAGT CCTCAGGACT CTACTCCCTC
     GACTGGTCGC CGCACGTGTG GAAGGGCCGA CAGGATGTCA GGAGTCCTGA GATGAGGGAG
168  L  T  S  G  V  H  T  F  P  A  V  L  Q  S  S  G  L  Y  S  L

1441 AGCAGCGTGG TGACCGTGCC CTCCAGCAGC TTGGGCACCC AGACCTACAT CTGCAACGTG
     TCGTCGCACC ACTGGCACGG GAGGTCGTCG AACCCGTGGG TCTGGATGTA GACGTTGCAC
188  S  S  V  V  T  V  P  S  S  S  L  G  T  Q  T  Y  I  C  N  V

1501 AATCACAAGC CCAGCAACAC CAAGGTCGAC AAGAAAGTTG AGCCCAAATC TTGTGACAAA
     TTAGTGTTCG GGTCGTTGTG GTTCCAGCTG TTCTTTCAAC TCGGGTTTAG AACACTGTTT
208  N  H  K  P  S  N  T  K  V  D  K  K  V  E  P  K  S  C  D  K

1561 ACTCACACAT GCCCGCCGTG CCCAGCACCA GAACTGCTGG GCGGCCGCAT GAAACAGCTA
     TGAGTGTGTA CGGGCGGCAC GGGTCGTGGT CTTGACGACC CGCCGGCGTA CTTTGTCGAT
228  T  H  T  C  P  P  C  P  A  P  E  L  L  G  G  R  M  K  Q  L
```

FIG. 37A

```
1621 GAGGACAAGG TCGAAGAGCT ACTCTCCAAG AACTACCACC TAGAGAATGA AGTGGCAAGA
     CTCCTGTTCC AGCTTCTCGA TGAGAGGTTC TTGATGGTGG ATCTCTTACT TCACCGTTCT
 248 E   D  K  V   E  E  L   L  S  K   N  Y  H   L  E  N   E  V  A  R

1681 CTCAAAAAGC TTGTCGGGGA GCGCTAA
     GAGTTTTTCG AACAGCCCCT CGCGATT
 268 L   K  K  L   V  G  E   R  O
```

```
                                                                    scrFI
                                                                    ncII
                                                                    mspI
                                                                    hpaII
                                                                    dsaV
                                                              xmaI/pspAI
                                                                    smaI
                                                                    scrFI
                                                                    ncII
                                                                    dsaV
                                                                    cauII                                        ddeI    nlaIII
                                                                    bsaJI    xhoI                                aluI    rsaI
                                                                    avaI     mnlI                                hindIII csp6I
                                                            rsaI  sau3AI taqI
                                                            csp6I mboI/ndeII[dam-]
                                                            nlaIV dpnI[dam+]                             bspMI
                                                            kpnI  nlaIV paeR7I                           scfI
                                                            bgiCI cauII dpnII[dam-]                      pstI
                                                            banI  bstYI/xhoII                            sse8387I
                                                            asp718 bsaJI alwI[dam-]             hphI     bspMI
                                                            acc65I bamHI avaI    hphI           maeIII   hphI bsgI
                                                                  alwI[dam-] mnlI mnlI          bstEII   hphI bsgI
                                                                                    mboII sfaNI
401 TGGTACCCG GGGATCCTCT CGAGGTTGAG GTGATTTTAT GAAAAAGAAT ATCGCATTTC TTCTGCATC TATGTGTCGTT TTTTCTATTG CTACAAACGC
    AGCCATGGGC CCCTAGGAGA GCTCCAACTC CACTAAAATA CTTTTTCTTA TAGCGTAAAG AAGAACGTAG ATACAAGCAA AAAAGATAAC GATGTTTGCG
-23                                                       M    K  R  N   I   A  F  L   L   A  S   H  F   V    P  S   I   A   T    N  A
                                                                     sstI
                                                                     sacI
                                                                     bglII
                                                                     hgiAI/aspHI
                                                                     ecl136II
                                                                     bsp1286
                                                                     bsiHKAI
                                                             bsmFI   bmyI
                                                    bsrI  avaI  aluI banII
                                                    tth111I/aspI acII
                                            ecoRV                           mnlI
    a mutation was found that inactivated the mluI site. The penultimate nucleotide was changed fr G to T ^

501 ATAGCCTGAT ATCCAGATGA CCCAGTCCCC GAGCTCCCTG TCCGCCTCTG TGGGCGATAG GGTCACCATC ACCTGCAGGT CAAGTCAAAG CTTAGTACAT
    TATGCGACTA TAGGTCTACT GGGTCAGGGG CTCGAGGGAC AGGCGGAGAC ACCCGCTATC CCAGTGGTAG TGGACGTCCA GTTCAGTTTC GAATCATGTA
  -2   Y    A   D   I   Q   M   T    Q   S   P    S   S   L    S   A   S  V   G   D   R   V   T    I   T    C    R   S     S   Q   S   L   V   H
```

FIG. 41B

```
                                                                                    scrFI
                                                                                    mvaI                                                                       hinfI
                                                                                    ecoRII                                                             hinfI    tflI
                                                                                    dsaV                                                                tagI    bsmFI
                                                                                    bstNI   aluI                                                                bpmI/gsuI[dcm-]                         rsaI
                                                                           bsrI     apyI[dcm+]                                                                  claI/bsp106      pleI                    csp6I
                                                                                                                                                                bspDI[dam-]      hinfI                   scaI    nlaIII
601 GGTATAGGTG CTACGTATT ACACTGGTAT CAACAGAAAC CAGGAAAAGC TCCGAAACTA CTGATTTACA AAGTATCCAA TCGATTCTCT GGAGTCCCTT
    CCATATCCAC GATGCATAAA TGTGACCATA GTTGTCTTTG GTCCTTTTCG AGGCTTTGAT GACTAAATGT TTCATAGGTT AGCTAAGAGA CCTCAGGGAA
 32  G  I  G   A   T  Y  L    H  W  Y   Q  Q  K   P  G  K   A  P  K  L  L  I  Y  K  V  S  N   R  F  S   G  V  P  S mspI
            hpaII
            balI
            bsaWI
            sau3AI
            mboI/ndeII[dam-]                                                fnu4HI
            dpnI[dam+]                                                      bsoFI
            dpnII[dam-]                                                     bbvI
            alwI[dam-]                                                                       scfI         mboII                                          mboII
            nlaIV                                                                            pstI         bpuAI                                          bpuAI     acII
            bstYI/xhoII                                                                      bsgI         bbsI                                           bbsI      mboII
            bamHI
            alwI[dam-] bsmFI
701 CTGCTTCTC TGGATCCGGT TCTCGGACGG ATTTCACTCT GACCATCAGC AGTCTGCAGC CAGAAGACTT CGCAACTTAT TACTGTTCAC AGAGTACTCA
    GAGCGAAGAG ACCTAGGCCA AGAGCCTGCC TAAAGTGAGA CTGGTAGTCG TCAGACGTCG GTCTTCTGAA GCGTTGAATA ATGACAAGTG TCTCATGAGT
 66  R  F  S   G  S  G    S  G  T  D  F  T  L    T  I  S  L  Q  P  E   D  F  A  T  Y  Y  C  S  Q   S  T  H styI
                                          bsaJI
                                 rsaI
                                 csp6I
                                 nlaIV
                                 kpnI
                                 hgiCI                sau3AI
                                 banI                 mboI/ndeII[dam-]  fnu4HI
                                 asp718               dpnI[dam+]        bsoFI
     bsrBI                       acc65I               dpnII[dam-]       bbvI                    bpuAI       aclI
     aclI                                                                                       bbsI        mboII
     bsmFI       maeII
801 TGTCCGGCTC ACGTTTGGAC AGGTACCAA TCCCATGGTG GGTGGAGATC AAACGAACTG TGGCTGCACC ATCTGTCTTC ATCTTCCCGC CATCTGATGA GCAGTTGAAA
    ACAGGCCGAG TGCAAACCTG TCCATGGTT AGGGTACCAC CCACCTCTAG TTTGCTTGAC ACCGACGTGG TAGACAGAAG TAGAAGGGCG GTAGACTACT CGTCAACTTT
 99  V  P  L    T  F  G  Q    G  T  K    V  E  I   K  R  T   V  A  A  P    S  V  F    I  F  P  P   S  D  E    Q  L  K
```

```
                  rsaI                        rmaI
                  bslWI/splI                  maeI
                  thaI                        bfaI                              mboII  sfaNI
      rsaI        fnuDII/mvnI                 xbaI mnlI mnlI
      csp6I speI  bstUI            rmaI
1201  AGTAGCAAC   TAGTCGTAAA AAGGTATCT AGAGGTTGAG GTGATTTTAT GAAAAAGAAT ATCGCATTTC TTCTTGCATC TATGTTCGTT TTTTCTATTG
      TCATCGTTG   ATCAGCATTT TTCCATAGA TCTCCAACTC CACTAAAATA CTTTTTCTTA TAGCGTAAAG AAGAACGTAG ATACAAGCAA AAAAGATAAC
                  mluI csp6I mnlI   maeI                            M  K  K  N  I  A  P  L  L  A  S  M  F  V  F  S  I  A
 -23              aflIII    ddeI    bfaI
                            aluI
                                                    scrFI
                                                    mvaI
                                                    ecoRII
                                                    dsaV
                                       scrFI        dsaV bstNI hglJII     bsp1286
                                       mvaI fnu4HI  bstNI bsoFI  bsaJI bmyI
                           rmaI        ecoRII       apyI[dcm+] apyI[dcm+]         aluI     alwNI[dcm-]
                           maeI                               haeIII/palI  bbvI                fnu4HI
                           bfaI                               acII haeI         banII          bsoFI
                           aluI                                                                bbvI
1301  CTACAAACGC GTACGCTGAG GTTCAGCTAG TGCAGTCTGG CGGTGGCCTG GTGCAGCCAG GGGGCTCACT CCGTTTGTCC TGTGCAGCTT CTGGCTACTC
      GATGTTTGCG CATGCGACTC CAAGTCGATC ACGTCAGACC GCCACCGGAC CACGTCGGTC CCCCGAGTGA GGCAAACAGG ACACGTCGAA GACCGATGAG
  -5  T  N  A  Y  A  E  V  Q  L  V  Q  S  G  G  G  L  V  Q  P  G  G  S  L  R  L  S  C  A  A  S  G  Y  S
                                             scrFI
                                             nciI
                                             mspI
                                             hpaII
                                             dsaV
                                             cauII
                                             bsiI
                                             xmaI/pspAI
                                             smaI
                                             scrFI     scrFI
                                             nciI      mvaI
                                             dsaV      ecoRII
                                             cauII
                                             bslI
```

```
                                        fnu4HI
                                        bsoFI
                                        haeIII/palI
                                        mcrI
                                        eagI/xmaIII/eclXI
                                        eaeI
                                        cfrI
                                        bsiEI                    sapI
                                        notI          rmaI       mboII                                       rmaI
              cac8I                     fnu4HI        maeI       earI/xsp632I                                maeI
              nlaIII                    bsoFI  nlaIII bfaI tth111I/aspI                                      bfaI
     nspI     bsp1286                   aciI aciI     aluI mnlI  taqI  aluI
     nspHI aciI bmyI
2001 TCACACATGC CCGCCGTGCC CAGCCGTGCC CAGCACCAGA ACTGCTGGGC GGCCGCATGA ACACAGCTAGA GGACAAGGTC GAAGAGCTAC TCTCCAAGAA CTACCACTA
     AGTGTGTACG GGCGGCACGG GTCGTGGTCT TGACGACCCG CCGGCGTACT TTGTCGATCT CCTGTTCCAG CTTCTCGATG AGAGGTTCTT GATGGTGGAT
229  H  T  C  P  P  C  P  A  P  E  L  L  G  G  R  M  K  Q  L  E  D  K  V  E  E  L  L  S  K  N  Y  H  L
              "junction between antibody and leucine zipper
                                                                                                 scrFI
                                                                                                 ncII
                                                                                                 mspI
                                                                                                 hpaII
                                              sphI                                               dsaV
                                              ddeI nlaIII                                        cauII
                                              celII/espI                           rmaI          acII
                                              blpI/bpu1102I                        maeI          fnu4HI
                                              hinPI nspI                           bfaI  bsmFI   bsoFI
                                              hhaI/cfoI    aluI    haeII sau96I pleI
                                      pleI              hindIII    nspHI haeIII/palI
                                      hinfI             cac8I      eco47III   asuI  hinfI
2101 GAGAATGAAG TGGCAAGACT CAAAAAGCTT GTCGGGGAGC GCTAAGCATG CGACGGCCCT AGAGTCCCTA ACGGTCCGTT GCCGCCGGGC GTTTTTTATT
     CTCTTACTTC ACCGTTCTGA GTTTTTCGAA CAGCCCCTCG CGATTCGTAC GCTGCCGGGA TCTCAGGGAT TGCCAGGCAA CGGCGGCCCG CAAAAAATAA
262  E  N  E  V  A  R  L  K  K  L  V  G  E  R  Q
                                         aluI
              tru9I                      hindIII
              mseI        taqI hindIII                        tru9I             nlaIV
     hpaI  nlaIII         claI/bspI06 tru9I                   mseI              hgiCI
     hincII/hindII aluI   bspDI(dam-) mseI  aciI                                banI
2201 GTTAACTCAT GTTTGACAGC TTATCATCGA TAAGCTTTAA TGCGGTAGTT TATCACAGTT AAATTGCTAA CGCAGTCAGG CACCGTGTAT GAAATCTAAC
     CAATTGAGTA CAAACTGTCG AATAGTAGCT ATTCGAAATT ACGCCATCAA ATAGTGTCAA TTTAACGATT GCGTCAGTCC GTGGCACATA CTTTAGATTG
```

FIG. 41H

```
                                                         sfaNI
                                                         scrFI                              haeIII/palI
                                                         mvaI                               sau96I
                                                         ecoRII                             scrFI
                                                         dsaV                               acII
                              mnlI                       bstNI                rsaI  mspI  mnlI
                              nlaIV                      bsaJI                      csp6I  hpaII                      fnu4HI
              mnlI hg1CI      bsaJI  hphI apyI[dcm+]                          mspI  dsaV  bsII                        bsoFI
        hinPI        bsaJI banI maeII foKI scrFI                              hpaII       cauII          ecoRV        haeIII/palI
        hhaI/cfoI foKI                                                        cfr10I/bsrFI asuI          acII         eaeI
                                                                                                                      cfrI
2301 AATGCGCTCA TGGTCATCCT CGGCACCGTC ACCCTGGATG CTGTAGGCAT AGGCTTGGTT TGCCGGGCCT ATGCGGGTAC TGCCGGGCCT CTTGCGGGAT ATCGTCCATT
     TTACGCGAGT AGCAGTAGGA GCCGTGGCAG TGGGACCTAC GACATCCGTA TCCGAACCAA ACGGCCCGGA TACGCCCATG ACGGCCCGGA GAACGCCCTA TAGCAGGTAA hinPI
                                                         hhaI/cfoI
                                                         rmaI
                                                         maeI
                        fnu4HI haeII                     nheI
                        bsoFI eco47III
              maeIII    bbvI bfaI                                                        hinPI             hg1AI/aspHI
     sfaNI bsrI    cac8I cac8I                                                           hhaI/cfoI         bsp1286
                                                                                         mstI bsII         bs1HKAI           acII    mcrI
                                                                          sfaNI          avIII/fspI        bmyI              bsiEI
2401 CCGACAGCAT CGCCAGTCAC TATGGCGTGC TGCTAGCGCT ATATGCGGTG ATGCAATTTC TATGCGCACC CGTTCTCGGA GCACTGTCCG ACCGCTTTGG
     GGCTGTCGTA GCGGTCAGTG ATACCGCACG ACGATCGCGA TATACGCCAC TACGTTAAAG ATACGCGTGG GCAAGAGCCT CGTGACAGGC TGGCGAAACC mnlI
                                                                      sau3AI
                                                        sau3AI        mboI/ndeII[dam-]
                                                        mboI/ndeII[dam-]  dpnI[dam+]
                                                        . dpnI[dam+]      dpnII[dam-]
                                                        dpnII[dam-]      alwI[dam-]
                                    thaI                                 nlaIV
                                    fnuDII/mvnI                          bstYI/xhoII         hgaI
     acII                           bstUI nlaIII                         bamHI              mspI
     fnu4HI                                                                                 hpaII  sfaNI
     bsoFI                                                     bsII     alwI[dam-]          tcctctacgc cggacgcatc
     acII bsrI     cac8I    nlaIV   taqI  bshI236I
2501 CGGCGCCCCA GTCCGGGTCG CTTCGCTACT TGGAGCCTCG ATCGACTACG CGATCATGGC GACCACACCC GTCCGTGTGA TCCTCTACGC CGGACGCATC
     GCCGCGGGGT CAGGCCCAGC GAAGCGATGA ACCTCGGAGC TAGCTGATGC GCTAGTACCG CTGGTGTGGG CAGGCACACT AGGAGATGCG GCCTGCGTAG
```

```
                                                                                fnu4HI
                                                                              mspI hinPI
                                                                                naeI haeII
                                                                                cfr10I/bsrFI
                                                                                cac8I eco47III
                                                               nlaIV bsoFI
                                                               hgiCI bbvI
                                                               banI hpaII hhaI/cfoI                     sau96I
         acII                                                                                            nlaIV
         thaI                                                   mboI                                     avaII
         fnuDII/mvnI                                            bpuAI                                    asuI        bsrI   acII
         bstUI     acII                                         bbsI              nlaIII                              maeIII bsmFI
         bshl236I  fnu4HI
         hinPI  bcgI    bsoFI
         hhaI/cfoI
2901 TGGGGCGGG GCATGACTAT CGTCGCCGCA CTTATGACTG TCTTCTTTAT CATGCAACTC GTAGGACAGG TGCCGGCAGC GCTCTGGGTC ATTTTCGGCG
     ACCCCGCCCC CGTACTGATA GCAGCGGCGT GAATACTGAC AGAAGAAATA GTACGTTGAG CATCCTGTCC ACGGCCGTCG CGAGACCCAG TAAAAGCCGC thaI
              fnuDII/mvnI                                                                                   thaI
              bstUI                                                                                         hgaI
         acII  bshl236I sau3AI                                                                              thaI fnuDII/mvnI
         sau96I hinPI   mboI/ndeII[dam-]                            acII       tfII                         fnuDII/mvnI
         avaII  hhaI/cfoI bpmI/gsuI[dcm-] mboII[dam+] dpnI[dam-]    cac8I      hinfI   cac8I mnlI           bstUI bstUI
         asuI  bpmI/gsuI[dcm-] dpnII[dam-]                                                                  bshl236I mnlI
3001 AGGACCGCTT TCGCTGGAGC GCGACGATGA TCGGCCTGTC GCTTGCCGTA TTCGGAATCT TGCACGCCCT CGCTCAAGCC TTCGTCACTG GTCCCGCCAC
     TCCTGGCGAA AGCGACCTCG CGCTGCTACT AGCCGGACAG CGAACGGCAT AAGCCTTAGA ACGTGCGGGA GCGAGTTCGG AAGCAGTGAC CAGGGCGGTG mcrI
                                                  eagI/xmaIII/eclXI
                                                  eaeI     hinPI
                                                  cfrI     hbaI/cfoI
                                                  bsIEI    thaI
                                         mspI     fnu4HI   fnuDII/mvnI
                                         naeI     thaI     bstUI                                              bshl236I mnlI   haeI
                                         cfr10I/bsrFI hpaI bstUI                                              nruI bshl236I fokI haeIII/paII
                      haeIII/paII        cac8I    bsoFI   bshl236I
          maeII  haeI  cac8I             bglI nlaIII haeIII/paII  maeII cac8I                                 cgtctcgcg cggaggctg gatgcctta
3101 CAAACGTTTC GGCGAGAGC AGGCCATTAT CGCCGGCCATG GCCCGGCCACG CCCTGGGCCA CGTCTCGCGA CGGAGGCTG GATGCCTTC
     GTTTGCAAAG CCGCTCTCG TCCGGTAATA GCGGCCGGTAC CGGGCCGGTGC GGGACCCGGT GCAGAACGCT GCCTCCGAC CTACCGGAAG
```

```
                                                      hinPI                            hgaI
                                                      hhaI/cfoI                        thaI acII
                                               mstI        pflMI                       fnuDII/mvnI
                                               avIII/fspI  bslI  styI                  bstUI
        hphI      pflMI                  acII  bsmI        bslI bsaJI                  bsh1236I
      tfII    bslI    nlaIV
      hinfI
3501  CTAACGGATT CACCACTCCA AGAATTGGAG ACTGTGAATG CCAATCAATT CTTGCGGAGA CCCTTGGCAG AACATATCCA TCGCGTCCGC
      GATTGCCTAA GTGGTGAGGT TCTTAACCTC TGACACTTAC GGTTAGTTAA GAACGCCTCT GGGAACCGTC TTGTATAGGT AGCGCAGGCG haeIII/palI
                                      mscI/balI
                                      haeI
                                      scrFI
                                      mvaI dsaI
                                      ecoRII
                                      dsaV
                                      bstNI                                                  mspI
                                      bslI bsaJI         sau3AI                              hpaII
                                      apyI[dcm+]         mboI/ndeII[dam-]                    scrFI           ncII
                       fnu4HI         sau96I    dpnI[dam+]                         nlaIV                    dsaV
                       thaI hinPI     avaII     dpnII[dam-]                        avaII cac8I              sau96I
             fnu4HI    fnuDII/mvnI    asuI eaeI hinPI hhaI/cfoI hgiAI/aspHI        asuI          rmaI
             bsoFI     bstUI          ppuMI     mstI nlaIII bsp1286                ppuMI         maeI
        fnu4HI                                  nlaIV cfrI     avIII/fspI bsiHKAI
        bsoFI   cac8I  hhaI/cfoI   fnu4HI                                          eco0109I/draII
        bbvI acII bsh1236I   avaI  bsoFI        eco0109I/draII  mslI bmyI          mnlI cauII-bfaI    acII
      bpmI/gsuI[dcm-] acII sfaNI    bbvI
3601  CATTCCAGGC AGCCGCCACGC GGGCCATCTC GGGCAGCGTT GGGTCCTGGC CACGGGTGCG CATGATCGTG CTCCTGTCGT TGAGGACCCG GCTAGGCTGG
      GTAGAGGTCG TCGGCGGTGCG CCCGGTAGAG CCCGTCGCAA CCCACCACGG GTGCCCACGC GTACTAGCAC GAGGACAGCA ACTCCTGGGC CGATCCGACC fnu4HI
                                                                                   bsoFI
                                         cac8I                                     bbvI
                                         thaI                                      fnu4HI
                            hphI         fnuDII/mvnI                               bsoFI
                       tfII              bstUI                                     bbvI
                       hinfI             bsh1236I maeII                                                   nlaIII
             bsrI                                                                                maeII    ddeI
3701  CGGGGTTGCC TTACTGGTTA GCAGAATGAA TCACCGATAC GCGAGCGAAC GTGAAGCGAC TGCTGCTGCA AAACGTCTGC GACCTGAGCA ACAACATGAA
      GCCCCAACGG AATGACCAAT CGTCTTACTT AGTGGCTATG CGCTCGCTTG CACTTCGCTG ACGACGACGT TTTGCAGACG CTGGACTCGT TGTTGTACTT
```

```
                                                                                  sau3AI
                                                                                  mboI/ndeII[dam-]
                                                                                  nam1[dam-]
                                                                                  dpnI[dam+]
                                                                                  dpnII[dam-]
                                                                                  bstYI/xhoII
                                                                                  alwI[dam-]
                                                                              mspI
                                                                              hpaII
                                                                              mroI bsaBI[dam-]          fnu4HI
                                                                              bspMI                    bsoFI
                                                                              bspEI[dam-]              bbvI
                                                                              bsaWI  sfaNI             sfaNI
                                                                              acIII[dam-]              foKI    cac8I
                                      acII                                    TTATGTTCCG GATCTGCATC GCAGGATGCT GCTGGCTACC
                                      thaI                                    AATACAAGGC CTAGACGTAG CGTCCTACGA CGACCGATGG
                                      fnuDII/mvnI hinPI
                                      bstUI     hhaI/cfoI
                                      bsh1236I  haeII    msII                       acII
            mboII                                                                  bsmFI   foKI
            bpuAI                                                                  sau96I  sfaNI
            bbsI                                                                   nlaIV acII
3801 TGGTCTTCGG TTTCCGTGTT TCGTAAAGTC TGGAAACGCG GAAGTCAGCG CCCTGCACCA              avaII fnu4HI
     ACCAGAAGCC AAAGGCACAA AGCATTTCAG ACCTTTGCGC CTTCAGTCGC GGGACGTGGT              asuI bsoFI                   bsrI
                                                                                                                acII             mnII
                            tru9I haeII                                       CTGGTCCCGC CGCATCCATA CGGCCAGTTG TTTACCCTCA
                            mseI eco47III                                     GACCAGGGCG GCGTAGGTAT GCCGGTCAAC AAATGGAGT
                            nspI
                            scrFI             cac8I
                            ncII              hinPI
                            mspI              hhaI/cfoI
                    bsrI    hpaII
                    bsII    dsaV nlaIII
              maeII         cauII                                                    mnII
         psp1406I maeIII nspHI          maeIII                                       foKI
                                                                                     sfaNI                      nlaIII           apoI   bsII
4001 CAACGTTCCA GTACCGGGC ATGTTCATCA TCAGTAACCC GTATCGTGAG CATCCTCTCT CGTTTCATCG GTATCATTAC CCCATGAAC AGAAATTCCC
     GTTGCAAGGT CATGGCCCCG TACAAGTAGT AGTCATTGGG CATAGCACTC GTAGGAGAGA GCAAAGTAGC CATAGTAATG GGGTACTTG TCTTTAAGGG

FIG. 41N
```

```
                                                                    cac8I
                                                                    sau96I
                                    sfaNI                       tru9I haeIII/palI                            tru9I
           mnlI         maeIII                      acII bslI nlaIII acII                              mseI      bpmI/gsuI[dcm-]
4101  CCTTACACGG AGGCATCAAG TGACCAACA GCCCTTAACA TGCCCCGCTT TATCAGAAGC CAGACATTAA CGCTTCTGA GAAACTCAAC
      GGAATGTGCC TCCGTAGTTC ACTGGTTTGT CGGGAATTGT ACGGGGCGAA ATAGTCTTCG GTCTGTAATT GCGAAGACCT CTTTGAGTTG
                                                                              fnu4HI    thaI
                                                                              bsoFI     fnuDII/mvnI
                                                                               aluI     bstUI
                                                                              pvuII     hinPI
                                                                              nspBII    hhaI/cfoI
                                                                              fnu4HI    thaI
                                                                              bsoFI     fnuDII/mvnI
                                                                              bcgI      bstUI
                                                                              bbvI      mnlI bshl236I                hphI
                                           xmnI                    msII    aluI   acII bbvI bshl236I     hphI
                                           tfiI
                                           hinfI
           acII                            asp700
           thaI
           fnuDII/mvnI
           bstUI
           bshl236I
    aluI hgaI fokI
4201  GAGCTGGACG CGGATGAACA GGCAGAGACATC TGTGAATCGC TTCACGACCA CGCTGATGAG CTTTACCGGA GCTGCCTCGC GCGTTTCGGT GATGACGGTG
      CTCGACCTGC GCCTACTTGT CCGTCTCTGTAG ACACTTAGCG AAGTGCTGGT GCGACTACTC GAAATGGCCT CGACGGAGCCG CGCAAAGCCA CTACTGCCAC
                                     esp3I                                  scrFI
                                     bsmBI                                  ncII
                                     bsmAI                                  mspI                                hgaI
                                     mspI   hpaII                           hpaII                               thaI
                           fnu4HI    scrFI                                                                      fnuDII/mvnI
                           bsoFI     ncII                                  sfaNI                                bstUI    acII
                           bbvI      dsaV                                  fokI dsaV                            bshl236I
                           nlaIII           aluI                          acII   cauII   drdI                   hinPI nspBII
           mnlI            nspI             maeIII                                                              hhaI/cfoI      acII
           nspHI aluI bslI
4301  AAAACCTCTG ACACATCAGC CTCCGGAGA CGGTCACAGC TGTCTCGTAA CGGATGCGG GGAGCAGACA AGCCCGTCAG GGGCGTGTTGG CGGGTGTTGG
      TTTTGGAGAC TGTGTACGTC GAGGGCCTCT GCCAGTGTCG AACAGACATT CCCTACGCC CCTCGTCTGT TCGGGCAGTC CCCGCACAACC GCCCACAACC
```

FIG. 41O

```
                              fnu4HI                                                                                     sfaNI                                        hgiAI/aspHI
                              bsoFI            maeII                                                                    fnu4HI                                         bsp1286
                               bbvI            maeIII                                                                   bsoFI                                  ddeI   baiHKAI
                         hinPI nlaIII bsrI bsaAI               bstl107I tru9I                                             aclI                                  rsaI  bmyI  ndeI
                         hhaI/cfoI tthlllI/aspI         aclI accI bsrI mseI                                                                                   csp6I   apaLI/snoI
                                                                                                                                                                      alw44I/snoI
4401 CGGGTGTCGG GGCGCAGCCA TGACCCAGTC ACGTAGGGAT AGCGGAGTGT ATACTGGCTT AACTATGGGG CATCAGAGCA GATTGTACTG AGAGTGCACC
     GCCCACAGCC CCGGTCGGT ACTGGGTCAG TGCATCCGCTA TCGCCTCACA TATGACCGAA TTGATACGCC GTAGTCTCGT CTAACATGAC TCTCACGTGG mboII                                    hinPI
                                                                             earI/ksp632I                             hhaI/cfoI
                                                                             sapI                                       fnu4HI              mcrI
                                                                     hinPI                                     pleI  bsoFI                  bslEI
                                                              sfaNI  hhaI/cfoI                                 hinfI bbvI
4501 ATATGCGGTG TGAAATACCG CACAGATGCG TAAGGAGAAA ATACCGCATC AGGCCCTCTT CCGCTTCCTC GCTCACTGAC TGCTGCGCT CGGTCGTTCG
     TATACGCCAC ACTTTATGGC GTGTCTACGC ATTCCTCTTT TATGGCGTAG TCCGGGAGAA GGCGAAGGAG CGAGTGACTG AGCGACGCGA GCCAGCAAGC fnu4HI
     bsoFI                                                                                                        nlaIII                              bslI
     aclI                                                                                                         nspI                                cac8I
     fnu4HI     aclI                                 thaI                                                         nspHI                              haeIII/palI
     bsoFI     barBI                     sfaNI     fnuDII/mvnI                                      tfiI          aflIII                              haeI
     bbvI cac8I                  aluI                                                               hinfI
4601 GCTGCGGCGA GCGGTATCAG CTCACTCAAA GGCGGTAATA CGGTTATCCA CAGAATCAGG GGATAACGCA GGAAAGAACA TGTGAGCAAA AGGCCAGCAA
     CGACGCCGCT CGCCATAGTC GAGTGAGTTT CCGCCATTAT GCCAATAGGT GTCTTAGTCC CCTATTGCGT CCTTTCTTGT ACACTCGTTT TCCGGTCGTT scrFI
     mvaI            bstUI
     ecoRII          bshl236I
     dsaV             aclI
     bstNI   bslI    fnu4HI                                                                                 hgaI
     apyI[dcm+]       bsoFI   cac8I                                                                         drdI
     haeIII/pal       haeIII/palI                                                          sfaNI          taqI                            mnlI
     haeI nlaIV                                                             aclI
4701 AAGGCCAGGA ACCGTAAAAA GGCCGCGTTG CTGGCGTTTT TCCATAGGCT CCGCCCCCCT GACGAGCATC ACAAAAATCG ACGCTCAAGT CAGAGGTGGC
     TTCCGGTCCT TGGCATTTTT CCGGCGCAAC GACCGCAAAA AGGTATCCGA GGCGGGGGGA CTGCTCGTAG TGTTTTTAGC TGCGAGTTCA GTCTCCACCG

FIG. 41P
```

```
                                                                                                                                  hglAI/aspBI
                                                                                                                                  bsp1286
                                                                                                                                  bslHKAI
                                                                                                                  hinPI            bmyI
                              scrFI                                                                               bssSI   acII mspI apaLI/snoI
            scrFI    mvaI   ecoRII                                            bslI       acII  fnu4HI hpaII       alw44I/snoI
            mvaI   ecoRII   dsaV                             apyI[dcm+]     alul mnlI  hhaI/cfoI   bsoFI bsaWI         aclI
            ecoRII  dsaV    bstNI         apyI[dcm+] bsaJI    alul mnlI  hhaI/cfoI
            dsaV    bstNI   apyI[dcm+]    bsaJI 4801 GAAACCCGAC AGGACTATAA AGATACCAGG CGTTTCCCCC TGGAAGCTCC CTCGTGGGCT CTCCGTTCC GACCCTGCCG CTTACCGGAT ACCTGTCGC
     CTTTGGGCTG TCCTGATATT TCTATGGTCC GCAAAGGGGG ACCTTCGAGG GAGCACCCGA GAGGCAAGG CTGGGACGGC GAATGGCCTA TGGACAGGCG alwNI[dcm-]
                                                                                                      fnu4HI
                                                                                                      bsoFI
                     fnu4HI                                    mspI                                  fnu4HI
                     bsoFI                                     hpaII                                  bsoFI
                     nspBII                                    scrFI                                 bbvI         maeIII
                acII  hinPI             maeIII                 ncII                           bsrI  bbvI   bsrI
            mcrI bbvI  mspI                                    dsaV                      rmaI
            bslEI  hhaI/cfoI hpaII                             cauII                     maeI
                                                           pleI                          bfaI
                                                           hinfI 4901 CTTTCTCCCT TCGGGAAGCG TGGCGCTTC TCATAGCTCA CGCTGTAGGT ATCTCAGTTC GGTGTAGGTC GTTCGCTCCA AGCTGGGCTG TGTGCACGAA
     GAAAGAGGGA AGCCCTTCGC ACCGCGAAAG AGTATCGAGT GCGACATCCA TAGAGTCAAG CCACATCCAG CAAGCGAGGT TCGACCCGAC ACACGTGCTT mspI
                                                              hpaII
                                                              scrFI
                                                              ncII                             bslI        hinPI
                                                              dsaV                          haeIII/palI   hhaI/cfoI
                                                              cauII                            haeI 5001 CCCCCCGTTC AGCCCGACCG CTGGCCCTTA TCCGGTAACT ATCGTCTTGA GTCCAACCCG GTAAGACACG ACTTATCGCC ACTGGCAGCA GCCACTGGTA
     GGGGGGCAAG TCGGGCTGGC GACCGGGAAT AGGCCATTGA TAGCAGAACT CAGGTTGGGC CATTCTGTGC TGAATAGCGG TGACCGTCGT CGGTGACCAT rmaI
                                                                              maeI
                                                                              bfaI
           mnlI  acII scfI 5101 ACAGGATTAG CAGAGCGAAG TATGTAGGCG GTTCTTGAAG TGGTGGCTA ACTACGGCTA CACTAGAAGG ACAGTATTTG GTATCTGCGC
     TGTCCTAATC GTCTCGCTTC ATACATCCGC CAAGAACTTC ACCACCGAT TGATGCCGAT GTGATCTTCC TGTCATAAAC CATAGACGCG
```

```
                                                                    mcrI
                                                                    bstEI
                                                                    bcgI
                                                                    fnu4HI              sau3AI
                                                                    bsoFI              mboI/ndeII[dam-]
                                                                    acII                dpnI[dam+]
                                                                                        dpnII[dam-]
                                                                                        bstYI/xhoI[dam-]
                                                      rsaI                              alwI[dam-]
                                            bsrI      scaI              ddeI
                               foKI         maeIII hphI csp6I
              nlaIII           sfaNI
6001 ATTCTCTTAC TGTCATGCCA TCCGTAAGAT GCTTTTCTGT GACTGGTGAG TACTCAACCA AGTCATTCTG AGAATAGTGT ATCGGGCGAC CGAGTTGCTC
     TAAGAGAATG ACAGTACGGT AGGCATTCTA CGAAAAGACA CTGACCACTC ATGAGTTGGT TCAGTAAGAC TCTTATCACA TACGCCCGCTG GCTCAACGAG bgaI
        hinfI/acyI                                                  hglAI/aspHI
        ahaII/bsaHI              hinPI                              bsp1286
     mspI                        hhaI/cfoI                          bslHKAI              maeII
     hpaII                       thaI                               bmyI                 psp1406I
     scrFI                       fnuDII/mvnI              tru9I                          xmnI
     ncII                        bstUI                    mseI     bmyI                           mboII
     dsaV                        bsh1236I                 ahaIII/draI                    asp700
     cauII hincII/hindII         acII
6101 TTGCCCGGCG TCAACACGGG ATAATACCGC AGCACATAGC AGAACTTTAA AAGTGCTCAT CATTGGAAAA CGTCTTCGG GGGAAAACT CTCAAGGATC
     AACGGGCCGC AGTTGTGCCC TATTATGGCG CGGTGTATCG TCTTGAAATT TTCACGAGTA GTAACCTTTT GCAAGAAGCC CCGCTTTGA GAGTTCCTAG hglAI/aspHI
            bsrI                        bsp1286
            sau3AI    taqI              bslHKAI       eco57I
            mboI/ndeII[dam-]            bmyI          mboII[dam-]
            dpnI[dam+]                  apaLI/snoI    sau3AI   sfaNI
            dpnII[dam-]                 alw44I/snoI   mboI/ndeII[dam-]
     nspBII bstYI/xhoI                                dpnII[dam-]
     acII   maeIII                      bssSI                            hphI        hphI
6201 TTACGCTGT TGAGATCCAG TTCGATGTAA CCCACTCGTG CACCCAACTG ATCTTCAGCA TCTTTTACTT TCACCAGCGT TTCTGGGTGA GCAAAAACAG
     AATGCGACA ACTCTAGGTC AAGCTACATT GGGTGAGCAC GTGGGTTGAC TAGAAGTCGT AGAAAATGAA AGTGGTCGCA AAGACCCACT CGTTTTTGTC mboII
        acII                                                            earI/ksp632I   sspI
        fnu4HI
        bsoFI                                               msII
6301 GAAGGCAAAA TGCCCAAAA AAGGGAATAA GGGCGACACG GAAATGTTGA ATACTCATAC TCTTCCTTTT TCAATATTAT TGAAGCATTT ATCAGGGTTA
     CTTCCGTTTT ACGGGTTTT TTCCCTTATT CCCGCTGTGC CTTTACAACT TATGAGTATG AGAAGGAAAA AGTTATAATA ACTTCGTAAA TAGTCCCAAT
```

FIG. 41T

```
                                                          hinPI
                                                          thaI
                                                          fnuDII/mvnI
                                                          bstUI                                    maeII
                                                          bshl236I                                 hinlI/acyI
                                                          acII                                     abaII/bsaHI
         nlaIII                                           nlaIV hhaI/cfoI                          aatII ddeI rcaI
         bspHI  acII
         bsmAI  barBI
6401 TTGTCTCATG AGCGGATACA TATTTGAATG TATTTAGAAA AATAAACAAA TAGGGGTTCC GGCACACATTT CCCCGAAAAG TGCCACCTGA CGTCTAAGAA
     AACAGAGTAC TCGCCTATGT ATAAACTTAC ATAAATCTTT TTATTTGTTT ATCCCCAAGG CGGGTGTAAA GGGGCTTTTC ACGGTGGACT GCAGATTCTT sau96I
                                       haeIII/palI
                                       asuI    mboII
                                       eco0109I/draII
                     nlaIII            mnlI    bpuAI
                     rcaI  tru9I             bssSI    bbsI
                     bspHI mseI
6501 ACCATTATTA TCATGACATT AACCTATAAA AATAGGGGTA TCACGAGGCC CTTTCGTCTT CAA
     TGGTAATAAT AGTACTGTAA TTGGATATTT TTATCCCCAT AGTGCTCCGG GAAAGCAGAA GTT
```

FIG. 41U

```
>length: 6563
aatII(GACGTC):         1645 6489
acc65I(GGTACC):        403 823
accI(GTMKAC):          1093 1963 4449
accIII(TCCGGA):        3867[dam-]
acII(CCGC):            178 542 805 877 1340 1750 1826 2011 2039 2043 2182 2242 2384 2492 2501 2504
                       2628 2781 2784 2787 2906 2926 3005 3094 3141 3226 3241 3309 3342 3367 3412
                       3436 3448 3490 3544 3597 3613 3619 3700 3838 3967 3970 3981 4139 4155 4210 4266
                       4351 4390 4400 4442 4467 4505 4518 4544 4561 4604 4611 4632 4723 4751 4878 4897
                       5018 5128 5263 5272 5634 5725 5916 5962 6083 6127 6204 6313 6412 6459
acyI                   see hinlI
aflIII(ACRYGT):        1307 4678
ageI(ACCGGT):          1788
ahaII/bsaHI(GRCGYC):   1645 1813 2616 2637 2751 3408 6107 6489
ahaIII/draI(TTTAAA):   5435 5454 6146
ahdI/eam1105I(GACNNNNNGTC): 346 5566
aluI(AGCT):            72 121 252 320 398 532 589 648 1126 1144 1167 1325 1386 1906 2054 2075 2126
                       2218 2233 2889 3292 4202 4259 4270 4319 4338 4619 4845 4935 4981 5238 5759 5859
                       5922
alw44I/snoI(GTGCAC):   1831 4494 4992 6238
alwI[dam-](GGATC):     412 413 712 713 1171 1471 2578 2579 3300 3870 5245 5319 5331 5416 5429 5893
                       6196 6214
alwNI[dcm-](CAGNNNCTG):1117 1385 5089
apaI(GGGCCC):          1695
apaLI/snoI(GTGCAC):    1831 4494 4992 6238
apoI(RAATTY):          1 391 4093
apyI[dcm+](CCWGG):     640 999 1347 1357 1449 1665 1713 1755 1764 2333 3262 3645 4705 4826 4839
aseI/asnI/vspI(ATTAAT):5742
asnI                   see aseI
asp700(GAANNNNTTC):    905 930 4234 6166
asp718(GGTACC):        403 823
aspHI                  see hgiAI
aspI                   see tthlllI
asuI(GGNCC):           1119 1195 1425 1434 1446 1512 1695 1696 1752 2155 2375 2727 3002 3090 3339 3463
```

FIG. 41V

Stop Template Primer

SL.97.2    5' CAT GGT ATA GGT TAA ACT TAT TTA CAC 3'

NNS Randomization Primer

SL.97.3    5' CAT GGT ATA GGT NNS ACT TAT TTA CAC 3'

FIG. 42

Randomization of Position N35 of Variable Light Chain CDR-1
Amino Acid Frequency

*Phage Display (NNS Codon Library) Sort #3*

| Amino Acid | Frequency | % Total | IC50 (nM) |
|---|---|---|---|
| Asparagine (wt) | 1 | 5.6 | 4.9 |
| Glycine | 6 | 16.6 | 3.1 |
| Aspartic Acid | 3 | 16.6 | 3.1 |
| Glutamic Acid | 4 | 22.2 | 0.1 |
| Alanine | 2 | 5.6 | 0.2 |
| Lysine | 1 | 5.6 | ND |
| Serine | 1 | 1.9 | ND |

FIG. 43A

Representative Conc versus Time Plot. Shown is the kinetic data for 6G4V11N35A.F(ab')2.

```
  1 ATGAAAAAGA ATATCGCATT TCTTCTTGCA TCTATGTTCG TTTTTTCTAT TGCTACAAAC
    TACTTTTTCT TATAGCGTAA AGAAGAACGT AGATACAAGC AAAAAAGATA ACGATGTTTG
-23 M  K  K   N  I  A  F   L  L  A   S  M  F  V   F  S  I   A  T  N

61 GCATACGCTG ATATCCAGAT GACCCAGTCC CCGAGCTCCC TGTCCGCCTC TGTGGGCGAT
    CGTATGCGAC TATAGGTCTA CTGGGTCAGG GGCTCGAGGG ACAGGCGGAG ACACCCGCTA
 -3 A  Y  A   D  I  Q  M   T  Q  S   P  S  S  L   S  A  S   V  G  D

121 AGGGTCACCA TCACCTGCAG GTCAAGTCAA AGCTTAGTAC ATGGTATAGG TGAGACGTAT
    TCCCAGTGGT AGTGGACGTC CAGTTCAGTT TCGAATCATG TACCATATCC ACTCTGCATA
 18 R  V  T   I  T  C  R   S  S  Q   S  L  V  H   G  I  G   E  T  Y

181 TTACACTGGT ATCAACAGAA ACCAGGAAAA GCTCCGAAAC TACTGATTTA CAAAGTATCC
    AATGTGACCA TAGTTGTCTT TGGTCCTTTT CGAGGCTTTG ATGACTAAAT GTTTCATAGG
 38 L  H  W   Y  Q  Q  K   P  G  K   A  P  K  L   L  I  Y   K  V  S

241 AATCGATTCT CTGGAGTCCC TTCTCGCTTC TCTGGATCCG GTTCTGGGAC GGATTTCACT
    TTAGCTAAGA GACCTCAGGG AAGAGCGAAG AGACCTAGGC CAAGACCCTG CCTAAAGTGA
 58 N  R  F   S  G  V  P   S  R  F   S  G  S  G   S  G  T   D  F  T

301 CTGACCATCA GCAGTCTGCA GCCAGAAGAC TTCGCAACTT ATTACTGTTC ACAGAGTACT
    GACTGGTAGT CGTCAGACGT CGGTCTTCTG AAGCGTTGAA TAATGACAAG TGTCTCATGA
 78 L  T  I   S  S  L  Q   P  E  D   F  A  T  Y   Y  C  S   Q  S  T

361 CATGTCCCGC TCACGTTTGG ACAGGGTACC AAGGTGGAGA TCAAACGAAC TGTGGCTGCA
    GTACAGGGCG AGTGCAAACC TGTCCCATGG TTCCACCTCT AGTTTGCTTG ACACCGACGT
 98 H  V  P   L  T  F  G   Q  G  T   K  V  E  I   K  R  T   V  A  A

421 CCATCTGTCT TCATCTTCCC GCCATCTGAT GAGCAGTTGA AATCTGGAAC TGCTTCTGTT
    GGTAGACAGA AGTAGAAGGG CGGTAGACTA CTCGTCAACT TTAGACCTTG ACGAAGACAA
118 P  S  V   F  I  F  P   P  S  D   E  Q  L  K   S  G  T   A  S  V

481 GTGTGCCTGC TGAATAACTT CTATCCCAGA GAGGCCAAAG TACAGTGGAA GGTGGATAAC
    CACACGGACG ACTTATTGAA GATAGGGTCT CTCCGGTTTC ATGTCACCTT CCACCTATTG
138 V  C  L   L  N  N  F   Y  P  R   E  A  K  V   Q  W  K   V  D  N

541 GCCCTCCAAT CGGGTAACTC CCAGGAGAGT GTCACAGAGC AGGACAGCAA GGACAGCACC
    CGGGAGGTTA GCCCATTGAG GGTCCTCTCA CAGTGTCTCG TCCTGTCGTT CCTGTCGTGG
158 A  L  Q   S  G  N  S   Q  E  S   V  T  E  Q   D  S  K   D  S  T

601 TACAGCCTCA GCAGCACCCT GACGCTGAGC AAAGCAGACT ACGAGAAACA CAAAGTCTAC
    ATGTCGGAGT CGTCGTGGGA CTGCGACTCG TTTCGTCTGA TGCTCTTTGT GTTTCAGATG
178 Y  S  L   S  S  T  L   T  L  S   K  A  D  Y   E  K  H   K  V  Y

661 GCCTGCGAAG TCACCCATCA GGGCCTGAGC TCGCCCGTCA CAAAGAGCTT CAACAGGGGA
    CGGACGCTTC AGTGGGTAGT CCCGGACTCG AGCGGGCAGT GTTTCTCGAA GTTGTCCCCT
198 A  C  E   V  T  H  Q   G  L  S   S  P  V  T   K  S  F   N  R  G

721 GAGTGTTAAG CTGATCCTCT ACGCCGGACG CATCGTGGCC CTAGTACGCA ACTAGTCGTA
    CTCACAATTC GACTAGGAGA TGCGGCCTGC GTAGCACCGG GATCATGCGT TGATCAGCAT
218 E  C  Q
```

FIG. 45

N35AH1upr

5'-CTAGTGCAGTCTGGGCGGTGGCCTGGTGCAGCCAGGGGCTCACTCCGTTGTCCTGTGCAGCTTCTGGCTACTCCTTC-3'

N35AH1lwr

5'-TCGAGAAGGAGTAGCCAGAAGCTGCACAGGACAAACGGAGTGAGCCCCTGGCTGCACCAGGCCACCGCCAGACTGCACTAG-3'

Bold indicates nucleotide change destroying PvuII site.

FIG. 47

```
> Wed May 7 18:27:36 1997
> /home/ruby/vc/Immbio/afan/ss.p6G425v11.N35A.choSD
> sites: std
> length: 8120 (circular)
> This has the pSVI backbone with the pRK7 cloning linker (p8V17) and the intron DHFR(ID)
> made from pSVI.WT6D.D by adding a linearization linker (LL) into the HpaI site cac8I
            aluI
            sstI
            sacI
            hgiJII
            hgiAI/aspHI
            ecl136II
            bsp1286
            bslHKAI
            bmyI                                                                                                      scrFI
            banII                                                  seu3AI  aluI                                       mvaI
            taqI                               rmaI                mboI/ndeII[dam-]                                   ecoRII
                                               maeI                dpnI[dam+]                                         dsaV
                                               bfaI                pvuI/bspCI                                         bstNI
                                                                   pleI dpnII[dam-]                                   apyI[dcm+]
                                                                   hinfI taqI[dam-]                                   bsaJI
                                                                         mcrI   pvuII                        bsmFI  nlaIV   cac8I
                                                                         bslEI  nspBII
                                                                         taqI[dam-]
    1 TTCGAGCTCG CCCGACATTG ATTATTGACT AGAGTCGATC GACAGCTGTG GAATGTGTGT CAGTTAGGGT GTGGAAAGTC CCCAGCTCCC CCAGCAGGCA
      AAGCTCGAGC GGGCTGTAAC TAATAACTGA TCTCAGCTAG CTGTCGACAC CTTACACACA GTCAATCCCA CACCTTTCAG GGGTCGAGGG GGTCGTCCGT sfaNI                                                                             sfaNI
                   ppu10I                                      scrFI   mvaI                          ppu10I
                   nsiI/avaIII                                         ecoRII                        nsiI/avaIII
                   nlaIII                                              dsaV                          nlaIII
                   sphI                                                bstNI                                  sphI
                   nspI                                                apyI[dcm+]                             nspI
                   nspHI                                               bsaJI                                  nspHI
                   cac8I                                sexAI          bsmFI nlaIV  cac8I                     cac8I
  101 GAAGTATGCA AAGCATGCAT CTCAATTAGT CAGCAACCAG GTGTGGAAAG TCCCCAGGCT CCCCAGCAGG CAGAAGTATG CAAAGCATGC ATCTCAATTA
      CTTCATACGT TTCGTACGTA GAGTTAATCA GTCGTTGGTC CACACCTTTC AGGGGTCCGA GGGGTCGTCC GTCTTCATAC GTTTCGTACG TAGAGTTAAT nlaIII
                                                                                        styI
                                                                                        ncoI
                                                                          bslI dsaI
            acII                                                          acII bsaJI
            bsmFI       acII   fokI       acII                bsrI  acII
  201 GTCAGCAACC ATAGTCCCGC CCCTAACTCT CCGCCATCCG GCCCCAGTTC CGCCCATTCT CCGCCCCATG CCGGGGGTAC GCTGACTAAT TTTTTTTATT
      CAGTCGTTGG TATCAGGGCG GGGATTGAGA GGCGGTAGGC CGGGGTCAAG GCGGGTAAGA GGCGGGGTAC GGCCCCCATG CGACTGATTA AAAAAAATAA
```

```
                     nlaIII
         sau3AI
         mboI/ndeII[dam-]
         dpnI[dam+]                          maeII
         dpnII[dam-]                         aflIII
     maeIII alwI[dam-]    apoI              maeIII                                                                mnlI
 901 GTGACAAGGA TCATGCAGGA ATTTGAAAGT GACACGTTTT TCCGAAAAT TGATTGGGGG AAATATAAAC CTCTCCCAGA TTTATATTTG ACTAAACCCC
     CACTGTTCCT AGTACGTCCT TAAACTTTCA CTGTGCAAAA AGGCTTTTTA ACTAACCCCC TTTATATTTG GAGAGGGTCT ATATATAAAC TGATTTGGGG scrFI
     nvaI
     ecoRII
     dsaV
     bstNI
     apyI[dcm+]
     sau96I
     avaII                                                                                   sfaNI
     asuI  mnlI     sfaNI                                 accI   mboII                       mboII
1001 AGGTCCAGGA GGAAAAGGC ATCAAGTATA AGTTTGAAGT TCAAACTTCA GATGCTCTTC TTCTGATTG TCCTTCTACG AAAGACTAAC AGGAAGATGC
     TCCAGGTCCT CCTTTTTCCG TAGTTCATAT TCAAACTTCA AGTTTGAAGT CTACGAGAAG AAGACTAAC AGGAAGATGC TTTCTGATTG TCCTTCTACG styI
                                 bsaJI
                                 sau3AI
                             nlaIII       mboI/ndeII[dam-]
                             styI         dpnI[dam+]
                             ncoI         dpnII[dam-]
             ppu10I         dsaI  bsmFI   alwI[dam-]
             nsiI/avaIII    bsaJI  cac8I  bstYI/xhoII
1101 ATGCATTTTT ATAAGACCAT GGGACTTTTG CTGGCCTTAG ATCCCTTGG CTTCGTTAGA ACCGAGCTAC AATTAATACA TAACCTTATG TATCATATAC
     TACGTAAAAA TATTCTGGTA CCCTGAAAAC GACCGGAATC TAGGGAACC GAAGCAATCT TGGCTCGATG TTAATTATGT ATTGGAATAC ATAGTATGTG
```

```
                          scrFI
                          mvaI
                          ecoRII              sfaNI
                          dsaV                ppul0I
                          bstNI               nsiI/avaIII                             mvaI     scrFI
                          apyI[dcm+]          nlaIII                                  ecoRII
                    bsmFI  bsaJI       nlaIV    cac8I       sphI                      dsaV
                                                            nspI                      bstNI
                                                            nspHI                     apyI[dcm+]
                                                            cac8I                     bsxAI    bsmFI
3001 GAAGTGTGT CAGTTAGGGT GTGGAAAGTC CCCAGGCTCC CCAGGCAGGCA GAAGTATGCA AAGCATGCAT CTCAATTAGT CAGGACCAG GTGTGGAAAG
     CTTACACACA GTCAATCCCA CACCTTTCAG GGGTCCGAGG GGTCGTCCGT CTTCATACGT TTCGTACGTA GAGTTAATCA GTCGTTGGTC CACACCTTTC nlaIV
        scrFI
        mvaI
        ecoRII              sfaNI
        dsaV                ppul0I
        bstNI               nsiI/avaIII
        apyI[dcm+]          nlaIII              nspI
  bsaJI       cac8I         sphI                nspHI                                        acII
                                                cac8I                               acII      fokI               acII
                                                                        fnu4HI       bsmFI     acII       acII
                                                                        bsoFI
                                                                        bglI
                                                                        sfiI
                                                                        haeIII/palI
                                        nlaIII                    mnlI  mnlI           ddeI
                                        styI                            bsaJI bsaJI mnlI eluI            mnlI
                              bslI dsaI  ncoI                   haeIII/palI acII     haeIII/palI          bseRI
3101 TCCCCAGGCT CCCCAGCAGG CAAAGCATGG CAGAAGTATG CCGCCCCATG ATCTCAATTA GTCAGCAACC ATAGTCCCGC GCCATCCCG CCCTAACTC
     AGGGGTCCGA GGGGTCGTCC GTTTCGTACG GTCTTCATAC GGCGGGGTAC TAGAGTTAAT CAGTCGTTGG TATCAGGGCG CGGTAGGGC GGGATTGAG bsrI acII
         acII bsaJI
3201 CGCCCAGTTC CGCCCATTCT CCGCCCCATG GCTGACTAAT TTTTTTATT TATGCAGAGG CCGAGGCCGC CTCGGCCTCT GAGTATTCC AGAAGTAGTG
     GCGGGTCAAG GCGGGTAAGA GGCGGGGTAC CGACTGATTA AAAAAAATAA ATACGTCTCC GGCTCCGGCG GAGCCGGAGA CTCGATAAGG TCTTCATCAC
```

FIG. 48K

```
                                                                        scrFI
                                                                        ncoI
                                                                        mspI
                                                                        hpaII
                                                                        dsaV
                                                                        haeIII/palI
                                                      alul              ncrI                tfiI
                                                      rmaI              eagI/xmaIII/eclXI   hinfI
                                                      maeI              eaeI                acII
                                                      bfaI              cfrI                thaI
                                                      nheI              bslEI               fnuDII/mvnI      pleI
                                                      cac8I             mspI cauII          bstUI            hinfI
                                                      aluI              hpaII               bsh1236I
       rmaI
       maeI
       styI
       bsaJI
       blnI
       avrII[dam-]
       haeIII/palI
       stuI
       haeI
       mnlI bfaI
mnlI
3301 AGGAGGCTTT TTTGGAGGCC TAGGCTTTTG CAAAAAGCTA GCTTATCCGG CGGGAACGG TGCATTGGAA CGCGGATTCC CCGTGCCAAG AGTCAGGTAA
     TCCTCCGAAA AAACCTCCGG ATCGAAAAC GTTTTTCGAT CGAATAGGCC GCCCTTGCC ACGTAACTT GGCCCTAAGG GGCACGGTTC TCAGTCCATT
     ^seq from pSV16B5-6G4VL: AvrII - HindIII frag                              U1 matched splice donor^ sau3AI
                                                                                           mboI/ndeII[dam-]
                                                                                           dpnI[dam+]
                                                                                           dpnII[dam-]
                                                                                           alwI[dam-]
                                                                                           taqI[dam-]
                                                      fnu4HI                                claI/bsp106[dam-]
                                                      bsoFI                                 bspDI[dam-]
                                                      acII                                  sau3AI
                                                      thaI                                  mboI/ndeII[dam-]
                    bstXI                             fnuDII/mvnI  tru9I                    dpnI[dam+]
       acII         sau96I  styI                      bstUI        maeI                     dpnII[dam-]
       rmaI  pleI   haeIII/palI                       bsh1236I     aseI/asnI/vspI           alwI[dam-]            fokI
  acII  sdfI hinfI  asuI    bsaJI
3401 GTACCGCCTA TAGAGTCTAT AGGCCCACCC CCTTGGCTTC GTTAGAACGC GGCTACAATT AATACATAAC CTTTTGGATC GATCCTACTG ACACTGACAT
     CATGGCGGAT ATCTCAGATA TCCGGGTGGG GGAACCGAAG CAATCTTGCG CCGATGTTAA TTATGTATTG GAAAACCTAG CTAGGATGAC TGTGACTGTA
                                        ^sp6 promoter                                       ^removed ATG
                                                                                                   ^U2 match
                                                                                                     lariat consensus^
                                                                                            IgG vH natural lariat restored^
```

```
                         rsaI                                                              sau3AI
                         csp6I                                                             mboI/ndeII[dam-]
                         nlaIV                                                             dpnI[dam+]
                         kpnI                                                              dpnII[dam-]
                         hgiCI                                                             pvuI/bspCI
                         banI                                                              ncrI
              rsaI       asp718                                                            bslEI
              mseI       acc65I       mnlI                                                 taqI[dam-]                              fnu4HI     haeI
      bsmI    bfaI       mnlI         ddeI    aciI                                         claI/bsp106[dam-]                       bsoFI      styI
                                                                                           bspDI[dam-]   tru9I                     bbvI       ncoI
                                                                                           sau3AI        mseI                      hinPI      dsaI  haeIII/palI
                                                                                           mboI/ndeII[dam-]                        hhaI/cfoI  nlaIII
                                                                                           dpnI[dam+]  xmnI    aseI/asnI/vspI      bsaJI
                                                                              nlaIII alwI[dam-]  dpnII[dam-]   asp700  GAATTAATTC GGGCAGCAC CATGGCCTGA
4401 TTTTCACTG CATTCTAGTT GTGGTTTGTC CAAACTCATC AATGTATCTT ATCATGTCTG GATCGATCGG GAATTAATTC CTTAATTAAG CCCGTCGTG GTACCGGACT
     AAAAGTGAC GTAAGATCAA CACCAAACAG GTTTGAGTAG TTACATAGAA TAGTACAGAC CTAGCTAGCC CTTAATTAAG CCCGTCGTG GTACCGGACT
                                                                                                           "sv40 origin"

aluI
                                                            pvuII
                                                            nspBII
                                sfaNI                                                                                    scrFI
                                ppu10I                                            scrFI                                  nvaI
                                nsiI/avaIII                                       nvaI                                   ecoRII
                                nlaIII                                            ecoRII                                 dsaV
                                sphI                                              dsaV                                   bstNI
                                nspI                                              bstNI                                  apyI[dcm+]
              mnlI    mnlI      nspHI                                             apyI[dcm+]                             bsaJI
              mnlI    mnlI      cac8I                                             bsaJI                bsmFI   nlaIV
4501 AATAACCTCT GAAAGAGGAA CTTGGTTAGG TACCCTTCTGA GGCGGAAAGA ACCAGCTGTG GAATGTGTGT CAGTTAGGCT GTGGAAAGTC CCCAGGCTCC
     TTATTGGAGA CTTTCTCCTT GAACCAATCC ATGGGAAGACT CCGCCTTTCT TGGTCGACAC GTCAATCCCA CACCTTTCAG GGGTCCGAGG sfaNI
                                                                                                               ppu10I
                                                                                                               nsiI/avaIII
                                                                              scrFI                            nlaIII
                                                                              nvaI                             sphI         nspI
                                                                              ecoRII                                        nspHI
                                                                              dsaV                                          cac8I
                                                                              bstNI
                                                                              apyI[dcm+]
                       cac8I                                                  sexAI      bsmFI    nlaIV
4601 CCAGCAGGCA AAGCATGCA AAGCATGCAT CTCAATAGT CAGCAACCAG GTGTGGAAAG TCCCAGGCT CCCCAGCCAGG GGGGTCGTCC CAGAAGTATG CAAAGCATGC
     GGTCGTCCGT CTTCATACGT TTCGTACGTA GAGTTAATCA GTCGTTGGTC CACACCTTTC AGGGTCCGAA GGGGTCGTCC CCCAGCAGG CAGAAGTATG CAAAGCATGC GTTTCGTACG
```

```
                                                               nlaIV
                                                               hgICI  taqI
                                                        nlaIV  banI  mnlI
       nspI                                             hgIJII
       hpaII                                            bspI286
       neaI                                             bmyI
       cfr10I/bsrFI                   alul              banII               nlaIV
       maeII                cac8I
5301 TTTCTCGCCA CGTTCGCCGG CTTTCCCGT CAAGCTCTAA ATCGGGGGCT CCCTTTAGGG TTCCGATTTA GTGCTTTACG GCACCTCGAC CCCAAAAAAC
     AAAGAGCGGT GCAAGCGGCC GAAAGGGCA GTTCGAGATT TAGCCCCCGA GGGAAATCCC AAGGCTAAAT CACGAAATGC CGTGGAGCTG GGGTTTTTTG
            maeII  haeIII/palI                                  maeII pleI                tru9I   pleI
            draIII saw96I                                       drdI hinfI maeII          maeI   hinfI
       hphI bssAI asuI                                                                           
5401 TTGATTGGG TGATGGTTCA CGTAGTGGGC CATCGCCCTG ATAGACGGTT TTTCGCCCTT TGACGTGGA GTCCACGTTC TTTAATAGTG GACTCTGTT
     AACTAAACCC ACTACCAAGT GCATCACCCG GTAGCGGGAC TATCTGCCAA AAAGCGGGAA ACTGCAACCT CAGTGCAAG AAATTATCAC CTGAGAACAA
                                                                                        tru9I
                                                bsII                                    maeI                  tru9I
                                                                                                       aluI   maeI
       bsrI                          bsII  avaI                             haeIII/palI
5501 CCAAACTGGA ACAACACTCA ACCTATCTC GGGCTATTCT TTTGATTTAT AAGGGATTTT GCCTATTGGT TAAAAAATGA GCTGATTTAA
     GGTTTGACCT TGTTGTGAGT TGGATAGAG CCCGATAAGA AAACTAAATA TTCCCTAAAA CGGATAACCA ATTTTTTACT CGACTAAATT
                    thaI                                                      hgIAI/aspHI
                    fnuDII/mvnI                                               bspI286
       tru9I  apoI tru9I                  maeII                               bslHKAI                       acII
       maeI   bstUI  maeI                 psp1406I                            bmyI  ddeI                    fnu4HI
       apoI   bsh1236I       sspI maeI    tru9I                               apaLI/snoI rsaI               bsoFI  tru9I
5601 CAAAAATTTA ACGCGAATTT TAACAATTA TTAACGTTTA CAATTTTATG GTGCACTCTC AGTACAATCT GCTCTGATGC CGCATAGTTA AGCCAACTCC
     GTTTTAAAT TGCGCTTAAA ATTGTTAAT AATTGCAAAT GTTAAAATAC CACGTGAGAG TCATGTTAGA CGAGACTACG GCGTATCAAT TCGGTTGAGG
                                                                      hinPI                   sfaNI
                                                                      hhaI/cfoI               mspI
                                                                      thaI                    hpaII
                                                                      fnuDII/mvnI             sarFI
                                                                      bstUI                   acII
       maeII                             aspBII bsh1236I     drdI                             dsaV fokI     acII
       maeII bsrI nlaIII hhaI/cfoI       acII hgeI                                            cauII  acII
       bssAI tth1111/aspI bbvI
5701 GCTATCGCTA CGTGACTGGG TCATGGCTGC GCCCGACAC CGGCTGACGC GCCGACTGCG GCCTGACGAG GCTTGTCTGC TCCGGGCATC CGCTTACAGA
     CGATAGCGAT GCACTGACCC AGTACCGACG CGGGCTGTG GCCGACTGCG CGGCACTGCG CGGACTGCTC CGAACAGACG AGGGCCGTAG GCGAATGTCT
```

```
                                                                                                      sau3AI
                     sau3AI                                                                           mboI/ndeII[dam-]
           mboII[dam-]                                                                                dpnI[dam+]
     sau3AI        mboI/ndeII[dam-]  thaI                                                             dpnII[dam-]
     mboI/ndeII[dam-]  dpnI[dam+]    fauDII/mvaI                                                      alwI[dam-]
     dpnI[dam+]     dpnII[dam-]      bstUI     cac8I                                                  mspI
     dpnII[dam-]    alwI[dam-]       bsh1236I  fnu4HI                                    acII         hpaII        aluI
     bstYI/xhoI     bstYI/xhoI       hinPI     bsoFI                            acII     nspBII       ACCAGCGGTG   GTTTGTTGC  CGGATCAAGA
     alwI[dam-]                      hhaI/cfoI bbvI
7101 TCAAAGGATC TTCTTGAGAT CCTTTTTTTC TGCGCGTAAT CTGCTGCTTG CAAACAAAAA ACCACCGCT ACCAGCGGTG GTTTGTTGC CGGATCAAGA
     AGTTTCCTAG AAGAACTCTA GGAAAAAAAG ACGCGCATTA GACGACGAAC GTTTGTTTT TTGGTGGCGA CAAACAACG GCCTAGTTCT
                                                                         rmaI
                                                      bsrI     hinPI     maeI                     haeIII/paII
                                                      maeIII   hhaI/cfoI bfaI            bsII     haeI
7201 GCTACCAACT CTTTTTCCGA AGTAACTGG CTTCAGCAGA GCGCAGATAC CAATATACTGT CCTTCTAGTG TAGCCGTAGT TAGGCCACCA CTTCAAGAAC
     CGATGGTTGA GAAAAAGGCT TCCATTGACC GAAGTCGTCT CGCGTCTATG GTTTATGACA GGAAGATCAC ATCGGCATCA ATCCGGTGGT GAAGTTCTTG
                                                                           fnu4HI
                                                                           bsoFI                       scrFI
                                                                           bbvI                        ncII
                                                                                                       mspI            pleI
                                                                                  fnu4HI               hpaII           hinfI
                                                                                  alwNI[dcm-]          dsaV
                                                                         maeIII   bsrI  bsoFI          cauII
7301 TCTGTCTAGC CGCCTACATA CCTCGCTCTG CTAATCCTGT TACCAGTGGC TGCTGCCAGT GGGCGATAAGT CGTGTCTTAC CGGGTTGGAC TCAAGACGAT
     AGACAGATCGTG GCGGATGTAT GGAGCGAGAC GATTAGGACA ATGGTCACCG ACGACGGTCA CCGCTATTCA GCACAGAATG GCCCAACCTG AGTTCTGCTA
                                                     hg1AI/aspHI
                                             acII    bsp1286
                                             nspBII  bs1HKAI
                                             fnu4HI  bmyI
                         mspI                bsoFI   apaLI/snoI
                         hpaII  bbvI mcrI    alw44I/snoI  aluI
                         bsaWI  hinPI bs1EI
     scfI     acII       maeIII hhaI/cfoI                                                               ddeI        scfI
7401 AGTTACCGGA TAAGGCGCAG CGGTCGGGCT GAACGGGGGG TTCGTGCACA CAGCCCAGCT TGGAGCGAAC GACCTACACC GAACTGAGAT ACCTACAGCG
     TCAATGGCCT ATTCCGCGTC GCCAGCCCGA CTTGCCCCCC AAGCACGTGT GTCGGGTCGA ACCTCGCTTG CTGGATGTGG CTTGACTCTA TGGATGTCGC
```

FIG. 48W

```
                                                                                        scrFI
                                                                                        mvaI
                                                                                        ecoRII
                                                                                        dsaV
                                                                          mspI          bstNI
                                                                          hpaII fnu4HI  bssSI             bsaJI
                        hinPI                                             bslI  bsoFI   hinPI mnlI
                        hhaI/cfoI                                  acII   bsaWI acII    hhaI/cfoI aluI apyI[dcm+]
                        haeII                                      GCGGACAGGT ATCCGGTAAG CGGCAGGGTC GGAACAGGAG AGCGCACGAG GGAGCTTCCA
7501 TGAGCATTGA GAAGGGCCA CGCTTCCCGA AGGGAGAAAG TCCCTCTTTC CGCCTGTCCA TAGGCCATTC GCCGTCCCAG CCTTGTCCTC TCGCGTGCTC CCTCGAAGGT
     ACTCGTAACT CTTTCGCCGT GCGAAGGGCT
                                                                                                                  nlaIV
     scrFI                                                                                                        acII
     mvaI
     ecoRII
     dsaV                                              mnlI drdI  hgaI            sfaNI  GATGCTCGTC AGGGGGGCGG AGCCTATGGA
     bstNI                                             ACTTGAGCGT CGATTTTTGT              CTACGAGCAG TCCCCCCGCC TCGGATACCT
     apyI[dcm+]       CCTGGTATCT TTATAGTCCT GTCGGGTTTC GCCACCTCTG
7601 GGGGGAAACG       GGACCATAGA AATATCAGGA CAGCCCAAAG CGGTGGAGAC TGAACTCGCA GCTAAAAACA
     CCCCCTTTGC
                                haeIII/palI
                haeII/palI      scrFI
                fnu4HI          mvaI bslI
                bsoFI           ecoRII
                acII            dsaV
                thaI  bslI      bstNI                      nlaIII
                fnuDII/mvnI     apyI[dcm+]      haeIII/palI nspI                                                 tfiI
                bstUI           nlaIV haeI      haeI       afIIII                                               hinfI
     cac8I      bsh1236I                       cacBI       TTGCTCTCACA TGTTCTTTTC TCGGTATCC CCTGATTCTG TGGATAACCG
7701 AAAACGCCAG CAACGGGCGC TTTTTACGGT TCCTGGCCTT         ACGACCGGAA AACGAGAGT ACAAGAAAGG ACGCAATAGG GGACTAAGAC ACCTATTGGC
     TTTTGCGGTC GTTGCGCCCG AAAAATGCCA AGGACCGGGA AACGACCGGA
                                fnu4HI
                                bsoFI                                                                sapI    hinPI
                                bbvI                                                                 mboII   hhaI/cfoI
                cac8I acII           bbvI pleI                                                       earI/xsp632I
                bsrBI fnu4HI         hinPI hinfI                                                     mnlI acII    haeII
     acII       acII  bsoFI          hhaI/cfoI  mcrI      bstEI                                      GAGGAAGCGG CTCCCTTCGCC GAGGAGCCGG AAGAGCGCCC AATACGCAAA
7801 TATTACCGCC TTTGAGTGAG CTGATACCGC TGCGCCAGCA CGAACGACCG AGCGGGGGTCG        CCGTTGCTGCT CAGTCACTCG GCGGAGGCCG TTATGCGTTT
     ATAATGGCGG AAACTCACTC GACTATGGCG ACGCGGTCGT GCTTGCTGGC TCGCCCCAGC GGCAACGACGA GTCAGTGAGC

FIG. 48X
```

```
                        thaI
                        fnuDII/mvnI
                        bstUI
                        bsh1236I
                        hinPI
                        hhaI/cfoI
                        thaI
                        fnuDII/mvnI                       cac8I
                        bstUI   haeIII/palI              aluI
                        bsh1236I         truI9I         pvuII
     mnlI       bsII   eaeI tfiI aseI/asnI/vspI                                                              truI9I
     aclI       aclI   cfrI hinfI mseI nspBII                       bsrI        cac8I       hinPI       mseI       maeIII
7901 CCGCCTCTCC CCGCGCGTTG GCCGATTCAT TAATCCAGCT GGCACGACAG GTTTCCCGAC TGGAAAGCGG GCAGTGAGCG CAACGCAATT AATGTGAGTT
     GGCGGAGAGG GGCGCGCAAC CGGCTAAGTA ATTAGGTCGA CCGTGCTGTC CAAAGGGCTG ACCTTTCGCC CGTCACTCGC GTTGCGTTAA TTACACTCAA
                         scrFI
                         mvaI
                         ecoRII
                         dsaV
                  nlaIV bstNI                            mspI              aclI
                  hgiCI apyI[dcm+]                       hpaII             bsrBI                            aluI
     mnlI         banI bsaJI                                                                                
8001 ACCTCACTCA TTAGGCACCC CAGGCTTTAC ACTTTATGCT TCCGGCTCGT ATGTTGTGTG GAATTGTGAG CGGATAACAA TTTCACACAG GAAACAGCTA
     TGGAGTGAGT AATCCGTGGG GTCCGAAATG TGAAATACGA AGGCCGAGCA TACAACACAC CTTAACACTC GCCTATTGTT AAAGTGTGTC CTTTGTCGAT
```

FIG. 48Y

```
                              tru9I
                              mseI
                              aseI/asnI/vspI
                      xmnI
              nlaIII  asp700
8101 TGACCATGAT TACGAATTAA
     ACTGGTACTA ATGCTTAATT >length: 8120 aatII(GACGTC):              1690 5947
acc65I(GGTACC):             2969 3967 4529
accI(GTMKAC):               823 1039 2738 4237
aclI(CCGC):                 217 229 238 250 260 271 317 422 454 485 574 1385 1795 1871 2248 2250 2758 2982
                            3167 3179 3188 3200 3210 3221 3267 3372 3404 3449 3686 3949 4021 4318 4542 4727
                            4739 4748 4760 4770 4781 4827 4910 4914 5070 5127 5153 5166 5203 5217 5220 5248
                            5275 5680 5699 5741 5751 5790 5979 6026 6125 6234 6311 6355 6476 6522 6713 6804
                            7166 7175 7310 7420 7541 7560 7687 7715 7806 7827 7877 7901 7911 7967 8070
acyI                        see hinII
afIII/bfrI(CTTAAG):         786
afIIII(ACRYGT):             932 7758
ageI(ACCGGT):               1833
ahaII/banHI(GRCGYC):        988 1690 1850 5117 5947 6329
ahaIII/draI(TTTAAA):        696 4935 6290 6982 7001
ahdI/eam1105I(GACNNNNNGTC): 2087 6865
aluI(AGCT):                 5 44 332 386 390 753 1097 1165 1370 1431 1951 2603 2751 2784 3282 3336 3340
                            3562 3566 3676 3733 3792 4270 4288 4311 4344 4554 4842 4896 4954 5047 5333 5590
                            5803 5822 6516 6579 6679 7200 7457 7593 7819 7937 8096
alw44I/snoI(GTGCAC):        1876 5651 6198 7444
```

FIG. 48Z

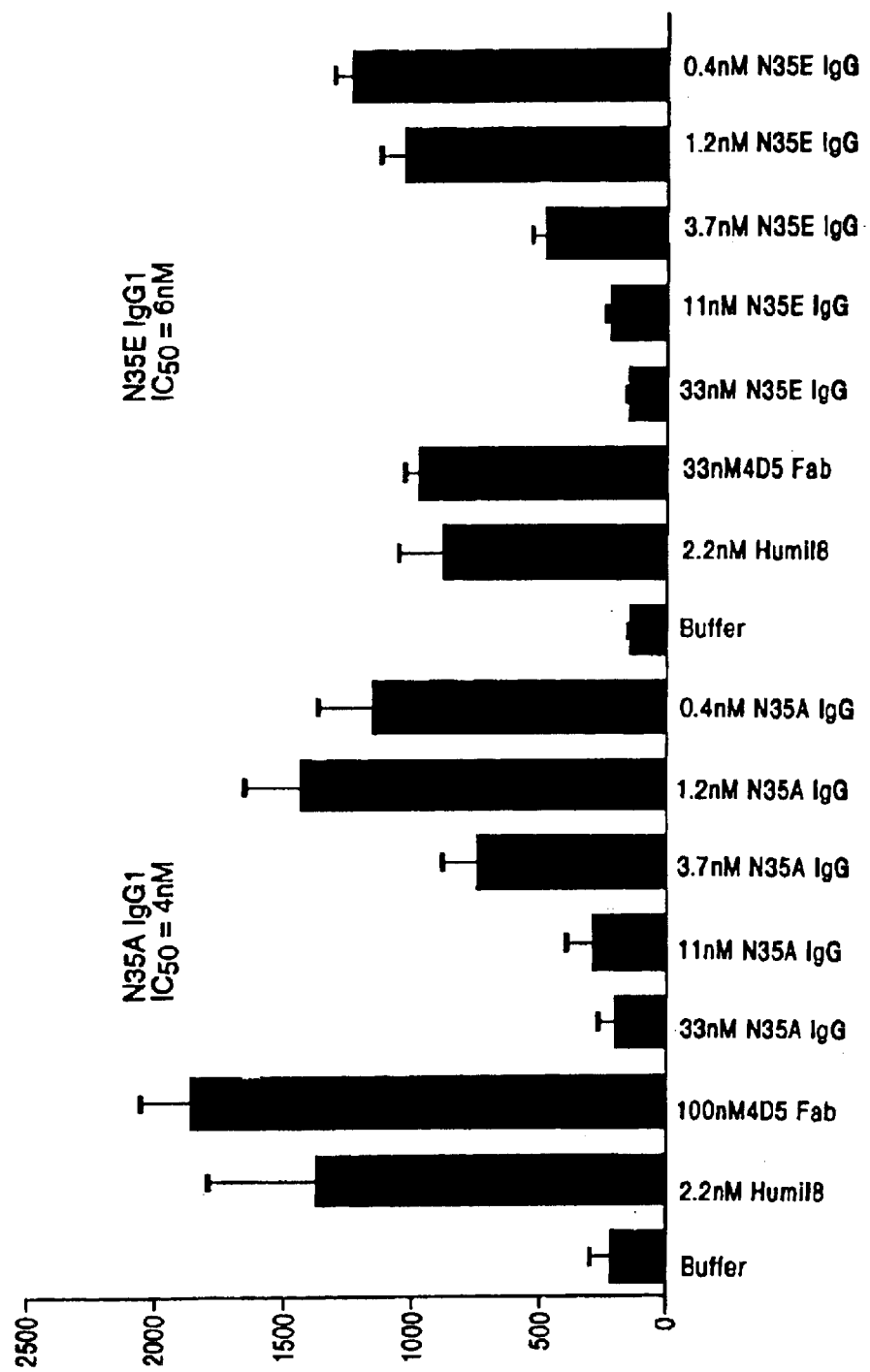

Representative Conc versus Time Plot. Shown is the kinetic data for 6G4V11N35A.IgG1

```
 781 AAAAGGGTAT CTAGAGGTTG AGGTGATTTT ATGAAAAAGA ATATCGCATT TCTTCTTGCA
     TTTTCCCATA GATCTCCAAC TCCACTAAAA TACTTTTTCT TATAGCGTAA AGAAGAACGT
  -1                                    M  K  K  N  I  A  F  L  L  A

841 TCTATGTTCG TTTTTTCTAT TGCTACAAAC GCGTACGCTG AGGTTCAGCT AGTGCAGTCT
     AGATACAAGC AAAAAAGATA ACGATGTTTG CGCATGCGAC TCCAAGTCGA TCACGTCAGA
 -11 S  M  F  V  F  S  I  A  T  N  A  Y  A  E  V  Q  L  V  Q  S

901 GGCGGTGGCC TGGTGCAGCC AGGGGGCTCA CTCCGTTTGT CCTGTGCAGC TTCTGGCTAC
     CCGCCACCGG ACCACGTCGG TCCCCCGAGT GAGGCAAACA GGACACGTCG AAGACCGATG
   8 G  G  G  L  V  Q  P  G  G  S  L  R  L  S  C  A  A  S  G  Y

961 TCCTTCTCGA GTCACTATAT GCACTGGGTC CGTCAGGCCC CGGGTAAGGG CCTGGAATGG
     AGGAAGAGCT CAGTGATATA CGTGACCCAG GCAGTCCGGG GCCCATTCCC GGACCTTACC
  28 S  F  S  S  H  Y  M  H  W  V  R  Q  A  P  G  K  G  L  E  W

1021 GTTGGATATA TTGATCCTTC CAATGGTGAA ACTACGTATA ATCAAAAGTT CAAGGGCCGT
     CAACCTATAT AACTAGGAAG GTTACCACTT TGATGCATAT TAGTTTTCAA GTTCCCGGCA
  48 V  G  Y  I  D  P  S  N  G  E  T  T  Y  N  Q  K  F  K  G  R

1081 TTCACTTTAT CTCGCGACAA CTCCAAAAAC ACAGCATACC TGCAGATGAA CAGCCTGCGT
     AAGTGAAATA GAGCGCTGTT GAGGTTTTTG TGTCGTATGG ACGTCTACTT GTCGGACGCA
  68 F  T  L  S  R  D  N  S  K  N  T  A  Y  L  Q  M  N  S  L  R

1141 GCTGAGGACA CTGCCGTCTA TTACTGTGCA AGAGGGGATT ATCGCTACAA TGGTGACTGG
     CGACTCCTGT GACGGCAGAT AATGACACGT TCTCCCCTAA TAGCGATGTT ACCACTGACC
  88 A  E  D  T  A  V  Y  Y  C  A  R  G  D  Y  R  Y  N  G  D  W

1201 TTCTTCGACG TCTGGGGTCA AGGAACCCTG GTCACCGTCT CCTCGGCCTC CACCAAGGGC
     AAGAAGCTGC AGACCCCAGT TCCTTGGGAC CAGTGGCAGA GGAGCCGGAG GTGGTTCCCG
 108 F  F  D  V  W  G  Q  G  T  L  V  T  V  S  S  A  S  T  K  G

1261 CCATCGGTCT TCCCCCTGGC ACCCTCCTCC AAGAGCACCT CTGGGGGCAC AGCGGCCCTG
     GGTAGCCAGA AGGGGGACCG TGGGAGGAGG TTCTCGTGGA GACCCCCGTG TCGCCGGGAC
 128 P  S  V  F  P  L  A  P  S  S  K  S  T  S  G  G  T  A  A  L

1321 GGCTGCCTGG TCAAGGACTA CTTCCCCGAA CCGGTGACGG TGTCGTGGAA CTCAGGCGCC
     CCGACGGACC AGTTCCTGAT GAAGGGGCTT GGCCACTGCC ACAGCACCTT GAGTCCGCGG
 148 G  C  L  V  K  D  Y  F  P  E  P  V  T  V  S  W  N  S  G  A

1381 CTGACCAGCG GCGTGCACAC CTTCCCGGCT GTCCTACAGT CCTCAGGACT CTACTCCCTC
     GACTGGTCGC CGCACGTGTG GAAGGGCCGA CAGGATGTCA GGAGTCCTGA GATGAGGGAG
 168 L  T  S  G  V  H  T  F  P  A  V  L  Q  S  S  G  L  Y  S  L

1441 AGCAGCGTGG TGACCGTGCC CTCCAGCAGC TTGGGCACCC AGACCTACAT CTGCAACGTG
     TCGTCGCACC ACTGGCACGG GAGGTCGTCG AACCCGTGGG TCTGGATGTA GACGTTGCAC
 188 S  S  V  V  T  V  P  S  S  S  L  G  T  Q  T  Y  I  C  N  V

1501 AATCACAAGC CCAGCAACAC CAAGGTCGAC AAGAAAGTTG AGCCCAAATC TTGTGACAAA
     TTAGTGTTCG GGTCGTTGTG GTTCCAGCTG TTCTTTCAAC TCGGGTTTAG AACACTGTTT
 208 N  H  K  P  S  N  T  K  V  D  K  K  V  E  P  K  S  C  D  K

1561 ACTCACACAT GCCCGCCGTGA
     TGAGTGTGTA CGGGCGGCACT
 228 T  H  T  C  P  P  Q
```

FIG. 53

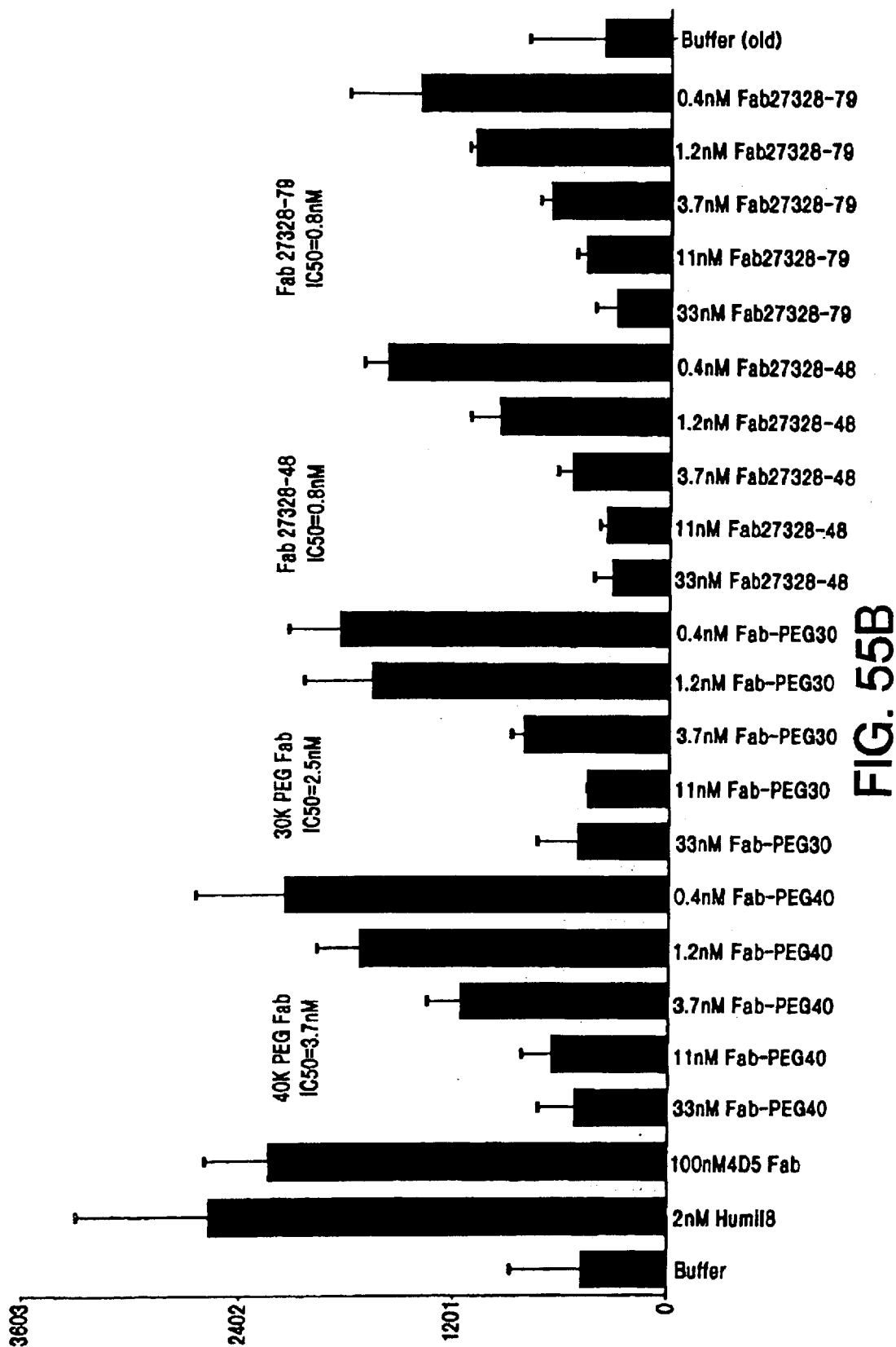

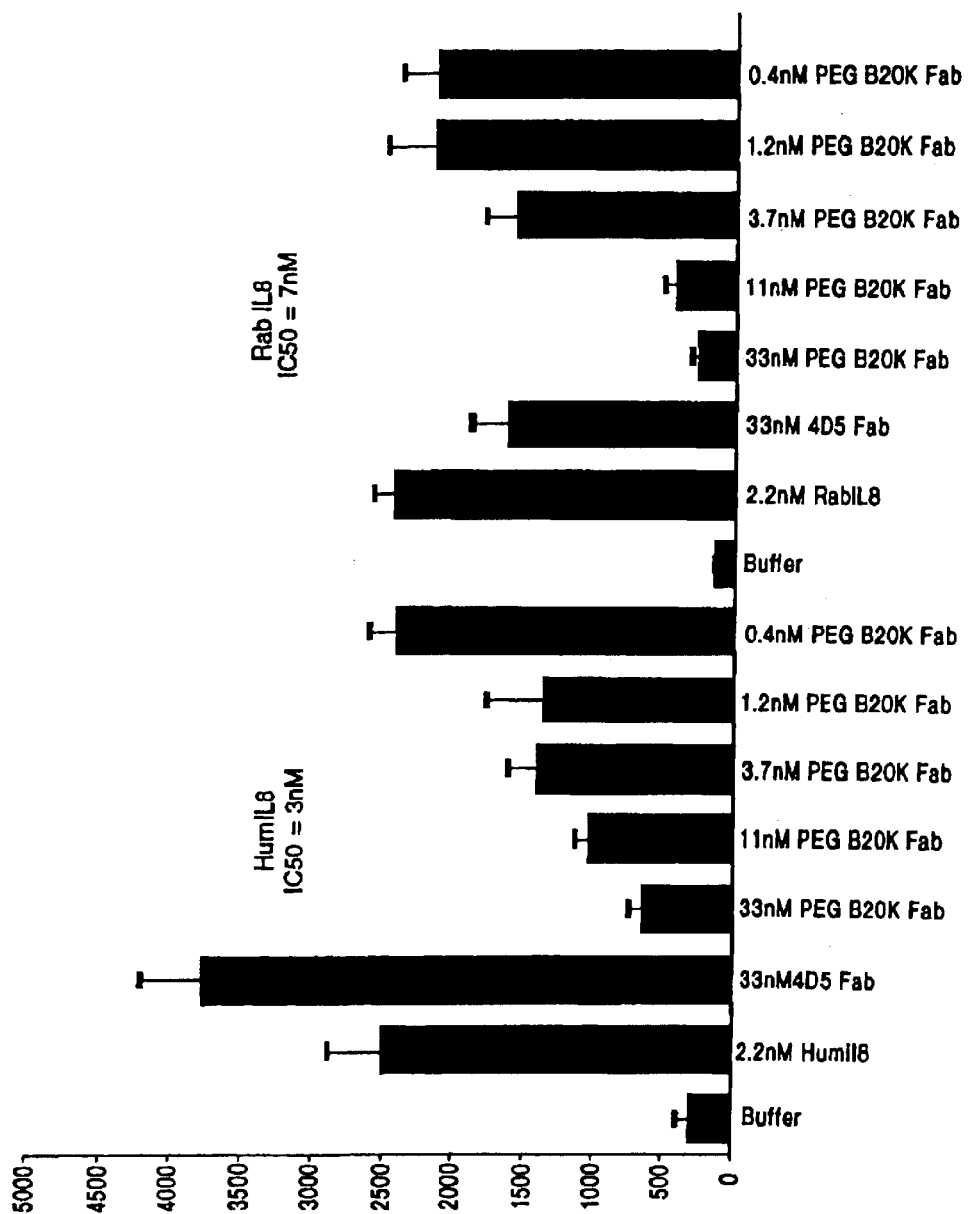

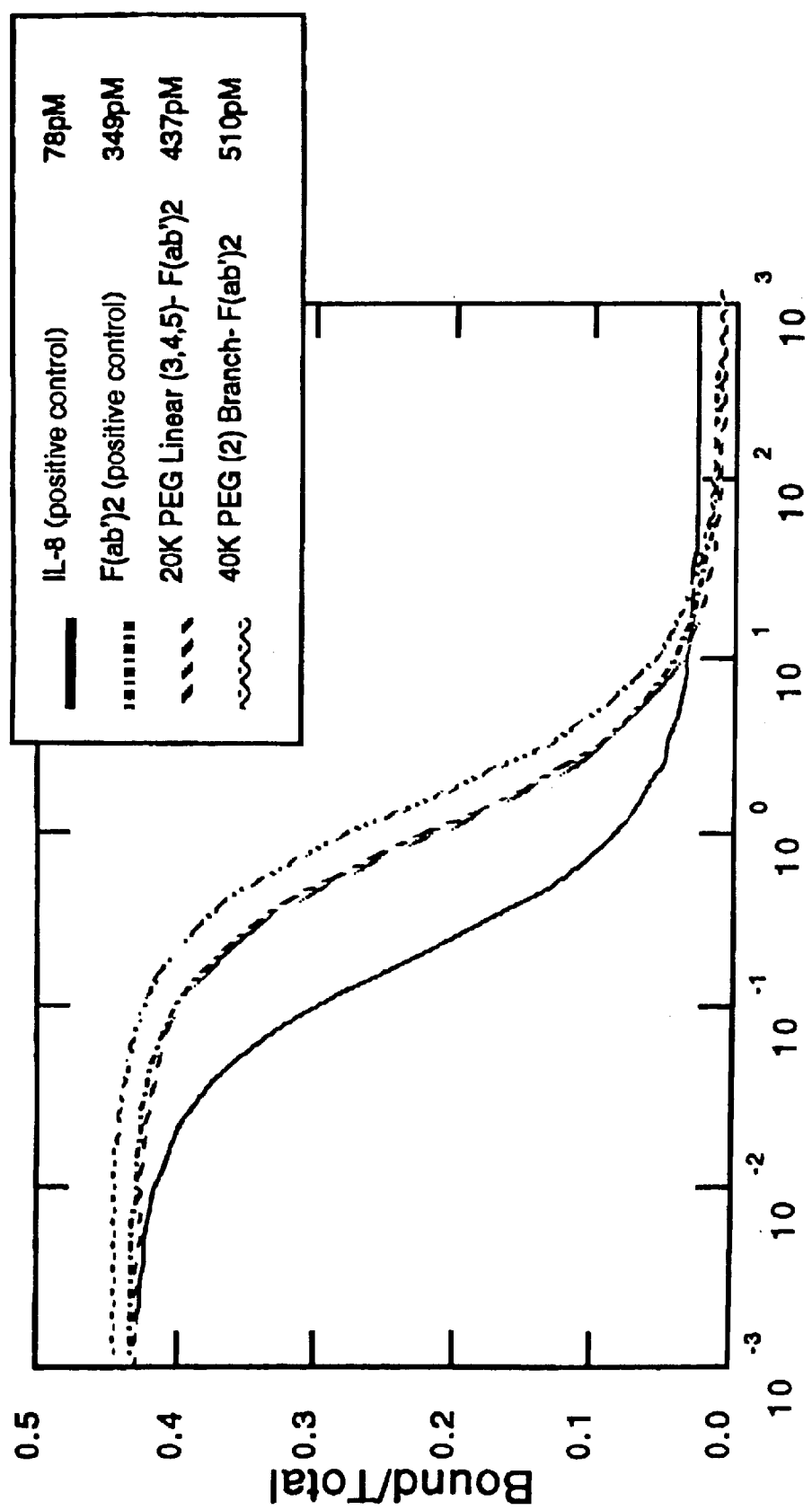

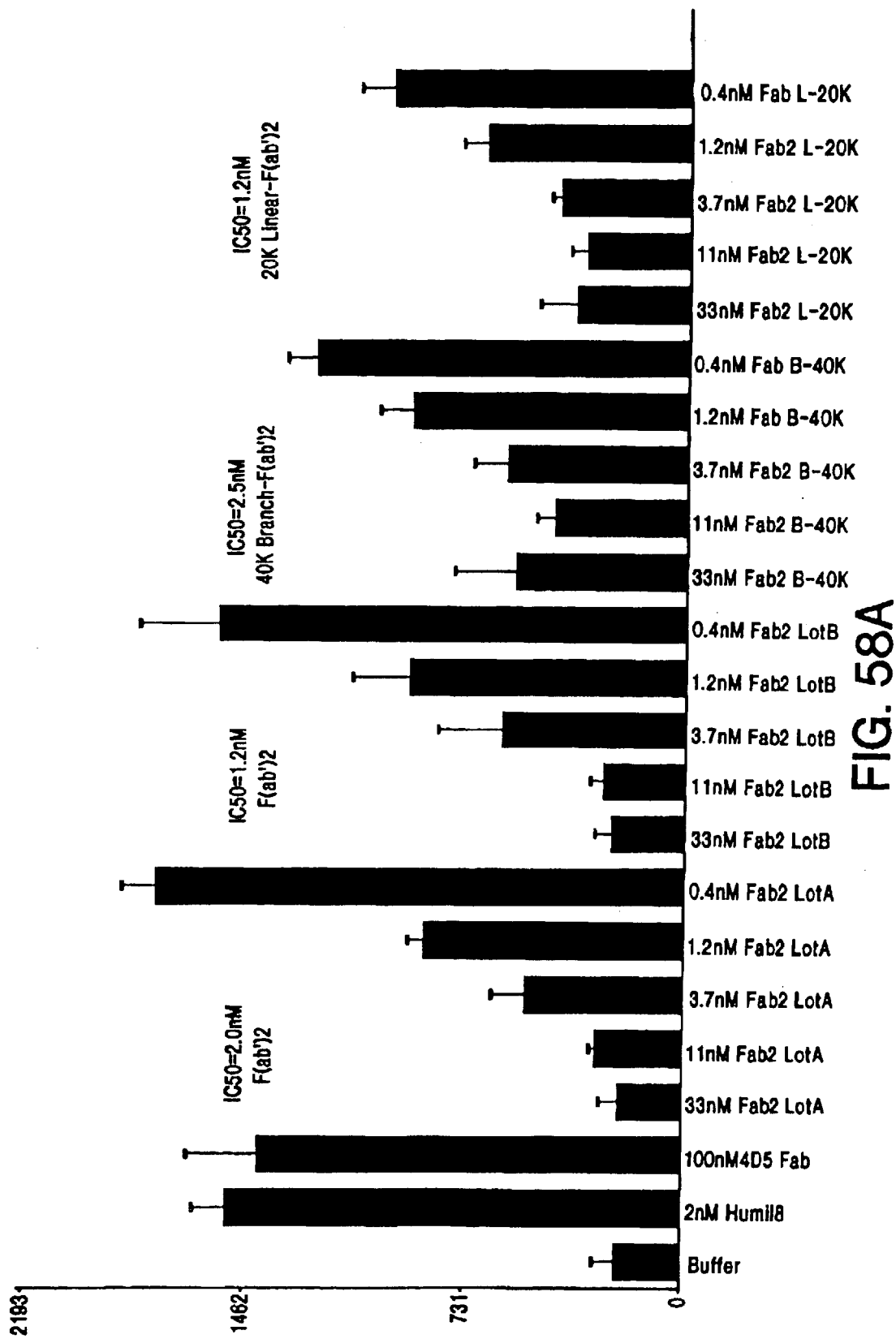

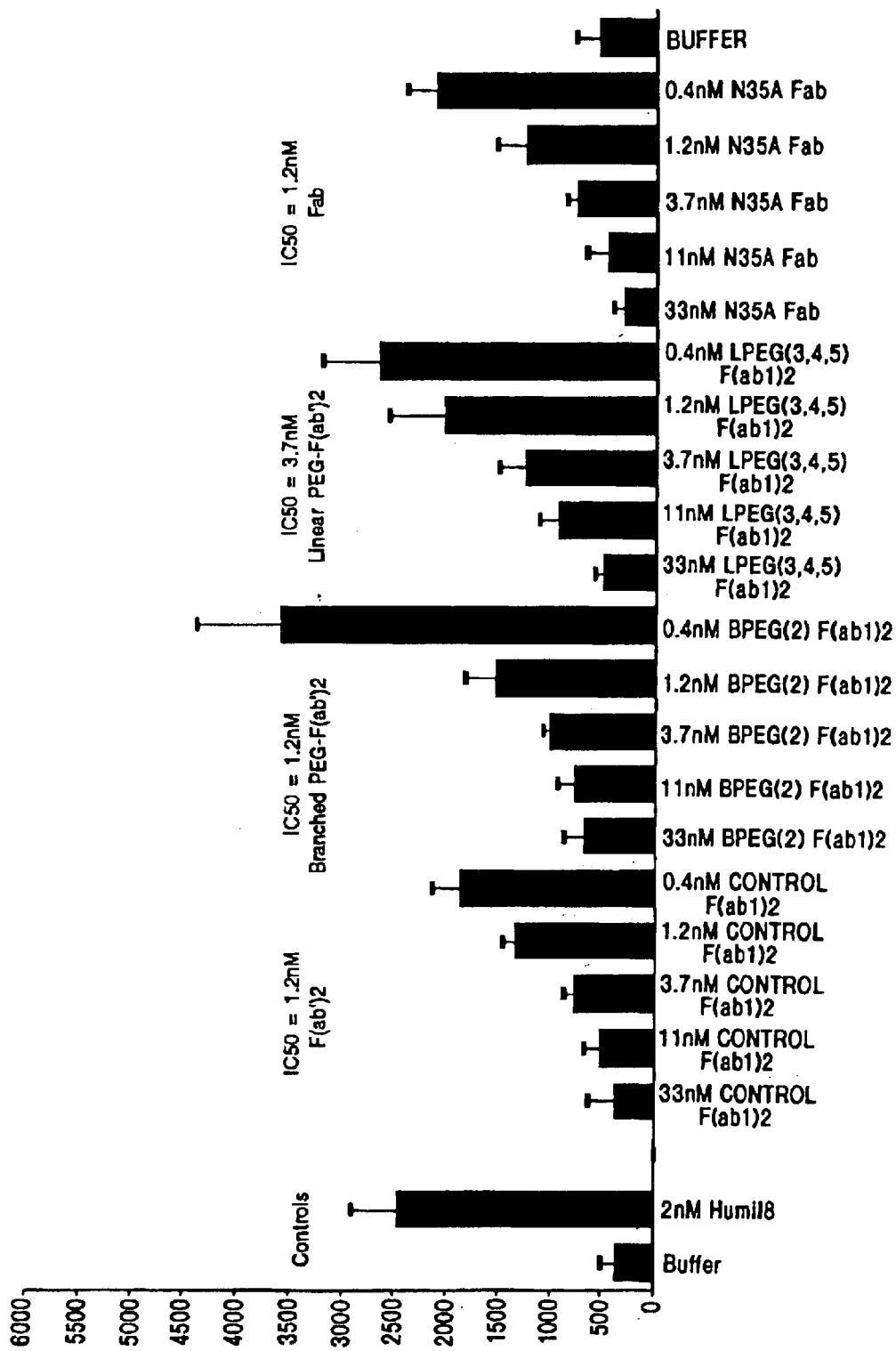

```
                         SEQUENCE LISTING (1) GENERAL INFORMATION:

(iii) NUMBER OF SEQUENCES: 72

(2) INFORMATION FOR SEQ ID NO: 1:

(i) SEQUENCE CHARACTERISTICS:
           (A) LENGTH: 22 base pairs
           (B) TYPE: Nucleic Acid
           (C) STRANDEDNESS: Single
           (D) TOPOLOGY: Linear (xi) SEQUENCE DESCRIPTION: SEQ ID NO: 1:

CAGTCCAACT GTTCAGGACG CC                                              22

(2) INFORMATION FOR SEQ ID NO: 2:

(i) SEQUENCE CHARACTERISTICS:
           (A) LENGTH: 22 base pairs
           (B) TYPE: Nucleic Acid
           (C) STRANDEDNESS: Single
           (D) TOPOLOGY: Linear (xi) SEQUENCE DESCRIPTION: SEQ ID NO: 2:

GTGCTGCTCA TGCTGTAGGT GC                                              22

(2) INFORMATION FOR SEQ ID NO: 3:

(i) SEQUENCE CHARACTERISTICS:
           (A) LENGTH: 23 base pairs
           (B) TYPE: Nucleic Acid
           (C) STRANDEDNESS: Single
           (D) TOPOLOGY: Linear (xi) SEQUENCE DESCRIPTION: SEQ ID NO: 3:

GAAGTTGATG TCTTGTGAGT GGC                                             23

(2) INFORMATION FOR SEQ ID NO: 4:

(i) SEQUENCE CHARACTERISTICS:
           (A) LENGTH: 24 base pairs
           (B) TYPE: Nucleic Acid
           (C) STRANDEDNESS: Single
           (D) TOPOLOGY: Linear (xi) SEQUENCE DESCRIPTION: SEQ ID NO: 4:

GCATCCTAGA GTCACCGAGG AGCC                                            24

(2) INFORMATION FOR SEQ ID NO: 5:

(i) SEQUENCE CHARACTERISTICS:
           (A) LENGTH: 22 base pairs
           (B) TYPE: Nucleic Acid
           (C) STRANDEDNESS: Single
           (D) TOPOLOGY: Linear (xi) SEQUENCE DESCRIPTION: SEQ ID NO: 5:

CACTGGCTCA GGGAAATAAC CC                                              22
```

(2) INFORMATION FOR SEQ ID NO: 6:

(i) SEQUENCE CHARACTERISTICS:
        (A) LENGTH: 22 base pairs
        (B) TYPE: Nucleic Acid
        (C) STRANDEDNESS: Single
        (D) TOPOLOGY: Linear (xi) SEQUENCE DESCRIPTION: SEQ ID NO: 6:

GGAGAGCTGG GAAGGTGTGC AC                                  22

(2) INFORMATION FOR SEQ ID NO: 7:

(i) SEQUENCE CHARACTERISTICS:
        (A) LENGTH: 35 base pairs
        (B) TYPE: Nucleic Acid
        (C) STRANDEDNESS: Single
        (D) TOPOLOGY: Linear (xi) SEQUENCE DESCRIPTION: SEQ ID NO: 7:

ACAAACGCGT ACGCTGACAT CGTCATGACC CAGTC                35

(2) INFORMATION FOR SEQ ID NO: 8:

(i) SEQUENCE CHARACTERISTICS:
        (A) LENGTH: 35 base pairs
        (B) TYPE: Nucleic Acid
        (C) STRANDEDNESS: Single
        (D) TOPOLOGY: Linear (xi) SEQUENCE DESCRIPTION: SEQ ID NO: 8:

ACAAACGCGT ACGCTGATAT TGTCATGACT CAGTC                35

(2) INFORMATION FOR SEQ ID NO: 9:

(i) SEQUENCE CHARACTERISTICS:
        (A) LENGTH: 35 base pairs
        (B) TYPE: Nucleic Acid
        (C) STRANDEDNESS: Single
        (D) TOPOLOGY: Linear (xi) SEQUENCE DESCRIPTION: SEQ ID NO: 9:

ACAAACGCGT ACGCTGACAT CGTCATGACA CAGTC                35

(2) INFORMATION FOR SEQ ID NO: 10:

(i) SEQUENCE CHARACTERISTICS:
        (A) LENGTH: 37 base pairs
        (B) TYPE: Nucleic Acid
        (C) STRANDEDNESS: Single
        (D) TOPOLOGY: Linear (xi) SEQUENCE DESCRIPTION: SEQ ID NO: 10:

GCTCTTCGAA TGGTGGGAAG ATGGATACAG TTGGTGC              37

(2) INFORMATION FOR SEQ ID NO: 11:

(i) SEQUENCE CHARACTERISTICS:
        (A) LENGTH: 39 base pairs
        (B) TYPE: Nucleic Acid
        (C) STRANDEDNESS: Single
        (D) TOPOLOGY: Linear (xi) SEQUENCE DESCRIPTION: SEQ ID NO: 11:

CGATGGGCCC GGATAGACCG ATGGGGCTGT TGTTTTGGC            39

(2) INFORMATION FOR SEQ ID NO: 12:

(i) SEQUENCE CHARACTERISTICS:
        (A) LENGTH: 39 base pairs
        (B) TYPE: Nucleic Acid
        (C) STRANDEDNESS: Single
        (D) TOPOLOGY: Linear (xi) SEQUENCE DESCRIPTION: SEQ ID NO: 12:

| | |
|---|---|
| CGATGGGCCC GGATAGACTG ATGGGGCTGT CGTTTTGGC | 39 |

(2) INFORMATION FOR SEQ ID NO: 13:

(i) SEQUENCE CHARACTERISTICS:
        (A) LENGTH: 39 base pairs
        (B) TYPE: Nucleic Acid
        (C) STRANDEDNESS: Single
        (D) TOPOLOGY: Linear (xi) SEQUENCE DESCRIPTION: SEQ ID NO: 13:

| | |
|---|---|
| CGATGGGCCC GGATAGACGG ATGGGGCTGT TGTTTTGGC | 39 |

(2) INFORMATION FOR SEQ ID NO: 14:

(i) SEQUENCE CHARACTERISTICS:
        (A) LENGTH: 39 base pairs
        (B) TYPE: Nucleic Acid
        (C) STRANDEDNESS: Single
        (D) TOPOLOGY: Linear (xi) SEQUENCE DESCRIPTION: SEQ ID NO: 14:

| | |
|---|---|
| CGATGGGCCC GGATAGACAG ATGGGGCTGT TGTTTTGGC | 39 |

(2) INFORMATION FOR SEQ ID NO: 15:

(i) SEQUENCE CHARACTERISTICS:
        (A) LENGTH: 39 base pairs
        (B) TYPE: Nucleic Acid
        (C) STRANDEDNESS: Single
        (D) TOPOLOGY: Linear (xi) SEQUENCE DESCRIPTION: SEQ ID NO: 15:

| | |
|---|---|
| CGATGGGCCC GGATAGACTG ATGGGGCTGT TGTTTTGGC | 39 |

(2) INFORMATION FOR SEQ ID NO: 16:

(i) SEQUENCE CHARACTERISTICS:
        (A) LENGTH: 369 base pairs
        (B) TYPE: Nucleic Acid
        (C) STRANDEDNESS: Double
        (D) TOPOLOGY: Linear (xi) SEQUENCE DESCRIPTION: SEQ ID NO: 16:

| | |
|---|---|
| GACATTGTCA TGACACAGTC TCAAAAATTC ATGTCCACAT CAGTAGGAGA | 50 |
| CAGGGTCAGC GTCACCTGCA AGGCCAGTCA GAATGTGGGT ACTAATGTAG | 100 |
| CCTGGTATCA ACAGAAACCA GGGCAATCTC CTAAAGCACT GATTTACTCG | 150 |
| TCATCCTACC GGTACAGTGG AGTCCCTGAT CGCTTCACAG GCAGTGGATC | 200 |
| TGGGACAGAT TTCACTCTCA CCATCAGCCA TGTGCAGTCT GAAGACTTGG | 250 |
| CAGACTATTT CTGTCAGCAA TATAACATCT ATCCTCTCAC GTTCGGTCCT | 300 |
| GGGACCAAGC TGGAGTTGAA ACGGGCTGAT GCTGCACCAC CAACTGTATC | 350 |
| CATCTTCCCA CCATTCGAA | 369 |

(2) INFORMATION FOR SEQ ID NO: 17:

(i) SEQUENCE CHARACTERISTICS:
        (A) LENGTH: 123 amino acids
        (B) TYPE: Amino Acid
        (D) TOPOLOGY: Linear (xi) SEQUENCE DESCRIPTION: SEQ ID NO: 17:

```
Asp Ile Val Met Thr Gln Ser Gln Lys Phe Met Ser Thr Ser Val
 1               5                  10                  15

Gly Asp Arg Val Ser Val Thr Cys Lys Ala Ser Gln Asn Val Gly
                20                  25                  30

Thr Asn Val Ala Trp Tyr Gln Gln Lys Pro Gly Gln Ser Pro Lys
                35                  40                  45

Ala Leu Ile Tyr Ser Ser Ser Tyr Arg Tyr Ser Gly Val Pro Asp
                50                  55                  60

Arg Phe Thr Gly Ser Gly Ser Gly Thr Asp Phe Thr Leu Thr Ile
                65                  70                  75

Ser His Val Gln Ser Glu Asp Leu Ala Asp Tyr Phe Cys Gln Gln
                80                  85                  90

Tyr Asn Ile Tyr Pro Leu Thr Phe Gly Pro Gly Thr Lys Leu Glu
                95                 100                 105

Leu Lys Arg Ala Asp Ala Ala Pro Pro Thr Val Ser Ile Phe Pro
               110                 115                 120

Pro Phe Glu
```

(2) INFORMATION FOR SEQ ID NO: 18:

(i) SEQUENCE CHARACTERISTICS:
        (A) LENGTH: 417 base pairs
        (B) TYPE: Nucleic Acid
        (C) STRANDEDNESS: Double
        (D) TOPOLOGY: Linear (xi) SEQUENCE DESCRIPTION: SEQ ID NO: 18:

```
TTCTATTGCT ACAAACGCGT ACGCTGAGGT GCAGCTGGTG GAGTCTGGGG          50
GAGGCTTAGT GCCGCCTGGA GGGTCCCTGA AACTCTCCTG TGCAGCCTCT         100
GGATTCATAT TCAGTAGTTA TGGCATGTCT TGGGTTCGCC AGACTCCAGG         150
CAAGAGCCTG GAGTTGGTCG CAACCATTAA TAATAATGGT GATAGCACCT         200
ATTATCCAGA CAGTGTGAAG GGCCGATTCA CCATCTCCCG AGACAATGCC         250
AAGAACACCC TGTACCTGCA AATGAGCAGT CTGAAGTCTG AGGACACAGC         300
CATGTTTTAC TGTGCAAGAG CCCTCATTAG TTCGGCTACT TGGTTTGGTT         350
ACTGGGGCCA AGGGACTCTG GTCACTGTCT CTGCAGCCAA ACAACAGCC          400
CCATCTGTCT ATCCGGG                                             417
```

(2) INFORMATION FOR SEQ ID NO: 19:

(i) SEQUENCE CHARACTERISTICS:
        (A) LENGTH: 130 amino acids
        (B) TYPE: Amino Acid
        (D) TOPOLOGY: Linear (xi) SEQUENCE DESCRIPTION: SEQ ID NO: 19:

```
Glu Val Gln Leu Val Glu Ser Gly Gly Gly Leu Val Pro Pro Gly
 1               5                  10                  15

Gly Ser Leu Lys Leu Ser Cys Ala Ala Ser Gly Phe Ile Phe Ser
                20                  25                  30
```

```
Ser Tyr Gly Met Ser Trp Val Arg Gln Thr Pro Gly Lys Ser Leu
            35                  40                  45

Glu Leu Val Ala Thr Ile Asn Asn Gly Asp Ser Thr Tyr Tyr
            50                  55                  60

Pro Asp Ser Val Lys Gly Arg Phe Thr Ile Ser Arg Asp Asn Ala
            65                  70                  75

Lys Asn Thr Leu Tyr Leu Gln Met Ser Ser Leu Lys Ser Glu Asp
            80                  85                  90

Thr Ala Met Phe Tyr Cys Ala Arg Ala Leu Ile Ser Ser Ala Thr
            95                 100                 105

Trp Phe Gly Tyr Trp Gly Gln Gly Thr Leu Val Thr Val Ser Ala
           110                 115                 120

Ala Lys Thr Thr Ala Pro Ser Val Tyr Pro
           125                 130

(2) INFORMATION FOR SEQ ID NO: 20:

(i) SEQUENCE CHARACTERISTICS:
        (A) LENGTH: 31 base pairs
        (B) TYPE: Nucleic Acid
        (C) STRANDEDNESS: Single
        (D) TOPOLOGY: Linear (xi) SEQUENCE DESCRIPTION: SEQ ID NO: 20:

ACAAACGCGT ACGCTGATAT CGTCATGACA G                              31

(2) INFORMATION FOR SEQ ID NO: 21:

(i) SEQUENCE CHARACTERISTICS:
        (A) LENGTH: 31 base pairs
        (B) TYPE: Nucleic Acid
        (C) STRANDEDNESS: Single
        (D) TOPOLOGY: Linear (xi) SEQUENCE DESCRIPTION: SEQ ID NO: 21:

GCAGCATCAG CTCTTCGAAG CTCCAGCTTG G                              31

(2) INFORMATION FOR SEQ ID NO: 22:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (xi) SEQUENCE DESCRIPTION: SEQ ID NO: 22:

CCACTAGTAC GCAAGTTCAC G                                         21

(2) INFORMATION FOR SEQ ID NO: 23:

(i) SEQUENCE CHARACTERISTICS:
        (A) LENGTH: 33 base pairs
        (B) TYPE: Nucleic Acid
        (C) STRANDEDNESS: Single
        (D) TOPOLOGY: Linear (xi) SEQUENCE DESCRIPTION: SEQ ID NO: 23:

GATGGGCCCT TGGTGGAGGC TGCAGAGACA GTG                            33

(2) INFORMATION FOR SEQ ID NO: 24:

(i) SEQUENCE CHARACTERISTICS:
        (A) LENGTH: 714 base pairs
```

(B) TYPE: Nucleic Acid
        (C) STRANDEDNESS: Double
        (D) TOPOLOGY: Linear (xi) SEQUENCE DESCRIPTION: SEQ ID NO: 24:

| | |
|---|---:|
| ATGAAGAAGA ATATCGCATT TCTTCTTGCA TCTATGTTCG TTTTTTCTAT | 50 |
| TGCTACAAAC GCGTACGCTG ATATCGTCAT GACACAGTCT CAAAAATTCA | 100 |
| TGTCCACATC AGTAGGAGAC AGGGTCAGCG TCACCTGCAA GGCCAGTCAG | 150 |
| AATGTGGGTA CTAATGTAGC CTGGTATCAA CAGAAACCAG GCAATCTCC | 200 |
| TAAAGCACTG ATTTACTCGT CATCCTACCG GTACAGTGGA GTCCCTGATC | 250 |
| GCTTCACAGG CAGTGGATCT GGGACAGATT TCACTCTCAC CATCAGCCAT | 300 |
| GTGCAGTCTG AAGACTTGGC AGACTATTTC TGTCAGCAAT ATAACATCTA | 350 |
| TCCTCTCACG TTCGGTCCTG GGACCAAGCT GGAGCTTCGA AGAGCTGTGG | 400 |
| CTGCACCATC TGTCTTCATC TTCCCGCCAT CTGATGAGCA GTTGAAATCT | 450 |
| GGAACTGCTT CTGTTGTGTG CCTGCTGAAT AACTTCTATC CCAGAGAGGC | 500 |
| CAAAGTACAG TGGAAGGTGG ATAACGCCCT CCAATCGGGT AACTCCCAGG | 550 |
| AGAGTGTCAC AGAGCAGGAC AGCAAGGACA GCACCTACAG CCTCAGCAGC | 600 |
| ACCCTGACGC TGAGCAAAGC AGACTACGAG AAACACAAAG TCTACGCCTG | 650 |
| CGAAGTCACC CATCAGGGCC TGAGCTCGCC CGTCACAAAG AGCTTCAACA | 700 |
| GGGGAGAGTG TTAA | 714 |

(2) INFORMATION FOR SEQ ID NO: 25:

(i) SEQUENCE CHARACTERISTICS:
        (A) LENGTH: 237 amino acids
        (B) TYPE: Amino Acid
        (D) TOPOLOGY: Linear (xi) SEQUENCE DESCRIPTION: SEQ ID NO: 25:

```
Met Lys Lys Asn Ile Ala Phe Leu Leu Ala Ser Met Phe Val Phe
  1               5                  10                  15

Ser Ile Ala Thr Asn Ala Tyr Ala Asp Ile Val Met Thr Gln Ser
                 20                  25                  30

Gln Lys Phe Met Ser Thr Ser Val Gly Asp Arg Val Ser Val Thr
                 35                  40                  45

Cys Lys Ala Ser Gln Asn Val Gly Thr Asn Val Ala Trp Tyr Gln
                 50                  55                  60

Gln Lys Pro Gly Gln Ser Pro Lys Ala Leu Ile Tyr Ser Ser Ser
                 65                  70                  75

Tyr Arg Tyr Ser Gly Val Pro Asp Arg Phe Thr Gly Ser Gly Ser
                 80                  85                  90

Gly Thr Asp Phe Thr Leu Thr Ile Ser His Val Gln Ser Glu Asp
                 95                 100                 105

Leu Ala Asp Tyr Phe Cys Gln Gln Tyr Asn Ile Tyr Pro Leu Thr
                110                 115                 120

Phe Gly Pro Gly Thr Lys Leu Glu Leu Arg Arg Ala Val Ala Ala
                125                 130                 135

Pro Ser Val Phe Ile Phe Pro Pro Ser Asp Glu Gln Leu Lys Ser
                140                 145                 150

Gly Thr Ala Ser Val Val Cys Leu Leu Asn Asn Phe Tyr Pro Arg
                155                 160                 165
```

```
Glu Ala Lys Val Gln Trp Lys Val Asp Asn Ala Leu Gln Ser Gly
            170                 175                 180

Asn Ser Gln Glu Ser Val Thr Glu Gln Asp Ser Lys Asp Ser Thr
            185                 190                 195

Tyr Ser Leu Ser Ser Thr Leu Thr Leu Ser Lys Ala Asp Tyr Glu
            200                 205                 210

Lys His Lys Val Tyr Ala Cys Glu Val Thr His Gln Gly Leu Ser
            215                 220                 225

Ser Pro Val Thr Lys Ser Phe Asn Arg Gly Glu Cys
            230                 235

(2) INFORMATION FOR SEQ ID NO: 26:

(i) SEQUENCE CHARACTERISTICS:
        (A) LENGTH: 756 base pairs
        (B) TYPE: Nucleic Acid
        (C) STRANDEDNESS: Double
        (D) TOPOLOGY: Linear (xi) SEQUENCE DESCRIPTION: SEQ ID NO: 26:
```

| | |
|---|---|
| ATGAAAAAGA ATATCGCATT TCTTCTTGCA TCTATGTTCG TTTTTTCTAT | 50 |
| TGCTACAAAC GCGTACGCTG AGGTGCAGCT GGTGGAGTCT GGGGGAGGCT | 100 |
| TAGTGCCGCC TGGAGGGTCC CTGAAACTCT CCTGTGCAGC CTCTGGATTC | 150 |
| ATATTCAGTA GTTATGGCAT GTCTTGGGTT CGCCAGACTC CAGGCAAGAG | 200 |
| CCTGGAGTTG GTCGCAACCA TTAATAATAA TGGTGATAGC ACCTATTATC | 250 |
| CAGACAGTGT GAAGGGCCGA TTCACCATCT CCCGAGACAA TGCCAAGAAC | 300 |
| ACCCTGTACC TGCAAATGAG CAGTCTGAAG TCTGAGGACA CAGCCATGTT | 350 |
| TTACTGTGCA AGAGCCCTCA TTAGTTCGGC TACTTGGTTT GGTTACTGGG | 400 |
| GCCAAGGGAC TCTGGTCACT GTCTCTGCAG CCTCCACCAA GGGCCCATCG | 450 |
| GTCTTCCCCC TGGCACCCTC CTCCAAGAGC ACCTCTGGGG GCACAGCGGC | 500 |
| CCTGGGCTGC CTGGTCAAGG ACTACTTCCC CGAACCGGTG ACGGTGTCGT | 550 |
| GGAACTCAGG CGCCCTGACC AGCGGCGTGC ACACCTTCCC GGCTGTCCTA | 600 |
| CAGTCCTCAG GACTCTACTC CCTCAGCAGC GTGGTGACCG TGCCCTCCAG | 650 |
| CAGCTTGGGC ACCCAGACCT ACATCTGCAA CGTGAATCAC AAGCCCAGCA | 700 |
| ACACCAAGGT GGACAAGAAA GTTGAGCCCA AATCTTGTGA CAAAACTCAC | 750 |
| ACATGA | 756 |

```
(2) INFORMATION FOR SEQ ID NO: 27:

(i) SEQUENCE CHARACTERISTICS:
        (A) LENGTH: 251 amino acids
        (B) TYPE: Amino Acid
        (D) TOPOLOGY: Linear (xi) SEQUENCE DESCRIPTION: SEQ ID NO: 27:

Met Lys Lys Asn Ile Ala Phe Leu Leu Ala Ser Met Phe Val Phe
 1               5                  10                  15

Ser Ile Ala Thr Asn Ala Tyr Ala Glu Val Gln Leu Val Glu Ser
            20                  25                  30

Gly Gly Gly Leu Val Pro Pro Gly Gly Ser Leu Lys Leu Ser Cys
            35                  40                  45

Ala Ala Ser Gly Phe Ile Phe Ser Ser Tyr Gly Met Ser Trp Val
            50                  55                  60
```

```
Arg Gln Thr Pro Gly Lys Ser Leu Glu Leu Val Ala Thr Ile Asn
                65                  70                  75

Asn Asn Gly Asp Ser Thr Tyr Tyr Pro Asp Ser Val Lys Gly Arg
                80                  85                  90

Phe Thr Ile Ser Arg Asp Asn Ala Lys Asn Thr Leu Tyr Leu Gln
                95                 100                 105

Met Ser Ser Leu Lys Ser Glu Asp Thr Ala Met Phe Tyr Cys Ala
               110                 115                 120

Arg Ala Leu Ile Ser Ser Ala Thr Trp Phe Gly Tyr Trp Gly Gln
               125                 130                 135

Gly Thr Leu Val Thr Val Ser Ala Ala Ser Thr Lys Gly Pro Ser
               140                 145                 150

Val Phe Pro Leu Ala Pro Ser Ser Lys Ser Thr Ser Gly Gly Thr
               155                 160                 165

Ala Ala Leu Gly Cys Leu Val Lys Asp Tyr Phe Pro Glu Pro Val
               170                 175                 180

Thr Val Ser Trp Asn Ser Gly Ala Leu Thr Ser Gly Val His Thr
               185                 190                 195

Phe Pro Ala Val Leu Gln Ser Ser Gly Leu Tyr Ser Leu Ser Ser
               200                 205                 210

Val Val Thr Val Pro Ser Ser Ser Leu Gly Thr Gln Thr Tyr Ile
               215                 220                 225

Cys Asn Val Asn His Lys Pro Ser Asn Thr Lys Val Asp Lys Lys
               230                 235                 240

Val Glu Pro Lys Ser Cys Asp Lys Thr His Thr
               245                 250
```

(2) INFORMATION FOR SEQ ID NO: 28:

(i) SEQUENCE CHARACTERISTICS:
        (A) LENGTH: 37 base pairs
        (B) TYPE: Nucleic Acid
        (C) STRANDEDNESS: Single
        (D) TOPOLOGY: Linear (xi) SEQUENCE DESCRIPTION: SEQ ID NO: 28:

CCAATGCATA CGCTGACATC GTGATGACCC AGACCCC                    37

(2) INFORMATION FOR SEQ ID NO: 29:

(i) SEQUENCE CHARACTERISTICS:
        (A) LENGTH: 37 base pairs
        (B) TYPE: Nucleic Acid
        (C) STRANDEDNESS: Single
        (D) TOPOLOGY: Linear (xi) SEQUENCE DESCRIPTION: SEQ ID NO: 29:

CCAATGCATA CGCTGATATT GTGATGACTC AGACTCC                    37

(2) INFORMATION FOR SEQ ID NO: 30:

(i) SEQUENCE CHARACTERISTICS:
    (A) LENGTH: 37 base pairs
    (B) TYPE: Nucleic Acid
    (C) STRANDEDNESS: Single
    (D) TOPOLOGY: Linear (xi) SEQUENCE DESCRIPTION: SEQ ID NO: 30:

CCAATGCATA CGCTGACATC GTGATGACAC AGACACC                    37

(2) INFORMATION FOR SEQ ID NO: 31:

(i) SEQUENCE CHARACTERISTICS:
       (A) LENGTH: 35 base pairs
       (B) TYPE: Nucleic Acid
       (C) STRANDEDNESS: Single
       (D) TOPOLOGY: Linear (xi) SEQUENCE DESCRIPTION: SEQ ID NO: 31:

AGATGTCAAT TGCTCACTGG ATGGTGGGAA GATGG                                      35

(2) INFORMATION FOR SEQ ID NO: 32:

(i) SEQUENCE CHARACTERISTICS:
       (A) LENGTH: 32 base pairs
       (B) TYPE: Nucleic Acid
       (C) STRANDEDNESS: Single
       (D) TOPOLOGY: Linear (xi) SEQUENCE DESCRIPTION: SEQ ID NO: 32:

CAAACGCGTA CGCTGAGATC CAGCTGCAGC AG                                         32

(2) INFORMATION FOR SEQ ID NO: 33:

(i) SEQUENCE CHARACTERISTICS:
       (A) LENGTH: 32 base pairs
       (B) TYPE: Nucleic Acid
       (C) STRANDEDNESS: Single
       (D) TOPOLOGY: Linear (xi) SEQUENCE DESCRIPTION: SEQ ID NO: 33:

CAAACGCGTA CGCTGAGATT CAGCTCCAGC AG                                         32

(2) INFORMATION FOR SEQ ID NO: 34:

(i) SEQUENCE CHARACTERISTICS:
       (A) LENGTH: 391 base pairs
       (B) TYPE: Nucleic Acid
       (C) STRANDEDNESS: Double
       (D) TOPOLOGY: Linear (xi) SEQUENCE DESCRIPTION: SEQ ID NO: 34:

GATATCGTGA TGACACAGAC ACCACTCTCC CTGCCTGTCA GTCTTGGAGA                      50

TCAGGCCTCC ATCTCTTGCA GATCTAGTCA GAGCCTTGTA CACGGTATTG                     100

GAAACACCTA TTTACATTGG TACCTGCAGA AGCCAGGCCA GTCTCCAAAG                     150

CTCCTGATCT ACAAAGTTTC CAACCGATTT TCTGGGGTCC CAGACAGGTT                     200

CAGTGGCAGT GGATCAGGGA CAGATTTCAC ACTCAGGATC AGCAGAGTGG                     250

AGGCTGAGGA TCTGGGACTT TATTTCTGCT CTCAAAGTAC ACATGTTCCG                     300

CTCACGTTCG GTGCTGGGAC CAAGCTGGAG CTGAAACGGG CTGATGCTGC                     350

ACCAACTGTA TCCATCTTCC CACCATCCAG TGAGCAATTG A                              391

(2) INFORMATION FOR SEQ ID NO: 35:

(i) SEQUENCE CHARACTERISTICS:
       (A) LENGTH: 131 amino acids
       (B) TYPE: Amino Acid
       (D) TOPOLOGY: Linear (xi) SEQUENCE DESCRIPTION: SEQ ID NO: 35:

Asp Ile Val Met Thr Gln Thr Pro Leu Ser Leu Pro Val Ser Leu
 1               5                  10                  15

```
Gly Asp Gln Ala Ser Ile Ser Cys Arg Ser Ser Gln Ser Leu Val
                20                  25                  30

His Gly Ile Gly Asn Thr Tyr Leu His Trp Tyr Leu Gln Lys Pro
                35                  40                  45

Gly Gln Ser Pro Lys Leu Leu Ile Tyr Lys Val Ser Asn Arg Phe
                50                  55                  60

Ser Gly Val Pro Asp Arg Phe Ser Gly Ser Gly Ser Gly Thr Asp
                65                  70                  75

Phe Thr Leu Arg Ile Ser Arg Val Glu Ala Glu Asp Leu Gly Leu
                80                  85                  90

Tyr Phe Cys Ser Gln Ser Thr His Val Pro Leu Thr Phe Gly Ala
                95                  100                 105

Gly Thr Lys Leu Glu Leu Lys Arg Ala Asp Ala Ala Pro Thr Val
                110                 115                 120

Ser Ile Phe Pro Pro Ser Ser Glu Gln Leu Lys
                125                 130
```

(2) INFORMATION FOR SEQ ID NO: 36:

(i) SEQUENCE CHARACTERISTICS:
        (A) LENGTH: 405 base pairs
        (B) TYPE: Nucleic Acid
        (C) STRANDEDNESS: Single
        (D) TOPOLOGY: Linear (xi) SEQUENCE DESCRIPTION: SEQ ID NO: 36:

```
GAGATTCAGC TGCAGCAGTC TGGACCTGAG CTGATGAAGC CTGGGGCTTC           50

AGTGAAGATA TCCTGCAAGG CTTCTGGTTA TTCATTCAGT AGCCACTACA          100

TGCACTGGGT GAAGCAGAGC CATGGAAAGA GCCTTGAGTG GATTGGCTAC          150

ATTGATCCTT CCAATGGTGA AACTACTTAC AACCAGAAAT TCAAGGGCAA          200

GGCCACATTG ACTGTAGACA CATCTTCCAG CACAGCCAAC GTGCATCTCA          250

GCAGCCTGAC ATCTGATGAC TCTGCAGTCT ATTTCTGTGC AAGAGGGGAC          300

TATAGATACA ACGGCGACTG GTTTTTCGAT GTCTGGGGCG CAGGGACCAC          350

GGTCACCGTC TCCTCCGCCA AAACCGACAG CCCCATCGGT CTATCCGGGC          400

CCATC                                                          405
```

(2) INFORMATION FOR SEQ ID NO: 37:

(i) SEQUENCE CHARACTERISTICS:
        (A) LENGTH: 135 amino acids
        (B) TYPE: Amino Acid
        (D) TOPOLOGY: Linear (xi) SEQUENCE DESCRIPTION: SEQ ID NO: 37:

```
Glu Ile Gln Leu Gln Gln Ser Gly Pro Glu Leu Met Lys Pro Gly
 1               5                  10                  15

Ala Ser Val Lys Ile Ser Cys Lys Ala Ser Gly Tyr Ser Phe Ser
                20                  25                  30

Ser His Tyr Met His Trp Val Lys Gln Ser His Gly Lys Ser Leu
                35                  40                  45

Glu Trp Ile Gly Tyr Ile Asp Pro Ser Asn Gly Glu Thr Thr Tyr
                50                  55                  60

Asn Gln Lys Phe Lys Gly Lys Ala Thr Leu Thr Val Asp Thr Ser
                65                  70                  75

Ser Ser Thr Ala Asn Val His Leu Ser Ser Leu Thr Ser Asp Asp
```

```
                80              85              90
Ser Ala Val Tyr Phe Cys Ala Arg Gly Asp Tyr Arg Tyr Asn Gly
                95                 100             105

Asp Trp Phe Phe Asp Val Trp Gly Ala Gly Thr Thr Val Thr Val
                110                115             120

Ser Ser Ala Lys Thr Asp Ser Pro Ile Gly Leu Ser Gly Pro Ile
                125                130             135
```

(2) INFORMATION FOR SEQ ID NO: 38:

(i) SEQUENCE CHARACTERISTICS:
        (A) LENGTH: 22 base pairs
        (B) TYPE: Nucleic Acid
        (C) STRANDEDNESS: Single
        (D) TOPOLOGY: Linear (xi) SEQUENCE DESCRIPTION: SEQ ID NO: 38:

```
CTTGGTGGAG GCGGAGGAGA CG                                              22
```

(2) INFORMATION FOR SEQ ID NO: 39:

(i) SEQUENCE CHARACTERISTICS:
        (A) LENGTH: 38 base pairs
        (B) TYPE: Nucleic Acid
        (C) STRANDEDNESS: Single
        (D) TOPOLOGY: Linear (xi) SEQUENCE DESCRIPTION: SEQ ID NO: 39:

```
GAAACGGGCT GTTGCTGCAC CAACTGTATT CATCTTCC                             38
```

(2) INFORMATION FOR SEQ ID NO: 40:

(i) SEQUENCE CHARACTERISTICS:
        (A) LENGTH: 31 base pairs
        (B) TYPE: Nucleic Acid
        (C) STRANDEDNESS: Single
        (D) TOPOLOGY: Linear (xi) SEQUENCE DESCRIPTION: SEQ ID NO: 40:

```
GTCACCGTCT CCTCCGCCTC CACCAAGGGC C                                    31
```

(2) INFORMATION FOR SEQ ID NO: 41:

(i) SEQUENCE CHARACTERISTICS:
        (A) LENGTH: 729 base pairs
        (B) TYPE: Nucleic Acid
        (C) STRANDEDNESS: Double
        (D) TOPOLOGY: Linear (xi) SEQUENCE DESCRIPTION: SEQ ID NO: 41:

```
ATGAAGAAGA ATATCGCATT TCTTCTTGCA TCTATGTTCG TTTTTTCTAT                50

TGCTACAAAT GCATACGCTG ATATCGTGAT GACACAGACA CCACTCTCCC                100

TGCCTGTCAG TCTTGGAGAT CAGGCCTCCA TCTCTTGCAG ATCTAGTCAG                150

AGCCTTGTAC ACGGTATTGG AAACACCTAT TTACATTGGT ACCTGCAGAA                200

GCCAGGCCAG TCTCCAAAGC TCCTGATCTA CAAAGTTTCC AACCGATTTT                250

CTGGGGTCCC AGACAGGTTC AGTGGCAGTG GATCAGGGAC AGATTTCACA                300

CTCAGGATCA GCAGAGTGGA GGCTGAGGAT CTGGGACTTT ATTTCTGCTC                350

TCAAAGTACA CATGTTCCGC TCACGTTCGG TGCTGGGACC AAGCTGGAGC                400

TGAAACGGGC TGTTGCTGCA CCAACTGTAT TCATCTTCCC ACCATCCAGT                450
```

```
GAGCAATTGA AATCTGGAAC TGCCTCTGTT GTGTGCCTGC TGAATAACTT          500

CTATCCCAGA GAGGCCAAAG TACAGTGGAA GGTGGATAAC GCCCTCCAAT          550

CGGGTAACTC CCAGGAGAGT GTCACAGAGC AGGACAGCAA GGACAGCACC          600

TACAGCCTCA GCAGCACCCT GACGCTGAGC AAAGCAGACT ACGAGAAACA          650

CAAAGTCTAC GCCTGCGAAG TCACCCATCA GGGCCTGAGC TCGCCCGTCA          700

CAAAGAGCTT CAACAGGGGA GAGTGTTAA                                 729
```

(2) INFORMATION FOR SEQ ID NO: 42:

(i) SEQUENCE CHARACTERISTICS:
        (A) LENGTH: 242 amino acids
        (B) TYPE: Amino Acid
        (D) TOPOLOGY: Linear (xi) SEQUENCE DESCRIPTION: SEQ ID NO: 42:

```
Met Lys Lys Asn Ile Ala Phe Leu Leu Ala Ser Met Phe Val Phe
 1               5                  10                  15

Ser Ile Ala Thr Asn Ala Tyr Ala Asp Ile Val Met Thr Gln Thr
                20                  25                  30

Pro Leu Ser Leu Pro Val Ser Leu Gly Asp Gln Ala Ser Ile Ser
                35                  40                  45

Cys Arg Ser Ser Gln Ser Leu Val His Gly Ile Gly Asn Thr Tyr
                50                  55                  60

Leu His Trp Tyr Leu Gln Lys Pro Gly Gln Ser Pro Lys Leu Leu
                65                  70                  75

Ile Tyr Lys Val Ser Asn Arg Phe Ser Gly Val Pro Asp Arg Phe
                80                  85                  90

Ser Gly Ser Gly Ser Gly Thr Asp Phe Thr Leu Arg Ile Ser Arg
                95                 100                 105

Val Glu Ala Glu Asp Leu Gly Leu Tyr Phe Cys Ser Gln Ser Thr
               110                 115                 120

His Val Pro Leu Thr Phe Gly Ala Gly Thr Lys Leu Glu Leu Lys
               125                 130                 135

Arg Ala Val Ala Ala Pro Thr Val Phe Ile Phe Pro Pro Ser Ser
               140                 145                 150

Glu Gln Leu Lys Ser Gly Thr Ala Ser Val Val Cys Leu Leu Asn
               155                 160                 165

Asn Phe Tyr Pro Arg Glu Ala Lys Val Gln Trp Lys Val Asp Asn
               170                 175                 180

Ala Leu Gln Ser Gly Asn Ser Gln Glu Ser Val Thr Glu Gln Asp
               185                 190                 195

Ser Lys Asp Ser Thr Tyr Ser Leu Ser Ser Thr Leu Thr Leu Ser
               200                 205                 210

Lys Ala Asp Tyr Glu Lys His Lys Val Tyr Ala Cys Glu Val Thr
               215                 220                 225

His Gln Gly Leu Ser Ser Pro Val Thr Lys Ser Phe Asn Arg Gly
               230                 235                 240

Glu Cys
```

(2) INFORMATION FOR SEQ ID NO: 43:

(i) SEQUENCE CHARACTERISTICS:
        (A) LENGTH: 762 base pairs
        (B) TYPE: Nucleic Acid
        (C) STRANDEDNESS: Double -continued (D) TOPOLOGY: Linear (xi) SEQUENCE DESCRIPTION: SEQ ID NO: 43:

```
ATGAAAAAGA ATATCGCATT TCTTCTTGCA TCTATGTTCG TTTTTTCTAT        50

TGCTACAAAC GCGTACGCTG AGATTCAGCT GCAGCAGTCT GGACCTGAGC       100

TGATGAAGCC TGGGGCTTCA GTGAAGATAT CCTGCAAGGC TTCTGGTTAT       150

TCATTCAGTA GCCACTACAT GCACTGGGTG AAGCAGAGCC ATGGAAAGAG       200

CCTTGAGTGG ATTGGCTACA TTGATCCTTC CAATGGTGAA ACTACTTACA       250

ACCAGAAATT CAAGGGCAAG GCCACATTGA CTGTAGACAC ATCTTCCAGC       300

ACAGCCAACG TGCATCTCAG CAGCCTGACA TCTGATGACT CTGCAGTCTA       350

TTTCTGTGCA AGAGGGGACT ATAGATACAA CGGCGACTGG TTTTTCGATG       400

TCTGGGGCGC AGGGACCACG GTCACCGTCT CCTCCGCCTC CACCAAGGGC       450

CCATCGGTCT TCCCCCTGGC ACCCTCCTCC AAGAGCACCT CTGGGGGCAC       500

AGCGGCCCTG GGCTGCCTGG TCAAGGACTA CTTCCCCGAA CCGGTGACGG       550

TGTCGTGGAA CTCAGGCGCC CTGACCAGCG GCGTGCACAC CTTCCCGGCT       600

GTCCTACAGT CCTCAGGACT CTACTCCCTC AGCAGCGTGG TGACCGTGCC       650

CTCCAGCAGC TTGGGCACCC AGACCTACAT CTGCAACGTG AATCACAAGC       700

CCAGCAACAC CAAGGTGGAC AAGAAAGTTG AGCCCAAATC TTGTGACAAA       750

ACTCACACAT GA                                               762
```

(2) INFORMATION FOR SEQ ID NO: 44:

(i) SEQUENCE CHARACTERISTICS:
        (A) LENGTH: 253 amino acids
        (B) TYPE: Amino Acid
        (D) TOPOLOGY: Linear (xi) SEQUENCE DESCRIPTION: SEQ ID NO: 44:

```
Met Lys Lys Asn Ile Ala Phe Leu Leu Ala Ser Met Phe Val Phe
 1               5                  10                  15

Ser Ile Ala Thr Asn Ala Tyr Ala Glu Ile Gln Leu Gln Gln Ser
                20                  25                  30

Gly Pro Glu Leu Met Lys Pro Gly Ala Ser Val Lys Ile Ser Cys
                35                  40                  45

Lys Ala Ser Gly Tyr Ser Phe Ser Ser His Tyr Met His Trp Val
                50                  55                  60

Lys Gln Ser His Gly Lys Ser Leu Glu Trp Ile Gly Tyr Ile Asp
                65                  70                  75

Pro Ser Asn Gly Glu Thr Thr Tyr Asn Gln Lys Phe Lys Gly Lys
                80                  85                  90

Ala Thr Leu Thr Val Asp Thr Ser Ser Thr Ala Asn Val His
                95                 100                 105

Leu Ser Ser Leu Thr Ser Asp Asp Ser Ala Val Tyr Phe Cys Ala
                110                 115                 120

Arg Gly Asp Tyr Arg Tyr Asn Gly Asp Trp Phe Phe Asp Val Trp
                125                 130                 135

Gly Ala Gly Thr Thr Val Thr Val Ser Ser Ala Ser Thr Lys Gly
                140                 145                 150

Pro Ser Val Phe Pro Leu Ala Pro Ser Ser Lys Ser Thr Ser Gly
                155                 160                 165
```

-continued

```
Gly Thr Ala Ala Leu Gly Cys Leu Val Lys Asp Tyr Phe Pro Glu
            170                 175                 180

Pro Val Thr Val Ser Trp Asn Ser Gly Ala Leu Thr Ser Gly Val
            185                 190                 195

His Thr Phe Pro Ala Val Leu Gln Ser Ser Gly Leu Tyr Ser Leu
            200                 205                 210

Ser Ser Val Val Thr Val Pro Ser Ser Leu Gly Thr Gln Thr
            215                 220                 225

Tyr Ile Cys Asn Val Asn His Lys Pro Ser Asn Thr Lys Val Asp
            230                 235                 240

Lys Lys Val Glu Pro Lys Ser Cys Asp Lys Thr His Thr
            245                 250
```

(2) INFORMATION FOR SEQ ID NO: 45:

(i) SEQUENCE CHARACTERISTICS:
        (A) LENGTH: 114 amino acids
        (B) TYPE: Amino Acid
        (D) TOPOLOGY: Linear (xi) SEQUENCE DESCRIPTION: SEQ ID NO: 45:

```
Asp Ile Val Met Thr Gln Thr Pro Leu Ser Leu Pro Val Ser Leu
 1               5                  10                  15

Gly Asp Gln Ala Ser Ile Ser Cys Arg Ser Ser Gln Ser Leu Val
            20                  25                  30

His Gly Ile Gly Asn Thr Tyr Leu His Trp Tyr Leu Gln Lys Pro
            35                  40                  45

Gly Gln Ser Pro Lys Leu Leu Ile Tyr Tyr Lys Val Ser Asn Arg
            50                  55                  60

Phe Ser Gly Val Pro Asp Arg Phe Ser Asp Ser Gly Ser Gly Thr
            65                  70                  75

Asp Phe Thr Leu Arg Ile Ser Arg Val Glu Ala Glu Asp Leu Gly
            80                  85                  90

Leu Tyr Phe Cys Ser Gln Ser Thr His Val Pro Leu Thr Phe Gly
            95                 100                 105

Ala Gly Thr Lys Leu Glu Leu Lys Arg
            110
```

(2) INFORMATION FOR SEQ ID NO: 46:

(i) SEQUENCE CHARACTERISTICS:
        (A) LENGTH: 114 amino acids
        (B) TYPE: Amino Acid
        (D) TOPOLOGY: Linear (xi) SEQUENCE DESCRIPTION: SEQ ID NO: 46:

```
Asp Ile Gln Met Thr Gln Ser Pro Ser Ser Leu Ser Ala Ser Val
 1               5                  10                  15

Gly Asp Arg Val Thr Ile Thr Cys Arg Ser Ser Gln Ser Leu Val
            20                  25                  30

His Gly Ile Gly Asn Thr Tyr Leu His Trp Tyr Gln Gln Lys Pro
            35                  40                  45

Gly Lys Ala Pro Lys Leu Leu Ile Tyr Tyr Lys Val Ser Asn Arg
            50                  55                  60

Phe Ser Gly Val Pro Ser Arg Phe Ser Gly Ser Gly Ser Gly Thr
            65                  70                  75

Asp Phe Thr Leu Thr Ile Ser Ser Leu Gln Pro Glu Asp Phe Ala
            80                  85                  90
```

-continued

```
Thr Tyr Tyr Cys Ser Gln Ser Thr His Val Pro Leu Thr Phe Gly
             95                  100                 105

Gln Gly Thr Lys Val Glu Ile Lys Arg
            110

(2) INFORMATION FOR SEQ ID NO: 47:

(i) SEQUENCE CHARACTERISTICS:
        (A) LENGTH: 109 amino acids
        (B) TYPE: Amino Acid
        (D) TOPOLOGY: Linear (xi) SEQUENCE DESCRIPTION: SEQ ID NO: 47:

Asp Ile Gln Met Thr Gln Ser Pro Ser Leu Ser Ala Ser Val
 1               5                  10                  15

Gly Asp Arg Val Thr Ile Thr Cys Arg Ala Ser Lys Thr Ile Ser
            20                  25                  30

Lys Tyr Leu Ala Trp Tyr Gln Gln Lys Pro Gly Lys Ala Pro Lys
            35                  40                  45

Leu Leu Ile Tyr Tyr Ser Gly Ser Thr Leu Glu Ser Gly Val Pro
            50                  55                  60

Ser Arg Phe Ser Gly Ser Gly Ser Gly Thr Asp Phe Thr Leu Thr
            65                  70                  75

Ile Ser Ser Leu Gln Pro Glu Asp Phe Ala Thr Tyr Tyr Cys Gln
            80                  85                  90

Gln His Asn Glu Tyr Pro Leu Thr Phe Gly Gln Gly Thr Lys Val
            95                  100                 105

Glu Ile Lys Arg (2) INFORMATION FOR SEQ ID NO: 48:

(i) SEQUENCE CHARACTERISTICS:
        (A) LENGTH: 117 amino acids
        (B) TYPE: Amino Acid
        (D) TOPOLOGY: Linear (xi) SEQUENCE DESCRIPTION: SEQ ID NO: 48:

Glu Ile Gln Leu Gln Gln Ser Gly Pro Glu Leu Met Lys Pro Gly
 1               5                  10                  15

Ala Ser Val Lys Ile Ser Cys Lys Ala Ser Gly Tyr Ser Phe Ser
            20                  25                  30

Ser His Tyr Met His Trp Val Lys Gln Ser His Gly Lys Ser Leu
            35                  40                  45

Glu Trp Ile Gly Tyr Ile Asp Pro Ser Asn Gly Glu Thr Thr Tyr
            50                  55                  60

Asn Gln Lys Phe Lys Gly Lys Ala Thr Leu Thr Val Asp Thr Ser
            65                  70                  75

Ser Ser Thr Ala Asn Val His Leu Ser Ser Leu Thr Ser Asp Asp
            80                  85                  90

Ser Ala Val Tyr Phe Cys Ala Ala Arg Gly Asp Tyr Arg Tyr Asn
            95                  100                 105

Gly Asp Trp Phe Phe Asp Val Trp Gly Ala Gly Thr
            110                 115

(2) INFORMATION FOR SEQ ID NO: 49:

(i) SEQUENCE CHARACTERISTICS:
        (A) LENGTH: 117 amino acids
```

(B) TYPE: Amino Acid
        (D) TOPOLOGY: Linear (xi) SEQUENCE DESCRIPTION: SEQ ID NO: 49:

Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Ser Phe Ser
                20                  25                  30

Ser His Tyr Met His Trp Val Arg Gln Ala Pro Gly Lys Gly Leu
                35                  40                  45

Glu Trp Val Gly Tyr Ile Asp Pro Ser Asn Gly Glu Thr Thr Tyr
                50                  55                  60

Asn Gln Lys Phe Lys Gly Arg Phe Thr Ile Ser Arg Asp Asn Ser
                65                  70                  75

Lys Asn Thr Leu Tyr Leu Gln Met Asn Ser Leu Arg Ala Glu Asp
                80                  85                  90

Thr Ala Val Tyr Tyr Cys Ala Ala Arg Gly Asp Tyr Arg Tyr Asn
                95                 100                 105

Gly Asp Trp Phe Phe Asp Val Trp Gly Gln Gly Thr
                110                115

(2) INFORMATION FOR SEQ ID NO: 50:

(i) SEQUENCE CHARACTERISTICS:
        (A) LENGTH: 116 amino acids
        (B) TYPE: Amino Acid
        (D) TOPOLOGY: Linear (xi) SEQUENCE DESCRIPTION: SEQ ID NO: 50:

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Ser Phe Thr
                20                  25                  30

Gly His Trp Met Asn Trp Val Arg Gln Ala Pro Gly Lys Gly Leu
                35                  40                  45

Glu Trp Val Gly Met Ile His Pro Ser Asp Ser Glu Thr Arg Tyr
                50                  55                  60

Ala Asp Ser Val Lys Gly Arg Phe Thr Ile Ser Arg Asp Asn Ser
                65                  70                  75

Lys Asn Thr Leu Tyr Leu Gln Met Asn Ser Leu Arg Ala Glu Asp
                80                  85                  90

Thr Ala Val Tyr Tyr Cys Ala Ala Arg Gly Ile Tyr Phe Tyr Gly
                95                 100                 105

Thr Thr Tyr Phe Asp Tyr Trp Gly Gln Gly Thr
                110                115

(2) INFORMATION FOR SEQ ID NO: 51:

(i) SEQUENCE CHARACTERISTICS:
        (A) LENGTH: 242 amino acids
        (B) TYPE: Amino Acid
        (D) TOPOLOGY: Linear (xi) SEQUENCE DESCRIPTION: SEQ ID NO: 51:

Met Lys Lys Asn Ile Ala Phe Leu Leu Ala Ser Met Phe Val Phe
 1               5                  10                  15

Ser Ile Ala Thr Asn Ala Tyr Ala Asp Ile Gln Met Thr Gln Ser
                20                  25                  30

-continued

```
Pro Ser Ser Leu Ser Ala Ser Val Gly Asp Arg Val Thr Ile Thr
                35                  40                  45

Cys Arg Ser Ser Gln Ser Leu Val His Gly Ile Gly Asn Thr Tyr
                50                  55                  60

Leu His Trp Tyr Gln Gln Lys Pro Gly Lys Ala Pro Lys Leu Leu
                65                  70                  75

Ile Tyr Lys Val Ser Asn Arg Phe Ser Gly Val Pro Ser Arg Phe
                80                  85                  90

Ser Gly Ser Gly Ser Gly Thr Asp Phe Thr Leu Thr Ile Ser Ser
                95                 100                 105

Leu Gln Pro Glu Asp Phe Ala Thr Tyr Tyr Cys Ser Gln Ser Thr
               110                 115                 120

His Val Pro Leu Thr Phe Gly Gln Gly Thr Lys Val Glu Ile Lys
               125                 130                 135

Arg Thr Val Ala Ala Pro Ser Val Phe Ile Phe Pro Pro Ser Asp
               140                 145                 150

Glu Gln Leu Lys Ser Gly Thr Ala Ser Val Val Cys Leu Leu Asn
               155                 160                 165

Asn Phe Tyr Pro Arg Glu Ala Lys Val Gln Trp Lys Val Asp Asn
               170                 175                 180

Ala Leu Gln Ser Gly Asn Ser Gln Glu Ser Val Thr Glu Gln Asp
               185                 190                 195

Ser Lys Asp Ser Thr Tyr Ser Leu Ser Ser Thr Leu Thr Leu Ser
               200                 205                 210

Lys Ala Asp Tyr Glu Lys His Lys Val Tyr Ala Cys Glu Val Thr
               215                 220                 225

His Gln Gly Leu Ser Ser Pro Val Thr Lys Ser Phe Asn Arg Gly
               230                 235                 240

Glu Cys
```

(2) INFORMATION FOR SEQ ID NO: 52:

(i) SEQUENCE CHARACTERISTICS:
        (A) LENGTH: 253 amino acids
        (B) TYPE: Amino Acid
        (D) TOPOLOGY: Linear (xi) SEQUENCE DESCRIPTION: SEQ ID NO: 52:

```
Met Lys Lys Asn Ile Ala Phe Leu Leu Ala Ser Met Phe Val Phe
 1               5                  10                  15

Ser Ile Ala Thr Asn Ala Tyr Ala Glu Val Gln Leu Val Gln Ser
                20                  25                  30

Gly Gly Gly Leu Val Gln Pro Gly Gly Ser Leu Arg Leu Ser Cys
                35                  40                  45

Ala Ala Ser Gly Tyr Ser Phe Ser Ser His Tyr Met His Trp Val
                50                  55                  60

Arg Gln Ala Pro Gly Lys Gly Leu Glu Trp Val Gly Tyr Ile Asp
                65                  70                  75

Pro Ser Asn Gly Glu Thr Thr Tyr Asn Gln Lys Phe Lys Gly Arg
                80                  85                  90

Phe Thr Leu Ser Arg Asp Asn Ser Lys Asn Thr Ala Tyr Leu Gln
                95                 100                 105

Met Asn Ser Leu Arg Ala Glu Asp Thr Ala Val Tyr Tyr Cys Ala
               110                 115                 120

Arg Gly Asp Tyr Arg Tyr Asn Gly Asp Trp Phe Phe Asp Val Trp
```

-continued

```
                125                 130                 135
Gly Gln Gly Thr Leu Val Thr Val Ser Ser Ala Ser Thr Lys Gly
                140                 145                 150

Pro Ser Val Phe Pro Leu Ala Pro Ser Ser Lys Ser Thr Ser Gly
                155                 160                 165

Gly Thr Ala Ala Leu Gly Cys Leu Val Lys Asp Tyr Phe Pro Glu
                170                 175                 180

Pro Val Thr Val Ser Trp Asn Ser Gly Ala Leu Thr Ser Gly Val
                185                 190                 195

His Thr Phe Pro Ala Val Leu Gln Ser Ser Gly Leu Tyr Ser Leu
                200                 205                 210

Ser Ser Val Val Thr Val Pro Ser Ser Ser Leu Gly Thr Gln Thr
                215                 220                 225

Tyr Ile Cys Asn Val Asn His Lys Pro Ser Asn Thr Lys Val Asp
                230                 235                 240

Lys Lys Val Glu Pro Lys Ser Cys Asp Lys Thr His Thr
                245                 250
```

(2) INFORMATION FOR SEQ ID NO: 53:

(i) SEQUENCE CHARACTERISTICS:
        (A) LENGTH: 159 amino acids
        (B) TYPE: Amino Acid
        (D) TOPOLOGY: Linear (xi) SEQUENCE DESCRIPTION: SEQ ID NO: 53:

```
Ser Gly Gly Gly Ser Gly Ser Gly Asp Phe Asp Tyr Glu Lys Met
 1               5                  10                  15

Ala Asn Ala Asn Lys Gly Ala Met Thr Glu Asn Ala Asp Glu Asn
                20                  25                  30

Ala Leu Gln Ser Asp Ala Lys Gly Lys Leu Asp Ser Val Ala Thr
                35                  40                  45

Asp Tyr Gly Ala Ala Ile Asp Gly Phe Ile Gly Asp Val Ser Gly
                50                  55                  60

Leu Ala Asn Gly Asn Gly Ala Thr Gly Asp Phe Ala Gly Ser Ser
                65                  70                  75

Asn Ser Gln Met Ala Gln Val Gly Asp Gly Asp Asn Ser Pro Leu
                80                  85                  90

Met Asn Asn Phe Arg Gln Tyr Leu Pro Ser Leu Pro Gln Ser Val
                95                  100                 105

Glu Cys Arg Pro Phe Val Phe Ser Ala Gly Lys Pro Tyr Glu Phe
                110                 115                 120

Ser Ile Asp Cys Asp Lys Ile Asn Leu Phe Arg Gly Val Phe Ala
                125                 130                 135

Phe Leu Leu Tyr Val Ala Thr Phe Met Tyr Val Phe Ser Thr Phe
                140                 145                 150

Ala Asn Ile Leu Arg Asn Lys Glu Ser
                155
```

(2) INFORMATION FOR SEQ ID NO: 54:

(i) SEQUENCE CHARACTERISTICS:
        (A) LENGTH: 780 base pairs
        (B) TYPE: Nucleic Acid
        (C) STRANDEDNESS: Single
        (D) TOPOLOGY: Linear (xi) SEQUENCE DESCRIPTION: SEQ ID NO: 54:

```
ATGAAAAAGA ATATCGCATT TCTTCTTGCA TCTATGTTCG TTTTTTCTAT         50

TGCTACAAAC GCATACGCTG ATATCCAGAT GACCCAGTCC CCGAGCTCCC        100

TGTCCGCCTC TGTGGGCGAT AGGGTCACCA TCACCTGCAG GTCAAGTCAA        150

AGCTTAGTAC ATGGTATAGG TAACACGTAT TTACACTGGT ATCAACAGAA        200

ACCAGGAAAA GCTCCGAAAC TACTGATTTA CAAAGTATCC AATCGATTCT        250

CTGGAGTCCC TTCTCGCTTC TCTGGATCCG GTTCTGGGAC GGATTTCACT        300

CTGACCATCA GCAGTCTGCA GCCAGAAGAC TTCGCAACTT ATTACTGTTC        350

ACAGAGTACT CATGTCCCGC TCACGTTTGG ACAGGGTACC AAGGTGGAGA        400

TCAAACGAAC TGTGGCTGCA CCATCTGTCT TCATCTTCCC GCCATCTGAT        450

GAGCAGTTGA AATCTGGAAC TGCTTCTGTT GTGTGCCTGC TGAATAACTT        500

CTATCCCAGA GAGGCCAAAG TACAGTGGAA GGTGGATAAC GCCCTCCAAT        550

CGGGTAACTC CCAGGAGAGT GTCACAGAGC AGGACAGCAA GGACAGCACC        600

TACAGCCTCA GCAGCACCCT GACGCTGAGC AAAGCAGACT ACGAGAAACA        650

CAAAGTCTAC GCCTGCGAAG TCACCCATCA GGGCCTGAGC TCGCCCGTCA        700

CAAAGAGCTT CAACAGGGGA GAGTGTTAAG CTGATCCTCT ACGCCGGACG        750

CATCGTGGCC CTAGTACGCA ACTAGTCGTA                              780
```

(2) INFORMATION FOR SEQ ID NO: 55:

(i) SEQUENCE CHARACTERISTICS:
        (A) LENGTH: 253 amino acids
        (B) TYPE: Amino Acid
        (D) TOPOLOGY: Linear (xi) SEQUENCE DESCRIPTION: SEQ ID NO: 55:

```
Met Lys Lys Asn Ile Ala Phe Leu Leu Ala Ser Met Phe Val Phe
 1               5                  10                  15

Ser Ile Ala Thr Asn Ala Tyr Ala Glu Val Gln Leu Val Glu Ser
                20                  25                  30

Gly Gly Gly Leu Val Gln Pro Gly Gly Ser Leu Arg Leu Ser Cys
                35                  40                  45

Ala Ala Ser Gly Tyr Ser Phe Ser Ser His Tyr Met His Trp Val
                50                  55                  60

Lys Gln Ala Pro Gly Lys Gly Leu Glu Trp Val Gly Tyr Ile Asp
                65                  70                  75

Pro Ser Asn Gly Glu Thr Thr Tyr Asn Gln Lys Phe Lys Gly Arg
                80                  85                  90

Phe Thr Leu Ser Arg Asp Asn Ser Lys Asn Thr Ala Tyr Leu Gln
                95                 100                 105

Met Asn Ser Leu Arg Ala Glu Asp Thr Ala Val Tyr Tyr Cys Ala
               110                 115                 120

Arg Gly Asp Tyr Arg Tyr Asn Gly Asp Trp Phe Phe Asp Val Trp
               125                 130                 135

Gly Gln Gly Thr Leu Val Thr Val Ser Ser Ala Ser Thr Lys Gly
               140                 145                 150

Pro Ser Val Phe Pro Leu Ala Pro Ser Ser Lys Ser Thr Ser Gly
               155                 160                 165

Gly Thr Ala Ala Leu Gly Cys Leu Val Lys Asp Tyr Phe Pro Glu
               170                 175                 180
```

-continued

```
Pro Val Thr Val Ser Trp Asn Ser Gly Ala Leu Thr Ser Gly Val
                185                 190                 195

His Thr Phe Pro Ala Val Leu Gln Ser Ser Gly Leu Tyr Ser Leu
                200                 205                 210

Ser Ser Val Val Thr Val Pro Ser Ser Leu Gly Thr Gln Thr
                215                 220                 225

Tyr Ile Cys Asn Val Asn His Lys Pro Ser Asn Thr Lys Val Asp
                230                 235                 240

Lys Lys Val Glu Pro Lys Ser Cys Asp Lys Thr His Thr
                245                 250
```

(2) INFORMATION FOR SEQ ID NO: 56:

(i) SEQUENCE CHARACTERISTICS:
        (A) LENGTH: 242 amino acids
        (B) TYPE: Amino Acid
        (D) TOPOLOGY: Linear (xi) SEQUENCE DESCRIPTION: SEQ ID NO: 56:

```
Met Lys Lys Asn Ile Ala Phe Leu Leu Ala Ser Met Phe Val Phe
 1               5                  10                  15

Ser Ile Ala Thr Asn Ala Tyr Ala Asp Ile Gln Met Thr Gln Ser
                20                  25                  30

Pro Ser Ser Leu Ser Ala Ser Val Gly Asp Arg Val Thr Ile Thr
                35                  40                  45

Cys Arg Ser Ser Gln Ser Leu Val His Gly Ile Gly Ala Thr Tyr
                50                  55                  60

Leu His Trp Tyr Gln Gln Lys Pro Gly Lys Ala Pro Lys Leu Leu
                65                  70                  75

Ile Tyr Lys Val Ser Asn Arg Phe Ser Gly Val Pro Ser Arg Phe
                80                  85                  90

Ser Gly Ser Gly Ser Gly Thr Asp Phe Thr Leu Thr Ile Ser Ser
                95                 100                 105

Leu Gln Pro Glu Asp Phe Ala Thr Tyr Tyr Cys Ser Gln Ser Thr
                110                115                 120

His Val Pro Leu Thr Phe Gly Gln Gly Thr Lys Val Glu Ile Lys
                125                130                 135

Arg Thr Val Ala Ala Pro Ser Val Phe Ile Phe Pro Pro Ser Asp
                140                145                 150

Glu Gln Leu Lys Ser Gly Thr Ala Ser Val Val Cys Leu Leu Asn
                155                160                 165

Asn Phe Tyr Pro Arg Glu Ala Lys Val Gln Trp Lys Val Asp Asn
                170                175                 180

Ala Leu Gln Ser Gly Asn Ser Gln Glu Ser Val Thr Glu Gln Asp
                185                190                 195

Ser Lys Asp Ser Thr Tyr Ser Leu Ser Ser Thr Leu Thr Leu Ser
                200                205                 210

Lys Ala Asp Tyr Glu Lys His Lys Val Tyr Ala Cys Glu Val Thr
                215                220                 225

His Gln Gly Leu Ser Ser Pro Val Thr Lys Ser Phe Asn Arg Gly
                230                235                 240

Glu Cys
```

(2) INFORMATION FOR SEQ ID NO: 57:

(i) SEQUENCE CHARACTERISTICS:

(A) LENGTH: 45 amino acids
(B) TYPE: Amino Acid
(D) TOPOLOGY: Linear (xi) SEQUENCE DESCRIPTION: SEQ ID NO: 57:

Cys Pro Pro Cys Pro Ala Pro Glu Leu Leu Gly Gly Arg Met Lys
 1               5                  10                  15

Gln Leu Glu Asp Lys Val Glu Glu Leu Leu Ser Lys Asn Tyr His
                20                  25                  30

Leu Glu Asn Glu Val Ala Arg Leu Lys Lys Leu Val Gly Glu Arg
                35                  40                  45

(2) INFORMATION FOR SEQ ID NO: 58:

(i) SEQUENCE CHARACTERISTICS:
        (A) LENGTH: 780 base pairs
        (B) TYPE: Nucleic Acid
        (C) STRANDEDNESS: Single
        (D) TOPOLOGY: Linear (xi) SEQUENCE DESCRIPTION: SEQ ID NO: 58:

| | | |
|---|---|---|
| ATGAAAAAGA ATATCGCATT TCTTCTTGCA TCTATGTTCG TTTTTTCTAT | | 50 |
| TGCTACAAAC GCATACGCTG ATATCCAGAT GACCCAGTCC CCGAGCTCCC | | 100 |
| TGTCCGCCTC TGTGGGCGAT AGGGTCACCA TCACCTGCAG GTCAAGTCAA | | 150 |
| AGCTTAGTAC ATGGTATAGG TGCTACGTAT TTACACTGGT ATCAACAGAA | | 200 |
| ACCAGGAAAA GCTCCGAAAC TACTGATTTA CAAAGTATCC AATCGATTCT | | 250 |
| CTGGAGTCCC TTCTCGCTTC TCTGGATCCG GTTCTGGGAC GGATTTCACT | | 300 |
| CTGACCATCA GCAGTCTGCA GCCAGAAGAC TTCGCAACTT ATTACTGTTC | | 350 |
| ACAGAGTACT CATGTCCCGC TCACGTTTGG ACAGGGTACC AAGGTGGAGA | | 400 |
| TCAAACGAAC TGTGGCTGCA CCATCTGTCT TCATCTTCCC GCCATCTGAT | | 450 |
| GAGCAGTTGA AATCTGGAAC TGCTTCTGTT GTGTGCCTGC TGAATAACTT | | 500 |
| CTATCCCAGA GAGGCCAAAG TACAGTGGAA GGTGGATAAC GCCCTCCAAT | | 550 |
| CGGGTAACTC CCAGGAGAGT GTCACAGAGC AGGACAGCAA GGACAGCACC | | 600 |
| TACAGCCTCA GCAGCACCCT GACGCTGAGC AAAGCAGACT ACGAGAAACA | | 650 |
| CAAAGTCTAC GCCTGCGAAG TCACCCATCA GGGCCTGAGC TCGCCCGTCA | | 700 |
| CAAAGAGCTT CAACAGGGGA GAGTGTTAAG CTGATCCTCT ACGCCGGACG | | 750 |
| CATCGTGGCC CTAGTACGCA ACTAGTCGTA | | 780 |

(2) INFORMATION FOR SEQ ID NO: 59:

(i) SEQUENCE CHARACTERISTICS:
        (A) LENGTH: 927 base pairs
        (B) TYPE: Nucleic Acid
        (C) STRANDEDNESS: Single
        (D) TOPOLOGY: Linear (xi) SEQUENCE DESCRIPTION: SEQ ID NO: 59:

| | | |
|---|---|---|
| AAAAGGGTAT CTAGAGGTTG AGGTGATTTT ATGAAAAAGA ATATCGCATT | | 50 |
| TCTTCTTGCA TCTATGTTCG TTTTTTCTAT TGCTACAAAC GCGTACGCTG | | 100 |
| AGGTTCAGCT AGTGCAGTCT GGCGGTGGCC TGGTGCAGCC AGGGGGCTCA | | 150 |
| CTCCGTTTGT CCTGTGCAGC TTCTGGCTAC TCCTTCTCGA GTCACTATAT | | 200 |
| GCACTGGGTC CGTCAGGCCC CGGGTAAGGG CCTGGAATGG GTTGGATATA | | 250 |

-continued

```
TTGATCCTTC CAATGGTGAA ACTACGTATA ATCAAAAGTT CAAGGGCCGT            300

TTCACTTTAT CTCGCGACAA CTCCAAAAAC ACAGCATACC TGCAGATGAA            350

CAGCCTGCGT GCTGAGGACA CTGCCGTCTA TTACTGTGCA AGAGGGGATT            400

ATCGCTACAA TGGTGACTGG TTCTTCGACG TCTGGGGTCA AGGAACCCTG            450

GTCACCGTCT CCTCGGCCTC CACCAAGGGC CCATCGGTCT TCCCCCTGGC            500

ACCCTCCTCC AAGAGCACCT CTGGGGGCAC AGCGGCCCTG GGCTGCCTGG            550

TCAAGGACTA CTTCCCCGAA CCGGTGACGG TGTCGTGGAA CTCAGGCGCC            600

CTGACCAGCG GCGTGCACAC CTTCCCGGCT GTCCTACAGT CCTCAGGACT            650

CTACTCCCTC AGCAGCGTGG TGACCGTGCC CTCCAGCAGC TTGGGCACCC            700

AGACCTACAT CTGCAACGTG AATCACAAGC CCAGCAACAC CAAGGTCGAC            750

AAGAAAGTTG AGCCCAAATC TTGTGACAAA ACTCACACAT GCCCGCCGTG            800

CCCAGCACCA GAACTGCTGG GCGGCCGCAT GAAACAGCTA GAGGACAAGG            850

TCGAAGAGCT ACTCTCCAAG AACTACCACC TAGAGAATGA AGTGGCAAGA            900

CTCAAAAAGC TTGTCGGGGA GCGCTAA                                    927
```

(2) INFORMATION FOR SEQ ID NO: 60:

(i) SEQUENCE CHARACTERISTICS:
        (A) LENGTH: 298 amino acids
        (B) TYPE: Amino Acid
        (D) TOPOLOGY: Linear (xi) SEQUENCE DESCRIPTION: SEQ ID NO: 60:

```
Met Lys Lys Asn Ile Ala Phe Leu Leu Ala Ser Met Phe Val Phe
 1               5                  10                  15

Ser Ile Ala Thr Asn Ala Tyr Ala Glu Val Gln Leu Val Gln Ser
                20                  25                  30

Gly Gly Gly Leu Val Gln Pro Gly Gly Ser Leu Arg Leu Ser Cys
                35                  40                  45

Ala Ala Ser Gly Tyr Ser Phe Ser Ser His Tyr Met His Trp Val
                50                  55                  60

Arg Gln Ala Pro Gly Lys Gly Leu Glu Trp Val Gly Tyr Ile Asp
                65                  70                  75

Pro Ser Asn Gly Glu Thr Thr Tyr Asn Gln Lys Phe Lys Gly Arg
                80                  85                  90

Phe Thr Leu Ser Arg Asp Asn Ser Lys Asn Thr Ala Tyr Leu Gln
                95                  100                 105

Met Asn Ser Leu Arg Ala Glu Asp Thr Ala Val Tyr Tyr Cys Ala
                110                 115                 120

Arg Gly Asp Tyr Arg Tyr Asn Gly Asp Trp Phe Phe Asp Val Trp
                125                 130                 135

Gly Gln Gly Thr Leu Val Thr Val Ser Ser Ala Ser Thr Lys Gly
                140                 145                 150

Pro Ser Val Phe Pro Leu Ala Pro Ser Ser Lys Ser Thr Ser Gly
                155                 160                 165

Gly Thr Ala Ala Leu Gly Cys Leu Val Lys Asp Tyr Phe Pro Glu
                170                 175                 180

Pro Val Thr Val Ser Trp Asn Ser Gly Ala Leu Thr Ser Gly Val
                185                 190                 195

His Thr Phe Pro Ala Val Leu Gln Ser Ser Gly Leu Tyr Ser Leu
                200                 205                 210
```

```
Ser Ser Val Val Thr Val Pro Ser Ser Leu Gly Thr Gln Thr
            215                 220                 225

Tyr Ile Cys Asn Val Asn His Lys Pro Ser Asn Thr Lys Val Asp
                230                 235                 240

Lys Lys Val Glu Pro Lys Ser Cys Asp Lys Thr His Thr Cys Pro
                245                 250                 255

Pro Cys Pro Ala Pro Glu Leu Leu Gly Gly Arg Met Lys Gln Leu
                260                 265                 270

Glu Asp Lys Val Glu Glu Leu Leu Ser Lys Asn Tyr His Leu Glu
                275                 280                 285

Asn Glu Val Ala Arg Leu Lys Lys Leu Val Gly Glu Arg
                290                 295

(2) INFORMATION FOR SEQ ID NO: 61:

(i) SEQUENCE CHARACTERISTICS:
        (A) LENGTH: 6563 base pairs
        (B) TYPE: Nucleic Acid
        (C) STRANDEDNESS: Single
        (D) TOPOLOGY: Linear (xi) SEQUENCE DESCRIPTION: SEQ ID NO: 61:
```

| | |
|---|---:|
| GAATTCAACT TCTCCATACT TTGGATAAGG AAATACAGAC ATGAAAAATC | 50 |
| TCATTGCTGA GTTGTTATTT AAGCTTGCCC AAAAAGAAGA AGAGTCGAAT | 100 |
| GAACTGTGTG CGCAGGTAGA AGCTTTGGAG ATTATCGTCA CTGCAATGCT | 150 |
| TCGCAATATG GCGCAAAATG ACCAACAGCG GTTGATTGAT CAGGTAGAGG | 200 |
| GGGCGCTGTA CGAGGTAAAG CCCGATGCCA GCATTCCTGA CGACGATACG | 250 |
| GAGCTGCTGC GCGATTACGT AAAGAAGTTA TTGAAGCATC CTCGTCAGTA | 300 |
| AAAAGTTAAT CTTTTCAACA GCTGTCATAA AGTTGTCACG GCCGAGACTT | 350 |
| ATAGTCGCTT TGTTTTTATT TTTTAATGTA TTTGTAACTA GAATTCGAGC | 400 |
| TCGGTACCCG GGGATCCTCT CGAGGTTGAG GTGATTTTAT GAAAAAGAAT | 450 |
| ATCGCATTTC TTCTTGCATC TATGTTCGTT TTTTCTATTG CTACAAACGC | 500 |
| ATACGCTGAT ATCCAGATGA CCCAGTCCCC GAGCTCCCTG TCCGCCTCTG | 550 |
| TGGGCGATAG GGTCACCATC ACCTGCAGGT CAAGTCAAAG CTTAGTACAT | 600 |
| GGTATAGGTG CTACGTATTT ACACTGGTAT CAACAGAAAC CAGGAAAAGC | 650 |
| TCCGAAACTA CTGATTTACA AAGTATCCAA TCGATTCTCT GGAGTCCCTT | 700 |
| CTCGCTTCTC TGGATCCGGT TCTGGGACGG ATTTCACTCT GACCATCAGC | 750 |
| AGTCTGCAGC CAGAAGACTT CGCAACTTAT TACTGTTCAC AGAGTACTCA | 800 |
| TGTCCCGCTC ACGTTTGGAC AGGGTACCAA GGTGGAGATC AAACGAACTG | 850 |
| TGGCTGCACC ATCTGTCTTC ATCTTCCCGC CATCTGATGA GCAGTTGAAA | 900 |
| TCTGGAACTG CTTCTGTTGT GTGCCTGCTG AATAACTTCT ATCCCAGAGA | 950 |
| GGCCAAAGTA CAGTGGAAGG TGGATAACGC CCTCCAATCG GGTAACTCCC | 1000 |
| AGGAGAGTGT CACAGAGCAG GACAGCAAGG ACAGCACCTA CAGCCTCAGC | 1050 |
| AGCACCCTGA CGCTGAGCAA AGCAGACTAC GAGAAACACA AAGTCTACGC | 1100 |
| CTGCGAAGTC ACCCATCAGG GCCTGAGCTC GCCCGTCACA AAGAGCTTCA | 1150 |
| ACAGGGGAGA GTGTTAAGCT GATCCTCTAC GCCGGACGCA TCGTGGCCCT | 1200 |
| AGTACGCAAC TAGTCGTAAA AAGGGTATCT AGAGGTTGAG GTGATTTTAT | 1250 |

-continued

```
GAAAAAGAAT ATCGCATTTC TTCTTGCATC TATGTTCGTT TTTTCTATTG      1300

CTACAAACGC GTACGCTGAG GTTCAGCTAG TGCAGTCTGG CGGTGGCCTG      1350

GTGCAGCCAG GGGGCTCACT CCGTTTGTCC TGTGCAGCTT CTGGCTACTC      1400

CTTCTCGAGT CACTATATGC ACTGGGTCCG TCAGGCCCCG GGTAAGGGCC      1450

TGGAATGGGT TGGATATATT GATCCTTCCA ATGGTGAAAC TACGTATAAT      1500

CAAAAGTTCA AGGGCCGTTT CACTTTATCT CGCGACAACT CCAAAAACAC      1550

AGCATACCTG CAGATGAACA GCCTGCGTGC TGAGGACACT GCCGTCTATT      1600

ACTGTGCAAG AGGGGATTAT CGCTACAATG GTGACTGGTT CTTCGACGTC      1650

TGGGGTCAAG GAACCCTGGT CACCGTCTCC TCGGCCTCCA CCAAGGGCCC      1700

ATCGGTCTTC CCCCTGGCAC CCTCCTCCAA GAGCACCTCT GGGGGCACAG      1750

CGGCCCTGGG CTGCCTGGTC AAGGACTACT TCCCCGAACC GGTGACGGTG      1800

TCGTGGAACT CAGGCGCCCT GACCAGCGGC GTGCACACCT TCCCGGCTGT      1850

CCTACAGTCC TCAGGACTCT ACTCCCTCAG CAGCGTGGTG ACCGTGCCCT      1900

CCAGCAGCTT GGGCACCCAG ACCTACATCT GCAACGTGAA TCACAAGCCC      1950

AGCAACACCA AGGTCGACAA GAAAGTTGAG CCCAAATCTT GTGACAAAAC      2000

TCACACATGC CCGCCGTGCC CAGCACCAGA ACTGCTGGGC GGCCGCATGA      2050

AACAGCTAGA GGACAAGGTC GAAGAGCTAC TCTCCAAGAA CTACCACCTA      2100

GAGAATGAAG TGGCAAGACT CAAAAAGCTT GTCGGGAGC GCTAAGCATG       2150

CGACGGCCCT AGAGTCCCTA ACGCTCGGTT GCCGCCGGGC GTTTTTTATT      2200

GTTAACTCAT GTTTGACAGC TTATCATCGA TAAGCTTTAA TGCGGTAGTT      2250

TATCACAGTT AAATTGCTAA CGCAGTCAGG CACCGTGTAT GAAATCTAAC      2300

AATGCGCTCA TCGTCATCCT CGGCACCGTC ACCCTGGATG CTGTAGGCAT      2350

AGGCTTGGTT ATGCCGGTAC TGCCGGGCCT CTTGCGGGAT ATCGTCCATT      2400

CCGACAGCAT CGCCAGTCAC TATGGCGTGC TGCTAGCGCT ATATGCGTTG      2450

ATGCAATTTC TATGCGCACC CGTTCTCGGA GCACTGTCCG ACCGCTTTGG      2500

CCGCCGCCCA GTCCTGCTCG CTTCGCTACT TGGAGCCACT ATCGACTACG      2550

CGATCATGGC GACCACACCC GTCCTGTGGA TCCTCTACGC CGGACGCATC      2600

GTGGCCGGCA TCACCGGCGC CACAGGTGCG GTTGCTGGCG CCTATATCGC      2650

CGACATCACC GATGGGGAAG ATCGGGCTCG CCACTTCGGG CTCATGAGCG      2700

CTTGTTTCGG CGTGGGTATG GTGGCAGGCC CCGTGGCCGG GGGACTGTTG      2750

GGCGCCATCT CCTTGCACGC ACCATTCCTT GCGGCGGCGG TGCTCAACGG      2800

CCTCAACCTA CTACTGGGCT GCTTCCTAAT GCAGGAGTCG CATAAGGGAG      2850

AGCGTCGTCC GATGCCCTTG AGAGCCTTCA ACCCAGTCAG CTCCTTCCGG      2900

TGGGCGCGGG GCATGACTAT CGTCGCCGCA CTTATGACTG TCTTCTTTAT      2950

CATGCAACTC GTAGGACAGG TGCCGGCAGC GCTCTGGGTC ATTTTCGGCG      3000

AGGACCGCTT TCGCTGGAGC GCGACGATGA TCGGCCTGTC GCTTGCGGTA      3050

TTCGGAATCT TGCACGCCCT CGCTCAAGCC TTCGTCACTG GTCCCGCCAC      3100

CAAACGTTTC GGCGAGAAGC AGGCCATTAT CGCCGGCATG GCGGCCGACG      3150

CGCTGGGCTA CGTCTTGCTG GCGTTCGCGA CGCGAGGCTG GATGGCCTTC      3200
```

| | |
|---|---|
| CCCATTATGA TTCTTCTCGC TTCCGGCGGC ATCGGGATGC CCGCGTTGCA | 3250 |
| GGCCATGCTG TCCAGGCAGG TAGATGACGA CCATCAGGGA CAGCTTCAAG | 3300 |
| GATCGCTCGC GGCTCTTACC AGCCTAACTT CGATCACTGG ACCGCTGATC | 3350 |
| GTCACGGCGA TTTATGCCGC CTCGGCGAGC ACATGGAACG GGTTGGCATG | 3400 |
| GATTGTAGGC GCCGCCCTAT ACCTTGTCTG CCTCCCCGCG TTGCGTCGCG | 3450 |
| GTGCATGGAG CCGGGCCACC TCGACCTGAA TGGAAGCCGG CGGCACCTCG | 3500 |
| CTAACGGATT CACCACTCCA AGAATTGGAG CCAATCAATT CTTGCGGAGA | 3550 |
| ACTGTGAATG CGCAAACCAA CCCTTGGCAG AACATATCCA TCGCGTCCGC | 3600 |
| CATCTCCAGC AGCCGCACGC GGCGCATCTC GGGCAGCGTT GGGTCCTGGC | 3650 |
| CACGGGTGCG CATGATCGTG CTCCTGTCGT TGAGGACCCG GCTAGGCTGG | 3700 |
| CGGGGTTGCC TTACTGGTTA GCAGAATGAA TCACCGATAC GCGAGCGAAC | 3750 |
| GTGAAGCGAC TGCTGCTGCA AAACGTCTGC GACCTGAGCA CAACATGAA | 3800 |
| TGGTCTTCGG TTTCCGTGTT TCGTAAAGTC TGGAAACGCG GAAGTCAGCG | 3850 |
| CCCTGCACCA TTATGTTCCG GATCTGCATC GCAGGATGCT GCTGGCTACC | 3900 |
| CTGTGGAACA CCTACATCTG TATTAACGAA GCGCTGGCAT TGACCCTGAG | 3950 |
| TGATTTTTCT CTGGTCCCGC CGCATCCATA CCGCCAGTTG TTTACCCTCA | 4000 |
| CAACGTTCCA GTAACCGGGC ATGTTCATCA TCAGTAACCC GTATCGTGAG | 4050 |
| CATCCTCTCT CGTTTCATCG GTATCATTAC CCCCATGAAC AGAAATTCCC | 4100 |
| CCTTACACGG AGGCATCAAG TGACCAAACA GGAAAAAACC GCCCTTAACA | 4150 |
| TGGCCCGCTT TATCAGAAGC CAGACATTAA CGCTTCTGGA GAAACTCAAC | 4200 |
| GAGCTGGACG CGGATGAACA GGCAGACATC TGTGAATCGC TTCACGACCA | 4250 |
| CGCTGATGAG CTTTACCGCA GCTGCCTCGC GCGTTTCGGT GATGACGGTG | 4300 |
| AAAACCTCTG ACACATGCAG CTCCCGGAGA CGGTCACAGC TTGTCTGTAA | 4350 |
| GCGGATGCCG GGAGCAGACA AGCCCGTCAG GGCGCGTCAG CGGGTGTTGG | 4400 |
| CGGGTGTCGG GGCGCAGCCA TGACCCAGTC ACGTAGCGAT AGCGGAGTGT | 4450 |
| ATACTGGCTT AACTATGCGG CATCAGAGCA GATTGTACTG AGAGTGCACC | 4500 |
| ATATGCGGTG TGAAATACCG CACAGATGCG TAAGGAGAAA ATACCGCATC | 4550 |
| AGGCGCTCTT CCGCTTCCTC GCTCACTGAC TCGCTGCGCT CGGTCGTTCG | 4600 |
| GCTGCGGCGA GCGGTATCAG CTCACTCAAA GGCGGTAATA CGGTTATCCA | 4650 |
| CAGAATCAGG GGATAACGCA GGAAAGAACA TGTGAGCAAA AGGCCAGCAA | 4700 |
| AAGGCCAGGA ACCGTAAAAA GGCCGCGTTG CTGGCGTTTT TCCATAGGCT | 4750 |
| CCGCCCCCCT GACGAGCATC ACAAAAATCG ACGCTCAAGT CAGAGGTGGC | 4800 |
| GAAACCCGAC AGGACTATAA AGATACCAGG CGTTTCCCCC TGGAAGCTCC | 4850 |
| CTCGTGCGCT CTCCTGTTCC GACCCTGCCG CTTACCGGAT ACCTGTCCGC | 4900 |
| CTTTCTCCCT TCGGGAAGCG TGGCGCTTTC TCATAGCTCA CGCTGTAGGT | 4950 |
| ATCTCAGTTC GGTGTAGGTC GTTCGCTCCA AGCTGGGCTG TGTGCACGAA | 5000 |
| CCCCCCGTTC AGCCCGACCG CTGCGCCTTA TCCGGTAACT ATCGTCTTGA | 5050 |
| GTCCAACCCG GTAAGACACG ACTTATCGCC ACTGGCAGCA GCCACTGGTA | 5100 |
| ACAGGATTAG CAGAGCGAGG TATGTAGGCG GTGCTACAGA GTTCTTGAAG | 5150 |
| TGGTGGCCTA ACTACGGCTA CACTAGAAGG ACAGTATTTG GTATCTGCGC | 5200 |

-continued

| | |
|---|---|
| TCTGCTGAAG CCAGTTACCT TCGGAAAAAG AGTTGGTAGC TCTTGATCCG | 5250 |
| GCAAACAAAC CACCGCTGGT AGCGGTGGTT TTTTTGTTTG CAAGCAGCAG | 5300 |
| ATTACGCGCA GAAAAAAAGG ATCTCAAGAA GATCCTTTGA TCTTTTCTAC | 5350 |
| GGGGTCTGAC GCTCAGTGGA ACGAAAACTC ACGTTAAGGG ATTTTGGTCA | 5400 |
| TGAGATTATC AAAAAGGATC TTCACCTAGA TCCTTTTAAA TTAAAAATGA | 5450 |
| AGTTTTAAAT CAATCTAAAG TATATATGAG TAAACTTGGT CTGACAGTTA | 5500 |
| CCAATGCTTA ATCAGTGAGG CACCTATCTC AGCGATCTGT CTATTTCGTT | 5550 |
| CATCCATAGT TGCCTGACTC CCCGTCGTGT AGATAACTAC GATACGGGAG | 5600 |
| GGCTTACCAT CTGGCCCCAG TGCTGCAATG ATACCGCGAG ACCCACGCTC | 5650 |
| ACCGGCTCCA GATTTATCAG CAATAAACCA GCCAGCCGGA AGGGCCGAGC | 5700 |
| GCAGAAGTGG TCCTGCAACT TTATCCGCCT CCATCCAGTC TATTAATTGT | 5750 |
| TGCCGGGAAG CTAGAGTAAG TAGTTCGCCA GTTAATAGTT TGCGCAACGT | 5800 |
| TGTTGCCATT GCTGCAGGCA TCGTGGTGTC ACGCTCGTCG TTTGGTATGG | 5850 |
| CTTCATTCAG CTCCGGTTCC CAACGATCAA GGCGAGTTAC ATGATCCCCC | 5900 |
| ATGTTGTGCA AAAAAGCGGT TAGCTCCTTC GGTCCTCCGA TCGTTGTCAG | 5950 |
| AAGTAAGTTG GCCGCAGTGT TATCACTCAT GGTTATGGCA GCACTGCATA | 6000 |
| ATTCTCTTAC TGTCATGCCA TCCGTAAGAT GCTTTTCTGT GACTGGTGAG | 6050 |
| TACTCAACCA AGTCATTCTG AGAATAGTGT ATGCGGCGAC CGAGTTGCTC | 6100 |
| TTGCCCGGCG TCAACACGGG ATAATACCGC GCCACATAGC AGAACTTTAA | 6150 |
| AAGTGCTCAT CATTGGAAAA CGTTCTTCGG GGCGAAAACT CTCAAGGATC | 6200 |
| TTACCGCTGT TGAGATCCAG TTCGATGTAA CCCACTCGTG CACCCAACTG | 6250 |
| ATCTTCAGCA TCTTTTACTT TCACCAGCGT TTCTGGGTGA GCAAAAACAG | 6300 |
| GAAGGCAAAA TGCCGCAAAA AAGGGAATAA GGGCGACACG GAAATGTTGA | 6350 |
| ATACTCATAC TCTTCCTTTT TCAATATTAT TGAAGCATTT ATCAGGGTTA | 6400 |
| TTGTCTCATG AGCGGATACA TATTTGAATG TATTTAGAAA AATAAACAAA | 6450 |
| TAGGGGTTCC GCGCACATTT CCCCGAAAAG TGCCACCTGA CGTCTAAGAA | 6500 |
| ACCATTATTA TCATGACATT AACCTATAAA AATAGGCGTA TCACGAGGCC | 6550 |
| CTTTCGTCTT CAA | 6563 |

(2) INFORMATION FOR SEQ ID NO: 62:

(i) SEQUENCE CHARACTERISTICS:
        (A) LENGTH: 242 amino acids
        (B) TYPE: Amino Acid
        (D) TOPOLOGY: Linear (xi) SEQUENCE DESCRIPTION: SEQ ID NO: 62:

```
Met Lys Lys Asn Ile Ala Phe Leu Leu Ala Ser Met Phe Val Phe
 1               5                  10                  15

Ser Ile Ala Thr Asn Ala Tyr Ala Asp Ile Gln Met Thr Gln Ser
                20                  25                  30

Pro Ser Leu Ser Ala Ser Val Gly Asp Arg Val Thr Ile Thr
                35                  40                  45

Cys Arg Ser Ser Gln Ser Leu Val His Gly Ile Gly Glu Thr Tyr
                50                  55                  60
```

```
Leu His Trp Tyr Gln Gln Lys Pro Gly Lys Ala Pro Lys Leu Leu
            65                  70                  75

Ile Tyr Lys Val Ser Asn Arg Phe Ser Gly Val Pro Ser Arg Phe
            80                  85                  90

Ser Gly Ser Gly Ser Gly Thr Asp Phe Thr Leu Thr Ile Ser Ser
            95                 100                 105

Leu Gln Pro Glu Asp Phe Ala Thr Tyr Tyr Cys Ser Gln Ser Thr
           110                 115                 120

His Val Pro Leu Thr Phe Gly Gln Gly Thr Lys Val Glu Ile Lys
           125                 130                 135

Arg Thr Val Ala Ala Pro Ser Val Phe Ile Phe Pro Pro Ser Asp
           140                 145                 150

Glu Gln Leu Lys Ser Gly Thr Ala Ser Val Val Cys Leu Leu Asn
           155                 160                 165

Asn Phe Tyr Pro Arg Glu Ala Lys Val Gln Trp Lys Val Asp Asn
           170                 175                 180

Ala Leu Gln Ser Gly Asn Ser Gln Glu Ser Val Thr Glu Gln Asp
           185                 190                 195

Ser Lys Asp Ser Thr Tyr Ser Leu Ser Ser Thr Leu Thr Leu Ser
           200                 205                 210

Lys Ala Asp Tyr Glu Lys His Lys Val Tyr Ala Cys Glu Val Thr
           215                 220                 225

His Gln Gly Leu Ser Ser Pro Val Thr Lys Ser Phe Asn Arg Gly
           230                 235                 240

Glu Cys
```

(2) INFORMATION FOR SEQ ID NO: 63:

(i) SEQUENCE CHARACTERISTICS:
        (A) LENGTH: 27 base pairs
        (B) TYPE: Nucleic Acid
        (C) STRANDEDNESS: Single
        (D) TOPOLOGY: Linear (xi) SEQUENCE DESCRIPTION: SEQ ID NO: 63:

```
CATGGTATAG GTTAAACTTA TTTACAC                                              27
```

(2) INFORMATION FOR SEQ ID NO: 64:

(i) SEQUENCE CHARACTERISTICS:
        (A) LENGTH: 27 base pairs
        (B) TYPE: Nucleic Acid
        (C) STRANDEDNESS: Single
        (D) TOPOLOGY: Linear (xi) SEQUENCE DESCRIPTION: SEQ ID NO: 64:

```
CATGGTATAG GTNNSACTTA TTTACAC                                              27
```

(2) INFORMATION FOR SEQ ID NO: 65:

(i) SEQUENCE CHARACTERISTICS:
        (A) LENGTH: 780 base pairs
        (B) TYPE: Nucleic Acid
        (C) STRANDEDNESS: Single
        (D) TOPOLOGY: Linear (xi) SEQUENCE DESCRIPTION: SEQ ID NO: 65:

```
ATGAAAAAGA ATATCGCATT TCTTCTTGCA TCTATGTTCG TTTTTTCTAT                     50
TGCTACAAAC GCATACGCTG ATATCCAGAT GACCCAGTCC CCGAGCTCCC                    100
```

| | |
|---|---|
| TGTCCGCCTC TGTGGGCGAT AGGGTCACCA TCACCTGCAG GTCAAGTCAA | 150 |
| AGCTTAGTAC ATGGTATAGG TGAGACGTAT TTACACTGGT ATCAACAGAA | 200 |
| ACCAGGAAAA GCTCCGAAAC TACTGATTTA CAAAGTATCC AATCGATTCT | 250 |
| CTGGAGTCCC TTCTCGCTTC TCTGGATCCG GTTCTGGGAC GGATTTCACT | 300 |
| CTGACCATCA GCAGTCTGCA GCCAGAAGAC TTCGCAACTT ATTACTGTTC | 350 |
| ACAGAGTACT CATGTCCCGC TCACGTTTGG ACAGGGTACC AAGGTGGAGA | 400 |
| TCAAACGAAC TGTGGCTGCA CCATCTGTCT TCATCTTCCC GCCATCTGAT | 450 |
| GAGCAGTTGA AATCTGGAAC TGCTTCTGTT GTGTGCCTGC TGAATAACTT | 500 |
| CTATCCCAGA GAGGCCAAAG TACAGTGGAA GGTGGATAAC GCCCTCCAAT | 550 |
| CGGGTAACTC CCAGGAGAGT GTCACAGAGC AGGACAGCAA GGACAGCACC | 600 |
| TACAGCCTCA GCAGCACCCT GACGCTGAGC AAAGCAGACT ACGAGAAACA | 650 |
| CAAAGTCTAC GCCTGCGAAG TCACCCATCA GGGCCTGAGC TCGCCCGTCA | 700 |
| CAAAGAGCTT CAACAGGGGA GAGTGTTAAG CTGATCCTCT ACGCCGGACG | 750 |
| CATCGTGGCC CTAGTACGCA ACTAGTCGTA | 780 |

(2) INFORMATION FOR SEQ ID NO: 66:

(i) SEQUENCE CHARACTERISTICS:
        (A) LENGTH: 78 base pairs
        (B) TYPE: Nucleic Acid
        (C) STRANDEDNESS: Single
        (D) TOPOLOGY: Linear (xi) SEQUENCE DESCRIPTION: SEQ ID NO: 66:

| | |
|---|---|
| CTAGTGCAGT CTGGCGGTGG CCTGGTGCAG CCAGGGGGCT CACTCCGTTT | 50 |
| GTCCTGTGCA GCTTCTGGCT ACTCCTTC | 78 |

(2) INFORMATION FOR SEQ ID NO: 67:

(i) SEQUENCE CHARACTERISTICS:
        (A) LENGTH: 82 base pairs
        (B) TYPE: Nucleic Acid
        (C) STRANDEDNESS: Single
        (D) TOPOLOGY: Linear (xi) SEQUENCE DESCRIPTION: SEQ ID NO: 67:

| | |
|---|---|
| TCGAGAAGGA GTAGCCAGAA GCTGCACAGG ACAAACGGAG TGAGCCCCCT | 50 |
| GGCTGCACCA GGCCACCGCC AGACTGCACT AG | 82 |

(2) INFORMATION FOR SEQ ID NO: 68:

(i) SEQUENCE CHARACTERISTICS:
        (A) LENGTH: 8120 base pairs
        (B) TYPE: Nucleic Acid
        (C) STRANDEDNESS: Single
        (D) TOPOLOGY: Linear (xi) SEQUENCE DESCRIPTION: SEQ ID NO: 68:

| | |
|---|---|
| TTCGAGCTCG CCCGACATTG ATTATTGACT AGAGTCGATC GACAGCTGTG | 50 |
| GAATGTGTGT CAGTTAGGGT GTGGAAAGTC CCCAGGCTCC CCAGCAGGCA | 100 |
| GAAGTATGCA AAGCATGCAT CTCAATTAGT CAGCAACCAG GTGTGGAAAG | 150 |
| TCCCCAGGCT CCCCAGCAGG CAGAAGTATG CAAAGCATGC ATCTCAATTA | 200 |
| GTCAGCAACC ATAGTCCCGC CCCTAACTCC GCCCATCCCG CCCCTAACTC | 250 |

| | |
|---|---|
| CGCCCAGTTC CGCCCATTCT CCGCCCCATG GCTGACTAAT TTTTTTTATT | 300 |
| TATGCAGAGG CCGAGGCCGC CTCGGCCTCT GAGCTATTCC AGAAGTAGTG | 350 |
| AGGAGGCTTT TTTGGAGGCC TAGGCTTTTG CAAAAAGCTA GCTTATCCGG | 400 |
| CCGGGAACGG TGCATTGGAA CGCGGATTCC CCGTGCCAAG AGTGACGTAA | 450 |
| GTACCGCCTA TAGAGCGATA AGAGGATTTT ATCCCCGCTG CCATCATGGT | 500 |
| TCGACCATTG AACTGCATCG TCGCCGTGTC CCAAAATATG GGGATTGGCA | 550 |
| AGAACGGAGA CCTACCCTGG CCTCCGCTCA GGAACGAGTT CAAGTACTTC | 600 |
| CAAAGAATGA CCACAACCTC TTCAGTGGAA GGTAAACAGA ATCTGGTGAT | 650 |
| TATGGGTAGG AAAACCTGGT TCTCCATTCC TGAGAAGAAT CGACCTTTAA | 700 |
| AGGACAGAAT TAATATAGTT CTCAGTAGAG AACTCAAAGA ACCACCACGA | 750 |
| GGAGCTCATT TTCTTGCCAA AAGTTTGGAT GATGCCTTAA GACTTATTGA | 800 |
| ACAACCGGAA TTGGCAAGTA AAGTAGACAT GGTTTGGATA GTCGGAGGCA | 850 |
| GTTCTGTTTA CCAGGAAGCC ATGAATCAAC CAGGCCACCT TAGACTCTTT | 900 |
| GTGACAAGGA TCATGCAGGA ATTTGAAAGT GACACGTTTT TCCCAGAAAT | 950 |
| TGATTTGGGG AAATATAAAC CTCTCCCAGA ATACCCAGGC GTCCTCTCTG | 1000 |
| AGGTCCAGGA GGAAAAAGGC ATCAAGTATA AGTTTGAAGT CTACGAGAAG | 1050 |
| AAAGACTAAC AGGAAGATGC TTTCAAGTTC TCTGCTCCCC TCCTAAAGCT | 1100 |
| ATGCATTTTT ATAAGACCAT GGGACTTTTG CTGGCTTTAG ATCCCCTTGG | 1150 |
| CTTCGTTAGA ACGCAGCTAC AATTAATACA TAACCTTATG TATCATACAC | 1200 |
| ATACGATTTA GGTGACACTA TAGATAACAT CCACTTTGCC TTTCTCTCCA | 1250 |
| CAGGTGTCCA CTCCCAGGTC CAACTGCACC TCGGTTCTAT CGATTGAATT | 1300 |
| CCACCATGGG ATGGTCATGT ATCATCCTTT TTCTAGTAGC AACTGCAACT | 1350 |
| GGAGTACATT CAGAAGTTCA GCTAGTGCAG TCTGGCGGTG GCCTGGTGCA | 1400 |
| GCCAGGGGGC TCACTCCGTT TGTCCTGTGC AGCTTCTGGC TACTCCTTCT | 1450 |
| CGAGTCACTA TATGCACTGG GTCCGTCAGG CCCCGGGTAA GGGCCTGGAA | 1500 |
| TGGGTTGGAT ATATTGATCC TTCCAATGGT GAAACTACGT ATAATCAAAA | 1550 |
| GTTCAAGGGC CGTTTCACTT TATCTCGCGA CAACTCCAAA ACACAGCAT | 1600 |
| ACCTGCAGAT GAACAGCCTG CGTGCTGAGG ACACTGCCGT CTATTACTGT | 1650 |
| GCAAGAGGGG ATTATCGCTA CAATGGTGAC TGGTTCTTCG ACGTCTGGGG | 1700 |
| TCAAGGAACC CTGGTCACCG TCTCCTCGGC CTCCACCAAG GGCCCATCGG | 1750 |
| TCTTCCCCCT GGCACCCTCC TCCAAGAGCA CCTCTGGGGG CACAGCGGCC | 1800 |
| CTGGGCTGCC TGGTCAAGGA CTACTTCCCC GAACCGGTGA CGGTGTCGTG | 1850 |
| GAACTCAGGC GCCCTGACCA GCGGCGTGCA CACCTTCCCG GCTGTCCTAC | 1900 |
| AGTCCTCAGG ACTCTACTCC CTCAGCAGCG TGGTGACTGT GCCCTCTAGC | 1950 |
| AGCTTGGGCA CCCAGACCTA CATCTGCAAC GTGAATCACA AGCCCAGCAA | 2000 |
| CACCAAGGTG GACAAGAAAG TTGAGCCCAA ATCTTGTGAC AAAACTCACA | 2050 |
| CATGCCCACC GTGCCCAGCA CCTGAACTCC TGGGGGGACC GTCAGTCTTC | 2100 |
| CTCTTCCCCC CAAAACCCAA GGACACCCTC ATGATCTCCC GGACCCCTGA | 2150 |
| GGTCACATGC GTGGTGGTGG ACGTGAGCCA CGAAGACCCT GAGGTCAAGT | 2200 |
| TCAACTGGTA CGTGGACGGC GTGGAGGTGC ATAATGCCAA GACAAAGCCG | 2250 |

```
CGGGAGGAGC AGTACAACAG CACGTACCGT GTGGTCAGCG TCCTCACCGT      2300

CCTGCACCAG GACTGGCTGA ATGGCAAGGA GTACAAGTGC AAGGTCTCCA      2350

ACAAAGCCCT CCCAGCCCCC ATCGAGAAAA CCATCTCCAA AGCCAAAGGG      2400

CAGCCCCGAG AACCACAGGT GTACACCCTG CCCCCATCCC GGGAAGAGAT      2450

GACCAAGAAC CAGGTCAGCC TGACCTGCCT GGTCAAAGGC TTCTATCCCA      2500

GCGACATCGC CGTGGAGTGG GAGAGCAATG GGCAGCCGGA GAACAACTAC      2550

AAGACCACGC CTCCCGTGCT GGACTCCGAC GGCTCCTTCT TCCTCTACAG      2600

CAAGCTCACC GTGGACAAGA GCAGGTGGCA GCAGGGGAAC GTCTTCTCAT      2650

GCTCCGTGAT GCATGAGGCT CTGCACAACC ACTACACGCA GAAGAGCCTC      2700

TCCCTGTCTC CGGGTAAATG AGTGCGACGG CCCTAGAGTC GACCTGCAGA      2750

AGCTTGGCCG CCATGGCCCA ACTTGTTTAT TGCAGCTTAT AATGGTTACA      2800

AATAAAGCAA TAGCATCACA AATTTCACAA ATAAAGCATT TTTTTCACTG      2850

CATTCTAGTT GTGGTTTGTC CAAACTCATC AATGTATCTT ATCATGTCTG      2900

GATCGATCGG GAATTAATTC GGCGCAGCAC CATGGCCTGA ATAACCTCT       2950

GAAAGAGGAA CTTGGTTAGG TACCTTCTGA GGCGGAAAGA ACCATCTGTG      3000

GAATGTGTGT CAGTTAGGGT GTGGAAAGTC CCCAGGCTCC CCAGCAGGCA      3050

GAAGTATGCA AAGCATGCAT CTCAATTAGT CAGCAACCAG GTGTGGAAAG      3100

TCCCCAGGCT CCCCAGCAGG CAGAAGTATG CAAAGCATGC ATCTCAATTA      3150

GTCAGCAACC ATAGTCCCGC CCCTAACTCC GCCCATCCCG CCCCTAACTC      3200

CGCCCAGTTC CGCCCATTCT CCGCCCCATG GCTGACTAAT TTTTTTTATT      3250

TATGCAGAGG CCGAGGCCGC CTCGGCCTCT GAGCTATTCC AGAAGTAGTG      3300

AGGAGGCTTT TTTGGAGGCC TAGGCTTTTG CAAAAAGCTA GCTTATCCGG      3350

CCGGGAACGG TGCATTGGAA CGCGGATTCC CCGTGCCAAG AGTCAGGTAA      3400

GTACCGCCTA TAGAGTCTAT AGGCCCACCC CCTTGGCTTC GTTAGAACGC      3450

GGCTACAATT AATACATAAC CTTTTGGATC GATCCTACTG ACACTGACAT      3500

CCACTTTTTC TTTTTCTCCA CAGGTGTCCA CTCCCAGGTC CAACTGCACC      3550

TCGGTTCGCG AAGCTAGCTT GGGCTGCATC GATTGAATTC CACCATGGGA      3600

TGGTCATGTA TCATCCTTTT TCTAGTAGCA ACTGCAACTG GAGTACATTC      3650

AGATATCCAG ATGACCCAGT CCCCGAGCTC CCTGTCCGCC TCTGTGGGCG      3700

ATAGGGTCAC CATCACCTGC AGGTCAAGTC AAAGCTTAGT ACATGGTATA      3750

GGTGCTACGT ATTTACACTG GTATCAACAG AAACCAGGAA AAGCTCCGAA      3800

ACTACTGATT TACAAAGTAT CCAATCGATT CTCTGGAGTC CCTTCTCGCT      3850

TCTCTGGATC CGGTTCTGGG ACGGATTTCA CTCTGACCAT CAGCAGTCTG      3900

CAGCCAGAAG ACTTCGCAAC TTATTACTGT TCACAGAGTA CTCATGTCCC      3950

GCTCACGTTT GGACAGGGTA CCAAGGTGGA GATCAAACGA ACTGTGGCTG      4000

CACCATCTGT CTTCATCTTC CCGCCATCTG ATGAGCAGTT GAAATCTGGA      4050

ACTGCTTCTG TTGTGTGCCT GCTGAATAAC TTCTATCCCA GAGAGGCCAA      4100

AGTACAGTGG AAGGTGGATA ACGCCCTCCA ATCGGGTAAC TCCCAGGAGA      4150

GTGTCACAGA GCAGGACAGC AAGGACAGCA CCTACAGCCT CAGCAGCACC      4200
```

-continued

| | |
|---|---|
| CTGACGCTGA GCAAAGCAGA CTACGAGAAA CACAAAGTCT ACGCCTGCGA | 4250 |
| AGTCACCCAT CAGGGCCTGA GCTCGCCCGT CACAAAGAGC TTCAACAGGG | 4300 |
| GAGAGTGTTA AGCTTGGCCG CCATGGCCCA ACTTGTTTAT TGCAGCTTAT | 4350 |
| AATGGTTACA AATAAAGCAA TAGCATCACA AATTTCACAA ATAAAGCATT | 4400 |
| TTTTTCACTG CATTCTAGTT GTGGTTTGTC CAAACTCATC AATGTATCTT | 4450 |
| ATCATGTCTG GATCGATCGG GAATTAATTC GGCGCAGCAC CATGGCCTGA | 4500 |
| AATAACCTCT GAAAGAGGAA CTTGGTTAGG TACCTTCTGA GGCGGAAAGA | 4550 |
| ACCAGCTGTG GAATGTGTGT CAGTTAGGGT GTGGAAAGTC CCCAGGCTCC | 4600 |
| CCAGCAGGCA GAAGTATGCA AAGCATGCAT CTCAATTAGT CAGCAACCAG | 4650 |
| GTGTGGAAAG TCCCCAGGCT CCCCAGCAGG CAGAAGTATG CAAAGCATGC | 4700 |
| ATCTCAATTA GTCAGCAACC ATAGTCCCGC CCCTAACTCC GCCCATCCCG | 4750 |
| CCCCTAACTC CGCCCAGTTC CGCCCATTCT CCGCCCATG GCTGACTAAT | 4800 |
| TTTTTTTATT TATGCAGAGG CCGAGGCCGC CTCGGCCTCT GAGCTATTCC | 4850 |
| AGAAGTAGTG AGGAGGCTTT TTTGGAGGCC TAGGCTTTTG CAAAAAGCTG | 4900 |
| TTACCTCGAG CGGCCGCTTA ATTAAGGCGC GCCATTTAAA TCCTGCAGGT | 4950 |
| AACAGCTTGG CACTGGCCGT CGTTTTACAA CGTCGTGACT GGGAAAACCC | 5000 |
| TGGCGTTACC CAACTTAATC GCCTTGCAGC ACATCCCCCC TTCGCCAGCT | 5050 |
| GGCGTAATAG CGAAGAGGCC CGCACCGATC GCCCTTCCCA ACAGTTGCGT | 5100 |
| AGCCTGAATG GCGAATGGCG CCTGATGCGG TATTTTCTCC TTACGCATCT | 5150 |
| GTGCGGTATT TCACACCGCA TACGTCAAAG CAACCATAGT ACGCGCCCTG | 5200 |
| TAGCGGCGCA TTAAGCGCGG CGGGTGTGGT GGTTACGCGC AGCGTGACCG | 5250 |
| CTACACTTGC CAGCGCCCTA GCGCCCGCTC CTTTCGCTTT CTTCCCTTCC | 5300 |
| TTTCTCGCCA CGTTCGCCGG CTTTCCCCGT CAAGCTCTAA ATCGGGGGCT | 5350 |
| CCCTTTAGGG TTCCGATTTA GTGCTTTACG GCACCTCGAC CCCAAAAAAC | 5400 |
| TTGATTTGGG TGATGGTTCA CGTAGTGGGC CATCGCCCTG ATAGACGGTT | 5450 |
| TTTCGCCCTT TGACGTTGGA GTCCACGTTC TTTAATAGTG GACTCTTGTT | 5500 |
| CCAAACTGGA ACAACACTCA ACCCTATCTC GGGCTATTCT TTTGATTTAT | 5550 |
| AAGGGATTTT GCCGATTTCG GCCTATTGGT TAAAAAATGA GCTGATTTAA | 5600 |
| CAAAAATTTA ACGCGAATTT TAACAAAATA TTAACGTTTA CAATTTTATG | 5650 |
| GTGCACTCTC AGTACAATCT GCTCTGATGC CGCATAGTTA AGCCAACTCC | 5700 |
| GCTATCGCTA CGTGACTGGG TCATGGCTGC GCCCCGACAC CCGCCAACAC | 5750 |
| CCGCTGACGC GCCCTGACGG GCTTGTCTGC TCCCGGCATC CGCTTACAGA | 5800 |
| CAAGCTGTGA CCGTCTCCGG GAGCTGCATG TGTCAGAGGT TTTCACCGTC | 5850 |
| ATCACCGAAA CGCGCGAGGC AGTATTCTTG AAGACGAAAG GGCCTCGTGA | 5900 |
| TACGCCTATT TTTATAGGTT AATGTCATGA TAATAATGGT TTCTTAGACG | 5950 |
| TCAGGTGGCA CTTTTCGGGG AAATGTGCGC GGAACCCCTA TTTGTTTATT | 6000 |
| TTTCTAAATA CATTCAAATA TGTATCCGCT CATGAGACAA TAACCCTGAT | 6050 |
| AAATGCTTCA ATAATATTGA AAAAGGAAGA GTATGAGTAT TCAACATTTC | 6100 |
| CGTGTCGCCC TTATTCCCTT TTTTGCGGCA TTTTGCCTTC CTGTTTTTGC | 6150 |
| TCACCCAGAA ACGCTGGTGA AAGTAAAAGA TGCTGAAGAT CAGTTGGGTG | 6200 |

| | |
|---|---|
| CACGAGTGGG TTACATCGAA CTGGATCTCA ACAGCGGTAA GATCCTTGAG | 6250 |
| AGTTTTCGCC CCGAAGAACG TTTTCCAATG ATGAGCACTT TTAAAGTTCT | 6300 |
| GCTATGTGGC GCGGTATTAT CCCGTGATGA CGCCGGGCAA GAGCAACTCG | 6350 |
| GTCGCCGCAT ACACTATTCT CAGAATGACT TGGTTGAGTA CTCACCAGTC | 6400 |
| ACAGAAAAGC ATCTTACGGA TGGCATGACA GTAAGAGAAT TATGCAGTGC | 6450 |
| TGCCATAACC ATGAGTGATA ACACTGCGGC CAACTTACTT CTGACAACGA | 6500 |
| TCGGAGGACC GAAGGAGCTA ACCGCTTTTT TGCACAACAT GGGGGATCAT | 6550 |
| GTAACTCGCC TTGATCGTTG GGAACCGGAG CTGAATGAAG CCATACCAAA | 6600 |
| CGACGAGCGT GACACCACGA TGCCAGCAGC AATGGCAACA ACGTTGCGCA | 6650 |
| AACTATTAAC TGGCGAACTA CTTACTCTAG CTTCCCGGCA ACAATTAATA | 6700 |
| GACTGGATGG AGGCGGATAA AGTTGCAGGA CCACTTCTGC GCTCGGCCCT | 6750 |
| TCCGGCTGGC TGGTTTATTG CTGATAAATC TGGAGCCGGT GAGCGTGGGT | 6800 |
| CTCGCGGTAT CATTGCAGCA CTGGGGCCAG ATGGTAAGCC CTCCCGTATC | 6850 |
| GTAGTTATCT ACACGACGGG GAGTCAGGCA ACTATGGATG AACGAAATAG | 6900 |
| ACAGATCGCT GAGATAGGTG CCTCACTGAT TAAGCATTGG TAACTGTCAG | 6950 |
| ACCAAGTTTA CTCATATATA CTTTAGATTG ATTTAAAACT TCATTTTTAA | 7000 |
| TTTAAAAGGA TCTAGGTGAA GATCCTTTTT GATAATCTCA TGACCAAAAT | 7050 |
| CCCTTAACGT GAGTTTTCGT TCCACTGAGC GTCAGACCCC GTAGAAAAGA | 7100 |
| TCAAAGGATC TTCTTGAGAT CCTTTTTTTC TGCGCGTAAT CTGCTGCTTG | 7150 |
| CAAACAAAAA AACCACCGCT ACCAGCGGTG GTTTGTTTGC CGGATCAAGA | 7200 |
| GCTACCAACT CTTTTTCCGA AGGTAACTGG CTTCAGCAGA GCGCAGATAC | 7250 |
| CAAATACTGT CCTTCTAGTG TAGCCGTAGT TAGGCCACCA CTTCAAGAAC | 7300 |
| TCTGTAGCAC CGCCTACATA CCTCGCTCTG CTAATCCTGT TACCAGTGGC | 7350 |
| TGCTGCCAGT GGCGATAAGT CGTGTCTTAC CGGGTTGGAC TCAAGACGAT | 7400 |
| AGTTACCGGA TAAGGCGCAG CGGTCGGGCT GAACGGGGGG TTCGTGCACA | 7450 |
| CAGCCCAGCT TGGAGCGAAC GACCTACACC GAACTGAGAT ACCTACAGCG | 7500 |
| TGAGCATTGA GAAAGCGCCA CGCTTCCCGA AGGGAGAAAG GCGGACAGGT | 7550 |
| ATCCGGTAAG CGGCAGGGTC GGAACAGGAG AGCGCACGAG GGAGCTTCCA | 7600 |
| GGGGGAAACG CCTGGTATCT TTATAGTCCT GTCGGGTTTC GCCACCTCTG | 7650 |
| ACTTGAGCGT CGATTTTTGT GATGCTCGTC AGGGGGGCGG AGCCTATGGA | 7700 |
| AAAACGCCAG CAACGCGGCC TTTTTACGGT TCCTGGCCTT TTGCTGGCCT | 7750 |
| TTTGCTCACA TGTTCTTTCC TGCGTTATCC CCTGATTCTG TGGATAACCG | 7800 |
| TATTACCGCC TTTGAGTGAG CTGATACCGC TCGCCGCAGC CGAACGACCG | 7850 |
| AGCGCAGCGA GTCAGTGAGC GAGGAAGCGG AAGAGCGCCC AATACGCAAA | 7900 |
| CCGCCTCTCC CCGCGCGTTG GCCGATTCAT TAATCCAGCT GGCACGACAG | 7950 |
| GTTTCCCGAC TGGAAAGCGG GCAGTGAGCG CAACGCAATT AATGTGAGTT | 8000 |
| ACCTCACTCA TTAGGCACCC CAGGCTTTAC ACTTTATGCT TCCGGCTCGT | 8050 |
| ATGTTGTGTG GAATTGTGAG CGGATAACAA TTTCACACAG GAAACAGCTA | 8100 |
| TGACCATGAT TACGAATTAA | 8120 |

-continued (2) INFORMATION FOR SEQ ID NO: 69:

(i) SEQUENCE CHARACTERISTICS:
        (A) LENGTH: 800 base pairs
        (B) TYPE: Nucleic Acid
        (C) STRANDEDNESS: Single
        (D) TOPOLOGY: Linear (xi) SEQUENCE DESCRIPTION: SEQ ID NO: 69:

```
AAAAGGGTAT CTAGAGGTTG AGGTGATTTT ATGAAAAAGA ATATCGCATT           50

TCTTCTTGCA TCTATGTTCG TTTTTTCTAT TGCTACAAAC GCGTACGCTG          100

AGGTTCAGCT AGTGCAGTCT GGCGGTGGCC TGGTGCAGCC AGGGGGCTCA          150

CTCCGTTTGT CCTGTGCAGC TTCTGGCTAC TCCTTCTCGA GTCACTATAT          200

GCACTGGGTC CGTCAGGCCC CGGGTAAGGG CCTGGAATGG GTTGGATATA          250

TTGATCCTTC CAATGGTGAA ACTACGTATA ATCAAAAGTT CAAGGGCCGT          300

TTCACTTTAT CTCGCGACAA CTCCAAAAAC ACAGCATACC TGCAGATGAA          350

CAGCCTGCGT GCTGAGGACA CTGCCGTCTA TTACTGTGCA AGAGGGGATT          400

ATCGCTACAA TGGTGACTGG TTCTTCGACG TCTGGGGTCA AGGAACCCTG          450

GTCACCGTCT CCTCGGCCTC CACCAAGGGC CCATCGGTCT TCCCCCTGGC          500

ACCCTCCTCC AAGAGCACCT CTGGGGGCAC AGCGGCCCTG GGCTGCCTGG          550

TCAAGGACTA CTTCCCCGAA CCGGTGACGG TGTCGTGGAA CTCAGGCGCC          600

CTGACCAGCG GCGTGCACAC CTTCCCGGCT GTCCTACAGT CCTCAGGACT          650

CTACTCCCTC AGCAGCGTGG TGACCGTGCC CTCCAGCAGC TTGGGCACCC          700

AGACCTACAT CTGCAACGTG AATCACAAGC CCAGCAACAC CAAGGTCGAC          750

AAGAAAGTTG AGCCCAAATC TTGTGACAAA ACTCACACAT GCCCGCCTGA          800
```

(2) INFORMATION FOR SEQ ID NO: 70:

(i) SEQUENCE CHARACTERISTICS:
        (A) LENGTH: 256 amino acids
        (B) TYPE: Amino Acid
        (D) TOPOLOGY: Linear (xi) SEQUENCE DESCRIPTION: SEQ ID NO: 70:

```
Met Lys Lys Asn Ile Ala Phe Leu Leu Ala Ser Met Phe Val Phe
 1               5                  10                  15

Ser Ile Ala Thr Asn Ala Tyr Ala Glu Val Gln Leu Val Gln Ser
                20                  25                  30

Gly Gly Gly Leu Val Gln Pro Gly Gly Ser Leu Arg Leu Ser Cys
                35                  40                  45

Ala Ala Ser Gly Tyr Ser Phe Ser Ser His Tyr Met His Trp Val
                50                  55                  60

Arg Gln Ala Pro Gly Lys Gly Leu Glu Trp Val Gly Tyr Ile Asp
                65                  70                  75

Pro Ser Asn Gly Glu Thr Thr Tyr Asn Gln Lys Phe Lys Gly Arg
                80                  85                  90

Phe Thr Leu Ser Arg Asp Asn Ser Lys Asn Thr Ala Tyr Leu Gln
                95                 100                 105

Met Asn Ser Leu Arg Ala Glu Asp Thr Ala Val Tyr Tyr Cys Ala
               110                 115                 120

Arg Gly Asp Tyr Arg Tyr Asn Gly Asp Trp Phe Phe Asp Val Trp
               125                 130                 135
```

-continued

```
Gly Gln Gly Thr Leu Val Thr Val Ser Ser Ala Ser Thr Lys Gly
            140                 145                 150
Pro Ser Val Phe Pro Leu Ala Pro Ser Ser Lys Ser Thr Ser Gly
            155                 160                 165
Gly Thr Ala Ala Leu Gly Cys Leu Val Lys Asp Tyr Phe Pro Glu
            170                 175                 180
Pro Val Thr Val Ser Trp Asn Ser Gly Ala Leu Thr Ser Gly Val
            185                 190                 195
His Thr Phe Pro Ala Val Leu Gln Ser Ser Gly Leu Tyr Ser Leu
            200                 205                 210
Ser Ser Val Val Thr Val Pro Ser Ser Ser Leu Gly Thr Gln Thr
            215                 220                 225
Tyr Ile Cys Asn Val Asn His Lys Pro Ser Asn Thr Lys Val Asp
            230                 235                 240
Lys Lys Val Glu Pro Lys Ser Cys Asp Lys Thr His Thr Cys Pro
            245                 250                 255
Pro (2) INFORMATION FOR SEQ ID NO: 71:

(i) SEQUENCE CHARACTERISTICS:
        (A) LENGTH: 452 amino acids
        (B) TYPE: Amino Acid
        (D) TOPOLOGY: Linear (xi) SEQUENCE DESCRIPTION: SEQ ID NO: 71:

Glu Val Gln Leu Val Gln Ser Gly Gly Gly Leu Val Gln Pro Gly
 1               5                  10                  15
Gly Ser Leu Arg Leu Ser Cys Ala Ala Ser Gly Tyr Ser Phe Ser
             20                  25                  30
Ser His Tyr Met His Trp Val Arg Gln Ala Pro Gly Lys Gly Leu
             35                  40                  45
Glu Trp Val Gly Tyr Ile Asp Pro Ser Asn Gly Glu Thr Thr Tyr
             50                  55                  60
Asn Gln Lys Phe Lys Gly Arg Phe Thr Leu Ser Arg Asp Asn Ser
             65                  70                  75
Lys Asn Thr Ala Tyr Leu Gln Met Asn Ser Leu Arg Ala Glu Asp
             80                  85                  90
Thr Ala Val Tyr Tyr Cys Ala Arg Gly Asp Tyr Arg Tyr Asn Gly
             95                 100                 105
Asp Trp Phe Phe Asp Val Trp Gly Gln Gly Thr Leu Val Thr Val
            110                 115                 120
Ser Ser Ala Ser Thr Lys Gly Pro Ser Val Phe Pro Leu Ala Pro
            125                 130                 135
Ser Ser Lys Ser Thr Ser Gly Gly Thr Ala Ala Leu Gly Cys Leu
            140                 145                 150
Val Lys Asp Tyr Phe Pro Glu Pro Val Thr Val Ser Trp Asn Ser
            155                 160                 165
Gly Ala Leu Thr Ser Gly Val His Thr Phe Pro Ala Val Leu Gln
            170                 175                 180
Ser Ser Gly Leu Tyr Ser Leu Ser Ser Val Val Thr Val Pro Ser
            185                 190                 195
Ser Ser Leu Gly Thr Gln Thr Tyr Ile Cys Asn Val Asn His Lys
            200                 205                 210
```

-continued

```
Pro Ser Asn Thr Lys Val Asp Lys Lys Val Glu Pro Lys Ser Cys
                215                 220                 225

Asp Lys Thr His Thr Cys Pro Pro Cys Pro Ala Pro Glu Leu Leu
                230                 235                 240

Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp
                275                 280                 285

Gly Val Glu Val His Asn Ala Lys Thr Lys Pro Arg Glu Glu Gln
                290                 295                 300

Tyr Asn Ser Thr Tyr Arg Val Val Ser Val Leu Thr Val Leu His
                305                 310                 315

Gln Asp Trp Leu Asn Gly Lys Glu Tyr Lys Cys Lys Val Ser Asn
                320                 325                 330

Lys Ala Leu Pro Ala Pro Ile Glu Lys Thr Ile Ser Lys Ala Lys
                335                 340                 345

Gly Gln Pro Arg Glu Pro Gln Val Tyr Thr Leu Pro Pro Ser Arg
                350                 355                 360

Glu Glu Met Thr Lys Asn Gln Val Ser Leu Thr Cys Leu Val Lys
                365                 370                 375

Gly Phe Tyr Pro Ser Asp Ile Ala Val Glu Trp Glu Ser Asn Gly
                380                 385                 390

Gln Pro Glu Asn Asn Tyr Lys Thr Thr Pro Pro Val Leu Asp Ser
                395                 400                 405

Asp Gly Ser Phe Phe Leu Tyr Ser Lys Leu Thr Val Asp Lys Ser
                410                 415                 420

Arg Trp Gln Gln Gly Asn Val Phe Ser Cys Ser Val Met His Glu
                425                 430                 435

Ala Leu His Asn His Tyr Thr Gln Lys Ser Leu Ser Leu Ser Pro
                440                 445                 450

Gly Lys (2) INFORMATION FOR SEQ ID NO: 72:

(i) SEQUENCE CHARACTERISTICS:
        (A) LENGTH: 219 amino acids
        (B) TYPE: Amino Acid
        (D) TOPOLOGY: Line (xi) SEQUENCE DESCRIPTION: SEQ ID NO: 72:

Asp Ile Gln Met Thr Gln Ser Pro Ser Ser Leu Ser Ala Ser Val
 1               5                  10                  15

Gly Asp Arg Val Thr Ile Thr Cys Arg Ser Ser Gln Ser Leu Val
                20                  25                  30

His Gly Ile Gly Ala Thr Tyr Leu His Trp Tyr Gln Gln Lys Pro
                35                  40                  45

Gly Lys Ala Pro Lys Leu Leu Ile Tyr Lys Val Ser Asn Arg Phe
                50                  55                  60

Ser Gly Val Pro Ser Arg Phe Ser Gly Ser Gly Ser Gly Thr Asp
                65                  70                  75

Phe Thr Leu Thr Ile Ser Ser Leu Gln Pro Glu Asp Phe Ala Thr
                80                  85                  90

Tyr Tyr Cys Ser Gln Ser Thr His Val Pro Leu Thr Phe Gly Gln
```

-continued

```
               95                  100                 105
Gly Thr Lys Val Glu Ile Lys Arg Thr Val Ala Ala Pro Ser Val
               110                 115                 120
Phe Ile Phe Pro Pro Ser Asp Glu Gln Leu Lys Ser Gly Thr Ala
               125                 130                 135
Ser Val Val Cys Leu Leu Asn Asn Phe Tyr Pro Arg Glu Ala Lys
               140                 145                 150
Val Gln Trp Lys Val Asp Asn Ala Leu Gln Ser Gly Asn Ser Gln
               155                 160                 165
Glu Ser Val Thr Glu Gln Asp Ser Lys Asp Ser Thr Tyr Ser Leu
               170                 175                 180
Ser Ser Thr Leu Thr Leu Ser Lys Ala Asp Tyr Glu Lys His Lys
               185                 190                 195
Val Tyr Ala Cys Glu Val Thr His Gln Gly Leu Ser Ser Pro Val
               200                 205                 210
Thr Lys Ser Phe Asn Arg Gly Glu Cys
               215
```

ANTIBODY FRAGMENT-POLYMER CONJUGATES AND HUMANIZED ANTI-IL-8 MONOCLONAL ANTIBODIES

This is a 35 U.S.C. §371 application of International Application No. PCT/US98/03337 filed Feb. 20, 1998, now inactive, which claims priority under 35 U.S.C. §§120 and 365 to non-provisional application U.S. Ser. No. 08/804,444 filed on Feb. 21, 1997, now granted a U.S. Pat. No. 6,117,980, and to its continuation-in-part application U.S. Ser. No. 09/012,116 filed on Jan. 22, 1998, now abandoned, of which the present application is a continuation.

FIELD OF THE INVENTION

A This application relates to the field of antibody fragments derivatized with polymers, and in particular to the use of such derivatization to increase the circulation half-lives of antibody fragment-polymer conjugates. This application also relates to humanized anti-interleukin-8 (IL-8) antibodies and to high affinity variants of such antibodies.

BACKGROUND

Modification of proteins with polyethylene glycol ("PEGylation") has the potential to increase residence time and reduce immunogenicity in vivo. For example, Knauf et al., *J. Biol. Chem.*, 263: 15064–15070 (1988) reported a study of the pharmacodynamic behavior in rats of various polyoxylated glycerol and polyethylene glycol modified species of interleukin-2. Despite the known advantage of PEGylation, PEGylated proteins have not been widely exploited for clinical applications. In the case of antibody fragments, PEGylation has not been shown to extend serum half-life to useful levels. Delgado et al., *Br. J. Cancer*, 73: 175–182 (1996), Kitamura et al., *Cancer Res.*, 51: 4310–4315 (1991), Kitamura et al., *Biochem. Biophys. Res. Comm.*, 171: 1387–1394 (1990), and Pedley et al., *Br. J. Cancer*, 70: 1126–1130 (1994) reported studies characterizing blood clearance and tissue uptake of certain anti-tumor antigen antibodies or antibody fragments derivatized with low molecular weight (5 kD) PEG. Zapata et al., *FASEB J.*, 9: A1479 (1995) reported that low molecular weight (5 or 10 kD) PEG attached to a sulfhydryl group in the hinge region of a Fab' fragment reduced clearance compared to the parental Fab' molecule.

Interleukin-8 (IL-8) is neutrophil chemotactic peptide secreted by a variety of cells in response to inflammatory mediators (for a review see Hebert et al. *Cancer Investigation* 11(6):743 (1993)). IL-8 can play an important role in the pathogenesis of inflammatory disorders, such as adult respiratory distress syndrome (ARDS), septic shock, and multiple organ failure. Immune therapy for such inflammatory disorders can include treatment of an affected patient with anti-IL-8 antibodies.

Sticherling et al. (*J. Immunol.* 143:1628 (1989)) disclose the production and characterization of four monoclonal antibodies against IL-8. WO 92/04372, published Mar. 19, 1992, discloses polyclonal antibodies which react with the receptor-interacting site of IL-8 and peptide analogs of IL-8, along with the use of such antibodies to prevent an inflammatory response in patients. St. John et al. (*Chest* 103:932 (1993)) review immune therapy for ARDS, septic shock, and multiple organ failure, including the potential therapeutic use of anti-IL-8 antibodies. Sekido et al. *Nature* 365:654 (1993)) disclose the prevention of lung reperfusion injury in rabbits by a monoclonal antibody against IL-8. Mulligan et al. (*J. Immunol.* 150:5585 (1993)), disclose protective effects of a murine monoclonal antibody to human IL-8 in inflammatory lung injury in rats.

WO 95/23865 (International Application No. PCT/US95/02589 published Sep. 8, 1995) demonstrates that anti-IL-8 monoclonal antibodies can be used therapeutically in the treatment of other inflammatory disorders, such as bacterial pneumonias and inflammatory bowel disease.

Anti-IL-8 antibodies are additionally useful as reagents for assaying IL-8. For example, Sticherling et al. (*Arch. Dermatol. Res.* 284:82 (1992)), disclose the use of anti-IL-8 monoclonal antibodies as reagents in immunohistochemical studies. Ko et al. (*J. Immunol. Methods* 149:227 (1992)) disclose the use of anti-IL-8 monoclonal antibodies as reagents in an enzyme-linked immunoabsorbent assay (ELISA) for IL-8.

SUMMARY OF THE INVENTION

One aspect of the invention is a conjugate consisting essentially of one or more antibody fragments covalently attached to one or more polymer molecules, wherein the apparent size of the conjugate is at least about 500 kD.

Another aspect of the invention is an anti-IL-8 monoclonal antibody or antibody fragment comprising the complementarity determining regions of the 6G4.2.5LV11N35E light chain polypeptide amino acid sequence of FIG. 45 (SEQ ID NO:62).

Further aspects of the invention are a nucleic acid molecule comprising a nucleic acid sequence encoding the above-described anti-IL-8 monoclonal antibody or antibody fragment; an expression vector comprising the nucleic acid molecule operably linked to control sequences recognized by a host cell transfected with the vector; a host cell transfected with the vector; and a method of producing the antibody fragment comprising culturing the host cell under conditions wherein the nucleic acid encoding the antibody fragment is expressed, thereby producing the antibody fragment, and recovering the antibody fragment from the host cell.

BRIEF DESCRIPTION OF THE FIGURES

FIG. 11A depicts myeloperoxidase levels in tissue; FIG. 11B depicts IL-8 levels in tissue; FIG. 11C depicts colon weight; FIG. 11D depicts gross inflammation; FIG. 11E depicts edema; FIG. 11F depicts extent of necrosis; FIG. 11G depicts severity of necrosis; FIG. 11H depicts neutrophil margination; FIG. 11I depicts neutrophil infiltration; and FIG. 11J depicts mononuclear infiltration.

FIG. 13 depicts the DNA sequences (SEQ ID NOS: 1–6) of three primers designed for each of the light and heavy chains. Multiple primers were designed in order to increase the chances of primer hybridization and efficiency of first strand cDNA synthesis for cloning the variable light and heavy regions of monoclonal antibody 5.12.14.

FIG. 14 depicts the DNA sequences (SEQ ID NOS: 7–10) of one forward primer and one reverse primer for the 5.12.14 light chain variable region amplification.

FIG. 15 depicts the DNA sequences (SEQ ID NOS: 11–15) of one forward primer and one reverse primer for the 5.12.14 heavy chain variable region amplification.

FIG. 16 depicts the DNA sequence (SEQ ID NO: 16) and the amino acid sequence (SEQ ID NO: 17) of the 5.12.14 light chain variable region and partial murine constant light region. CDRs are indicated by either X-ray crystallography (underlined amino acids) or by Kabat sequence comparison (amino acids denoted with asterisk). Important restriction sites are indicated in italics. The signal peptide of STII is amino acids −23 to −1. The murine variable light region is amino acids 1 to 109. The partial murine constant light region is amino acids 110 to 123 (in italics).

FIG. 17 depicts the DNA sequence (SEQ ID NO: 18) and the amino acid sequence (SEQ ID NO: 19) of the 5.12.14 heavy chain variable region and partial murine constant heavy region. CDRs are indicated by either X-ray crystallography (underlined amino acids) or by Kabat sequence comparison (amino acids denoted with asterisk). Important restriction sites are indicated in italics. The signal peptide of STII is amino acids −23 to −1. The murine variable heavy region is amino acids 1 to 120. The partial murine constant heavy region is amino acids 121 to 130.

FIG. 18 depicts the DNA sequences (SEQ ID NOS: 20–23) of amplification primers used to convert murine light and heavy chain constant region residues to their human equivalents.

FIG. 19 depicts the DNA sequence (SEQ ID NO: 24) and the amino acid sequence (SEQ ID NO: 25) for the 5.12.14 light chain variable region and the human IgG1 light chain constant region. CDRs are indicated by either X-ray crystallography (underlined amino acids) or by Kabat sequence comparison (amino acids denoted with asterisk). The human constant region is denoted in italics. The signal peptide of STII is amino acids −23 to −1. The murine variable light region is amino acids 1 to 109. The human constant light region is amino acids 110 to 215.

FIGS. 20A–20B depict the DNA sequence (SEQ ID NO: 26) and the amino acid sequence (SEQ ID NO: 27) for the 5.12.14 heavy chain variable region and the heavy chain constant region of human IgG1. CDRs are indicated by either X-ray crystallography (underlined amino acids) or by Kabat sequence comparison (amino acids denoted with asterisk). The human constant region is denoted in italics. The signal peptide of STII is amino acids −23 to −1. The murine variable heavy region is amino acids 1 to 120. The human constant heavy region is amino acids 121 to 229.

FIG. 21 depicts the DNA sequences (SEQ ID NOS: 1–6) of three primers designed for each of the light and heavy chains. Multiple primers were designed in order to increase the chances of primer hybridization and efficiency of first strand cDNA synthesis for cloning the variable light and heavy regions of monoclonal antibody 6G4.2.5.

FIG. 22 depicts the DNA sequences (SEQ ID NOS: 28–31) of one forward primer and one reverse primer for the 6G4.2.5 light chain variable region amplification.

FIG. 23 depicts the DNA sequences (SEQ ID NOS: 32,33,11,15,14, and 13) of one forward primer and one reverse primer for the 6G4.2.5 heavy chain variable region amplification.

FIG. 24 depicts the DNA sequence (SEQ ID NO: 34) and the amino acid sequence (SEQ ID NO: 35) of the 6G4.2.5 light chain variable region and partial murine constant light region. CDRs are indicated by either X-ray crystallography (underlined amino acids) or by Kabat sequence comparison (amino acids denoted with asterisk). Useful cloning sites are in italics. The signal peptide of STII is amino acids −23 to −1. The murine variable light region is amino acids 1 to 114. The partial murine constant light region is amino acids 115 to 131.

FIG. 25 depicts the DNA sequence (SEQ ID NO: 36) and the amino acid sequence (SEQ ID NO: 37) of the 6G4.2.5 heavy chain variable region and partial murine constant heavy region. CDRs are indicated by either X-ray crystallography (underlined amino acids) or by Kabat sequence comparison (amino acids denoted with asterisk). Useful cloning sites are in italics. The signal peptide of STII is amino acids −23 to −1. The murine variable heavy region is amino acids 1 to 122. The partial murine constant heavy region is amino acids 123 to 135.

FIG. 26 depicts the DNA sequences (SEQ ID NOS: 38–40) of primers to convert the murine light chain and heavy chain constant regions to their human equivalents.

FIGS. 27A–27B depict the DNA sequence (SEQ ID NO: 41) and the amino acid sequence (SEQ ID NO: 42) for the chimeric 6G4.2.5 light chain. CDRs are indicated by either X-ray crystallography (underlined amino acids) or by Kabat sequence comparison (amino acids denoted with asterisk). The human constant region is denoted in italics. The signal peptide of STII is amino acids −23 to −1. The murine variable heavy region is amino acids 1 to 114. The human constant heavy region is amino acids 115 to 220.

FIGS. 28A–28B depict the DNA sequence (SEQ ID NO: 43) and the amino acid sequence (SEQ ID NO: 44) for the chimeric 6G4.2.5 heavy chain. CDRs are indicated by either X-ray crystallography (underlined amino acids) or by Kabat sequence comparison (amino acids denoted with asterisk). The human constant region is denoted in italics. The signal peptide of STII is amino acids −23 to −1. The murine variable heavy region is amino acids 1 to 122. The human constant heavy region is amino acids 123 to 231.

FIG. 29 depicts an amino acid sequence alignment of murine 6G425 light chain variable domain (SEQ ID NO: 45), humanized 6G425 F(ab)-1 light chain variable domain (SEQ ID NO: 46), and human light chain κI consensus framework (SEQ ID NO: 47) amino acid sequences, and an amino acid sequence alignment of murine 6G425 heavy chain variable domain (SEQ ID NO: 48), humanized 6G425 F(ab)-1 heavy chain variable domain (SEQ ID NO: 49), and human IgG1 subgroup III heavy chain variable domain (SEQ ID NO: 50) amino acid sequences, used in the humanization of 6G425. Light chain CDRs are labeled L1, L2, L3; heavy chain CDRs are labeled H1, H2, and H3. = and + indicate CDR sequences as defined by X-ray crystallographic contacts and sequence hypervariability, respectively. # indicates a difference between the aligned sequences. Residue numbering is according to Kabat et al. Lower case lettering denotes the insertion of an amino acid residue relative to the humIII consensus sequence numbering.

FIG. 31A depicts the amino acid sequences of the humanized anti-IL-8 6G4.2.5V11 light chain in an N-terminal fusion with the STII leader peptide (SEQ ID NO: 51), the humanized anti-IL-8 6G4.2.5V11 heavy chain in an N-terminal fusion with the STII leader peptide (SEQ ID NO: 52), and a peptide linker in a C-terminal fusion with M13 phage gene-III coat protein (SEQ ID NO: 53).

FIG. 31B depicts the nucleic acid sequence (SEQ ID NO: 54) and the translated amino acid sequence (SEQ ID NO: 51) of the humanized anti-IL-8 6G4.2.5V11 light chain in an N-terminal fusion with the STII leader peptide.

FIG. 31C depicts the amino acid sequences of the humanized anti-IL-8 6G4.2.5V19 light chain in an N-terminal fusion with the STII leader peptide (SEQ ID NO: 51), and the humanized anti-IL-8 6G4.2.5V19 heavy chain in an N-terminal fusion with the STII leader peptide (SEQ ID NO: 55).

FIG. 35 depicts the amino acid sequences of the humanized anti-IL-8 6G4.2.5V11N35A light chain in an N-terminal fusion with the STII leader peptide (SEQ ID NO: 56), the humanized anti-IL-8 6G4.2.5V11N35A heavy chain in an N-terminal fusion with the STII leader peptide (SEQ ID NO: 52), and the GCN4 leucine zipper peptide (SEQ ID NO: 57). The Ala residue (substituted for the wild type Asn residue) at amino acid position 35 in the 6G4.2.5V11N35A light chain appears in bold case. A putative pepsin cleavage site in the GCN4 leucine zipper sequence is underlined.

FIG. 36 depicts the DNA sequence (SEQ ID NO: 58) and the amino acid sequence (SEQ ID NO: 56) of the humanized anti-IL-8 6G4.2.5V11N35A light chain in an N-terminal fusion with the STII leader peptide. Complementarity determining regions L1, L2, and L3 are underlined.

FIGS. 37A–37B depict the DNA sequence (SEQ ID NO: 59) and the amino acid sequence (SEQ ID NO: 60) of the humanized anti-IL-8 6G4.2.5V11N35A heavy chain in an N-terminal fusion with the STII leader peptide and in a C-terminal fusion with the GCN4 leucine zipper sequence. Complementarity determining regions H1, H2, and H3 are underlined.

Figure 41A:
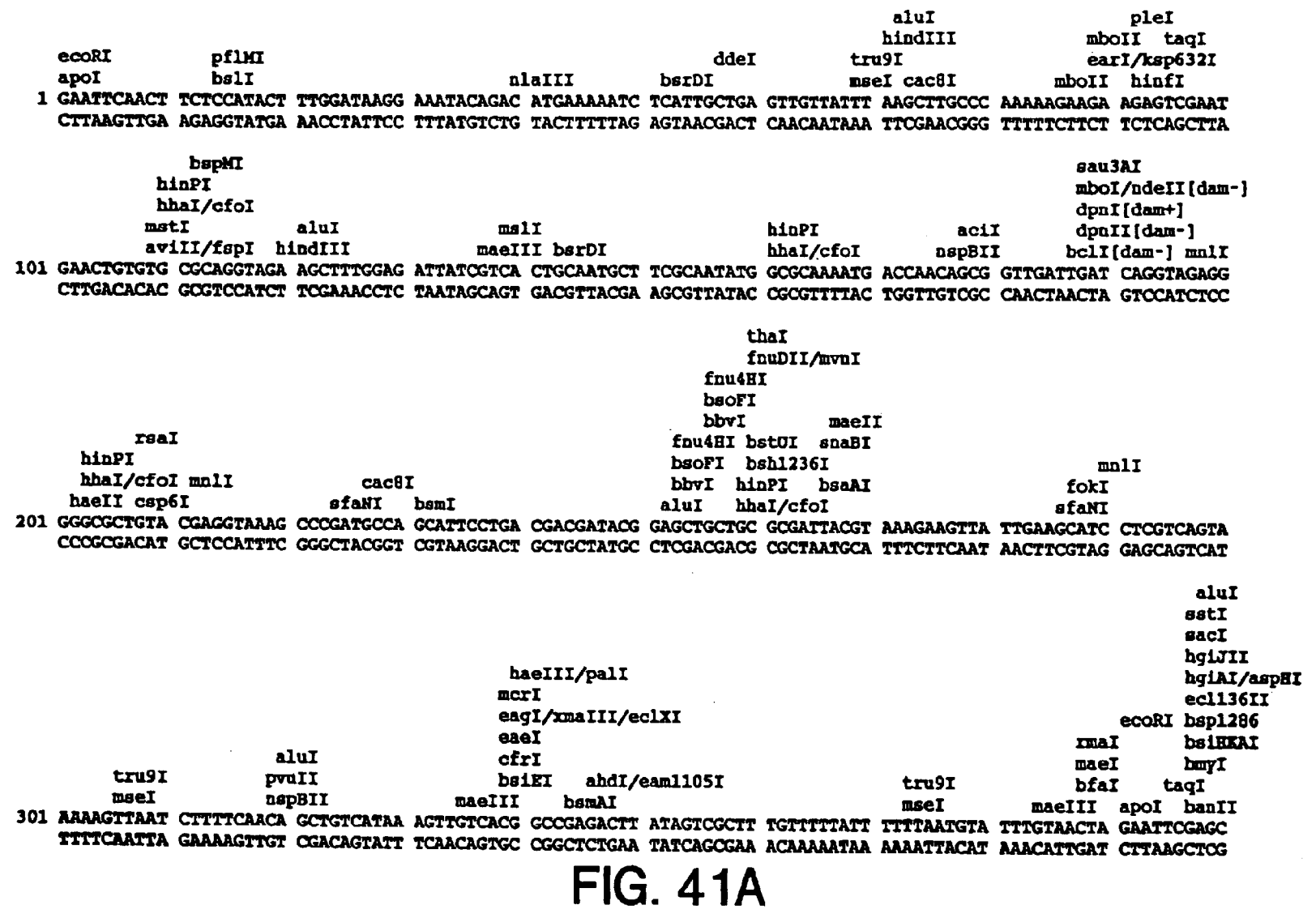
Figure 41D:
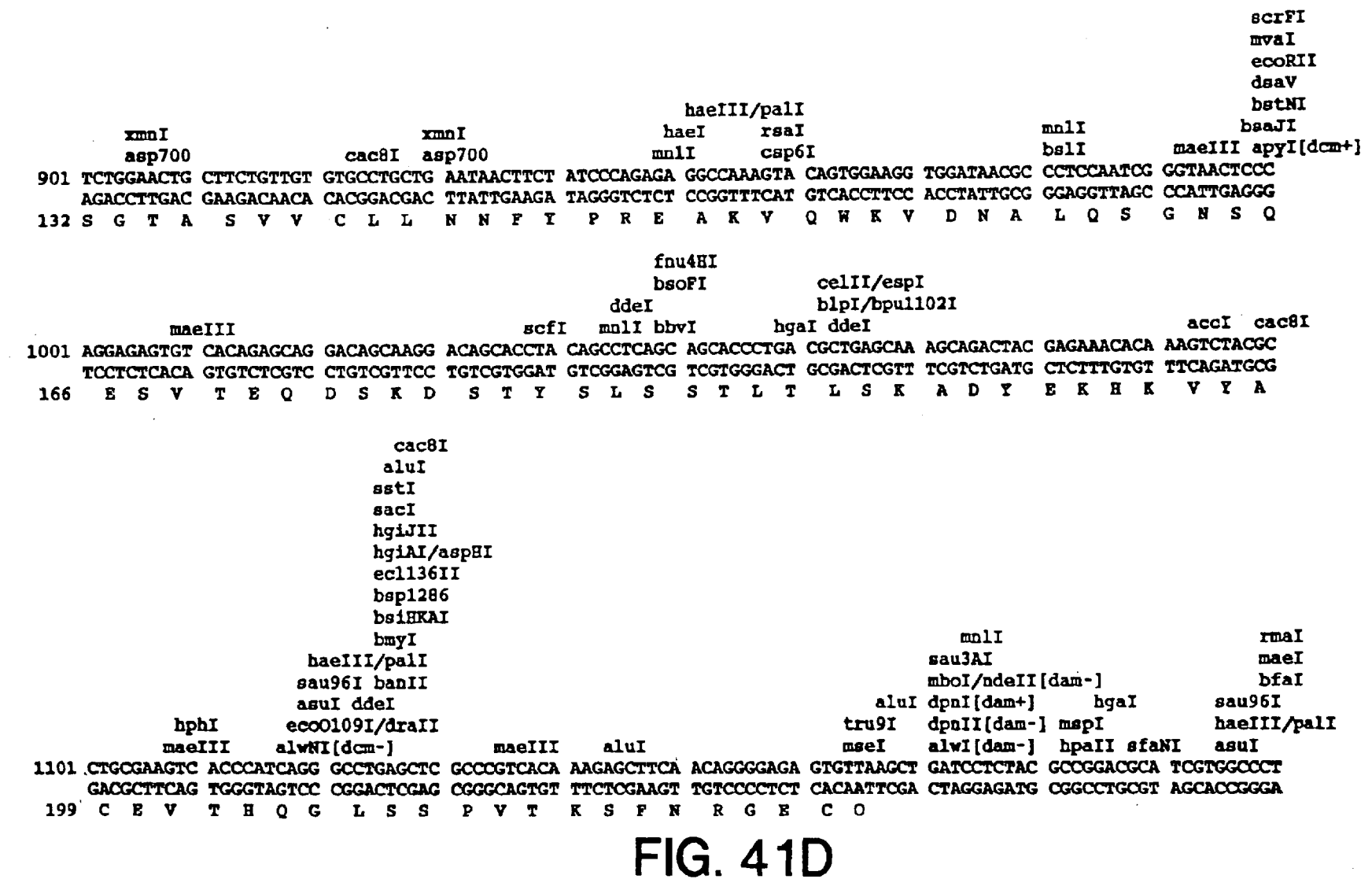
Figure 41F:
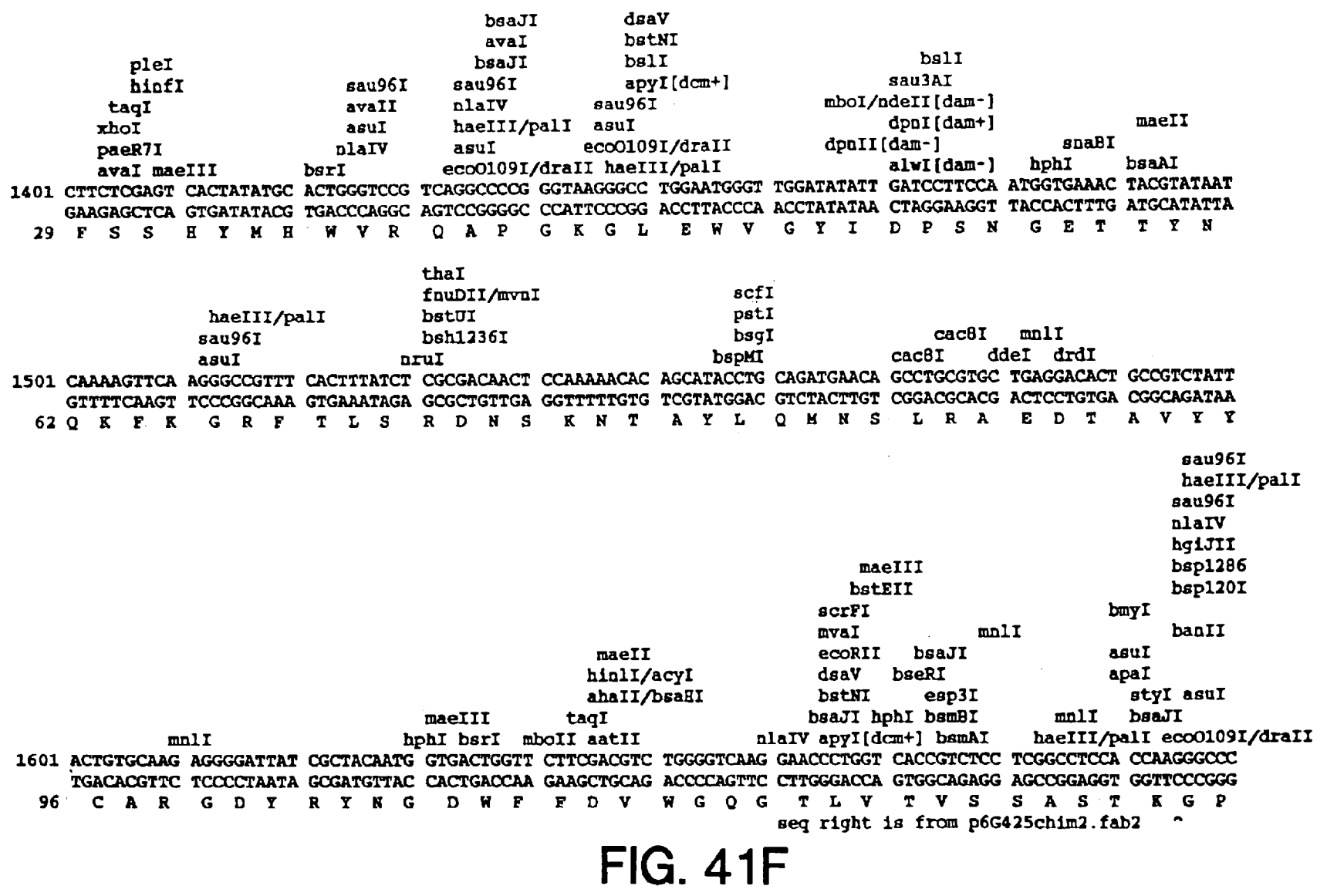
Figure 41G:
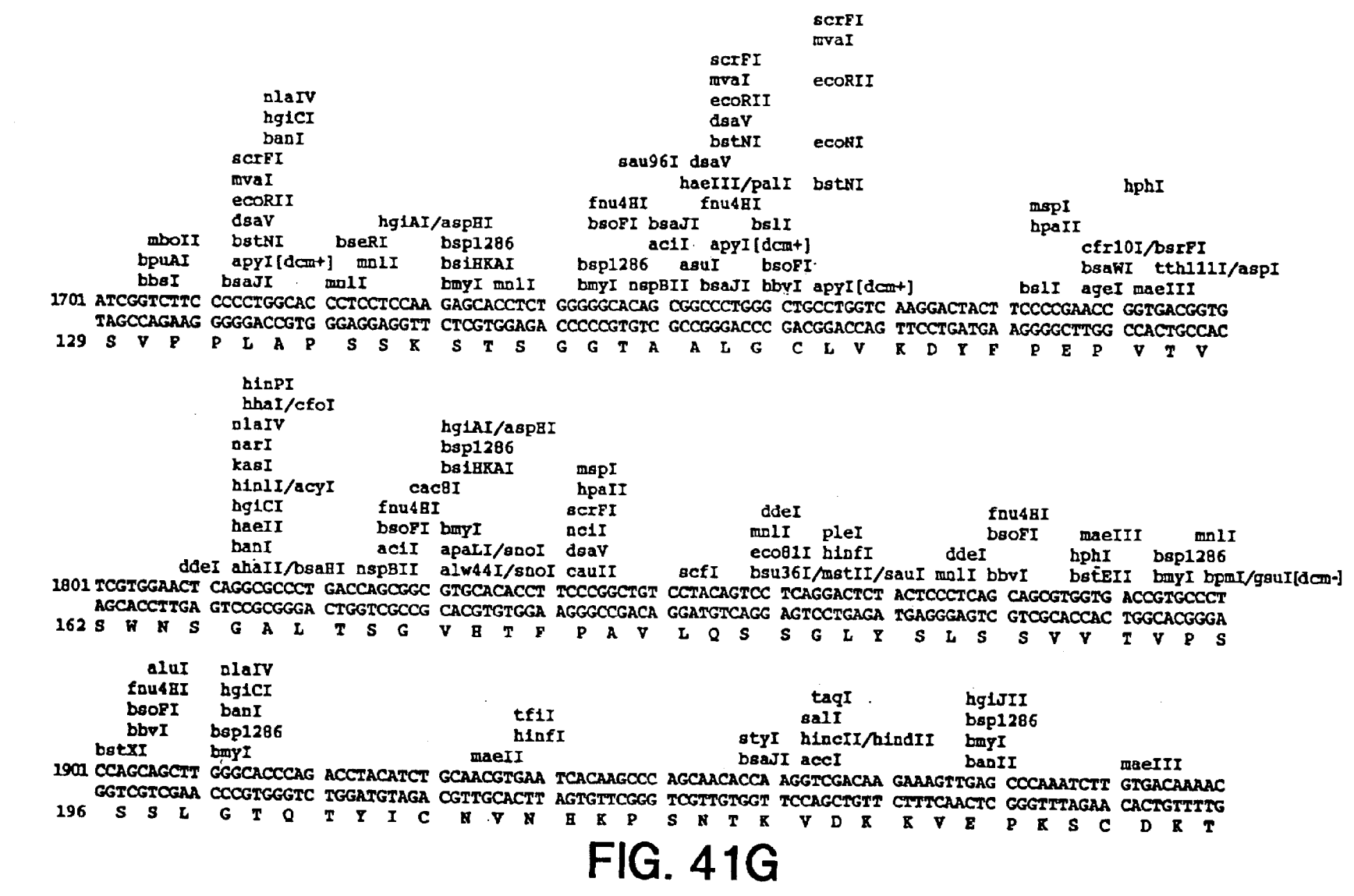
Figure 41J:
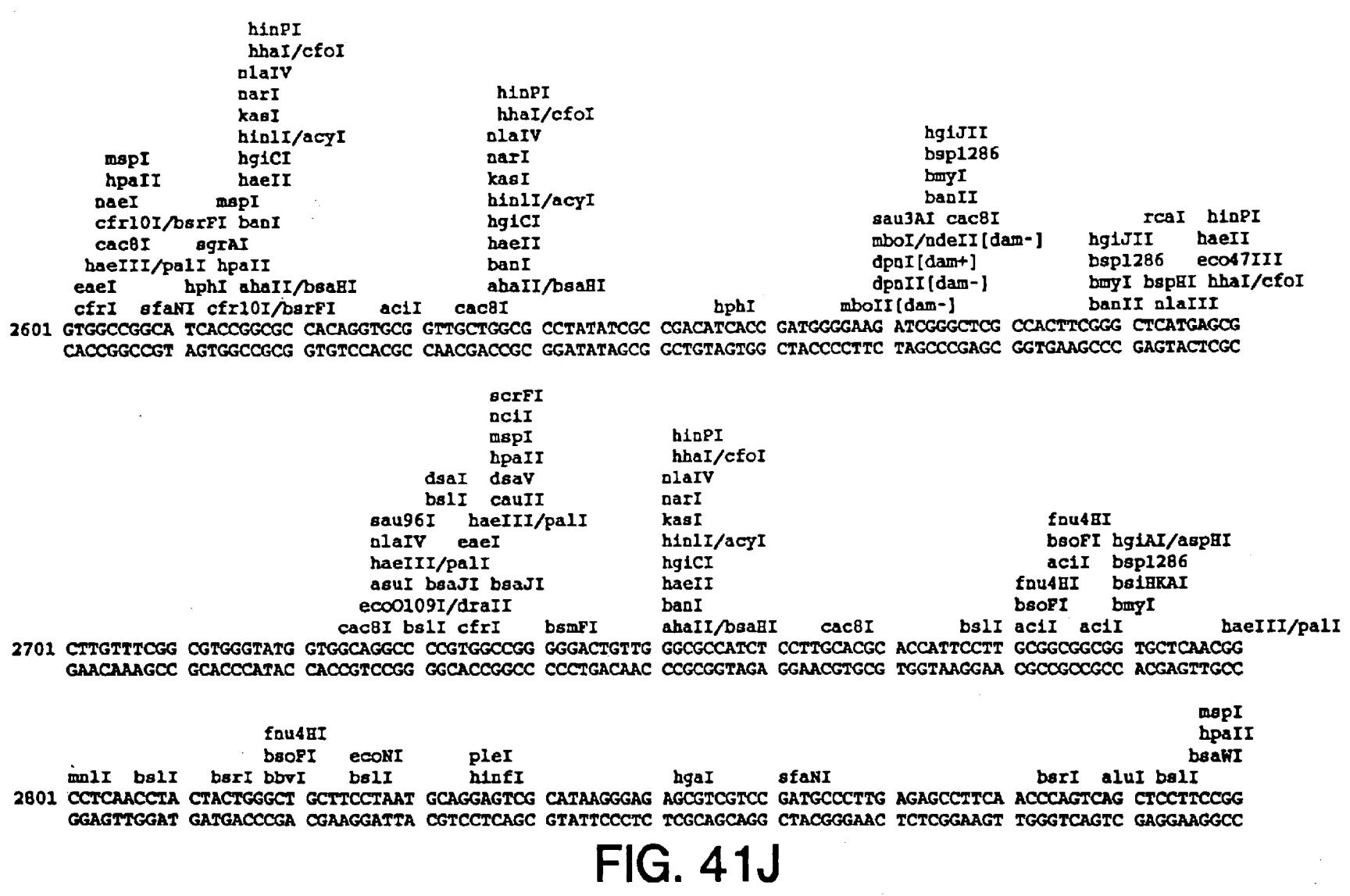
Figure 41L:
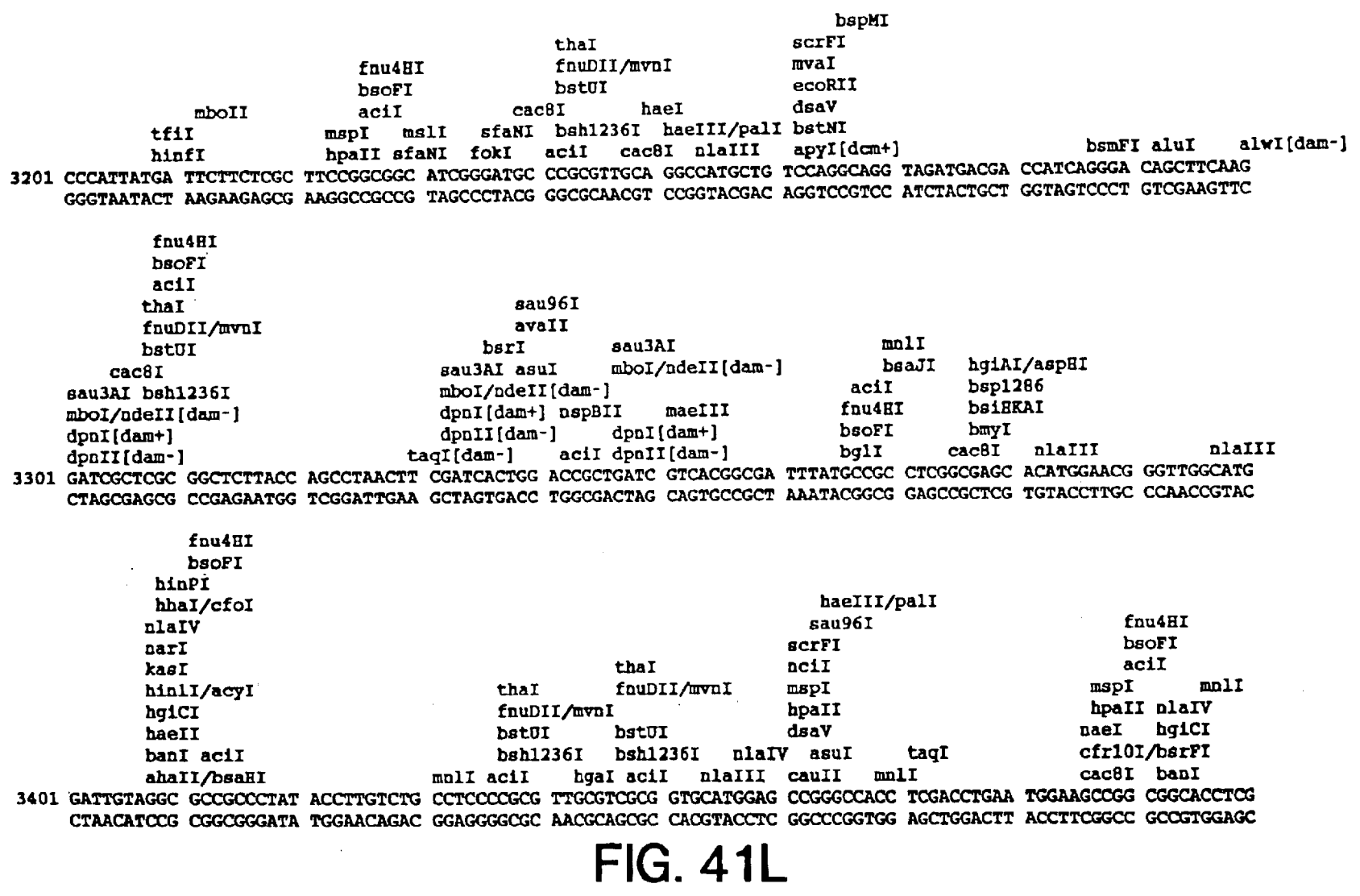
Figure 41R:
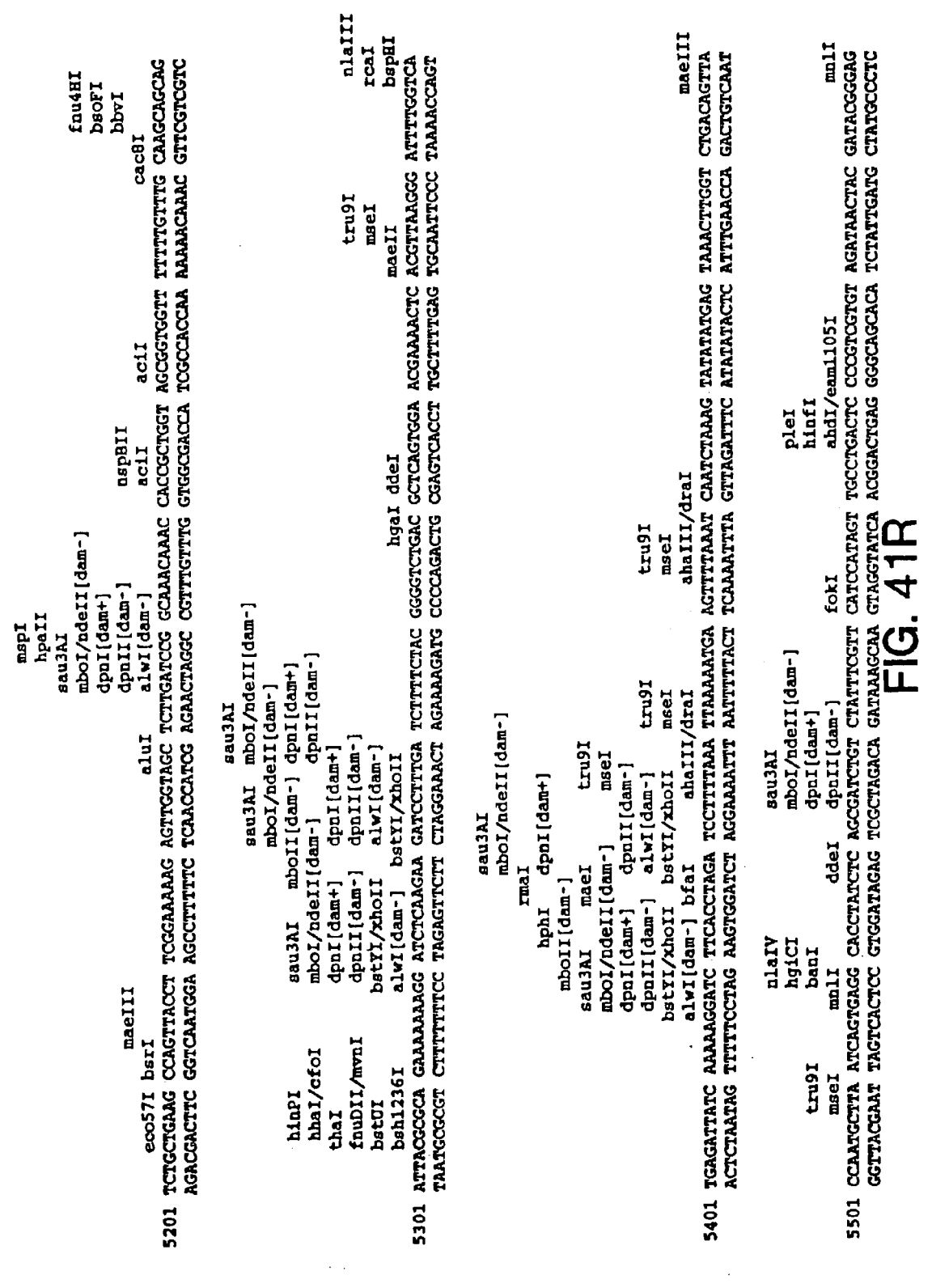
Figure 41S:
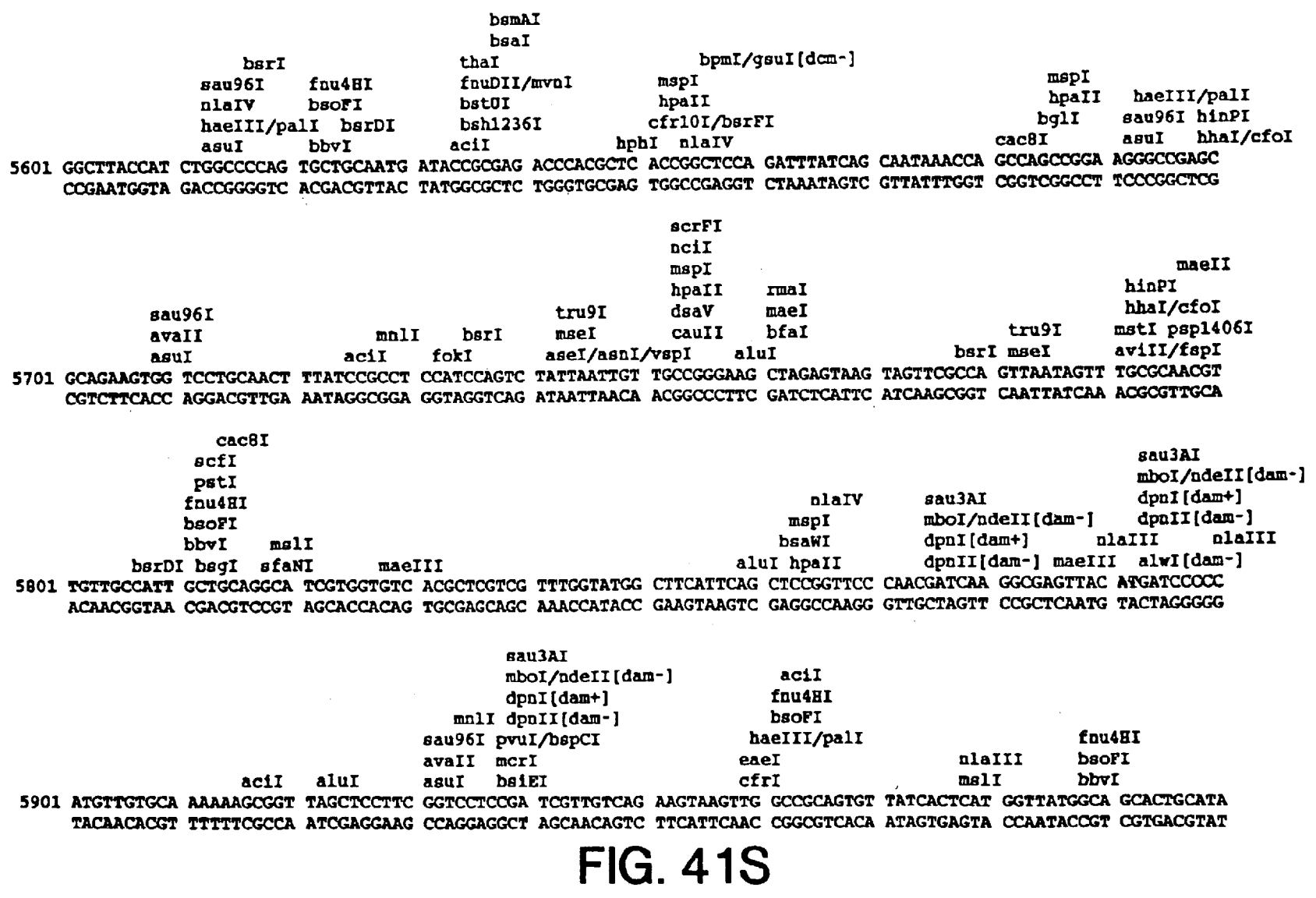

FIGS. 41A–41V depict the nucleic acid sequence (SEQ ID NO: 61) of the p6G4V11N35A.F(ab')$_2$ vector.

FIG. 42 depicts the nucleic acid sequences of the stop template primer (SEQ ID NO: 63) and the NNS randomization primer (SEQ ID NO: 64) used for random mutagenesis of amino acid position 35 in variable light chain CDR-L1 of humanized antibody 6G4V11.

FIG. 43A is a table of data describing the frequencies of different phage display clones obtained from the randomization of amino acid position 35 in variable light chain CDR-L1 of humanized antibody 6G4V11.

FIG. 44 also contains a table of data providing the equilibrium constant for 6G4V11N35A Fab binding to IL-8 (rate constants were not determined "ND"), and the equilibrium and rate constants for 6G4V11N35A F(ab') and 6G4V11N35E Fab binding to IL-8.

FIG. 45 depicts the DNA sequence (SEQ ID NO: 65) and amino acid sequence (SEQ ID NO: 62) of the 6G4V11N35E light chain in an N-terminal fusion with the STII leader peptide. Complementarity determining regions L1, L2 and L3 are underlined.

FIG. 47 depicts the DNA sequence of the sense (SEQ ID NO: 66) and anti-sense (SEQ ID NO: 67) strands of a PvuII-XhoI synthetic nucleotide encoding amino acids Leu4 to Phe29 of the 6G4V11N35A heavy chain.

Figure 48B:
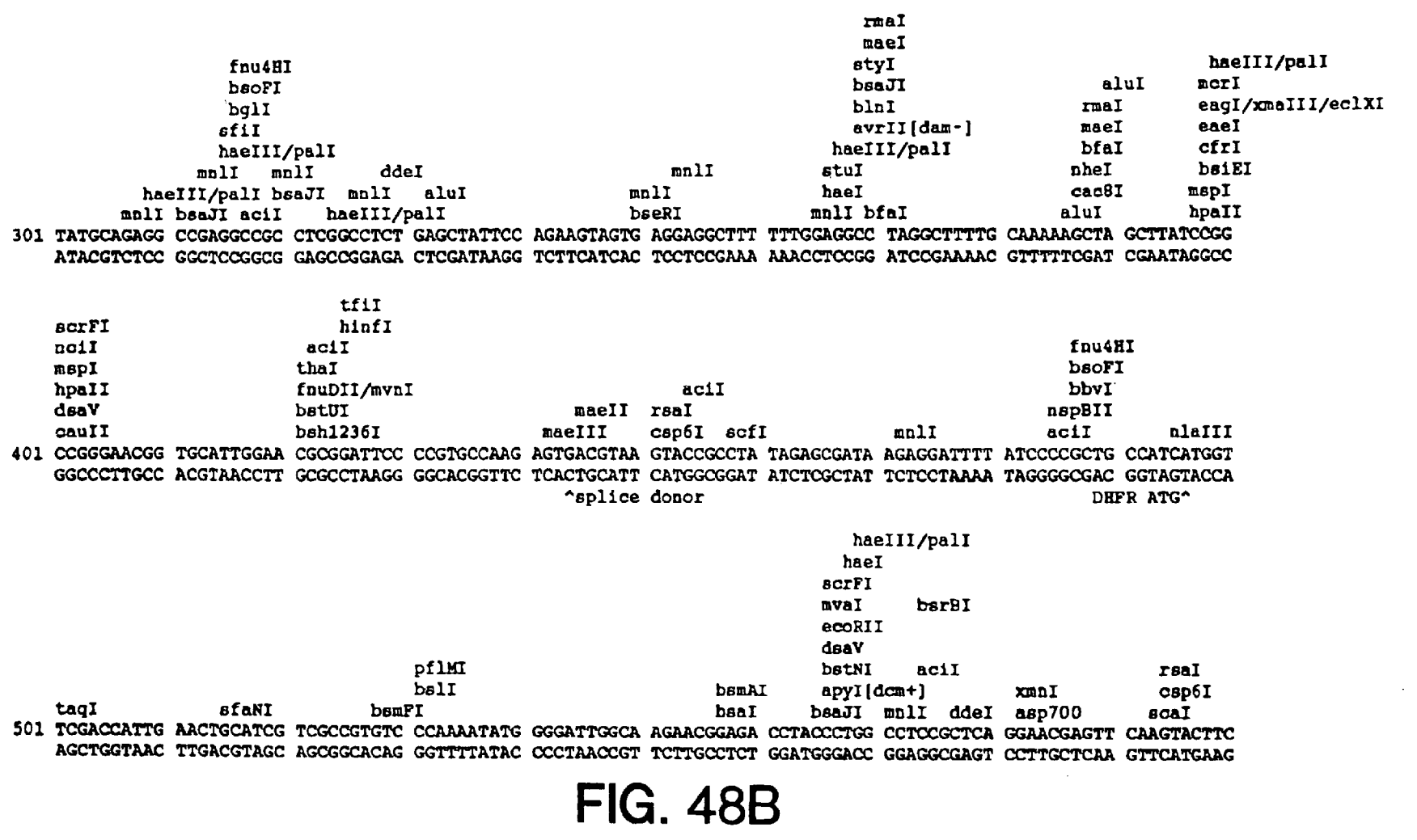
Figure 48C:
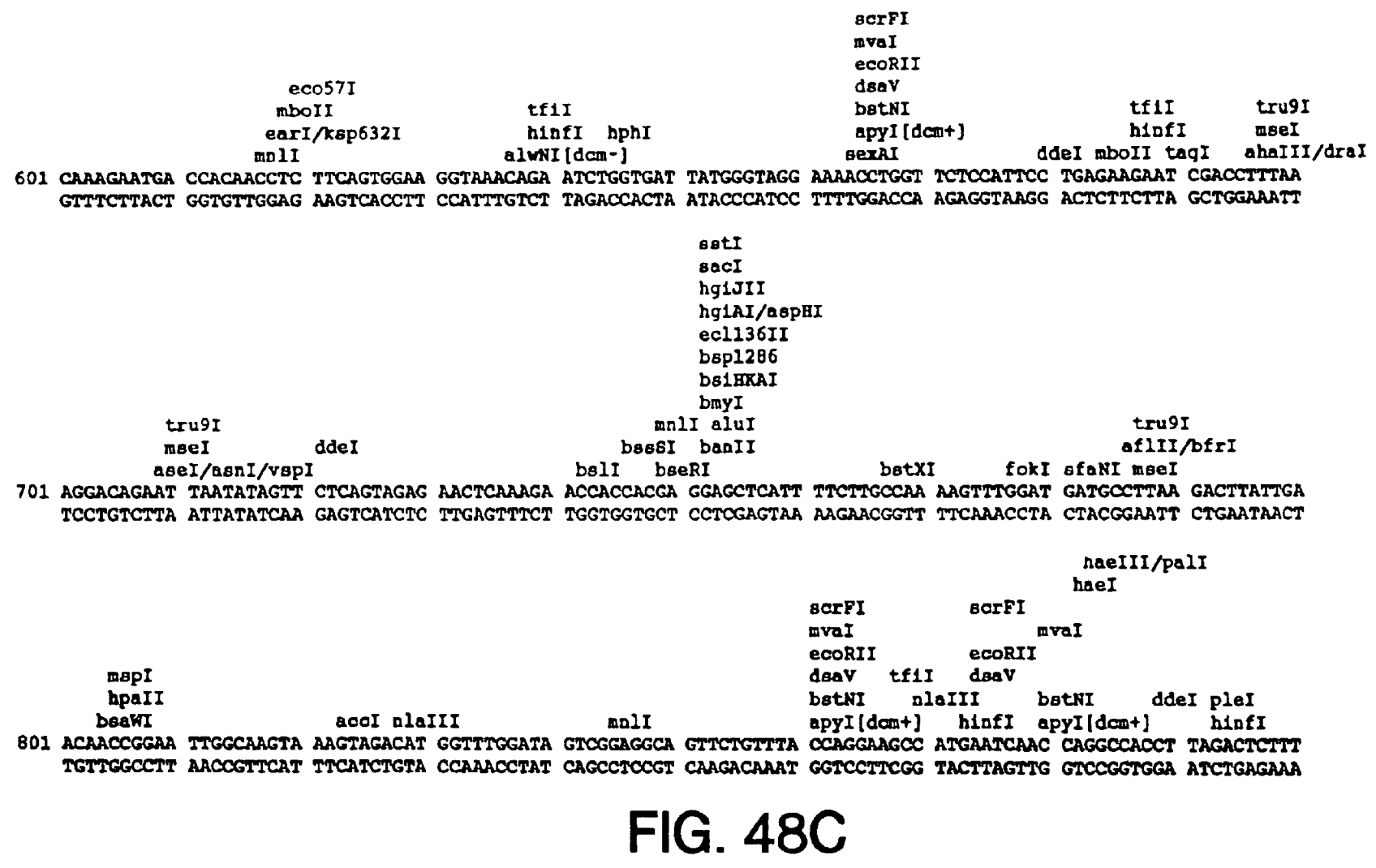
Figure 48E:
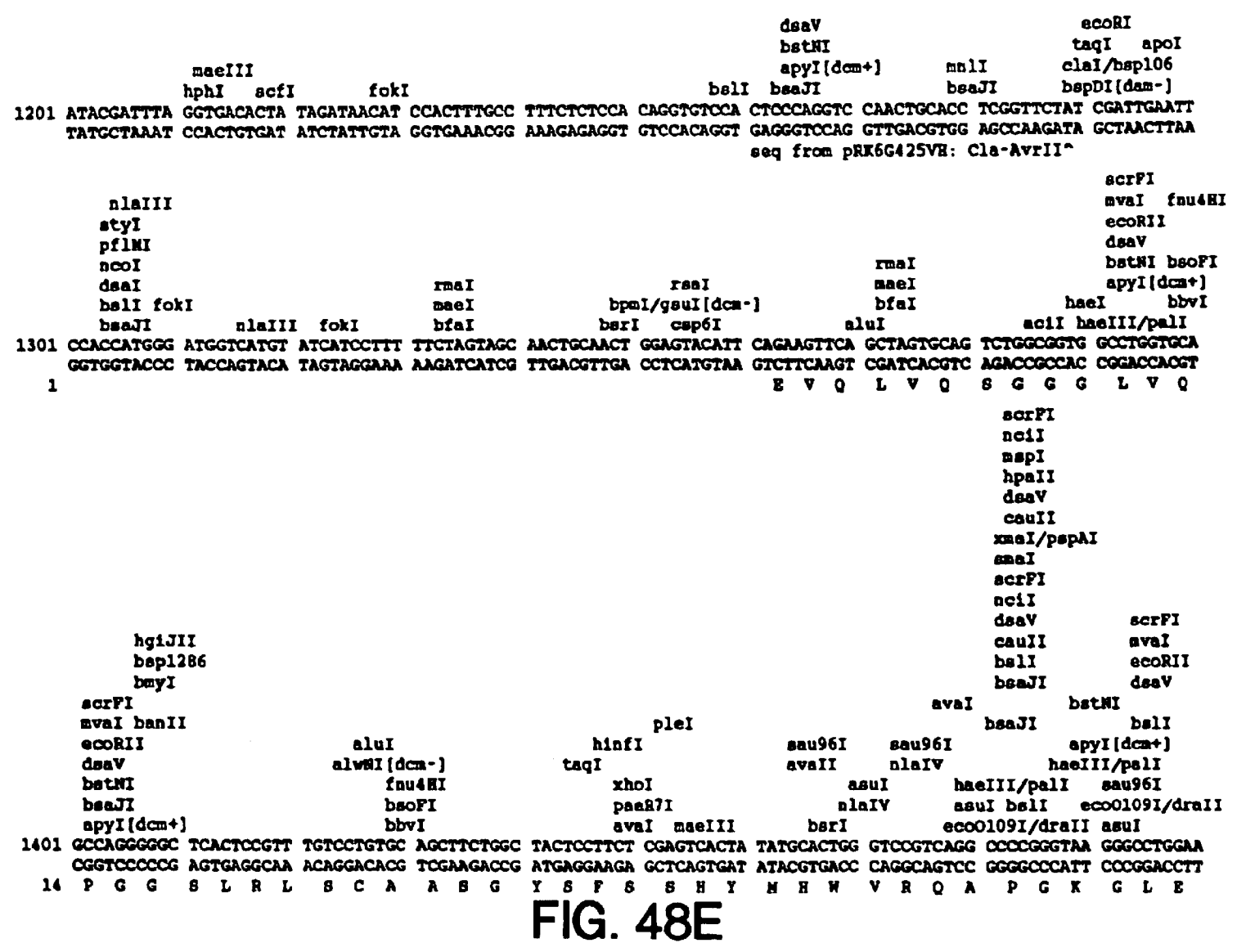
Figure 48F:
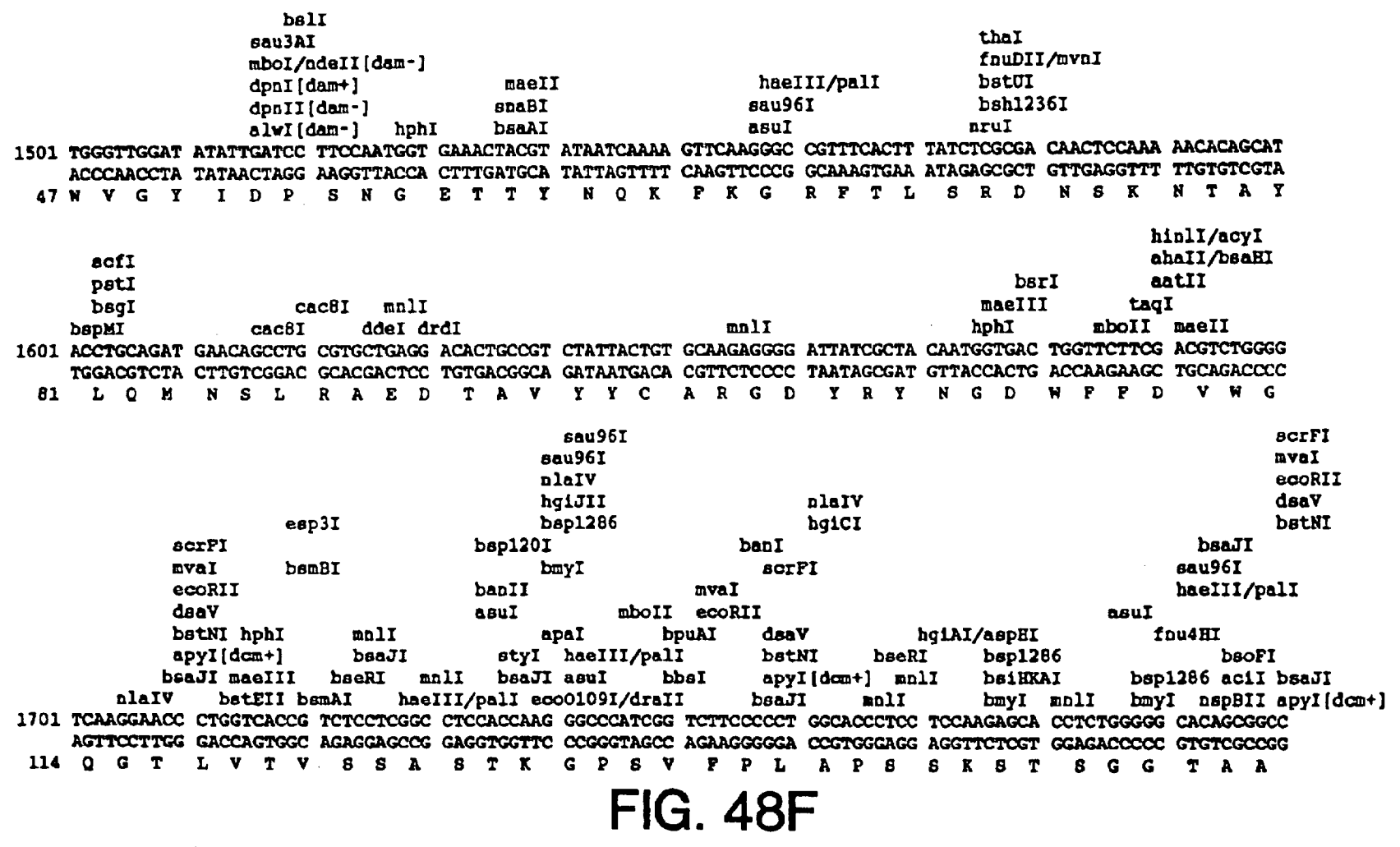
Figure 48G:
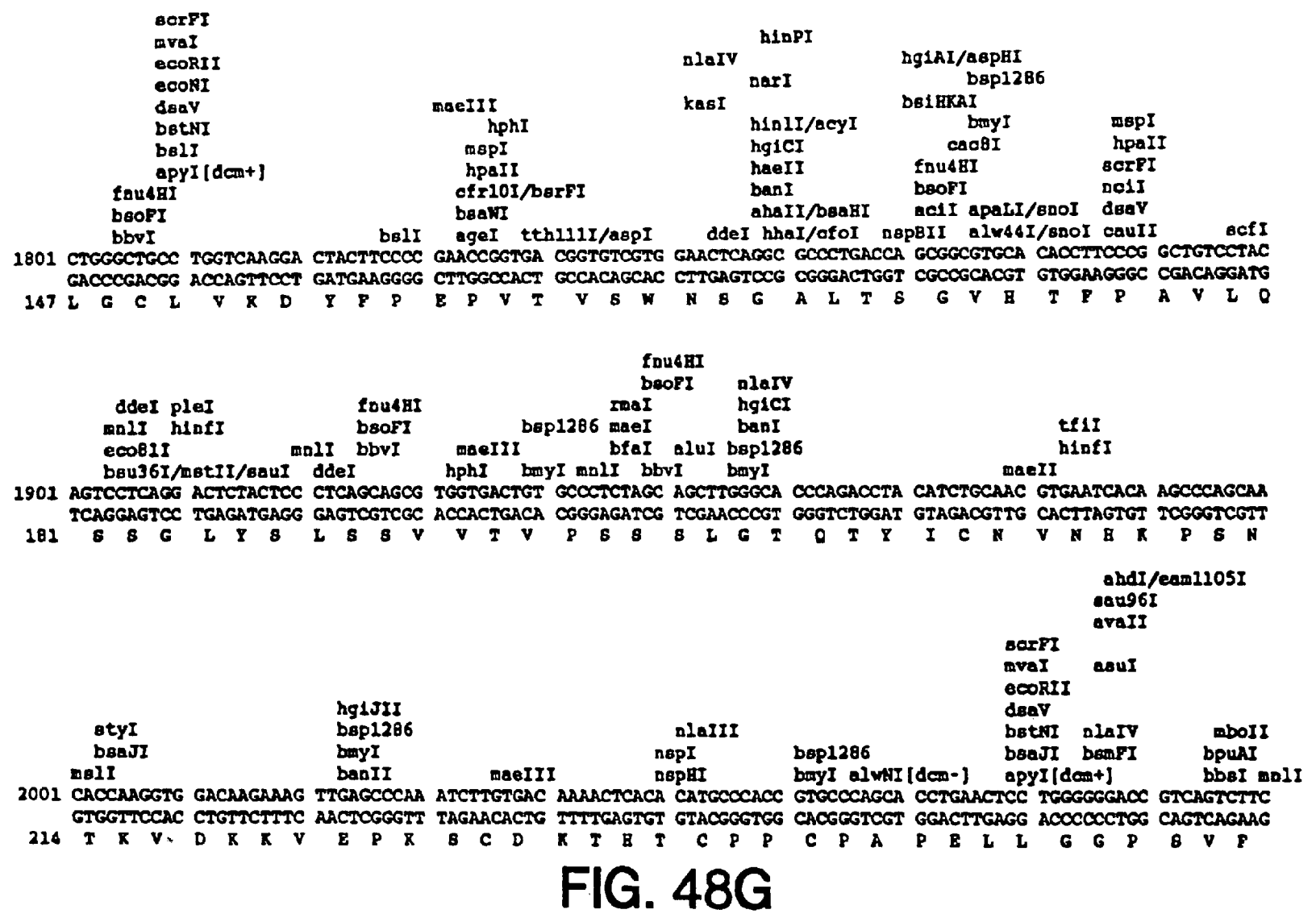
Figure 48H:
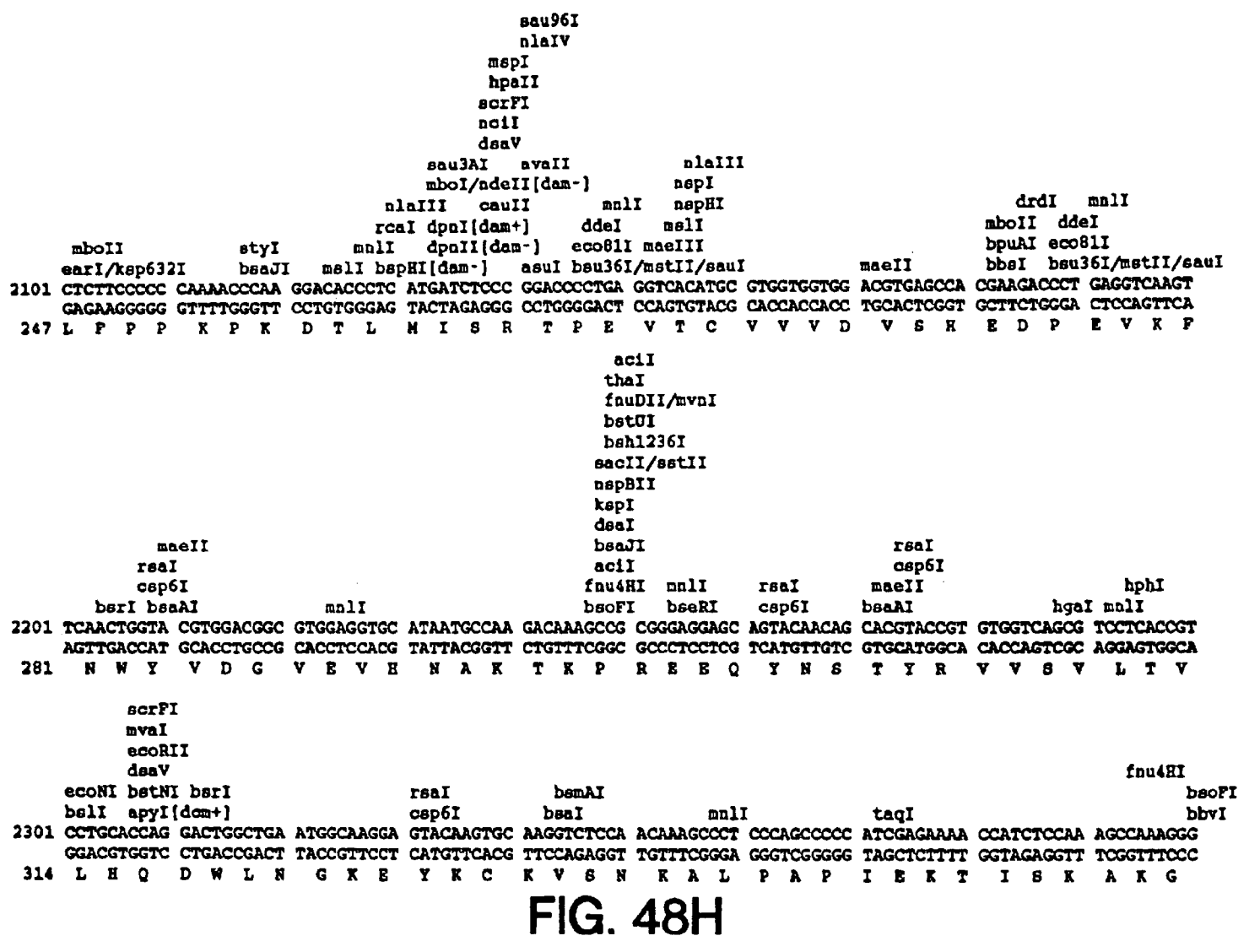
Figure 48I:
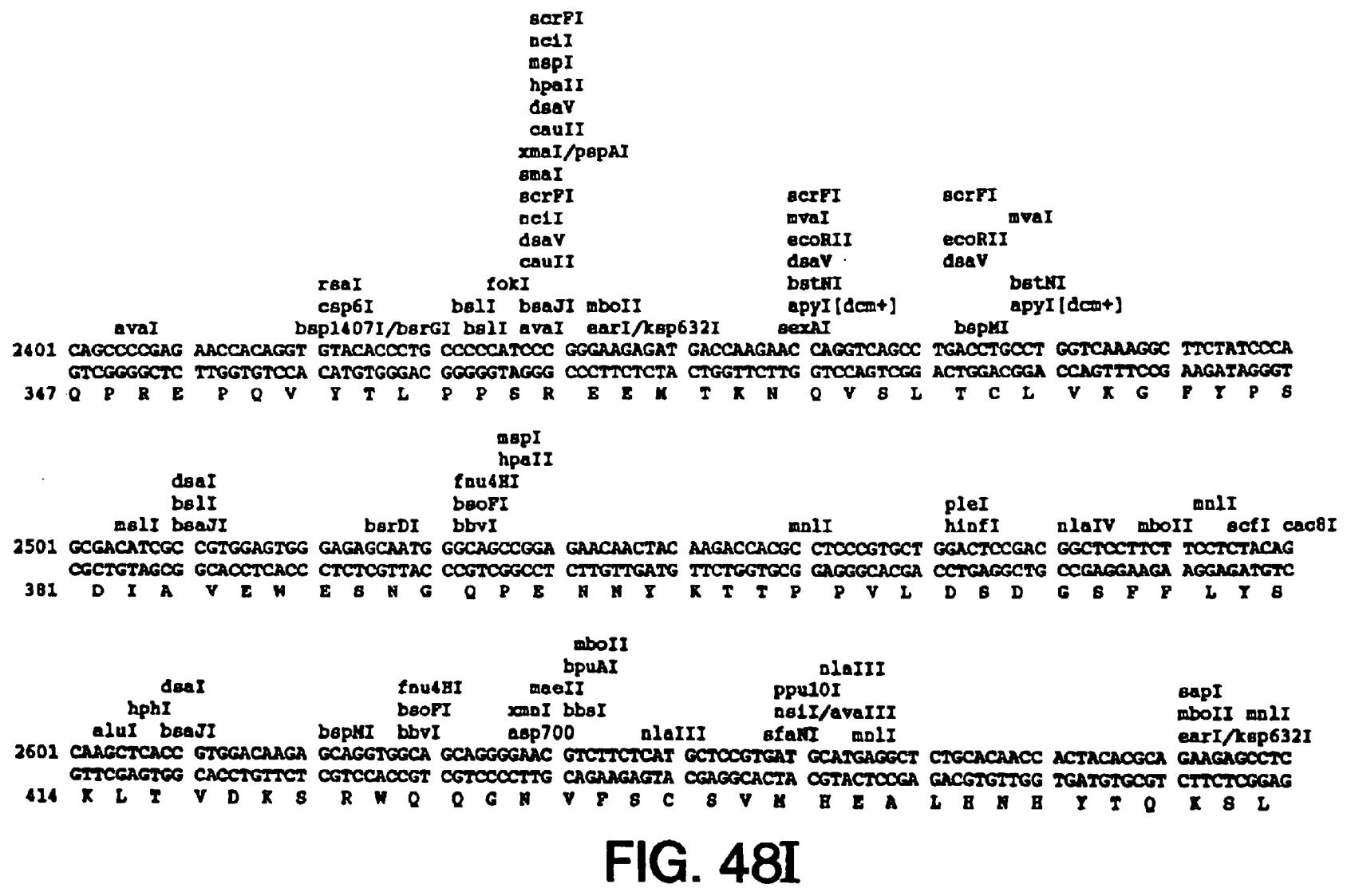
Figure 48J:
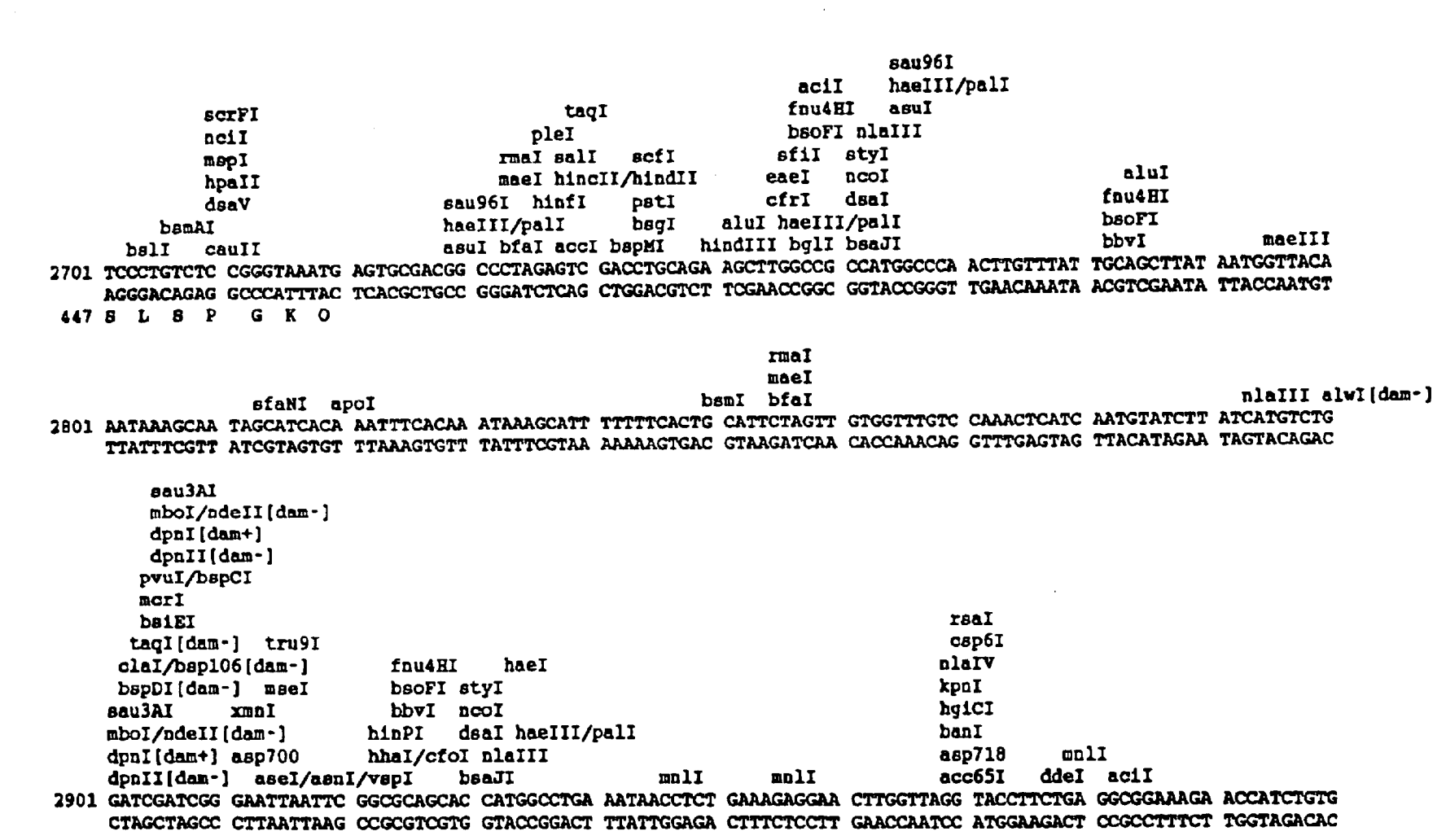
Figure 48M:
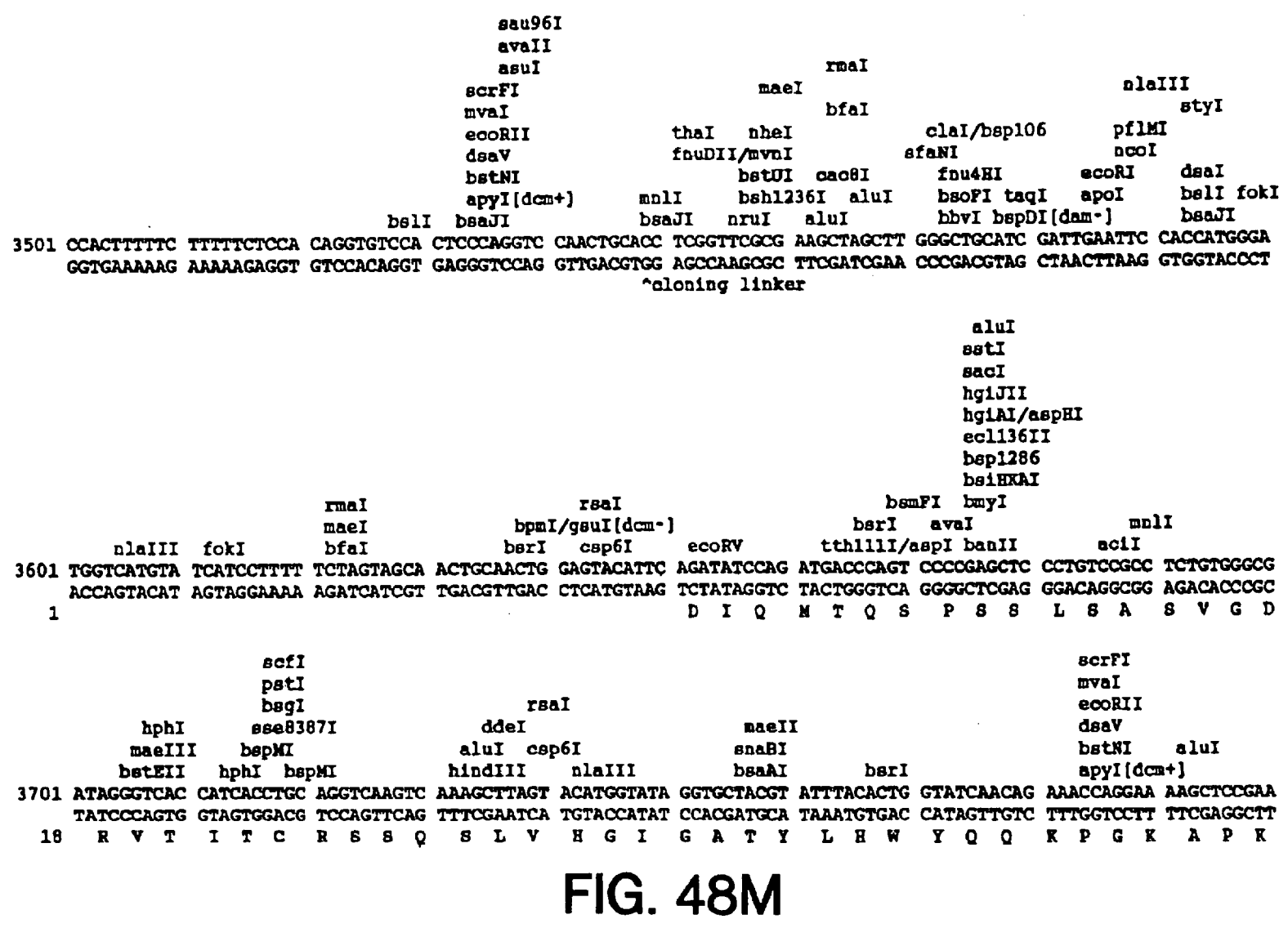
Figure 48N:
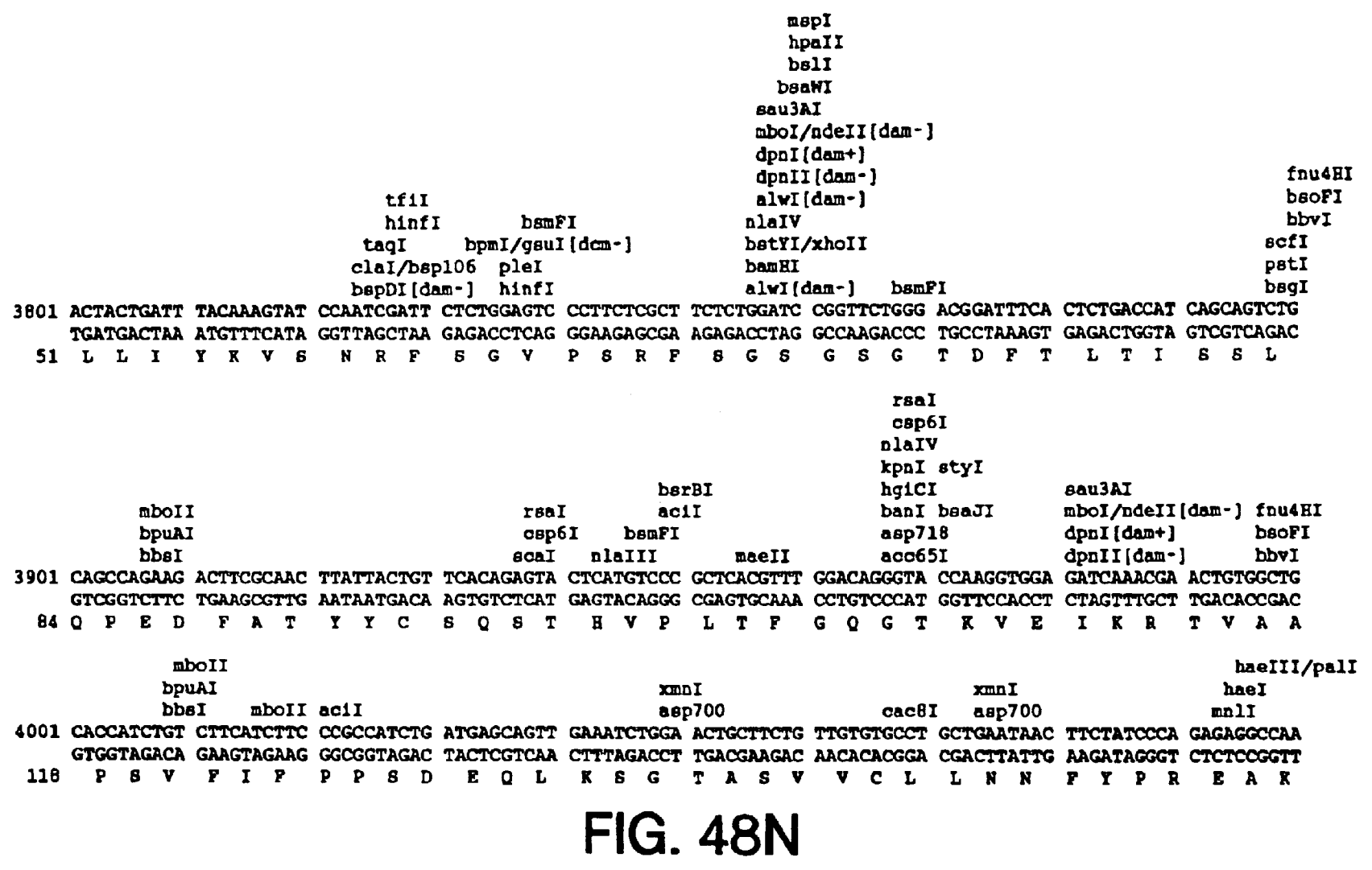
Figure 48Q:
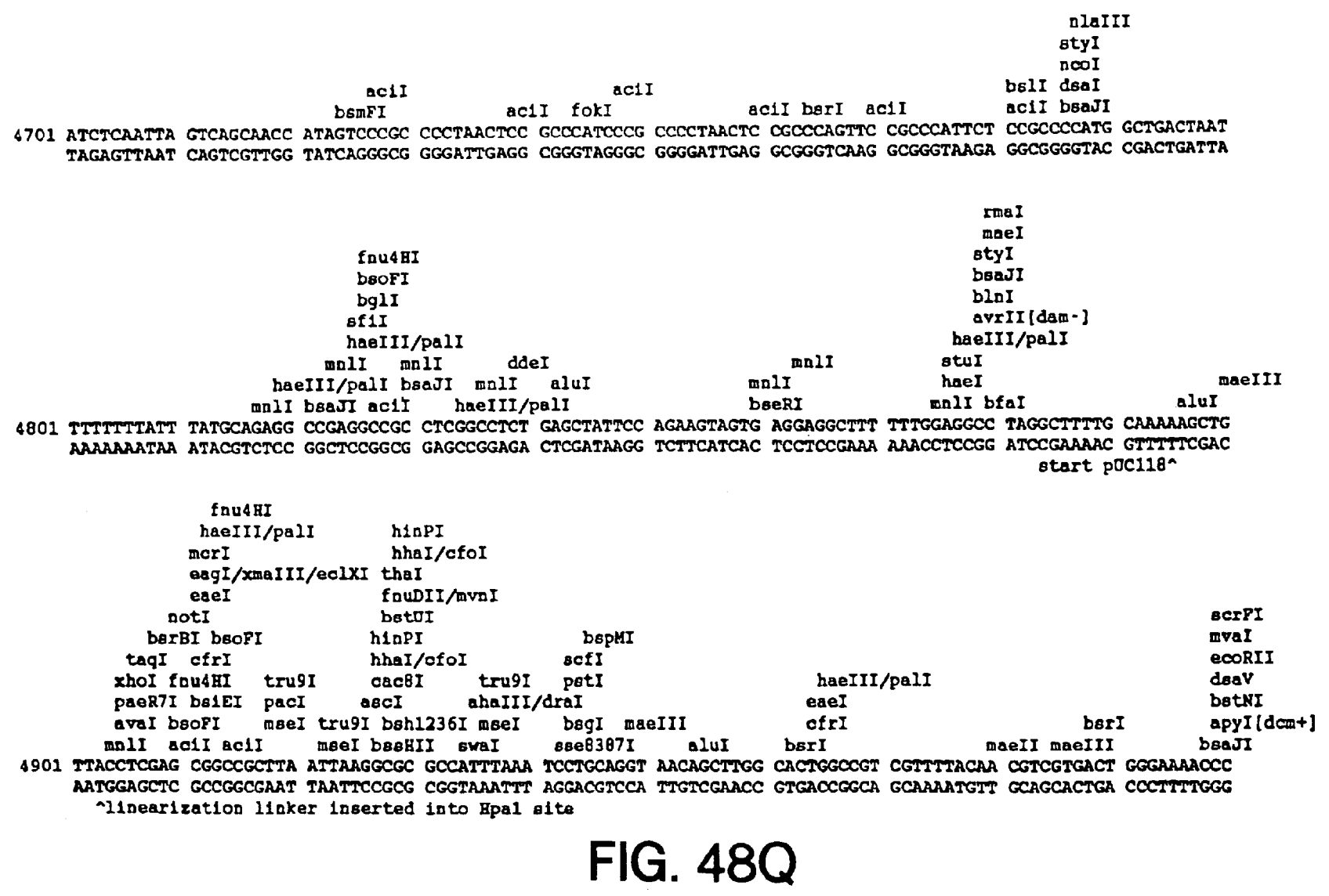
Figure 48R:
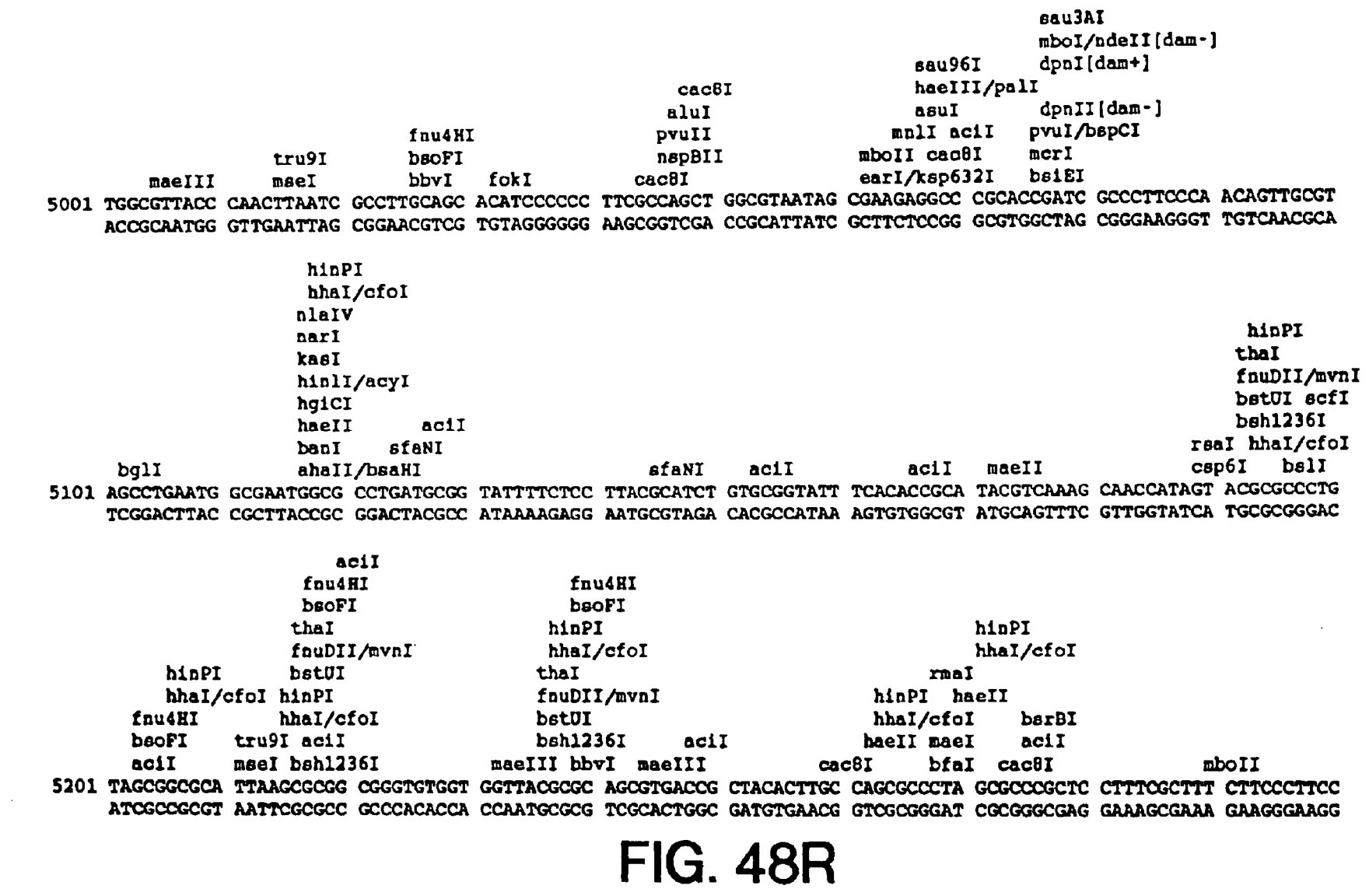
Figure 48T:
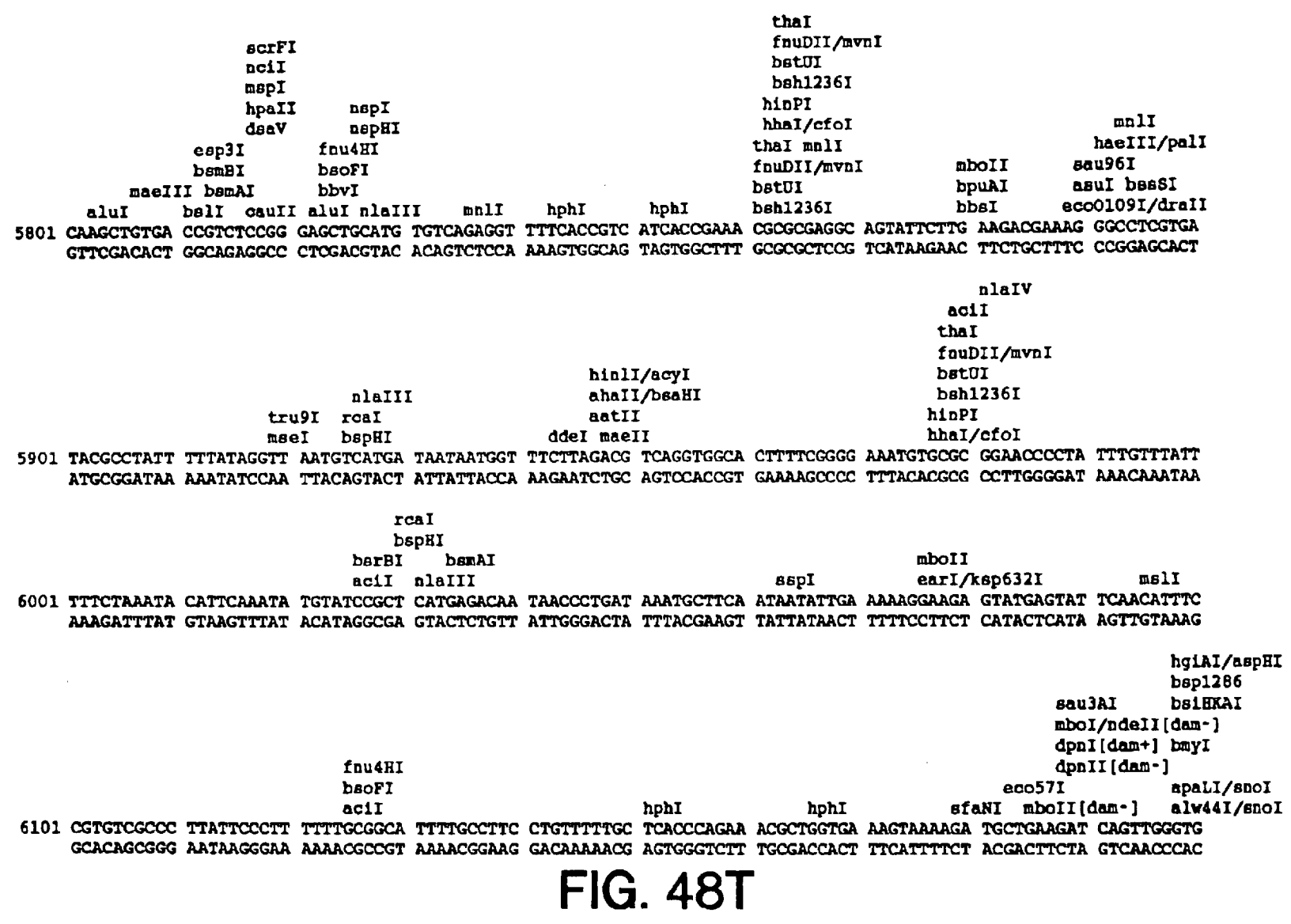
Figure 48U:
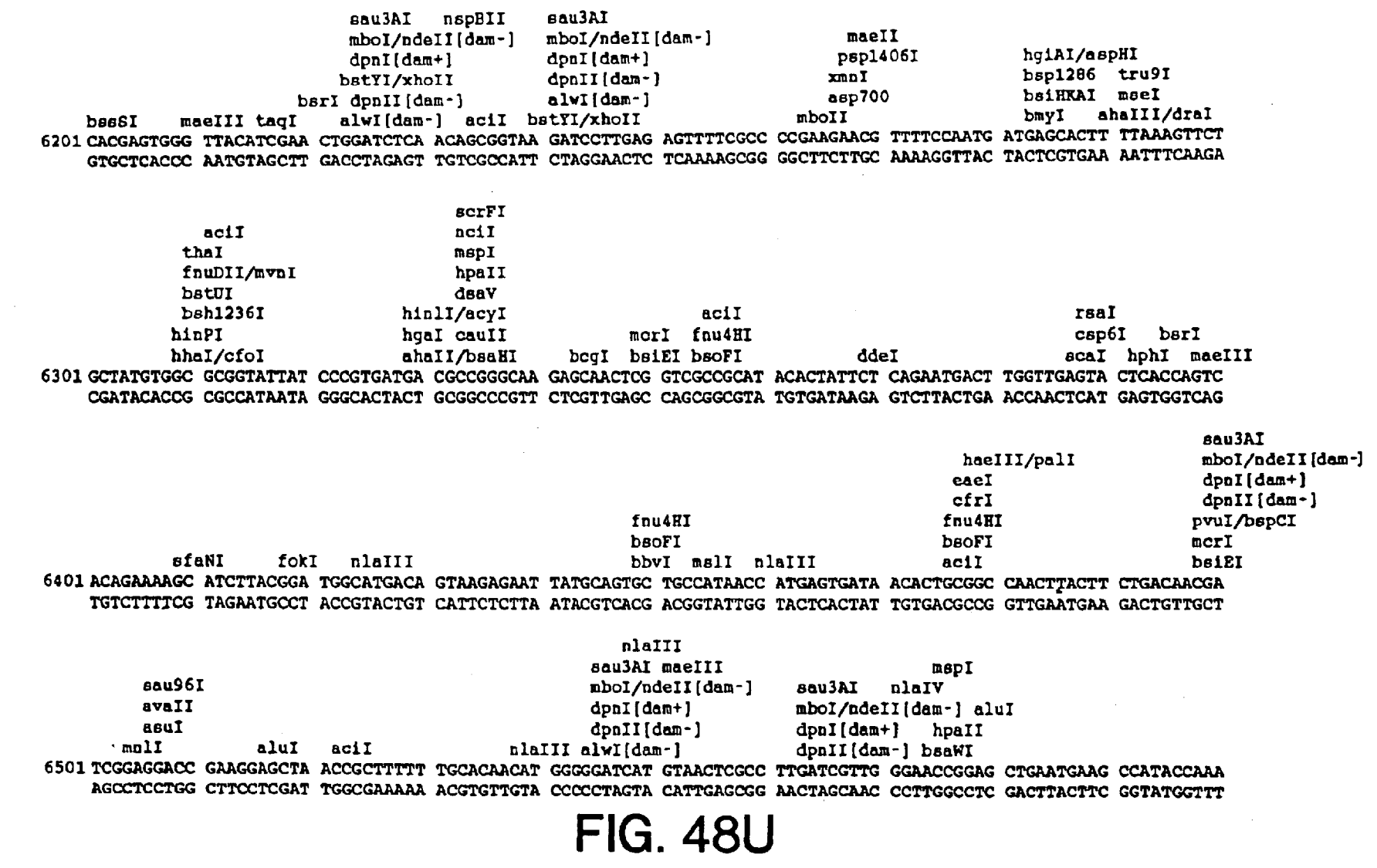
Figure 48V:
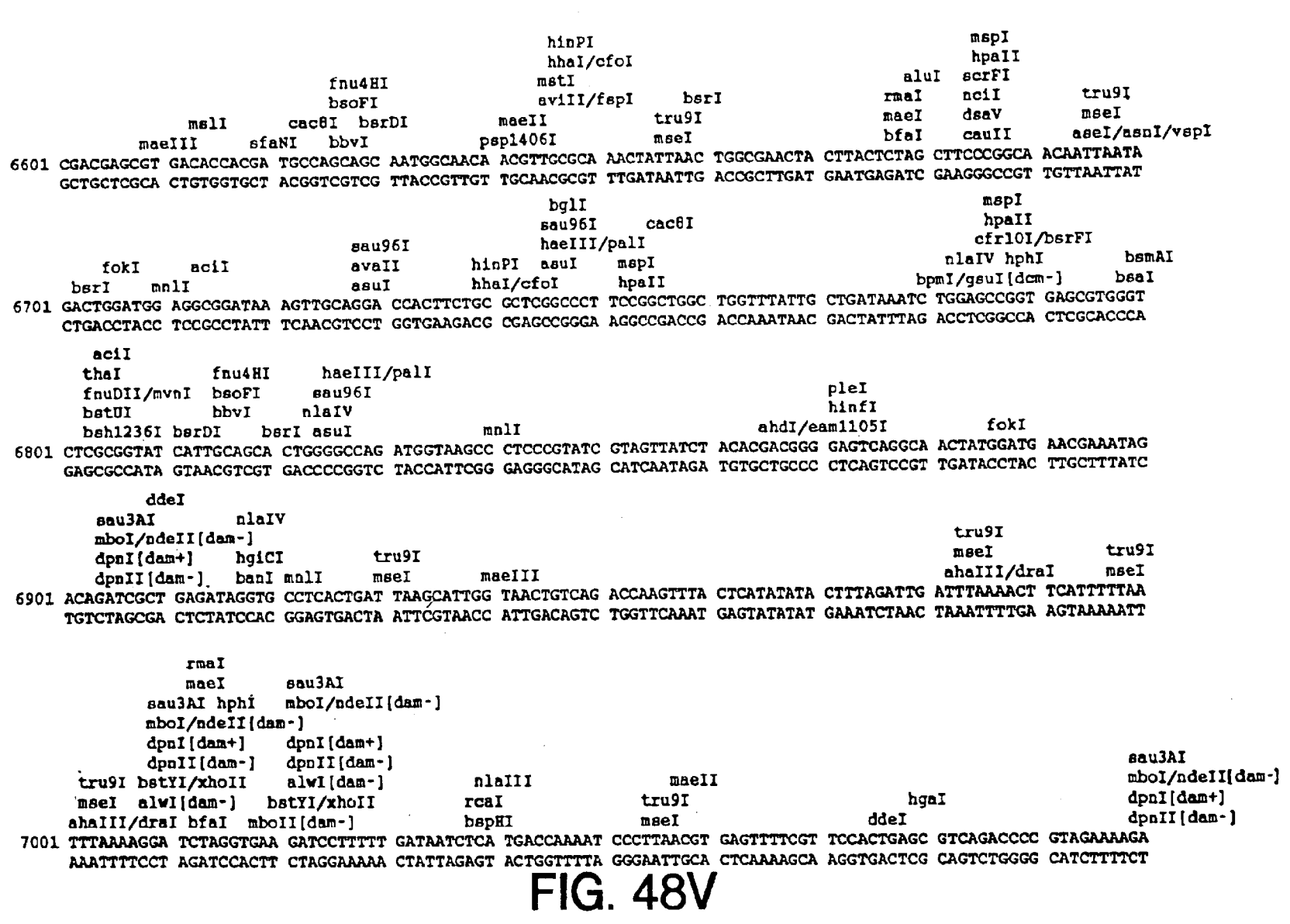

FIGS. 48A–48Z depict the DNA sequence (SEQ ID NO: 68) of plasmid p6G4V11N35A.choSD9.

FIGS. 50A–50B are graphs depicting the ability of full length 6G4V11N35A IgG1 and 6G4V11N35E IgG1 to inhibit human IL-8 (FIG. 50A) and rabbit IL-8 (FIG. 50B) mediated neutrophil chemotaxis.

FIG. 51 also contains a table of data providing the equilibrium and rate constants for full length murine 6G4.2.5 IgG2a, 6G4V11N35A IgG1 and 6G4V11N35E IgG1 binding to IL-8.

FIG. 53 depicts the DNA sequence (SEQ ID NO: 69) and amino acid sequence (SEQ ID NO: 70) of the 6G4V11N35A Fab' heavy chain (6G4V11N35A Fab heavy chain modified to contain a cysteine residue in the hinge region).

FIGS. 55A–55C are graphs depicting the ability of PEG-maleimide modified 6G4V11N35A Fab' molecules to inhibit human IL-8 and rabbit IL-8 mediated neutrophil chemotaxis.

FIGS. 57A–57B contain graphs of displacement curves depicting the inhibition of $^{125}$I-IL-8 binding to neutrophils exhibited by PEG-succinimide modified 6G4V1 N35A Fab'$_2$ molecules.

FIGS. 58A–58B are graphs depicting the ability of PEG-succinimide modified 6G4V11N35A F(ab')$_2$ molecules to inhibit human IL-8 mediated neutrophil chemotaxis.

DESCRIPTION OF THE PREFERRED EMBODIMENTS

I. Definitions

Figure 1:
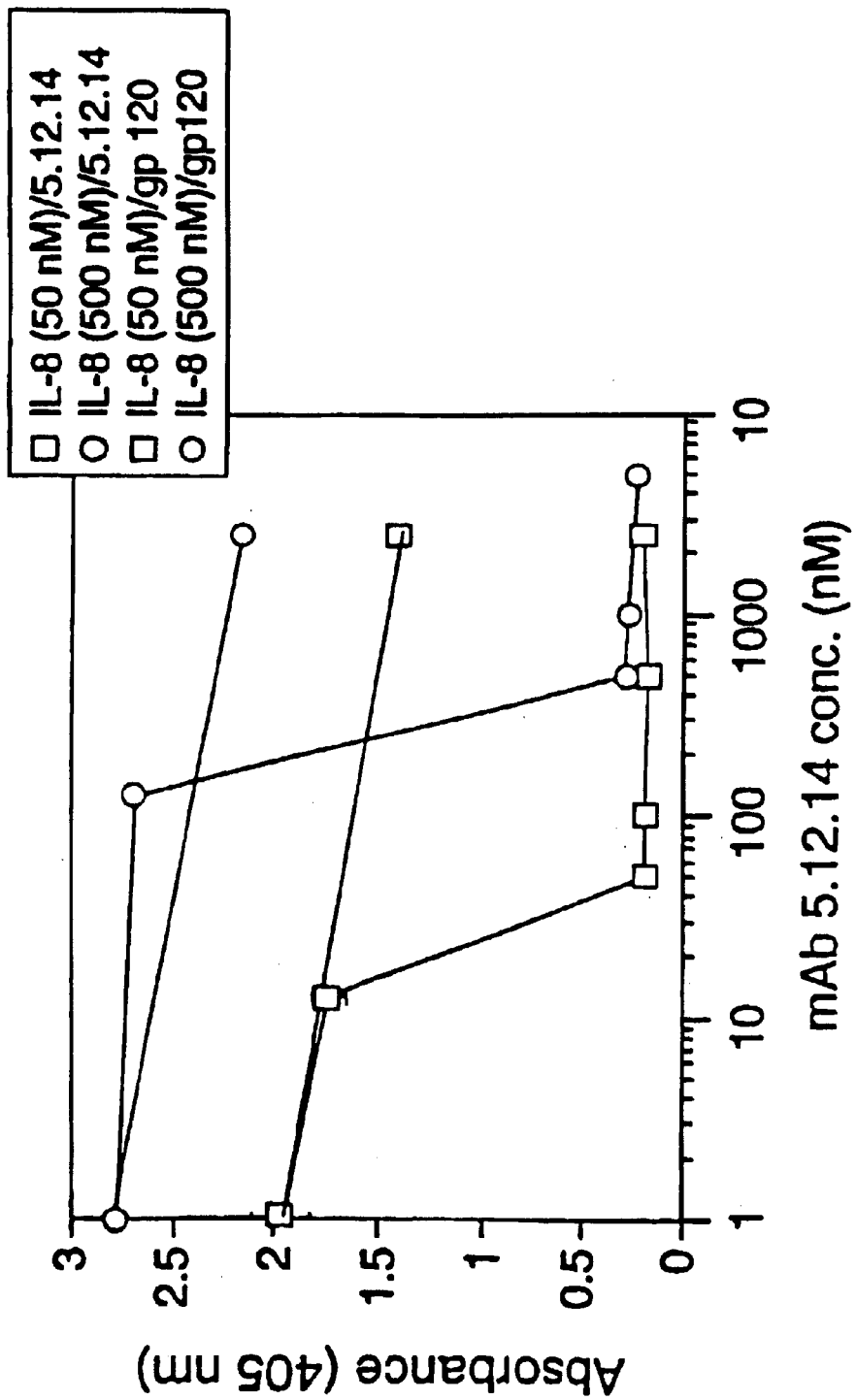
FIG. 1 is a graph depicting the blocking of IL-8 mediated elastase release from neutrophils by anti-IL-8 monoclonal antibody 5.12.14.

In general, the following words or phrases have the indicated definition when used in the description, examples, and claims.

"Polymerase chain reaction" or "PCR" refers to a procedure or technique in which minute amounts of a specific piece of nucleic acid, RNA and/or DNA, are amplified as described in U.S. Pat. No. 4,683,195 issued 28 Jul. 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., Cold Spring Harbor Symp. Quant. Biol. 51:263 (1987); Erlich, ed., PCR Technology (Stockton Press, NY, 1989). As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Clothia et al., *J. Mol. Biol.* 186:651 (1985); Novotny and Haber, *Proc. Natl. Acad. Sci. U.S.A.* 82:4592 (1985)).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species (scFv), one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site. For a review of scFv see Pluckthun, in *The Pharmacology of Monoclonal Antibodies*, vol. 113, Rosenburg and Moore eds., Springer-Verlag, New York, pp. 269–315 (1994).

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (k) and lambda (l), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG$_1$, IgG$_2$, IgG$_3$, IgG4, IgA$_1$, and IgA$_2$. The heavy-chain constant domains that correspond to the different classes of immunoglobulins are called α, δ, ε, γ, and μ, respectively. The subunit structures and three-dimensional configurations of different classes of immunoglobulins are well known.

The term "antibody" is used in the broadest sense and specifically covers single monoclonal antibodies (including agonist and antagonist antibodies) and antibody compositions with polyepitopic specificity.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s). Suitable leucine zipper sequences include the jun and fos leucine zippers taught by Kostelney et al., *J. Immunol.*, 148: 1547–1553 (1992) and the GCN4 leucine zipper described in the Examples below.

Unless specifically indicated to the contrary, the term "conjugate" as described and claimed herein is defined as a heterogeneous molecule formed by the covalent attachment of one or more antibody fragment(s) to one or more polymer molecule(s), wherein the heterogeneous molecule is water soluble, i.e. soluble in physiological fluids such as blood, and wherein the heterogeneous molecule is free of any structured aggregate. In the context of the foregoing definition, the term "structured aggregate" refers to (1) any aggregate of molecules in aqueous solution having a spheroid or spheroid shell structure, such that the heterogeneous molecule is not in a micelle or other emulsion structure, and is not anchored to a lipid bilayer, vesicle or liposome; and (2) any aggregate of molecules in solid or insolubilized form, such as a chromatography bead matrix, that does not release the heterogeneous molecule into solution upon contact with an aqueous phase. Accordingly, the term "conjugate" as defined herein encompasses the aforementioned heterogeneous molecule in a precipitate, sediment, bioerodible matrix or other solid capable of releasing the heterogeneous molecule into aqueous solution upon hydration of the solid.

Unless specifically indicated to the contrary, the terms "polymer", "polymer molecule", "nonproteinaceous polymer", and "nonproteinaceous polymer molecule" are used interchangeably and are defined as a molecule formed by covalent linkage of two or more monomers, wherein none of the monomers is contained in the group consisting of alanine (Ala), cysteine (Cys), aspartic acid (Asp), glutamic acid (Glu), phenylalanine (Phe), glycine (Gly), histidine (His), isoleucine (Ile), lysine (Lys), leucine (Leu), methionine (Met), asparagine (Asn), proline (Pro), glutamine (Gln), arginine (Arg), serine (Ser), threonine (Thr), valine (Val), tryptophan (Trp), and tyrosine (Tyr) residues.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each mAb is directed against a single determinant on the antigen. In addition to their specificity, the monoclonal antibodies are advantageous in that they can be synthesized by hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816,567 to Cabilly et al.). The "monoclonal antibodies" also include clones of antigen-recognition and binding-site containing antibody fragments (Fv clones) isolated from phage antibody libraries using the techniques described in Clackson et al., *Nature*, 352:624–628 (1991) and Marks et al., *J. Mol. Biol.*, 222:581–597 (1991), for example.

The monoclonal antibodies herein include hybrid and recombinant antibodies produced by splicing a variable (including hypervariable) domain of an anti-IL-8 antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity. (See, e.g., U.S. Pat. No. 4,816,567 to Cabilly et al.; Mage and Lamoyi, in *Monoclonal Antibody Production Techniques and Applications*, pp. 79–97 (Marcel Dekker, Inc., New York, 1987).)

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al., supra; Morrison et al., *Proc. Natl. Acad. Sci. U.S.A.* 81:6851(1984)).

"Humanized" forms of non-human (e.g., murine) antibodies are specific chimeric immunoglobulins, immunoglobulin chains or fragments thereof (such as Fv, Fab, Fab', F(ab')$_2$, or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Furthermore, humanized antibodies can comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details see Jones et al., *Nature* 321:522 (1986); Reichmann et al., *Nature* 332:323 (1988); and Presta, *Curr. Op. Struct. Biol.* 2:593 (1992).

"Treatment" refers to both therapeutic treatment and prophylactic or preventative measures.

Those in need of treatment include those already with the disorder as well as those prone to have the disorder or those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal herein is human.

As used herein, protein, peptide and polypeptide are used interchangeably to denote an amino acid polymer or a set of two or more interacting or bound amino acid polymers.

As used herein, the term "inflammatory disorders" refers to pathological states resulting in inflammation, typically caused by neutrophil chemotaxis. Examples of such disorders include inflammatory skin diseases including psoriasis; responses associated with inflammatory bowel disease (such as Crohn's disease and ulcerative colitis); ischemic reperfusion; adult respiratory distress syndrome; dermatitis; meningitis; encephalitis; uveitis; autoimmune diseases such as rheumatoid arthritis, Sjorgen's syndrome, vasculitis; diseases involving leukocyte diapedesis; central nervous system (CNS) inflammatory disorder, multiple organ injury syndrome secondary to septicaemia or trauma; alcoholic hepatitis, bacterial pneumonia, antigen-antibody complex mediated diseases; inflammations of the lung, including pleurisy, alveolitis, vasculitis, pneumonia, chronic bronchitis, bronchiectasis, and cystic fibrosis; etc. The preferred indications are bacterial pneumonia and inflammatory bowel disease such as ulcerative colitis.

The terms "hydrodynamic size", "apparent size", "apparent molecular weight", "effective size" and "effective molecular weight" of a molecule are used synonymously herein refer to the size of a molecule as determined by comparison to a standard curve produced with globular protein molecular weight standards in a size exclusion chromatography system, wherein the standard curve is created by mapping the actual molecular weight of each standard against its elution time observed in the size exclusion chromatography system. Thus, the apparent size of a test molecule is derived by using the molecule's elution time to extrapolate a putative molecular weight from the standard curve. Preferably, the molecular weight standards used to create the standard curve are selected such that the apparent size of the test molecule falls within the linear portion of the standard curve.

II. Modes for Carrying Out the Invention

In one part, the invention arises from the surprising and unexpected discovery that antibody fragment-polymer conjugates having an effective or apparent size significantly greater than the antibody fragment-polymer conjugates described in the art confers an increase in serum half-life, an increase in mean residence time in circulation (MRT), and/or a decrease in serum clearance rate over underivatized antibody fragment which far exceed the modest changes in such biological property or properties obtained with the art-known antibody fragment-polymer conjugates. The present inventors have determined for the first time that increasing the effective size of an antibody fragment to at least about 500,000 D, or increasing the effective size of an antibody fragment by at least about 8 fold over the effective size of the parental antibody fragment, or derivatizing an antibody fragment with a polymer of at least about 20,000 D in molecular weight, yields a molecule with a commercially useful pharmacokinetic profile. The greatly extended serum half-life, extended MRT, and/or reduced serum clearance rate of the conjugates of the invention makes such conjugates viable alternatives to intact antibodies used for therapeutic treatment of many disease indications. Antibody fragments provide significant advantages over intact antibodies, notably the fact that recombinant antibody fragments can be made in bacterial cell expression systems. Bacterial cell expression systems provide several advantages over mammalian cell expression systems, including reduced time and cost at both the research and development and manufacturing stages of a product.

In another part, the present invention also arises from the humanization of the 6G4.2.5 murine anti-rabbit IL-8 monoclonal antibody ("6G4.2.5") described in WO 95/23865 (PCT/US95/02589 published Sep. 8, 1995), the entire disclosure of which is specifically incorporated herein by reference. The hybridoma producing antibody 6G4.2.5 was deposited on Sep. 28, 1994 with the American Type Culture Collection and assigned ATCC Accession No. HB 11722 as described in the Examples below. In one aspect, the invention provides a humanized derivative of the 6G4.2.5 antibody, variant 11 (referred to herein as "6G4.2.5v11"), in which the murine CDRs of 6G4.2.5 are grafted onto a consensus framework for human light chain κI and human IgG1 heavy chain subgroup III, followed by importing three framework residues from the murine 6G4.2.5 parent heavy chain variable domain sequence into analogous sites in the heavy chain variable domain of the human template sequence, as described in the Examples below. In another aspect, the invention provides variants of the 6G4.2.5v11 antibody with certain amino acid substitution(s) yielding increased affinity for human IL-8 and/or promoting greater efficiency in recombinant manufacturing processes.

It will be understood that in the context of this Section (II) and all subsections thereof, every reference to "an antibody fragment" or "the antibody fragment" contained in a conjugate shall be a reference to one or more antibody fragment(s) in the conjugate (consistent with the definition of the term "conjugate" set forth in Section (I) above), except where the number of antibody fragment(s) in the conjugate is expressly indicated. It will be understood that in the context of this Section (II) and all subsections thereof, every reference to "a polymer", "a polymer molecule", "the polymer", or "the polymer molecule" contained in a conjugate shall be a reference to one or more polymer molecule(s) in the conjugate (consistent with the definition of the term "conjugate" set forth in Section (I) above), except where the number of polymer molecule(s) in the conjugate is expressly indicated.

1. Large Effective Size Antibody Fragment-polymer Conjugates

In one aspect, the invention provides an antibody fragment covalently attached to a polymer to form a conjugate having an effective or apparent size of at least about 500,000 Daltons (D). In another aspect, the invention provides an antibody fragment covalently attached to a polymer to form a conjugate having an apparent size that is at least about 8 fold greater than the apparent size of the parental antibody fragment. In yet another aspect, the invention provides an antibody fragment covalently attached to a polymer of at least about 20,000 D in molecular weight (MW). It will be appreciated that the unexpectedly and surprisingly large increase in antibody fragment serum half-life, increase in MRT, and/or decrease in serum clearance rate can be achieved by using any type of polymer or number of polymer molecules which will provide the conjugate with an effective size of at least about 500,000 D, or by using any type of polymer or number of polymer molecules which will provide the conjugate with an effective size that is at least about 8 fold greater than the effective size of the parental antibody fragment, or by using any type or number of polymers wherein each polymer molecule is at least about 20,000 D in MW. Thus, the invention is not dependent on the use of any particular polymer or molar ratio of polymer to antibody fragment in the conjugate.

In addition, the beneficial aspects of the invention extend to antibody fragments without regard to antigen specificity. Although variations from antibody to antibody are to be expected, the antigen specificity of a given antibody will not substantially impair the extraordinary improvement in serum half-life, MRT, and/or serum clearance rate for antibody fragments thereof that can be obtained by derivatizing the antibody fragments as taught herein.

In one embodiment, the conjugate has an effective size of at least about 500,000 D, or at least about 800,000 D, or at least about 900,000 D, or at least about 1,000,000 D, or at least about 1,200,000 D, or at least about 1,400,000 D, or at least about 1,500,000 D, or at least about 1,800,000 D, or at least about 2,000,000 D, or at least about 2,500,000 D.

In another embodiment, the conjugate has an effective size of at or about 500,000 D to at or about 10,000,000 D, or an effective size of at or about 500,000 D to at or about 8,000,000 D, or an effective size of at or about 500,000 D to at or about 5,000,000 D, or an effective size of at or about 500,000 D to at or about 4,000,000 D, or an effective size of at or about 500,000 D to at or about 3,000,000 D, or an effective size of at or about 500,000 D to at or about 2,500,000 D, or an effective size of at or about 500,000 D to at or about 2,000,000 D, or an effective size of at or about 500,000 D to at or about 1,800,000 D, or an effective size of at or about 500,000 D to at or about 1,600,000 D, or an effective size of at or about 500,000 D to at or about 1,500,000 D, or an effective size of at or about 500,000 D to at or about 1,000,000 D.

In another embodiment, the conjugate has an effective size of at or about 800,000 D to at or about 10,000,000 D, or an effective size of at or about 800,000 D to at or about 8,000,000 D, or an effective size of at or about 800,000 D to at or about 5,000,000 D, or an effective size of at or about 800,000 D to at or about 4,000,000 D, or an effective size of at or about 800,000 D to at or about 3,000,000 D, or an effective size of at or about 800,000 D to at or about 2,500,000 D, or an effective size of at or about 800,000 D to at or about 2,000,000 D, or an effective size of at or about 800,000 D to at or about 1,800,000 D, or an effective size of at or about 800,000 D to at or about 1,600,000 D, or an effective size of at or about 800,000 D to at or about 1,500,000 D, or an effective size of at or about 800,000 D to at or about 1,000,000 D.

In another embodiment, the conjugate has an effective size of at or about 900,000 D to at or about 10,000,000 D, or an effective size of at or about 900,000 D to at or about 8,000,000 D, or an effective size of at or about 900,000 D to at or about 5,000,000 D, or an effective size of at or about 900,000 D to at or about 4,000,000 D, or an effective size of at or about 900,000 D to at or about 3,000,000 D, or an effective size of at or about 900,000 D to at or about 2,500,000 D, or an effective size of at or about 900,000 D to at or about 2,000,000 D, or an effective size of at or about 900,000 D to at or about 1,800,000 D, or an effective size of at or about 900,000 D to at or about 1,600,000 D, or an effective size of at or about 900,000 D to at or about 1,500,000 D.

In another embodiment, the conjugate has an effective size of at or about 1,000,000 D to at or about 10,000,000 D, or an effective size of at or about 1,000,000 D to at or about 8,000,000 D, or an effective size of at or about 1,000,000 D to at or about 5,000,000 D, or an effective size of at or about 1,000,000 D to at or about 4,000,000 D, or an effective size of at or about 1,000,000 D to at or about 3,000,000 D, or an effective size of at or about 1,000,000 D to at or about 2,500,000 D, or an effective size of at or about 1,000,000 D to at or about 2,000,000 D, or an effective size of at or about 1,000,000 D to at or about 1,800,000 D, or an effective size of at or about 1,000,000 D to at or about 1,600,000 D, or an effective size of at or about 1,000,000 D to at or about 1,500,000 D.

In a further embodiment, the conjugate has an effective size that is at least about 8 fold greater, or at least about 10 fold greater, or at least about 12 fold greater, or at least about 15 fold greater, or at least about 18 fold greater, or at least about 20 fold greater, or at least about 25 fold greater, or at least about 28 fold greater, or at least about 30 fold greater, or at least about 40 fold greater, than the effective size of the parental antibody fragment.

In another embodiment, the conjugate has an effective size that is about 8 fold to about 100 fold greater, or is about 8 fold to about 80 fold greater, or is about 8 fold to about 50 fold greater, or is about 8 fold to about 40 fold greater, or is about 8 fold to about 30 fold greater, or is about 8 fold to about 28 fold greater, or is about 8 fold to about 25 fold greater, or is about 8 fold to about 20 fold greater, or is about 8 fold to about 18 fold greater, or is about 8 fold to about 15 fold greater, than the effective size of the parental antibody fragment.

In another embodiment, the conjugate has an effective size that is about 12 fold to about 100 fold greater, or is about 12 fold to about 80 fold greater, or is about 12 fold to about 50 fold greater, or is about 12 fold to about 40 fold greater, or is about 12 fold to about 30 fold greater, or is about 12 fold to about 28 fold greater, or is about 12 fold to about 25 fold greater, or is about 12 fold to about 20 fold greater, or is about 12 fold to about 18 fold greater, or is about 12 fold to about 15 fold greater, than the effective size of the parental antibody fragment.

In another embodiment, the conjugate has an effective size that is about 15 fold to about 100 fold greater, or is about 15 fold to about 80 fold greater, or is about 15 fold to about 50 fold greater, or is about 15 fold to about 40 fold greater, or is about 15 fold to about 30 fold greater, or is about 15 fold to about 28 fold greater, or is about 15 fold to about 25 fold greater, or is about 15 fold to about 20 fold greater, or is about 15 fold to about 18 fold greater, than the effective size of the parental antibody fragment.

In another embodiment, the conjugate has an effective size that is about 18 fold to about 100 fold greater, or is about 18 fold to about 80 fold greater, or is about 18 fold to about 50 fold greater, or is about 18 fold to about 40 fold greater, or is about 18 fold to about 30 fold greater, or is about 18 fold to about 28 fold greater, or is about 18 fold to about 25 fold greater, or is about 18 fold to about 20 fold greater, than the effective size of the parental antibody fragment.

In another embodiment, the conjugate has an effective size that is about 20 fold to about 100 fold greater, or is about 20 fold to about 80 fold greater, or is about 20 fold to about 50 fold greater, or is about 20 fold to about 40 fold greater, or is about 20 fold to about 30 fold greater, or is about 20 fold to about 28 fold greater, or is about 20 fold to about 25 fold greater, than the effective size of the parental antibody fragment.

In another embodiment, the conjugate has an effective size that is about 25 fold to about 100 fold greater, or is about 25 fold to about 80 fold greater, or is about 25 fold to about 50 fold greater, or is about 25 fold to about 40 fold greater, or is about 25 fold to about 30 fold greater, or is about 25 fold to about 28 fold greater, than the effective size of the parental antibody fragment.

In another embodiment, the conjugate has an effective size that is about 28 fold to about 100 fold greater, or is about 28 fold to about 80 fold greater, or is about 28 fold to about 50 fold greater, or is about 28 fold to about 40 fold greater, or is about 28 fold to about 30 fold greater, than the effective size of the parental antibody fragment.

In another embodiment, the conjugate has an effective size that is about 30 fold to about 100 fold greater, or is about 30 fold to about 80 fold greater, or is about 30 fold to about 50 fold greater, or is about 30 fold to about 40 fold greater, than the effective size of the parental antibody fragment.

In another embodiment, the conjugate has an effective size that is about 40 fold to about 100 fold greater, or is about 40 fold to about 80 fold greater, or is about 40 fold to about 50 fold greater, than the effective size of the parental antibody fragment.

In still another embodiment, the conjugate is an antibody fragment covalently attached to at least one polymer having an actual MW of at least about 20,000 D.

In a further embodiment, the conjugate is an antibody fragment covalently attached to at least one polymer having an actual MW of at least about 30,000 D.

In yet another embodiment, the conjugate is an antibody fragment covalently attached to at least one polymer having an actual MW of at least about 40,000 D.

In another embodiment, the conjugate is an antibody fragment covalently attached to at least one polymer having an actual MW that is at or about 20,000 D to at or about 300,000 D, or is at or about 30,000 D to at or about 300,000 D, or is at or about 40,000 D to at or about 300,000 D.

In another embodiment, the conjugate is an antibody fragment covalently attached to at least one polymer having an actual MW that is at or about 20,000 D to at or about 100,000 D, or is at or about 30,000 D to at or about 100,000 D, or is at or about 40,000 D to at or about 100,000 D.

In another embodiment, the conjugate is an antibody fragment covalently attached to at least one polymer having an actual MW that is at or about 20,000 D to at or about 70,000 D, or is at or about 30,000 D to at or about 70,000 D, or is at or about 40,000 D to at or about 70,000 D.

In another embodiment, the conjugate is an antibody fragment covalently attached to at least one polymer having an actual MW that is at or about 20,000 D to at or about 50,000 D, or is at or about 30,000 D to at or about 50,000 D, or is at or about 40,000 D to at or about 50,000 D.

In another embodiment, the conjugate is an antibody fragment covalently attached to at least one polymer having an actual MW that is at or about 20,000 D to at or about 40,000 D, or is at or about 30,000 D to at or about 40,000 D.

The conjugates of the invention can be made using any suitable technique now known or hereafter developed for derivatizing antibody fragments with polymers. It will be appreciated that the invention is not limited to conjugates utilizing any particular type of linkage between an antibody fragment and a polymer.

The conjugates of the invention include species wherein a polymer is covalently attached to a non-specific site or non-specific sites on the parental antibody fragment, i.e. polymer attachment is not targeted to a particular region or a particular amino acid residue in the parental antibody fragment. In such embodiments, the coupling chemistry can, for example, utilize the free epsilon amino groups of lysine residues in the parental antibody as attachment sites for the polymer, wherein such lysine residue amino groups are randomly derivatized with polymer.

In addition, the conjugates of the invention include species wherein a polymer is covalently attached to a specific site or specific sites on the parental antibody fragment, i.e. polymer attachment is targeted to a particular region or a particular amino acid residue or residues in the parental antibody fragment. In such embodiments, the coupling chemistry can, for example, utilize the free sulfhydryl group of a cysteine residue not in a disulfide bridge in the parental antibody fragment. In one embodiment, one or more cysteine residue(s) is (are) engineered into a selected site or sites in the parental antibody fragment for the purpose of providing a specific attachment site or sites for polymer. The polymer can be activated with any functional group that is capable of reacting specifically with the free sulfhydryl or thiol group(s) on the parental antibody, such as maleimide, sulfhydryl, thiol, triflate, tesylate, aziridine, exirane, and 5-pyridyl functional groups. The polymer can be coupled to the parental antibody fragment using any protocol suitable for the chemistry of the coupling system selected, such as the protocols and systems described in Section (II)(1)(b) or in Section (T) of the Examples below.

In another embodiment, polymer attachment is targeted to the hinge region of the parental antibody fragment. The location of the hinge region varies according to the isotype of the parental antibody. Typically, the hinge region of IgG, IgD and IgA isotype heavy chains is contained in a proline rich peptide sequence extending between the $C_H1$ and $C_H2$ domains. In a preferred embodiment, a cysteine residue or residues is (are) engineered into the hinge region of the parental antibody fragment in order to couple polymer specifically to a selected location in the hinge region.

In one aspect, the invention encompasses a conjugate having any molar ratio of polymer to antibody fragment that endows the conjugate with an apparent size in the desired range as taught herein. The apparent size of the conjugate will depend in part upon the size and shape of the polymer used, the size and shape of the antibody fragment used, the number of polymer molecules attached to the antibody fragment, and the location of such attachment site(s) on the antibody fragment. These parameters can easily be identified and maximized to obtain the a conjugate with the desired apparent size for any type of antibody fragment, polymer and linkage system.

In another aspect, the invention encompasses a conjugate with a polymer to antibody fragment molar ratio of no more than about 10:1, or no more than about 5:1, or no more than about 4:1, or no more than about 3:1, or no more than about 2:1, or no more than 1:1.

In yet another aspect, the invention encompasses a conjugate wherein the antibody fragment is attached to about 10 or fewer polymer molecules, each polymer molecule having a molecular weight of at least about 20,000 D, or at least about 30,000 D, or at least about 40,000 D. In another embodiment, the conjugate contains an antibody fragment attached to about 5 or fewer polymer molecules, each polymer molecule having a molecular weight of at least about 20,000 D, or at least about 30,000 D, or at least about 40,000 D. In still another embodiment, the conjugate contains an antibody fragment attached to about 4 or fewer polymer molecules, each polymer molecule having a molecular weight of at least about 20,000 D, or at least about 30,000 D, or at least about 40,000 D. In a further embodiment, the conjugate contains an antibody fragment attached to about 3 or fewer polymer molecules, each polymer molecule having a molecular weight of at least about 20,000 D, or at least about 30,000 D, or at least about 40,000 D. In an additional embodiment, the conjugate contains an antibody fragment attached to about 2 or fewer polymer molecules, each polymer molecule having a molecular weight of at least about 20,000 D, or at least about 30,000 D, or at least about 40,000 D. Also provided herein is a conjugate containing an antibody fragment attached to a single polymer molecule having a molecular weight of at least about 20,000 D, or at least about 30,000 D, or at least about 40,000 D.

In still another aspect, the invention encompasses a conjugate wherein every polymer molecule in the conjugate has a molecular weight that is at or about 20,000 D to at or about 300,000 D, or is at or about 30,000 D to at or about 300,000 D, or is at or about 40,000 D to at or about 300,000 D, and wherein the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In still another aspect, the invention encompasses a conjugate wherein every polymer molecule in the conjugate has a molecular weight that is at or about 20,000 D to at or about 100,000 D, or is at or about 30,000 D to at or about 100,000 D, or is at or about 40,000 D to at or about 100,000 D, and wherein the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In still another aspect, the invention encompasses a conjugate wherein every polymer molecule in the conjugate has a molecular weight that is at or about 20,000 D to at or about 70,000 D, or is at or about 30,000 D to at or about 70,000 D, or is at or about 40,000 D to at or about 70,000 D, and wherein the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In still another aspect, the invention encompasses a conjugate wherein every polymer molecule in the conjugate has a molecular weight that is at or about 20,000 D to at or about 50,000 D, or is at or about 30,000 D to at or about 50,000 D, or is at or about 40,000 D to at or about 50,000 D, and wherein the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In still another aspect, the invention encompasses a conjugate wherein every polymer molecule in the conjugate has a molecular weight that is at or about 20,000 D to at or about 40,000 D, or is at or about 30,000 D to at or about 40,000 D, and wherein the conjugate contains no more than about 10 polymer molecules, or no more than about S polymer molecules, or no more than about 4 polymer molecules, or no more than about 3 polymer molecules, or no more than about 2 polymer molecules, or no more than 1 polymer molecule.

It is believed that the serum half-life, MRT and/or serum clearance rate of any antibody fragment can be greatly improved by derivatizing the antibody fragment with polymer as taught herein. In one embodiment, the conjugate contains an antibody fragment selected from the group consisting of Fab, Fab', Fab'-SH, Fv, scFv and F(ab')$_2$.

In a preferred embodiment, the conjugate contains an antibody fragment selected from the group consisting of Fab, Fab', and Fab'-SH, wherein every polymer molecule in the conjugate is attached to the hinge region of the antibody fragment.

In another preferred embodiment, the conjugate contains an antibody fragment selected from the group consisting of Fab, Fab', and Fab'-SH, every polymer molecule in the conjugate molecule is attached to the hinge region of the antibody fragment, and the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In yet another preferred embodiment, the conjugate contains a F(ab')$_2$ antibody fragment attached to no more than about 2 polymer molecules, wherein every polymer molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In a further embodiment, the conjugate contains an antibody fragment selected from the group consisting of Fab, Fab', and Fab'-SH, wherein the antibody fragment is attached to no more than 1 polymer molecule and the polymer is coupled to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In an additional embodiment, the conjugate contains an antibody fragment selected from the group consisting of Fab, Fab', and Fab'-SH, every polymer molecule in the conjugate is at least about 20,000 D in molecular weight, or at least about 30,000 in molecular weight, or at least about 40,000 D in molecular weight, every polymer molecule in the conjugate is attached to the hinge region of the antibody fragment, and the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In another embodiment, the conjugate contains an antibody fragment selected from the group consisting of Fab, Fab', and Fab'-SH, every polymer molecule in the conjugate is at or about 20,000 D to at or about 300,000 D in molecular weight, or is at or about 30,000 D to at or about 300,000 D in molecular weight, or is at or about 40,000 D to at or about 300,000 D in molecular weight, every polymer molecule in the conjugate is attached to the hinge region of the antibody fragment, and the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In another embodiment, the conjugate contains an antibody fragment selected from the group consisting of Fab, Fab', and Fab'-SH, every polymer molecule in the conjugate is at or about 20,000 D to at or about 100,000 D in molecular weight, or is at or about 30,000 D to at or about 100,000 D in molecular weight, or is at or about 40,000 D to at or about 100,000 D in molecular weight, every polymer molecule in the conjugate is attached to the hinge region of the antibody fragment, and the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In another embodiment, the conjugate contains an antibody fragment selected from the group consisting of Fab, Fab', and Fab'-SH, every polymer molecule in the conjugate is at or about 20,000 D to at or about 70,000 D in molecular weight, or is at or about 30,000 D to at or about 70,000 D in molecular weight, or is at or about 40,000 D to at or about 70,000 D in molecular weight, every polymer molecule in the conjugate is attached to the hinge region of the antibody fragment, and the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In another embodiment, the conjugate contains an antibody fragment selected from the group consisting of Fab, Fab', and Fab'-SH, every polymer molecule in the conjugate is at or about 20,000 D to at or about 50,000 D in molecular weight, or is at or about 30,000 D to at or about 50,000 D in molecular weight, or is at or about 40,000 D to at or about 50,000 D in molecular weight, every polymer molecule in the conjugate is attached to the hinge region of the antibody fragment, and the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In another embodiment, the conjugate contains an antibody fragment selected from the group consisting of Fab, Fab', and Fab'-SH, every polymer molecule in the conjugate is at or about 20,000 D to at or about 40,000 D in molecular weight, or is at or about 30,000 D to at or about 40,000 D in molecular weight, every polymer molecule in the conjugate is attached to the hinge region of the antibody fragment, and the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In a further embodiment, the conjugate contains a F(ab')$_2$ antibody fragment attached to no more than about 2 polymer molecules, wherein every polymer molecule in the conjugate is at least about 20,000 D in molecular weight, or at least about 30,000 D in molecular weight, or at least about 40,000 D in molecular weight, and wherein every polymer molecule in the conjugate is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another embodiment, the conjugate contains a F(ab')$_2$ antibody fragment attached to no more than about 2 polymer molecules, wherein every polymer molecule in the conjugate is at or about 20,000 D to at or about 300,000 D in molecular weight, or is at or about 30,000 D to at or about 300,000 D in molecular weight, or is at or about 40,000 D to at or about 300,000 D in molecular weight, and wherein every polymer molecule in the conjugate is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another embodiment, the conjugate contains a F(ab')$_2$ antibody fragment attached to no more than about 2 polymer molecules, wherein every polymer molecule in the conjugate is at or about 20,000 D to at or about 100,000 D in molecular weight, or is at or about 30,000 D to at or about 100,000 D in molecular weight, or is at or about 40,000 D to at or about 100,000 D in molecular weight, and wherein every polymer molecule in the conjugate is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another embodiment, the conjugate contains a F(ab')$_2$ antibody fragment attached to no more than about 2 polymer molecules, wherein every polymer molecule in the conjugate is at or about 20,000 D to at or about 70,000 D in molecular weight, or is at or about 30,000 D to at or about 70,000 D in molecular weight, or is at or about 40,000 D to at or about 70,000 D in molecular weight, and wherein every polymer molecule in the conjugate is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another embodiment, the conjugate contains a F(ab')$_2$ antibody fragment attached to no more than about 2 polymer molecules, wherein every polymer molecule in the conjugate is at or about 20,000 D to at or about 50,000 D in molecular weight, or is at or about 30,000 D to at or about 50,000 D in molecular weight, or is at or about 40,000 D to at or about 50,000 D in molecular weight, and wherein every polymer molecule in the conjugate is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another embodiment, the conjugate contains a F(ab')$_2$ antibody fragment attached to no more than about 2 polymer molecules, wherein every polymer molecule in the conjugate is at or about 20,000 D to at or about 40,000 D in molecular weight, or is at or about 30,000 D to at or about 40,000 D in molecular weight, and wherein every polymer molecule in the conjugate is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In yet another embodiment, the conjugate contains an antibody fragment selected from the group consisting of Fab, Fab', and Fab'-SH, wherein the antibody fragment is attached to no more than 1 polymer molecule, wherein the polymer molecule is at least about 20,000 D in molecular weight, or at least about 30,000 D in molecular weight, or at least about 40,000 D in molecular weight, wherein the polymer molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another embodiment, the conjugate contains an antibody fragment selected from the group consisting of Fab, Fab', and Fab'-SH, wherein the antibody fragment is attached to no more than 1 polymer molecule, wherein the polymer molecule is at or about 20,000 D to at or about 300,000 D in molecular weight, or is at or about 30,000 D to at or about 300,000 D in molecular weight, or is at or about 40,000 D to at or about 300,000 D in molecular weight, wherein the polymer molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another embodiment, the conjugate contains an antibody fragment selected from the group consisting of Fab, Fab', and Fab'-SH, wherein the antibody fragment is attached to no more than 1 polymer molecule, wherein the polymer molecule is at or about 20,000 D to at or about 100,000 D in molecular weight, or is at or about 30,000 D to at or about 100,000 D in molecular weight, or is at or about 40,000 D to at or about 100,000 D in molecular weight, wherein the polymer molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another embodiment, the conjugate contains an antibody fragment selected from the group consisting of Fab, Fab', and Fab'-S", wherein the antibody fragment is attached to no more than 1 polymer molecule, wherein the polymer molecule is at or about 20,000 D to at or about 70,000 D in molecular weight, or is at or about 30,000 D to at or about 70,000 D in molecular weight, or is at or about 40,000 D to at or about 70,000 D in molecular weight, wherein the polymer molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another embodiment, the conjugate contains an antibody fragment selected from the group consisting of Fab, Fab', and Fab'-SH, wherein the antibody fragment is attached to no more than 1 polymer molecule, wherein the polymer molecule is at or about 20,000 D to at or about 50,000 D in molecular weight, or is at or about 30,000 D to at or about 50,000 D in molecular weight, or is at or about 40,000 D to at or about 50,000 D in molecular weight, wherein the polymer molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another embodiment, the conjugate contains an antibody fragment selected from the group consisting of Fab, Fab', and Fab'-SH, wherein the antibody fragment is attached to no more than 1 polymer molecule, wherein the polymer molecule is at or about 20,000 D to at or about 40,000 D in molecular weight, or is at or about 30,000 D to at or about 40,000 D in molecular weight, wherein the polymer molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In still another embodiment, the conjugate contains an antibody fragment selected from the group consisting of Fab, Fab', and Fab'-SH, wherein the antibody fragment is attached to no more than 1 polymer molecule, wherein the polymer molecule is at least about 20,000 D in molecular weight, or at least about 30,000 D in molecular weight, or at least about 40,000 D in molecular weight, and wherein the polymer molecule is attached to the hinge region of the antibody fragment.

In another embodiment, the conjugate contains an antibody fragment selected from the group consisting of Fab, Fab', and Fab'-SH, wherein the antibody fragment is attached to no more than 1 polymer molecule, wherein the polymer molecule is at or about 20,000 D to at or about 300,000 D in molecular weight, or is at or about 30,000 D to at or about 300,000 D in molecular weight, or is at or about 40,000 D to at or about 300,000 D in molecular weight, and wherein the polymer molecule is attached to the hinge region of the antibody fragment.

In another embodiment, the conjugate contains an antibody fragment selected from the group consisting of Fab, Fab', and Fab'-SH, wherein the antibody fragment is attached to no more than 1 polymer molecule, wherein the polymer molecule is at or about 20,000 D to at or about 100,000 D in molecular weight, or is at or about 30,000 D to at or about 100,000 D in molecular weight, or is at or about 40,000 D to at or about 100,000 D in molecular weight, and wherein the polymer molecule is attached to the hinge region of the antibody fragment.

In another embodiment, the conjugate contains an antibody fragment selected from the group consisting of Fab, Fab', and Fab'-SH, wherein the antibody fragment is attached to no more than 1 polymer molecule, wherein the polymer molecule is at or about 20,000 D to at or about 70,000 D in molecular weight, or is at or about 30,000 D to at or about 70,000 D in molecular weight, or is at or about 40,000 D to at or about 70,000 D in molecular weight, and wherein the polymer molecule is attached to the hinge region of the antibody fragment.

In another embodiment, the conjugate contains an antibody fragment selected from the group consisting of Fab, Fab', and Fab'-SH, wherein the antibody fragment is attached to no more than 1 polymer molecule, wherein the polymer molecule is at or about 20,000 D to at or about 50,000 D in molecular weight, or is at or about 30,000 D to at or about 50,000 D in molecular weight, or is at or about 40,000 D to at or about 50,000 D in molecular weight, and wherein the polymer molecule is attached to the hinge region of the antibody fragment.

In another embodiment, the conjugate contains an antibody fragment selected from the group consisting of Fab, Fab', and Fab'-SH, wherein the antibody fragment is attached to no more than 1 polymer molecule, wherein the polymer molecule is at or about 20,000 D to at or about 40,000 D in molecular weight, or is at or about 30,000 D to at or about 40,000 D in molecular weight, and wherein the polymer molecule is attached to the hinge region of the antibody fragment.

Although any type of polymer is contemplated for use in constructing the conjugates of the invention, including the polymers and chemical linkage systems described in Section (II)(1)(b) below, polyethylene glycol (PEG) polymers are preferred for use herein.

In one embodiment, the conjugate is an antibody fragment covalently attached to at least one PEG having an actual MW of at least about 20,000 D.

In another embodiment, the conjugate is an antibody fragment covalently attached to at least one PEG having an actual MW of at least about 30,000 D.

In yet another embodiment, the conjugate is an antibody fragment covalently attached to at least one PEG having an actual MW of at least about 40,000 D.

In another embodiment, the conjugate is an antibody fragment covalently attached to at least one PEG having an actual MW that is at or about 20,000 D to at or about 300,000 D, or is at or about 30,000 D to at or about 300,000 D, or is at or about 40,000 D to at or about 300,000 D.

In another embodiment, the conjugate is an antibody fragment covalently attached to at least one PEG having an actual MW that is at or about 20,000 D to at or about 100,000 D, or is at or about 30,000 D to at or about 100,000 D, or is at or about 40,000 D to at or about 100,000 D.

In another embodiment, the conjugate is an antibody fragment covalently attached to at least one PEG having an actual MW that is at or about 20,000 D to at or about 70,000 D, or is at or about 30,000 D to at or about 70,000 D, or is at or about 40,000 D to at or about 70,000 D.

In another embodiment, the conjugate is an antibody fragment covalently attached to at least one PEG having an actual MW that is at or about 20,000 D to at or about 50,000 D, or is at or about 30,000 D to at or about 50,000 D, or is at or about 40,000 D to at or about 50,000 D.

In another embodiment, the conjugate is an antibody fragment covalently attached to at least one PEG having an actual MW that is at or about 20,000 D to at or about 40,000 D, or is at or about 30,000 D to at or about 40,000 D.

In another aspect, the invention encompasses a conjugate with a PEG to antibody fragment molar ratio of no more than about 10:1, or no more than about 5:1, or no more than about 4:1, or no more than about 3:1, or no more than about 2:1, or no more than 1:1.

In yet another aspect, the invention encompasses a conjugate wherein the antibody fragment is attached to about 10 or fewer PEG molecules, each PEG molecule having a molecular weight of at least about 20,000 D, or at least about 30,000 D, or at least about 40,000 D. In another embodiment, the conjugate contains an antibody fragment attached to about 5 or fewer PEG molecules, each PEG molecule having a molecular weight of at least about 20,000 D, or at least about 30,000 D, or at least about 40,000 D. In still another embodiment, the conjugate contains an antibody fragment attached to about 4 or fewer PEG molecules, each PEG molecule having a molecular weight of at least about 20,000 D, or at least about 30,000 D, or at least about 40,000 D. In a further embodiment, the conjugate contains an antibody fragment attached to about 3 or fewer PEG molecules, each PEG molecule having a molecular weight of at least about 20,000 D, or at least about 30,000 D, or at least about 40,000 D. In an additional embodiment, the conjugate contains an antibody fragment attached to about 2 or fewer PEG molecules, each PEG molecule having a molecular weight of at least about 20,000 D, or at least about 30,000 D, or at least about 40,000 D. Also provided herein is a conjugate containing an antibody fragment attached to a single PEG molecule having a molecular weight of at least about 20,000 D, or at least about 30,000 D, or at least about 40,000 D.

In another aspect, the invention encompasses a conjugate wherein the antibody fragment is derivatized with PEG, wherein every PEG molecule in the conjugate is at or about 20,000 D to at or about 300,000 D in molecular weight, or is at or about 30,000 D to at or about 300,000 D in molecular weight, or is at or about 40,000 D to at or about 300,000 D in molecular weight, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another aspect, the invention encompasses a conjugate wherein the antibody fragment is derivatized with PEG, wherein every PEG molecule in the conjugate is at or about 20,000 D to at or about 100,000 D in molecular weight, or is at or about 30,000 D to at or about 100,000 D in molecular weight, or is at or about 40,000 D to at or about 100,000 D in molecular weight, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another aspect, the invention encompasses a conjugate wherein the antibody fragment is derivatized with PEG, wherein every PEG molecule in the conjugate is at or about 20,000 D to at or about 70,000 D in molecular weight, or is at or about 30,000 D to at or about 70,000 D in molecular weight, or is at or about 40,000 D to at or about 70,000 D in molecular weight, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another aspect, the invention encompasses a conjugate wherein the antibody fragment is derivatized with PEG, wherein every PEG molecule in the conjugate is at or about 20,000 D to at or about 50,000 D in molecular weight, or is at or about 30,000 D to at or about 50,000 D in molecular weight, or is at or about 40,000 D to at or about 50,000 D in molecular weight, and wherein the conjugate contains no more than about 10 PEG molecules, or no more than about S PEG molecules, or no more than about 4 PEG molecules, or no more than about 3 PEG molecules, or no more than about 2 PEG molecules, or no more than 1 PEG molecule.

In another aspect, the invention encompasses a conjugate wherein the antibody fragment is derivatized with PEG, wherein every PEG molecule in the conjugate is at or about 20,000 D to at or about 40,000 D in molecular weight, or is at or about 30,000 D to at or about 40,000 D in molecular weight, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In still another aspect, the invention encompasses a conjugate containing an antibody fragment selected from the group consisting of Fab, Fab', Fab'-SH and F(ab')$_2$, wherein the antibody fragment is attached to about 10 or fewer PEG molecules, each PEG molecule having a molecular weight of at least about 20,000 D, or at least about 30,000 D, or at least about 40,000 D. In another embodiment, the foregoing conjugate contains an antibody fragment attached to about 5 or fewer PEG molecules, each PEG molecule having a molecular weight of at least about 20,000 D, or at least about 30,000 D, or at least about 40,000 D. In still another embodiment, the foregoing conjugate contains an antibody fragment attached to about 4 or fewer PEG molecules, each PEG molecule having a molecular weight of at least about 20,000 D, or at least about 30,000 D, or at least about 40,000 D. In a further embodiment, the foregoing conjugate contains an antibody fragment attached to about 3 or fewer PEG molecules, each PEG molecule having a molecular weight of at least about 20,000 D, or at least about 30,000 D, or at least about 40,000 D. In an additional embodiment, the foregoing conjugate contains an antibody fragment attached to about 2 or fewer PEG molecules, each PEG molecule having a molecular weight of at least about 20,000 D, or at least about 30,000 D, or at least about 40,000 D. Also provided herein is the foregoing conjugate that contains an antibody fragment attached to a single PEG molecule having a molecular weight of at least about 20,000 D, or at least about 30,000 D, or at least about 40,000 D.

In another aspect, the invention encompasses a conjugate containing an antibody fragment selected from the group consisting of Fab, Fab', Fab'-SH and F(ab')$_2$, wherein the antibody fragment is derivatized with PEG, wherein every PEG molecule in the conjugate is at or about 20,000 D to at or about 300,000 D in molecular weight, or is at or about 30,000 D to at or about 300,000 D in molecular weight, or is at or about 40,000 D to at or about 300,000 D in molecular weight, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another aspect, the invention encompasses a conjugate containing an antibody fragment selected from the group consisting of Fab, Fab', Fab'-SH and F(ab')$_2$ wherein the antibody fragment is derivatized with PEG, wherein every PEG molecule in the conjugate is at or about 20,000 D to at or about 100,000 D in molecular weight, or is at or about 30,000 D to at or about 100,000 D in molecular weight, or is at or about 40,000 D to at or about 100,000 D in molecular weight, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another aspect, the invention encompasses a conjugate containing an antibody fragment selected from the group consisting of Fab, Fab', Fab'-SH and F(ab')$_2$, wherein the antibody fragment is derivatized with PEG, wherein every PEG molecule in the conjugate is at or about 20,000 D to at or about 70,000 D in molecular weight, or is at or about 30,000 D to at or about 70,000 D in molecular weight, or is at or about 40,000 D to at or about 70,000 D in molecular weight, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another aspect, the invention encompasses a conjugate containing an antibody fragment selected from the group consisting of Fab, Fab', Fab'-SH and F(ab')$_2$, wherein the antibody fragment is derivatized with PEG, wherein every PEG molecule in the conjugate is at or about 20,000 D to at or about 50,000 D in molecular weight, or is at or about 30,000 D to at or about 50,000 D in molecular weight, or is at or about 40,000 D to at or about 50,000 D in molecular weight, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another aspect, the invention encompasses a conjugate containing an antibody fragment selected from the group consisting of Fab, Fab', Fab'-SH and F(ab')$_2$, wherein the antibody fragment is derivatized with PEG, wherein every PEG molecule in the conjugate is at or about 20,000 D to at or about 40,000 D in molecular weight, or is at or about 30,000 D to at or about 40,000 D in molecular weight, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In a preferred embodiment, the conjugate contains an antibody fragment selected from the group consisting of Fab, Fab', and Fab'-SH, wherein the antibody fragment is derivatized with PEG having a molecular weight of at least about 20,000 D, or at least about 30,000 D, or at least about 40,000 D, and wherein every PEG molecule in the conjugate is attached to the hinge region of the antibody fragment.

In another preferred embodiment, the conjugate contains an antibody fragment selected from the group consisting of Fab, Fab', and Fab'-SH, wherein the antibody fragment is derivatized with PEG having a molecular weight that is at or about 20,000 D to about 300,000 D, or is at or about 30,000 D to at or about 300,000 D, or is at or about 40,000 D to at or about 300,000 D, and wherein every PEG molecule in the conjugate is attached to the hinge region of the antibody fragment.

In another preferred embodiment, the conjugate contains an antibody fragment selected from the group consisting of Fab, Fab', and Fab'-SH, wherein the antibody fragment is derivatized with PEG having a molecular weight that is at or about 20,000 D to about 100,000 D, or is at or about 30,000 D to at or about 100,000 D, or is at or about 40,000 D to at or about 100,000 D, and wherein every PEG molecule in the conjugate is attached to the hinge region of the antibody fragment.

In another preferred embodiment, the conjugate contains an antibody fragment selected from the group consisting of Fab, Fab', and Fab'-SH, wherein the antibody fragment is derivatized with PEG having a molecular weight that is at or about 20,000 D to about 70,000 D, or is at or about 30,000 D to at or about 70,000 D, or is at or about 40,000 D to at or about 70,000 D, and wherein every PEG molecule in the conjugate is attached to the hinge region of the antibody fragment.

In another preferred embodiment, the conjugate contains an antibody fragment selected from the group consisting of Fab, Fab', and Fab'-SH, wherein the antibody fragment is derivatized with PEG having a molecular weight that is at or about 20,000 D to about 50,000 D, or is at or about 30,000 D to at or about 50,000 D, or is at or about 40,000 D to at or about 50,000 D, and wherein every PEG molecule in the conjugate is attached to the hinge region of the antibody fragment.

In another preferred embodiment, the conjugate contains an antibody fragment selected from the group consisting of Fab, Fab', and Fab'-SH, wherein the antibody fragment is derivatized with PEG having a molecular weight that is at or about 20,000 D to about 40,000 D, or is at or about 30,000 D to at or about 40,000 D, and wherein every PEG molecule in the conjugate is attached to the hinge region of the antibody fragment.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at least about 20,000 D in molecular weight, or at least about 30,000 D in molecular weight, or at least about 40,000 D in molecular weight, wherein every PEG molecule in the conjugate molecule is attached to the hinge region of the antibody fragment, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at or about 20,000 D to at or about 300,000 D in molecular weight, or is at or about 30,000 D to at or about 300,000 D in molecular weight, or is at or about 40,000 D to at or about 300,000 D in molecular weight, wherein every PEG molecule in the conjugate molecule is attached to the hinge region of the antibody fragment, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at or about 20,000 D to at or about 100,000 D in molecular weight, or is at or about 30,000 D to at or about 100,000 D in molecular weight, or is at or about 40,000 D to at or about 100,000 D in molecular weight, wherein every PEG molecule in the conjugate molecule is attached to the hinge region of the antibody fragment, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at or about 20,000 D to at or about 70,000 D in molecular weight, or is at or about 30,000 D to at or about 70,000 D in molecular weight, or is at or about 40,000 D to at or about 70,000 D in molecular weight, wherein every PEG molecule in the conjugate molecule is attached to the hinge region of the antibody fragment, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at or about 20,000 D to at or about 50,000 D in molecular weight, or is at or about 30,000 D to at or about 50,000 D in molecular weight, or is at or about 40,000 D to at or about 50,000 D in molecular weight, wherein every PEG molecule in the conjugate molecule is attached to the hinge region of the antibody fragment, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at or about 20,000 D to at or about 40,000 D in molecular weight, or is at or about 30,000 D to at or about 40,000 D in molecular weight, wherein every PEG molecule in the conjugate molecule is attached to the hinge region of the antibody fragment, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In yet another preferred embodiment, the conjugate contains a F(ab')$_2$ antibody fragment derivatized with PEG, wherein every PEG molecule in the conjugate is at least about 20,000 D in molecular weight, or at least about 30,000 D in molecular weight, or at least about 40,000 D in molecular weight, wherein the antibody fragment is attached to no more than about 2 PEG molecules, and wherein every PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another preferred embodiment, the conjugate contains a F(ab')$_2$ antibody fragment derivatized with PEG, wherein every PEG molecule in the conjugate is at or about 20,000 D to at or about 300,000 D in molecular weight, or is at or about 30,000 D to at or about 300,000 D in molecular weight, or is at or about 40,000 D to at or about 300,000 D in molecular weight, wherein the antibody fragment is attached to no more than about 2 PEG molecules, and wherein every PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another preferred embodiment, the conjugate contains a F(ab')$_2$ antibody fragment derivatized with PEG, wherein every PEG molecule in the conjugate is at or about 20,000 D to at or about 100,000 D in molecular weight, or is at or about 30,000 D to at or about 100,000 D in molecular weight, or is at or about 40,000 D to at or about 100,000 D in molecular weight, wherein the antibody fragment is attached to no more than about 2 PEG molecules, and wherein every PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another preferred embodiment, the conjugate contains a F(ab')$_2$ antibody fragment derivatized with PEG, wherein every PEG molecule in the conjugate is at or about 20,000 D to at or about 70,000 D in molecular weight, or is at or about 30,000 D to at or about 70,000 D in molecular weight, or is at or about 40,000 D to at or about 70,000 D in molecular weight, wherein the antibody fragment is attached to no more than about 2 PEG molecules, and wherein every PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another preferred embodiment, the conjugate contains a F(ab')$_2$ antibody fragment derivatized with PEG, wherein every PEG molecule in the conjugate is at or about 20,000 D to at or about 50,000 D in molecular weight, or is at or about 30,000 D to at or about 50,000 D in molecular weight, or is at or about 40,000 D to at or about 50,000 D in molecular weight, wherein the antibody fragment is attached to no more than about 2 PEG molecules, and wherein every PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another preferred embodiment, the conjugate contains a F(ab')$_2$ antibody fragment derivatized with PEG, wherein every PEG molecule in the conjugate is at or about 20,000 D to at or about 40,000 D in molecular weight, or is at or about 30,000 D to at or about 40,000 D in molecular weight, wherein the antibody fragment is attached to no more than about 2 PEG molecules, and wherein every PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In still another preferred embodiment, the conjugate contains an antibody fragment selected from the group consisting of Fab, Fab', and Fab'-SH, wherein the antibody fragment is derivatized with PEG, wherein every PEG molecule in the conjugate is at least about 20,000 D in molecular weight, or at least about 30,000 in molecular weight, or at least about 40,000 D in molecular weight, wherein the antibody fragment is attached to no more than 1 PEG molecule, and wherein the PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at or about 20,000 D to at or about 300,000 D in molecular weight, or is at or about 30,000 D to at or about 300,000 D in molecular weight, or is at or about 40,000 D to at or about 300,000 D in molecular weight, wherein the antibody fragment is attached to no more than 1 PEG molecule, and wherein the PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at or about 20,000 D to at or about 100,000 D in molecular weight, or is at or about 30,000 D to at or about 100,000 D in molecular weight, or is at or about 40,000 D to at or about 100,000 D in molecular weight, wherein the antibody fragment is attached to no more than 1 PEG molecule, and wherein the PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at or about 20,000 D to at or about 70,000 D in molecular weight, or is at or about 30,000 D to at or about 70,000 D in molecular weight, or is at or about 40,000 D to at or about 70,000 D in molecular weight, wherein the antibody fragment is attached to no more than 1 PEG molecule, and wherein the PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at or about 20,000 D to at or about 50,000 D in molecular weight, or is at or about 30,000 D to at or about 50,000 D in molecular weight or is at or about 40,000 D to at or about 50,000 D in molecular weight, wherein the antibody fragment is attached to no more than 1 PEG molecule, and wherein the PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at or about 20,000 D to at or about 40,000 D in molecular weight, or is at or about 30,000 D to at or about 40,000 D in molecular weight, wherein the antibody fragment is attached to no more than 1 PEG molecule, and wherein the PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

It will be appreciated that all of the above-described embodiments of the invention utilizing PEG polymers include conjugates wherein the PEG polymer(s) is (are) linear or branched. In a preferred embodiment, the conjugate contains an antibody fragment selected from the group consisting of Fab, Fab', and Fab'-SH, wherein the antibody fragment is attached to no more than 1 PEG molecule, and wherein the PEG molecule is branched and at least about 40,000 D in molecular weight. In a particularly surprising and unexpected finding, the inventors discovered that the foregoing conjugate exhibits a serum half-life, MRT and serum clearance rate approaching that of full length antibody as shown in Example X below.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is branched and has a molecular weight that is at or about 40,000 D to at or about 300,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is branched and has a molecular weight that is at or about 40,000 D to at or about 100,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is branched and has a molecular weight that is at or about 40,000 D to at or about 70,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is branched and has a molecular weight that is at or about 40,000 D to at or about 50,000 D.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is branched and at least 40,000 D in molecular weight, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is branched and has a molecular weight that is at or about 40,000 D to at or about 300,000 D, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is branched and has a molecular weight that is at or about 40,000 D to at or about 100,000 D, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is branched and has a molecular weight that is at or about 40,000 D to at or about 70,000 D, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is branched and has a molecular weight that is at or about 40,000 D to at or about 50,000 D, and the PEG molecule is attached to the hinge region of the antibody fragment.

In one aspect, the invention provides any of the above-described conjugates wherein the conjugate contains no more than one antibody fragment. Additionally provided herein is any of the above-described conjugates wherein the conjugate contains one or more antibody fragment(s) covalently linked to one or more polymer molecule(s), such as conjugates containing two or more antibody fragments covalently linked together by polymer molecule(s). In one embodiment, a polymer molecule is used to link together two antibody fragments to form a dumbbell-shaped structure. Also encompassed herein are conjugates formed by more than two antibody fragments joined by polymer molecule(s) to form a rosette or other shapes. The antibody fragments in such structures can be of the same or different fragment type and can have the same antigen specificity or have different antigen specificities. Such structures can be made by using a polymer molecule derivatized with multiple functional groups permitting the direct attachment, or the attachment by means of bi- or multi-functional linkers, of two or more antibody fragments to the polymer backbone.

In another aspect, the invention encompasses any of the above-described conjugates utilizing an antibody fragment comprising an antigen recognition site that binds to rabbit IL-8 and/or human IL-8. In yet another aspect, the invention encompasses any of the above-described conjugates utilizing an antibody fragment comprising 6G4.2.5LV/L1N35A or 6G4.2.5LV/L1N35E as defined below. In still another aspect, the invention encompasses any of the above-described conjugates utilizing an antibody fragment comprising 6G4.5.2.5HV11 as defined below. In a further aspect, the invention encompasses any of the above-described conjugates utilizing an antibody fragment comprising hu6G4.2.5LV/L1N35A or hu6G4.2.5LV/L1N35E as defined below. In an additional aspect, the invention encompasses any of the above-described conjugates utilizing an antibody fragment comprising hu6G4.2.5HV. Further encompassed herein are any of the above-described conjugates utilizing an antibody fragment comprising 6G4.2.5LV/L1N35A or 6G4.2.5LV/L1N35E and further comprising the CDRs of 6G4.2.5HV as defined below. Also encompassed herein are any of the above described conjugates utilizing an antibody fragment comprising hu6G4.2.5LV/L1N35A or hu6G4.2.5LV/L1N35E and further comprising hu6G4.2.5HV as defined below. Additionally encompassed herein are any of the above-described conjugates utilizing an antibody fragment comprising 6G4.2.5LV11N35A or 6G4.2.5LV11N35E as defined below. Further provided herein are any of the above-described conjugates utilizing an antibody fragment comprising 6G4.2.5LV11N35A or 6G4.2.5LV11N35E and further comprising 6G4.2.5HV11 as defined below.

a. Production of Antibody Fragments

Antibody fragments can be produced by any method known in the art. Generally, an antibody fragment is derived from a parental intact antibody. The parental antibody can be generated by raising polyclonal sera against the desired antigen by multiple subcutaneous (sc) or intraperitoneal (ip) injections of antigen and an adjuvant, such as monophosphoryl lipid A (MPL)/trehalose dicrynomycolate (TDM) (Ribi Immunochem. Research, Inc., Hamilton, Mont.), at multiple sites. Two weeks later the animals are boosted. 7 to 14 days later animals are bled and the serum is assayed for anti-antigen titer. Animals are boosted until titer plateaus. Sera are harvested from animals, and polyclonal antibodies are isolated from sera by conventional immunoglobulin purification procedures, such as protein A-Sepharose chromatography, hydroxylapatite chromatography, gel filtration, dialysis, or antigen affinity chromatography. The desired antibody fragments can be generated from purified polyclonal antibody preparations by conventional enzymatic methods, e.g. F(ab')$_2$ fragments are produced by pepsin cleavage of intact antibody, and Fab fragments are produced by briefly digesting intact antibody with papain.

Alternatively, antibody fragments are derived from monoclonal antibodies generated against the desired antigen. Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp.59–103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51–63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp.59–103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (eg., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Review articles on recombinant expression in bacteria of antibody-encoding DNA include Skerra et al., *Curr. Opinion in Immunol.*, 5: 256 (1993) and Pluckthun, *Immunol. Revs.*, 130: 151(1992).

In a preferred embodiment, the antibody fragment is derived from a humanized antibody. Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. It will be appreciated that variable domain sequences obtained from any non-human animal phage display library-derived Fv clone or from any non-human animal hybridoma-derived antibody clone provided as described herein can serve as the "import" variable domain used in the construction of the humanized antibodies of the invention. Humanization can be essentially performed following the method of Winter and co-workers (Jones et al., *Nature*, 321: 522 (1986); Riechmann et al., *Nature*, 332: 323 (1988); Verhoeyen et al., *Science*, 239: 1534 (1988)), by substituting non-human animal, e.g. rodent, CDRs or CDR sequences for the corresponding sequences of a human antibody. Accordingly, such "humanized" antibodies are chimeric antibodies (Cabilly et al., supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in non-human animal, e.g. rodent, antibodies.

The choice of human variable domains, both light and heavy, to be used in making the humanized antibodies is very important to reduce antigenicity. According to the so-called "best-fit" method, the sequence of the variable domain of a non-human animal, e.g. rodent, antibody is screened against the entire library of known human variable-domain sequences. The human sequence which is closest to that of the non-human animal is then accepted as the human framework (FR) for the humanized antibody (Sims et al., *J. Immunol.*, 151: 2296 (1993); Chothia and Lesk, *J. Mol. Biol.*, 196: 901 (1987)). Another method uses a particular framework derived from the consensus sequence of all human antibodies of a particular subgroup light or heavy chains. The same framework can be used for several different humanized antibodies (Carter et al., *Proc. Natl. Acad. Sci USA*, 89: 4285 (1992); Presta et al., *J. Immunol.*, 151: 2623 (1993)). It is also important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind to its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

In addition, antibody fragments for use herein can be derived from human monoclonal antibodies. Human monoclonal antibodies against the antigen of interest can be made by the hybridoma method. Human myeloma and mouse-human heteromyeloma cell lines for the production of human monoclonal antibodies have been described, for example, by Kozbor *J. Immunol.*, 133: 3001 (1984); Brodeur et al., *Monoclonal Antibody Production Techniques and Applications*, pp. 51–63 (Marcel Dekker, Inc., New York, 1987); and Boerner et al., *J. Immunol.*, 147: 86 (1991).

It is now possible to produce transgenic animals (e.g. mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci USA*, 90: 2551 (1993); Jakobovits et al., *Nature*, 362: 255 (1993); Bruggermann et al., *Year in Immunol.*, 7: 33 (1993).

Alternatively, phage display technology (McCafferty et al., *Nature* 348:552 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M 13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson et al., *Current Opinion in Structural Biology* 3:564 (1993). Several sources of V-gene segments can be used for phage display. Clackson et al., *Nature* 352:624 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581 (1991), or Griffith et al., *EMBO J.* 12:725 (1993).

In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., *Bio/Technol.* 10:779 (1992)). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the nM range. A strategy for making very large phage antibody repertoires has been described by Waterhouse et al., *Nucl. Acids Res.* 21:2265 (1993).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described above is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

The invention also encompasses the use of bispecific and heteroconjugate antibody fragments having specificities for at least two different antigens. Bispecific and heteroconjugate antibodies can be prepared as full length antibodies or as antibody fragments (e.g. F(ab')$_2$ bispecific antibody fragments). Antibody fragments having more than two valencies (e.g. trivalent or higher valency antibody fragments) are also contemplated for use herein. Bispecific antibodies, heteroconjugate antibodies, and multi-valent antibodies can be prepared as described in Section (II)(3(C) below.

As described above, DNA encoding the monoclonal antibody or antibody fragment of interest can be isolated from its hybridoma or phage display clone of origin, and then manipulated to create humanized and/or affinity matured constructs. In addition, known techniques can be employed to introduce an amino acid residue or residues into any desired location on the polypeptide backbone of the antibody fragment, e.g. a cysteine residue placed in the hinge region of the heavy chain, thereby providing a site for specific attachment of polymer molecule(s). In one embodiment, the native cysteine residue in either the light or heavy chain of the antibody fragment that would ordinarily form the disulfide bridge linking the light and heavy chains is substituted with another amino acid, such as serine, in order to leave the partner cysteine residue in the opposite chain with a free suflhydryl for specific attachment of polymer molecule.

Upon construction of the desired antibody or antibody fragment-encoding clone, the clone can be used for recombinant production of the antibody fragment as described in Section (II)(4) below. Finally, the antibody or antibody fragment product can be recovered from host cell culture and purified as described in Section (II)(4)(F) below. In the case of embodiments utilizing an antibody fragment engineered to lack a cysteine residue that ordinarily forms the disulfide bridge between the light and heavy chains as described above, preferred recombinant production systems include bacterial expression and product recovery procedures utilizing the low pH osmotic shock method described in the "Alternative Fab'-SH Purification" section of Example T below. If a full length antibody is produced, the desired antibody fragment can be obtained therefrom by subjecting the intact antibody to enzymatic digestion according to known methods, e.g. as described in Section (II)(4)(G) below.

b. Construction of Antibody Fragment-polymer Conjugates

The antibody fragment-polymer conjugates of the invention can be made by derivatizing the desired antibody fragment with an inert polymer. It will be appreciated that any inert polymer which provides the conjugate with the desired apparent size or which has the selected actual MW as taught herein is suitable for use in constructing the antibody fragment-polymer conjugates of the invention.

Many inert polymers are suitable for use in pharmaceuticals. See, e.g., Davis et al., *Biomedical Polymers: Polymeric Materials and Pharmaceuticals for Biomedical Use*, pp.441–451 (1980). In all embodiments of the invention, a non-proteinaceous polymer is used. The nonproteinaceous polymer ordinarily is a hydrophilic synthetic polymer, i.e., a polymer not otherwise found in nature. However, polymers which exist in nature and are produced by recombinant or in vitro methods are also useful, as are polymers which are isolated from native sources. Hydrophilic polyvinyl polymers fall within the scope of this invention, e.g. polyvinylalcohol and polyvinylpyrrolidone. Particularly useful are polyalkylene ethers such as polyethylene glycol (PEG); polyoxyalkylenes such as polyoxyethylene, polyoxypropylene, and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin or heparon. The polymer prior to cross-linking need not be, but preferably is, water soluble, but the final conjugate must be water soluble. Preferably, the conjugate exhibits a water solubility of at least about 0.01 mg/ml, and more preferably at least about 0.1 mg/ml, and still more preferably at least about 1 mg/ml. In addition, the polymer should not be highly immunogenic in the conjugate form, nor should it possess viscosity that is incompatible with intravenous infusion or injection if the conjugate is intended to be administered by such routes.

In one embodiment, the polymer contains only a single group which is reactive. This helps to avoid cross-linking of protein molecules. However, it is within the scope herein to maximize reaction conditions to reduce cross-linking, or to purify the reaction products through gel filtration or ion exchange chromatography to recover substantially homogenous derivatives. In other embodiments, the polymer contains two or more reactive groups for the purpose of linking multiple antibody fragments to the polymer backbone. Again, gel filtration or ion exchange chromatography can be used to recover the desired derivative in substantially homogeneous form.

The molecular weight of the polymer can range up to about 500,000 D, and preferably is at least about 20,000 D, or at least about 30,000 D, or at least about 40,000 D. The molecular weight chosen can depend upon the effective size of the conjugate to be achieved, the nature (e.g. structure, such as linear or branched) of the polymer, and the degree of derivatization, i.e. the number of polymer molecules per antibody fragment, and the polymer attachment site or sites on the antibody fragment.

The polymer can be covalently linked to the antibody fragment through a multifunctional crosslinking agent which reacts with the polymer and one or more amino acid residues of the antibody fragment to be linked. However, it is also within the scope of the invention to directly crosslink the polymer by reacting a derivatized polymer with the antibody fragment, or vice versa.

The covalent crosslinking site on the antibody fragment includes the N-terminal amino group and epsilon amino groups found on lysine residues, as well as other amino, imino, carboxyl, sulfhydryl, hydroxyl or other hydrophilic groups. The polymer may be covalently bonded directly to the antibody fragment without the use of a multifunctional (ordinarily bifunctional) crosslinking agent. Covalent binding to amino groups is accomplished by known chemistries based upon cyanuric chloride, carbonyl diimidazole, aldehyde reactive groups (PEG alkoxide plus diethyl acetal of bromoacetaldehyde; PEG plus DMSO and acetic anhydride, or PEG chloride plus the phenoxide of 4-hydroxybenzaldehyde, activated succinimidyl esters, activated dithiocarbonate PEG, 2,4,5-trichlorophenylcloroformate or P-nitrophenylcloroformate activated PEG.) Carboxyl groups are derivatized by coupling PEG-amine using carbodiimide. Sulfhydryl groups are derivatized by coupling to maleimido-substituted PEG (e.g. alkoxy-PEG amine plus sulfosuccinimidyl 4-(N-maleimidomethyl)cyclohexane-1-carboxylate) as described in WO 97/10847 published Mar. 27, 1997, or PEG-maleimide commercially available from Shearwater Polymers, Inc., Huntsville, Ala.). Alternatively, free amino groups on the antibody fragment (e.g. epsilon amino groups on lysine residues) can be thiolated with 2-imino-thiolane (Traut's reagent) and then coupled to maleimide-containing derivatives of PEG as described in Pedley et al., *Br. J. Cancer*, 70: 1126–1130 (1994).

The polymer will bear a group which is directly reactive with an amino acid side chain, or the N- or C-terminus of the polypeptide linked, or which is reactive with the multifunctional cross-linking agent. In general, polymers bearing such reactive groups are known for the preparation of immobilized proteins. In order to use such chemistries here, one should employ a water soluble polymer otherwise derivatized in the same fashion as insoluble polymers heretofore employed for protein immobilization. Cyanogen bromide activation is a particularly useful procedure to employ in crosslinking polysaccharides.

"Water soluble" in reference to the starting polymer means that the polymer or its reactive intermediate used for conjugation is sufficiently water soluble to participate in a derivatization reaction.

The degree of substitution with such a polymer will vary depending upon the number of reactive sites on the antibody fragment, the molecular weight, hydrophilicity and other characteristics of the polymer, and the particular antibody fragment derivatization sites chosen. In general, the conjugate contains from 1 to about 10 polymer molecules, but greater numbers of polymer molecules attached to the antibody fragments of the invention are also contemplated. The desired amount of derivatization is easily achieved by using an experimental matrix in which the time, temperature and other reaction conditions are varied to change the degree of substitution, after which the level of polymer substitution of the conjugates is determined by size exclusion chromatography or other means known in the art.

The polymer, e.g. PEG, is cross-linked to the antibody fragment by a wide variety of methods known per se for the covalent modification of proteins with nonproteinaceous polymers such as PEG. Certain of these methods, however, are not preferred for the purposes herein. Cyanuronic chloride chemistry leads to many side reactions, including protein cross-linking. In addition, it may be particularly likely to lead to inactivation of proteins containing sulfhydryl groups. Carbonyl diimidazole chemistry (Beauchamp et al., *Anal Biochem.* 131, 25–33 [1983]) requires high pH (>8.5), which can inactivate proteins. Moreover, since the "activated PEG" intermediate can react with water, a very large molar excess of "activated PEG" over protein is required. The high concentrations of PEG required for the carbonyl diimidazole chemistry also led to problems in purification, as both gel filtration chromatography and hydrophilic interaction chromatography are adversely affected. In addition, the high concentrations of "activated PEG" may precipitate protein, a problem that per se has been noted previously (Davis, U.S. Pat. No. 4,179,337). On the other hand, aldehyde chemistry (Royer, U.S. Pat. No. 4,002,531) is more efficient since it requires only a 40-fold molar excess of PEG and a 1–2 hr incubation. However, the manganese dioxide suggested by Royer for preparation of the PEG aldehyde is problematic "because of the pronounced tendency of PEG to form complexes with metal-based oxidizing agents" (Harris et al., *J. Polym. Sci. Polym. Chem. Ed.* 22, 341–52 [1984]). The use of a Moffatt oxidation, utilizing DMSO and acetic anhydride, obviates this problem. In addition, the sodium borohydride suggested by Royer must be used at high pH and has a significant tendency to reduce disulfide bonds. In contrast, sodium cyanoborohydride, which is effective at neutral pH and has very little tendency to reduce disulfide bonds is preferred. In another preferred embodiment, maleimido-activated PEG is used for coupling to free thiols on the antibody fragment.

Functionalized PEG polymers to modify the antibody fragments of the invention are available from Shearwater Polymers, Inc. (Huntsville, Ala.). Such commercially available PEG derivatives include, but are not limited to, amino-PEG, PEG amino acid esters, PEG-hydrazide, PEG-thiol, PEG-succinate, carboxymethylated PEG, PEG-propionic acid, PEG amino acids, PEG succinimidyl succinate, PEG succinimidyl propionate, succinimidyl ester of carboxymethylated PEG, succinimidyl carbonate of PEG, succinimidyl esters of amino acid PEGs, PEG-oxycarbonylimidazole, PEG-nitrophenyl carbonate, PEG tresylate, PEG-glycidyl ether, PEG-aldehyde, PEG vinylsulfone, PEG-maleimide, PEG-orthopyridyldisulfide, heterofunctional PEGs, PEG vinyl derivatives, PEG silanes, and PEG phospholides. The reaction conditions for coupling these PEG derivatives will vary depending on the protein, the desired degree of PEGylation, and the PEG derivative utilized. Some factors involved in the choice of PEG derivatives include: the desired point of attachment (such as lysine or cysteine R-groups), hydrolytic stability and reactivity of the derivatives, stability, toxicity and antigenicity of the linkage, suitability for analysis, etc. Specific instructions for the use of any particular derivative are available from the manufacturer.

The conjugates of this invention are separated from the unreacted starting materials by gel filtration or ion exchange HPLC. Heterologous species of the conjugates are purified from one another in the same fashion.

The conjugates may also be purified by ion-exchange chromatography. The chemistry of many of the electrophilically activated PEG's results in a reduction of amino group charge of the PEGylated product. Thus, high resolution ion exchange chromatography can be used to separate the free and conjugated proteins, and to resolve species with different levels of PEGylation. In fact, the resolution of different species (e.g. containing one or two PEG residues) is also possible due to the difference in the ionic properties of the unreacted amino acids. In one embodiment, species with difference levels of PEGylation are resolved according to the methods described in WO 96/34015 (International Application No. PCT/US96/05550 published Oct.31, 1996).

In a preferred embodiment, the conjugate is generated by utilizing the derivatization and purification methods described in Section (T) of the Examples below.

In one aspect, the invention provides any of the above-described conjugates formed by its component parts, i.e. one or more antibody fragment(s) covalently attached to one or more polymer molecule(s), without any extraneous matter in the covalent molecular structure of the conjugate.

c. Other Derivatives of Large Effective Size Conjugates

In another aspect, any of the above-described conjugates can be modified to contain one or more component(s) in addition to the antibody fragment component(s) and polymer component(s) that form the conjugate, wherein the modification does not alter the essential functional property of the conjugate, namely, the substantially improved serum half-life, MRT and/or serum clearance rate as compared to that of the parental antibody fragment from which the conjugate is derived. In one embodiment, the invention provides any of the above-described conjugates modified to incorporate one or more nonproteinaceous functional group (s). For example, the conjugate can be modified to incorporate nonproteinaceous labels or reporter molecules, such as radiolabels, including any radioactive substance used in medical treatment or imaging or used as an effector function or tracer in an animal model, such as radioisotopic labels $^{99}$Tc, $^{90}$Y, $^{111}$In, $^{32}$P, $^{14}$C, $^{125}$I, $^{3}$H, $^{131}$I, $^{11}$C, $^{15}$O, $^{13}$N, $^{18}$F, $^{35}$S, $^{51}$Cr, $^{57}$To, $^{226}$Ra, $^{60}$Co, $^{59}$Fe, $^{75}$Se, $^{152}$Eu, $^{67}$Cu, $^{217}$Ci, $^{211}$At, $^{212}$Pb, $^{47}$Sc, $^{109}$Pd, $^{234}$Th, $^{40}$K, and the like, non-radioisotopic labels such as $^{157}$Gd, $^{55}$Mn, $^{52}$Tr, $^{56}$Fe, etc., fluorescent or chemiluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}$Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels, stable free radicals, and the like.

Conventional methods are available to bind these labels covalently to the polypeptide antibody fragment or polymer component of the conjugate. In one aspect, any conjugate of the invention is modified by derivatizing the antibody fragment component with any of the above-described nonproteinaceous labels, wherein the label is directly or indirectly (through a coupling agent) attached to the antibody fragment, and wherein such derivatization of the antibody fragment does not contribute or introduce any polymer moiety into the molecular structure of the conjugate. For instance, coupling agents such as dialdehydes, carbodiimides, dimaleimides, bis-imidates, bis-diazotized benzidine, and the like can be used to tag the antibody fragment with the above-described fluorescent or chemiluminescent labels. See, for example, U.S. Pat. No. 3,940,475 (fluorimetry), Morrison, *Meth. Enzymol.*, 32b, 103 (1974), Svyanen et al., *J. Biol. Chem.*, 2, 3762 (1973), and Bolton and Hunter, Biochem. J., 133, 529 (1973).

In the case of embodiments utilizing radiolabels, both direct and indirect labeling can be used to incorporate the selected radionuclide into the conjugate. As used herein in the context of radiolabeling, the phrases "indirect labeling" and "indirect labeling approach" both mean that a chelating agent is covalently attached to the antibody fragment moiety or polymer moiety of the conjugate and at least one raidonuclide is inserted into the chelating agent. Preferred chelating agents and radionuclides are set forth in Srivagtava, S. C. and Mease, R. C., "Progress in Research on Ligands, Nuclides and Techniques for Labeling Monoclonal Antibodies," *Nucl. Med. Bio.*, 8(6): 599–603 (1991). A particularly preferred chelating agent is 1-isothiocycmatobenzyl-3-methyldiothelene triaminepent acetic acid ("MX-DTPA"). As used herein in the context of radiolabeling, the phrases "direct labeling" and "direct labeling approach" both mean that a radionuclide is covalently attached directly to the antibody fragment moiety (typically via an amino acid residue) or to the polymer moiety of the conjugate. Preferred radionuclides for use in direct labeling of conjugate are provided in Srivagtava and Mease, supra. In one embodiment, the conjugate is directly labeled with $^{131}$I covalently attached to tyrosine residues. In another embodiment, the antibody fragment component of the conjugate is directly or indirectly labeled with any of the above-described radiolabels, wherein such labeling of the antibody fragment does not contribute or introduce any polymer moiety into the molecular structure of the conjugate.

d. Therapeutic Compositions and Administration of Large Effective Size Conjugates The conjugate of the invention is useful for treating the disease indications that are treated with the parent intact antibody. For example, a conjugate derived from an anti-IL-8 antibody or fragment is useful in the treatment of inflammatory disorders as described in Section (II)(5)(B) below. Therapeutic formulations of the conjugate of the invention can be prepared by utilizing the same procedures described for the formulation of the anti-IL-8 antibodies and fragments of the invention in Section (II)5)(B) below. The conjugate of the invention can be administered in place of the parent antibody for a given disease indication by modifying the formulation, dosage, administration protocol, and other aspects of a therapeutic regimen as required by the different pharmacodynamic characteristics of the conjugate and as dictated by common medical knowledge and practice.

e. Reagent Uses for Large Effective Size Conjugates

The conjugate of the invention also finds application as a reagent in an animal model system for in vivo study of the biological functions of the antigen recognized by the conjugate. The conjugate would enable the practitioner to inactivate or detect the cognate antigen in circulation or in tissue for a far greater period of time than would be possible with art-known constructs while removing any Fc interaction (which could attend the use of an intact antibody) from the system. In addition, the increased half-life of the conjugate of the invention can be applied advantageously to the induction of tolerance for the underivatized antibody fragment in a test animal by employing the Wie et al., *Int. Archs. Allergy Appl. Immunol.*, 64: 84–99 (1981) method for allergen tolerization, which would permit the practitioner to repeatedly challenge the tolerized animal with the underivatized parental antibody fragment without generating an immune response against the parental fragment.

2. Humanized 6G4.2.5 Monclonal Antibodies and Antibody Fragments

In one embodiment, the invention provides an antibody fragment or full length antibody comprising a heavy chain comprising the amino acid sequence of amino acids 1–230 (herein referred to as "6G4.2.5HV11") of the humanized anti-IL-8 6G4.2.5v11 heavy chain polypeptide amino acid sequence of FIGS. 37A–37B (SEQ ID NO: 60).

The invention encompasses a single chain antibody fragment comprising the 6G4.2.5HV11, with or without any additional amino acid sequence. In one embodiment, the invention provides a single chain antibody fragment comprising the 6G4.2.5HV11 without any associated light chain amino acid sequence, i.e. a single chain species that makes up one half of a Fab fragment.

Further provided herein are an antibody or antibody fragment comprising the 6G4.2.51V11, and further comprising a light chain comprising the amino acid sequence of amino acids 1–219 (herein referred to as "6G4.2.5LV11") of the humanized anti-IL-8 6G4.2.5v11 light chain polypeptide amino acid sequence of FIG. 31B (SEQ ID NO: 51).

In one embodiment, the invention provides a single chain antibody fragment wherein the 6G4.2.5HV11 and the 6G4.2.5LV11 are contained in a single chain polypeptide species. In a preferred embodiment, the single chain antibody fragment comprises the 6G4.2.5HV11 joined to the 6G4.2.5LV11 by means of a flexible peptide linker sequence, wherein the heavy chain and light chain domains can associate in a "dimeric" structure analogous to that formed in a two-chain Fab species. In another embodiment, the single chain antibody fragment is a species comprising the 6G4.2.5HV11 joined to the 6G4.2.5LV11 by a linker that is too short to permit intramolecular pairing of complementary domains, i.e. a single chain polypeptide monomer that forms a diabody upon dimerization with another monomer.

In yet another embodiment, the invention provides an antibody fragment comprising a plurality of polypeptide chains, wherein one polypeptide chain comprises the 6G4.2.5HV11 and a second polypeptide chain comprises the 6G4.2.5LV11 and the two polypeptide chains are covalently linked by one or more interchain disulfide bonds. In a preferred embodiment, the foregoing two-chain antibody fragment is selected from the group consisting of Fab, Fab', Fab'-SH, and F(ab')$_2$.

The invention also provides an antibody or antibody fragment comprising a heavy chain containing the 6G4.2.5HV11 and optionally further comprising a light chain containing the 6G4.2.5LV11, wherein the heavy chain, and optionally the light chain, is (are) fused to an additional moiety, such as additional immunoglobulin constant domain sequence. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al. (supra).

In a preferred embodiment, the antibody or antibody fragment comprises the 6G4.2.5HV11 in a heavy chain that is fused to or contains a leucine zipper sequence. The leucine zipper can increase the affinity and/or production efficiency of the antibody or antibody fragment of interest. Suitable leucine zipper sequences include the jun and fos leucine zippers taught by Kostelney et al., *J. Immunol.*, 148: 1547–1553 (1992) and the GCN4 leucine zipper described in the Examples below. In a preferred embodiment, the antibody or antibody fragment comprises the 6G4.2.514V11 fused at its C-terminus to the GCN4 leucine zipper to yield the amino acid sequence of amino acids 1–275 (herein referred to as "6G4.2.5HV11GCN4") of the heavy chain polypeptide amino acid sequence of FIGS. 37A–37B (SEQ ID NO: 60).

3. Variants of Humanized 6G4.2.5 Monoclonal Antibodies and Antibody Fragments The invention additionally encompasses humanized anti-IL-8 monoclonal antibody and antibody fragments comprising variants of the 6G4.2.5 complementarity determining regions (CDRs) or variants of the 6G4.2.5v11 variable domains which exhibit higher affinity for human IL-8 and/or possess properties that yield greater efficiency in recombinant production processes.

A. 6G4.2.5LV Variants

In one aspect, the invention provides humanized anti-IL-8 monoclonal antibodies and antibody fragments comprising the complementarity determining regions (referred to herein as the "CDRs of 6G4.2.5LV") L1, L2, and L3 of the 6G4.2.5 light chain variable domain amino acid sequence of FIG. 24, wherein L1 corresponds to amino acids 24–39 of the amino acid sequence of FIG. 24, L2 corresponds to amino acids 55–61 of the amino acid sequence of FIG. 24 (SEQ ID NO: 35), and L3 corresponds to amino acids 94–102 of the amino acid sequence of FIG. 24 (SEQ ID NO: 35).

In addition, the invention provides a variant 6G4.2.5 humanized antibody or antibody fragment comprising a humanized light chain variable domain comprising a variant (hereinafter referred to a "6G4.2.5LV CDRs variant") of the complementarity determining regions L1, L2, and L3 of the 6G4.2.5 variable light chain domain amino acid sequence of FIG. 24 (SEQ ID NO: 35). In one embodiment, the invention provides a variant 6G4.2.5 humanized antibody or antibody fragment comprising a 6G4.2.5LV CDRs variant (herein referred to as "6G4.2.5LV/L1N35$X_{35}$") wherein L1 corresponds to amino acids 24–39 of the amino acid sequence of FIG. 24 (SEQ ID NO: 35) with the proviso that any amino acid other than Asn (denoted as "$X_{35}$") is substituted for Asn at amino acid position 35, L2 corresponds to amino acids 55–61 of the amino acid sequence of FIG. 24 (SEQ ID NO: 35), and L3 corresponds to amino acids 94–102 of the amino acid sequence of FIG. 24 (SEQ ID NO: 35). In a preferred embodiment, the invention provides a variant 6G4.2.5 humanized antibody or antibody fragment comprising a 6G4.2.5LV CDRs variant (herein referred to as "6G4.2.5LV/L1N35A") wherein L1 corresponds to amino acids 24–39 of the amino acid sequence of FIG. 24 (SEQ ID NO: 35) with the proviso that Ala is substituted for Asn at amino acid position 35, L2 corresponds to amino acids 55–61 of the amino acid sequence of FIG. 24 (SEQ ID NO: 35), and L3 corresponds to amino acids 94–102 of the amino acid sequence of FIG. 24 (SEQ ID NO: 35). In another preferred embodiment, the invention provides a variant 6G4.2.5 humanized antibody or antibody fragment comprising a 6G4.2.5LV CDRs variant (herein referred to as "6G4.2.5LV/L1N35E") wherein L1 corresponds to amino acids 24–39 of the amino acid sequence of FIG. 24 (SEQ ID NO: 35) with the proviso that Glu is substituted for Asn at amino acid position 35, L2 corresponds to amino acids 55–61 of the amino acid sequence of FIG. 24 (SEQ ID NO: 35), and L3 corresponds to amino acids 94–102 of the amino acid sequence of FIG. 24 (SEQ ID NO: 35).

In a second aspect, the invention provides a variant 6G4.2.5 humanized antibody or antibody fragment comprising a 6G4.2.5LV CDRs variant (herein referred to as "6G4.2.5LV/L1S26$X_{26}$") wherein L1 corresponds to amino acids 24–39 of the amino acid sequence of FIG. 24 (SEQ ID NO: 35) with the proviso that any amino acid other than Ser (denoted as "$X_{26}$") is substituted for Ser at amino acid position 26, L2 corresponds to amino acids 55–61 of the amino acid sequence of FIG. 24 (SEQ ID NO: 35), and L3 corresponds to amino acids 94–102 of the amino acid sequence of FIG. 24 (SEQ ID NO: 35). In a preferred embodiment, the invention provides a variant 6G4.2.5 humanized antibody or antibody fragment comprising a 6G4.2.5LV CDRs variant (herein referred to as "6G4.2.5LV/L1S26A") wherein L1 corresponds to amino acids 24–39 of the amino acid sequence of FIG. 24 (SEQ ID NO: 35) with the proviso that Ala is substituted for Ser at amino acid position 26, L2 corresponds to amino acids 55–61 of the amino acid sequence of FIG. 24 (SEQ ID NO: 35), and L3 corresponds to amino acids 94–102 of the amino acid sequence of FIG. 24 (SEQ ID NO: 35).

In a third aspect, the invention provides a variant 6G4.2.5 humanized antibody or antibody fragment comprising a 6G4.2.5LV CDRs variant (herein referred to as "6G4.2.5LV/L3H98$X_{98}$") wherein L1 corresponds to amino acids 24–39 of the amino acid sequence of FIG. 24 (SEQ ID NO: 35), L2 corresponds to amino acids 55–61 of the amino acid sequence of FIG. 24 (SEQ ID NO: 35), and L3 corresponds to amino acids 94–102 of the amino acid sequence of FIG. 24 (SEQ ID NO: 35) with the proviso that any amino acid other than His (denoted as "$X_{98}$") is substituted for His at amino acid position 98. In a preferred embodiment, the invention provides a variant 6G4.2.5 humanized antibody or antibody fragment comprising a 6G4.2.5LV CDRs variant (herein referred to as "6G4.2.5LV/L3H98A") wherein L1 corresponds to amino acids 24–39 of the amino acid sequence of FIG. 24 (SEQ ID NO: 35), L2 corresponds to amino acids 55–61 of the amino acid sequence of FIG. 24 (SEQ ID NO: 35), and L3 corresponds to amino acids 94–102 of the amino acid sequence of FIG. 24 (SEQ ID NO: 35) with the proviso that Ala is substituted for His at amino acid position 98.

In a fourth aspect, the invention provides a variant 6G4.2.5 humanized antibody or antibody fragment comprising a 6G4.2.5LV CDRs variant (herein referred to as "6G4.2.5LV/L1S26$X_{26}$,N35$X_{35}$") wherein L1 corresponds to amino acids 24–39 of the amino acid sequence of FIG. 24 (SEQ ID NO: 35) with the proviso that any amino acid other than Ser (denoted as "$X_{26}$") is substituted for Ser at amino acid position 26 and any amino acid other than Asn (denoted as "$X_{35}$") is substituted for Asn at amino acid position 35, L2 corresponds to amino acids 55–61 of the amino acid sequence of FIG. 24 (SEQ ID NO:35), and L3 corresponds to amino acids 94–102 of the amino acid sequence of FIG. 24 (SEQ ID NO:35). In a preferred embodiment, the invention provides a variant 6G4.2.5 humanized antibody or antibody fragment comprising a 6G4.2.5LV CDRs variant (herein referred to as "6G4.2.5LV/L1S26A,N35A") wherein L1 corresponds to amino acids 24–39 of the amino acid sequence of FIG. 24 (SEQ ID NO:35) with the proviso that Ala is substituted for Ser at amino acid position 26 and Ala is substituted for Asn at amino acid position 35, L2 corresponds to amino acids 55–61 of the amino acid sequence of FIG. 24 (SEQ ID NO 35), and L3 corresponds to amino acids 94–102 of the amino acid sequence of FIG. 24 (SEQ ID NO 35).

In a fifth aspect, the invention provides a variant 6G4.2.5 humanized antibody or antibody fragment comprising a 6G4.2.5LV CDRs variant (herein referred to as "6G4.2.5LV/L1N35$X_{35}$/L3H98$X_{98}$") wherein L1 corresponds to amino acids 2439 of the amino acid sequence of FIG. 24 (SEQ ID NO 35) with the proviso that any amino acid other than Asn (denoted as "$X_{35}$") is substituted for Asn at amino acid position 35, L2 corresponds to amino acids 55–61 of the amino acid sequence of FIG. 24 (SEQ ID NO 35), and L3 corresponds to amino acids 94–102 of the amino acid sequence of FIG. 24 (SEQ ID NO 35) with the proviso that any amino acid other than His (denoted as "$X_{98}$") is substituted for His at amino acid position 98. In a preferred embodiment, the invention provides a variant 6G4.2.5 humanized antibody or antibody fragment comprising a 6G4.2.5LV CDRs variant (herein referred to as "6G4.2.5LV/L1N35A/L3H98A") wherein L1 corresponds to amino acids 24–39 of the amino acid sequence of FIG. 24 (SEQ ID NO 35) with the proviso that Ala is substituted for Asn at amino acid position 35, L2 corresponds to amino acids 55–61 of the amino acid sequence of FIG. 24 (SEQ ID NO 35), and L3 corresponds to amino acids 94–102 of the amino acid sequence of FIG. 24 (SEQ ID NO 35) with the proviso that Ala is substituted for His at amino acid position 98.

In a sixth aspect, the invention provides a variant 6G4.2.5 humanized antibody or antibody fragment comprising a 6G4.2.5LV CDRs variant (herein referred to as "6G4.2.5LV/L1S$_{26}$X26/L3H98X$_{98}$") wherein L1 corresponds to amino acids 24–39 of the amino acid sequence of FIG. 24 (SEQ ID NO 35) with the proviso that any amino acid other than Ser (denoted as "$X_{26}$") is substituted for Ser at amino acid position 26, L2 corresponds to amino acids 55–61 of the amino acid sequence of FIG. 24 (SEQ ID NO 35), and L3 corresponds to amino acids 94–102 of the amino acid sequence of FIG. 24 (SEQ ID NO 35) with the proviso that any amino acid other than His (denoted as "$X_{98}$") is substituted for His at amino acid position 98. In a preferred embodiment, the invention provides a variant 6G4.2.5 humanized antibody or antibody fragment comprising a 6G4.2.5LV CDRs variant (herein referred to as "6G4.2.5LV/L1S26A/L3H98A") wherein L1 corresponds to amino acids 24–39 of the amino acid sequence of FIG. 24 (SEQ ID NO 35) with the proviso that Ala is substituted for Ser at amino acid position 26, L2 corresponds to amino acids 55–61 of the amino acid sequence of FIG. 24 SEQ ID NO 35), and L3 corresponds to amino acids 94–102 of the amino acid sequence of FIG. 24 (SEQ ID NO: 35) with the proviso that Ala is substituted for His at amino acid position 98.

In a seventh aspect, the invention provides a variant 6G4.2.5 humanized antibody or antibody fragment comprising a 6G4.2.5LV CDRs variant (here referred to as "6G4.2.5LV/L1S26X$_{26}$N35X$_{35}$/L3H98X$_{98}$") wherein L1 corresponds to amino acids 24–39 of the amino acid sequence of FIG. 24 (SEQ ID NO: 35) with the proviso that any amino acid other than Ser (denoted as "$X_{26}$") is substituted for Ser at amino acid position 26 and any amino acid other than Asn (denoted as "$X_{35}$") is substituted for Asn at amino acid position 35, L2 corresponds to amino acids 55–61 of the amino acid sequence of FIG. 24 (SEQ ID NO: 35), and L3 corresponds to amino acids 94–102 of the amino acid sequence of FIG. 24 (SEQ ID NO: 35) with the proviso that any amino acid other than His (denoted as "$X_{98}$") is substituted for His at amino acid position 98. In a preferred embodiment, the invention provides a variant 6G4.2.5 humanized antibody or antibody fragment comprising a 6G4.2.5LV CDRs variant (here referred to as "6G4.2.5LV/L1S26A,N35A/L3H98A") wherein L1 corresponds to amino acids 24–39 of the amino acid sequence of FIG. 24 (SEQ ID NO: 35) with the proviso that Ala is substituted for Ser at amino acid position 26 and Ala is substituted for Asn at amino acid position 35, L2 corresponds to amino acids 55–61 of the amino acid sequence of FIG. 24 (SEQ ID NO: 35), and L3 corresponds to amino acids 94–102 of the amino acid sequence of FIG. 24 (SEQ ID NO: 35) with the proviso that Ala is substituted for His at amino acid position 98.

The humanized light chain variable domains of the invention can be constructed by using any of the techniques for antibody humanization known in the art. Humanization can be essentially performed following the method of Winter and co-workers (Jones et al., *Nature* 321:522 (1986); Riechmann et al., *Nature* 332:323 (1988); Verhoeyen et al., *Science* 239:1534 (1988)), by substituting the CDRs of 6G4.2.5LV or the CDRs of a 6G4.2.5LV CDRs variant for the corresponding sequences of a human antibody light chain variable domain. Accordingly, such "humanized" derivatives containing the CDRs of 6G4.2.5LV or the CDRs of a 6G4.2.5VL CDRs variant are chimeric (Cabilly et al., supra). The humanized light chain variable domain comprising the CDRs of 6G4.2.5LV or the CDRs of a 6G4.2.5LV CDRs variant can also contain some FR residues that are substituted by residues from analogous sites in the murine 6G4.2.5 antibody light chain variable domain ("6G4.2.5LV"). The complete amino acid sequence of 6G4.2.5LV is set out as amino acids 1–114 of the amino acid sequence of FIG. 24 (SEQ ID NO: 35).

The invention further provides a humanized antibody or antibody fragment comprising a humanized light chain variable domain comprising the CDRs of 6G4.2.5LV or the CDRs of a 6G4.2.5LV CDRs variant as described above, and further comprising a humanized heavy chain variable domain comprising the complementarity determining regions (CDRs) H1, H2, and H3 of the 6G4.2.5 (murine monoclonal antibody) variable heavy chain domain amino acid sequence of FIG. 25 (SEQ ID NO: 37), wherein H1 correspond to amino acids 26–35 of the amino acid sequence of FIG. 25 (SEQ ID NO: 37), wherein H2 corresponds to amino acids 50–66 of the amino acid sequence of FIG. 25 (SEQ ID NO: 37), and wherein H3 corresponds to amino acids 99–111 of the amino acid sequence of FIG. 25 (SEQ ID NO: 37). The above-described H1, H2, and H3 CDRs of the 6G4.2.5 heavy chain variable domain ("6G4.2.5HV") are collectively referred to as the "CDRs of 6G4.2.5HV".

In another embodiment, the invention provides a humanized antibody or antibody fragment comprising a humanized light chain variable domain comprising the CDRs of 6G4.2.5LV or the CDRs of a 6G4.2.51,V CDRs variant as described above, and further comprising a humanized heavy chain variable domain comprising a variant (herein referred to as a "6G4.2.5HV CDRs variant") of the H1, H2, and H3 CDRs of the 6G4.2.5 (murine monoclonal antibody) variable heavy chain domain amino acid sequence of FIG. 25 (SEQ ID NO: 37). In one 6G4.2.5HV CDRs variant (referred to herein as "6G4.2.5HV/H1S31Z$_{31}$"), H1 correspond to amino acids 26–35 of the amino acid sequence of FIG. 25 (SEQ ID NO: 37) with the proviso that any amino acid other than Ser (denoted as "$Z_{31}$") is substituted for Ser at amino acid position 31, H2 corresponds to amino acids 50–66 of the amino acid sequence of FIG. 25 35 (SEQ ID NO: 37), and H3 corresponds to amino acids 99–111 of the amino acid sequence of FIG. 25 (SEQ ID NO: 37). In a preferred 6G4.2.5HV CDRs variant (referred to herein as "6G4.2.5HV/H1S31A"), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37).

In a second 6G4.2.5HV CDRs variant (referred to herein as "6G4.2.5HV/H2S54Z$_{54}$"), H1 corresponds to amino acids 26–35 of the amino acid sequence of FIG. 25 (SEQ ID NO: 37), H2 corresponds to amino acids 50–66 of the amino acid sequence of FIG. 25 (SEQ ID NO: 37) with the proviso that any amino acid other than Ser (denoted as "$Z_{54}$") is substituted for Ser at amino acid position 54, and H3 corresponds to amino acids 99–111 of the amino acid sequence of FIG. 25 (SEQ ID NO: 37). In a preferred 6G4.2.5HV CDRs variant (referred to herein as "6G4.2.5HV/H2S54A"), H1 corresponds to amino acids 26–35 of the amino acid sequence of FIG. 25 (SEQ ID NO: 37), H2 corresponds to amino acids 50–66 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37).

In a third 6G4.2.5HV CDRs variant (referred to herein as "6G4.2.5HV/H3D100E"), wherein H1 correspond to amino acids 26–35 of the amino acid sequence of FIG. 25 (SEQ ID NO: 37), wherein H2 corresponds to amino acids 50–66 of the amino acid sequence of FIG. 25 (SEQ ID NO: 37), and wherein H3 corresponds to amino acids 99–111 of the amino acid sequence of FIG. 25 (SEQ ID NO: 37) with the proviso that Glu is substituted for Asp at amino acid position 100.

In a fourth 6G4.2:5HV CDRs variant (referred to herein as "6G4.2.5HV/H3R102K"), wherein H1 correspond to amino acids 26–35 of the amino acid sequence of FIG. 25 (SEQ ID NO: 37), wherein H2 corresponds to amino acids 50–66 of the amino acid sequence of FIG. 25 (SEQ ID NO: 37), and wherein H3 corresponds to amino acids 99–111 of the amino acid sequence of FIG. 25 (SEQ ID NO: 37) with the proviso that Lys is substituted for Arg at amino acid position 102.

In a fifth 6G4.2.5HV CDRs variant (referred to herein as "6G4.2.5HV/H3D106E"), wherein H1 correspond to amino acids 26–35 of the amino acid sequence of FIG. 25 (SEQ ID NO: 37), wherein H2 corresponds to amino acids 50–66 of the amino acid sequence of FIG. 25 (SEQ ID NO: 37), and wherein H3 corresponds to amino acids 99–111 of the amino acid sequence of FIG. 25 (SEQ ID NO: 37) with the proviso that Glu is substituted for Asp at amino acid position 106.

In a seventh 6G4.2.5HV CDRs variant (referred to herein as "6G4.2.5HV/H3D100E,R102K"), wherein H1 correspond to amino acids 26–35 of the amino acid sequence of FIG. 25 (SEQ ID NO: 37), wherein H2 corresponds to amino acids 50–66 of the amino acid sequence of FIG. 25 (SEQ ID NO: 37), and wherein H3 corresponds to amino acids 99–111 of the amino acid sequence of FIG. 25 (SEQ ID NO: 37) with the proviso that Glu is substituted for Asp at amino acid position 100 and Lys is substituted for Arg at amino acid position 102.

In an eighth 6G4.2.5HV CDRs variant (referred to herein as "6G4.2.5HV/H3R102K,D106E"), wherein H1 correspond to amino acids 26–35 of the amino acid sequence of FIG. 25 (SEQ ID NO: 37), wherein H2 corresponds to amino acids 50–66 of the amino acid sequence of FIG. 25 (SEQ ID NO: 37), and wherein H3 corresponds to amino acids 99–111 of the amino acid sequence of FIG. 25 (SEQ ID NO: 37) with the proviso that Lys is substituted for Arg at amino acid position 102 and Glu is substituted for Asp at amino acid position 106.

In a ninth 6G4.2.5HV CDRs variant (referred to herein as "6G4.2.5HV/H3D100E,D106E"), wherein H1 correspond to amino acids 26–35 of the amino acid sequence of FIG. 25 (SEQ ID NO: 37), wherein H2 corresponds to amino acids 50–66 of the amino acid sequence of FIG. 25 (SEQ ID NO: 37), and wherein H3 corresponds to amino acids 99–111 of the amino acid sequence of FIG. 25 (SEQ ID NO: 37) with the proviso that Glu is substituted for Asp at amino acid position 100 and Glu is substituted for Asp at amino acid position 106.

In a tenth 6G4.2.5HV CDRs variant (referred to herein as "6G4.2.5HV/H3D100E,R102K,D106E"), wherein H1 correspond to amino acids 26–35 of the amino acid sequence of FIG. 25 (SEQ ID NO: 37), wherein H2 corresponds to amino acids 50-66 of the amino acid sequence of FIG. 25 (SEQ ID NO: 37), and wherein H3 corresponds to amino acids 99–111 of the amino acid sequence of FIG. 25 (SEQ ID NO: 37) with the proviso that Glu is substituted for Asp at amino acid position 100, Lys is substituted for Arg at amino acid position 102, and Glu is substituted for Asp at amino acid position 106.

In an eleventh 6G4.2.5HV CDRs variant (referred to herein as "6G4.2.5HV/H1S31$Z_{31}$/H2S54$Z_{54}$"), H1 correspond to amino acids 26–35 of the amino acid sequence of FIG. 25 (SEQ ID NO: 37) with the proviso that any amino acid other than Ser (denoted as "$Z_{31}$") is substituted for Ser at amino acid position 31, H2 corresponds to amino acids 50–66 of the amino acid sequence of FIG. 25 (SEQ ID NO: 37) with the proviso that any amino acid other than Ser (denoted as "$Z_{54}$") is substituted for Ser at amino acid position 54, and H3 corresponds to amino acids 99–111 of the amino acid sequence of FIG. 25 (SEQ ID NO: 37). In a preferred 6G4.2.5HV CDRs variant (referred to herein as "6G4.2.5HV/H1S31A/H2S54A"), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37).

In a twelfth 6G4.2.5HV CDRs variant (referred to herein as "6G4.2.5HV/H1S31$Z_{31}$/H3D100E), H1 correspond to amino acids 26–35 of the amino acid sequence of FIG. 25 (SEQ ID NO: 37) with the proviso that any amino acid other than Ser (denoted as "$Z_{31}$") is substituted for Ser at amino acid position 31, H2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37) with the proviso that Glu is substituted for Asp at amino acid position 100. In a preferred 6G4.2.5HV CDRs variant (referred to herein as "6G4.2.5HV/H1S31A/H3D100E"), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37) with the proviso that Glu is substituted for Asp at amino acid position 100.

In a thirteenth 6G4.2.5HV CDRs variant (referred to herein as "6G4.2.5HV/H1S31$Z_{31}$/H3R102K"), H1 correspond to amino acids 26–35 of the amino acid sequence of FIG. 25 (SEQ ID NO: 37) with the proviso that any amino acid other than Ser (denoted as "$Z_{31}$") is substituted for Ser at amino acid position 31, H2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37) with the proviso that Lys is substituted for Arg at amino acid position 102. In a preferred 6G4.2.5HV CDRs variant (referred to herein as "6G4.2.5HV/H1S31A/H3R102K"), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37) with the proviso that Lys is substituted for Arg at amino acid position 102.

A fourteenth 6G4.2.5HV CDRs variant (referred to herein as "6G4.2.5HV/H1S31Z$_{31}$/H3D106E"), H1 correspond to amino acids 26–35 of the amino acid sequence of FIG. 25 (SEQ ID NO: 37) with the proviso that any amino acid other than Ser (denoted as "Z$_{31}$") is substituted for Ser at amino acid position 31, H2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37) with the proviso that Glu is substituted for Asp at amino acid position 106. In a preferred 6G4.2.5HV CDRs variant (referred to herein as "6G4.2.5HV/H1S31A/H3D106E"), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37) with the proviso that Glu is substituted for Asp at amino acid position 106.

A fifteenth 6G4.2.5HV CDRs variant (referred to herein as "6G4.2.5HV/H1S31Z$_{31}$/H3D100E,R102K"), H1 correspond to amino acids 26–35 of the amino acid sequence of FIG. 25 (SEQ ID NO: 37) with the proviso that any amino acid other than Ser (denoted as -Z$_{31}$") is substituted for Ser at amino acid position 31, H2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37) with the proviso that Glu is substituted for Asp at amino acid position 100 and Lys is substituted for Arg at amino acid position 102. In a preferred 6G4.2.5HV CDRs variant (referred to herein as "6G4.2.5HV/H1S31A/H3D100E,R102K"), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37) with the proviso that Glu is substituted for Asp at amino acid position 100 and Lys is substituted for Arg at amino acid position 102.

In a sixteenth 6G4.2.5HV CDRs variant (referred to herein as "6G4.2.5HV/H1S31Z$_{31}$/H3R102K,D106E"), H1 correspond to amino acids 26–35 of the amino acid sequence of FIG. 25 (SEQ ID NO: 37) with the proviso that any amino acid other than Ser (denoted as "Z$_{31}$") is substituted for Ser at amino acid position 31, H2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37) with the proviso that Lys is substituted for Arg at amino acid position 102 and Glu is substituted for Asp at amino acid position 106. In a preferred 6G4.2.5HV CDRs variant (referred to herein as "6G4.2.5HV/H1S31A/H3R102K,D106E"), H1 correspond to amino acids 26–35 of the amino acid sequence of FIG. 25 (SEQ ID NO: 37) with the proviso that Ala is substituted for Ser at amino acid position 31, R2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37) with the proviso that Lys is substituted for Arg at amino acid position 102 and Glu is substituted for Asp at amino acid position 106.

In a seventeenth 6G4.2.5HV CDRs variant (referred to herein as "6G4.2.5HV/H1S31Z$_{31}$/H3D100E,D106E"), H1 correspond to amino acids 26–35 of the amino acid sequence of FIG. 25 (SEQ ID NO: 37) with the proviso that any amino acid other than Ser (denoted as "Z$_{31}$") is substituted for Ser at amino acid position 31 H2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37) with the proviso that Glu is substituted for Asp at amino acid position 100 and Glu is substituted for Asp at amino acid position 106. In a preferred 6G4.2.5HV CDRs variant (referred to herein as "6G4.2.5HV/H1S31A/H3D100E,D106E"), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37) with the proviso that Glu is substituted for Asp at amino acid position 100 and Glu is substituted for Asp at amino acid position 106.

In an eighteenth 6G4.2.5HV CDRs variant (referred to herein as "6G4.2.5HV/H1S31Z$_{31}$/H3D100E,R102K, D106E"), H1 correspond to amino acids 26–35 of the amino acid sequence of FIG. 25 (SEQ ID NO: 37) with the proviso that any amino acid other than Ser (denoted as "Z$_{31}$") is substituted for Ser at amino acid position 31, H2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37) with the proviso that Glu is substituted for Asp at amino acid position 100, Lys is substituted for Arg at amino acid position 102 and Glu is substituted for Asp at amino acid position 106. In a preferred 6G4.2.5HV CDRs variant (referred to herein as "6G4.2.5HV/H1S31A/ H3D100E,R102K,D106E"), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37) with the proviso that Glu is substituted for Asp at amino acid position 100, Lys is substituted for Arg at amino acid position 102 and Glu is substituted for Asp at amino acid position 106.

In a nineteenth 6G4.2.5HV CDRs variant (referred to herein as "6G4.2.5HV/H2S54Z$_{54}$/H3D100E"), H1 corresponds to amino acids 26–35 of the amino acid sequence of FIG. 25 (SEQ ID NO: 37), H2 corresponds to amino acids 50–66 of the amino acid sequence of FIG. 25 (SEQ ID NO:. 37) with the proviso that any amino acid other than Ser (denoted as "Z$_{54}$") is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100. In a preferred 6G4.2.5HV CDRs variant (referred to herein as "6G4.2.5HV/H2S54A/H3D100E"), H1 corresponds to amino acids 26–35 of the amino acid sequence of FIG. 25 (SEQ ID NO: 37), H2 corresponds to amino acids 50–66 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100.

In a twentieth 6G4.2.5HV CDRs variant (referred to herein as "6G4.2.5HV/H2S54Z$_{54}$/H3R102K"), H1 corresponds to amino acids 26–35 of the amino acid sequence of FIG. 25 (SEQ ID NO: 37), H2 corresponds to amino acids 50–66 of the amino acid sequence of FIG. 25 (SEQ ID NO:

37) with the proviso that any amino acid other than Ser (denoted as "$Z_{54}$") is substituted for Ser at amino acid position 54, and H3 corresponds to amino acids 99–111 of the amino acid sequence of FIG. 25 (SEQ ID NO: 37) with the proviso that Lys is substituted for Arg at amino acid position 102. In a preferred 6G4.2.5HV CDRs variant (referred to herein as "6G4.2.5HV/H2S54A/H3R102K"), H1 corresponds to amino acids 26–35 of the amino acid sequence of FIG. 25 (SEQ ID NO: 37), H2 corresponds to amino acids 50–66 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37) with the proviso that Lys is substituted for Arg at amino acid position 102.

In a twenty-first 6G4.2.5HV CDRs variant (referred to herein as "6G4.2.5HV/H2S54$Z_{54}$/H3D106E"), H1 corresponds to amino acids 26–35 of the amino acid sequence of FIG. 25 (SEQ ID NO: 37), R2 corresponds to amino acids 5066 of the amino acid sequence of FIG. 25 (SEQ ID NO: 37) with the proviso that any amino acid other than Ser (denoted as "$Z_{54}$") is substituted for Ser at amino acid position 54, and H3 corresponds to amino acids 99–111 of the amino acid sequence of FIG. 25 (SEQ ID NO: 37) with the proviso that Glu is substituted for Asp at amino acid position 106. In a preferred 6G4.2.5HV CDRs variant (referred to herein as "6G4.2.5HV/H2S54A/H3D106E"), H1 corresponds to amino acids 26–35 of the amino acid sequence of FIG. 25 (SEQ ID NO: 37), H2 corresponds to amino acids 5066 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37) with the proviso that Glu is substituted for Asp at amino acid position 106.

In a twenty-second 6G4.2.5HV CDRs variant (referred to herein as "6G4.2.5HV/H2S54$Z_{54}$/H3D100E,R102K"), H1 corresponds to amino acids 26–35 of the amino acid sequence of FIG. 25 (SEQ ID NO: 37), H2 corresponds to amino acids 50–66 of the amino acid sequence of FIG. 25 (SEQ ID NO: 37) with the proviso that any amino acid other than Ser (denoted as "$Z_{54}$") is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100 and Lys is substituted for Arg at amino acid position 102. In a preferred 6G4.2.5HV CDRs variant (referred to herein as "6G4.2.5HV/H2S54A/H3D100E, R102K"), H1 corresponds to amino acids 26–35 of the amino acid sequence of FIG. 25 (SEQ ID NO: 37), H2 corresponds to amino acids 50–66 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100 and Lys is substituted for Arg at amino acid position 102.

In a twenty-third 6G4.2.5HV CDRs variant (referred to herein as "6G4.2.5HV/H2S54$Z_{54}$/H3R102K,D106E"), H1 corresponds to amino acids 26–35 of the amino acid sequence of FIG. 25 (SEQ ID NO: 37), H2 corresponds to amino acids 50–66 of the amino acid sequence of FIG. 25 (SEQ ID NO: 37) with the proviso that any amino acid other than Ser (denoted as "$Z_{54}$") is substituted for Ser at amino acid position 54, and H3 corresponds to amino acids 99–111 of the amino acid sequence of FIG. 25 (SEQ ID NO: 37) with the proviso that Lys is substituted for Arg at amino acid position 102 and Glu is substituted for Asp at amino acid position 106. In a preferred 6G4.2.5HV CDRs variant (referred to herein as "6G4.2.5HV/H2S54A/H3R102K, D106E"), H1 corresponds to amino acids 26–35 of the amino acid sequence of FIG. 25 (SEQ ID NO: 37), H2 corresponds to amino acids 50–66 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37) with the proviso that Lys is substituted for Arg at amino acid position 102 and Glu is substituted for Asp at amino acid position 106.

In a twenty-fourth 6G4.2.5HV CDRs variant (referred to herein as "6G4.2.5HV/H2S54$Z_{54}$/H3D100E,D106E"), H1 corresponds to amino acids 26–35 of the amino acid sequence of FIG. 25 (SEQ ID NO: 37), H2 corresponds to amino acids 50–66 of the amino acid sequence of FIG. 25 (SEQ ID NO: 37) with the proviso that any amino acid other than Ser (denoted as "$Z_{54}$") is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100 and Glu is substituted for Asp at amino acid position 106. In a preferred 6G4.2.5HV CDRs variant (referred to herein as "6G4.2.5HV/H2S54A/H3D100E, D106E"), H1 corresponds to amino acids 26–35 of the amino acid sequence of FIG. 25 (SEQ ID NO: 37), H2 corresponds to amino acids 50–66 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100 and Glu is substituted for Asp at amino acid position 106.

In a twenty-fifth 6G4.2.5HV CDRs variant (referred to herein as "6G4.2.5HV/H2S54$Z_{54}$/H3D100E,R102K, D106E"), H1 corresponds to amino acids 26–35 of the amino acid sequence of FIG. 25 (SEQ ID NO: 37), H2 corresponds to amino acids 50–66 of the amino acid sequence of FIG. 25 (SEQ ID NO: 37) with the proviso that any amino acid other than Ser (denoted as "$Z_{54}$") is substituted for Ser at amino acid position 54, and 13 corresponds to amino acids 99–111 of the amino acid sequence of FIG. 25 (SEQ ID NO: 37) with the proviso that Glu is substituted for Asp at amino acid position 100, Lys is substituted for Arg at amino acid position 102 and Glu is substituted for Asp at amino acid position 106. In a preferred 6G4.2.5HV CDRs variant (referred to herein as "6G4.2.5HV/H2S54A/ H3D100E,R102K,D106E"), H1 corresponds to amino acids 26–35 of the amino acid sequence of FIG. 25 (SEQ ID NO: 37), H2 corresponds to amino acids 50–66 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100, Lys is substituted for Arg at amino acid position 102 and Glu is substituted for Asp at amino acid position 106.

In a twenty-sixth 6G4.2.5HV CDRs variant (referred to herein as "6G4.2.5HV/H1S31$Z_{31}$/R2S54$Z_{54}$/H3D100E"), H1 correspond to amino acids 26–35 of the amino acid sequence of FIG. 25 (SEQ ID NO: 37) with the proviso that any amino acid other than Ser (denoted as "$Z_{31}$") is substituted for Ser at amino acid position 31, R2 corresponds to amino acids 50–66 of the amino acid sequence of FIG. 25 (SEQ ID NO: 37) with the proviso that any amino acid other than Ser (denoted as "$Z_{54}$") is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100. In a preferred 6G4.2.5HV CDRs variant (referred to herein as "6G4.2.5HV/H1S31A/H2S54A/H3D100E"), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100.

In a twenty-seventh 6G4.2.5HV CDRs variant (referred to herein as "6G4.2.5HV/H1S31$Z_{31}$/H2S54$Z_{54}$/H3R102K"), H1 correspond to amino acids 26–35 of the amino acid sequence of FIG. 25 (SEQ ID NO: 37) with the proviso that any amino acid other than Ser (denoted as "$Z_{31}$") is substituted for Ser at amino acid position 31, 12 corresponds to amino acids 50–66 of the amino acid sequence of FIG. 25 (SEQ ID NO: 37) with the proviso that any amino acid other than Ser (denoted as "$Z_{54}$") is substituted for Ser at amino acid position 54, and H3 corresponds to amino acids 99–111 of the amino acid sequence of FIG. 25 (SEQ ID NO: 37) with the proviso that Lys is substituted for Arg at amino acid position 102. In a preferred 6G4.2.5IV CDRs variant (referred to herein as "6G4.2.5HV/H1S31A/H2S54A/H3R102K"), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37) with the proviso that Lys is substituted for Arg at amino acid position 102.

In a twenty-eighth 6G4.2.5HV CDRs variant (referred to herein as "6G4.2.5HV/H1S31$Z_{31}$/H2S54$Z_{54}$/H3D106E"), H1 correspond to amino acids 26–35 of the amino acid sequence of FIG. 25 (SEQ ID NO: 37) with the proviso that any amino acid other than Ser (denoted as "$Z_{31}$") is substituted for Ser at amino acid position 31, H2 corresponds to amino acids 50–66 of the amino acid sequence of FIG. 25 (SEQ ID NO: 37) with the proviso that any amino acid other than Ser (denoted as "$Z_{54}$") is substituted for Ser at amino acid position 54, and H3 corresponds to amino acids 99–111 of the amino acid sequence of FIG. 25 (SEQ ID NO: 37) with the proviso that Glu is substituted for Asp at amino acid position 106. In a preferred 6G4.2.5HV CDRs variant (referred to herein as "6G4.2.5HV/H1S31A/H2S54A/H3D106E), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO 37) with the proviso that Ala is substituted for Ser at amino acid position 54, and H3 corresponds to amino acids 99–111 of the amino acid sequence of FIG. 25 (SEQ ID NO 37) with the proviso that Glu is substituted for Asp at amino acid position 106.

In a twenty-ninth 6G4.2.5HV CDRs variant (referred to herein as "6G4.2.5HV/H1S31$Z_{31}$/H2S54$Z_{54}$/H3D100E,R102K"), H1 correspond to amino acids 26–35 of the amino acid sequence of FIG. 25 (SEQ ID NO: 37) with the proviso that any amino acid other than Ser (denoted as "$Z_{31}$") is substituted for Ser at amino acid position 31, 1H2 corresponds to amino acids 50–66 of the amino acid sequence of FIG. 25 (SEQ ID NO: 37) with the proviso that any amino acid other than Ser (denoted as "$Z_{54}$") is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100 and Lys is substituted for Arg at amino acid position 102. In a preferred 6G4.2.5HV CDRs variant (referred to herein as "6G4.2.5HV/H1S31A/H2S54A/H3D100E,R102K"), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100 and Lys is substituted for Arg at amino acid position 102.

In a thirtieth 6G4.2.5HV CDRs variant (referred to herein as "6G4.2.5HV/H1S31$Z_{31}$/H2S54$Z_{54}$/H3R102K,D106E"), H1 correspond to amino acids 26–35 of the amino acid sequence of FIG. 25 (SEQ ID NO: 37) with the proviso that any amino acid other than Ser (denoted as "$Z_{31}$") is substituted for Ser at amino acid position 31, H2 corresponds to amino acids 50–66 of the amino acid sequence of FIG. 25 (SEQ ID NO: 37) with the proviso that any amino acid other than Ser (denoted as "$Z_{54}$") is substituted for Ser at amino acid position 54, and H3 corresponds to amino acids 99–111 of the amino acid sequence of FIG. 25 (SEQ ID NO: 37) with the proviso that Lys is substituted for Arg at amino acid position 102 and Glu is substituted for Asp at amino acid position 106. In a preferred 6G4.2.5HV CDRs variant (referred to herein as "6G4.2.5HV/H1S31A/H2S54A/H3R102K,D106E"), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37) with the proviso that Lys is substituted for Arg at amino acid position 102 and Glu is substituted for Asp at amino acid position 106.

In a thirty-first 6G4.2.5HV CDRs variant (referred to herein as "6G4.2.5HV/H1S31$Z_{31}$/H2S54$Z_{54}$/H3D100E,D106E"), H1 correspond to amino acids 26–35 of the amino acid sequence of FIG. 25 (SEQ ID NO: 37) with the proviso that any amino acid other than Ser (denoted as "$Z_{31}$") is substituted for Ser at amino acid position 31, H2 corresponds to amino acids 50–66 of the amino acid sequence of FIG. 25 (SEQ ID NO: 37) with the proviso that any amino acid other than Ser (denoted as "$Z_{54}$") is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100 and Glu is substituted for Asp at amino acid position 106. In a preferred 6G4.2.5HV CDRs variant (referred to herein as "6G4.2.5HV/H1S31A/H2S54A/H3D100E,D106E"), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100 and Glu is substituted for Asp at amino acid position 106.

In a thirty-second 6G4.2.5HV CDRs variant (referred to herein as "6G4.2.5HV/H1S31$Z_{31}$/H2S54$Z_{54}$/H3D100E, R102K,D106E"), H1 correspond to amino acids 26–35 of the amino acid sequence of FIG. 25 (SEQ ID NO: 37) with the proviso that any amino acid other than Ser (denoted as "$Z_{31}$") is substituted for Ser at amino acid position 31, H2 corresponds to amino acids 50–66 of the amino acid sequence of FIG. 25 (SEQ ID NO: 37) with the proviso that any amino acid other than Ser (denoted as "$Z_{54}$") is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100, Lys is substituted for Arg at amino acid position 102 and Glu is substituted for Asp at amino acid position 106. In a preferred 6G4.2.5HV CDRs variant (referred to herein as "6G4.2.5HV/H1S31A/H2S54A/H3D100E,R102K,D106E"), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100, Lys is substituted for Arg at amino acid position 102 and Glu is substituted for Asp at amino acid position 106.

As in the humanization of the light chain variable domain described above, a humanized heavy chain variable domain is constructed by substituting the CDRs of 6G4.2.5HV or the CDRs of a 6G4.2.5HV CDRs variant for the corresponding sequences in a human heavy chain variable domain. The humanized heavy chain variable domain comprising the CDRs of 6G4.2.5HV or the CDRs of a 6G4.2.5HV CDRs variant can also contain some FR residues that are substituted by residues from analogous sites in the murine 6G4.2.5 antibody heavy chain variable domain. The complete amino acid sequence of 6G4.2.5HV is set out as amino acids 1–122 of the amino acid sequence of FIG. 25 (SEQ ID NO: 37).

The choice of human variable domains, both light and heavy, to be used in making the humanized antibodies and antibody fragments is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.* 151: 2296 (1993); Chothia and Lesk, *J. Mol. Biol.* 196:901 (1987)). Another method uses a particular framework derived from the consensus sequence of all human antibodies of a particular subgroup of light or heavy chains. The same framework can be used for several different humanized antibodies (Carter et al., *Proc. Natl. Acad. Sci. U.S.A.* 89:4285 (1992); Presta et al., *J. Immunol.* 151:2623 (1993)).

It is also important that the antibodies and antibody fragments of the invention be humanized with retention of high affinity for human IL-8 and other favorable biological properties. To achieve this goal, according to a preferred method, the humanized antibodies and antibody fragments of the invention are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way; FR residues can be selected and combined from the consensus and parental sequences so that the desired antibody characteristic, such as increased affinity for the target antigen(s), is achieved.

Any and all humanized light chain variable domain amino acid sequences which comprise the CDRs of 6G4.2.5LV are collectively referred to herein as "hu6G4.2.5LV".

Any and all humanized light chain variable domain amino acid sequences which comprise the CDRs of 6G4.2.5LV/L1N35$X_{35}$ are collectively referred to herein as "hu 6G4.2.5LV/L1N35$X_{35}$".

Any and all humanized light chain variable domain amino acid sequences which comprise the CDRs of 6G4.2.5LV/L1N35A are collectively referred to herein as "hu6G4.2.5LV/L1N35A".

Any and all humanized light chain variable domain amino acid sequences which comprise the CDRs of 6G4.2.5LV/L1N35E are collectively referred to herein as "hu6G4.2.5LV/L1N35E".

Any and all humanized light chain variable domain amino acid sequences which comprise the CDRs of 6G4.2.5LV/L1S26$X_{26}$ are collectively referred to herein as "hu6G4.2.5LV/L1S26$X_{26}$".

Any and all humanized light chain variable domain amino acid sequences which comprise the CDRs of 6G4.2.5LV/L1S26A are collectively referred to herein as "hu6G4.2.5LV/L1S26A".

Any and all humanized light chain variable domain amino acid sequences which comprise the CDRs of 6G4.2.5LV/L3H98$X_{98}$ are collectively referred to herein as "hu6G4.2.5LV/L3H98$X_{98}$".

Any and all humanized light chain variable domain amino acid sequences which comprise the CDRs of 6G4.2.5LV/L3H98A are collectively referred to herein as "hu6G4.2.5LV/L3H98A".

Any and all humanized light chain variable domain amino acid sequences which comprise the CDRs of 6G4.2.5LV/L1S26$X_{26}$,N35$X_{35}$ are collectively referred to herein as "hu6G4.2.5LV/L1S26$X_{26}$,N35$X_{35}$".

Any and all humanized light chain variable domain amino acid sequences which comprise the CDRs of 6G4.2.5LV/L1S26A,N35A are collectively referred to herein as "hu6G4.2.5LV/L1S26A,N35A".

Any and all humanized light chain variable domain amino acid sequences which comprise the CDRs of 6G4.2.5LV/L1N35$X_{35}$/L3H98$X_{98}$ are collectively referred to herein as "hu6G4.2.5LV/L1N35$X_{35}$/L3H98$X_{98}$".

Any and all humanized light chain variable domain amino acid sequences which comprise the CDRs of 6G4.2.5LV/L1N35A/L3H98A are collectively referred to herein as "hu6G4.2.5LV/L1N35A/L3H98A".

Any and all humanized light chain variable domain amino acid sequences which comprise the CDRs of 6G4.2.5LV/L1S26$X_{26}$/L3H98$X_{98}$ are collectively referred to herein as "hu6G4.2.5LV/L1S26$X_{26}$/L3H98$X_{98}$".

Any and all humanized light chain variable domain amino acid sequences which comprise the CDRs of 6G4.2.5LV/L1S26A/L3H98A are collectively referred to herein as "hu6G4.2.5LV/L1S26A/L3H98A".

Any and all humanized light chain variable domain amino acid sequences which comprise the CDRs of 6G4.2.5LV/L1S26X$_{26}$,N35X$_{35}$/L3H98X$_{98}$ are collectively referred to herein as "hu6G4.2.5LV/L1S26X$_{26}$,N35X$_{35}$/L3H98X$_{98}$".

Any and all humanized light chain variable domain amino acid sequences which comprise the CDRs of 6G4.2.5LV/L1S26A,N35A/L3H98A are collectively referred to herein as "hu6G4.2.5LV/L1S26A,N35A/L3H98A".

The humanized light chain variable domain amino acid sequences of hu6G4.2.5LV/L1N35X$_{35}$, hu6G4.2.5LV/L1S26X$_{26}$, hu6G4.2.5LV/L1S26X$_{26}$/L3H98X$_{98}$, hu6G4.2.5LV/L1S26X$_{26}$,N35X$_{35}$, hu6G4.2.5LV/L1N35X$_{35}$/L3H98X$_{98}$, hu6G4.2.5LV/L1S26X$_{26}$/L3H98X$_{98}$, and hu6G4.2.5LV/L1S26X$_{26}$,N35X$_{35}$/L3H98X$_{98}$ are collectively referred to herein as "hu6G4.2.5LV/vL1-3X".

The humanized light chain variable domain amino acid sequences of hu6G4.2.5LV/L1N35A, hu6G4.2.5LV/L1S26A, hu6G4.2.5LV/L1S26A/L3H98A, hu6G4.2.5LV/L1S26A,N35A, hu6G4.2.5LV/L1N35A/L3H98A, hu6G4.2.5LV/L1S26A/L3H98A, hu6G4.2.5LV/L1S26A,N35A/L3H98A are collectively referred to herein as "hu6G4.2.5LV/vL1-3A".

Any and all humanized heavy chain variable domain amino acid sequences which comprise the CDRs of 6G4.2.5HV are collectively referred to herein as "hu6G4.2.5HV".

Any and all humanized heavy chain variable domain amino acid sequences which comprise the CDRs of 6G4.2.5HV/H1S31Z$_{31}$ are collectively referred to herein as "hu6G4.2.5HV/H1S31Z$_{31}$".

Any and all humanized heavy chain variable domain amino acid sequences which comprise the CDRs of 6G4.2.5HV/H1S31A are collectively referred to herein as "hu6G4.2.5HV/H1S31A".

Any and all humanized heavy chain variable domain amino acid sequences which comprise the CDRs of 6G4.2.5HV/H2S54Z$_{54}$ are collectively referred to herein as "hu6G4.2.5HV/H2S54Z$_{54}$".

Any and all humanized heavy chain variable domain amino acid sequences which comprise the CDRs of 6G4.2.5HV/H2S54A are collectively referred to herein as "hu6G4.2.5HV/H2S54A".

Any and all humanized heavy chain variable domain amino acid sequences which comprise the CDRs of 6G4.2.5HV/H3D100E are collectively referred to herein as "hu6G4.2.5HV/H3D100E".

Any and all humanized heavy chain variable domain amino acid sequences which comprise the CDRs of 6G4.2.5HV/H3R102K are collectively referred to herein as "hu6G4.2.5HV/H3R102K".

Any and all humanized heavy chain variable domain amino acid sequences which comprise the CDRs of 6G4.2.5HV/H3D106E are collectively referred to herein as "hu6G4.2.5HV/H3D106E".

Any and all humanized heavy chain variable domain amino acid sequences which comprise the CDRs of 6G4.2.5HV/H3D100E,R102K are collectively referred to herein as "hu6G4.2.5HV/H3D100E,R102K".

Any and all humanized heavy chain variable domain amino acid sequences which comprise the CDRs of 6G4.2.5HV/H3R102K,D106E are collectively referred to herein as "hu6G4.2.5HV/H3R102K,D106E".

Any and all humanized heavy chain variable domain amino acid sequences which comprise the CDRs of 6G4.2.5HV/H3D100E,D106E are collectively referred to herein as "hu6G4.2.5HV/H3D100E,D106E".

Any and all humanized heavy chain variable domain amino acid sequences which comprise the CDRs of 6G4.2.5HV/H3D100E,R102K,D106E are collectively referred to herein as "hu6G4.2.5HV/H3D100E,R102K,D106E.

Any and all humanized heavy chain variable domain amino acid sequences which comprise the CDRs of 6G4.2.5HV/H1S31Z$_{31}$/H2S54Z$_{54}$ are collectively referred to herein as "hu6G4.2.5HV/H1S31Z$_{31}$/H2S54Z$_{54}$".

Any and all humanized heavy chain variable domain amino acid sequences which comprise the CDRs of 6G4.2.5HV/H1S31Z$_{31}$/H3D100E are collectively referred to herein as "hu6G4.2.5HV/H1S31Z$_{31}$/H3D100E".

Any and all humanized heavy chain variable domain amino acid sequences which comprise the CDRs of 6G4.2.5HV/H1S31Z$_{31}$/H3R102K are collectively referred to herein as hu6G4.2.5HV/H1S3l1Z$_{31}$/H3R102K".

Any and all humanized heavy chain variable domain amino acid sequences which comprise the CDRs of 6G4.2.5HV/H1S31Z$_{31}$/H3D106E are collectively referred to herein as "hu6G4.2.5HV/H1S31Z$_{31}$/H3D106E".

Any and all humanized heavy chain variable domain amino acid sequences which comprise the CDRs of 6G4.2.5HV/H1S31Z$_{31}$/H3D100E,R102K are collectively referred to herein as "hu6G4.2.5HV/H1S31Z$_{31}$/H3D100E, R102K".

Any and all humanized heavy chain variable domain amino acid sequences which comprise the CDRs of 6G4.2.5HV/H1S31Z$_{31}$/H3R102K,D106E are collectively referred to herein as "hu6G4.2.5HV/H1S31Z$_{31}$/H3R102K, D106E".

Any and all humanized heavy chain variable domain amino acid sequences which comprise the CDRs of 6G4.2.5HV/H1S31Z$_{31}$/H3D100E,D106E are collectively referred to herein as "hu6G4.2.5HV/H1S31Z$_{31}$/H3D100E, D106E".

Any and all humanized heavy chain variable domain amino acid sequences which comprise the CDRs of 6G4.2.5HV/H1S31Z$_{31}$/H3D100E,R102K,D106E are collectively referred to herein as "hu6G4.2.5HV/H1S31Z$_{31}$/H3D100E,R102K,D106E".

Any and all humanized heavy chain variable domain amino acid sequences which comprise the CDRs of 6G4.2.5HV/H2S54Z$_{54}$/H3D100E are collectively referred to herein as "hu6G4.2.5HV/H2S54Z$_{54}$/H3D100E".

Any and all humanized heavy chain variable domain amino acid sequences which comprise the CDRs of 6G4.2.5HV/H2S54Z$_{54}$/H3R102K are collectively referred to herein as "hu6G4.2.5HV/H2S54Z$_{54}$/H3R102K".

Any and all humanized heavy chain variable domain amino acid sequences which comprise the CDRs of 6G4.2.5HV/H2S54Z54/H3D106E are collectively referred to herein as "hu6G4.2.5HV/H2S54Z$_{54}$/H3D106E".

Any and all humanized heavy chain variable domain amino acid sequences which comprise the CDRs of 6G4.2.5HV/H2S54Z$_{54}$/H3R102K,D106E are collectively referred to herein as "hu6G4.2.5HV/H2S54Z$_{54}$/H3R102K, D106E".

Any and all humanized heavy chain variable domain amino acid sequences which comprise the CDRs of 6G4.2.5HV/H2S54Z$_{54}$/H3D100E,D106E are collectively referred to herein as "hu6G4.2.5HV/R2S54Z$_{54}$/H3D100E, D106E".

Any and all humanized heavy chain variable domain amino acid sequences which comprise the CDRs of 6G4.2.5HV/H2S54Z$_{54}$/H3D100E,R102K,D106E are collectively referred to herein as "hu6G4.2.5HV/H2S54Z$_{54}$/H3D100E,R102K,D106E".

Any and all humanized heavy chain variable domain amino acid sequences which comprise the CDRs of 6G4.2.5HV/H1S31$Z_{31}$/H2S54$Z_{54}$/H3D100E are collectively referred to herein as "hu6G4.2.5HV/H1S31$Z_{31}$/H2S54$Z_{54}$/H3D100E".

Any and all humanized heavy chain variable domain amino acid sequences which comprise the CDRs of 6G4.2.5HV/H1S31$Z_{31}$/H2S54$Z_{54}$/H3R102K are collectively referred to herein as "hu6G4.2.5HV/H1S31$Z_{31}$/H2S54$Z_{54}$/H3R102K".

Any and all humanized heavy chain variable domain amino acid sequences which comprise the CDRs of 6G4.2.5HV/H1S31$Z_{31}$/H2S54$Z_{54}$/H3D106E are collectively referred to herein as "hu6G4.2.5HV/H1S31$Z_{31}$/H2S54$Z_{54}$/H3D106E".

Any and all humanized heavy chain variable domain amino acid sequences which comprise the CDRs of 6G4.2.5HV/H1S31$Z_{31}$/H2S54$Z_{54}$/H3D100E,R102K are collectively referred to herein as "hu6G4.2.5HV/H1S31$Z_{31}$/H2S54$Z_{54}$/H3D100E,R102K".

Any and all humanized heavy chain variable domain amino acid sequences which comprise the CDRs of 6G4.2.5HV/H1S31$Z_{31}$/H2S54$Z_{54}$/H3R102K,D106E are collectively referred to herein as "hu6G4.2.5HV/H1S31$Z_{31}$/H2S54$Z_{54}$/H3R102K,D106E".

Any and all humanized heavy chain variable domain amino acid sequences which comprise the CDRs of 6G4.2.5HV/H1S31$Z_{31}$/H2S54Z54/H3D100E,D106E are collectively referred to herein as "hu6G4.2.5HV/H1S31$Z_{31}$/H2S54$Z_{54}$/H3D100E,D106E".

Any and all humanized heavy chain variable domain amino acid sequences which comprise the CDRs of 6G4.2.5HV/H1S31$Z_{31}$/H2S54$Z_{54}$/H3D100E,R102K,D106E are collectively referred to herein as "hu6G4.2.5HV/H1S31$Z_{31}$/H2S54$Z_{54}$/H3D100E,R102K,D106E".

Any and all humanized heavy chain variable domain amino acid sequences which comprise the CDRs of 6G4.2.5HV/H1S31A/H2S54A are collectively referred to herein as "hu6G4.2.5HV/H1S31A/H2S54A".

Any and all humanized heavy chain variable domain amino acid sequences which comprise the CDRs of 6G4.2.5HV/H1S31A/H3D100E are collectively referred to herein as "hu6G4.2.5HV/H1S31A/H3D100E".

Any and all humanized heavy chain variable domain amino acid sequences which comprise the CDRs of 6G4.2.5HV/H1S31A/H3R102K are collectively referred to herein as "hu6G4.2.5HV/H1S31A/H3R102K".

Any and all humanized heavy chain variable domain amino acid sequences which comprise the CDRs of 6G4.2.5HV/H1S31A/H3D106E are collectively referred to herein as "hu6G4.2.5HV/H1S31A/H3D106E".

Any and all humanized heavy chain variable domain amino acid sequences which comprise the CDRs of 6G4.2.5HV/H1S31A/H3D100E,R102K are collectively referred to herein as "hu6G4.2.5HV/H1S31A/H3D100E,R102K".

Any and all humanized heavy chain variable domain amino acid sequences which comprise the CDRs of 6G4.2.5HV/H1S31A/H3R102K,D106E are collectively referred to herein as "hu6G4.2.5HV/H1S31A/H3R102K,D106E".

Any and all humanized heavy chain variable domain amino acid sequences which comprise the CDRs of 6G4.2.5HV/H1S31A/H3D100E,D106E are collectively referred to herein as "hu6G4.2.5HV/H1S31A/H3D100E,D106E".

Any and all humanized heavy chain variable domain amino acid sequences which comprise the CDRs of 6G4.2.5HV/H1S31A/H3D100E,R102K,D106E are collectively referred to herein as "hu6G4.2.5HV/H1S31A/H3D100E,R102K,D106E".

Any and all humanized heavy chain variable domain amino acid sequences which comprise the CDRs of 6G4.2.5HV/H2S54A/H3D100E are collectively referred to herein as "hu6G4.2.5HV/H2S54A/H3D100E".

Any and all humanized heavy chain variable domain amino acid sequences which comprise the CDRs of 6G4.2.5HV/H2S54A/H3R102K are collectively referred to herein as "hu6G4.2.5HV/H2S54A/H3R102K".

Any and all humanized heavy chain variable domain amino acid sequences which comprise the CDRs of 6G4.2.5HV/H2S54A/H3D106E are collectively referred to herein as "hu6G4.2.5HV/H2S54A/H3D106E".

Any and all humanized heavy chain variable domain amino acid sequences which comprise the CDRs of 6G4.2.5HV/H2S54A/H3R102K,D106E are collectively referred to herein as "hu6G4.2.5HV/H2S54A/H3R102K,D106E".

Any and all humanized heavy chain variable domain amino acid sequences which comprise the CDRs of 6G4.2.5HV/H2S54A/H3D100E,D106E are collectively referred to herein as "hu6G4.2.5HV/H2S54A/H3D100E,D106E".

Any and all humanized heavy chain variable domain amino acid sequences which comprise the CDRs of 6G4.2.5HV/H2S54A/H3D100E,R102K,D106E are collectively referred to herein as "hu6G4.2.5HV/H2S54A/H3D100E,R102K,D106E".

Any and all humanized heavy chain variable domain amino acid sequences which comprise the CDRs of 6G4.2.5HV/H1S31A/H2S54A/H3D100E are collectively referred to herein as "hu6G4.2.5HV/H1S31A/H2S54A/H3D100E".

Any and all humanized heavy chain variable domain amino acid sequences which comprise the CDRs of 6G4.2.5HV/H1S31A/H2S54A/H3R102K are collectively referred to herein as "hu6G4.2.5HV/H1S31A/H2S54A/H3R102K".

Any and all humanized heavy chain variable domain amino acid sequences which comprise the CDRs of 6G4.2.5HV/H1S31A/H2S54A/H3D106E are collectively referred to herein as "hu6G4.2.5HV/H1S31A/H2S54A/H3D106E".

Any and all humanized heavy chain variable domain amino acid sequences which comprise the CDRs of 6G4.2.5HV/H1S31A/H2S54A/H3D100E,R102K are collectively referred to herein as "hu6G4.2.5HV/H1S31A/H2S54A/H3D100E,R102K".

Any and all humanized heavy chain variable domain amino acid sequences which comprise the CDRs of 6G4.2.5HV/H1S31A/H2S54A/H3R102K,D106E are collectively referred to herein as "hu6G4.2.5HV/H1S31A/H2S54A/H3R102K,D106E".

Any and all humanized heavy chain variable domain amino acid sequences which comprise the CDRs of 6G4.2.5HV/H1S31A/H2S54A/H3D100E,D106E are collectively referred to herein as "hu6G4.2.5HV/H1S31A/H2S54A/H3D100E,D106E".

Any and all humanized heavy chain variable domain amino acid sequences which comprise the CDRs of 6G4.2.5HV/H1S31A/H2S54A/H3D100E,R102K,D106E are collectively referred to herein as "hu6G4.2.5HV/H1S31A/H2S54A/H3D100E,R102K,D106E".

The humanized heavy chain variable domain amino acid sequences of hu6G4.2.5HV/H1S31$Z_{31}$, hu6G4.2.5HV/

H2S54Z$_{54}$, hu6G4.2.5HV/H3D100E, hu6G4.2.5HV/ H3R102K, hu6G4.2.5HV/H3D106E, hu6G4.2.5HV/ H3D100E,R102K, hu6G4.2.5HV/H3R102K,D106E, hu6G4.2.5HV/H3D100E,D106E, hu6G4.2.5HV/H3D100E, R102K,D106E, hu6G4.2.5HV/H1S31Z$_{31}$/H2S54Z$_{54}$, hu6G4.2.5HV/H1S31Z$_{31}$/H3D100E, hu6G4.2.5HV/ H1S31Z$_{31}$/H3R102K, hu6G4.2.5HV/H1S31Z$_{31}$/H3D106E, hu6G4.2.5HV/H1S31Z$_{31}$/H3D100E,R102K, hu6G4.2.5HV/ H1S31Z$_{31}$/H3R102K,D106E, hu6G4.2.5HV/H1S31Z$_{31}$/ H3D100E,D106E, hu6G4.2.5HV/H1S31Z$_{31}$/H3D100E, R102K,D106E, hu6G4.2.5HV/H2S54Z$_{54}$/H3D100E, hu6G4.2.5HV/H2S54Z$_{54}$/H3R102K, hu6G4.2.5HV/ H2S54Z$_{54}$/H3D106E, hu6G4.2.5HV/H2S54Z$_{54}$/H3R102K, D106E, hu6G4.2.5HV/H2S54Z$_{54}$/H3D100E,D106E, hu6G4.2.5HV/H2S54Z$_{54}$/H3D100E,R102K,D106E, hu6G4.2.5HV/H1S31Z$_{31}$/H2S54Z$_{54}$/H3D100E, hu6G4.2.5HV/H1S31Z$_{31}$/H2S54Z$_{54}$/H3R102K, hu6G4.2.5HV/H1S31Z$_{31}$/H2S54Z$_{54}$/H3D106E, hu6G4.2.5HV/H1S31Z$_{31}$/H2S54Z$_{54}$/H3D100E,R102K, hu6G4.2.5HV/H1S31Z$_{31}$/H2S54Z$_{54}$/H3R102K,D106E, hu6G4.2.5HV/H1S31Z$_{31}$/H2S54Z$_{54}$/H3D100E,D106E, and hu6G4.2.5HV/H1S31Z$_{31}$/H2S54Z$_{54}$/H3D100E,R102K, D106E are collectively referred to herein as "hu6G4.2.5HV/ vH1-3Z".

The humanized heavy chain variable domain amino acid sequences of hu6G4.2.5HV/H1S31A, hu6G4.2.5HV/H2S54A, hu6G4.2.5HV/H3D100E, hu6G4.2.5HV/H3R102K, hu6G4.2.5HV/H3D106E, hu6G4.2.5HV/H3D100E,R102K, hu6G4.2.5HV/H3R102K,D106E, hu6G4.2.5HV/H3D100E,D106E, hu6G4.2.5HV/H3D100E, R102K,D106E, hu6G4.2.5HV/H1S31A/H2S54A, hu6G4.2.5HV/H1S31A/H3D100E, hu6G4.2.5HV/H1S31A/H3R102K, hu6G4.2.5HV/H1S31A/H3D106E, hu6G4.2.5HV/H1S31A/H3D100E,R102K, hu6G4.2.5HV/H1S31A/H3R102K,D106E, hu6G4.2.5HV/H1S31A/H3D100E,D106E, hu6G4.2.5HV/H1S31A/H3D100E, R102K,D106E, hu6G4.2.5HV/H2S54A/H3D100E, hu6G4.2.5HV/H2S54A/H3R102K, hu6G4.2.5HV/H2S54A/H3D106E, hu6G4.2.5HV/H2S54A/H3R102K, D106E, hu6G4.2.5HV/H2S54A/H3D100E,D106E, hu6G4.2.5HV/H2S54A/H3D100E,R102K,D106E, hu6G4.2.5HV/H1S31A/H2S54A/H3D100E, hu6G4.2.5HV/H1S31A/H2S54A/H3R102K, hu6G4.2.5HV/H1S31A/H2S54A/H3D106E, hu6G4.2.5HV/H1S31A/H2S54A/H3D100E,R102K, hu6G4.2.5HV/H1S31A/H2S54A/H3R102K,D106E, hu6G4.2.5HV/H1S31A/H2S54A/H3D100E,D106E, and hu6G4.2.5HV/H1S31A/H2S54A/H3D100E,R102K,D106E are collectively referred to herein as "hu6G4.2.5HV/vH1-3A".

The invention provides a humanized antibody or antibody fragment that comprises a light chain variable domain comprising the hu6G4.2.5LV/vL1-3X. In another embodiment, the invention provides a humanized antibody or antibody fragment that comprises a light chain variable domain comprising the hu6G4.2.5LV/vL1-3A. In yet another embodiment, the invention provides a humanized antibody or antibody fragment that comprises a light chain variable domain comprising the hu6G4.2.5LV/$L1N35X_{35}$. In still another embodiment, the invention provides a humanized antibody or antibody fragment that comprises a light chain variable domain comprising the hu6G4.2.5LV/L1N35A. In a further embodiment, the invention provides a humanized antibody or antibody fragment that comprises a light chain variable domain comprising the hu6G4.2.5LV/L1N35E.

The invention additionally provides a humanized antibody or antibody fragment that comprises a light chain variable domain comprising the hu6G4.2.5LV/vL1-3X, and further comprises a heavy chain variable domain comprising the hu6G4.2.5HV or hu6G4.2.5HV/vH1-3Z. In another embodiment, the invention provides a humanized antibody or antibody fragment that comprises a light chain variable domain comprising the hu6G4.2.5LV/vL1-3A, and further comprises a heavy chain variable domain comprising the hu6G4.2.5HV or hu6G4.2.5HV/vH1-3Z. In yet another embodiment, the invention provides a humanized antibody or antibody fragment that comprises a light chain variable domain comprising the hu6G4.2.5LV/vL1-3A, and further comprises a heavy chain variable domain comprising the hu6G4.2.5HV/vH1-3A.

In a further embodiment, the invention provides a humanized antibody or antibody fragment that comprises a light chain variable domain comprising the hu6G4.2.5LV/$L1N35X_{35}$, and further comprises a heavy chain variable domain comprising the hu6G4.2.5HV or hu6G4.2.5HV/vH1-3Z. In another embodiment, the invention provides a humanized antibody or antibody fragment that comprises a light chain variable domain comprising the hu6G4.2.5LV/$N35X_{35}$, and further comprises a heavy chain variable domain comprising the hu6G4.2.5HV/vH1-3A. In a preferred embodiment, the antibody or antibody fragment comprises a light chain variable domain comprising the hu6G4.2.5LV/$L1N35X_{35}$ and further comprises a humanized heavy chain comprising the amino acid sequence of 6G4.2.5HV11.

In an additional embodiment, the invention provides a humanized antibody or antibody fragment that comprises a light chain variable domain comprising the hu6G4.2.5LV/L1N35A, and further comprises a heavy chain variable domain comprising the hu6G4.2.5HV or hu6G4.2.5HV/vH1-3Z. In another embodiment, the invention provides a humanized antibody or antibody fragment that comprises a light chain variable domain comprising the hu6G4.2.5LV/N35A, and further comprises a heavy chain variable domain comprising the hu6G4.2.5HV/vH1-3A. In still another embodiment, the humanized antibody or antibody fragment comprises a light chain variable domain comprising the hu6G4.2.5LV/L1N35A, and further comprises a heavy chain variable domain comprising the hu6G4.2.5HV. In a further embodiment, the humanized antibody or antibody fragment comprises a light chain variable domain comprising the hu6G4.2.5LV/L1N35E, and further comprises a heavy chain variable domain comprising the hu6G4.2.5HV. In a preferred embodiment, the antibody or antibody fragment comprises a light chain variable domain comprising the hu6G4.2.5LV/L1N35A and further comprises a humanized heavy chain comprising the amino acid sequence of 6G4.2.5HV11. In another preferred embodiment, the antibody or antibody fragment comprises a light chain variable domain comprising the hu6G4.2.5LV/L1N35E and further comprises a humanized heavy chain comprising the amino acid sequence of 6G4.2.5HV11.

The invention encompasses a single chain antibody fragment comprising the hu6G4.2.5LV/vL1-3X, with or without any additional amino acid sequence. In one embodiment, the invention provides a single chain antibody fragment comprising the hu6G4.2.5LV/vL1-3X without any associated heavy chain variable domain amino acid sequence, i.e. a single chain species that makes up one half of an Fv fragment. In another embodiment, the invention provides a single chain antibody fragment comprising the hu6G4.2.5LV/vL1-3A without any associated heavy chain variable domain amino acid sequence. In still another embodiment, the invention provides a single chain antibody fragment comprising the hu6G4.2.5LV/L1N35X$_{35}$ without any associated heavy chain variable domain amino acid sequence. In a preferred embodiment, the invention provides a single chain antibody fragment comprising the hu6G4.2.5LV/L1N35A without any associated heavy chain variable domain amino acid sequence. In another preferred embodiment, the invention provides a single chain antibody fragment comprising the hu6G4.2.5LV/L1N35E without any associated heavy chain variable domain amino acid sequence.

In one embodiment, the invention provides a single chain antibody fragment wherein the hu6G4.2.5LV/vL1-3X and the hu6G4.2.5HV or hu6G4.2.5HV/vH1-3Z are contained in a single chain polypeptide species. In a preferred embodiment, the single chain antibody fragment is a scFv species comprising the hu6G4.2.5LV/vL1-3X joined to the hu6G4.2.5HV or hu6G4.2.5HV/vH1-3Z by means of a flexible peptide linker sequence, wherein the heavy chain and light chain variable domains can associate in a "dimeric" structure analogous to that formed in a two-chain Fv species. In another embodiment, the single chain antibody fragment is a species comprising the hu6G4.2.5LV/vL1-3X joined to the hu6G4.2.5HV or hu6G4.2.5HV/vH1-3Z by a linker that is too short to permit intramolecular pairing of the two variable domains, i.e. a single chain polypeptide monomer that forms a diabody upon dimerization with another monomer.

In another embodiment, the invention provides a single chain antibody fragment wherein the hu6G4.2.5LV/vL1-3A and the hu6G4.2.5HV or hu6G4.2.5HV/vH1-3Z are contained in a single chain polypeptide species. In a preferred embodiment, the single chain antibody fragment is a scFv species comprising the hu6G4.2.5LV/vL1-3A joined to the hu6G4.2.5HV or hu6G4.2.5HV/vH1-3Z by means of a flexible peptide linker sequence, wherein the heavy chain and light chain variable domains can associate in a "dimeric" structure analogous to that formed in a two-chain Fv species. In another embodiment, the single chain antibody fragment is a species comprising the hu6G4.2.5LV/vL1-3A joined to the hu6G4.2.5HV or hu6G4.2.5HV/vH1-3Z by a linker that is too short to permit intramolecular pairing of the two variable domains, i.e. a single chain polypeptide monomer that forms a diabody upon dimerization with another monomer.

In yet another embodiment, the invention provides a single chain antibody fragment wherein the hu6G4.2.5LV/vL1-3A and the hu6G4.2.5HV/vH1-3A are contained in a single chain polypeptide species. In a preferred embodiment, the single chain antibody fragment is a scFv species comprising the hu6G4.2.5LV/vL1-3A joined to the hu6G4.2.5HV/vH1-3A by means of a flexible peptide linker sequence, wherein the heavy chain and light chain variable domains can associate in a "dimeric" structure analogous to that formed in a two-chain Fv species. In another embodiment, the single chain antibody fragment is a species comprising the hu6G4.2.5LV/vL1-3A joined to the hu6G4.2.5HV/vH1-3A by a linker that is too short to permit intramolecular pairing of the two variable domains, i.e. a single chain polypeptide monomer that forms a diabody upon dimerization with another monomer.

In still another embodiment, the invention provides a single chain antibody fragment wherein the hu6G4.2.5LV/L1N35X$_{35}$ and the hu6G4.2.5HV or hu6G4.2.5HV/vH1-3Z are contained in a single chain polypeptide species. In a preferred embodiment, the single chain antibody fragment is a scFv species comprising the hu6G4.2.5LV/L1N35X$_{35}$ joined to the hu6G4.2.5HV or hu6G4.2.5HV/vH1-3Z by means of a flexible peptide linker sequence, wherein the heavy chain and light chain variable domains can associate in a "dimeric" structure analogous to that formed in a two-chain Fv species. In another embodiment, the single chain antibody fragment is a species comprising the hu6G4.2.5LV/L1N35X$_{35}$ joined to the hu6G4.2.5HV or hu6G4.2.5HV/vH1-3Z by a linker that is too short to permit intramolecular pairing of the two variable domains, i.e. a single chain polypeptide monomer that forms a diabody upon dimerization with another monomer.

In a further embodiment, the invention provides a single chain antibody fragment wherein the hu6G4.2.5LV/L1N35X$_{35}$ and the hu6G4.2.5HV/vH1-3A are contained in a single chain polypeptide species. In a preferred embodiment, the single chain antibody fragment is a scFv species comprising the hu6G4.2.5LV/L1N35X$_{35}$ joined to the hu6G4.2.5HV/vH1-3A by means of a flexible peptide linker sequence, wherein the heavy chain and light chain variable domains can associate in a "dimeric" structure analogous to that formed in a two-chain Fv species. In another embodiment, the single chain antibody fragment is a species comprising the hu6G4.2.5LV/L1N35X$_{35}$ joined to the hu6G4.2.5HV/vH1-3A by a linker that is too short to permit intramolecular pairing of the two variable domains, i.e. a single chain polypeptide monomer that forms a diabody upon dimerization with another monomer.

In an additional embodiment, the invention provides a single chain antibody fragment wherein the hu6G4.2.5LV/L1N35A and the hu6G4.2.5HV or hu6G4.2.5HV/vH1-3Z are contained in a single chain polypeptide species. In a preferred embodiment, the single chain antibody fragment is a scFv species comprising the hu6G4.2.5LV/L1N35A joined to the hu6G4.2.5HV or hu6G4.2.5HV/vH1-3Z by means of a flexible peptide linker sequence, wherein the heavy chain and light chain variable domains can associate in a "dimeric" structure analogous to that formed in a two-chain Fv species. In another embodiment, the single chain antibody fragment is a species comprising the hu6G4.2.5LV/L1N35A joined to the hu6G4.2.5HV or hu6G4.2.5HV/vH1-3Z by a linker that is too short to permit intramolecular pairing of the two variable domains, i.e. a single chain polypeptide monomer that forms a diabody upon dimerization with another monomer.

Also provided herein is a single chain antibody fragment wherein the hu6G4.2.5LV/L1N35E and the hu6G4.2.5HV are contained in a single chain polypeptide species. In a preferred embodiment, the single chain antibody fragment is a scFv species comprising the hu6G4.2.5LV/L1N35E joined to the hu6G4.2.5HV by means of a flexible peptide linker sequence, wherein the heavy chain and light chain variable domains can associate in a "dimeric" structure analogous to that formed in a two-chain Fv species. In another embodiment, the single chain antibody fragment is a species comprising the hu6G4.2.5LV/L1N35E joined to the hu6G4.2.5HV by a linker that is too short to permit intramolecular pairing of the two variable domains, i.e. a single chain polypeptide monomer that forms a diabody upon dimerization with another monomer.

In still another embodiment, the invention provides a single chain antibody fragment wherein the hu6G4.2.5LV/L1N35A and the hu6G4.2.5HV/vH1-3A are contained in a single chain polypeptide species. In a preferred embodiment, the single chain antibody fragment is a scFv species comprising the hu6G4.2.5LV/L1N35A joined to the hu6G4.2.5HV/vH1-3A by means of a flexible peptide linker sequence, wherein the heavy chain and light chain variable domains can associate in a "dimeric" structure analogous to that formed in a two-chain Fv species. In another embodiment, the single chain antibody fragment is a species comprising the hu6G4.2.5LV/L1N35A joined to the hu6G4.2.5HV/vH1-3A by a linker that is too short to permit intramolecular pairing of the two variable domains, i.e. a single chain polypeptide monomer that forms a diabody upon dimerization with another monomer.

In yet another embodiment, the invention provides an antibody fragment comprising a plurality of polypeptide chains, wherein one polypeptide chain comprises the hu6G4.2.5LV/vL1-3X and a second polypeptide chain comprises the hu6G4.2.5HV or hu6G4.2.5HV/vH1-3Z and the two polypeptide chains are covalently linked by one or more interchain disulfide bonds.

In still another embodiment, the invention provides an antibody fragment comprising a plurality of polypeptide chains, wherein one polypeptide chain comprises the hu6G4.2.5LV/vL1-3X and a second polypeptide chain comprises the hu6G4.2.5HV/vH1-3A and the two polypeptide chains are covalently linked by one or more interchain disulfide bonds. In a preferred embodiment, the invention provides an antibody fragment comprising a plurality of polypeptide chains, wherein one polypeptide chain comprises the hu6G4.2.5LV/vL1-3X and a second polypeptide chain comprises the amino acid sequence of 6G4.2.5HV11 and the two polypeptide chains are covalently linked by one or more interchain disulfide bonds.

In a further embodiment, the invention provides an antibody fragment comprising a plurality of polypeptide chains, wherein one polypeptide chain comprises the hu6G4.2.5LV/vL1-3A and a second polypeptide chain comprises the hu6G4.2.5HV or hu6G4.2.5HV/vH1-3Z and the two polypeptide chains are covalently linked by one or more interchain disulfide bonds.

In still another embodiment, the invention provides an antibody fragment comprising a plurality of polypeptide chains, wherein one polypeptide chain comprises the hu6G4.2.5LV/vL1-3A and a second polypeptide chain comprises the hu6G4.2.5HV/vH1-3A and the two polypeptide chains are covalently linked by one or more interchain disulfide bonds. In a preferred embodiment, the invention provides an antibody fragment comprising a plurality of polypeptide chains, wherein one polypeptide chain comprises the hu6G4.2.5LV/vL1-3A and a second polypeptide chain comprises the amino acid sequence of 6G4.2.5HV11 and the two polypeptide chains are covalently linked by one or more interchain disulfide bonds.

The invention also encompasses an antibody fragment comprising a plurality of polypeptide chains, wherein one polypeptide chain comprises the hu6G4.2.5LV/L1N35$X_{35}$ and a second polypeptide chain comprises the hu6G4.2.5HV or hu6G4.2.5HV/vH1-3Z and the two polypeptide chains are covalently linked by one or more interchain disulfide bonds.

In still another embodiment, the invention provides an antibody fragment comprising a plurality of polypeptide chains, wherein one polypeptide chain comprises the hu6G4.2.5LV/L1N35$X_{35}$ and a second polypeptide chain comprises the hu6G4.2.5HV/vH1-3A and the two polypeptide chains are covalently linked by one or more interchain disulfide bonds. In a preferred embodiment, the invention provides an antibody fragment comprising a plurality of polypeptide chains, wherein one polypeptide chain comprises the hu6G4.2.5LV/L1N35$X_{35}$ and a second polypeptide chain comprises the amino acid sequence of 6G4.2.5HV11 and the two polypeptide chains are covalently linked by one or more interchain disulfide bonds.

The invention further encompasses an antibody fragment comprising a plurality of polypeptide chains, wherein one polypeptide chain comprises the hu6G4.2.5LV/L1N35A and a second polypeptide chain comprises the hu6G4.2.5HV or hu6G4.2.5HV/vH1-3Z and the two polypeptide chains are covalently linked by one or more interchain disulfide bonds.

The invention also encompasses an antibody fragment comprising a plurality of polypeptide chains, wherein one polypeptide chain comprises the hu6G4.2.5LV/L1N35E and a second polypeptide chain comprises the hu6G4.2.5HV and the two polypeptide chains are covalently linked by one or more interchain disulfide bonds.

In still another embodiment, the invention provides an antibody fragment comprising a plurality of polypeptide chains, wherein one polypeptide chain comprises the hu6G4.2.5LV/L1N35A and a second polypeptide chain comprises the hu6G4.2.5HV/vH1-3A and the two polypeptide chains are covalently linked by one or more interchain disulfide bonds. In a preferred embodiment, the invention provides an antibody fragment comprising a plurality of polypeptide chains, wherein one polypeptide chain comprises the hu6G4.2.5LV/L1N35A and a second polypeptide chain comprises the amino acid sequence of 6G4.2.5HV11 and the two polypeptide chains are covalently linked by one or more interchain disulfide bonds. In another preferred embodiment, the invention provides an antibody fragment comprising a plurality of polypeptide chains, wherein one polypeptide chain comprises the hu6G4.2.5LV/L1N35E and a second polypeptide chain comprises the amino acid sequence of 6G4.2.5HV11 and the two polypeptide chains are covalently linked by one or more interchain disulfide bonds.

In a preferred embodiment, any of the foregoing two-chain antibody fragments are selected from the group consisting of Fab, Fab', Fab'-SH, Fv, and F(ab')$_2$. In another preferred embodiment, the antibody fragment is selected from the group consisting of Fab, Fab', Fab'-SH, Fv, and F(ab')$_2$, wherein the antibody fragment comprises one polypeptide chain comprising the hu6G4.2.5LV/L1N35$X_{35}$ and a second polypeptide chain comprising the hu6G4.2.5HV. In yet another preferred embodiment, the antibody fragment is selected from the group consisting of Fab, Fab', Fab'-SH, Fv, and F(ab')$_2$, wherein the antibody fragment comprises one polypeptide chain comprising the hu6G4.2.5LV/L1N35A and a second polypeptide chain comprising the hu6G4.2.5HV. In a further preferred embodiment, the antibody fragment is selected from the group consisting of Fab, Fab', Fab'-SH, Fv, and F(ab')$_2$, wherein the antibody fragment comprises one polypeptide chain comprising the hu6G4.2.5LV/L1N35E and a second polypeptide chain comprising the hu6G4.2.5HV. In still another preferred embodiment, the antibody fragment is a F(ab')$_2$ that comprises one polypeptide chain comprising the hu6G4.2.5LV/L1N35A and a second polypeptide chain comprising the amino acid sequence of 6G4.2.5HV11. In an additional preferred embodiment, the antibody fragment is a F(ab')$_2$ that comprises one polypeptide chain comprising the hu6G4.2.5LV/L1N35E and a second polypeptide chain comprising the amino acid sequence of 6G4.2.5HV11.

The invention also provides an antibody or antibody fragment comprising a light chain variable domain containing the hu6G4.2.5LV/vL1-3X and optionally further comprising a heavy chain variable domain containing the hu6G4.2.5HV or hu6G4.2.5HV/vH1-3Z, wherein the light chain variable domain, and optionally the heavy chain variable domain, is (are) fused to an additional moiety, such as a immunoglobulin constant domain. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

The invention additionally provides an antibody or antibody fragment comprising a light chain variable domain containing the hu6G4.2.5LV/vL1-3X and optionally further comprising a heavy chain variable domain containing the hu6G4.2.5HV/vH1-3A, wherein the light chain variable domain, and optionally the heavy chain variable domain, is (are) fused to an additional moiety, such as a immunoglobulin constant domain. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

The invention further provides an antibody or antibody fragment comprising a light chain variable domain containing the hu6G4.2.5LV/L1N35$X_{35}$ and optionally further comprising a heavy chain variable domain containing the hu6G4.2.5HV or hu6G4.2.5HV/vH1-3Z, wherein the light chain variable domain, and optionally the heavy chain variable domain, is (are) fused to an additional moiety, such as a immunoglobulin constant domain. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

The invention additionally provides an antibody or antibody fragment comprising a light chain variable domain containing the hu6G4.2.5LV/L1N35$X_{35}$ and optionally further comprising a heavy chain variable domain containing the hu6G4.2.5HV/vH1-3A, wherein the light chain variable domain, and optionally the heavy chain variable domain, is (are) fused to an additional moiety, such as a immunoglobulin constant domain. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al. The invention also encompasses an antibody or antibody fragment comprising a light chain variable domain containing the hu6G4.2.5LV/L1N35A and optionally further comprising a heavy chain variable domain containing the hu6G4.2.5HV or hu6G4.2.5HV/vH1-3Z, wherein the light chain variable domain, and optionally the heavy chain variable domain, is (are) fused to an additional moiety, such as a immunoglobulin constant domain. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

The invention additionally provides an antibody or antibody fragment comprising a light chain variable domain containing the hu6G4.2.5LV/L1N35A and optionally further comprising a heavy chain variable domain containing the hu6G4.2.5HV/vH1-3A, wherein the light chain variable domain, and optionally the heavy chain variable domain, is (are) fused to an additional moiety, such as a immunoglobulin constant domain. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

The invention additionally encompasses an antibody or antibody fragment comprising a light chain variable domain containing the hu6G4.2.5LV/L1N35A and optionally further comprising a heavy chain containing the amino acid sequence of 6G4.2.5HV11, wherein the light chain variable domain, and optionally the heavy chain, is (are) fused to an additional moiety, such as immunoglobulin constant domain sequences. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

The invention further encompasses an antibody or antibody fragment comprising a light chain variable domain containing the hu6G4.2.5LV/L1N35E and optionally further comprising a heavy chain containing the amino acid sequence of 6G4.2.5HV11, wherein the light chain variable domain, and optionally the heavy chain, is (arc) fused to an additional moiety, such as immunoglobulin constant domain sequences. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and I&E constant regions, and that such constant regions can be obtained from any human or animal species. Preferably, the constant domain sequence is human in origin. Suitable human constant domain sequences can be obtained from Kabat et al.

In a preferred embodiment, the antibody or antibody fragment comprises a light chain variable domain containing the hu6G4.2.5LV/vL1-3X, and further comprises the hu6G4.2.5HV or hu6G4.2.5HV/vH1-3Z in a heavy chain that is fused to or contains a leucine zipper sequence. The leucine zipper can increase the affinity or production efficiency of the antibody or antibody fragment of interest. Suitable leucine zipper sequences include the jun and fos leucine zippers taught by Kostelney et al., *J. Immunol.*, 148:

1547–1553 (1992) and the GCN4 leucine zipper described in the Examples below.

In particular, the invention provides an antibody or antibody fragment comprising a light chain comprising the amino acid sequence of amino acids 1–219 of the variant humanized anti-IL-8 6G4.2.5v11 light chain polypeptide amino acid sequence of FIG. 31B (SEQ ID NO: 51) with the proviso that any amino acid other than Asn (denoted as "$X_{35}$") is substituted for Asn at amino acid position 35 (herein referred to as "6G4.2.5LV11N35$X_{35}$").

In another embodiment, the invention provides an antibody or antibody fragment comprising a light chain comprising the amino acid sequence of amino acids 1–219 of the variant humanized anti-IL-8 6G4.2.5v11 light chain polypeptide amino acid sequence of FIG. 31B (SEQ ID NO: 51) with the proviso that any amino acid other than Ser (denoted as "$X_{26}$") is substituted for Ser at amino acid position 26 (herein referred to as "6G4.2.5LV11S26$X_{26}$").

In yet another embodiment, the invention provides an antibody or antibody fragment comprising a light chain comprising the amino acid sequence of amino acids 1–219 of the variant humanized anti-IL-8 6G4.2.5v11 light chain polypeptide amino acid sequence of FIG. 31B (SEQ ID NO: 51) with the proviso that any amino acid other than His (denoted as "$X_{98}$") is substituted for His at amino acid position 98 (herein referred to as "6G4.2.5LV11H98$X_{98}$").

In still another embodiment, the invention provides an antibody or antibody fragment comprising a light chain comprising the amino acid sequence of amino acids 1–219 of the variant humanized anti-IL-8 6G4.2.5v11 light chain polypeptide amino acid sequence of FIG. 31B (SEQ ID NO: 51) with the proviso that any amino acid other than Ser (denoted as "$X_{26}$") is substituted for Ser at amino acid position 26 and any amino acid other than Asn (denoted as "$X_{35}$") is substituted for Asn at amino acid position 35 (herein referred to as "6G4.2.5LV11S26$X_{26}$/N35$X_{35}$").

In a further embodiment, the invention provides an antibody or antibody fragment comprising a light chain comprising the amino acid sequence of amino acids 1–219 of the variant humanized anti-IL-8 6G4.2.5v11 light chain polypeptide amino acid sequence of FIG. 31B (SEQ ID NO: 51) with the proviso that any amino acid other than Asn (denoted as "$X_{35}$") is substituted for Asn at amino acid position 35 and any amino acid other than His (denoted as "$X_{98}$") is substituted for His at amino acid position 98 (herein referred to as "6G4.2.5LV11N35$X_{35}$/H98$X_{98}$").

In an additional embodiment, the invention provides an antibody or antibody fragment comprising a light chain comprising the amino acid sequence of amino acids 1–219 of the variant humanized anti-IL-8 6G4.2.5v11 light chain polypeptide amino acid sequence of FIG. 31B (SEQ ID NO: 51) with the proviso that any amino acid other than Ser (denoted as "$X_{26}$") is substituted for Ser at amino acid position 26 and any amino acid other than His (denoted as "$X_{98}$") is substituted for His at amino acid position 98 (herein referred to as "6G4.2.5LV11S26$X_{26}$/H98$X_{98}$").

The invention also encompasses an antibody or antibody fragment comprising a light chain comprising the amino acid sequence of amino acids 1–219 of the variant humanized anti-IL-8 6G4.2.5v11 light chain polypeptide amino acid sequence of FIG. 31B (SEQ ID NO: 51) with the proviso that any amino acid other than Ser (denoted as "$X_{26}$") is substituted for Ser at amino acid position 26, any amino acid other than Asn (denoted as "$X_{35}$") is substituted for Asn at amino acid position 35 and any amino acid other than His (denoted as "$X_{98}$") is substituted for His at amino acid position 98 (herein referred to as "6G4.2.5LV11S26$X_{26}$/N35$X_{35}$/H98$X_{98}$")

Additionally, the invention provides an antibody or antibody fragment comprising a light chain comprising the amino acid sequence of amino acids 1–219 of the variant humanized anti-IL-8 6G4.2.5v11 light chain polypeptide amino acid sequence (SEQ ID NO: 56) of FIG. 36 (herein referred to as "6G4.2.5LV11N35A").

Further provided herein is an antibody or antibody fragment comprising a light chain comprising the amino acid sequence of amino acids 1–219 of the variant humanized anti-IL-8 6G4.2.5v11 light chain polypeptide amino acid sequence (SEQ ID NO: 62) of FIG. 45 (herein referred to as "6G4.2.5LV11N35E").

In another embodiment, the invention provides an antibody or antibody fragment comprising a light chain comprising the amino acid sequence of amino acids 1–219 of the variant humanized anti-IL-8 6G4.2.5v11 light chain polypeptide amino acid sequence of FIG. 31B (SEQ ID NO: 51) with the proviso that Ala is substituted for Ser at amino acid position 26 (herein referred to as "6G4.2.5LV11S26A").

In yet another embodiment, the invention provides an antibody or antibody fragment comprising a light chain comprising the amino acid sequence of amino acids 1–219 of the variant humanized anti-IL-8 6G4.2.5v11 light chain polypeptide amino acid sequence of FIG. 31B (SEQ ID NO: 51) with the proviso that Ala is substituted for His at amino acid position 98 (herein referred to as "6G4.2.5LV11H98A").

In still another embodiment, the invention provides an antibody or antibody fragment comprising a light chain comprising the amino acid sequence of amino acids 1–219 of the variant humanized anti-IL-8 6G4.2.5v11 light chain polypeptide amino acid sequence of FIG. 31B (SEQ ID NO: 51) with the proviso that Ala is substituted for Ser at amino acid position 26 and Ala is substituted for Asn at amino acid position 35 (herein referred to as "6G4.2.5LV11S26A/N35A").

In a further embodiment, the invention provides an antibody or antibody fragment comprising a light chain comprising the amino acid sequence of amino acids 1–219 of the variant humanized anti-IL-8 6G4.2.5v11 light chain polypeptide amino acid sequence of FIG. 31B (SEQ ID NO: 51) with the proviso that Ala is substituted for Ser at amino acid position 26 and Ala is substituted for His at amino acid position 98 (herein referred to as "6G4.2.5LV11S26A/H98A").

The invention also encompasses an antibody or antibody fragment comprising a light chain comprising the amino acid sequence of amino acids 1–219 of the variant humanized anti-IL-8 6G4.2.5v11 light chain polypeptide amino acid sequence of FIG. 31B (SEQ ID NO: 51) with the proviso that Ala is substituted for Asn at amino acid position 35 and Ala is substituted for His at amino acid position 98 (herein referred to as "6G4.2.5LV11N35A/H98A").

The invention further encompasses an antibody or antibody fragment comprising a light chain comprising the amino acid sequence of amino acids 1–219 of the variant humanized anti-IL-8 6G4.2.5v11 light chain polypeptide amino acid sequence of FIG. 31B (SEQ ID NO: 51) with the proviso that Ala is substituted for Ser at amino acid position 26, Ala is substituted for Asn at amino acid position 35, and Ala is substituted for His at amino acid position 98 (herein referred to as "6G4.2.5LV11S26A/N35A/H98A").

The invention provides a single chain antibody fragment comprising a variant light chain selected from the group consisting of 6G4.2.5LV11N35$X_{35}$, 6G4.2.5LV11S26$X_{26}$, 6G4.2.5LV11H98$X_{98}$, 6G4.2.5LV11S26$X_{26}$/N35$X_{35}$, 6G4.2.5LV11N35$X_{35}$/H98$X_{98}$, 6G4.2.5LV11S26$X_{26}$/H98$X_{98}$, and 6G4.2.5LV11S26$X_{26}$N35$X_{35}$/H98$X_{98}$, with or without any additional amino acid sequence. It will be understood that the group consisting of 6G4.2.5LV11N35$X_{35}$, 6G4.2.5LV11S26$X_{26}$, 6G4.2.5LV11H98$X_{98}$, 6G4.2.5LV11S26$X_{26}$/N35$X_{35}$, 6G4.2.5LV11N35$X_{35}$/H98$X_{98}$, 6G4.2.5LV11S26$X_{26}$/H98$X_{98}$, and 6G4.2.5LV11S26$X_{26}$N35$X_{35}$/H98$X_{98}$, is collectively referred to herein as the "group of 6G4.2.5LV11X variants", and that individual members of this group are generically referred to herein as a "6G4.2.5LV11X variant." In one embodiment, the invention provides a single chain antibody fragment comprising a 6G4.2.5LV11X variant without any associated heavy chain amino acid sequence, i.e. a single chain species that makes up one half of a Fab fragment. In a preferred embodiment, the invention provides a 6G4.2.5LV11N35$X_{35}$ variant without any associated heavy chain amino acid sequence.

The invention encompasses a single chain antibody fragment comprising a variant light chain selected from the group consisting of 6G4.2.5LV11N35A, 6G4.2.5LV11S26A, 6G4.2.5LV11H98A, 6G4.2.5LV11S26A/N35A, 6G4.2.5LV11N35A/H98A, 6G4.2.5LV11S26A/H98A, and 6G4.2.5LV11S26A/N35A/H98A, with or without any additional amino acid sequence. It will be understood that the group consisting of 6G4.2.5LV11N35A, 6G4.2.5LV11S26A, 6G4.2.5LV11H98A, 6G4.2.5LV11S26A/N35A, 6G4.2.5LV11N35A/H98A, 6G4.2.5LV11S26A/H98A, and 6G4.2.5LV11S26A/N35A/H98A is collectively referred to herein as the "group of 6G4.2.5LV11A variants", and that individual members of this group are generically referred to herein as a "6G4.2.5LV11A variant." In one embodiment, the invention provides a single chain antibody fragment comprising a 6G4.2.5LV11A variant without any associated heavy chain amino acid sequence, i.e. a single chain species that makes up one half of a Fab fragment. In a preferred embodiment, the invention provides the 6G4.2.5LV11N35A without any associated heavy chain amino acid sequence.

Further provided herein are an antibody or antibody fragment comprising a light chain comprising a 6G4.2.5LV11X variant, and further comprising a heavy chain comprising the 6G4.2.5HV11. In a preferred embodiment, the invention provides an antibody or antibody fragment comprising a 6G4.2.5LV11N35$X_{35}$ variant and further comprising the 6G4.2.5HV11. In a preferred embodiment, the invention provides an antibody or antibody fragment comprising the 6G4.2.5LV11N35A and further comprising the 6G4.2.5HV 1. In another preferred embodiment, the invention provides an antibody or antibody fragment comprising the 6G4.2.5LV11N35E and further comprising the 6G4.2.5HV11.

In one embodiment, the invention provides a single chain antibody fragment wherein a 6G4.2.5LV11X variant and the 6G4.2.5HV11 are contained in a single chain polypeptide species. In a preferred embodiment, the single chain antibody fragment comprises a 6G4.2.5LV11X variant joined to the 6G4.2.5HV11 by means of a flexible peptide linker sequence, wherein the heavy chain and light chain domains can associate in a "dimeric" structure analogous to that formed in a two-chain Fab species. In another embodiment, the single chain antibody fragment is a species comprising a 6G4.2.5LV11X variant joined to the 6G4.2.5HV11 by a linker that is too short to permit intramolecular pairing of complementary domains, i.e. a single chain polypeptide monomer that forms a diabody upon dimerization with another monomer.

In still another embodiment, the invention provides a single chain antibody fragment wherein a 6G4.2.5LV11N35$X_{35}$ variant and the 6G4.2.5HV11 are contained in a single chain polypeptide species. In a preferred embodiment, the single chain antibody fragment comprises a 6G4.2.5LV11N35$X_{35}$ variant joined to the 6G4.2.5HV11 by means of a flexible peptide linker sequence, wherein the heavy chain and light chain domains can associate in a "dimeric" structure analogous to that formed in a two-chain Fab species. In another embodiment, the single chain antibody fragment is a species comprising a 6G4.2.5LV11N35$X_{35}$ variant joined to the 6G4.2.5HV11 by a linker that is too short to permit intramolecular pairing of complementary domains, i.e. a single chain polypeptide monomer that forms a diabody upon dimerization with another monomer.

In a further embodiment, the invention provides a single chain antibody fragment wherein the 6G4.2.5LV11N35A and the 6G4.2.5HV11 are contained in a single chain polypeptide species. In a preferred embodiment, the single chain antibody fragment comprises the 6G4.2.5LV11N35A joined to the 6G4.2.5HV11 by means of a flexible peptide linker sequence, wherein the heavy chain and light chain domains can associate in a "dimeric" structure analogous to that formed in a two-chain Fab species. In another embodiment, the single chain antibody fragment is a species comprising the 6G4.2.5LV11N35A joined to the 6G4.2.5HV11 by a linker that is too short to permit intramolecular pairing of complementary domains, i.e. a single chain polypeptide monomer that forms a diabody upon dimerization with another monomer.

In an additional embodiment, the invention provides a single chain antibody fragment wherein the 6G4.2.5LV11N35E and the 6G4.2.5HV11 are contained in a single chain polypeptide species. In a preferred embodiment, the single chain antibody fragment comprises the 6G4.2.5LV11N35E joined to the 6G4.2.5HV11 by means of a flexible peptide linker sequence, wherein the heavy chain and light chain domains can associate in a "dimeric" structure analogous to that formed in a two-chain Fab species. In another embodiment, the single chain antibody fragment is a species comprising the 6G4.2.5LV11N35E joined to the 6G4.2.5HV11 by a linker that is too short to permit intramolecular pairing of complementary domains, i.e. a single chain polypeptide monomer that forms a diabody upon dimerization with another monomer.

In yet another embodiment, the invention provides an antibody fragment comprising a plurality of polypeptide chains, wherein one polypeptide chain comprises a 6G4.2.5LV11X variant and a second polypeptide chain comprises the 6G4.2.5HV11 and the two polypeptide chains are covalently linked by one or more interchain disulfide bonds. In still another embodiment, the invention provides an antibody fragment comprising a plurality of polypeptide chains, wherein one polypeptide chain comprises a 6G4.2.5LV11N35$X_{35}$ variant and a second polypeptide chain comprises the 6G4.2.5HV11 and the two polypeptide chains are covalently linked by one or more interchain disulfide bonds. In a preferred embodiment, any of the foregoing two-chain antibody fragments is selected from the group consisting of Fab, Fab', Fab'-SH, and $F(ab')_2$. In still another preferred embodiment, the two-chain antibody fragment is a $F(ab')_2$ wherein one polypeptide chain comprises the 6G4.2.5LV11N35A and the second polypeptide chain comprises the 6G4.2.5HV11. In a further preferred embodiment, the antibody fragment is a Fab, Fab', Fab'-SH, or $F(ab')_2$ wherein one polypeptide chain comprises the 6G4.2.5LV11N35E and the second polypeptide chain comprises the 6G4.2.5HV11. A particularly preferred embodiment, the antibody fragment is the 6G4V11N35A F(ab')$_2$ GCN4 leucine zipper species described in the Examples below. In another particularly preferred embodiment, the antibody fragment is the 6G4V11N35E F(ab')$_2$ GCN4 leucine zipper species described in the Examples below. In yet another particularly preferred embodiment, the antibody fragment is the 6G4V11N35E Fab described in the Examples below.

The invention also provides an antibody or antibody fragment comprising a light chain containing a 6G4.2.5LV11X variant and optionally further comprising a heavy chain containing the 6G4.2.5HV11, wherein the light chain, and optionally the heavy chain, is (are) fused to an additional moiety, such as additional immunoglobulin constant domain sequence. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

The invention additionally provides an antibody or antibody fragment comprising a light chain containing a 6G4.2.5LV11N35X$_{35}$ variant and optionally further comprising a heavy chain containing the 6G4.2.5HV11, wherein the light chain, and optionally the heavy chain, is (are) fused to an additional moiety, such as additional immunoglobulin constant domain sequence. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

The invention further provides an antibody or antibody fragment comprising a light chain containing the 6G4.2.5LV11N35A and optionally further comprising a heavy chain containing the 6G4.2.5HV11, wherein the light chain, and optionally the heavy chain, is (are) fused to an additional moiety, such as additional immunoglobulin constant domain sequence. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

The invention further provides an antibody or antibody fragment comprising a light chain containing the 6G4.2.5LV11N35E and optionally further comprising a heavy chain containing the 6G4.2.5HV11, wherein the light chain, and optionally the heavy chain, is (are) fused to an additional moiety, such as additional immunoglobulin constant domain sequence. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al. In a preferred embodiment, the antibody or antibody fragment comprises a light chain containing a 6G4.2.5LV11X variant, and further comprises the 6G4.2.5HV11 in a heavy chain that is fused to or contains a leucine zipper sequence. The leucine zipper can increase the affinity or production efficiency of the antibody or antibody fragment of interest. Suitable leucine zipper sequences include the jun and fos leucine zippers taught by Kostelney et al., *J. Immunol.*, 148: 1547–1553 (1992) and the GCN4 leucine zipper described in the Examples below. In another preferred embodiment, the antibody or antibody fragment comprises a light chain containing the 6G4.2.5LV11N35A, and further comprises a heavy chain containing the 6G4.2.5HV11 fused to the GCN4 leucine zipper. In yet another preferred embodiment, the antibody or antibody fragment comprises a light chain containing the 6G4.2.5LV11N35E, and further comprises a heavy chain containing the 6G4.2.5HV11 fused to the GCN4 leucine zipper.

B. 6G4.2.5HV Variants

The invention provides humanized antibodies and antibody fragments comprising the CDRs of a 6G4.2.5HV CDR variant. The use of a 6G4.2.5HV CDRs variant in the humanized antibodies and antibody fragments of the invention confer the advantages of higher affinity for human IL-8 and/or improved recombinant manufacturing economy.

A heavy chain variable domain comprising the CDRs of a 6G4.2.5HV CDRs variant can be humanized in conjunction with a light chain comprising the CDRs of 6G4.2.5LV or the CDRs of a 6G4.2.5LV CDRs variant, essentially as described in Section (II)(2)(A) above. In one embodiment, the invention provides a humanized antibody or antibody fragment comprising a 6G4.2.5HV CDRs variant selected from the group consisting of 6G4.2.5HV/H1S31Z$_{31}$, 6G4.2.5HV/H2S54Z$_{54}$, and 6G4.2.5HV/H1S31Z$_{31}$/H2S54Z$_{54}$. In addition, the invention provides a humanized antibody or antibody fragment comprising a 6G4.2.5HV CDRs variant selected from the group consisting of 6G4.2.5HV/H1S31A, 6G4.2.5HV/H2S54A, and 6G4.2.5HV/H1S31A/H2S54A. In particular, the 6G4.2.5HV CDRs variants can be used to construct a humanized antibody or antibody comprising the hu6G4.2.5HV/vH1-3Z as described in Section (II)(2)(A) above.

The invention additionally provides a humanized antibody or antibody fragment that comprises a heavy chain variable domain comprising the hu6G4.2.5HV/vH1-3Z, and further comprises a light chain variable domain comprising the hu6G4.2.5LV or hu6G4.2.5LV/vL1-3X.

The invention further encompasses a single chain humanized antibody fragment comprising the hu6G4.2.5HV/vH1-3Z, with or without any additional amino acid sequence. In one embodiment, the invention provides a single chain antibody fragment comprising the hu6G4.2.5HV/vH1-3Z without any associated heavy chain variable domain amino acid sequence, i.e. a single chain species that makes up one half of an Fv fragment.

In one embodiment, the invention provides a single chain humanized antibody fragment wherein the hu6G4.2.5HV/vH1-3Z and the hu6G4.2.5LV or hu6G4.2.5LV/vL1-3X are contained in a single chain polypeptide species. In a preferred embodiment, the single chain antibody fragment is a scFv species comprising the hu6G4.2.5HV/vH1-3Z joined to the hu6G4.2.5LV or hu6G4.2.5LV/vL1-3X by means of a flexible peptide linker sequence, wherein the heavy chain and light chain variable domains can associate in a "dimeric" structure analogous to that formed in a two-chain Fv species. In another embodiment, the single chain antibody fragment is a species comprising the hu6G4.2.5HV/vH1-3Z joined to the hu6G4.2.5LV or hu6G4.2.5LV/vL1-3X by a linker that is too short to permit intramolecular pairing of the two variable domains, i.e. a single chain polypeptide monomer that forms a diabody upon dimerization with another monomer.

In yet another embodiment, the invention provides a humanized antibody fragment comprising a plurality of polypeptide chains, wherein one polypeptide chain comprises the hu6G4.2.5HV/vH1-3Z and a second polypeptide chain comprises the hu6G4.2.5LV or hu6G4.2.5LV/vL1-3X and the two polypeptide chains are covalently linked by one or more interchain disulfide bonds. In a preferred embodiment, the foregoing two-chain antibody fragment is selected from the group consisting of Fab, Fab', Fab'-SH, Fv, and F(ab')$_2$.

The invention also provides a humanized antibody or antibody fragment comprising a heavy chain variable domain containing the hu6G4.2.5HV/vH1-3Z and optionally further comprising a light chain variable domain containing the hu6G4.2.5LV or hu6G4.2.5LV/vL1-3X, wherein the heavy chain variable domain, and optionally the light chain variable domain, is (are) fused to an additional moiety, such as an immunoglobulin constant domain. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

In a preferred embodiment, the humanized antibody or antibody fragment comprises the hu6G4.2.5HV/vH1-3Z in a heavy chain that is fused to or contains a leucine zipper sequence. The leucine zipper can increase the affinity or production efficiency of the antibody or antibody fragment of interest. Suitable leucine zipper sequences include the jun and fos leucine zippers taught by Kostelney et al., *J. Immunol.*, 148: 1547–1553 (1992) and the GCN4 leucine zipper described in the Examples below.

In addition, the invention provides a humanized antibody or antibody fragment comprising a heavy chain comprising the amino acid sequence of amino acids 1–230 of the 6G4.2.5HV11 polypeptide amino acid sequence of FIGS. 37A–37B (SEQ ID NO: 60) with the proviso that Ala is substituted for Ser at amino acid position 31 (hereinafter referred to as "6G4.2.5HV11S31A").

In another embodiment, the invention provides a humanized antibody or antibody fragment comprising a heavy chain comprising the amino acid sequence of amino acids 1–230 of the 6G4.2.5HV11 polypeptide amino acid sequence of FIGS. 37A–37B (SEQ ID NO: 60) with the proviso that Ala is substituted for Ser at amino acid position 54 (hereinafter referred to as "6G4.2.5HV11S54A").

In yet another embodiment, the invention provides a humanized antibody or antibody fragment comprising a heavy chain comprising the amino acid sequence of amino acids 1–230 of the 6G4.2.5HV11 polypeptide amino acid sequence of FIGS. 37A–37B (SEQ ID NO: 60) with the proviso that Ala is substituted for Ser at amino acid position 31 and Ala is substituted for Ser at amino acid position 54 (hereinafter referred to as "6G4.2.5HV11S31A/S54A").

Further provided herein is a humanized antibody or antibody fragment that comprises any of the light and heavy chain combinations listed in Tables 1–2 below.

TABLE 1

| Heavy Chain | Light Chain |
| --- | --- |
| 6G4.2.5HV11S31A | 6G4.2.5LV11 |
| 6G4.2.5HV11S31A | 6G4.2.5LV11N35A |
| 6G4.2.5HV11S31A | 6G4.2.5LV11S26A |
| 6G4.2.5HV11S31A | 6G4.2.5LV11H98A |
| 6G4.2.5HV11S31A | 6G4.2.5LV11S26A/N35A |
| 6G4.2.5HV11S31A | 6G4.2.5LV11S26A/H98A |
| 6G4.2.5HV11S31A | 6G4.2.5LV11N35A/H98A |
| 6G4.2.5HV11S31A | 6G4.2.5LV11S26A/N35A/H98A |
| 6G4.2.5HV11S54A | 6G4.2.5LV11 |
| 6G4.2.5HV11S54A | 6G4.2.5LV11N35A |
| 6G4.2.5HV11S54A | 6G4.2.5LV11S26A |
| 6G4.2.5HV11S54A | 6G4.2.5LV11H98A |
| 6G4.2.5HV11S54A | 6G4.2.5LV11S26A/N35A |
| 6G4.2.5HV11S54A | 6G4.2.5LV11S26A/H98A |
| 6G4.2.5HV11S54A | 6G4.2.5LV11N35A/H98A |
| 6G4.2.5HV11S54A | 6G4.2.5LV11S26A/N35A/R98A |
| 6G4.2.5HV11S31A/S54A | 6G4.2.5LV11 |
| 6G4.2.5HV11S31A/S54A | 6G4.2.5LV11N35A |
| 6G4.2.5HV11S31A/S54A | 6G4.2.5LV11S26A |
| 6G4.2.5HV11S31A/S54A | 6G4.2.5LV11H98A |
| 6G4.2.5HV11S31A/S54A | 6G4.2.5LV11S26A/N35A |
| 6G4.2.5HV11S31A/S54A | 6G4.2.5LV11S26A/H98A |
| 6G4.2.5HV11S31A/S54A | 6G4.2.5LV11N3SA/H98A |
| 6G4.2.5HV11S31A/S54A | 6G4.2.5LV11S26A/N35A/H98A |

TABLE 2

| Heavy Chain | Light Chain |
| --- | --- |
| 6G4.2.5HV11S31A | 6G4.2.5LV11 |
| 6G4.2.5HV11S31A | 6G4.2.5LV11N35X$_{35}$ |
| 6G4.2.5HV11S31A | 6G4.2.5LV11S26X$_{26}$ |
| 6G4.2.5HV11S31A | 6G4.2.5LV11H98X$_{98}$ |
| 6G4.2.5HV11S31A | 6G4.2.5LV11S26X$_{26}$/N35X$_{35}$ |
| 6G4.2.5HV11S31A | 6G4.2.5LV11S26X$_{26}$/H98X$_{98}$ |
| 6G4.2.5HV11S31A | 6G4.2.5LV11N35X$_{35}$/H98X$_{98}$ |
| 6G4.2.5HV11S31A | 6G4.2.5LV11S26X$_{26}$/N35X$_{35}$/H98X$_{98}$ |
| 6G4.2.5HV11S54A | 6G4.2.5LV11 |
| 6G4.2.5HV11S54A | 6G4.2.5LV11N35X$_{35}$ |
| 6G4.2.5HV11S54A | 6G4.2.5LV11526X$_{26}$ |
| 6G4.2.5HV11S54A | 6G4.2.5LV11H98X$_{98}$ |
| 6G4.2.5HV11S54A | 6G4.2.5LV11S26X$_{26}$/N35X$_{35}$ |
| 6G4.2.5HV11S54A | 6G4.2.5LV11S26X$_{26}$/H98X$_{98}$ |
| 6G4.2.5HV11S54A | 6G4.2.5LV11N35X$_{35}$/H98X$_{98}$ |
| 6G4.2.5HV11S54A | 6G4.2.5LV11S26X$_{26}$/N35X$_{35}$/H98X$_{98}$ |
| 6G4.2.5HV11S31A/S54A | 6G4.2.5LV11 |
| 6G4.2.5HV11S31A/S54A | 6G4.2.5LV11N35X$_{35}$ |
| 6G4.2.5HV11S31A/S54A | 6G4.2.5LV11526X$_{26}$ |
| 6G4.2.5HV11S31A/S54A | 6G4.2.5LV11H98X$_{98}$ |
| 6G4.2.5HV11S31A/S54A | 6G4.2.5LV11S26X$_{26}$/N35X$_{35}$ |
| 6G4.2.5HV11S31A/S54A | 6G4.2.5LV11S26X$_{26}$/H98X$_{98}$ |
| 6G4.2.5HV11S31A/S54A | 6G4.2.5LV11N35X$_{35}$/H98X$_{98}$ |
| 6G4.2.5HV11S31A/S54A | 6G4.2.5LV11S26X$_{26}$/N35X$_{35}$/H98X$_{98}$ |

The invention encompasses a single chain humanized antibody fragment comprising a variant heavy chain selected from the group consisting of 6G4.2.5HV11S31A, 6G4.2.5HV11S54A, and 6G4.2.5HV11S31A/S54A, with or without any additional amino acid sequence. It will be understood that the group consisting of 6G4.2.5HV11S31A, 6G4.2.5HV11S54A, and 6G4.2.5HV11S31A/S54A is collectively referred to herein as the "group of 6G4.2.5HV11A variants", and that individual members of this group are generically referred to herein as a "6G4.2.5HV11A variant."

In one embodiment, the invention provides a single chain humanized antibody fragment comprising a 6G4.2.5HV11A variant without any associated light chain amino acid sequence, i.e. a single chain species that makes up one half of a Fab fragment.

Further provided herein are a humanized antibody or antibody fragment comprising a heavy chain comprising a 6G4.2.5HV11A variant, and further comprising a light chain comprising a 6G4.2.5LV11A variant or a 6G4.2.5LV11X variant. In another embodiment, the humanized antibody or antibody fragment comprises any combination of light and heavy chains listed in Tables 1 and 2 above. In one embodiment, the invention provides a humanized antibody or antibody fragment comprising a 6G4.2.5HV11A variant and further comprising the 6G4.2.5LV11N35$X_{35}$. In a preferred embodiment, the invention provides a humanized antibody or antibody fragment comprising a 6G4.2.5HV11A variant and further comprising the 6G4.2.5LV11N35A.

In yet another embodiment, the invention provides a single chain humanized antibody fragment wherein a 6G4.2.5HV11A variant and the 6G4.2.5LV11 are contained in a single chain polypeptide species. In another embodiment, the invention provides a single chain humanized antibody fragment wherein any pair of light and heavy chains listed in Tables 1–2 above is contained in a single chain polypeptide species. In yet another embodiment, the invention provides a single chain humanized antibody fragment wherein a 6G4.2.5HV11A variant and a 6G4.2.5LV11X variant are contained in a single chain polypeptide species. In still another embodiment, the invention provides a single chain humanized antibody fragment wherein a 6G4.2.5HV11A variant and a 6G4.2.5LV11N35$X_{35}$ variant are contained in a single chain polypeptide species. In an additional embodiment, the invention provides a single chain humanized antibody fragment wherein a 6G4.2.5HV11A variant and the 6G4.2.5LV11N35A variant are contained in a single chain polypeptide species.

In a preferred embodiment, the single chain humanized antibody fragment comprises a 6G4.2.5HV11A variant joined to a 6G4.2.5LV11X variant, 6G4.2.5LV11N35$X_{35}$ variant, 6G4.2.5LV11N35A variant, or 6G4.2.5LV11 by means of a flexible peptide linker sequence, wherein the heavy chain and light chain domains can associate in a "dimeric" structure analogous to that formed in a two-chain Fab species. In a further embodiment, the single chain humanized antibody fragment is a species comprising a 6G4.2.5HV11A variant joined to a 6G4.2.5LV11X variant, 6G4.2.5LV11N35$X_{35}$ variant, 6G4.2.5LV11N35A variant, or 6G4.2.5LV11 by a linker that is too short to permit intramolecular pairing of complementary domains, i.e. a single chain polypeptide monomer that forms a diabody upon dimerization with another monomer.

In still another embodiment, the single chain humanized antibody fragment comprises any pair of light and heavy chains listed in Table 1 above joined by means of a flexible peptide linker sequence, wherein the heavy chain and light chain domains can associate in a "dimeric" structure analogous to that formed in a two-chain Fab species. In an additional embodiment, the single chain humanized antibody fragment comprises any pair of light and heavy chains listed in Tables 1–2 above joined by a linker that is too short to permit intramolecular pairing of complementary domains, i.e. a single chain polypeptide monomer that forms a diabody upon dimerization with another monomer.

In yet another embodiment, the invention provides a humanized antibody fragment comprising a plurality of polypeptide chains, wherein one polypeptide chain comprises a 6G4.2.5HV11A variant and a second polypeptide chain comprises a 6G4.2.5LV11X variant, 6G4.2.5LV11N35$X_{35}$ variant, 6G4.2.5LV11N35A variant, or 6G4.2.5LV11, and the two polypeptide chains are covalently linked by one or more interchain disulfide bonds. In a preferred embodiment, the foregoing two-chain antibody fragment is selected from the group consisting of Fab, Fab', Fab'-SH, and F(ab')$_2$.

In an additional embodiment, the invention provides a two-chain humanized antibody fragment comprising any pair of heavy and light chains listed in Tables 1–2 above, wherein each chain is contained on a separate molecule. In another embodiment, the two-chain antibody fragment comprising any pair of heavy and light chains listed in Tables 1–2 above is selected from the group consisting of Fab, Fab', Fab'-SH, and F(ab')$_2$. In a preferred embodiment, the two-chain humanized antibody fragment is a F(ab')$_2$ comprising any pair of heavy and light chains listed in Tables 1–2 above. In another preferred embodiment, the two-chain humanized antibody fragment is a F(ab')$_2$ wherein one polypeptide chain comprises a 6G4.2.5HV11A variant and the second polypeptide chain comprises the 6G4.2.5LV11N35A.

The invention also provides a humanized antibody or antibody fragment comprising a heavy chain containing a 6G4.2.5HV11A variant and optionally further comprising a light chain containing a 6G4.2.5LV11X variant, 6G4.2.5LV11N35$X_{35}$ variant, 6G4.2.5LV11N35A, or 6G4.2.5HV11, wherein the heavy chain, and optionally the light chain, is (are) fused to an additional moiety, such as additional immunoglobulin constant domain sequence. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al. (supra).

In a preferred embodiment, the humanized antibody or antibody fragment comprises a 6G4.2.5HV11A variant in a heavy chain that is fused to or contains a leucine zipper sequence. The leucine zipper can increase the affinity or production efficiency of the antibody or antibody fragment of interest. Suitable leucine zipper sequences include the jun and fos leucine zippers taught by Kostelney et al., *J. Immunol.*, 148: 1547–1553 (1992) and the GCN4 leucine zipper described in the Examples below.

C. Bispecific Antibodies

Bispecific antibodies are monoclonal, preferably human or humanized, antibodies that have binding specificities for at least two different antigens. In the present case, one of the binding specificities is for IL-8, the other one is for any other antigen. For example, bispecific antibodies specifically binding a IL-8 and neurotrophic factor, or two different types of IL-8 polypeptides are within the scope of the present invention.

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, *Nature* 305:537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published 13 May 1993, and in Traunecker et al., *EMBO J.* 10:3655 (1991).

According to a different and more preferred approach, antibody-variable domains with the desired binding specificities (antibody-antigen combining sites) are fused to immunoglobulin constant-domain sequences. The fusion preferably is with an immunoglobulin heavy-chain constant domain, comprising at least part of the hinge, CH2, and CH3 regions. It is preferred to have the first heavy-chain constant region (CH1), containing the site necessary for light-chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the maximum yields. It is, however, possible to insert the coding sequences for two or all three polypeptide chains in one expression vector when the production of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation. For further details of generating bispecific antibodies, see, for example, Suresh et al., *Methods in Enzymology* 121:210 (1986).

According to another approach, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/00373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217–225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad Sci. USA*, 90:6444–6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., *J. Immunol.*, 152:5368(1994).

Antibodies with more than two valencies are contemplated. For example, trispecific antibodies can be prepared. Tutt et al. *J. Immunol.* 147: 60 (1991).

4. Production of Humanized Anti-IL-8 6G4.2.5 Monoclonal Antibody, Antibody Fragments, and Variants The antibodies and antibody fragments of the invention can be produced using any convenient antibody manufacturing process known in the art. Typically, the antibody or antibody fragment is made using recombinant expression systems. A multiple polypeptide chain antibody or antibody fragment species can be made in a single host cell expression system wherein the host cell produces each chain of the antibody or antibody fragment and assembles the polypeptide chains into a multimeric structure to form the antibody or antibody fragment in vivo, followed by recovery of the antibody or antibody fragment from the host cell. For example, suitable recombinant expression systems for the production of complete antibody or antibody fragment are described in Lucas et al., *Nucleic Acids Res.*, 24: 1774–1779 (1996). Alternatively, the separate polypeptide chains of the desired antibody or antibody fragment can be made in separate expression host cells, separately recovered from the respective host cells, and then mixed in vitro under conditions permitting the formation of the multi-subunit antibody or antibody fragment of interest. For example, U.S. Pat. No. 4,816,567 to Cabilly et al. and Carter et al., *Bio/Technology*, 10: 163–167 (1992) provide methods for recombinant production of antibody heavy and light chains in separate expression hosts followed by assembly of antibody from separate heavy and light chains in vitro.

The following discussion of recombinant expression methods applies equally to the production of single chain antibody polypeptide species and multi-subunit antibody and antibody fragment species. All recombinant procedures for the production of antibody or antibody fragment provided below shall be understood to describe: (1) manufacture of single chain antibody species as the desired end-product; (2) manufacture of multi-subunit antibody or antibody fragment species by production of all subunits in a single host cell, subunit assembly in the host cell, optionally followed by host cell secretion of the multi-subunit end-product into the culture medium, and recovery of the multi-subunit end-product from the host cell and/or culture medium; and (3) manufacture of multi-subunit antibody or antibody fragment by production of subunits in separate host cells (optionally followed by host cell secretion of subunits into the culture medium), recovery of subunits from the respective host cells and/or culture media, followed by in vitro subunit assembly to form the multi-subunit end-product. In the case of a multi-subunit antibody or antibody fragment produced in a single host cell, it will be appreciated that production of the various subunits can be effected by expression of multiple polypeptide-encoding nucleic acid sequences carried on a single vector or by expression of polypeptide-encoding nucleic acid sequences carried on multiple vectors contained in the host cell.

A. Construction of DNA Encoding Humanized 6G4.2.5 Monoclonal Antibodies, Antibody Fragments, and Variants Following the selection of the humanized antibody or antibody fragment of the invention according to the methods described above, the practitioner can use the genetic code to design DNAs encoding the desired antibody or antibody fragment. In one embodiment, codons preferred by the expression host cell are used in the design of a DNA encoding the antibody or antibody fragment of interest. DNA encoding the desired antibody or antibody fragment can be prepared by a variety of methods known in the art. These methods include, but are not limited to, chemical synthesis by any of the methods described in Engels et al., *Agnew. Chem. Int. Ed. Engl.*, 28: 716–734 (1989), the entire disclosure of which is incorporated herein by reference, such as the triester, phosphite, phosphoramidite and H-phosphonate methods.

A variation on the above procedures contemplates the use of gene fusions, wherein the gene(s) encoding the antibody or antibody fragment is associated, in the vector, with a gene encoding another protein or a fragment of another protein. This results in the antibody or antibody fragment being produced by the host cell as a fusion with another protein. The "other" protein is often a protein or peptide which can be secreted by the cell, making it possible to isolate and purify the desired protein from the culture medium and eliminating the necessity of destroying the host cells which arises when the desired protein remains inside the cell. Alternatively, the fusion protein can be expressed intracellularly. It is advantageous to use fusion proteins that are highly expressed.

The use of gene fusions, though not essential, can facilitate the expression of heterologous proteins in *E. coli* as well as the subsequent purification of those gene products (Harris, T. J. R. in *Genetic Engineering*, Williamson, R., Ed., Academic, London, Vol. 4, p. 127(1983); Uhlen, M. & Moks, T., *Methods Enzymol.* 185:129–143 (1990)). Protein A fusions are often used because the binding of protein A, or more specifically the Z domain of protein A, to IgG provides an "affinity handle" for the purification of the fused protein (Nilsson, B. & Abrahmsen, L. *Methods Enzymol.* 185:144–161 (1990)). It has also been shown that many heterologous proteins are degraded when expressed directly in *E. coli*, but are stable when expressed as fusion proteins (Marston, F. A. O., *Biochem J.* 240: 1 (1986)).

Fusion proteins can be cleaved using chemicals, such as cyanogen bromide, which cleaves at a methionine, or hydroxylamine, which cleaves between an Asn and Gly. Using standard recombinant DNA methodology, the nucleotide base pairs encoding these amino acids may be inserted just prior to the 5' end of the antibody or antibody fragment gene(s).

Alternatively, one can employ proteolytic cleavage of fusion proteins, which has been recently reviewed (Carter, P. (1990) in *Protein Purification: From Molecular Mechanisms to Large-Scale Processes*, Ladisch, M. R., Willson, R. C., Painton, C. C., and Builder, S. E., eds., American Chemical Society Symposium Series No. 427, Ch 13, 181–193).

Proteases such Factor Xa, thrombin, subtilisin and mutants thereof, have been successfully used to cleave fusion proteins. Typically, a peptide linker that is amenable to cleavage by the protease used is inserted between the "other" protein (e.g., the Z domain of protein A) and the protein of interest, such as humanized anti-IL-8 antibody or antibody fragment. Using recombinant DNA methodology, the nucleotide base pairs encoding the linker are inserted between the genes or gene fragments coding for the other proteins. Proteolytic cleavage of the partially purified fusion protein containing the correct linker can then be carried out on either the native fusion protein, or the reduced or denatured fusion protein.

Various techniques are also available which may now be employed to produce variant humanized antibodies or antibody fragments, which encodes for additions, deletions, or changes in amino acid sequence of the resultant protein(s) relative to the parent humanized antibody or antibody fragment.

By way of illustration, with expression vectors encoding humanized antibody or antibody fragment in hand, site specific mutagenesis (Kunkel et al., *Methods Enzymol.* 204:125–139 (1991); Carter, P., et al., *Nucl. Acids. Res.* 13:4331 (1986); Zoller, M. J. et al., *Nucl. Acids Res.* 10:6487 (1982)), cassette mutagenesis (Wells, J. A., et al., *Gene* 34:315 (1985)), restriction selection mutagenesis (Wells, J. A., et al., *Philos. Trans. R. Soc. London SerA* 317, 415 (1986)) or other known techniques may be performed on the antibody or antibody fragment DNA. The variant DNA can then be used in place of the parent DNA by insertion into the aforementioned expression vectors. Growth of host bacteria containing the expression vectors with the mutant DNA allows the production of variant humanized antibodies or antibody fragments, which can be isolated as described herein.

B. Insertion of DNA into a Cloning Vehicle

The DNA encoding the antibody or antibody fragment is inserted into a replicable vector for further cloning (amplification of the DNA) or for expression. Many vectors are available, and selection of the appropriate vector will depend on (1) whether it is to be used for DNA amplification or for DNA expression, (2) the size of the DNA to be inserted into the vector, and (3) the host cell to be transformed with the vector. Each vector contains various components depending on its function (amplification of DNA or expression of DNA) and the host cell for which it is compatible. The vector components generally include, but are not limited to, one or more of the following: a signal sequence, an origin of replication, one or more marker genes, an enhancer element, a promoter, and a transcription termination sequence.

(i) Signal Sequence Component

In general, a signal sequence may be a component of the vector, or it may be a part of the antibody or antibody fragment DNA that is inserted into the vector. Preferably, a heterologous signal sequence selected and fused to the antibody or antibody fragment DNA such that the signal sequence in the corresponding fusion protein is recognized, transported and processed (i.e., cleaved by a signal peptidase) in the host cell's protein secretion system. In the case of prokaryotic host cells, the signal sequence is selected, for example, from the group of the alkaline phosphatase, penicillinase, lpp, or heat-stable enterotoxin II leaders. In a preferred embodiment, the STII signal sequence is used as described in the Examples below. For yeast secretion the native signal sequence may be substituted by, e.g., the yeast invertase leader, α factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the $2\mu$ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e. they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using *Bacillus* species as hosts, for example, by including in the vector a DNA sequence that is homologous to a sequence found in *Bacillus* genomic DNA. Transfection of *Bacillus* with this vector results in homologous recombination with the genome and insertion of the antibody or antibody fragment DNA.

(iii) Selection Gene Component

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g. ampicillin, neomycin, methotrexate, or tetracycline, (D) complement auxotrophic deficiencies, or (c) supply critical nutrients not available from complex media, e.g. the gene encoding Dalanine racemase for *Bacilli*.

One example of a selection scheme utilizes a drug to arrest growth of a host cell. Those cells that are successfully transformed with a heterologous gene express a protein conferring drug resistance and thus survive the selection regimen. Examples of such dominant selection use the drugs neomycin (Southern et al., *J. Molec. Appl. Genet.*, 1: 327 (1982)), mycophenolic acid (Mulligan et al., *Science*, 209: 1422 (1980)) or hygromycin (Sugden et al., *Mol. Cell. Biol.* 5: 410413 (1985)). The three examples given above employ bacterial genes under eukaryotic control to convey resistance to the appropriate drug (G418 or neomycin (geneticin), xgpt (mycophenolic acid), and hygromycin, respectively.)

Another example of suitable selectable markers for mammalian cells are those that enable the identification of cells competent to take up the antibody or antibody fragment nucleic acid, such as dihydrofolate reductase (DHFR) or thymidine kinase. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes the antibody or antibody fragment. Amplification is the process by which genes in greater demand for the production of a protein critical for growth are reiterated in tandem within the chromosomes of successive generations of recombinant cells. Increased quantities of the antibody or antibody fragment are synthesized from the amplified DNA.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc. Natl. Acad. Sci. USA*, 77: 4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding the antibody or antibody fragment. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060). Alternatively, host cells (particularly wild-type hosts that contain endogenous DHFR) transformed or co-transformed with DNA sequences encoding the antibody or antibody fragment, wild-type DHFR protein, and another selectable marker such as aminoglycoside 3' phosphotransferase (APH) can be selected by cell growth in medium containing a selection agent for the selectable marker such as an aminoglycosidic antibiotic, e.g., kanamycin, neomycin, or G4 18. See U.S. Pat. No. 4,965,199.

A suitable selection gene for use in yeast is the trp1 gene present in the yeast plasmid YRp7. Stinchcomb et al., Nature, 282: 39 (1979); Kingsman et al., Gene, 1: 141 (1979); or Tschemper et al., Gene, 10: 157 (1980). The trp1 gene provides a selection marker for a mutant strain of yeast lacking the ability to grow in tryptophan, for example, ATCC No. 44076 or PEP4-1. Jones, Genetics 85: 12 (1977). The presence of the trp1 lesion in the yeast host cell genome then provides an effective environment for detecting transformation by growth in the absence of tpyptophan. Similarly, Leu2-deficient yeast strains (ATCC 20,622 or 38,626) are complemented by known plasmids bearing the Leu2 gene.

(iv) Promoter Component

Expression vectors usually contain a promoter that is recognized by the host organism and is operably linked to the antibody or antibody fragment nucleic acid. Promoters are untranslated sequences located upstream (5') to the start codon of a structural gene (generally within about 100 to 1000 bp) that control the transcription and translation of a particular nucleic acid sequence, such as the antibody or antibody fragment encoding sequence, to which they are operably linked. Such promoters typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known.

Promoters suitable for use with prokaryotic hosts include the β-lactamase and lactose promoter systems (Chang et al., Nature, 275: 615 (1978); and Goeddel et al., Nature 281: 544 (1979)), alkaline phosphatase, a tryptophan (trp) promoter system (Goeddel, Nucleic Acids Res. 8: 4057 (1980) and EP 36,776) and hybrid promoters such as the tac promoter (deBoer et al., Proc. Natl. Acad. Sci. USA, 80: 21–25 (1983)). However, other known bacterial promoters are suitable. Their nucleotide sequences have been published, thereby enabling a skilled worker to operably ligate them to DNA encoding the antibody or antibody fragment (Siebenlist et al., Cell, 20: 269 (1980)) using linkers or adaptors to supply any required restriction sites. Promoters for use in bacterial systems also generally will contain a Shine-Dalgarno (S.D.) sequence operably linked to the DNA encoding the antibody or antibody fragment.

Suitable promoting sequences for use with yeast hosts include the promoters for 3-phosphoglycerate kinase (Hitzeman et al., J. Biol. Chem., 255: 2073 (1980)) or other glycolytic enzymes (Hess et al., J. Adv. Enzyme Reg., 7: 149 (1968); and Holland, Biochemistry 17: 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657A. Yeast enhancers also are advantageously used with yeast promoters.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into mammalian expression vectors.

Vector driven transcription of antibody or antibody fragment encoding DNA in mammalian host cells can be controlled by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g. the actin promoter or an immunoglobulin promoter, and from heat-shock promoters, provided such promoters are compatible with the host cell systems.

The early and late promoters of the SV40 virus are conveniently obtained as an SV40 restriction fragment that also contains the SV40 viral origin of replication. Fiers et al., Nature, 273: 113 (1978); Mulligan and Berg, Science, 209: 1422–1427 (1980); Pavlakis et al., Proc. Natl. Acad. Sci. USA, 78: 7398–7402 (1981). The immediate early promoter of the human cytomegalovirus is conveniently obtained as a HindIII E restriction fragment. Greenaway et al., Gene, 18: 355–360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., Nature, 295: 503–508 (1982) on expressing cDNA encoding immune interferon in monkey cells, Reyes et al., Nature, 297: 598–601 (1982) on expression of human-interferon cDNA in mouse cells under the control of a thymidine kinase promoter from herpes simplex virus, Canaani and Berg, Proc. Natl. Acad. Sci. USA, 79: 5166–5170 (1982) on expression of the human interferon 1 gene in cultured mouse and rabbit cells, and Gorman et al., Proc. Natl. Acad. Sci. USA, 79: 6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

(v) Enhancer Element Component

Transcription of a DNA encoding antibody or antibody fragment by higher eukaryotic host cells is often increased by inserting an enhancer sequence into the vector. Enhancers are cis-acting elements of DNA, usually about from 10–300 bp, that act on a promoter to increase its transcription. Enhancers are relatively orientation and position independent having been found 5' (Laimins et al., Proc. Natl. Acad. Sci. USA, 78: 993 (1981)) and 3' (Lusky et al., Mol. Cell Bio., 3: 1108 (1983)) to the transcription unit, within an intron (Banerji et al., Cell, 33: 729 (1983)) as well as within the coding sequence itself (Osborne et al., Mol. Cell Bio., 4: 1293 (1984)). Many enhancer sequences are now known from mammalian genes (globin, elastase, albumin, -fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature*, 297: 17–18 (1982) on enhancing elements for activation of eukaryotic promoters. The enhancer may be spliced into the vector at a position 5' or 3' to the antibody or antibody fragment DNA, but is preferably located at a site 5' from the promoter.

(vi) Transcription Termination Component

Expression vectors used in eukaryotic host cells (yeast, fungi, insect, plant, animal, human, or nucleated cells from other multicellular organisms) can also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding the antibody or antibody fragment. The 3' untranslated regions also include transcription termination sites.

Suitable vectors containing one or more of the above listed components and the desired coding and control sequences are constructed by standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.*, 9: 309 (1981) or by the method of Maxam et al., *Methods in Enzymology*, 65; 499 (1980).

Particularly useful in the practice of this invention are expression vectors that provide for the transient expression in mammalian cells of DNA encoding the antibody or antibody fragment. In general, transient expression involves the use of an expression vector that is able to replicate efficiently in a host cell, such that the host cell accumulates many copies of the expression vector and, in turn, synthesizes high levels of a desired polypeptide encoded by the expression vector.

Other methods, vectors, and host cells suitable for adaptation to the synthesis of the antibody or antibody fragment in recombinant vertebrate cell culture are described in Gething et al., *Nature*, 293: 620–625 (1981); Mantei et al., *Nature*, 281: 40–46 (1979); Levinson et al., EP 117,060; and EP 117,058. A particularly useful plasmid for mammalian cell culture expression of the IgE peptide antagonist is pRK5 (EP pub. no. 307,247) or pSV16B (PCT pub. no. WO 91108291 published 13 Jun. 1991).

C. Selection and Transformation of Host Cells

Suitable host cells for cloning or expressing the vectors herein are the prokaryote, yeast, or higher eukaryote cells described above. Suitable prokaryotes include eubacteria, such as Gram-negative or Gram-positive organisms, for example, *E. coli, Bacilli* such as *B. subtilis, Pseudomonas* species such as *P. aeruginosa, Salmonella typhimurium*, or *Serratia marcescens*. One preferred *E. coli* cloning host is *E. coli* 294 (ATCC 31,446), although other strains such as *E. coli* B, *E. coli* 1776 (ATCC 31,537), and *E. coli* W3110 (ATCC 27,325) are suitable. These examples are illustrative rather than limiting. Preferably the host cell should secrete minimal amounts of proteolytic enzymes. In a preferred embodiment, the *E. coli* strain 49D6 is used as the expression host as described in the Examples below. Review articles describing the recombinant production of antibodies in bacterial host cells include Skerra et al., *Curr. Opinion in Immunol.*, 5: 256 (1993) and Pluckthun, Immunol. Revs., 130: 151 (1992).

In addition to prokaryotes, eukaryotic microbes such as filamentous fungi or yeast are suitable hosts for vectors containing antibody or antibody fragment DNA. *Saccharomyces cerevisiae*, or common baker's yeast, is the most commonly used among lower eukaryotic host microorganisms. However, a number of other genera, species, and strains are commonly available and useful herein, such as *S. pombe* (Beach and Nurse, *Nature*, 290: 140 (1981)), *Kluyveromyces lactis* (Louvencourt et al., *J. Bacteriol.*, 737 (1983)), *yarrowia* (EP 402,226), *Pichia pastoris* (EP 183, 070), *Trichoderma reesia* (EP 244,234), *Neurospora crassa* (Case et al., *Proc. Natl. Acad. Sci. USA*, 76: 5259–5263 (1979)), and *Aspergillus* hosts such as *A. nidulans* (Ballance et al., *Biochem. Biophys. Res. Commun.*, 112: 284–289 (1983); Tilburn et al., *Gene*, 26: 205–221 (1983); Yelton et al., *Proc. Natl. Acad. Sci. USA*, 81: 1470–1474 (1984)) and *A. niger* (Kelly and Hynes, *EMBO J.*, 4: 475–479 (1985)).

Host cells derived from multicellular organisms can also be used in the recombinant production of antibody or antibody fragment Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* host cells have been identified. See, e.g., Luckow et al., *Bio/Technology*, 6: 47–55 (1988); Miller et al., in *Genetic Engineering*, Setlow, J. K. et al., 8: 277–279 (Plenum Publishing, 1986), and Maeda et al., *Nature*, 315: 592–594 (1985). A variety of such viral strains are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the antibody or antibody fragment DNA. During incubation of the plant cell culture with *A. tumefaciens*, the DNA encoding antibody or antibody fragment is transferred to the plant cell host such that it is transfected, and will, under appropriate conditions, express the antibody or antibody fragment DNA. In addition, regulatory and signal sequences compatible with plant cells are available, such as the nopaline synthase promoter and polyadenylation signal sequences. Depicker et al., *J. Mol. Appl. Gen.*, 1: 561 (1982). In addition, DNA segments isolated from the upstream region of the T-DNA 780 gene are capable of activating or increasing transcription levels of plant-expressible genes in recombinant DNA-containing plant tissue. See EP 321,196 published 21 Jun. 1989.

Vertebrate cell culture is preferred for the recombinant production of full length antibodies. The propagation of vertebrate cells in culture (tissue culture) has become a routine procedure in recent years (*Tissue Culture*, Academic Press, Kruse and Patterson, editors (1973)). Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.*, 36: 59 (1977)); baby hamster kidney cells (BHK, ATCC CCL 10); Chinese hamster ovary cells/DHFR (CHO, Urlaub and Chasin, *Proc. Natl. Acad. Sci. USA*, 77: 4216 (1980)); mouse sertoli cells (TM4, Mather, *Biol. Reprod.* 23: 243–251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.*, 383: 44–68 (1982));

MRC 5 cells; FS4 cells; and a human hepatoma cell line (Hep G2). Preferred host cells are human embryonic kidney 293 and Chinese hamster ovary cells. Myeloma cells that do not otherwise produce immunoglobulin protein are also usefull host cells for the recombinant production of full length antibodies.

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ precipitation and electroporation. Successful transfection is generally recognized when any indication of the operation of this vector occurs within the host cell.

Transformation means introducing DNA into an organism so that the DNA is replicable, either as an extrachromosomal element or by chromosomal integrant Depending on the host cell used, transformation is done using standard techniques appropriate to such cells. The calcium treatment employing calcium chloride, as described in section 1.82 of Sambrook et al., supra, is generally used for prokaryotes or other cells that contain substantial cell-wall barriers. Infection with *Agrobacterium tumefaciens* is used for transformation of certain plant cells, as described by Shaw et al., *Gene*, 23: 315 (1983) and WO 89/05859 published 29 Jun. 1989. For mammalian cells without such cell walls, the calcium phosphate precipitation method described in sections 16.30–16.37 of Sambrook et al., supra, is preferred. General aspects of mammalian cell host system transformations have been described by Axel in U.S. Pat. No. 4,399,216 issued 16 Aug. 1983. Transformations into yeast are typically carried out according to the method of Van Solingen et al., *J. Bact.*, 130: 946 (1977) and Hsiao et al., *Proc. Natl. Acad. Sci. (USA)*, 76: 3829 (1979). However, other methods for introducing DNA into cells such as by nuclear injection, electroporation, or by protoplast fusion may also be used.

D. Culturing the Host Cells

Prokaryotic cells used to produce the antibody or antibody fragment are cultured in suitable media as described generally in Sambrook et al., supra.

The mammalian host cells used to produce the antibody or antibody fragment can be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham and Wallace, *Meth. Enz.*, 58: 44 (1979), Barnes and Sato, *Anal. Biochem.*, 102 255 (1980), U.S. Pat. Nos. 4,767,704; 4,657,866; 4,927, 762; or 4,560,655; WO 90103430; WO 87/00195; U.S. Pat. No. Re. 30,985; or U.S. Pat. No. 5,122,469, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The host cells referred to in this disclosure encompass cells in in vitro culture as well as cells that are within a host animal.

E. Detecting Gene Amplification/Expression

Gene amplification and/or expression may be measured in a sample directly, for example, by conventional Southern blotting, northern blotting to quantitate the transcription of mRNA (Thomas, *Proc. Natl. Acad. Sci. USA*, 77: 5201–5205 (1980)), dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product, where the labels are usually visually detectable, such as enzymatic labels, fluorescent labels, luminescent labels, and the like. A particularly sensitive staining technique suitable for use in the present invention is described by Hsu et al., *Am. J. Clin. Path.*, 75: 734–738 (1980).

F. Purification of the Antibody or Antibody Fragment

In the case of a host cell secretion system, the antibody or antibody fragment is recovered from the culture medium. Alternatively, the antibody can be produced intracellularly, or produced in the periplasmic space of a bacterial host cell. If the antibody is produced intracellularly, as a first step, the host cells are lysed, and the resulting particulate debris is removed, for example, by centrifugation or ultrafiltration.

Carter et al., *Bio/Technology* 10:163–167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fe domain that is present in the antibody. Protein A can be used to purify antibodies that are based on human γ1, γ2, or γ4 heavy chains (Lindmnark et at, *J. Immunol. Meth.* 62:1–13 (1983)). Protein G is recommended for all mouse isotypes and for human γ3 (Guss et al., *EMBO J.* 5: 15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin Sepharose™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5–4.5, preferably performed at low salt concentrations (e.g. from about 0–0.25M salt).

G. Production of Antibody Fragments

Various techniques have been developed for the production of the humanized antibody fragments of the invention, including Fab, Fab', Fab'-SH, or $F(ab')_2$ fragments. Traditionally, these fragments were derived via proteolytic digestion of intact antibodies (see, e.g., Morimoto et al., *Journal of Biochemical and Biophysical Methods* 24:107–117 (1992) and Brennan et al., *Science*, 229:81 (1985)). However, these fragments can now be produced directly by recombinant host cells. For example, Fab'-SH fragments can be directly recovered from *E. coli* and chemically coupled to form $F(ab')_2$ fragments (Carter et al., *Bio/Technology*, 10:163–167 (1992)). According to another approach, $F(ab')_2$ fragments can be isolated directly from recombinant host cell culture. Other techniques for the production of antibody fragments will be apparent to the skilled practitioner.

5. Uses of Anti-IL-8 Antibodies

A. Diagnostic Uses

For diagnostic applications requiring the detection or quantitation of IL-8, the antibodies or antibody fragments of the invention typically will be labeled with a detectable moiety. The detectable moiety can be any one which is capable of producing, either directly or indirectly, a detectable signal. For example, the detectable moiety can be a radioisotope, such as $^3H$, $^{14}C$, $^{32}P$, $^{35}S$, or $^{125}I$; a fluorescent or chemiluminescent compound, such as fluorescein isothiocyanate, rhodamine, or luciferin; radioactive isotopic labels, such as, e.g., $^{125}I$, $^{32}P$, $^{14}C$, or $^3H$; or an enzyme, such as alkaline phosphatase, beta-galactosidase, or horseradish peroxidase.

Any method known in the art for separately conjugating the antibody or antibody fragment to the detectable moiety can be employed, including those methods described by Hunter et al., *Nature* 144:945 (1962); David et al., *Biochemistry* 13:1014 (1974); Pain et al., *J. Immunol. Meth.* 40:219 (1981); and Nygren, *J. Histochem. and Cytochem.* 30:407 (1982).

The antibodies and antibody fragments of the present invention can be employed in any known assay method, such as competitive binding assays, direct and indirect sandwich assays, and immunoprecipitation assays. For example, see Zola, *Monoclonal Antibodies: A Manual of Techniques*, pp. 147–158 (CRC Press, Inc., 1987).

Competitive binding assays rely on the ability of a labeled standard (which can be a IL-8 or an immunologically reactive portion thereof) to compete with the test sample analyte (IL-8) for binding with a limited amount of antibody or antibody fragment. The amount of IL-8 in the test sample is inversely proportional to the amount of standard that becomes bound to the antibodies. To facilitate determining the amount of standard that becomes bound, the antibodies or antibody fragments generally are insolubilized before or after the competition, so that the standard and analyte that are bound to the antibodies can conveniently be separated from the standard and analyte which remain unbound.

Sandwich assays involve the use of two antibodies, each capable of binding to a different antigenic portion, or epitope, of the protein (IL-8) to be detected. In a sandwich assay, the test sample analyte is bound by a first antibody which is immobilized on a solid support, and thereafter a second antibody binds to the analyte, thus forming an insoluble three-part complex (U.S. Pat. No. 4,376,110). The second antibody can itself be labeled with a detectable moiety (direct sandwich assays) or can be measured using an anti-immunoglobulin antibody that is labeled with a detectable moiety (indirect sandwich assay). For example, one type of sandwich assay is an ELISA assay, in which case the detectable moiety is an enzyme (e.g., horseradish peroxidase).

IL-8 antibodies and antibody fragments also are useful for the affinity purification of IL-8 from recombinant cell culture or natural sources. For example, these antibodies can be fixed to a solid support by techniques well known in the art so as to purify IL-8 from a source such as culture supernatant or tissue.

B. Therapeutic Compositions and Administration of Anti-IL-8 Antibody

The humanized anti-IL-8 antibodies and antibody fragments of the invention are useful in the treatment of inflammatory disorders, such as adult respiratory distress syndrome (ARDS), hypovolemic shock, ulcerative colitis, and rheumatoid arthritis.

Therapeutic formulations of the humanized anti-IL-8 antibodies and antibody fragments are prepared for storage by mixing the antibody or antibody fragment having the desired degree of purity with optional physiologically acceptable carriers, excipients, or stabilizers (*Remington's Pharmaceu-* tical Sciences, supra), in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The humanized anti-IL-8 mAb or antibody fragment to be used for in vivo administration must be sterile. This is readily accomplished by filtration through sterile filtration membranes, prior to or following lyophilization and reconstitution. The humanized anti-IL-8 mAb or antibody fragment ordinarily will be stored in lyophilized form or in solution.

Therapeutic humanized anti-IL-8 mAb or antibody fragment compositions generally are placed into a container having a sterile access port, for example, an intravenous solution bag or vial having a stopper pierceable by a hypodermic injection needle.

The route of humanized anti-IL-8 mAb or antibody fragment administration is in accord with known methods, eg., inhalation, injection or infusion by intravenous, intraperitoneal, intracerebral, intramuscular, intraocular, intraarterial, or intralesional routes, by enema or suppository, or by sustained release systems as noted below. Preferably the antibody is given systemically or at a site of inflammation.

Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman et al., *Biopolymers* 22:547 (1983)), poly(2-hydroxyethyl-methacrylate) (Langer et al., *J. Biomed. Mater. Res.* 15:167 (1981) and Langer, *Chem. Tech.* 12:98 (1982)), ethylene vinyl acetate (Langer et al., supra) or poly-D-(–)-3-hydroxybutyric acid (EP 133,988). Sustained-release humanized anti-IL-8 antibody or antibody fragment compositions also include liposomally entrapped antibody or antibody fragment. Liposomes containing an antibody or antibody fragment are prepared by methods known per se: DE 3,218,121; Epstein et al., *Proc. Natl. Acad. Sci. U.S.A.* 82:3688 (1985); Hwang et al., *Proc. Natl. Acad. Sci. U.S.A.* 77:4030 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamelar type in which the lipid content is greater than about 30 mole percent cholesterol, the selected proportion being adjusted for the most efficacious antibody or antibody fragment therapy.

An "effective amount" of the humanized anti-IL-8 antibody or antibody fragment to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. Typically, the clinician will administer the humanized anti-IL-8 antibody or antibody fragment until a dosage is reached that achieves the desired effect. The progress of this therapy is easily monitored by conventional assays.

In the treatment and prevention of an inflammatory disorder with a humanized anti-IL-8 antibody or antibody fragment of the invention, the antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the antibody, the particular type of antibody, the method of administration, the scheduling of administration, and other factors known to medical practitioners. The "therapeutically effective amount" of antibody to be administered will be governed by such considerations, and is the minimum amount necessary to prevent, ameliorate, or treat the inflammatory disorder, including treating acute or chronic respiratory diseases and reducing inflammatory responses. Such amount is preferably below the amount that is toxic to the host or renders the host significantly more susceptible to infections.

As a general proposition, the initial pharmaceutically effective amount of the antibody or antibody fragment administered parenterally per dose will be in the range of about 0.1 to 50 mg/kg of patient body weight per day, with the typical initial range of antibody used being 0.3 to 20 mg/kg/day, more preferably 0.3 to 15 mg/kg/day.

As noted above, however, these suggested amounts of antibody or antibody fragment are subject to a great deal of therapeutic discretion. The key factor in selecting an appropriate dose and scheduling is the result obtained, as indicated above.

The antibody or antibody fragment need not be, but is optionally formulated with one or more agents currently used to prevent or treat the inflammatory disorder in question. For example, in rheumatoid arthritis, the antibody can be given in conjunction with a glucocorticosteroid. The effective amount of such other agents depends on the amount of antibody or antibody fragment present in the formulation, the type of disorder or treatment, and other factors discussed above. These are generally used in the same dosages and with administration routes as used hereinbefore or about from 1 to 99% of the heretofore employed dosages.

The following examples are offered by way of illustration and not by way of limitation. The disclosures of all references cited in the specification, and the disclosures of all citations in such references, are expressly incorporated herein by reference.

EXAMPLES

A. Generation and Characterization of Monoclonal Antibodies Against Human IL-8

Balb/c mice were immunized in each hind footpad or intraperitoneally with 10 µg of recombinant human IL-8 (produced as a fusion of (ser-IL-8)$_{72}$ with ubiquitin (Hebert et al. *J. Immunology* 145:3033–3040 (1990)); IL-8 is available commercially from PeproTech, Inc., Rocky Hill, N.J.) resuspended in MPL/TDM (Ribi Immunochem. Research Inc., Hamilton, Mont.) and boosted twice with the same amount of IL-8. In these experiments, "IL-8" is intended to mean (ser-IL-8)$_{72}$ unless otherwise specified. A final boost of 10 µg of IL-8 was given 3 days before the fusion. Spleen cells or popliteal lymph node cells were fused with mouse myeloma P3X63Ag8U.1 (ATCC CRL1597), a non-secreting clone of the myeloma P3X63Ag8, using 35% polyethylene glycol as described before. Ten days after the fusion, culture supernatant was screened for the presence of monoclonal antibodies to IL-8 by ELISA.

The ELISA was performed as follows. Nunc 96-well immunoplates (Flow Lab, McLean, Va.) were coated with 50 µl/well of 2 µg/ml IL-8 in phosphate-buffered saline (PBS) overnight at 4° C. The remaining steps were carried out at room temperature. Nonspecific binding sites were blocked with 0.5% bovine serum albumin (BSA) for 1 hour (hr). Plates were then incubated with 50 µl/well of hybridoma culture supernatants from 672 growing parental fusion wells for 1 hr, followed by the incubation with 50 µl/well of 1:1000 dilution of a 1 mg/ml stock solution of alkaline phosphatase-conjugated goat anti-mouse Ig (Tago Co., Foster City, Calif.) for 1 hr. The level of enzyme-linked antibody bound to the plate was determined by the addition of 100 µl/well of 0.5 mg/ml of r-nitrophenyl phosphate in sodium bicarbonate buffer, pH 9.6. The color reaction was measured at 405 nm with an ELISA plate reader (Titertrek Multiscan, Flow Lab, McLean, Va.). Between each step, plates were washed three times in PBS containing 0.05% Tween 20.

Culture supernatants which promoted 4-fold more binding of IL-8 than did control medium were selected as positives. According to this criterion, 16 of 672 growing parental fusion wells (2%) were positive. These positive hybridoma cell lines were cloned at least twice by using the limiting dilution technique.

Seven of the positive hybridomas were further characterized as follows. The isotypes of the monoclonal antibodies were determined by coating Nunc 96-well immunoplates (Flow Lab, McLean, Va.) with IL-8 overnight, blocking with BSA, incubating with culture supernatants followed by the addition of predetermined amount of isotype-specific alkaline phosphatase-conjugated goat anti-mouse Ig (Fisher Biotech, Pittsburgh, Pa.). The level of conjugated antibodies bound to the plate was determined by the addition of r-nitrophenyl phosphate as described above.

All the monoclonal antibodies tested belonged to either $IgG_1$ or $IgG_2$ immunoglobulin isotype. Ascites fluid containing these monoclonal antibodies had antibody titers in the range of 10,000 to 100,000 as determined by the reciprocal of the dilution factor which gave 50% of the maximum binding in the ELISA.

To assess whether these monoclonal antibodies bound to the same epitopes, a competitive binding ELISA was performed. At a ratio of biotinylated mAb to unlabeled mAb of 1:100, the binding of biotinylated mAb 5.12.14 was significantly inhibited by its homologous mAb but not by mAb 4.1.3, while the binding of biotinylated mAb 4.1.3 was inhibited by mAb 4.1.3 but not by mAb 5.12.14. Monoclonal antibody 5.2.3 behaved similarly to mAb 4.1.3, while monoclonal antibodies 4.8 and 12.3.9 were similar to mAb 5.12.14. Thus, mAb 4.1.3 and mAb 5.2.3 bind to a different epitope(s) than the epitope recognized by monoclonal antibodies 12.3.9, 4.8 and 5.12.14.

Immunodot blot analysis was performed to assess antibody reactivity to IL-8 immobilized on nitrocellulose paper. All seven antibodies recognized IL-8 immobilized on paper, whereas a control mouse IgG antibody did not.

The ability of these monoclonal antibodies to capture soluble $^{125}$I-IL-8 was assessed by a radioimmune precipitation test (RIP). Briefly, tracer $^{125}$I-IL-8 ($4 \times 10^4$ cpm) was incubated with various dilutions of the monoclonal anti-IL-8 antibodies in 0.2 ml of PBS containing 0.5% BSA and 0.05% Tween 20 (assay buffer) for 1 hr at room temperature. One hundred microliters of a predetermined concentration of goat anti-mouse Ig antisera (Pel-Freez, Rogers, Ariz.) were added and the mixture was incubated at room temperature for 1 hr. Immune complexes were precipitated by the addition of 0.5 ml of 6% polyethylene glycol (M.W. 8000) kept at 4° C. After centrifugation at 2,000×g for 20 min at 4° C., the supernatant was removed by aspiration and the radioactivity remaining in the pellet was counted in a gamma counter. Percent specific binding was calculated as (precipitated cpm—background cpm)/(total cpm—background cpm). Monoclonal antibodies 4.1.3, 5.2.3, 4.8, 5.12.14 and 12.3.9 captured $^{125}$I-IL-8 very efficiently, while antibodies 9.2.4 and 8.9.1 were not able to capture soluble $^{125}$I-IL-8 in the RIP even though they could bind to IL-8 coated onto ELISA plates (Table 1).

The dissociation constants of these monoclonal antibodies were determined using a competitive binding RIP assay. Briefly, competitive inhibition of the binding each antibody to $^{125}$I-IL-8 (20,000–40,000 cpm per assay) by various amounts of unlabeled IL-8 was determined by the RIP described above. The dissociation constant (affinity) of each mAb was determined by using Scatchard plot analysis (Munson, et al., *Anal. Biochem.* 107:220 (1980)) as provided in the VersaTerm-PRO computer program (Synergy Software, Reading, Pa.).The $K_d$'s of these monoclonal antibodies (with the exception of 9.2.4 and 8.9.1) were in the range from $2 \times 10^{-8}$ to $3 \times 10^{-10}$ M. Monoclonal antibody 5.12.14 with a $K_d$ of $3 \times 10^{-10}$ M showed the highest affinity among all the monoclonal antibodies tested (Table 3).

TABLE 3

Characterization of Anti-IL-8 Monoclonal Antibodies

| Antibody | % Specific Binding to IL-8 | $K_d$ (M) | Isotype | pI |
|---|---|---|---|---|
| 4.1.3 | 58 | $2 \times 10^{-9}$ | $IgG_1$ | 4.3–6.1 |
| 5.2.3 | 34 | $2 \times 10^{-8}$ | $IgG_1$ | 5.2–5.6 |
| 9.2.4 | 1 | — | $IgG_1$ | 7.0–7.5 |
| 8.9.1 | 2 | — | $IgG_1$ | 6.8–7.6 |
| 4.8 | 62 | $3 \times 10^{-8}$ | $IgG_{2a}$ | 6.1–7.1 |
| 5.12.14 | 98 | $3 \times 10^{-10}$ | $IgG_{2a}$ | 6.2–7.4 |
| 12.3.9 | 86 | $2 \times 10^{-9}$ | $IgG_{2a}$ | 6.5–7.1 |

To assess the ability of these monoclonal antibodies to neutralize IL-8 activity, the amount of $^{125}$I-IL-8 bound to human neutrophils in the presence of various amounts of culture supernatants and purified monoclonal antibodies was measured. Neutrophils were prepared by using Mono-Poly Resolving Medium (M-PRM) (Flow Lab. Inc., McLean, Va.). Briefly fresh, heparinized human blood was loaded onto M-PRM at a ratio of blood to medium, 3.5:3.0, and centrifuged at 300×g for 30 min at room temperature. Neutrophils enriched at the middle layer were collected and washed once in PBS. Such a preparation routinely contained greater than 95% neutrophils according to the Wright's Giemsa staining. The receptor binding assay was done as follows. 50 µl of $^{125}$I-IL-8 (5 ng/ml) was incubated with 50 µl of unlabeled IL-8 (100 µg/ml) or monoclonal antibodies in PBS containing 0.1% BSA for 30 min at room temperature. The mixture was then incubated with 100 µl of neutrophils ($10^7$ cells/ml) for 15 min at 37° C. The $^{125}$I-IL-8 bound was separated from the unbound material by loading mixtures onto 0.4 ml of PBS containing 20% sucrose and 0.1% BSA and by centrifugation at 300×g for 15 min. The supernatant was removed by aspiration and the radioactivity associated with the pellet was counted in a gamma counter.

Monoclonal antibodies 4.1.3, 5.2.3, 4.8, 5.12.14, and 12.3.9 inhibited greater than 85% of the binding of IL-8 to human neutrophils at a 1:25 molar ratio of IL-8 to mAb. On the other hand, monoclonal antibodies 9.2.4 and 8.9.1 appeared to enhance the binding of IL-8 to its receptors on human neutrophils. Since a control mouse IgG also enhanced the binding of IL-8 on neutrophils, the enhancement of IL-8 binding to its receptors by mAb 9.2.4 and 8.9.1 appears to be nonspecific. Thus, monoclonal antibodies, 4.1.3, 5.1.3, 4.8, 5.12.14, and 12.3.9 are potential neutralizing monoclonal antibodies while monoclonal antibodies 8.9.1 and 9.2.4 are non-neutralizing monoclonal antibodies.

The ability of the anti-IL-8 antibodies to block neutrophil chemotaxis induced by IL-8 was tested as follows. Neutrophil chemotaxis induced by IL-8 was determined using a Boyden chamber method (Larsen, et al. *Science* 243:1464 (1989)). One hundred μl of human neutrophils ($10^6$ cells/ml) resuspended in RPMI containing 0.1% BSA were placed in the upper chamber and 29 μl of the IL-8 (20 nM) with or without monoclonal antibodies were placed in the lower chamber. Cells were incubated for 1 hr at 37° C. Neutrophils migrated into the lower chamber were stained with Wright's Giemsa stain and counted under the microscope (100× magnification). Approximately 10 different fields per experimental group were examined. Neutralizing monoclonal antibodies 5.12.14 and 4.1.3 blocked almost 70% of the neutrophil chemotactic activity of IL-8 at 1:10 ratio of IL-8 to mAb.

The isoelectric focusing (IEF) pattern of each mAb was determined by applying purified antibodies on an IEF polyacrylamide gel (pH 3–9, Pharmacia) using the Fast gel system (Pharmacia, Piscataway, N.J.). The IEF gel was pretreated with pharmalyte containing 1% Triton X100 (Sigma, St. Louis, Mo.) for 10 min before loading the samples. The IEF pattern was visualized by silver staining according to the instructions from the manufacturer. All of the monoclonal antibodies had different IEF patterns, confirming that they originated from different clones. The pi values for the antibodies are listed in Table 3.

All these monoclonal antibodies bound equally well to both (ala-IL-8)77 and (ser-IL-8)72 forms of IL-8. Because IL-8 has greater than 30% sequence homology with certain other members of the platelet factor 4 (PF4) family of inflammatory cytokines such as β-TG (Van Damme et al., *Eur. J. Biochem.* 181:337(1989); Tanaka et al., *FEB* 236(2):467 (1988)) and PF4 (Deuel et al., *Proc. Natl. Acad. Sci. U.S.A.* 74:2256 (1977)), they were tested for possible cross reactivity to β-TG and PF4, as well as to another neutrophil activating factor, C5a. No detectable binding to any of these proteins was observed, with the exception of mAb 4.1.3, which had a slight cross reactivity to β-TG.

One of the antibodies, mAb 5.12.14, was further studied to determine whether it could block the IL-8 mediated release of elastase by neutrophils. Briefly, human neutrophils were resuspended in Hanks balanced salt solution (Gibco, Grand Island, N.Y.) containing 1.0% BSA, Fraction V (Sigma, St. Louis, Mo.), 2 mg/ml alpha-D-glucose (Sigma), 4.2 mM sodium bicarbonate (Sigma) and 0.01 M HEPES, pH 7.1 (JRH Bioscience, Lenexa, Kans.). A stock of cytochalasin B (Sigma) was prepared (5 mg/ml in dimethylsulfoxide (Sigma) and stored at 2–8° C. Cytochalasin B was added to the neutrophil preparation to produce a final concentration of 5 μg/ml, and incubated for 15 min at 37° C. Human IL-8 was incubated with mAb 5.12.14 (20 μl), or a negative control antibody, in 1 ml polypropylene tubes (DBM Scientific, San Fernando, Calif.) for 30 min at 37° C. The final assay concentrations of IL-8 were 50 and 500 nM. The monoclonal antibodies were diluted to produce the following ratios (IL-8:Mab): 1:50, 1:10, 1:2, 1:1, and 1:0.25. Cytochalasin B-treated neutrophils were added (100 μl/tube) and incubated for 2 hours at 25° C. The tubes were centrifuged (210×g, 2–8° C.) for 10 min, and supernatants were transferred to 96 well tissue culture plates (30 μl/well). Elastase substrate stock, 10 mM methoxysuccinyl-alanyl-alanyl-propyl-valyl-p-nitroanilide (Calbiochem, La Jolla, Calif.) in DMSO was prepared and stored at 2–8° C. Elastase substrate solution (1.2 mM substrate, 1.2 M NaCl (Mallinckrodt, Paris, Ky.), 0.12 M HEPES pH 7.2 in distilled water) was added (170 pi/well) to the supernatants and incubated for 0.5 to 2 hours at 37° C. (until control O.D. of 1.0 was reached). Absorbance was measured at 405 nm (SLT 340 ATTC plate reader, SLT Lab Instruments, Austria).

The results are shown in FIG. 1. At a 1:1 ratio of IL-8 to mAb 5.12.14, the antibody was able to effectively block the release of elastase from neutrophils.

The hybridoma producing antibody 5.12.14 was deposited on Feb. 15, 1993 with the American Type Culture Collection, 12301 Parklawn Drive, Rockville, Md., U.S.A. (ATCC) and assigned ATTC Accession No. HB 11553.

B. Generation and Characterization of Monoclonal Antibodies Against Rabbit IL-8

Antibodies against rabbit IL-8 were generated in essentially the same process as anti-human IL-8 antibodies using rabbit IL-8 as immunogen (kindly provided by C. Broaddus; see also Yoshimura et al. *J. Immunol.* 146:3483 (1991)). The antibody was characterized as described above for binding to other cytokines coated onto ELISA plates; no measurable binding was found to MGSA, fMLP, C5a, b-TG, TNF, PF4, or IL-1.

The hybridoma producing antibody 6G4.2.5 was deposited on Sep. 28, 1994, with the American Type Culture Collection, 12301 Parklawn Drive, Rockville, Md., U.S.A. (ATCC) and assigned ATFC Accession No. HB 11722.

Recombinant human-murine chimeric Fabs for S.12.14 and 6G4.2.5 were constructed as described below. A chimeric 6G.4.25 Fab is compared with a chimeric 5.12.14 Fab in detail below.

1. Inhibition of IL-8 Binding to Human Neutrophils by 5.12.14-Fab and 6G4 2.5-Fab The ability of the two chimeric Fabs, 5.12.14-Fab and 6G4.2.5-Fab, to efficiently bind IL-8 and prevent IL-8 from binding to IL-8 receptors on human neutrophils was determined by performing a competition binding assay which allows the calculation of the $IC_{50}$-concentration required to achieve 50% inhibition of IL-8 binding.

Figure 2:
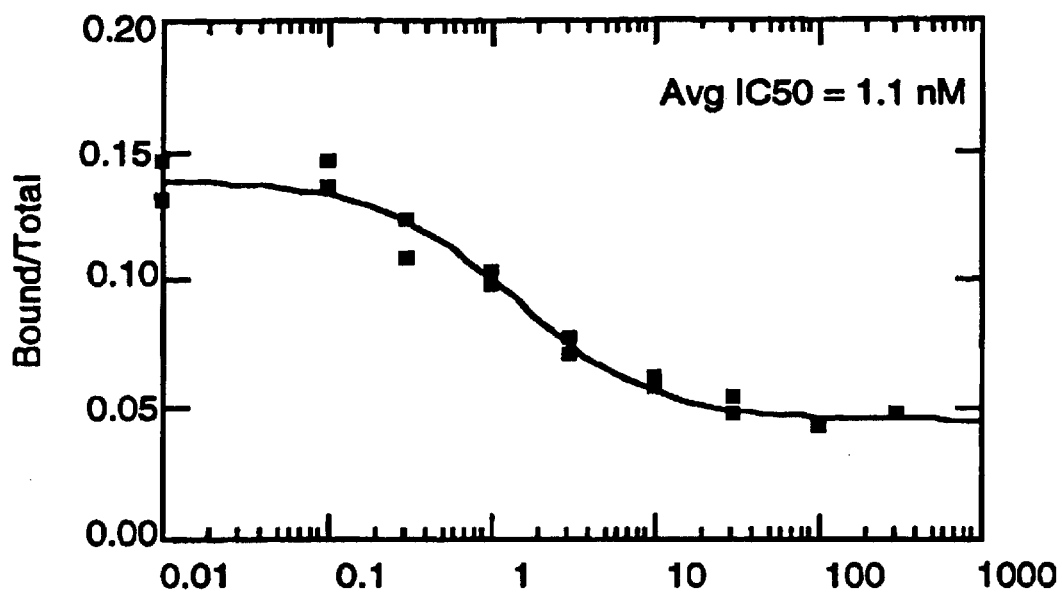
FIG. 2 is a graph depicting the inhibition of $^{125}$I-IL-8 binding to neutrophils by unlabeled IL-8.
Figure 3:
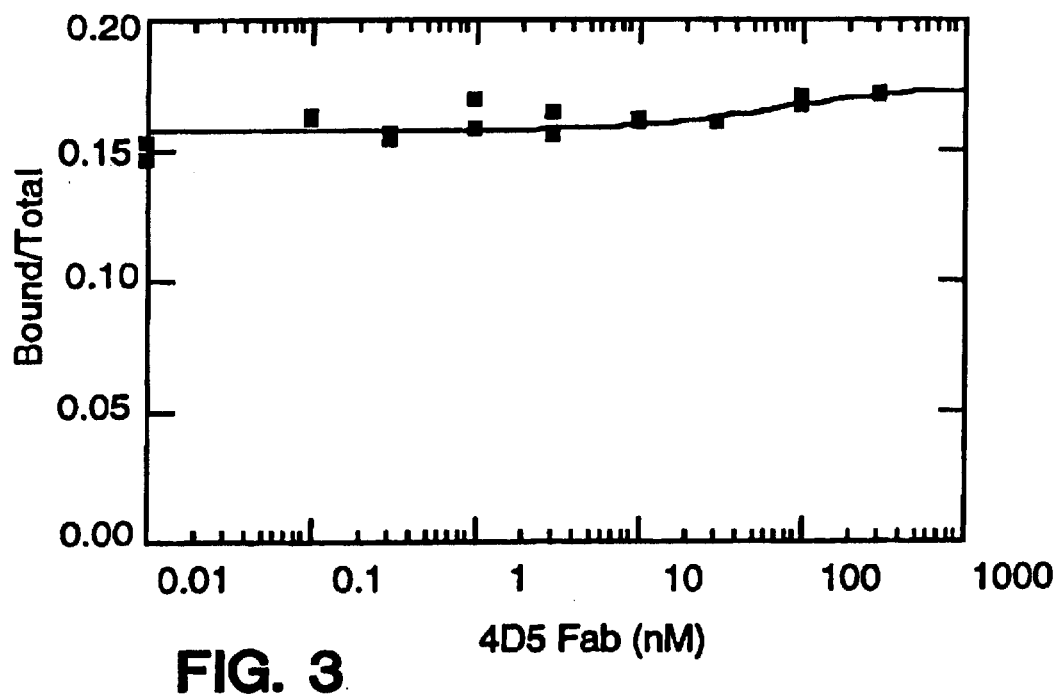
FIG. 3 demonstrates that a isotype matched negative control Fab (denoted as "4D5 Fab") does not inhibit the binding of $^{125}$I-IL-8 to human neutrophils.
Figure 4:
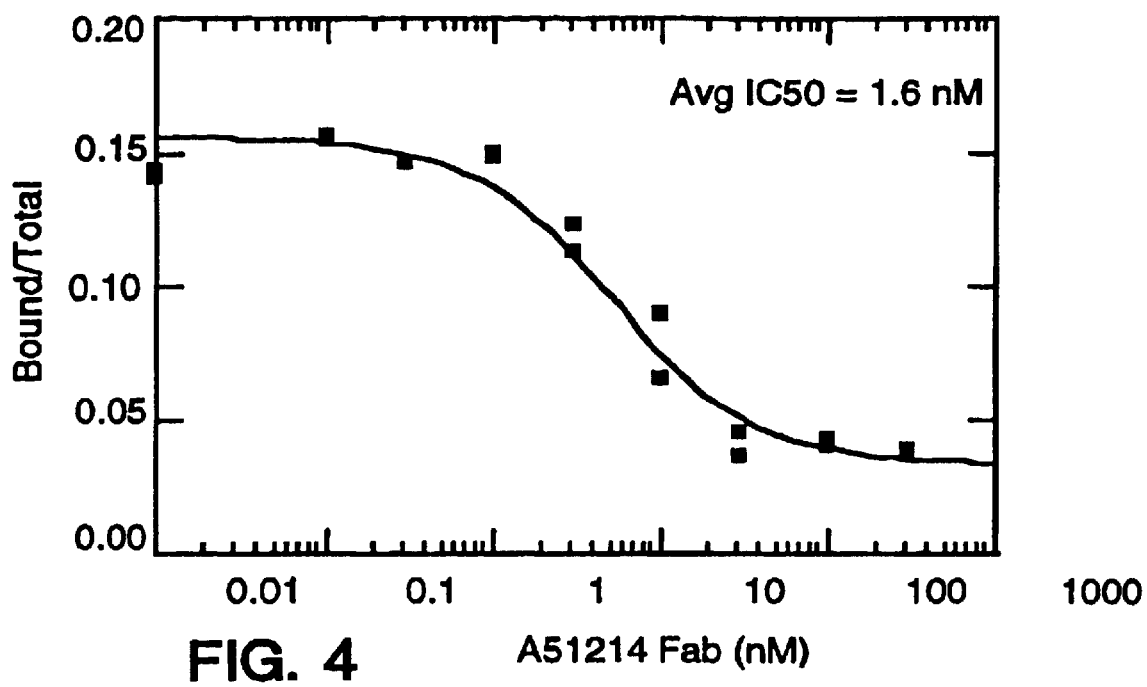
FIG. 4 is a graph depicting the inhibition of binding of $^{125}$I-IL-8 to human neutrophils by chimeric 5.12.14 Fab with an average $IC_{50}$ of 1.6 nM.
Figure 5:
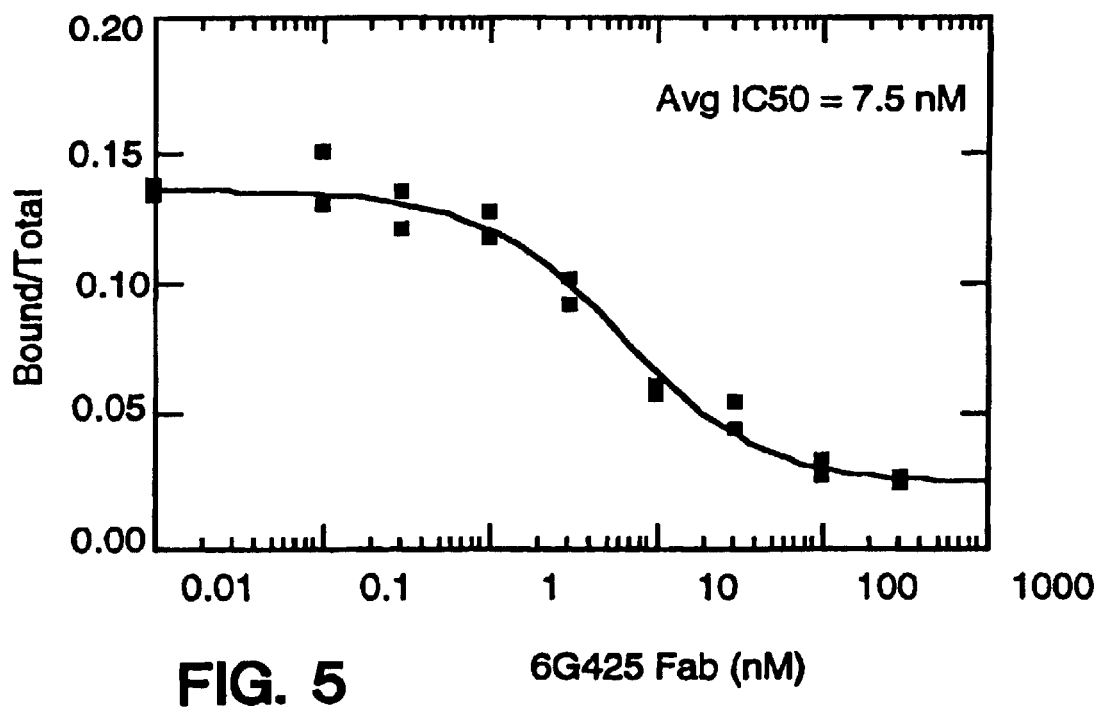
FIG. 5 is a graph depicting the inhibition of binding of $^{125}$I-IL-8 to human neutrophils by chimeric 6G.4.25 Fab with an average $IC_{50}$ of 7.5 nM.

Human neutrophils ($5\times10^5$) were incubated for 1 hour at 4° C. with 0.5 nM $^{125}$I-IL-8 in the presence of various concentrations (0 to 300 nM) of 5.12.14-Fab, 6G4.2.5-Fab, an isotype control (4D5-Fab) or unlabeled IL-8. After the incubation, the unbound $^{125}$I-IL-8 was removed by centrifugation through a solution of 20% sucrose and 0.1% bovine serum albumin in phosphate buffered saline and the amount of $^{125}$I-IL-8 bound to the cells was determined by counting the cell pellets in a gamma counter. FIG. 2 demonstrates the inhibition of $^{125}$I-IL-8 binding to neutrophils by unlabeled IL-8. FIG. 3 demonstrates that a negative isotype matched Fab does not inhibit the binding of $^{125}$I-IL-8 to human neutrophils. Both the anti-IL-8 Fabs, 5.12.14 Fab (FIG. 4) and 6G.4.25 Fab (FIG. 5) were able to inhibit the binding of $^{125}$I-IL-8 to human neutrophils with an average $IC_{50}$ of 1.6 nM and 7.5 nM, respectively.

2. Inhibition of IL-8-Mediated Neutrophil Chemotaxis by 5.12.14-Fab and 6G4.2.5-Fab Human neutrophils were isolated, counted and resuspended at $5\times10^6$ cells/ml in Hank's balanced salt solution (abbreviated HBSS; without calcium and magnesium) with 0.1% bovine serum albumin. The neutrophils were labeled by adding calcein AM (Molecular Probe, Eugene, Oreg.) at a final concentration of 2.0 μM. Following a 30 minute incubation at 37° C., cells were washed twice with HBSS-BSA and resuspended at $5 \times 10^6$ cells/ml.

Chemotaxis experiments were carried out in a Neuro Probe (Cabin John, Md.) 96-well chamber, model MBB96. Experimental samples (buffer only control, IL-8 alone or IL-8+Fabs) were loaded in a Polyfiltronics 96-well View plate (Neuro Probe Inc.) placed in the lower chamber. 100 μl of the calcein AM-labeled neutrophils were added to the upper chambers and allowed to migrate through a 5 micrometer porosity PVP free polycarbonate framed filter (Ncuro Probe Inc.) toward the bottom chamber sample. The chemotaxis apparatus was then incubated for 40 to 60 minutes at 37° C. with 5% $CO_2$. At the end of the incubation, neutrophils remaining in the upper chamber were aspirated and upper chambers were washed three times with PBS. Then the polycarbonate filter was removed, non-migrating cells were wiped off with a squeegee wetted with PBS, and the filter was air dried for 15 minutes.

The relative number of neutrophils migrating through the filter (Neutrophil migration index) was determined by measuring fluorescence intensity of the filter and the fluorescence intensity of the contents of the lower chamber and adding the two values together. Fluorescence intensity was measured with a CytoFluor 2300 fluorescent plate reader (Millipore Corp. Bedford, Mass.) configured to read a Corning 96-well plate using the 485-20 nm excitation filter and a 530-25 emission filter, with the sensitivity set at 3.

Figure 6:
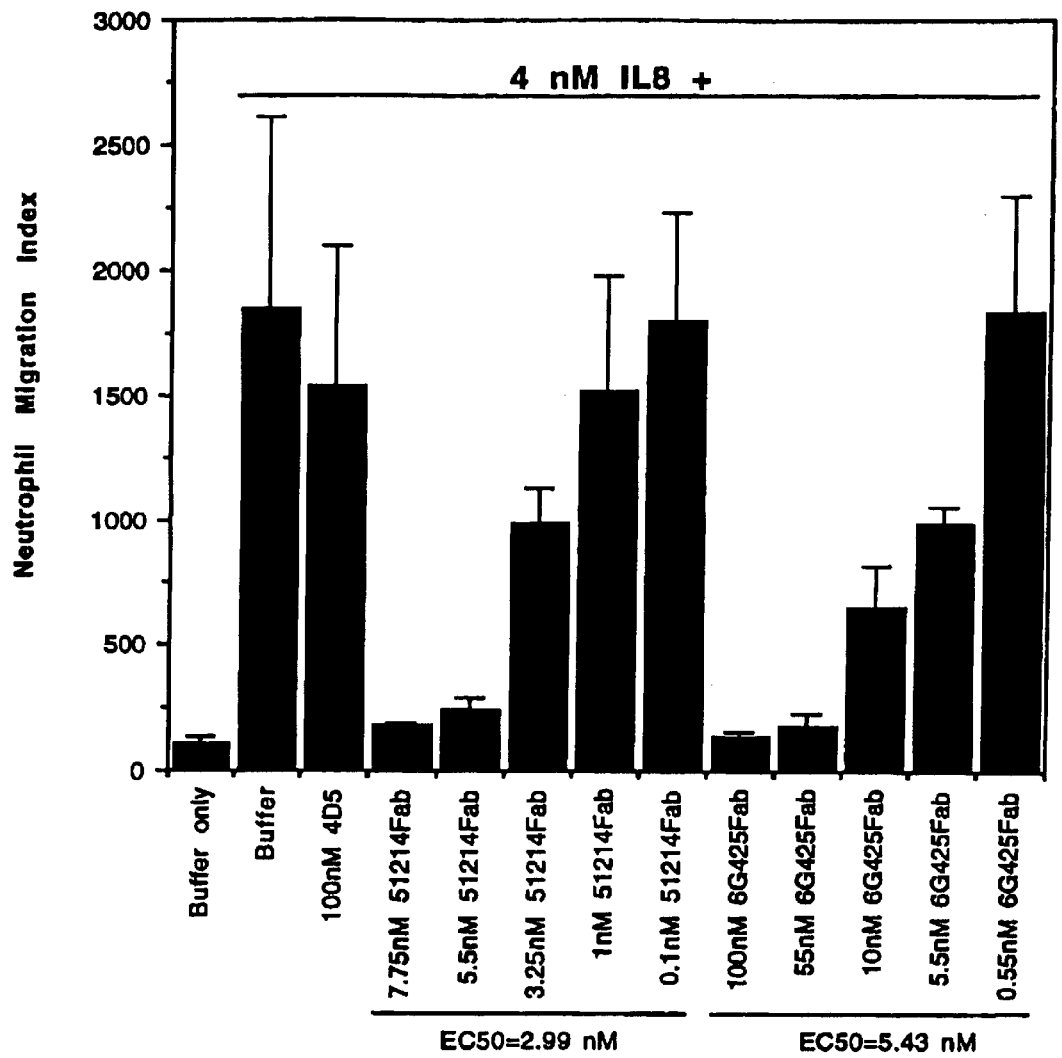
FIG. 6 demonstrates the inhibition of human IL-8 mediated neutrophil chemotaxis by chimeric 6G4.2.5 Fab and chimeric 5.12.14 Fab.
Figure 7:
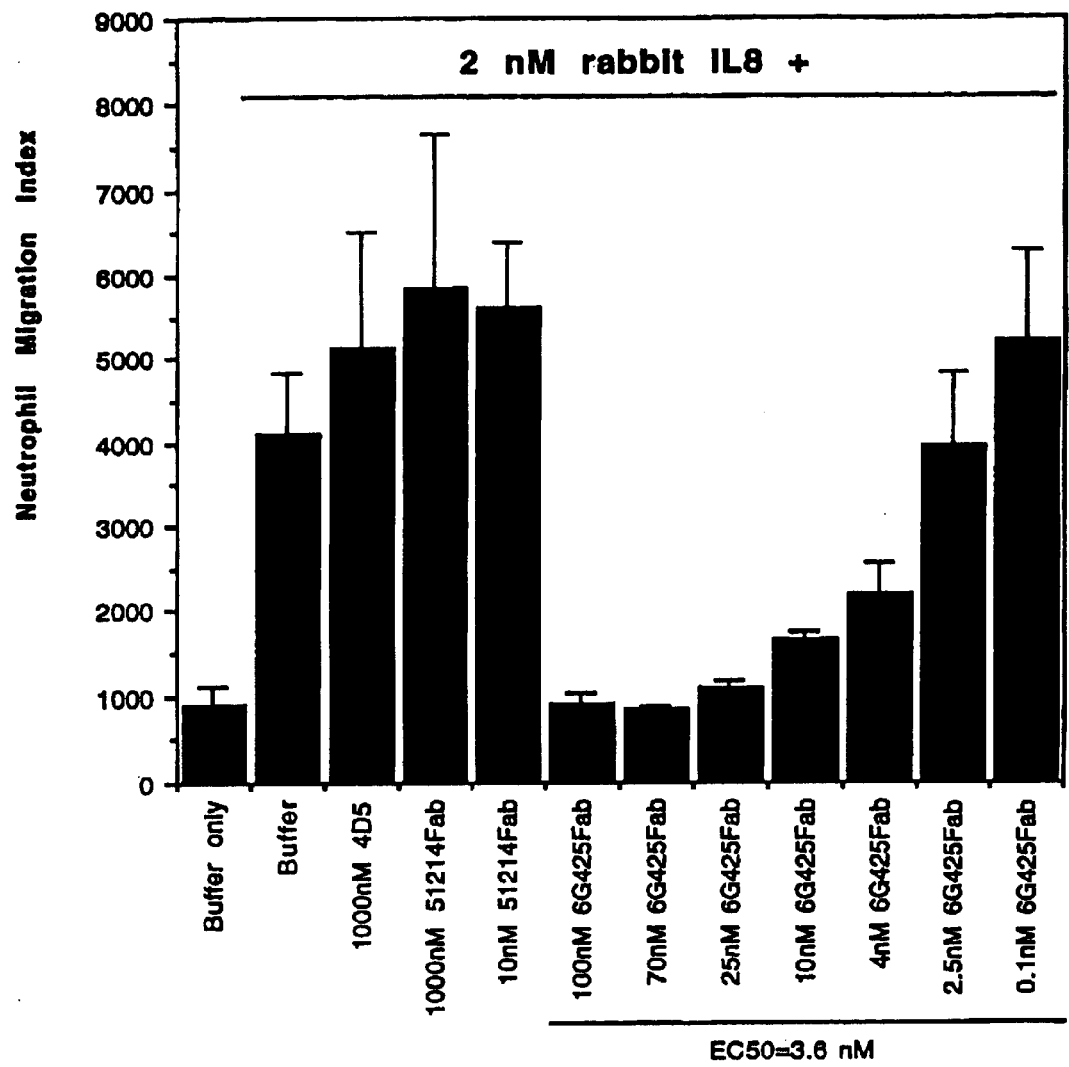
FIG. 7 demonstrates the relative abilities of chimeric 6G4.2.5 Fab and chimeric 5.12.14 Fab to inhibit rabbit IL-8 mediated neutrophil chemotaxis.

The results are shown in FIGS. 6 and 7. FIG. 6 demonstrates the inhibition of human IL-8 mediated neutrophil chemotaxis by chimeric 6G4.2.5 and 5.12.14 Fabs. FIG. 7 demonstrates the relative abilities of chimeric 6G4.2.5 and 5.12.14 Fabs to inhibit rabbit IL-8 mediated neutrophil chemotaxis.

3. Inhibition of IL-8-Mediated Neutrophil Elastase Release by Various Concentrations of 6G4.2.5 and 5.12.14 Fabs Blood was drawn from healthy male donors into heparinized syringes. Neutrophils were isolated by dextran sedimentation, centrifugation over Lymphocyte Separation Medium (Organon Teknika, Durham, N.C.), and hypotonic lysis of contaminating red blood cells as described by Berman et al. (*J. Cell Biochem.* 52:183 (1993)). The final neutrophil pellet was suspended at a concentration of $1 \times 10^7$ cells/ml in assay buffer, which consisted of Hanks Balanced Salt Solution (GIBCO, Grand Island, N.Y.) supplemented with 1.0% BSA (fraction V, Sigma, St. Louis, Mo.), 2 mg/ml glucose, 4.2 mM sodium bicarbonate, and 0.01 M HEPES, pH 7.2. The neutrophils were stored at 4° C. for not longer than 1 hr.

Figure 8:
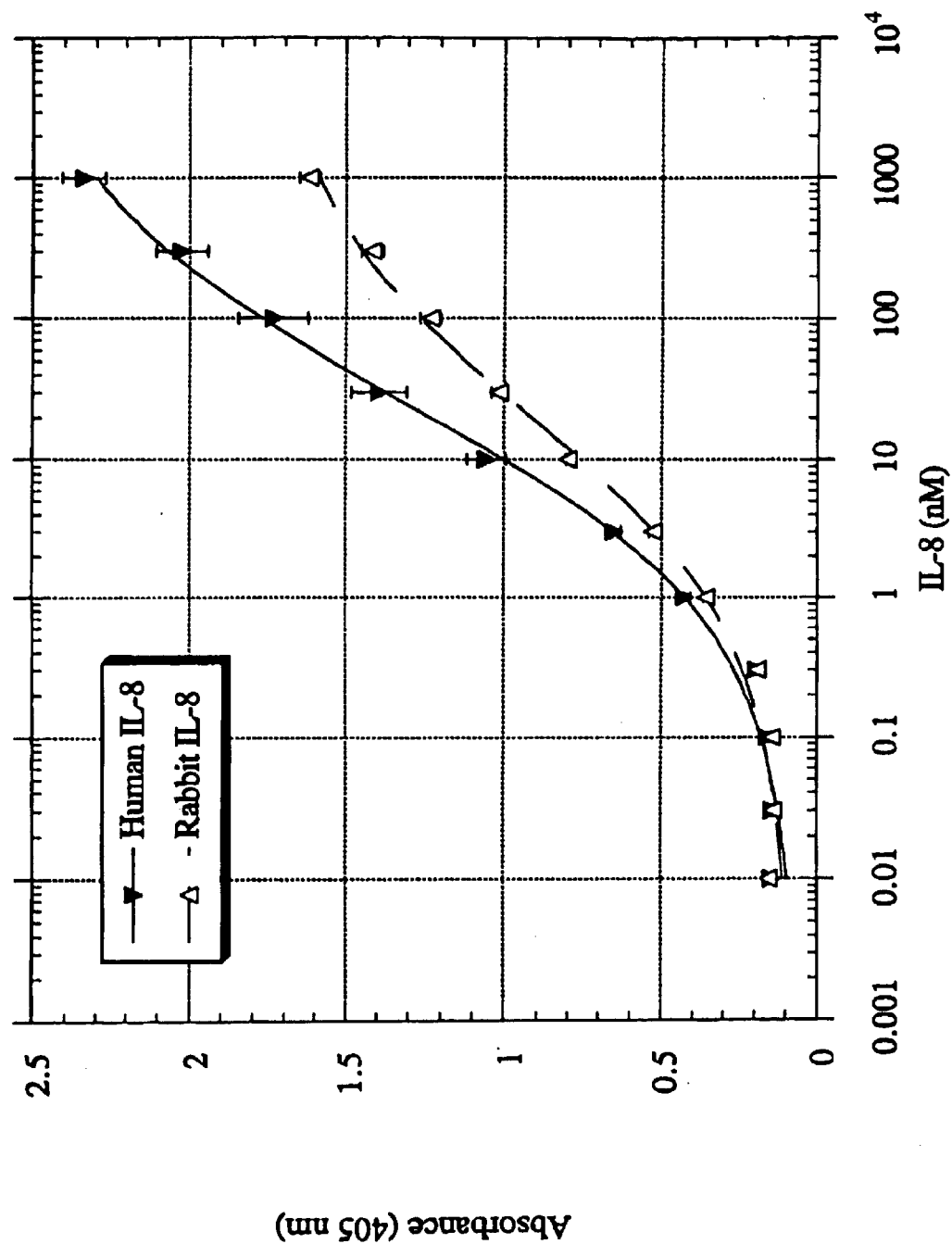
FIG. 8 depicts the stimulation of elastase release from human neutrophils by various concentrations of human and rabbit IL-8. The relative extent of elastase release was quantitated by measurement of absorbance at 405 nm. The data represent mean±SEM of triplicate samples.
Figure 9:
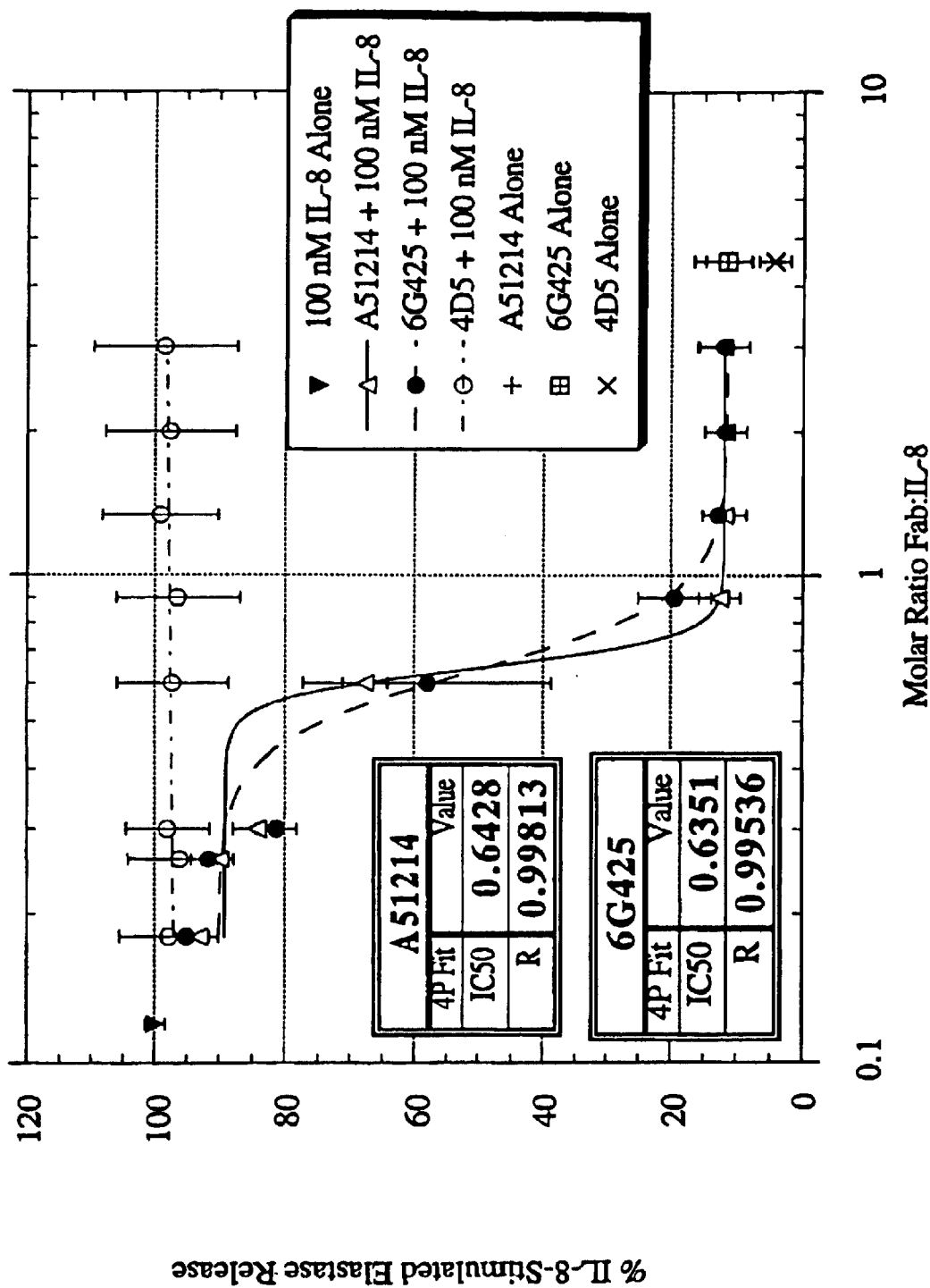
FIG. 9 is a graph depicting the ability of chimeric 6G4.2.5 Fab and chimeric 5.12.14 Fab to inhibit elastase release from human neutrophils stimulated by human IL-8. The results were normalized to reflect the percentage of elastase release elicited by 100 nM IL-8 alone. The data represent the mean±SEM of three separate experiments performed on different days with different blood donors. $IC_{50}$ values were calculated by four parameter fit.
Figure 10:
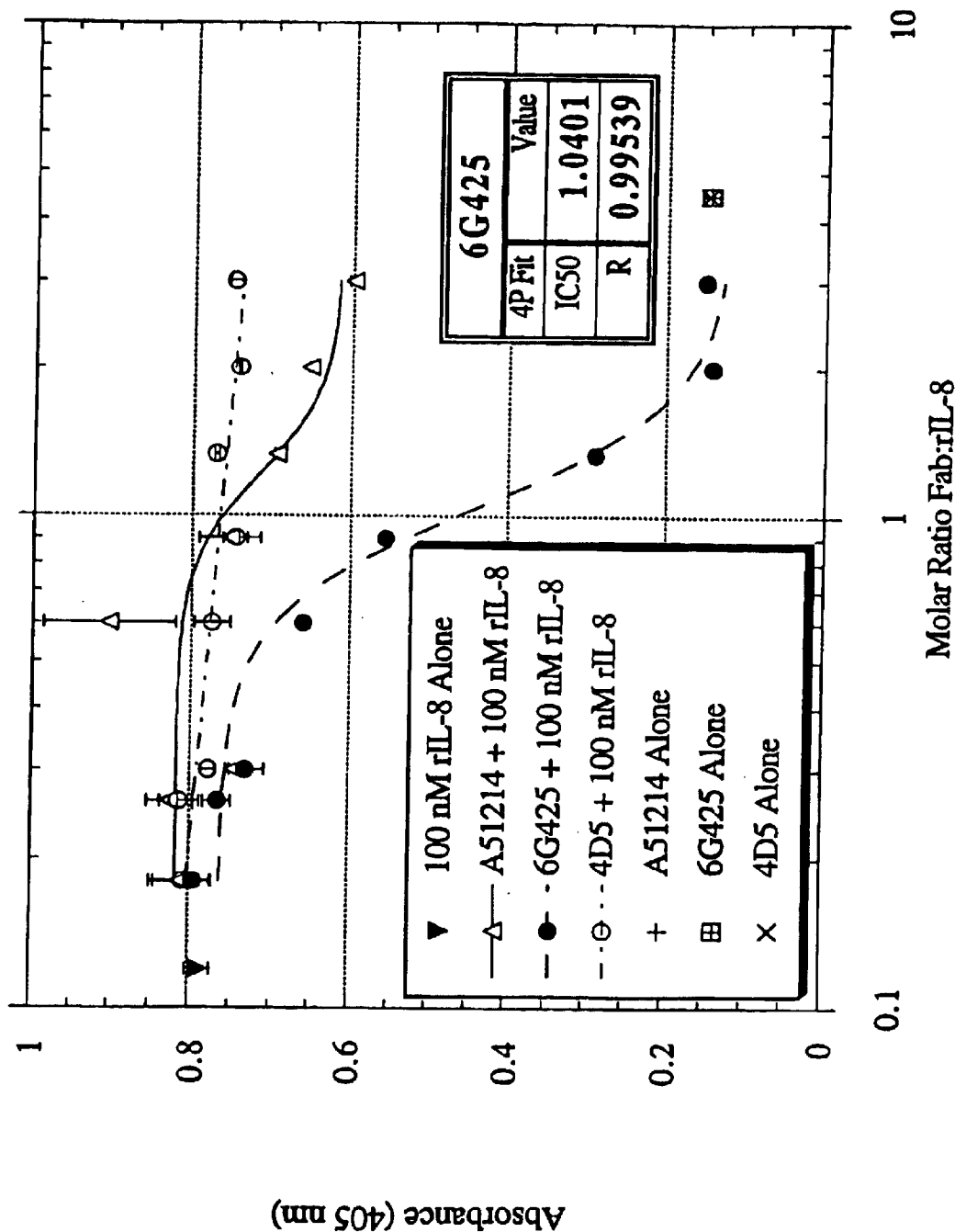
FIG. 10 is a graph depicting the relative abilities of chimeric 6G4.2.5 Fab and chimeric 5.12.14 Fab to inhibit elastase release from human neutrophils stimulated by rabbit IL-8. The results were normalized to reflect the percentage of elastase release elicited by 100 nM IL-8 alone. The data represent the mean±SEM of three separate experiments performed on different days with different blood donors. $IC_{50}$ values were calculated by four parameter fit.
Figure 11B:
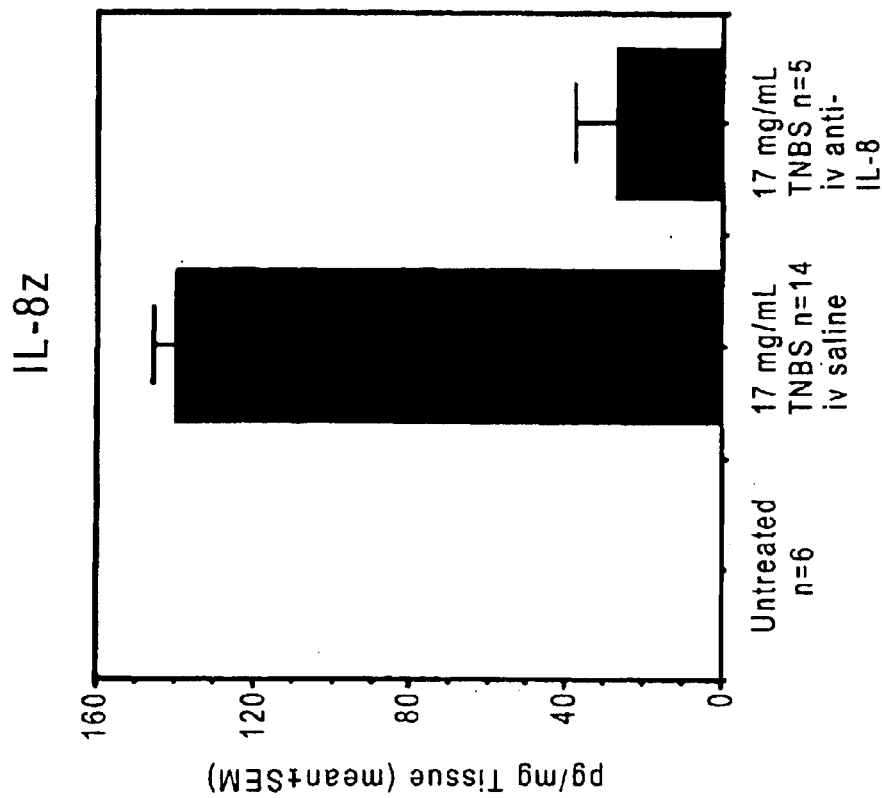
FIGS. 11A–11J are a set of graphs depicting the following Parameters in a rabbit ulcerative colitis model.
Figure 11A:
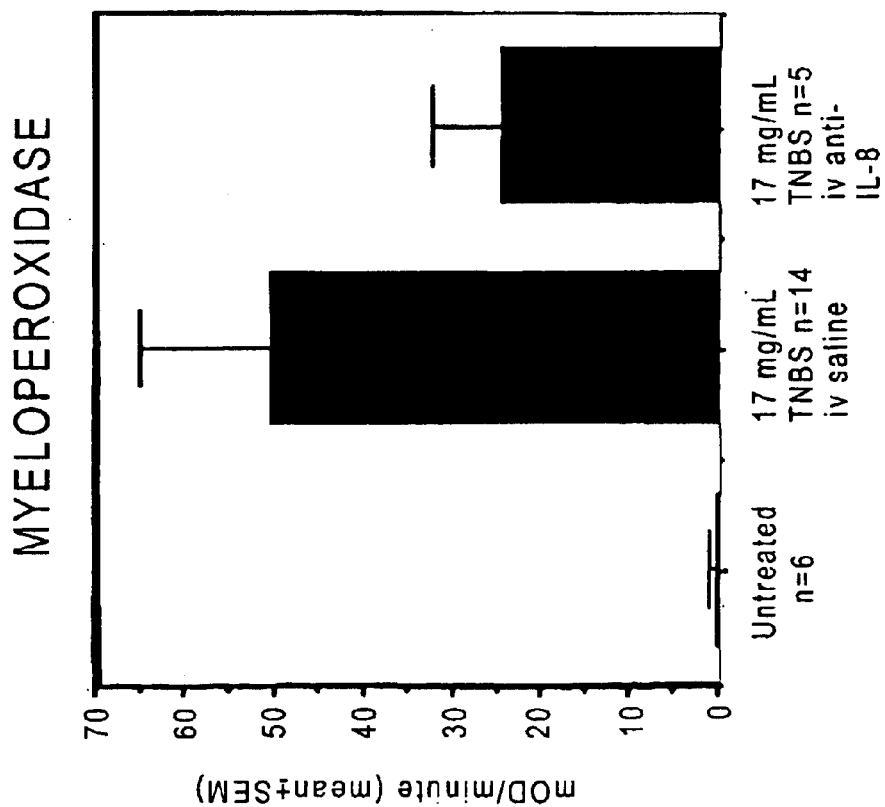
Figure 11D:
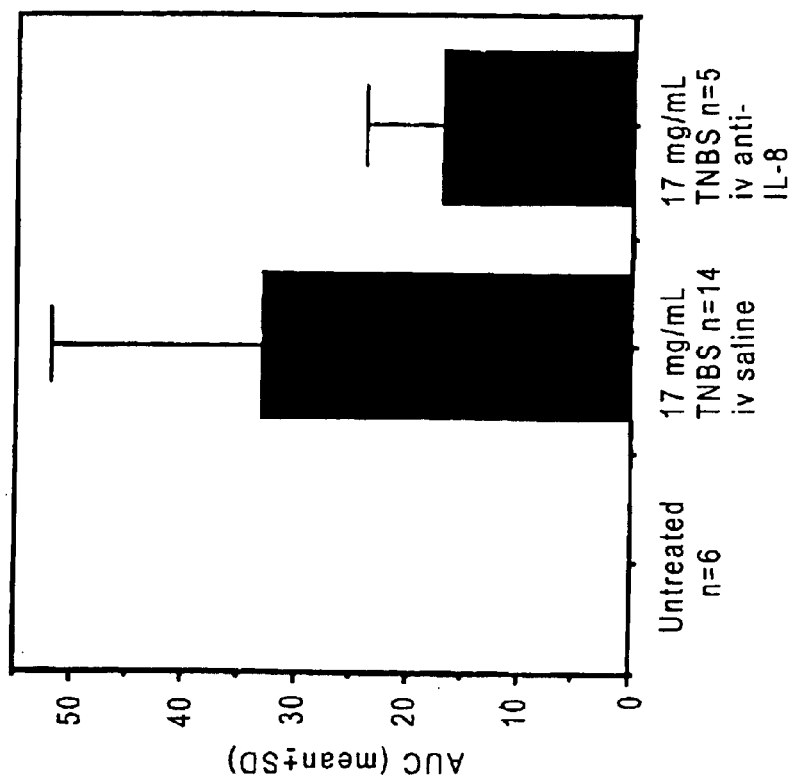
Figure 11C:
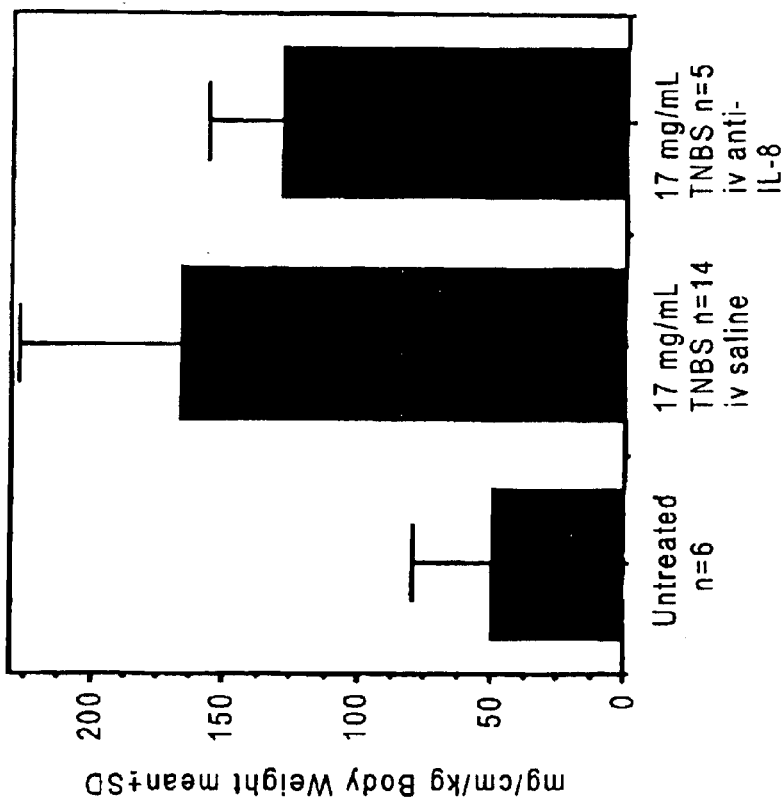
Figure 11F:
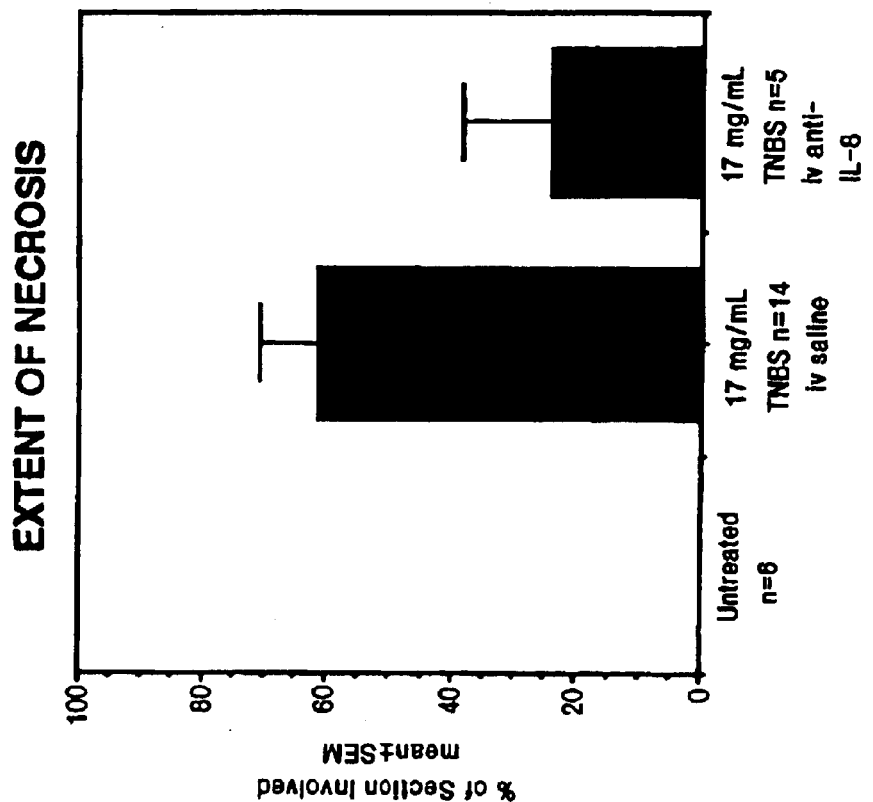
Figure 11E:
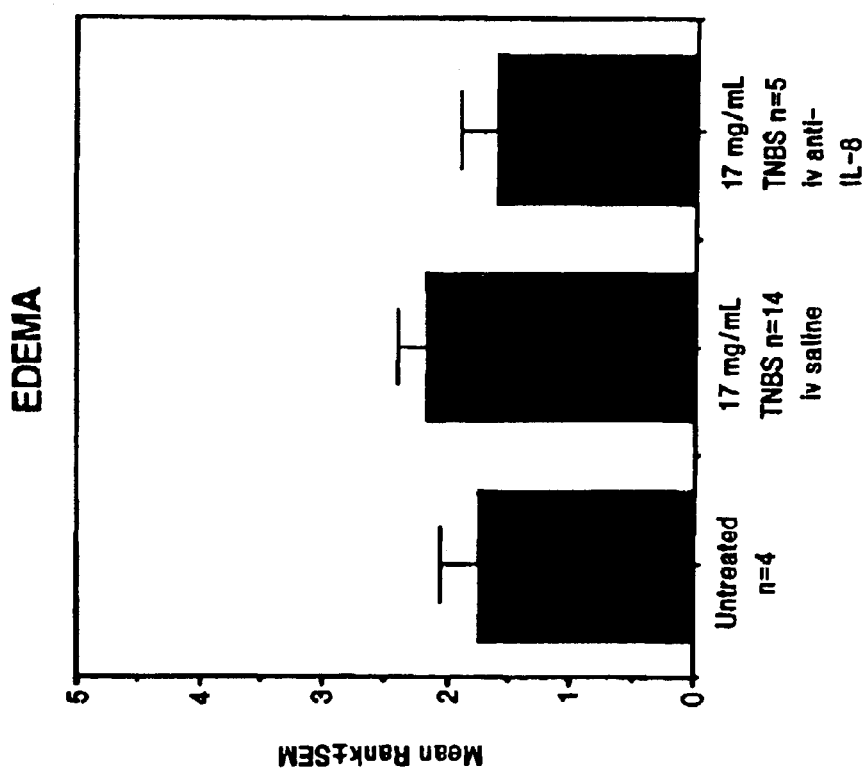
Figure 11H:
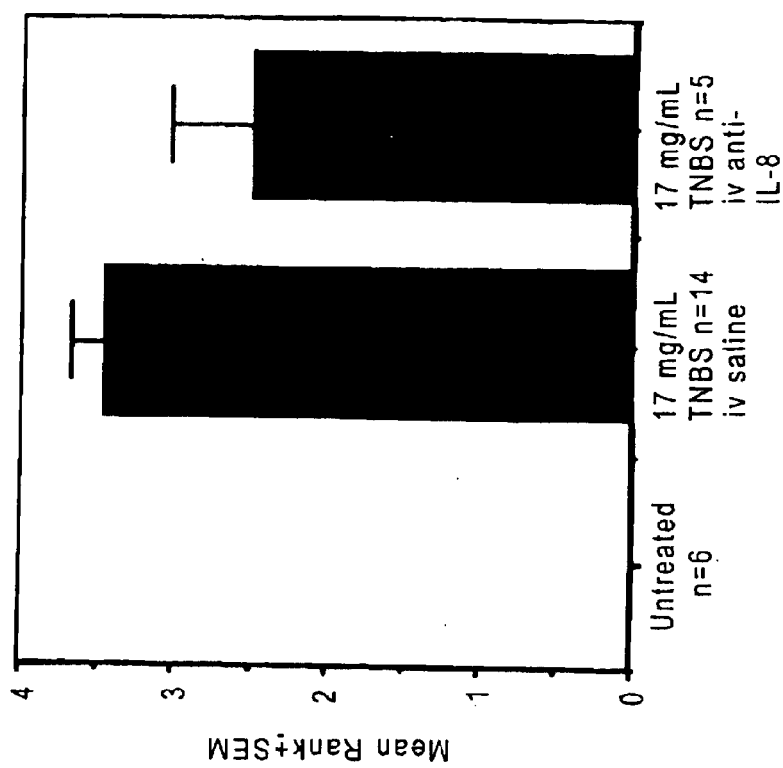
Figure 11G:
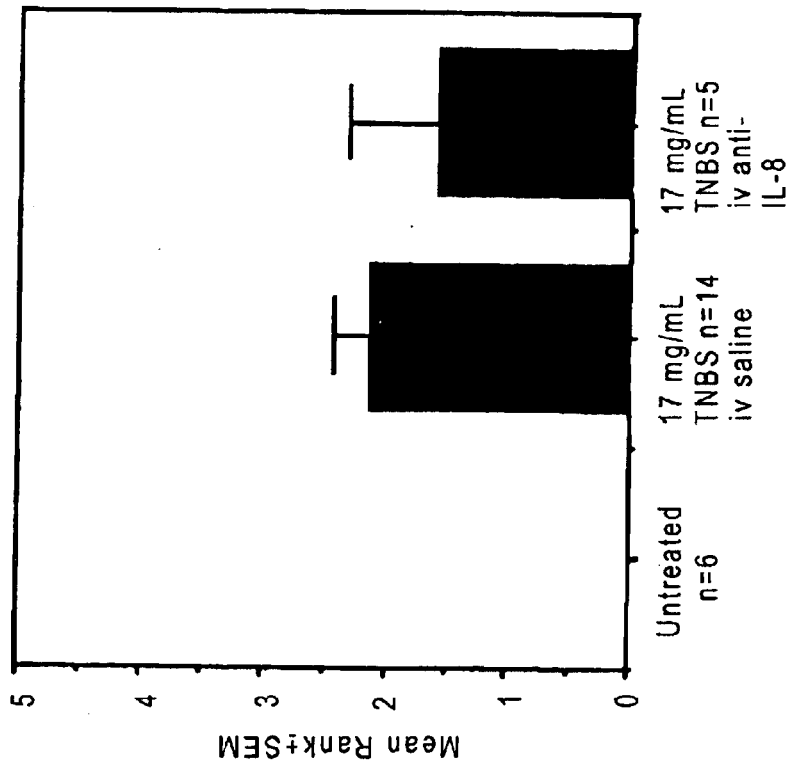
Figure 11J:
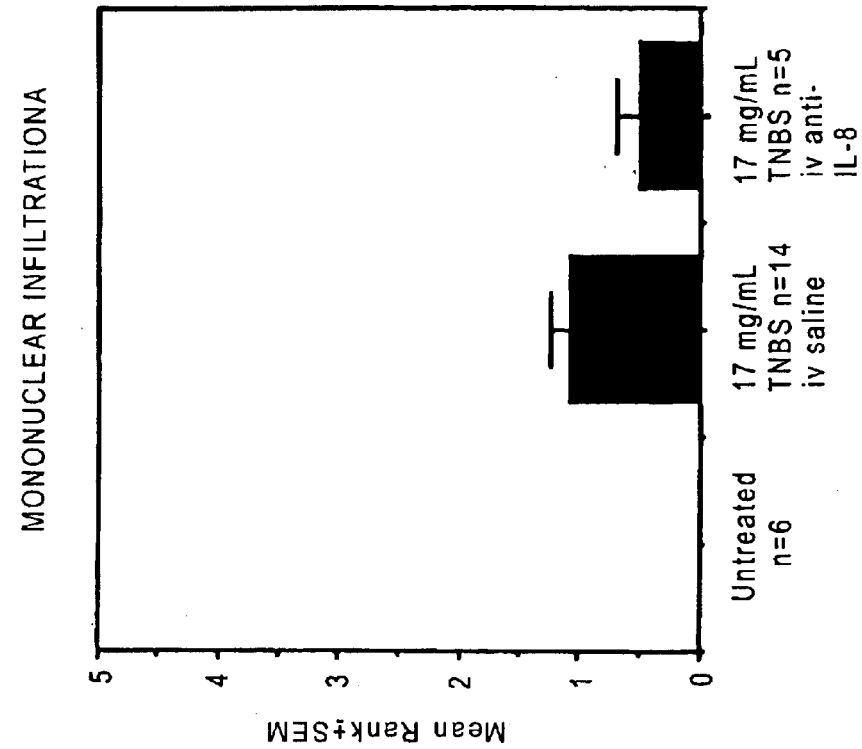
Figure 11I:
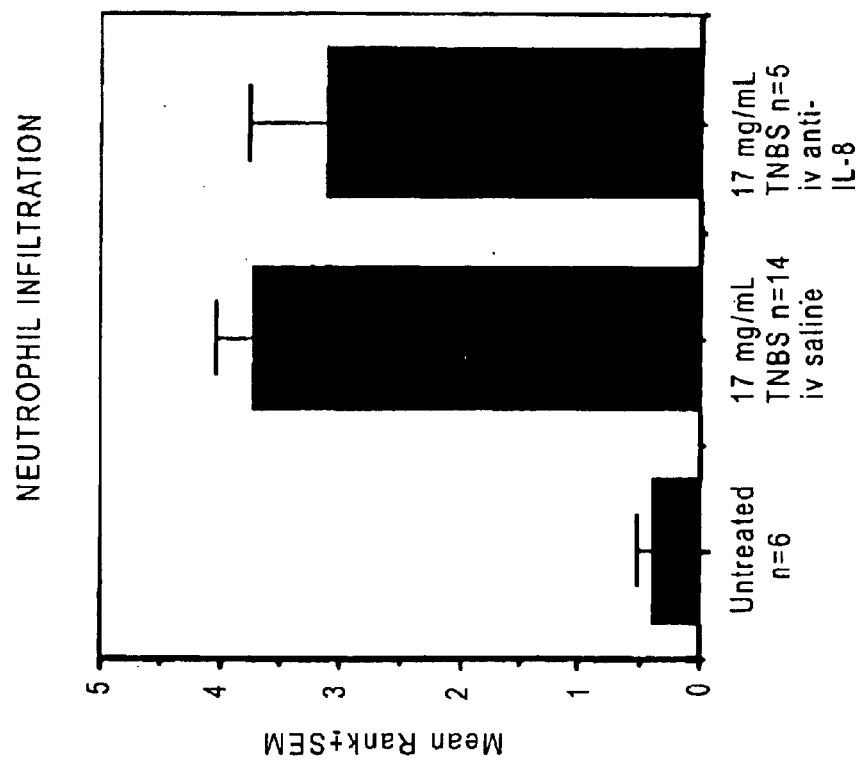
Figure 12:
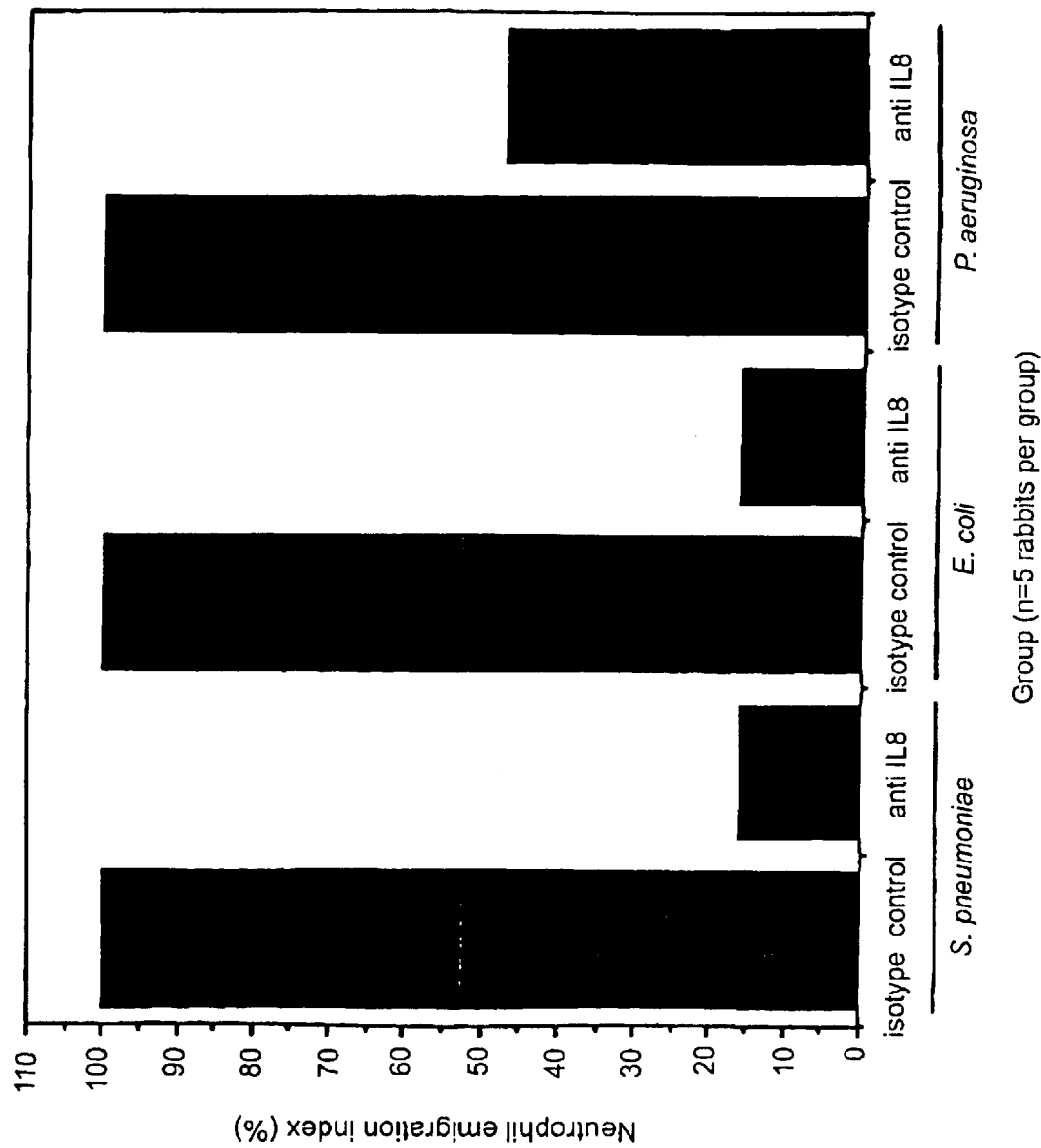
FIG. 12 is a graph depicting the effect of anti-IL-8 monoclonal antibody treatment on the number of neutrophils in bronchoalveolar lavage (BAL) fluid in animals infected with *Streptococcus pneumoniae, Escherichia coli,* or *Pseudomonas aeruginosa*. Treatment with 6G4.2.5 significantly reduced the number of neutrophils present in the BAL fluid compared to animals treated with isotype control mouse IgG (FIG. 12).

IL-8 (10 μl) was mixed with anti-IL-8 Fab, an isotype control Fab, or buffer (20 μl) in 1 ml polypropylene tubes and incubated in a 37° C. water bath for 30 min. IL-8 was used at final concentrations ranging from 0.01 to 1000 nM in dose response studies (FIG. 8) and at a final concentration of 100 nM in the experiments addressing the effects of the Fabs on elastase release (FIGS. 9 and 10). Fab concentrations ranged from approximately 20 nM to 300 nM, resulting in Fab:IL-8 molar ratios of 0.2:1 to 3:1. Cytochalasin B (Sigma) was added to the neutrophil suspension at a concentration of 5 μg/ml (using a 5 mg/ml stock solution made up in DMSO), and the cells were incubated for 15 min in a 37° C. water bath. Cytochalasin B-treated neutrophils (100 μl) were then added to the IL-8/Fab mixtures. After a 3 hr incubation at room temperature, the neutrophils were pelleted by centrifugation (200×g for 5 min), and aliquots of the cell-free supernatants were transferred to 96 well plates (30 μl/well). The elastase substrate, methoxysuccinyl-alanyl-alanyl-prolyl-valyl-p-nitroanilide (Calbiochem, La Jolla, Calif.), was prepared as a 10 mM stock solution in DMSO and stored at 4° C. Elastase substrate working solution was prepared just prior to use (1.2 mM elastase substrate, 1.2 M NaCl, 0.12 M HEPES, pH 7.2), and 170 μl was added to each sample-containing well. The plates were placed in a 37° C. tissue culture incubator for 30 min or until an optical density reading for the positive controls reached at least 1.0. Absorbance was measured at 405 nm using an SLT 340 plate reader (SLT Lab Instruments, Austria).

FIG. 9 demonstrates the ability of the chimeric anti-IL-8 Fabs to inhibit elastase release from human neutrophils stimulated by human IL-8; FIG. 10 demonstrates the relative abilities of the chimeric anti-IL-8 Fabs to inhibit elastase release from human neutrophils stimulated by rabbit IL-8.

C. Molecular Cloning of the Variable Light and Heavy Regions of the Murine 5.12.14 (Anti-IL-8) Monoclonal Antibody Total RNA was isolated from $1 \times 10^8$ cells (hybridoma cell line ATCC HB11722) using the procedure described by Chomczynski and Sacchi (*Anal. Biochem.* 162:156 (1987)). First strand cDNA was synthesized by specifically priming the mRNA with synthetic DNA oligonucleotides designed to hybridize with regions of the murine RNA encoding the constant region of the kappa light chain or the IgG2a heavy chain (the DNA sequence of these regions are published in *Sequences of Proteins of Immunological Interest*, Kabat, E. A. et al. (1991) NIH Publication 91-3242, V 1–3.). Three primers (SEQ ID NOS: 1–6) were designed for each of the light and heavy chains to increase the chances of primer hybridization and efficiency of first strand cDNA synthesis (FIG. 13). Amplification of the first strand cDNA to double-stranded (ds) DNA was accomplished using two sets of synthetic DNA oligonucleotide primers: one forward primer (SEQ ID NOS: 7–9) and one reverse primer (SEQ ID NO: 10) for the light chain variable region amplification (FIG. 14) and one forward primer (SEQ ID NOS: 11–14) and one reverse primer (SEQ ID NOS: 11, 15, 14 and 13) for the heavy chain variable region amplification (FIG. 15). The N-terminal sequence of the first eight amino acids of either the light or heavy chains of 5.12.14 was used to generate a putative murine DNA sequence corresponding to this region. (A total of 29 amino acids was sequenced from the N-terminus of both the light chain and heavy chain variable regions using the Edman degradation protein sequencing technique.) This information was used to design the forward amplification primers which were made degenerate in the third position for some codons to increase the chances of primer hybridization to the natural murine DNA codons and also included the unique restriction site, MluI, for both the light chain variable region forward primer and the heavy chain variable region forward primer to facilitate ligation to the 3' end of the STII element in the cloning vector. The reverse amplification primers were designed to anneal with the murine DNA sequence corresponding to a portion of the constant region of the light or heavy chains near the variable/constant junction. The light chain variable region reverse primer contained a unique BstBI restriction site and the heavy chain variable region reverse primer contained a unique ApaI restriction site for ligation to the 5' end of either the human IgG1 constant light or IgG1 constant heavy regions in the vectors, pB13.1 (light chain) and pB14 (heavy chain). The polymerase chain reaction using these primer sets yielded DNA fragments of approximately 400 bp. The cDNA encoding the 5.12.14 light chain variable region was cloned into the vector pB13.1, to form pA51214VL and the 5.12.14 heavy chain variable region was cloned into the vector, pB14, to form pA51214VH. The cDNA inserts were characterized by DNA sequencing and are presented in the DNA sequence (SEQ ID NO: 16) and amino acid sequence (SEQ ID NO: 17) of FIG. 16 (murine light chain variable region) and in the DNA sequence (SEQ ID NO: 18) and amino acid (SEQ ID NO: 19) of FIG. 17 (murine heavy chain variable region).

D. Construction of a 5.12.14 Fab Vector

In the initial construct, pAD1214VL, the amino acids between the end of the 5.12.14 murine light chain variable sequence and the unique cloning site, BstBI in the human IgG1 constant light sequence were of murine origin corresponding to the first 13 amino acids of the murine IgG1 constant region (FIG. 16). Therefore, this plasmid contained a superfluous portion of the murine constant region separating the 5.12.14 murine light chain variable region and the human light chain IgG1 constant region. This intervening sequence would alter the amino acid sequence of the chimera and most likely produce an incorrectly folded Fab. This problem was addressed by immediately truncating the cDNA clone after A109 and re-positioning the BstBI site to the variable/constant junction by the polymerase chain reaction. FIG. 18 shows the amplification primers used to make these modifications. The forward primer, VL.front (SEQ ID NO: 20), was designed to match the last five amino acids of the STII signal sequence, including the MluI cloning site, and the first 4 amino acids of the 5.12.14 murine light chain variable sequence. The sequence was altered from the original cDNA in the third position of the first two codons D1 (T to C) and I2 (C to T) to create a unique EcoRV cloning site which was used for later constructions. The reverse primer, VL.rear (SEQ ID NO: 21), was designed to match the first three amino acids of the human IgG1 constant light sequence and the last seven amino acids of the 5.12.14 light chain variable sequence which included a unique BstBI cloning site. In the process of adding the BstBI site, the nucleotide sequence encoding several amino acids were altered: L106 (TTG to CTT), K107 (AAA to CGA) resulting in a conservative amino acid substitution to arginine, and R108 (CGG to AGA). The PCR product encoding the modified 5.12.14 light chain variable sequence was then subcloned into pB13.1 in a two-part ligation. The MluI-BstBI digested 5.12.14 PCR product encoding the light chain variable region was ligated into MluI-BstBI digested vector to form the plasmid, pA51214VL'. The modified cDNA was characterized by DNA sequencing. The coding sequence for the 5.12.14 light chain is shown in FIG. 19.

Likewise, the DNA sequence between the end of the heavy chain variable region and the unique cloning site, ApaI, in the human IgG1 heavy chain constant domain of pA51214VH was reconstructed to change the amino acids in this area from murine to human. This was done by the polymerase chain reaction. Amplification of the murine 5.12.14 heavy chain variable sequence was accomplished using the primers shown in FIG. 18. The forward PCR primer (SEQ ID NO: 22) was designed to match nucleotides 867–887 in pA51214VH upstream of the STII signal sequence and the putative cDNA sequence encoding the heavy chain variable region and included the unique cloning site SpeI. The reverse PCR primer (SEQ ID NO: 23) was designed to match the last four amino acids of the 5.12.14 heavy chain variable sequence and the first six amino acids corresponding to the human IgG1 heavy constant sequence which also included the unique cloning site, ApaI. The PCR product encoding the modified 5.12.14 heavy chain variable sequence was then subcloned to the expression plasmid, pMHM24.2.28 in a two-part ligation. The vector was digested with SpeI-ApaI and the SpeI-ApaI digested 5.12.14 PCR product encoding the heavy chain variable region was ligated into it to form the plasmid, pA51214VH'. The modified cDNA was characterized by DNA sequencing. The coding sequence for the 5.12.14 heavy chain is shown in the DNA sequence (SEQ ID NO: 26) and amino acid sequence (SEQ ID NO: 27) of FIGS. 20A–20B.

The first expression plasmid, pantIL-8.1, encoding the chimeric Fab of 5.12.14 was made by digesting pA51214VH' with EcoRV and Bpu1102I to replace the EcoRV-Bpu1102I fragment with a EcoRV-Bpu1102I fragment encoding the murine 5.12.14 light chain variable region of pA51214VL'. The resultant plasmid thus contained the murine-human variable/constant regions of both the light and heavy chains of 5.12.14.

Preliminary analysis of Fab expression using pantIL-8.1 showed that the light and heavy chains were produced intracellularly but very little was being secreted into the periplasmic space of *E. coli*. To correct this problem, a second expression plasmid was constructed.

The second expression plasmid, pantIL-8.2, was constructed using the plasmid, pmy187, as the vector. Plasmid pantIL-8.2 was made by digesting pmy187 with MluI and SphI and the MluI (partial) SphI fragment encoding the murine 5.12.14 murine-human chimeric Fab of pantIL-8.1 was ligated into it The resultant plasmid thus contained the murine-human variable/constant regions of both the light and heavy chains of 5.12.14.

The plasmid pantIL-8.2 was deposited on Feb. 10, 1995 with the American Type Culture Collection, 12301 Parklawn Drive, Rockville, Md., U.S.A. (ATCC) and assigned ATTC Accession No. ATCC 97056.

E. Molecular Cloning of the Variable Light and Heavy Regions of the Murine 6G4.2.5 Monoclonal Antibody Total RNA was isolated from $1 \times 10^8$ cells (hybridoma cell line 6G4.2.5) using the procedure described by Chomczynski and Sacchi (*Anal. Biochem.* 162:156 (1987)). First strand cDNA was synthesized by specifically priming the mRNA with synthetic DNA oligonucleotides designed to hybridize with regions of the murine RNA encoding the constant region of the kappa light chain or the IgG2a heavy chain (the DNA sequence of these regions are published in *Sequences of Proteins of Immunological Interest*, Kabat et al. (1991) NIH Publication 91-3242, V 1–3). Three primers (SEQ ID NOS: SEQ ID NOS: 1–6) were designed for each the light and heavy chains to increase the chances of primer hybridization and efficiency of first strand cDNA synthesis (FIG. 21). Amplification of the first strand cDNA to double-stranded (ds) DNA was accomplished using two sets of synthetic DNA oligonucleotide primers: one forward primer (SEQ ID NOS: 28–30) and one reverse primer (SEQ ID NO: 31) for the light chain variable region amplification (FIG.

22) and one forward primer (SEQ ID NOS: 32–33) and one reverse primer (SEQ ID NOS: 11,15,14 and 13) for the heavy chain variable region amplification (FIG. 23). The N-terminal sequence of the first eight amino acids of either the light or heavy chains of 6G4.2.5 was used to generate a putative murine DNA sequence corresponding to this region. (A total of 29 amino acids were sequenced from the N-terminus of both the light chain and heavy chain variable regions using the Edman degradation protein sequencing technique.) This information was used to design the forward amplification primers which were made degenerate in the third position for some codons to increase the chances of primer hybridization to the natural murine DNA codons and also included the unique restriction site, NsiI, for the light chain variable region forward primer and the unique restriction site, MluI, for the heavy chain variable region forward primer to facilitate ligation to the 3' end of the STII element in the vector, pchimFab. The reverse amplification primers were designed to anneal with the murine DNA sequence corresponding to a portion of the constant region of the light or heavy chains near the variable/constant junction. The light chain variable region reverse primer contained a unique MunI restriction site and the heavy chain variable region reverse primer contained a unique ApaI restriction site for ligation to the 5' end of either the human IgG1 constant light or IgG1 constant heavy regions in the vector, pchimFab. The polymerase chain reaction using these primer sets yielded DNA fragments of approximately 400 bp and were cloned individually into the vector, pchimFab, to form p6G425VL and p6G425VH. The cDNA inserts were characterized by DNA sequencing and are presented in the DNA sequence (SEQ ID NO: 34) and amino acid sequence (SEQ ID NO: 35) of FIG. 24 (murine light chain variable region) and the DNA sequence (SEQ ID NO: 36) and amino acid sequence (SEQ ID NO: 37) of FIG. 25 (murine heavy chain variable region).

F. Construction of A 6G4.2.5 Chimeric Fab Vector

In the initial construct, p6G425VL, the amino acids between the end of the 6G4.2.5 murine light chain variable sequence and the unique cloning site, MunI, in the human IgG1 constant light sequence were of murine origin. These amino acids must match the human IgG1 amino acid sequence to allow proper folding of the chimeric Fab. Two murine amino acids, D115 and S121, differed dramatically from the amino acids found in the loops of the β-strands of the human IgG1 constant domain and were converted to the proper human amino acid residues, V115 and F121, by site-directed mutagenesis using the primers (SEQ ID NOS: 38,39,40) shown in FIG. 26. These specific mutations were confirmed by DNA sequencing and the modified plasmid named p6G425VL'. The coding sequence is shown in the DNA sequence (SEQ ID NO: 41) and amino acid sequence (SEQ ID NO: 42) of FIGS. 27A–27B.

Likewise, the DNA sequence between the end of the heavy chain variable region and the unique cloning site, ApaI, in the human IgG1 heavy chain constant domain of p6G425VH was reconstructed to change the amino acids in this area from murine to human. This process was facilitated by the discovery of a BstEII site near the end of the heavy chain variable region. This site and the ApaI site were used for the addition of a synthetic piece of DNA encoding the corresponding IgG human amino acid sequence. The synthetic oligo-nucleotides shown in FIG. 26 were designed as complements of one another to allow the formation of a 27 bp piece of ds DNA. The construction was performed as a three-part ligation because the plasmid, p6G425VH, contained an additional BstEII site within the vector sequence. A 5309 bp fragment of p6G425VH digested with MluI-ApaI was ligated to a 388 bp fragment carrying the 6G4.2.5 heavy chain variable region and a 27 bp synthetic DNA fragment encoding the first six amino acids of the human IgG1 constant region to form the plasmid, p6G425VH". The insertion of the synthetic piece of DNA was confirmed by DNA sequencing. The coding sequence is shown in the DNA sequence (SEQ ID NO: 43) and amino acid sequence (SEQ ID NO: 44) of FIGS. 28A–28B.

The expression plasmid, p6G425chim2, encoding the chimeric Fab of 6G4.2.5 was made by digesting p6G425chimVL' with MluI and ApaI to remove the STII-murine HPC4 heavy chain variable region and replacing it with the MluI-ApaI fragment encoding the STII-murine 6G4.2.5 heavy chain variable region of p6G425chimVH'. The resultant plasmid thus contained the murine-human variable/constant regions of both the light and heavy chains of 6G4.2.5.

The plasmid p6G425chim2 was deposited on Feb. 10, 1995 with the American Type Culture Collection, 12301 Parklawn Drive, Rockville, Md., U.S.A. (ATCC) and assigned ATTC Accession No. 97055.

G. Construction of Humanized Versions of Anti-IL-8 Antibody 6G4.2.5

The murine cDNA sequence information obtained from the hybridoma cell line, 6G4.2.5, was used to construct recombinant humanized variants of the murine anti-IL-8 antibody. The first humanized variant, F(ab)-1, was made by grafting synthetic DNA oligonucleotide primers encoding the murine CDRs of the heavy and light chains onto a phagemid vector, pEMX1 (Werther et al., *J. Immunol*, 157:4986–4995 (1996)), which contains a human 6-subgroup I light chain and a human IgG1 subgroup III heavy chain (FIG. 29). Amino acids comprising the framework of the antibody that were potentially important for maintaining the conformations necessary for high affinity binding to IL-8 by the complementarity-determining regions (CDR) were identified by comparing molecular models of the murine and humanized 6G4.2.5 (F(ab)-1) variable domains using methods described by Carter et al., *PNAS* 89:4285 (1992) and Eigenbrot, et. al., J. Mol. Biol. 229:969 (1993). Additional humanized framework variants (F(ab) 2-9) were constructed from the information obtained from these models and are presented in Table 2 below. In these variants, the site-directed mutagenesis methods of Kunkel, *Proc. Natl. Acad. Sci USA*), 82:488 (1985) were utilized to exchange specific human framework residues with their corresponding 6G4.2.5 murine counterparts. Subsequently, the entire coding sequence of each variant was confirmed by DNA sequencing. Expression and purification of each F(ab) variant was performed as previously described by Werther et. al., supra, with the exception that hen egg white lysozyme was omitted from the purification protocol. The variant antibodies were analyzed by SDS-PAGE, electrospray mass spectroscopy and amino acid analysis.

TABLE 4

Humanized 6G425 Variants
IC50[c]
+- - -+

| Variant | Version | Template | Changes[a] | Purpose[b] | Mean | S.D. | N |
|---|---|---|---|---|---|---|---|
| F(ab)-1 | version 1 | | CDR Swap | | 63.0 | 12.3 | 4 |
| F(ab)-2 | version 2 | F(ab)-1 | PheH67Ala | packaging w/ CDR H2 | 106.0 | 17.0 | 2 |
| F(ab)-3 | version 3 | F(ab)-1 | ArgH71Val | packaging w/ CDRsH1, H2 | 79.8 | 42.2 | 4 |
| F(ab)-4 | version 6 | F(ab)-1 | IleH69Leu | packaging w/ CDR H2 | 44.7 | 9.0 | 3 |
| F(ab)-5 | version 7 | F(ab)-1 | LeuH78Ala | packaging w/ CDRs H1, H2 | 52.7 | 31.0 | 9 |
| F(ab)-6 | version 8 | F(ab)-1 | IleH69Lea LeuH78Ala | combine F(ab)-4 and -5 | 34.6 | 6.7 | 7 |
| F(ab)-7 | version 16 | F(ab)-6 | LeuH80Val | packaging w/ CDR H1 | 38.4 | 9.1 | 2 |
| F(ab)-8 | version 19 | F(ab)-6 | ArgH38Lys | packaging w/ CDR H2 | 14.0 | 5.7 | 2 |
| F(ab)-9 | version 11 | F(ab)-6 | GluH6Gln | packaging w/ CDR H3 | 19.0 | 5.1 | 7 |
| Chimeric[d] F(ab) | | | | | 11.4 | 7.0 | 13 |
| rhu4D5[e] F(ab) | | | | | >200 $\mu$M | | 5 |

[a]Amino acid changes made relative to the template used. Murine residues are in bold italics and residue numbering is according to Kabat et al.
[b]Purpose for making changes based upon interactions observed in molecular models of the humanized and murine variable domains.
[c]nM concentration of variant necessary to inhibit binding of iodinated IL-8 to human neutrophils in the competitive binding assay.
[d]Chimeric F(ab) is a (F(ab) which carries the murine heavy and light chain variable domains fused to the human light chain kI constant domain and the human heavy chain subgroup III constant domain I respectively.
[e]rhu4D5F(ab) is of the same isotype as the humanized 6G425 F(ab)s and is a humanized anti-HER2 F(ab) and therefore should not bind to IL8.

Figure 30A:
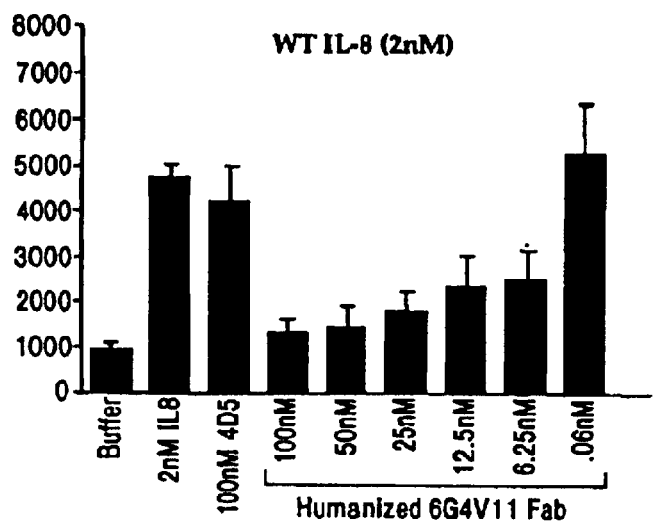
FIG. 30 is a graph with three panels (A, B and C) depicting the ability of F(ab)-9 (humanized 6G4V11 Fab) to inhibit human wild type IL-8, human monomeric IL-8, and rhesus IL-8 mediated neutrophil chemotaxis, respectively. Panel A presents inhibition data for F(ab)-9 samples at concentrations of 0.06 nM, 6.25 nM, 12.5 nM, 25 nM, 50 nM, and 100 nM, for an isotype control antibody (denoted "4D5") sample at a concentration of 100 nM, and for a no antibody control sample, in the presence of 2 nM human wild type IL-8. Panel B presents inhibition data for F(ab')-9 samples at concentrations of 6.25 nM, 12.5 nM, 25 nM, and 50 nM, for an isotype control antibody (denoted "4D5") sample at a concentration of 100 nM, and for a no antibody control sample, in the presence of 4 nM human monomeric IL-8 (denoted as "BD59" and as "monomeric IL-8"). Panel C presents inhibition data for F(ab)-9 samples at concentrations of 1 nM, 12.5 nM, 25 nM, and 50 nM, for an isotype control antibody (denoted "4D5") sample at a concentration of 100 nM, and for a no antibody control sample, in the presence of 2 nM rhesus IL-8. In addition, all panels A, B an C each presents data for a no IL-8 buffer control sample (denoted as "Buffer") in the respective inhibition assay.
Figure 30B:
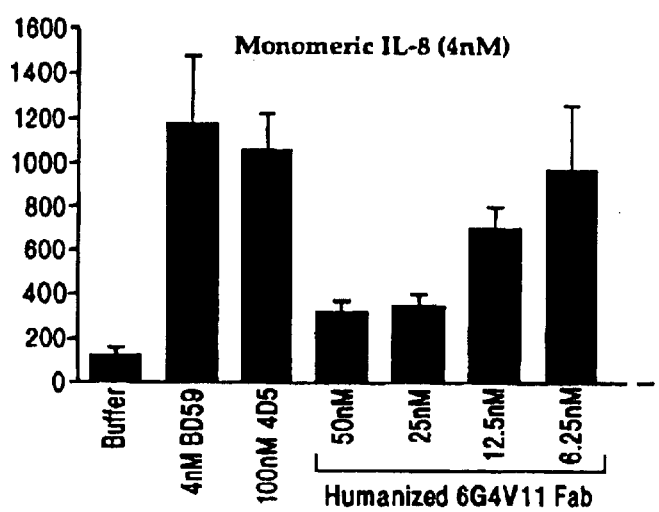
Figure 30C:
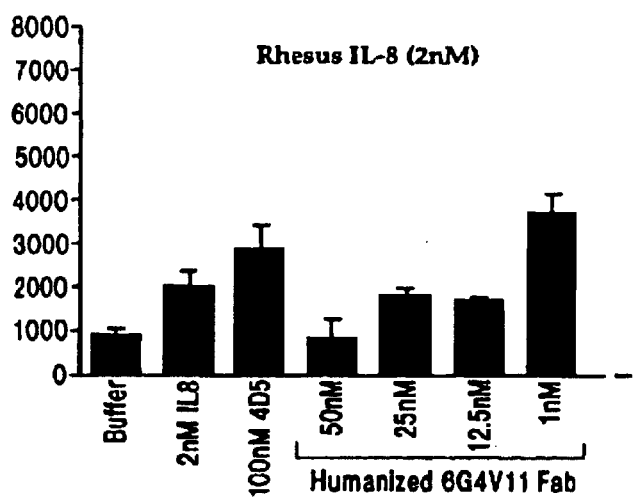

The first humanized variant, F(ab)-1, was an unaltered CDR swap in which all the murine CDR amino acids defined by both x-ray crystallography and sequence hypervariability were transferred to the human framework. When the purified F(ab) was tested for its ability to inhibit $^{125}$I-IL-8 binding to human neutrophils according to the methods described in Section (B)(1) above, a 5.5 fold reduction in binding affinity was evident as shown in Table 4 above. Subsequent versions of F(ab)-1 were engineered to fashion the 3-dimensional structure of the CDR loops into a more favorable conformation for binding IL-8. The relative affinities of the F(ab) variants determined from competition binding experiments using human neutrophils as described in Section (B)(1) above are presented in Table 4 above. A slight decrease in IL-8 binding (<2 fold) was observed for F(ab)-2-3 while only slight increases in IL-8 binding were noted for F(ab)-3-5. Variant F(ab)-6 had the highest increase in affinity for IL-8 (approximately 2 fold), exhibiting an IL-8 binding affinity of 34.6 nM compared to the F(ab)-1 IL-8 binding affinity of 63 nM. The substitutions of murine Leu for Ile at H69 and murine Ala for Leu at H78 are predicted to influence the packing of CDRs H1 and H2. Further framework substitutions using the F(ab)-6 variant as template were made to bring the binding affinity closer to that of the chimeric F(ab). In-vitro binding experiments revealed no change in affinity for F(ab)-7 (38.4 nM) but a significant improvement in affinity for F(ab)-8/9 of 14 nM and 19 nM, respectively. By analysis of a 3-D computer-generated model of the anti-IL-8 antibody, it was hypothesized that the substitution of murine Lys for Arg at H38 in F(ab)-8 influences CDR-H2 while a change at H6 of murine Gin for Glu in F(ab)-9 affects CDR-H3. Examination of the human antibody sequences with respect to amino acid variability revealed that the frequency of Arg at residue H38 is >99% whereas residue H6 is either Gln ~20% or Glu ~80% (Kabat et. al., Sequences of Proteins of Immunological Interest 5th Ed. (1991)). Therefore, to reduce the likelihood of causing an immune response to the antibody, F(ab)-9 was chosen over F(ab)-8 for further affinity maturation studies. Variant F(ab)-9 was also tested for its ability to inhibit IL-8-mediated chemotaxis (FIG. 30). This antibody was able to block neutrophil migration induced by wild-type human IL-8, human monomeric IL-8 and Rhesus IL-8 with $IC_{50}$=s of approximately 12 nM, 15 nM, and 22 nM, respectively, in IL-8 mediated neutrophil chemotaxis inhibition assays performed as described in Section (B)(2) above. The amino acid sequence for variant F(ab)-8 is provided in FIG. 31c. The F(ab)-8 was found to block human and rhesus IL-8-mediated chemotaxis with $IC_{50}$=s of 0.12 nM and 10 nM, respectively, in IL-8 mediated neutrophil chemotaxis inhibition assays performed as described in Section (B)(2) above.

H. Construction of an Anti-IL-8-Gene III Fusion Protein for Phage Display and Alanine Scanning Mutagenesis An expression plasmid, pPh6G4.V11, encoding a fusion protein (heavy chain of the humanized 6G4.2.5 version 11 antibody and the M13 phage gene-III coat protein) and the light chain of the humanized 6G4.2.5 version 11 antibody was assembled to produce a monovalent display of the anti-IL-8 antibody on phage particles. The construct was made by digesting the plasmid, pFPHX, with EcoRV and ApaI to remove the existing irrelevant antibody coding sequence and replacing it with a 1305 bp EcoRV-ApaI fragment from the plasmid, p6G4.V11, encoding the humanized 6G4.2.5 version 11 anti-IL-8 antibody. The translated sequence of the hunanized 6G4.2.5 version 11 heavy chain (SEQ ID NO: 52), peptide linker and gene III coat protein (SEQ ID NO: 53) is shown in FIG. 31A. The pFPHX plasmid is a derivative of phGHam-3 which contains an in-frame amber codon (TAG) between the human growth hormone and gene-III DNA coding sequences. When transformed into an amber suppressor strain of E. coli, the codon (TAG) is read as Glutamate producing a growth hormone (hGH)-gene III fusion protein. Likewise, in a normal strain of E coli, the codon (TAG) is read as a stop preventing translational read-through into the gene-III sequence and thus allowing the production of soluble hGH. The pGHam-3 plasmid is described in *Methods: A Companion to Methods in Enzymology* 3:205 (1991). The final product, pPh6G4.V11, was used as the template for the alanine scanning mutagenesis of the CDRs and for the construction of randomized CDR libraries of the humanized 6G4.V11 antibody.

I. Alanine Scanning Mutagenesis of Humanized Antibody 6G4.2.5 Version 11

The solvent exposed amino acid residues in the CDRs of the humanized anti-IL-8 6G4.2.5 version 11 antibody (h6G4V11) were identified by analysis of a 3-D computer-generated model of the anti-IL-8 antibody. In order to determine which solvent exposed amino acids in the CDRs affect binding to interleukin-8, each of the solvent exposed amino acids was individually changed to alanine, creating a panel of mutant antibodies wherein each mutant contained an alanine substitution at a single solvent exposed residue. The alanine scanning mutagenesis was performed as described by Leong et. al., *J. Biol. Chem.*, 269: 19343 (1994)).

The $IC_{50}$'s (relative affinities) of h6G4V11 wt and mutated antibodies were established using a Competition Phage ELISA Assay described by Cunningham et. al., (*EMBO J.* 13:2508 (1994)) and Lee et. al., (*Science* 270:1657 (1995)). The assay measures the ability of each antibody to bind IL-8 coated onto a 96-well plate in the presence of various concentrations of free IL-8 (0.2 to 1 uM) in solution. The first step of the assay requires that the concentrations of the phage carrying the wild type and mutated antibodies be normalized, allowing a comparison of the relative affinities of each antibody. The normalization was accomplished by titering the phage on the IL-8 coated plates and establishing their $EC_{50}$. Sulfhydryl coated 96-well binding plates (Coming-Costar; Wilmington, Mass.) were incubated with a 0.1 mg/ml solution of K64C IL-8 (Lysine 64 is substituted with Cysteine to allow the formation of a disulfide bond between the free thiol group of K64C IL-8 and the sulfhydryl coated plate, which results in the positioning of the IL-8 receptor binding domains towards the solution interface) in phosphate buffered saline (PBS) pH 6.5 containing 1 mM EDTA for 1 hour at 25EC followed by three washes with PBS and a final incubation with a solution of PBS containing 1.75 mg/ml of L-cysteine-HCl and 0.1M $NaHCO_3$ to block any free reactive sulfhydryl groups on the plate. The plates were washed once more and stored covered at 4EC with 200 ul of PBS/well. Phage displaying either the reference antibody, h6G4V11, or the mutant h6G4V11 antibodies were grown and harvested by PEG precipitation. The phage were resuspended in 500 ul 10 mM Tris-HCl pH 7.5, 1 mM EDTA and 100 mM NaCl and held at 4EC for no longer than 3 hours. An aliquot of each phage was diluted 4-fold in PBS containing 0.05% Tween-20 (BioRad, Richmond, Calif.) and 0.5% BSA RIA grade (Sigma, St. Louis, Mo.) (PBB) and added to IL-8 coated plates blocked for at least 2 hours at 25EC with 50 mg/ml skim milk powder in 25 mM Carbonate Buffer pH 9.6. The phage were next serially diluted in 3 fold steps down the plate from well A through H. The plates were incubated for 1 hour at 25EC followed by nine quick washes with PBS containing 0.05% Tween-20 (PBST). The plates were then incubated with a 1:3200 dilution of rabbit anti-phage antibody and a 1:1600 dilution of secondary goat-anti-rabbit Fc HRP-conjugated antibody for 15 minutes at 25EC followed by nine quick washes with PBST. The plates were developed with 80 ul/well of 1 mg/ml OPD (Sigma, St. Louis, Mo.) in Citrate Phosphate buffer pH 5.0 containing 0.015% $H_2O_2$ for 4 minutes at 25EC and the reaction stopped with the addition of 40 ul of 4.5M $H_2SO_4$. The plates were analyzed at wavelength $8_{492}$ in a SLT model 340ATTC plate reader (SLT Lab Instruments). The individual $EC_{50}$=s were determined by analyzing the data using the program Kaleidagraph (Synergy Software, Reading, Pa.) and a 4-parameter fit equation. The phage held at 4EC were then immediately diluted in PBB to achieve a final concentration corresponding to their respective $EC_{50}$ or target $OD_{492}$ for the competition segment of the experiment, and dispensed into a 96 well plate containing 4-fold serial dilutions of soluble IL-8 ranging from 1 uM in well A and ending with 0.2 uM in well H. Using a 12-channel pipet, 100 ul of the phage/IL-8 mixture was transferred to an IL-8 coated 96-well plate and executed as described above. Each sample was done in triplicate—3 columns/sample.

TABLE 5

Relative Affinities (IC50) for Alanine-scan Anti-IL-8 6G4V11 CDR Mutants

| CDR | Amino Acid Residue | Avg IC50 (nM) | Std Dev |
| --- | --- | --- | --- |
| VII | Reference | 11.5 | 6.4 |
| CDR-L1 | S26 | 6.3 | 2.9 |
|  | Q27 | 10.2 | 2.4 |
|  | S28 | 14.2 | 5.2 |
|  | V30 | 29.1 | 12.3 |
|  | H31 | 580.3 | 243.0 |
|  | I33 | 64.2 | 14.6 |
|  | N35 | 3.3 | 0.7 |
|  | T36 | 138.0 | nd |
|  | Y37 | NDB | nd |
| CDR-L2 | K55 | 24.2 | 14.9 |
|  | V56 | 15.5 | 3.8 |
|  | S57 | 12.4 | 4.0 |
|  | N58 | 17.6 | 3.7 |
|  | R59 | nd | nd |
| CDR-L3 | S96 | 10.8 | 4.4 |
|  | T97 | 70.6 | 55.2 |
|  | H98 | 8.0 | 1.2 |
|  | V99 | 19.6 | 1.9 |
| CDR-H1 | S28 | 8.6 | 3.1 |
|  | S30 | nd | nd |
|  | S31 | 7.8 | 2.5 |
|  | H32 | 13.3 | 5.8 |
|  | Y53 | 48.2 | 15.8 |
| CDR-H2 | Y50 | 35.6 | 13.0 |
|  | D52 | 13.3 | 7.5 |
|  | S53 | 6.0 | 3.4 |
|  | N54 | 96.0 | 5.8 |
|  | E56 | 15.8 | 4.5 |
|  | T57 | 8.4 | 1.6 |
|  | T58 | 11.3 | 1.8 |

TABLE 5-continued

Relative Affinities (IC50) for Alanine-scan Anti-IL-8 6G4V11 CDR Mutants

| CDR | Amino Acid Residue | Avg IC50 (nM) | Std Dev |
|---|---|---|---|
| | Y59 | 9.1 | 3.7 |
| | Q61 | 12.6 | 6.4 |
| | K64 | 18.5 | 12.1 |
| CDR-H3 | D96 | NDB | nd |
| | Y97 | NDB | nd |
| | R98 | 36.6 | 15.3 |
| | Y99 | 199.5 | nd |
| | N100 | 278.3 | 169.4 |
| | D102 | 159.2 | 44 |
| | W103 | NDB | nd |
| | F104 | NDB | nd |
| | F105 | 209.4 | 72.3 |
| | D106 | 25.3 | 21.7 |

Each sample performed in triplicate/experiment.
NDB = No Detectable Binding/nd = value not determined*
Residue numbering is according to Kabat et al.

Figure 32:
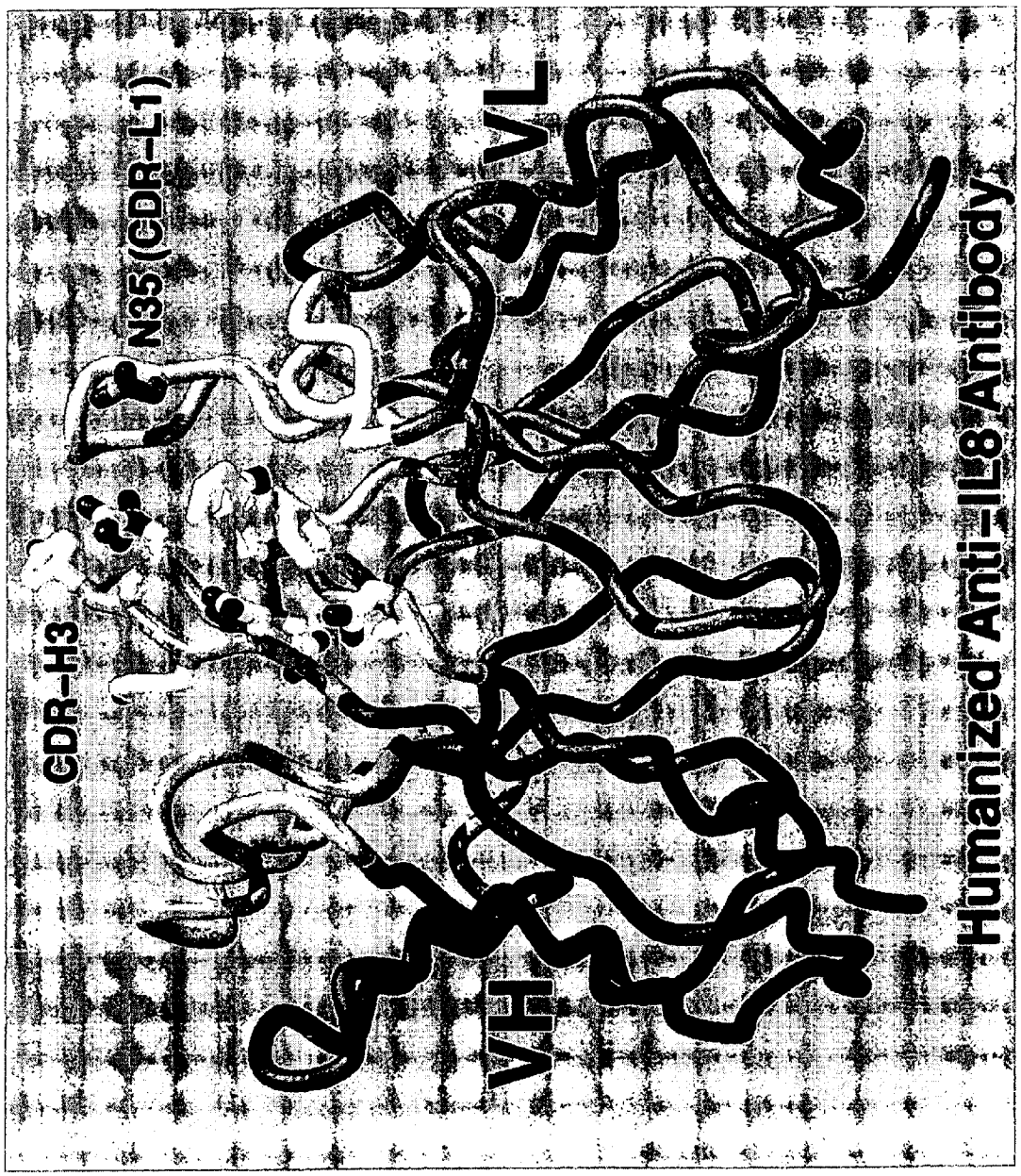
FIG. 32 is a three dimensional computer model of the humanized anti-IL-8 6G4.2.5V11 antibody. Heavy chain CDR loops and variable domain regions appear in purple, and CDR-H3 side chain residues appear in yellow. Heavy chain constant domain regions appear in red. Light chain CDR loops and variable domain regions appear in off-white, and the Asn residue at amino acid position 35 (N35) in CDR L1 appears in green. Light chain constant domain regions appear in amber.

The results of the alanine-scan are summarized in Table 5 above. The alanine substitutions in of many of the mutant antibodies had little or no adverse effects (<3 fold) on the binding affinity for IL-8. Mutants that were found to exhibit no detectable binding of IL-8 (NDB) presumably contained disruptions in the conformational structure of the antibody conferred by crucial structural or buried amino acids in the CDR. Based on the results of the scan, CDR-H3 (heavy chain, 3rd CDR) was identified as the dominant binding epitope for binding IL-8. Alanine substitutions in this CDR resulted in a 3 to >26 fold decrease in binding affinity. The amino acids, Y597, Y599 and D602 are of particular interest because it was determined from the computer generated model of the anti-IL-8 antibody that these residues are solvent exposed and that these residues might participate in hydrogen bonding or charge interactions with IL-8 or other amino acids of the antibody that influence either binding to IL-8 or the conformation of the CDR-H3 loop structure. (See the model depicted in FIG. 32). Unexpected increases in binding affinity (1.8>2.7 fold) were noted for S528 and S531 of CDR-H1 and S553 of CDR-H2.

Surprisingly, a significant increase in binding affinity was observed in the alanine mutant N35A located in CDR-L1 (light chain, 1st CDR). A 3–6 fold increase in affinity was observed compared to the wild-type h6G4V11 antibody. This augmentation of IL-8 binding could be the result of the close proximity of N35A to CDR-H3. The alanine substitution may have imparted a slight change in the conformation of CDR-L1 which alters the packing interaction of neighboring amino acid residues on CDR-H3, thereby tweaking the loop of CDR-H3 into a conformation that facilitates more appropriate contacts with IL-8. Similarly, N35A may also influence the orientation of amino acids in CDR-L1 or its interaction directly with IL-8. Unexpected increases in affinity (~2 fold) were also observed for S26 of CDR-L1 and H98 of CDR-L3.

J. Characterization of Humanized Anti-IL-8 Antibody 6G4V11N35A

Figure 33:
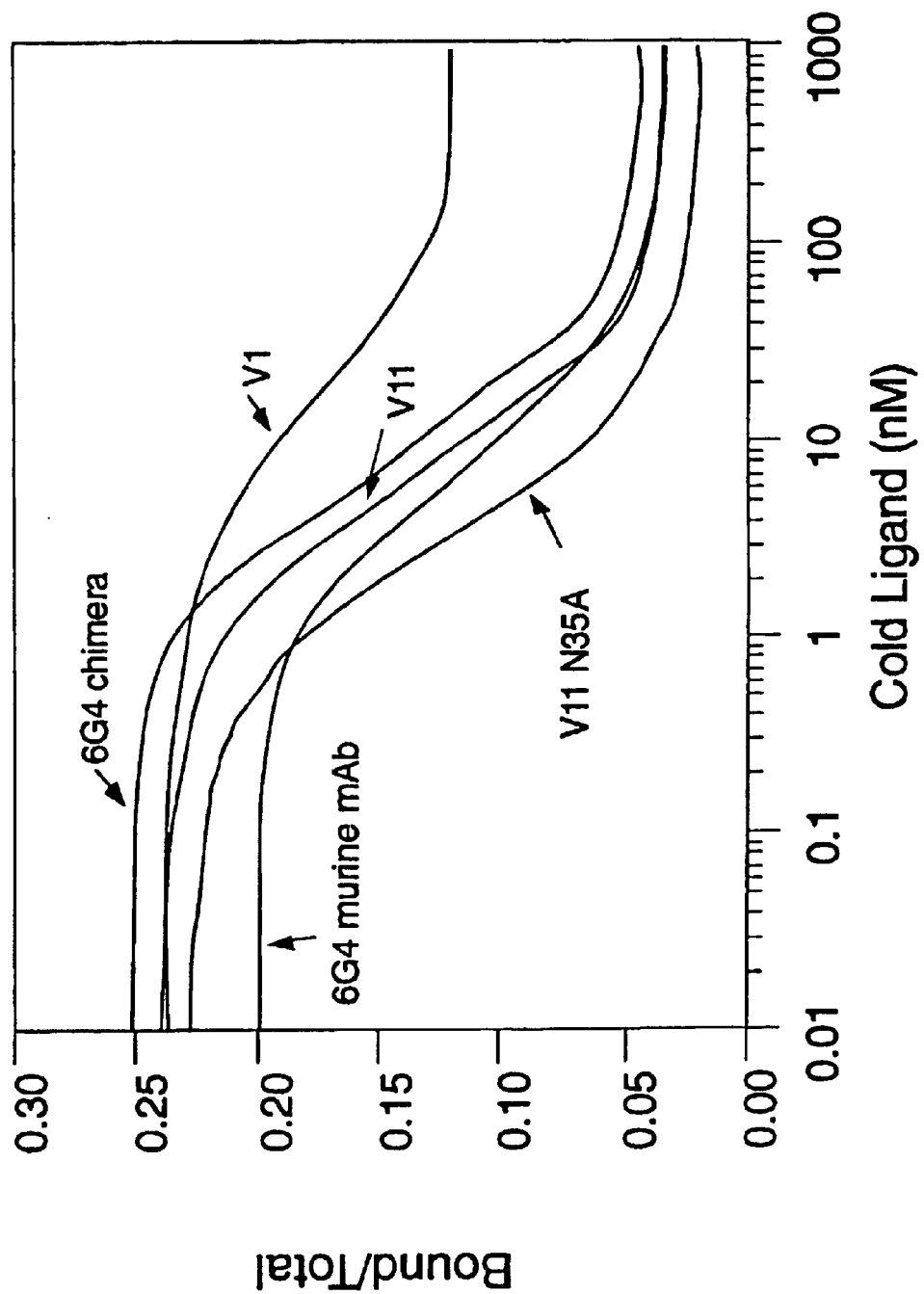
FIG. 33 is a Scatchard plot depicting the inhibition of $^{125}$I-IL-8 binding to human neutrophils exhibited by intact murine 6G4.2.5 antibody (denoted 6G4 murine mAb), 6G4.2.5 murine-human chimera Fab (denoted 6G4chimera), humanized 6G4.2.5 Fab versions I and II (denoted VI and VII), and variant 6G4.2.5V11N35A Fab (denoted V11N35A).
Figure 34A:
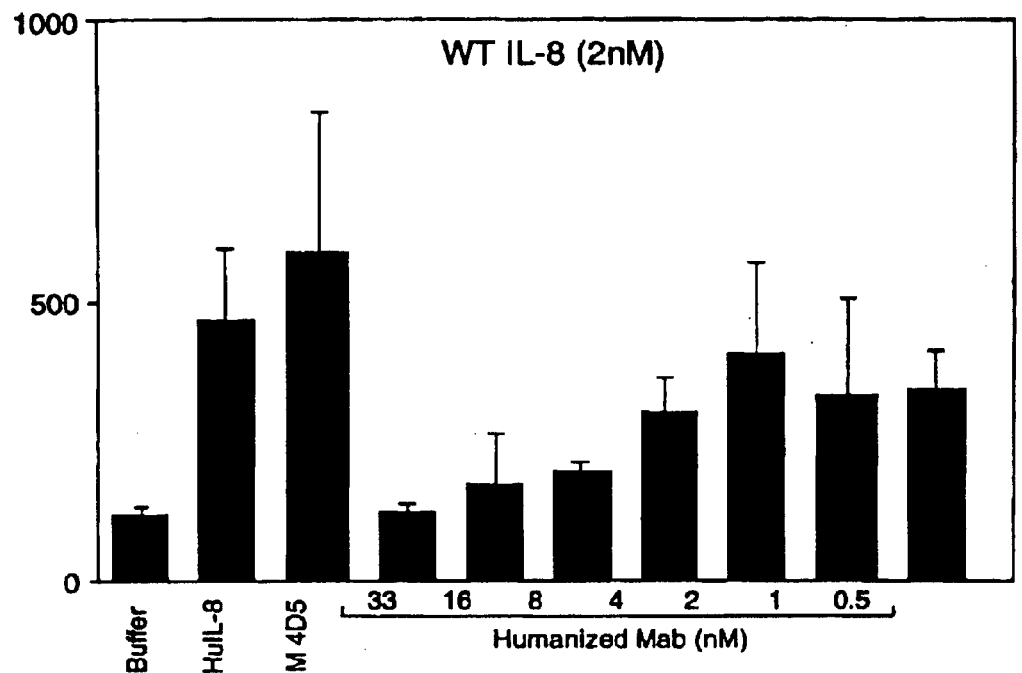
FIG. 34 is a graph with four panels (A, B, C, and D) depicting the ability of 6G4.2.5V11N35A Fab to inhibit human wild type IL-8, human monomeric IL-8, rabbit IL-8, and rhesus IL-8 mediated neutrophil chemotaxis, respectively. Panel A presents inhibition data for 6G4.2.5V11N35A Fab samples at concentrations of 0.5, 1, 2, 4, 8, 16, and 33 nM, for an isotype control antibody (denoted "4D5") sample at a concentration of 33 nM, and for a no antibody control (denoted "HuIL-8") sample, in the presence of 2 nM human wild type IL-8. Panel B presents inhibition data for 6G4.2.5V11N35A Fab samples at concentrations of 0.5, 1, 2, 4, 8, 16, and 33 nM, for an intact 6G4.2.5 mAb sample at a concentration of 33 nM, for an isotype control antibody (denoted as "4D5") sample at a concentration of 33 nM, and for a no antibody control (denoted "BD59") sample, in the presence of 2 nM human monomeric IL-8. Panel C presents inhibition data for 6G4.2.5V11N35A Fab samples at concentrations of 0.5, 1, 2, 4, 8, 16, and 33 nM, for an intact 6G4.2.5 mAb sample at a concentration of 33 nM, for an isotype control antibody (denoted "4D5") sample at a concentration of 33 nM, and for a no antibody control (denoted "Rab IL-8") sample, in the presence of 2 nM rabbit IL-8. Panel D presents inhibition data for 6G4.2.5V11N35A Fab samples at concentrations of 0.5, 1, 2, 4, 8, 16, and 33 nM, for an intact 6G4.2.5 mAb sample at a concentration of 33 nM, for an isotype control antibody (denoted as "4D5") sample at a concentration of 33 nM, and for a no antibody control (denoted "Rhe IL-8") sample, in the presence of 2 nM rhesus IL-8. In addition, panels B, C and D each presents data for human wild type IL-8 control (denoted "HuIL-8") samples at a concentration of 2 nM in the respective assay, and panels A, B, C, and D each presents data for a no IL-8 buffer control (denoted "Buffer") sample in the respective assay.
Figure 34B:
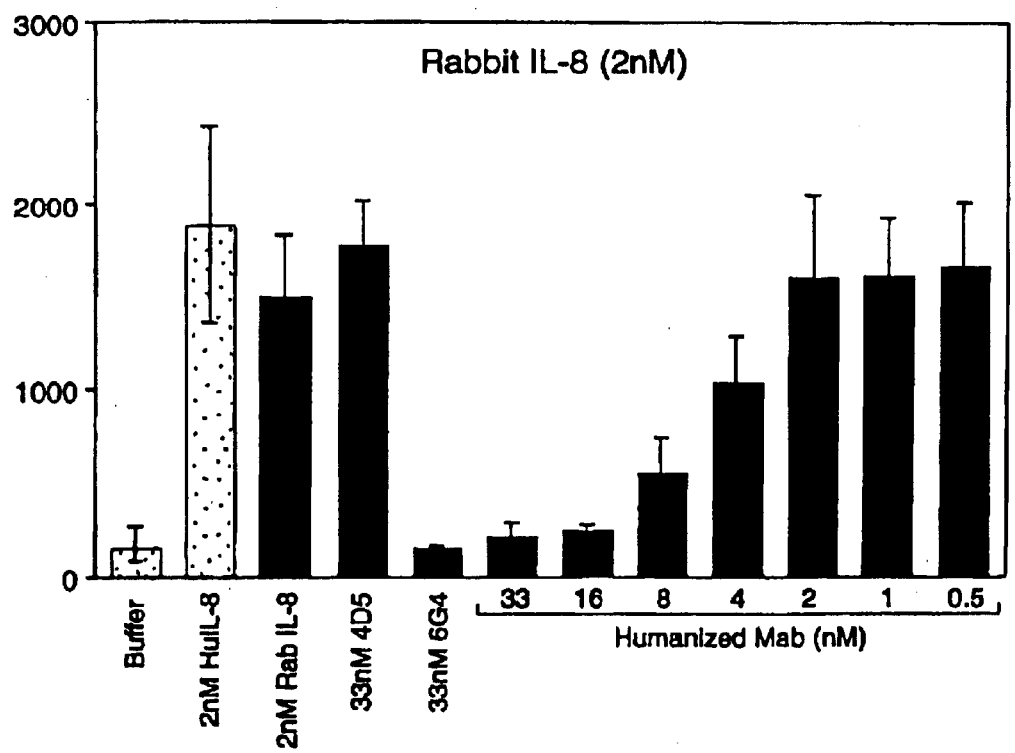
Figure 34C:
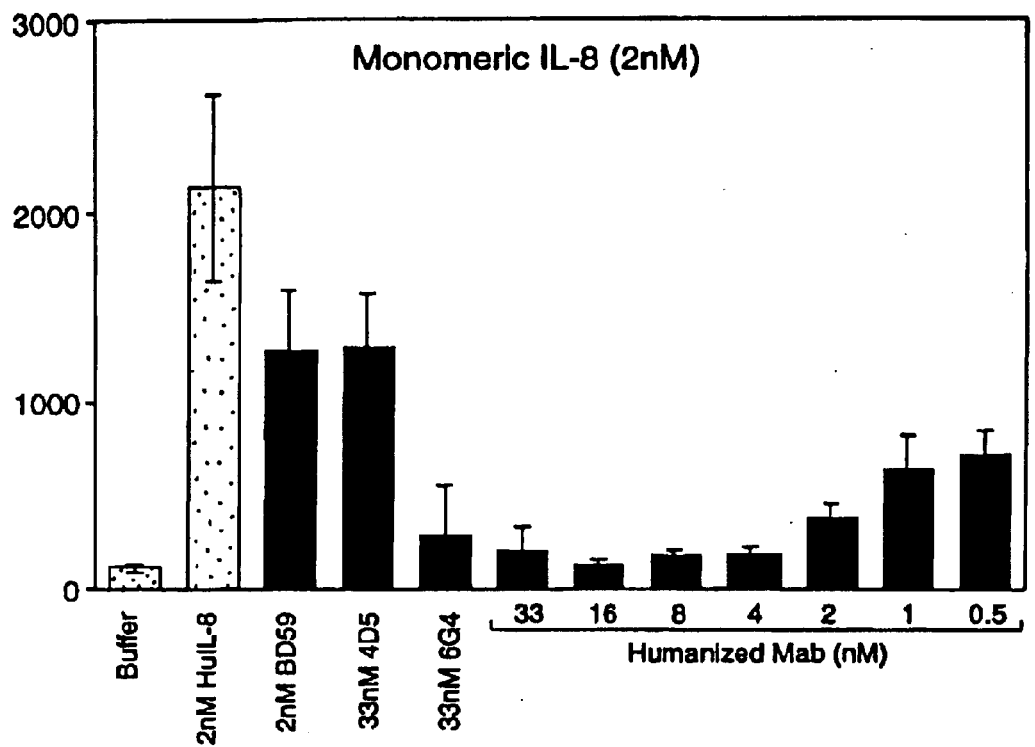
Figure 34D:
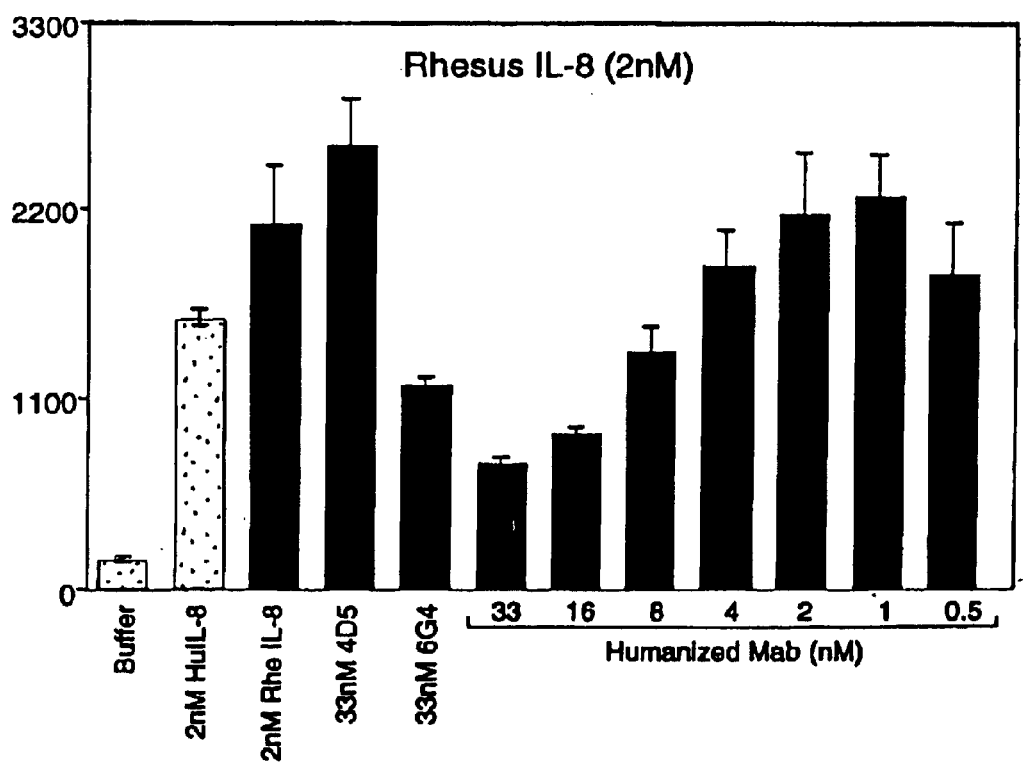

Soluble 6G4V11N35A Fab antibody was made by transforming an amber non-suppressor strain of E. coli, 34B8, with pPh6G4.V11 and growing the culture in low phosphate medium for 24 hours. The periplasmic fraction was collected and passed over a Hi-Trap Protein-G column (Pharmacia, Piscataway, N.J.) followed by a desalting and concentration step. The protein was analyzed by SDS-PAGE, mass spectrometry and amino acid analysis. The protein had the correct size and amino acid composition (FIG. 35). The 6G4V11N35A Fab was tested for its ability to inhibit $^{125}$I-IL-8 binding to human neutrophils and to inhibit IL-8 mediated neutrophil chemotaxis as described in Section (B)(1) and (B)(2) above. As shown in FIG. 33, hybridoma-derived intact murine antibody (6G4 murine mAB), recombinant 6G4 murine-human chimera Fab, recombinant humanized Fab versions 1 and 11, and 6G4V11N35A Fab were found to inhibit $^{125}$I-IL-8 binding to human neutrophils with an average IC$_{50}$ of 5 nM, 8 nM, 40 nM, 10 nM and 3 nM, respectively. The 6G4V11N35A Fab had at least a 2-fold higher affinity than the 6G4.2.5 chimera Fab and a 3-fold higher affinity than 6G4V11. As shown in FIG. 34, the 6G4V11N35A Fab was found to inhibit IL-8 mediated neutrophil chemotaxis induced by both wild type and monomeric human IL-8, and by two different animal species of IL-8, namely, rabbit and rhesus. The irrelevant isotype control Fab (4D5) did not inhibit neutrophil migration. The average IC$_{50}$ values were 3 nM (wt IL-8), 1 nM (monomeric IL-8), 5 nM (Rabbit IL-8), and 10 nM (Rhesus IL-8).

K. Construction of a 6G4V11N35A F(ab')$_2$ Leucine Zipper

Production of a F(ab')$_2$ version of the humanized anti-IL-8 6G4V11N35A Fab was accomplished by constructing a fusion protein with the yeast GCN4 leucine zipper. The expression plasmid p6G4V11N35A.F(ab')$_2$ was made by digesting the plasmid p6G425chim2.fab2 with the restriction enzymes bsaI and apaI to remove the DNA sequence encoding the 6G4.2.5 murine-human chimeric Fab and replacing it with a 2620 bp bsaI-apaI fragment from pPh6G4.V11N35A. The plasmid p6G425chim2.fab2 is a derivative of pS1130 which encodes a fusion protein (the GCN4 leucine zipper fused to the heavy chain of anti-CD18) and the light chain of anti-CD18 antibody. The expression plasmid p6G4V11N35A.F(ab')$_2$ was deposited on Feb. 20, 1996 with the American Type Culture Collection, 12301 Parklawn Drive, Rockville, Md., U.S.A. (ATCC) and assigned ATCC Accession No. 97890. A pepsin cleavage site in the hinge region of the antibody facilitates the removal of the leucine zipper leaving the two immunoglobin monomers joined by the cysteines that generate the interchain disulfide bonds. The DNA and protein sequence of the h6G4V11N35A.F(ab')$_2$ are depicted in FIGS. 35–37.

An expression host cell was obtained by transforming E. coli strain 49D6 with p6G4V11N35A.F(ab')$_2$ essentially as described in Section (II)(3)(C) above. The transformed host E. coli 49D6 (p6G4V11N35A.F(ab')$_2$) was deposited on Feb. 20, 1997 at the ATCC and assigned ATCC Accession No. 98332. Transformed host cells were grown in culture, and the 6G4V11N35A F(ab')$_2$ product was harvested from the host cell periplasmic space essentially as described in Section (II)(3)(F) above.

L. Characterization of the Humanized 6G4V11N35A F(ab')$_2$ Leucine Zipper

Figure 38:
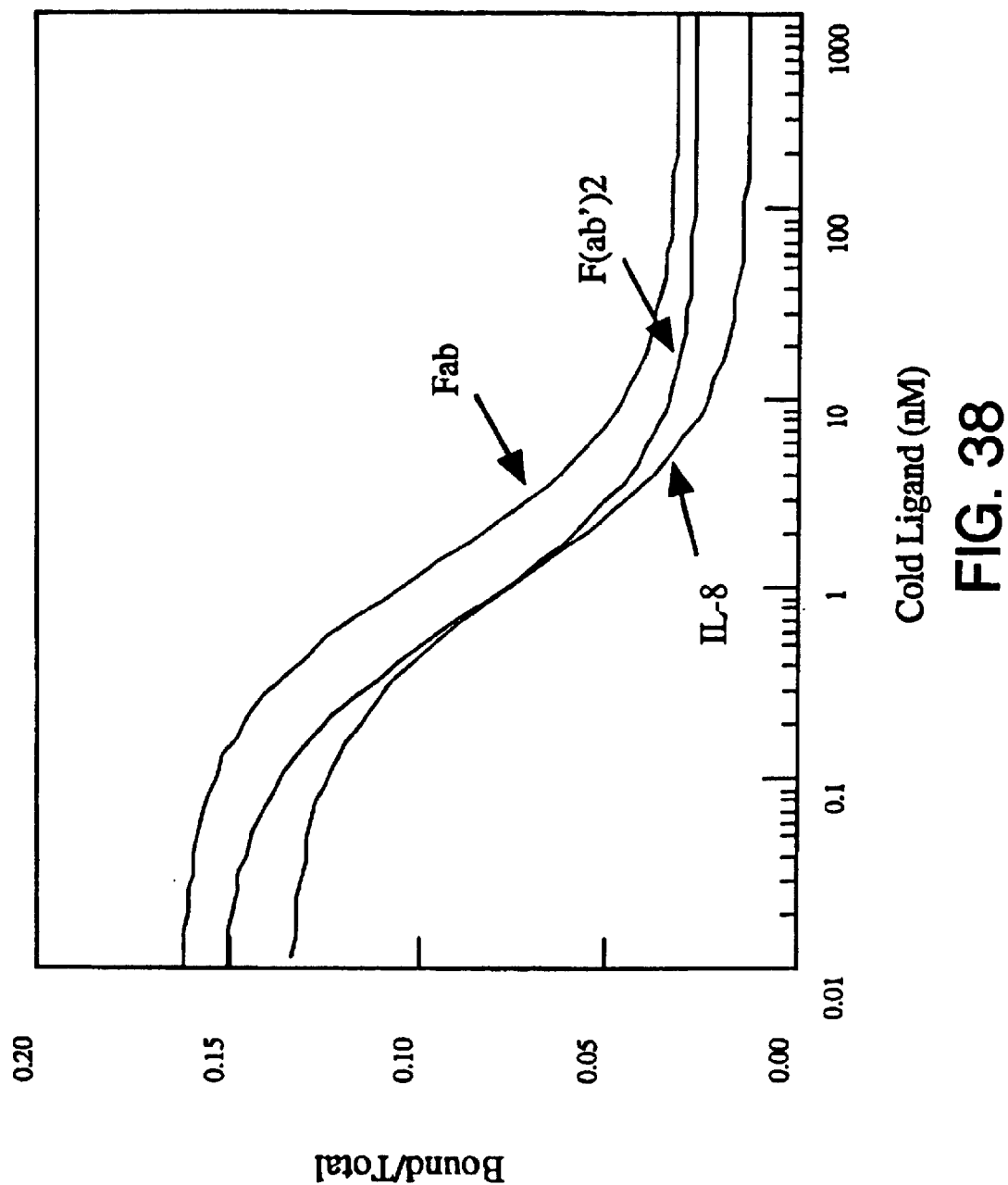
FIG. 38 is a Scatchard plot depicting the inhibition of $^{125}$I-IL-8 binding to human neutrophils exhibited by 6G4.2.5V11N35A Fab (denoted Fab), 6G4.2.5V11N35A F(ab')$_2$ (denoted F(ab')$_2$), and human wild type IL-8 control (denoted IL-8).

The 6G4V11N35A Fab and F(ab')$_2$ were tested for their ability to inhibit $^{125}$I-IL-8 binding to neutrophils according to the procedures described in Section (B)(1) above. The displacement curves from a representative binding experiment performed in duplicate is depicted in FIG. 38. Scatchard analysis of this data shows that 6G4V11N35A F(ab')$_2$ inhibited $^{125}$I-IL-8 binding to human neutrophils with an average IC$_{50}$ of 0.7 nM (+/−0.2). This is at least a 7 fold increase in affinity compared to the hybridoma-derived intact murine antibody (average IC$_{50}$ of 5 nM) and at least a 2.8 fold increase in affinity over the Fab version (average IC$_{50}$ of 2 nM).

Figure 39:
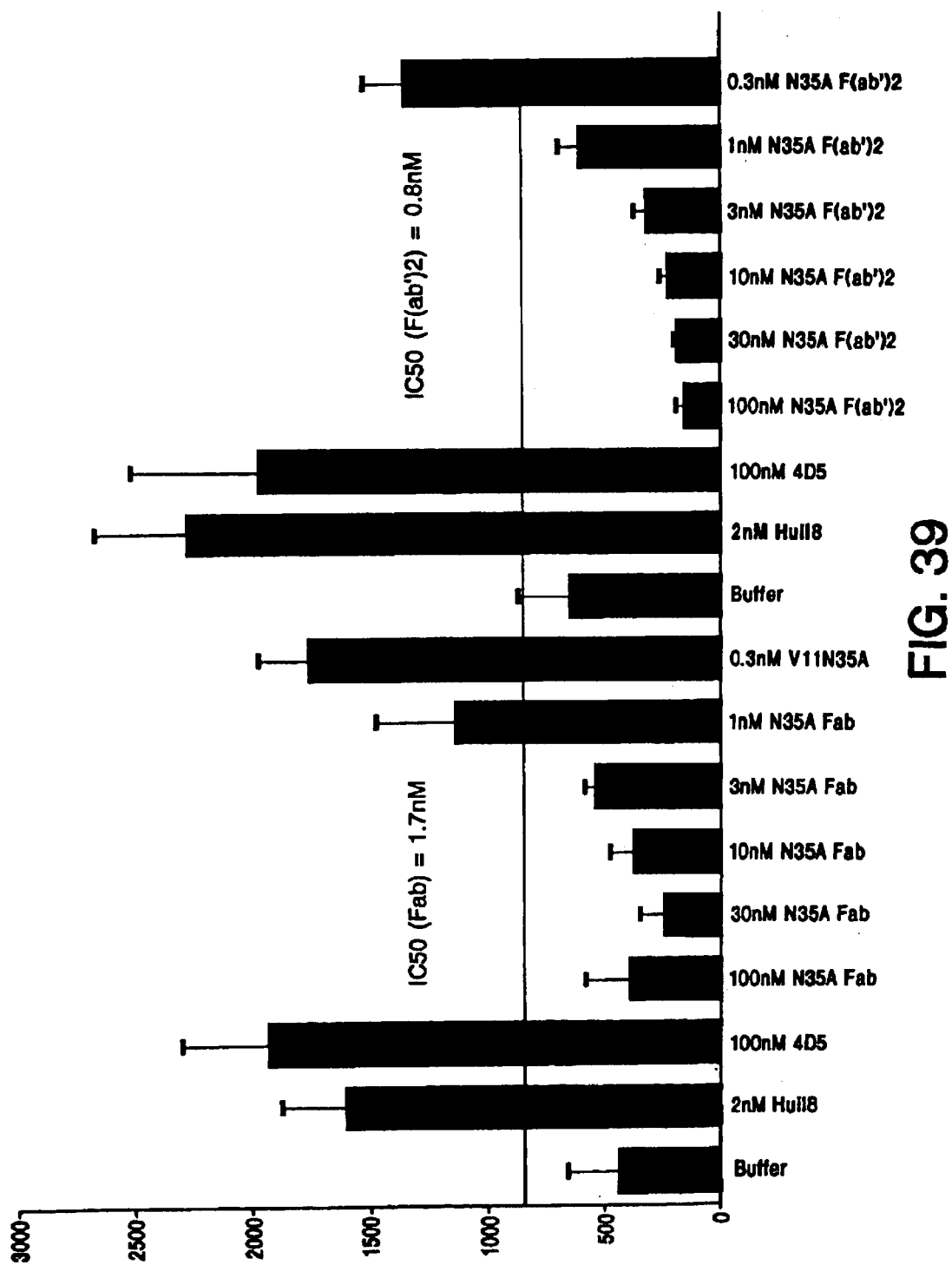
FIG. 39 is a graph depicting a comparison of the wild type human IL-8 mediated neutrophil chemotaxis inhibition activities of the 6G4.2.5V11N35A F(ab')$_2$ and 6G4.2.5V11N35A Fab. Inhibition data are presented for 6G4.2.5V11N35A Fab samples (denoted "N35A Fab") and 6G4.2.5V11N35A F(ab')$_2$ samples (denoted N35A F(ab')$_2$) at concentrations of 0.3, 1, 3, 10, 30, and 100 nM, for an isotype control antibody (denoted as "4D5") sample at a concentration of 100 nM, and for a no antibody control sample, in the presence of 2 nM human wild type IL-8. In addition, inhibition data are presented for no IL-8 buffer control samples (denoted "Buffer").
Figure 40:
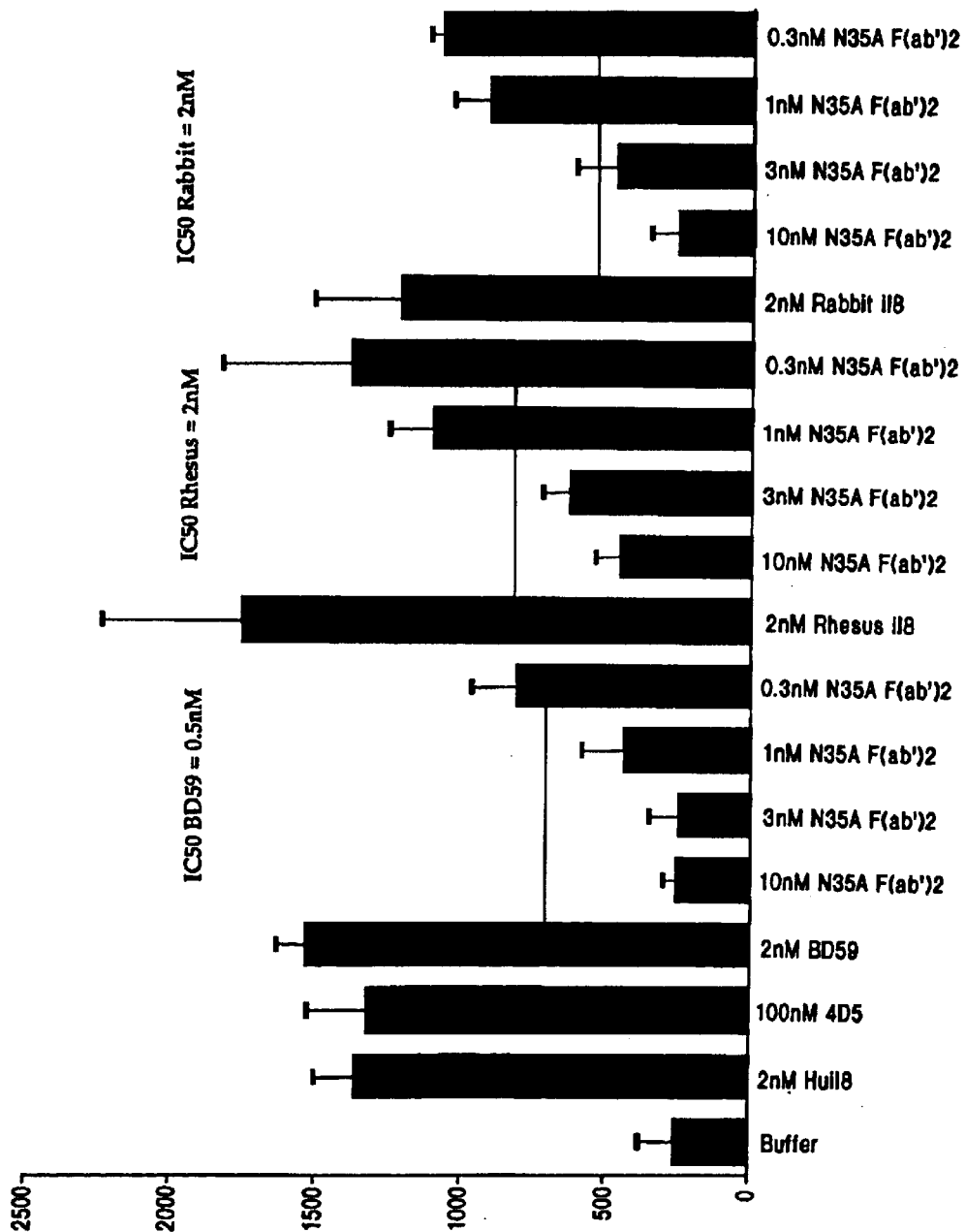
FIG. 40 is a graph depicting the ability of 6G4.2.5V11N35A F(ab')$_2$ to inhibit human monomeric IL-8, rhesus IL-8, and rabbit IL-8 mediated neutrophil chemotaxis. Human monomeric IL-8 mediated neutrophil chemotaxis data are presented for 6G4.2.5V11N35A F(ab')$_2$ samples at concentrations of 0.3, 1, 3, and 10 nM, for an isotype control antibody (denoted as "4D5") sample at a concentration of 100 nM, and for a no antibody control sample (denoted as "BD59"), in the presence of human monomeric. IL-8 (denoted as "BD59") at a concentration of 0.5 nM. Rhesus IL-8 mediated neutrophil chemotaxis data are presented for 6G4.2.5V11N35A F(ab')$_2$ samples at concentrations of 0.3, 1, 3, and 10 nM, and for a no antibody control sample, in the presence of rhesus IL-8 at a concentration of 2 nM. Rabbit IL-8 mediated neutrophil chemotaxis data are presented for 6G4.2.5V11N35A F(ab')$_2$ samples at concentrations of 0.3, 1, 3, and 10 nM, and for a no antibody control sample, in the presence of rabbit IL-8 at a concentration of 2 nM. In addition, inhibition data are presented for a no IL-8 buffer control sample (denoted as "Buffer") and for a 2 nM human wild type IL-8 (denoted as "HuIL-8").

The 6G4V11N35A F(ab')$_2$ was also tested for its ability to inhibit IL-8 mediated neutrophil chemotaxis according to the procedures described in Section (B)(2) above. The results of a representative chemotaxis experiment performed in quadruplicate are depicted in FIG. 39. As shown in FIG. 39, the 6G4V11N35A F(ab')$_2$ inhibited human IL-8 mediated neutrophil chemotaxis. The 6G4V11N35A F(ab')$_2$ exhibited an average IC$_{50}$ value of 1.5 nM versus 2.7 nM for the 6G4V11N35A Fab, which represents an approximately 2 fold improvement in the antibody's ability to neutralize the effects of IL-8. The irrelevant isotype control Fab (4D5) did not inhibit neutrophil migration. Furthermore, the 6G4V11N35A F(ab')$_2$ antibody retained its ability to inhibit IL-8 mediated neutrophil chemotaxis by monomeric IL-8 and by two different animal species of IL-8, namely rabbit and rhesus, in neutrophil chemotaxis experiments conducted as described above. An individual experiment is shown in FIG. 40. The average IC50 values were 1 nM (monomeric IL-8), 4 nM (Rabbit IL-8), and 2.0 nM (Rhesus IL-8).

M. Random Mutagenesis of Light Chain Amino Acid (N35A) IN CDR-L1 of Humanized Antibody 6G4V11

A 3-fold improvement in the IC$_{50}$ for inhibiting $^{125}$I-IL-8 binding to human neutrophils was observed when alanine was substituted for asparagine at position 35 in CDR-L1 (light chain) of the humanized 6G4V11 mAb as described in Section (I) above. This result might be attributed to an improvement in the contact between the antigen-antibody binding interfaces as a consequence of the replacement of a less bulky nonpolar side chain (R-group) that may have altered the conformation of CDR-L1 or neighboring CDR-H3 (heavy chain) to become more accessible for antigen docking. The acceptance of alanine at position 35 of CDR-L1 suggested that this position contributed to improved affinity and that an assessment of the re-modeling of CDR loops /antigen-binding region(s) by other amino acids at this location was warranted. Selection of an affinity matured version of the humanized 6G4.V11 mAB (Kunkel, T. A., *Proc. Natl. Acad. Sci. USA*, 82:488 (1995)) was accomplished by randomly mutagenizing position 35 of CDR-L1 and constructing an antibody-phage library. The codon for Asparagine (N) at position 35 of CDR-L1, was targeted for randomization to any of the 20 known amino acids.

Initially, a stop template, pPh6G4.V11-stop, was made to eliminate contaminating wild-type N35 sequence from the library. This was accomplished by performing site-directed mutagenesis (Muta-Gene Kit, Biorad, Ricmond, Calif.) of pPH6G4V11 (described in Section (H) above) to replace the codon (AAC) for N35 with a stop codon (TAA) using the primer SL.97.2 (SEQ ID NO:63)(FIG. 42). The incorporation of the stop codon was confirmed by DNA sequencing. Subsequently, uracil containing single-stranded DNA derived from *E. coli* CJ236 transformed with the stop template was used to generate an antibody-phage library following the method described by Lowman (*Methods in Molecular Biology*, 87 Chapter 25: 1–15 (1997). The variants generated from this library were predicted to produce a collection of antibodies containing one of the 20 known amino acids at position N35 in CDR-L1. The amino acid substitutions were accomplished by site-directed mutagenesis using the degenerate oligonucleotide primer (SL.97.3) with the sequence NNS (N=A/G/T/C; S=G/C;) (SEQ ID NO: 64)(FIG. 42). This codon usage should allow for the expression of any of the 20 amino acids—including the amber stop codon (TAG). The collection of antibody-phage variants was transfected into *E. coli* strain XL-1 blue (Stratagene, San Diego, Calif.) by electroporation and grown at 37° C. overnight to amplify the library. Selection of tight binding humanized 6G4V11 Fab's were accomplished by panning the library on IL-8 coated 96-well plates as described in Section (i) above. Prior to panning, the number of phage/library was normalized to 1.1×10$^{13}$ phage/ml (which produces a maximum OD$_{270}$ reading=1 OD unit) and IL-8 coated plates were incubated with blocking solution (25 mN Carbonate buffer containing 50 mg/ml skim milk) for 2 hours before the addition of phage (each sort used eight IL-8 coated wells/library ). After the blocking and washing steps, every sort began with the addition of 100 ul of antibody-phage (titered at 1.1×10$^{13}$ phage/ml) to each of eight IL-8 coated wells followed by an 1 hour incubation at 25° C. The non-specifically bound antibody-phage were removed by 10 quick washes with PBS0.05% Tween 20 (PBS-Tween). For sort #1, a low stringency wash (100 ul PBS-Tween/well for 10 minutes at 25° C.) was employed to capture the small proportion of tight binding antibody-phage bound to the immobilized IL-8. The antibody-phage variants specifically bound to IL-8 were eluted with 100 ul/well of 200 mM Glycine pH 2.0 for 5 minutes at 25° C. The eluted antibody-phage variants from the 8 wells were then pooled and neutralized with 1M Tris-HCl pH 8.0 (1/3 the elution volume). The phage were titered and propagated as described in Section (I) above. The stringency of the washes were successively increased with each round of panning depending upon the percent recovery of phage at the end of a sort. The wash conditions were as follows: sort #2 (4×15 minute intervals; total time=60 minutes) and sort #3 (either #3a: 8×15 minute intervals or #3b: 12×10 minute intervals; total time=120 minutes). The total number of phage recovered was progressively reduced after each sort suggesting that non- or weak-binders were being selected against The recovery of the negative control (the antibody-phage stop variant) was constant throughout the panning (approximately 0.0001 to 0.00001 percent).

Eighteen random variants from sort #3 were analyzed by DNA sequencing to look for an amino acid consensus at position 35 of CDR-L1. The data presented in FIG. 43A showed that Glycine occupied position 35 in 33% of the variants sequenced. However, after correcting for the number of NNS codon combinations/amino acid, the frequency of Glycine was reduced to 16.6%. Glutamic Acid was represented with the highest frequency (22%) followed by Aspartic Acid and Glycine (16.6%). The frequencies of recovery of the wild-type Asparagine and substituted Alanine were only 5.6%. Interestingly, the high frequency of Glycine may suggest that a much wider range of conformations might be allowed for the loop of CDR-L1 which may be attributed to the reduction in steric hindrance of bond angle (φ-ψ) pairing as a result of the single hydrogen atom as the side chain. Conversely, Glutamic Acid at position 35 might restrict the flexibility of the loop by imposing less freedom of rotation imposed by the more rigid and bulky charged polar side chain.

Figures 1, 43B:
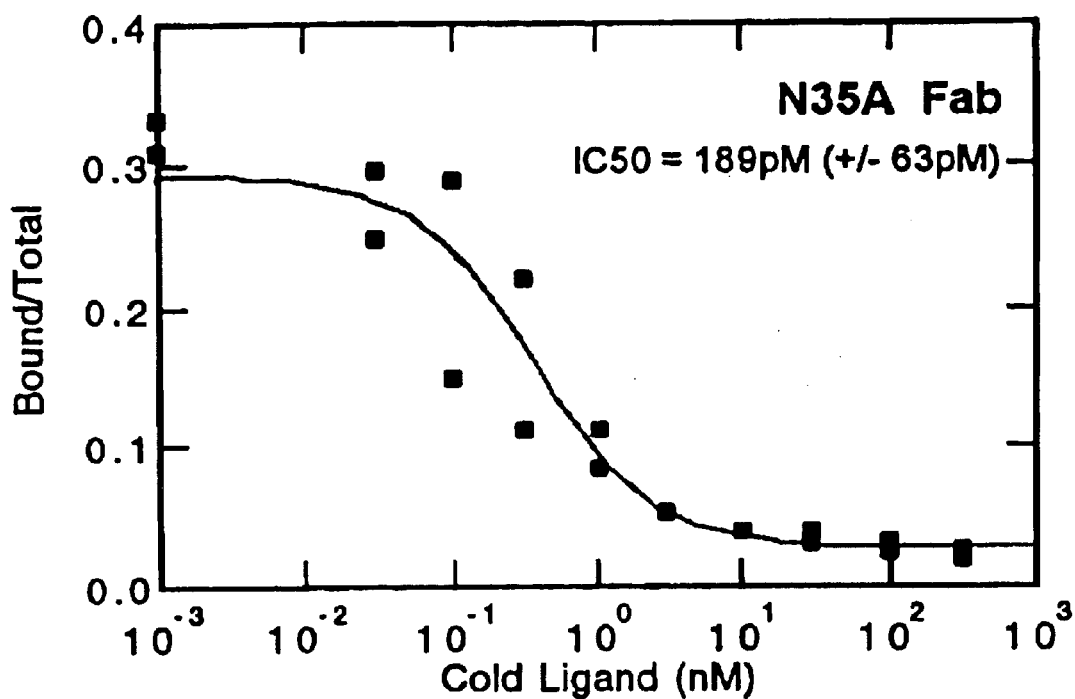
FIG. 43B contains graphs of displacement curves depicting the inhibition of $^{125}$I-IL-8 binding to neutrophils exhibited by the 6G4V11N35A, 6G4V11N35D, 6G4V11N35E and 6G4V11N35G Fab's.
Figures 2, 43B:
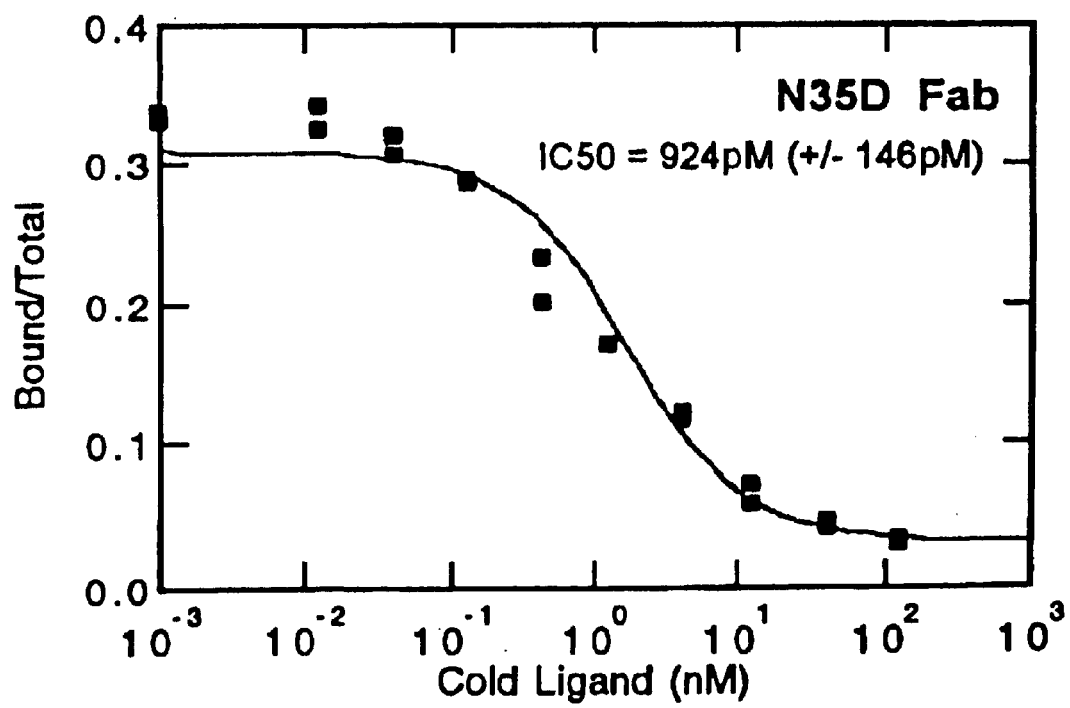
Figures 3, 43B:
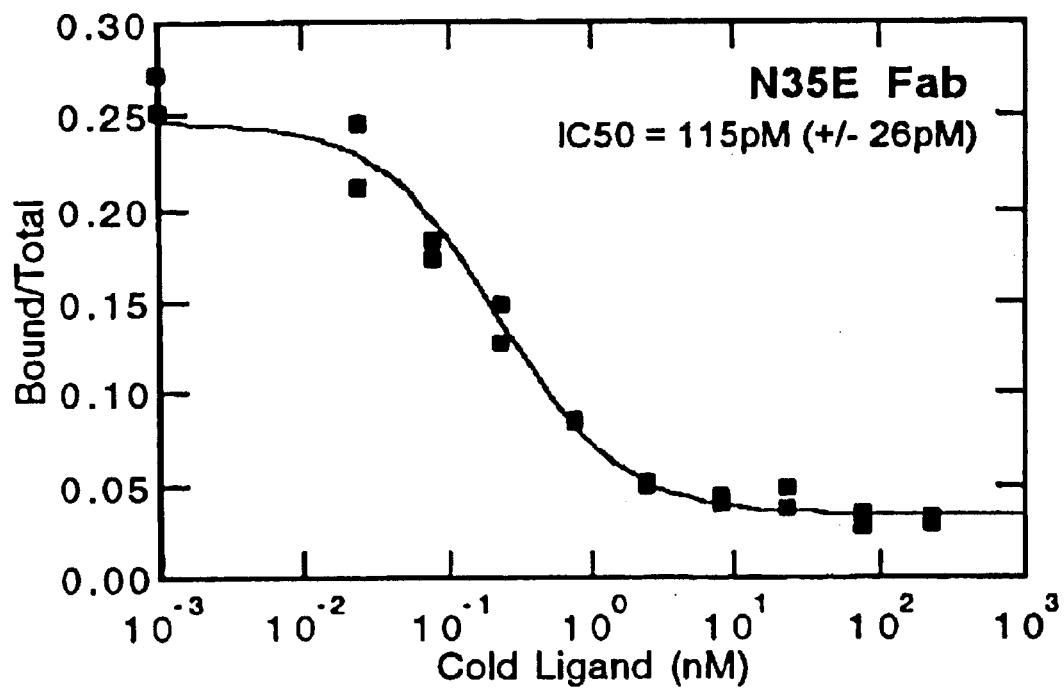
Figures 4, 43B:
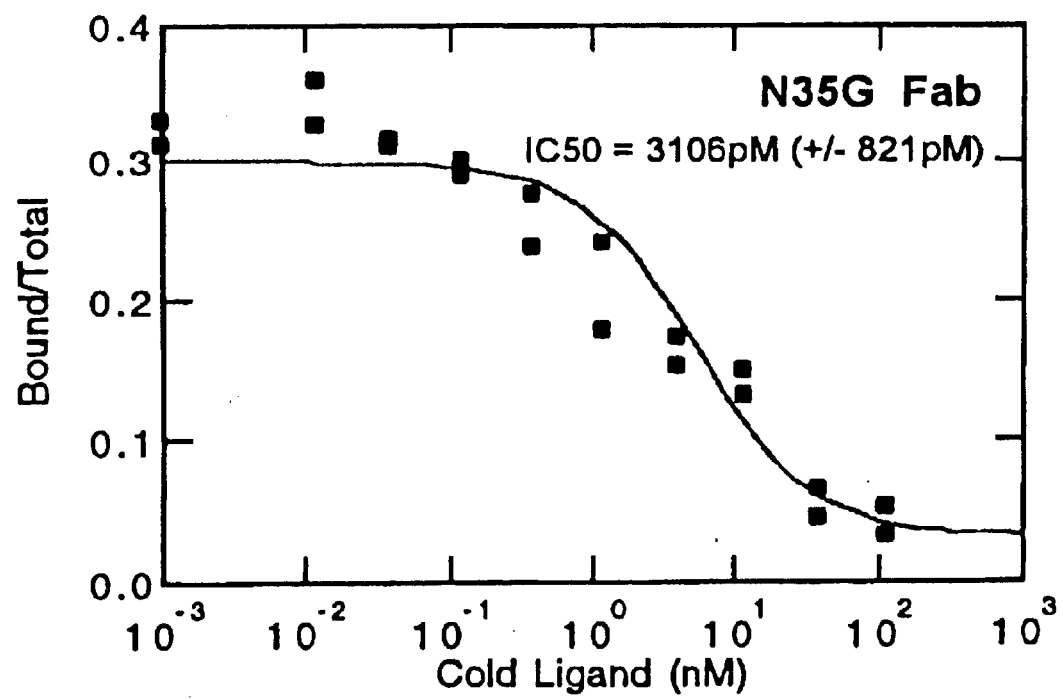

Soluble Fab's of the affinity matured variants (N3SG, N35D, N35E and N35A) were made as described in Section (J) above for evaluating their ability to block IL-8 binding. As shown in FIG. 43B, variants N35A, N35D, N35E and N35G were found to inhibit $^{125}$I-IL-8 binding to human neutrophils with an approximate IC$_{50}$ of 0.2 nM, 0.9 nM, 0.1 nM and 3.0 nM, respectively. All of the affinity matured variants showed an improvement in binding IL-8 ranging from 3–100 fold compared to the humanized 6G4V11 mAb. The affinity-matured variant, 6G4V11N35E, was 2-fold more potent in blocking IL-8 binding to human neutrophils than the alanine-scan variant, 6G4V11N35A. Equilibrium and kinetic measurements of variants 6G4V11N35A and 6G4V11N35E were determined using KinEXA™ automated immunoassay system (Sapidyne Instruments Inc., Idaho City, Id.) as described by Blake et al., *J. Biol. Chem.* 271: 27677 (1996). The procedure for preparing the antigen-coated particles was modified as follows: 1 ml of activated agarose beads (Reacti-Gel 6X; Pierce, Rockford, Ill.) were coated with antigen in 50 mM Carbonate buffer pH 9.6 containing 20 ug/ml of human IL-8 and incubated with gentle agitation on a rocker overnight at 25° C. The IL-8 coated beads were then washed twice with 1M Tris-HCl pH 7.5 to inactivate any unreactive groups on the beads and blocked with Superblock (Pierce, Rockford, Ill.) for 1 hour at 25 C to reduce non-specific binding. The beads were resuspended in assay buffer (0.1% bovine serum albumin in PBS) to a final volume of 30 ml. A 550 ul aliquot of the IL-8 coated bead suspension was used each time to pack a fresh 4 mm high column in the KinEXA observation cell. The amount of unbound antibody from the antibody-antigen mixtures captured by the IL-8-coated beads in both the equilibrium and kinetic experiments was quantified using a fluorescently labeled secondary antibody. Murine 6G4.2.5 was detected with a R-PE AffiniPure F(ab')$_2$ goat anti-mouse IgG, Fc fragment specific 2° antibody (Jackson Immuno Research Laboratories, West Grove, Pa.) and humanized affinity matured N35A (Fab and F(ab')$_2$) and N35E Fab were detected with a R-PE AffiniPure F(ab')$_2$ donkey anti-human IgG (H+L) 2° antibody (Jackson Immunoresearch Laboratories, West Grove, Pa.); both at a 1:1000 dilution.

Equilibrium measurements were determined by incubating a constant amount of anti-IL-8 antibody (0.005 ug/ml) with various concentrations of human IL-8 (0, 0.009, 0.019, 0.039, 0.078, 0.156, 0.312, 0.625, 1.25, 2.5 nM). The antibody-antigen mixture was incubated for2 hours at 25° C. to allow the molecules to reach equilibrium. Subsequently, each sample was passed over a naive IL-8 coated bead pack in the KinEXA observation cell at a flow rate of 0.5 ml/minute for a total of 9 minutes/sample. The equilibrium constant (Kd) was calculated using the software provided by Sapidyne Instruments Inc.

Rates of association (ka) and dissociation (kd) were determined by incubating together a constant amount of antibody and antigen, and measuring the amount of uncomplexed anti-IL-8 bound to the IL-8 coated beads over time. The concentration of antibody used in the kinetic experiments was identical to that used in the equilibrium experiment described above. Generally, the amount of human IL-8 used was the concentration derived from the binding curves of the equilibrium experiment that resulted in 700/0 inhibition of anti-IL-8 binding to the IL-8 coated beads. Measurements were made every 15 minutes to collect approximately nine data points. The ka was calculated using the software provided by Sapidyne Instruments, Inc. The off rate was determined using the equation: kd=Kd/ka.

Figure 44:
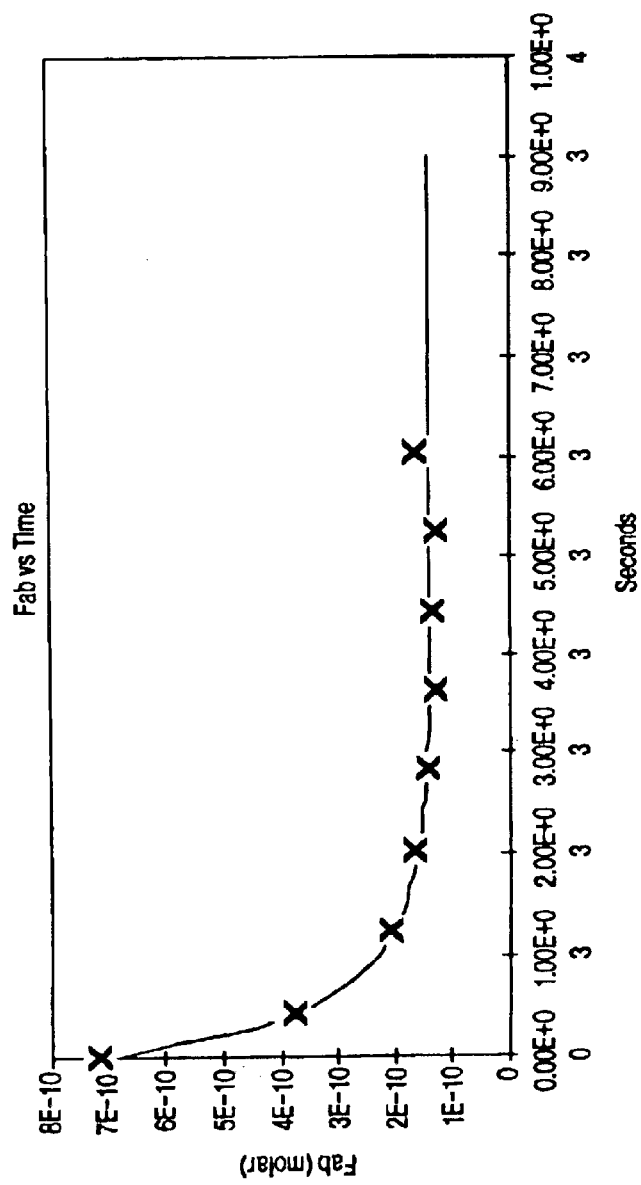
FIG. 44 contains a graph depicting the typical kinetics of an anti-IL-8 antibody fragment (6G4V11N35A F(ab')$_2$) binding to IL-8.

FIG. 44 shows the equilibrium constants (Kd) for the affinity matured variants 6G4V11N35E and 6G4V11N35A Fab's were approximately 54 pM and 114 pM, respectively. The improvement in affinity of 6G4V11N35E Fab for IL-8 can be attributed to a 2-fold faster rate of association ($K_{on}$) of 4.7×10$^6$ for 6G4V11N35E Fab versus 2.0×10$^6$ for 6G4V11N35A F(ab')$_2$. (The Kd of the 6G4V11N35A F(ab')$_2$ and 6G4V11N35A Fab are similar.) The dissociation rates ($K_{off}$) were not significantly different. Molecular modeling suggests that substitution of Aspargine with Glutamic Acid might either affect the antibody's interaction with IL-8 directly or indirectly by neutralizing the charge of neighboring residues R98 (CDR-H3) or K50 (CDR-L2) in the CDR's to facilitate contact with IL-8. Another effect might be the formation of a more stable loop conformation for CDR-L1 that could have facilitated more appropriate contacts of other CDR-L1 loop residues with IL-8. The DNA (SEQ ID NO: 65) and amino acid (SEQ ID NO:62) sequences of p6G4V11N35E.Fab showing the Asparagine to Glutamic Acid substitution in the light chain are presented in FIG. 45.

N. Characterization of Humanized Anti-IL-8 Variant 6G4V11N35E Fab

Figure 46:
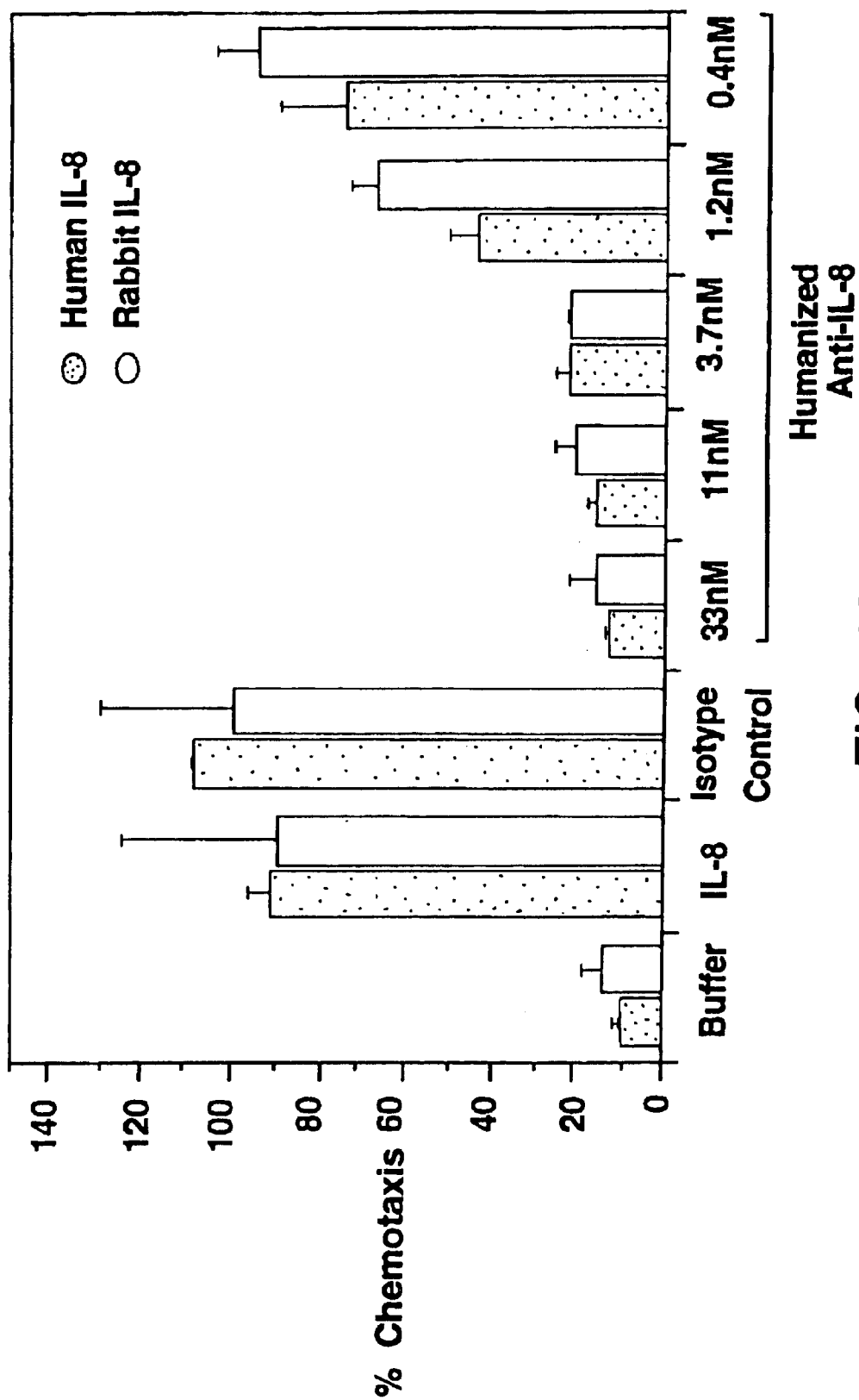
FIG. 46 is a graph depicting the ability of 6G4V11N35E Fab to inhibit human IL-8 (dark columns) and rabbit IL-8 (light columns) mediated neutrophil chemotaxis. Data are presented for 6G4V11N35E Fab samples at concentrations of 0.4, 1.2, 3.7, 11 and 33 nM, and for an isotype control antibody (4D5) sample at a concentration of 100 nM, in the presence of 2 nM human IL-8 or 2 nM rabbit IL-8. In addition, inhibition data are presented for a no IL-8 buffer control sample (denoted "Buffer") and for human and rabbit IL-8 control samples (denoted "IL-8").
Figure 49A:
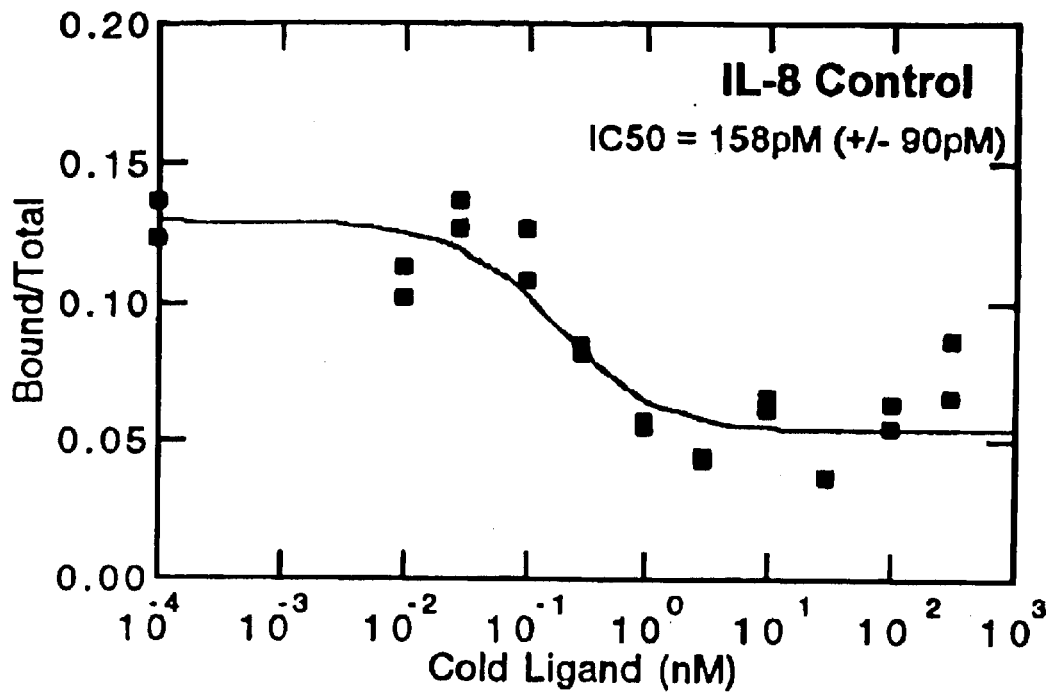
FIG. 49 contains graphs of displacement curves depicting the inhibition of $^{125}$I-IL-8 binding to neutrophils exhibited by the full length IgG1 forms of variants 6G4V11N35A and 6G4V11N35E.
Figure 49B:
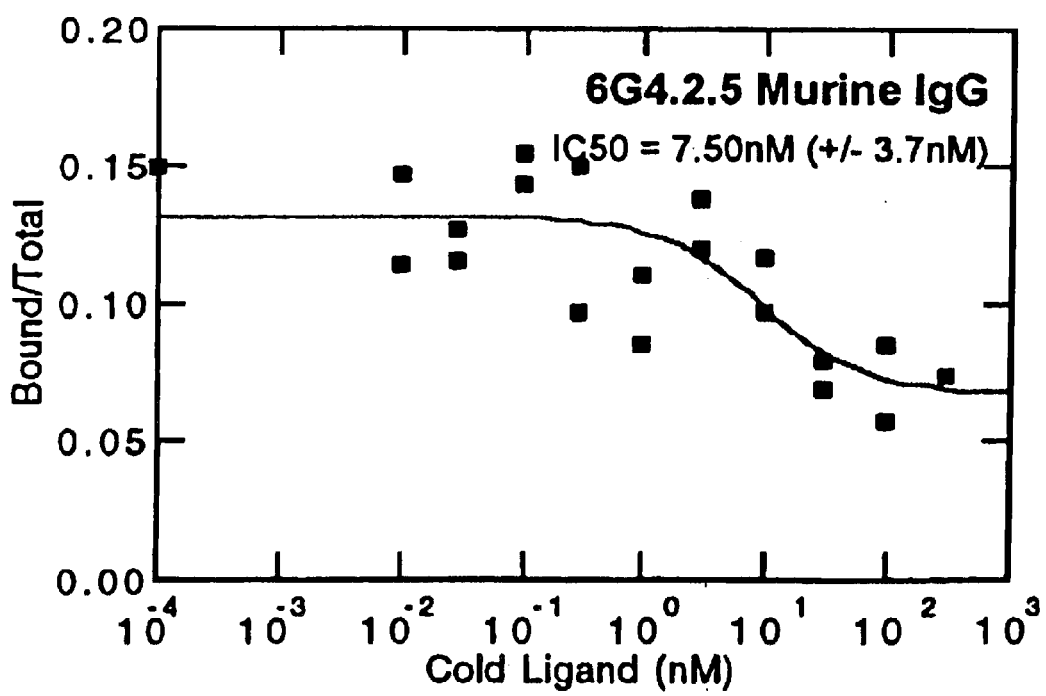
Figure 49C:
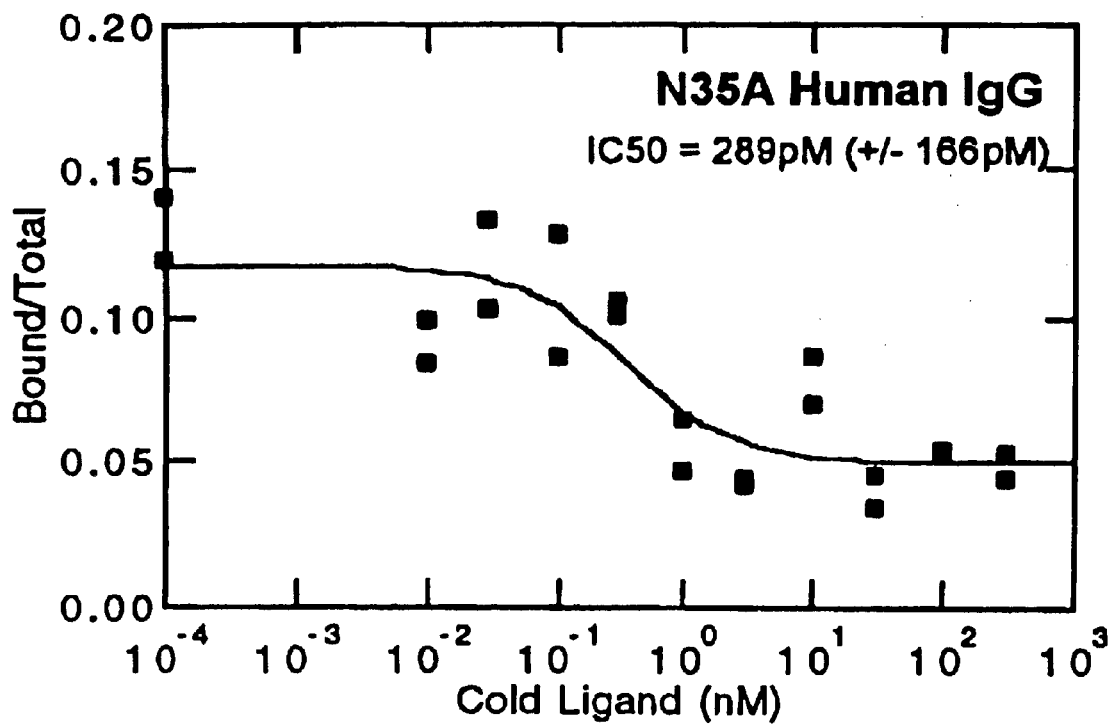
Figure 49D:
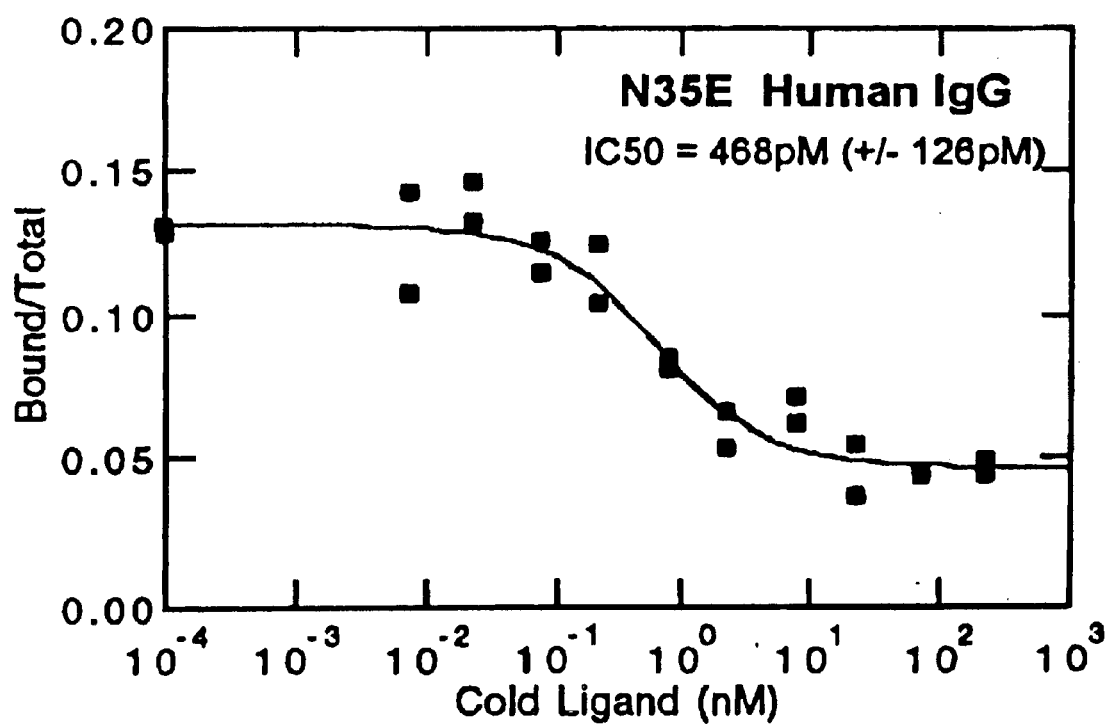

The affinity matured Fab variant,6G4V11N35E, was tested for its ability to inhibit IL-8 mediated neutrophil chemotaxis as described in Section (B)(2) above. The reuseable 96-well chemotaxis chamber described in Section (B)(2) was replaced with endotoxin-free disposable chemotaxis chambers containing 5-micron PVP-free polycarbonate filters (ChemoTx101-5, Neuro Probe, Inc. Cabin John, Md.). As illustrated in FIG. 46, variant N35E effectively blocks IL-8 mediated neutrophil chemotaxis induced by a 2 nM stimulus of either rabbit or human IL-8. In fact, the level of inhibition at antibody concentrations between 3.7 nM–33 nM was not significantly different from the buffer control indicating variant N35E could completely inhibit this response. The IC$_{50}$'s for both rabbit and human IL-8 were approximately 2.8 nM and 1.2 nM, respectively. The irrelevant isotype control Fab (4D5) did not inhibit neutrophil migation indicating the results observed for the affinity matured variant, N35E, is IL-8 specific.

O. Construction of Humanized 6G4V11N35E F(ab')$_2$ Leucine Zipper

A F(ab')$_2$ expression plasmid for 6G4V11N35E was constructed using methods similar to those described in Section (K) above. The expression plasmid, p6G4V11N35E.F(ab')$_2$, was made by digesting the plasmid p6G4V11N35A.F(ab')$_2$ (described in Section (K) above) with the restriction enzymes ApaI and NdeI to isolate a 2805 bp fragment encoding the heavy chain constant domain -GCN4 leucine zipper and ligating it to a 3758 bp ApaI-NdeI fragment of the pPH6G4V11N35E phage display clone (encoding 6G4V11N35E Fab) obtained as described in Section (M) above. The integrity of the entire coding sequence was confirmed by DNA sequencing.

P. Construction of the Full Length Humanized 6G4V11N35A IpG Expression Plasmid

The full length IgG1 version of the humanized anti-1L8 variant 6G4V11N35A was made using a dicistronic DHFR-Intron expression vector (Lucas et al., *Nucleic Acids Res.*, 24: 1774–1779 (1996)) which contained the full length recombinant murine-human chimera of the 6G4.2.5 anti-IL8 mAb. The expression plasmid encoding the humanized variant 6G4V11N35A was assembled as follows. First an intermediate plasmid (pSL-3) was made to shuttle the sequence encoding the variable heavy chain of humanized anti-IL-8 variant 6G4V11N35A to pRK56G4chim.2Vh— which contains the variable heavy region of the chimeric 6G4.5 anti-IL8 antibody. The vector pRK56G4chim.Vh was digested with PvuII and ApaI to remove the heavy chain variable region of the chimeric antibody and religated with an 80 bp PvuII-XhoI synthetic oligonucleotide (encoding Leu4 to Phe29 of 6G4V11N35A) (FIG. 47) and a 291 bp XhoI-ApaI fragment from p6G4V11N35A.7 carrying the remainder of the variable heavy chain sequence of 6G4V11N35A to create pSL-3. This intermediate plasmid was used in conjunction with 2 other plasmids, p6G4V11N35A.F(ab')$_2$ and p6G425chim2.choSD, to create the mammalian expression plasmid, p6G4V11N35AchoSD.9 (identified as p6G425V11N35A.choSD in a deposit made on Dec. 16, 1997 with the ATCC and assigned ATCC Accession No. 209552). This expression construct was assembled in a 4-part ligation using the following DNA fragments: a 5,203 bp ClaI-BlpI fragment encoding the regulatory elements of the mammalian expression plasmid (p6G425chim2.choSD), a 451 bp ClaI-ApaI fragment containing the heavy chain variable region of the humanized 6G4V11N35A antibody (pSL-3), a 1,921 bp ApaI-EcoRV fragment carrying the heavy chain constant region of 6G4V11N35A (p6G425chim2.choSD) and a 554 bp EcoRV-BlpI fragment encoding the light chain variable and constant regions of 6G4V11N35A (p6G4V11N35A.F(ab')$_2$). The DNA sequence (SEQ ID NO: 68) of clone p6G4V11N35A.choSD.9 was confirmed by DNA sequencing and is presented in FIG. 48.

Q. Construction of the Full Length Humanized 6G4V11N35E IgG Expression Plasmid A mammalian expression vector for the humanized 6G4V11N35E was made by swapping the light chain variable region of 6G4V11N35A with 6G4V11N35E as follows: a 7,566 bp EcoRV-BlpI fragment (void of the 554 bp fragment encoding the light chain variable region of 6G4V11N35A) from p6G4V11N35A.choSD.9 was ligated to a 554 bp EcoRV-BlpI fragment (encoding the light chain variable region of 6G4V11N35E) from pPH6G4V11N35E.7. The mutation at position N35 of the light chain of p6G4V11N35E.choSD.10 was confirmed by DNA sequencing.

R. Stable CHO Cell Lines for Variants N35A and N35E

For stable expression of the final humanized IgG1 variants (6G4V11N35A and 6G4V11N35E), Chinese hamster ovary (CHO) DP-12 cells were transfected with the above-described dicistronic vectors (p6G4V11N35A.choSD.9 and p6G4V11N35E.choSD.10, respectively) designed to coexpress both heavy and light chains (Lucas et al., *Nucleic Acid Res.* 24:1774–79 (1996)). Plasmids were introduced into CHO DP12 cells via lipofection and selected for growth in GHT-free medium (Chisholm, V. High efficiency gene transfer in mammalian cells. In: Glover, D M, Hames, B D. *DNA Cloning* 4. *Mammalian systems*. Oxford Univ. Press, Oxford pp 1–41 (1996)). Approximately 20 unamplified clones were randomly chosen and reseeded into 96 well plates. Relative specific productivity of each colony was monitored using an ELISA to quantitate the full length human IgG accumulated in each well after 3 days and a fluorescent dye, Calcien AM, as a surrogate marker of viable cell number per well. Based on these data, several unamplified clones were chosen for further amplification in the presence of increasing concentrations of methotrexate. Individual clones surviving at 10, 50, and 100 nM methotrexate were chosen and transferred to 96 well plates for productivity screening: One clone for each antibody (clone#1933 aIL8.92 NB 28605/12 for 6G4V11N35A; clone#1934 aIL8.42 NB 28605/14 for 6G4V11N35E), which reproducibly exhibited high specific productivity, was expanded in T-flasks and used to inoculate a spinner culture. After several passages, the suspension-adapted cells were used to inoculate production cultures in GHT-containing, serum-free media supplemented with various hormones and protein hydrolysates. Harvested cell culture fluid containing recombinant humanized anti-IL8 was purified using protein A-Sepharose CL-4B. The purity after this step was approximately 99%. Subsequent purification to homogeneity was carried out using an ion exchange chromatography step. Production titer of the humanized 6G4V11N35E IgG1 antibody after the first round of amplification and 6G4V11N35A IgG1 after the second round of amplification were 250 mg/L and 150 mg/L, respectively.

S. Characterization of the Humanized 6G4V11N35A/E IgG Variants

Figure 50B:
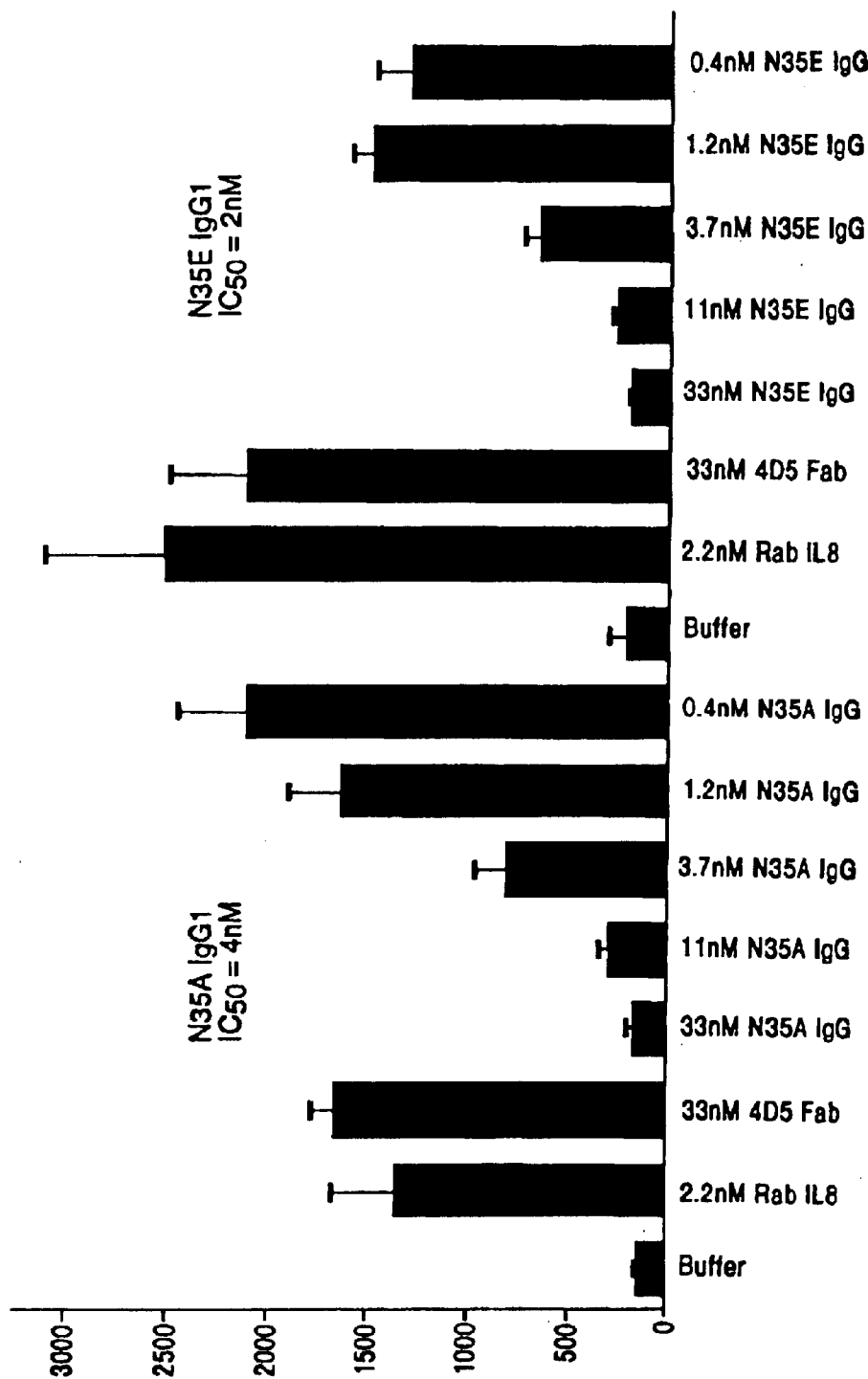

The humanized full length IgG variants of 6G4.2.5 were tested for their ability to inhibit $^{125}$I-IL-8 binding and to neutralize activation of human neutrophils; the procedures are described in Sections (B)(1) and (B)(2) above. As shown in FIG. 49, the full length IgG1 forms of variants 6G4V11N35A and 6G4V11N35E equally inhibited $^{125}$I-IL-8 binding to human neutrophils with approximate IC$_{50}$'s of 0.3 nM and 0.5 nM, respectively. This represents a 15–25 fold improvement in blocking binding of IL-8 compared to the full length murine mAb (IC$_{50}$ =7.5 nM). Similarly, the two anti-IL-8 variants showed equivalent neutralizing capabilities with respect to inhibiting IL-8 mediated human neutrophil chemotaxis (FIGS. 50A–50B). The IC$_{50}$'s of 6G4V11N35A IgG1 and 6G4V11N35E IgG1 for human IL-8 were 4.0 nM and 6.0 nM, respectively, and for rabbit IL-8 were 4.0 nM and 2.0 nM, respectively. The irrelevant isotype control Fab (4D5) did not inhibit neutrophil migration.

Figure 51:
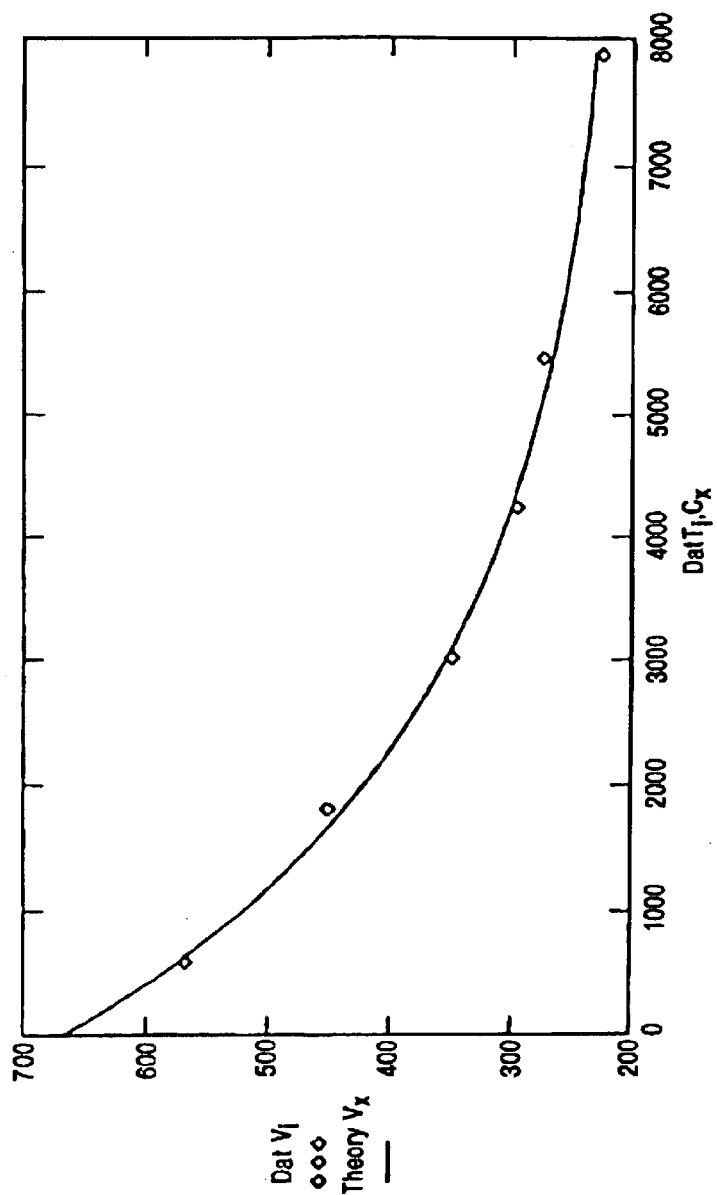
FIG. 51 contains a graph depicting the typical kinetics of a full length anti-IL8 antibody (6G4V11N35A IgG1) binding to IL-8.
Figure 52A:
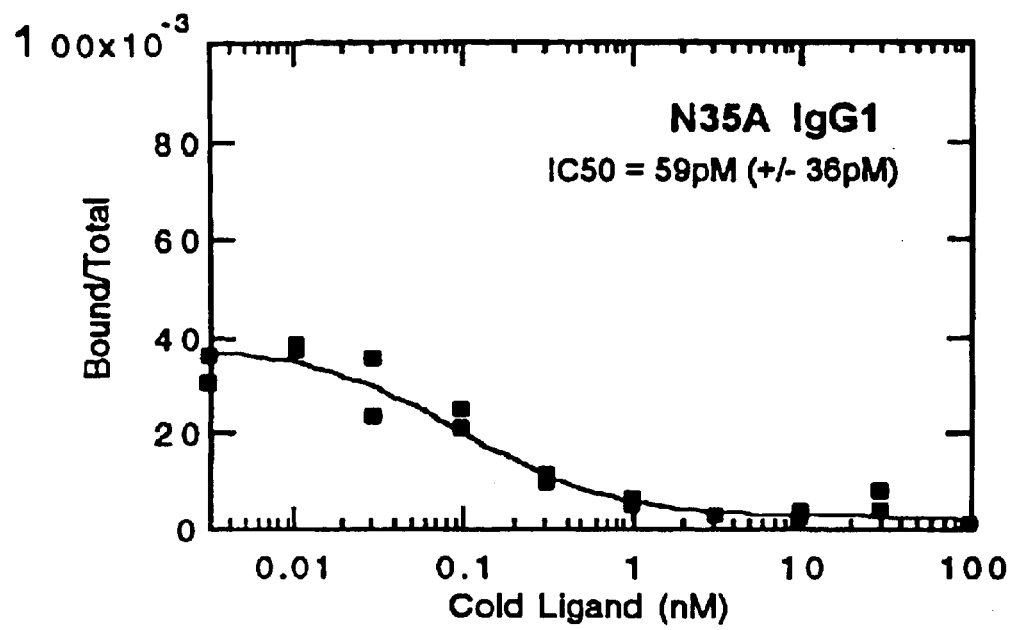
FIG. 52 contains graphs of displacement curves depicting the results of an unlabeled IL-8/$^{125}$I-IL-8 competition radioimmunoassay performed with full length 6G4V11N35A IgG1 and 6G4V11N35E IgG1.
Figure 52B:
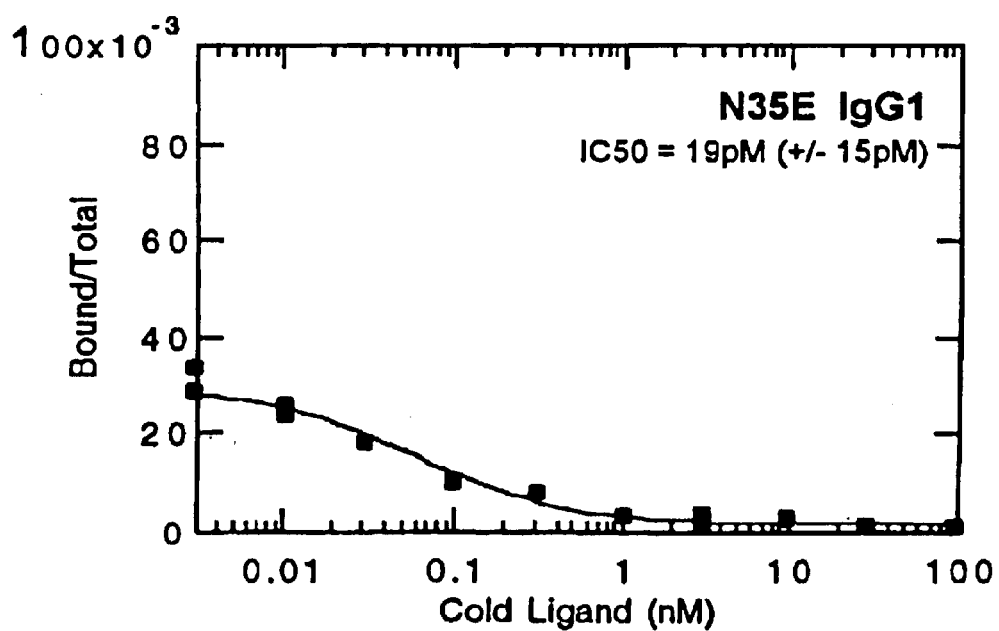

The affinity for IL-8 of these variants relative to the murine 6G4.2.5 mAb was determined using KinExA as described in Section (M). FIG. 51 shows the equilibrium constant (Kd) for the full length affinity matured variants 6G4V11N35E IgG1 and 6G4V11N35A IgG1 were approximately 49 pM and 88 pM, respectively. The Kd for 6G4V11N35A IgG1 was determined directly from the kinetic experiment. As reported with their respective Fabs, this improvement in affinity might be attributed to an approximate 2-fold increase in the on-rate of 6G4V11N35E IgG1 (ka=3.0×10$^6$) compared to that of 6G4V11N35A IgG1 (ka 8.7×10$^5$). In addition, these results were confirmed by a competition radio-immune assay using iodinated human IL-8. 50 pM of 6G4V11N35A IgG1 or 6G4V11N35E IgG1 was incubated for 2 hours at 25° C. with 30–50 pM of $^{125}$I-IL-8 and varying concentrations (0 to 100 nM) of unlabeled IL-8. The antibody-antigen mixture was then incubated for 1 hour at 4 C with 10 ul of a 70% slurry of Protein-A beads (pre-blocked with 0.1% BSA). The beads were briefly spun in a microcentrifuge and the supernatant discarded to remove the unbound $^{125}$I-IL-8. The amount of $^{125}$I-IL-8 specifically bound to the anti-IL-8 antibodies was determined by counting the protein-A pellets in a gamma counter. The approximate Kd values were similar to those determined by KinEXA. The average Kd for 6G4V11N35A IgG1 and 6G4V11N35E IgG1 were 54 pM (18–90 pM) and 19 pM (5–34 pM), respectively (FIG. 52).

T. Construction of Humanized 6G4V11N35A/E Fab's for Modification by Polyethylene Glycol A Fab' expression vector for 6G4V11N35A was constructed by digesting p6G4V11N35A.F(ab')$_2$ with the restriction enzymes ApaI and NdeI to remove the 2805 bp fragment encoding the human IgG1constant domain fused with the yeast GCN4 leucine zipper and replacing it with the 2683 bp ApaI-NdeI fragment from the plasmid pcDNA.18 described in Eigenbrot et al., *Proteins: Struct. Funct. Genet.*, 18: 49–62 (1994). The pcDNA.18 ApaI-NdeI fragment carries the coding sequence for the human constant IgG1 heavy domain, including the free cysteine in the hinge region that was used to attach the PEG molecule. The 3758 bp ApaI-NdeI fragment (encodes the light chain and heavy variable domain of 6G4V11N35A) isolated from p6G4V11N35A.F(ab')$_2$ was ligated to the 2683 bp ApaI-NdeI fragment of pcDNA.18 to create p6G4V11N35A.PEG-1. The integrity of the entire coding sequence was confirmed by DNA sequencing. The nucleotide and translated amino acid sequences of heavy chain constant domain with the cysteine in the hinge are presented in FIG. 53.

A Fab' expression plasmid for 6G4V11N35E was made similarly by digesting pPH6G4V11N35E (from Section (O) above) with the restriction enzymes ApaI and NdeI to isolate the 3758 bp ApaI-NdeI DNA fragment carrying the intact light chain and heavy variable domain of 6G4V11N35E and ligating it to the 2683 bp ApaI-NdeI DNA fragment from p6G4V11N35A.PEG-1 to create p6G4V11N35E.PEG-3. The integrity of the entire coding sequence was confirmed by DNA sequencing.

Anti-IL-8 6G4V11N35A Fab' variant was modified with 20 kD linear methoxy-PEG-maleimide, 30 kD linear methoxy-PEG-maleimide, 40 kD linear methoxy-PEG-maleimide, or 40 kD branched methoxy-PEG-maleimide as described below. All PEG's used were obtained commercially from Shearwater Polymers, Inc.

a. Materials and Methods

Fab'-SH Purification

A Fab'-SH antibody fragment of the affinity matured antibody 6G4V11N35A was expressed in *E. coli* grown to high cell density in the fermentor as described by Carter et al., *Bio/Technology* 10, 163–167 (1992). Preparation of Fab'-SH fragments was accomplished by protecting the Fab'-SH fragments with 4',4'-dithiodipyridine (PDS), partially purifying the protected Fab'-PDS fragments, deprotect the Fab'-PDS with dithiothreitol (DTT) and finally isolate the free Fab'-SH by using gel permeation chromatography.

Protection of Fab'-SH with PDS

Fermentation paste samples were dissolved in 3 volumes of 20 mM MES, 5 mM EDTA, pH 6.0 containing 10.7 mg of 4',4'-dithiodipyridine per gram fermentation paste, resulting in a suspension with a pH close to 6.0 The suspension was passed through a homogenizer followed by addition of 5% PEI (w/v), pH 6 to the homogenate to a final concentration of 0.25%. The mixture was then centrifuged to remove solids and the clear supernatant was conditioned to a conductivity of less than 3 mS by the addition of cold water.

Partial Purification of the Fab'-SH Molecule Using Ion Exchange Chromatography

The conditioned supernatant was loaded onto an ABX (Baker) column equilibrated in 20 mM MES, pH 6.0. The column was washed with the equilibration buffer followed by elution of the Fab'-SH with a 15 column volume linear gradient from 20 mM MES, pH 6.0 to 20 mM MES, 350 mM sodium chloride. The column was monitored by absorbance at 280nm, and the eluate was collected in fractions.

Deprotection of the Fab'-SH Antibody Fragments with DTT

The pH of the ABX pool was adjusted to 4.0 by the addition of dilute HCl. The pH adjusted solution was then deprotected by adding DTT to a final concentration of 0.2 mM. The solution was incubated for about 30 minutes and then applied to a gel filtration Sephadex G25 column, equilibrated with 15 mM sodium phosphate, 25 mM MES, pH 4.0. After elution, the pH of the pool was raised to pH 5.5 and immediately flash frozen at −70° C. for storage or derivatized with PEG-MAL as described below.

Alternative Fab'-SH Purification

Alternatively Fab'-SH fragments can be purified using the following procedure. 100 g fermentation paste is thawed in the presence of 200 ml 50 mM acetic acid, pH 2.8, 2 mM EDTA, 1 mM PMSF. After mixing vigorously for 30 min at room temperature, the extract is incubated with 100 mg hen egg white lysozyme. DEAE fast flow resin (approximately 100 mL) is equilibrated with 10 mM MES, pH 5.5, 1 mM EDTA on a sintered glass funnel. The osmotic shock extract containing the Fab'-SH fragment is then filtered through the resin.

A protein G Sepharose column is equilibrated with 10 mM MES, pH 5.5, 1 mM EDTA and then loaded with the DEAE flow-through sample. The column is washed followed by three 4 column volume washes with 10 mM MES, pH 5.5, 1 mM EDTA. The Fab'-SH antibody fragment containing a free thiol is eluted from the column with 100 mM acetic acid, pH 2.8, 1 mM EDTA. After elution, the pH of the pool is raised to pH 5.5 and immediately flash frozen at −70° C. for storage or derivatized with PEG-MAL as described below.

Preparation of Fab'-S-PEG

The free thiol content of the Fab'-SH preparation obtained as described above was determined by reaction with 5,5'-dithiobis(2-nitrobenzoic acid) (DTNB) analysis according to the method of Creighton in *Protein Structure: A Practical Approach*, Creighton, T. E., ed, IRL Press (Oxford, UK: 1990), pp. 155–167. The concentration of free thiol was calculated from the increase on absorbance at 412 nm, using $e_{412}=14,150$ cm$^{-1}$ M$^{-1}$ for the thionitrobenzoate anion and a $M_r=48,690$ and $e_{280}=1.5$ for the Fab'-SH antibody. To the Fab'-SH protein G Sepharose pool, or the deprotected Fab'-SH gel permeation pool, 5 molar equivalents of PEG-MAL were added and the pH was immediately adjusted to pH 6.5 with 10% NaOH.

The Fab'-S-PEG was purified using a 2.5×20 cm cation exchange column (Poros 50-HS). The column was equilibrated with a buffer containing 20 mM MES, pH 5.5. The coupling reaction containing the PEGylated antibody fragment was diluted with deionized water to a conductivity of approximately 2.0 mS. The conditioned coupling reaction was then loaded onto the equilibrated Poros 50 HS column. Unreacted PEG-MAL was washed from the column with 2 column volumes of 20 mM MES, pH 5.5. The Fab'-S-PEG was eluted from the column using a linear gradient from 0 to 400 mM NaCl, in 20 mM MES pH 5.5, over 15 column volumes.

Alternatively a Bakerbond ABX column can be used to purify the Fab'-S-PEG molecule. The column is equilibrated with 20 mM MES, pH 6.0 (Buffer A). The coupling reaction is diluted with deionized water until the conductivity equaled that of the Buffer A (approximately 2.0 mS) and loaded onto the column. Unreacted PEG-MAL is washed from the column with 2 column volumes of 20 mM MES, pH 6.0. The Fab'-S-PEG is eluted from the column using a linear gradient from 0 to 100 mM (NH$_4$SO$_4$, in 20 mM MES pH 6.0, over 15 column volumes.

Size Exclusion Chromatography

The hydrodynamic or effective size of each molecule was determined using a Pharmacia Superose-6 HR 10/30 column (10×300 mm). The mobile phase was 200 mM NaCl, 50 mM sodium phosphate pH 6.0. Flow rate was at 0.5 ml/min and the column was kept at ambient temperature. Absorbance at 280 nm was monitored where PEG contributed little signal. Biorad MW standards containing cyanocobalamin, myoglobin, ovalbumin, IgG, Thyroglobulin monomer and dimer were used to generate a standard curve from which the effective size of the pegylated species was estimated.

b. Results

Size Exclusion Chromatography

Figure 60:
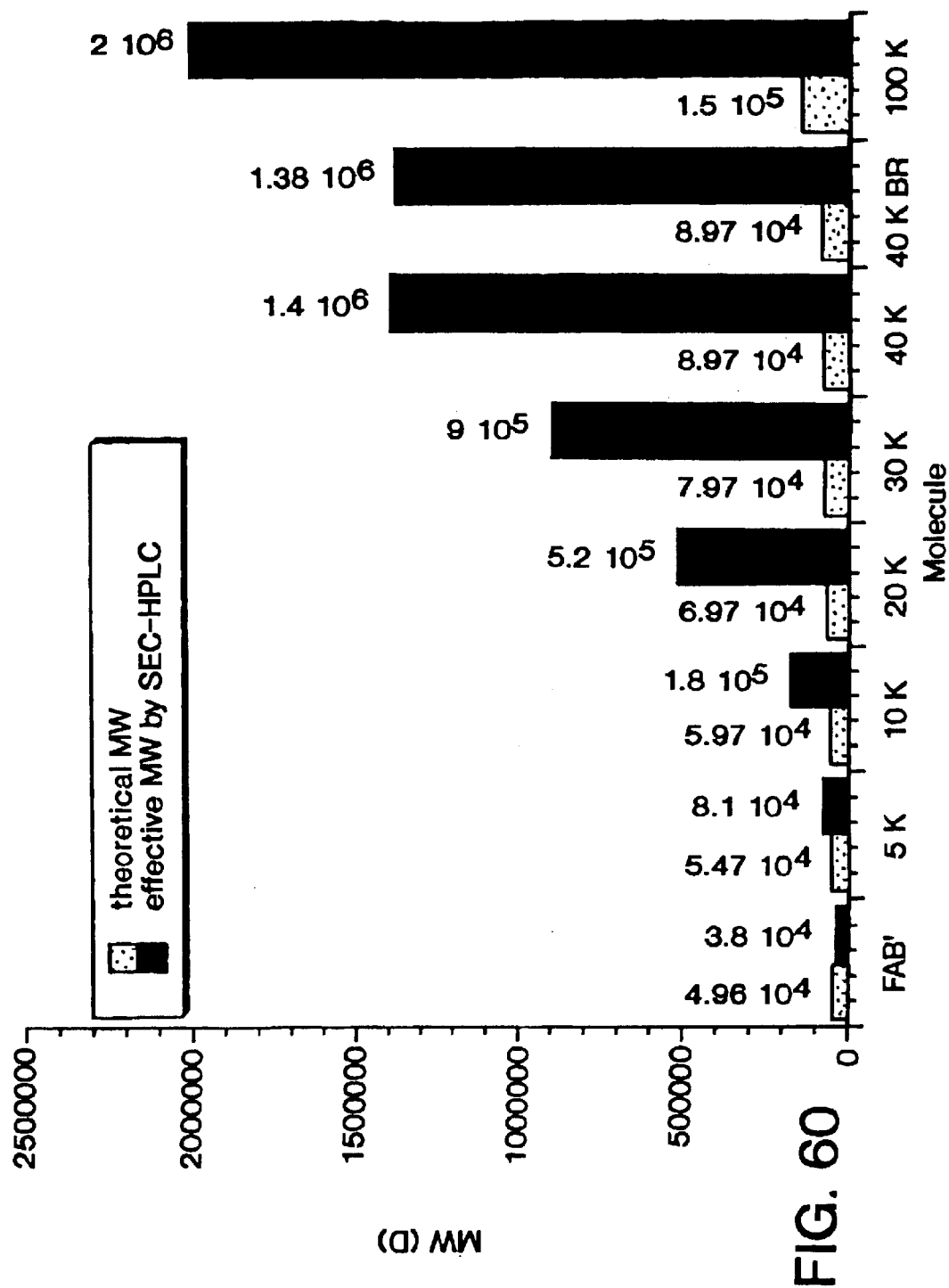
FIG. 60 is a graph depicting the theoretical molecular weight (dotted bars) and effective size (solid bars) of PEG-maleimide modified 6G4V11N35A Fab' molecules as determined by SEC-HPLC.

The effective size of each modified species was characterized using size exclusion chromatography. The results are shown in FIG. 60 below. The theoretical molecular weight of the anti-IL8 Fab fragments modified with PEG 5 kD, 10 kD, 20 kD, 30 kD, 40 kD (linear), 40 kD (branched) or 100,000 kD is shown along with the apparent molecular weight of the PEGylated fragments obtained by HPLC size exclusion chromatography. When compared to the theoretical molecular weight of the Fab'-S-PEG fragments, the apparent molecular weight (calculated by size exclusion HPLC) increases dramatically by increasing the size of the PEG attached to the fragments. Attachment of a small molecular weight PEG, for example PEG 10,000 D only increases the theoretical molecular weight of the PEGylated antibody fragment (59,700 D) by 3 fold to an apparent molecular weight of 180,000 D. In contrast attachment of a larger molecular weight PEG for example 100,000 D PEG to the antibody fragment increases the theoretical molecular weight of the PEGylated antibody fragment (158,700 D) by 12 fold to an apparent molecular weight of 2,000,000 D.

SDS-PAGE

Figure 61A:
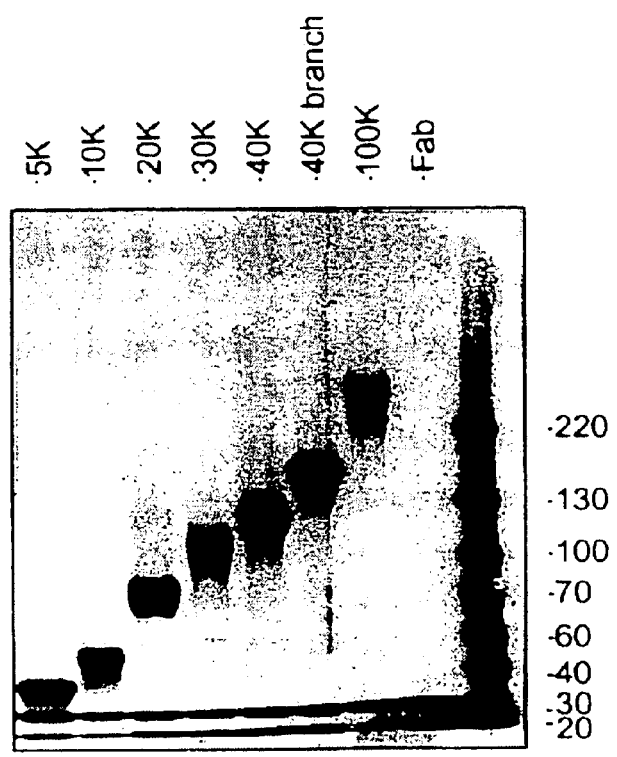
FIG. 61 is an SDS-PAGE gel depicting the electrophoretic mobility of various PEG-maleimide modified 6G4V11N35A Fab' molecules.
Figure 61B:
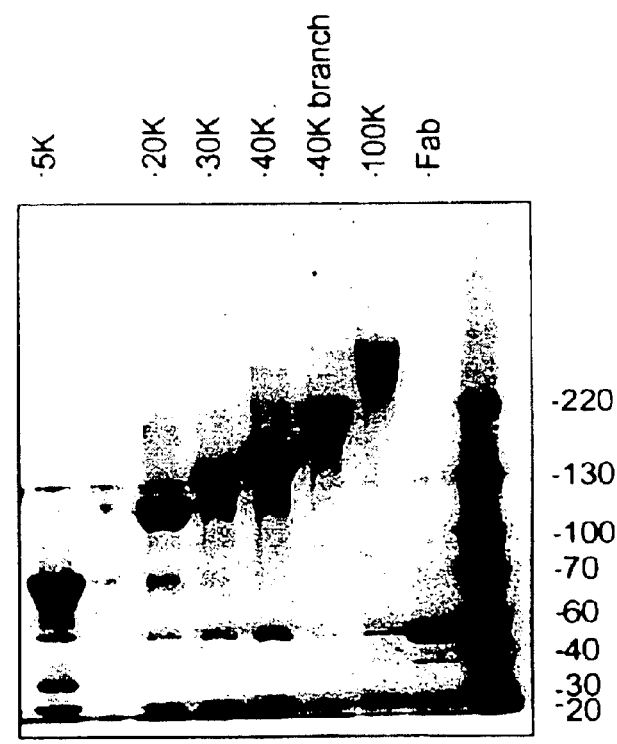

In FIG. 61, the upper panel shows the size of the anti-IL-8 Fab fragments modified with PEG of molecular weight 5 kD (linear), 10 kD (linear), 20 kD (linear), 30 kD (linear), 40 kD (linear), 40 kD (branched) or 100 kD (linear) under reduced conditions. The unmodified Fab is shown in lane 2 from right to left. Both the heavy and light chains of the Fab had a molecular weight of approximately 30 kD as determined by PAGE. Each PEGylated fragment sample produced two bands: (1) a first band (attributed to the light chain) exhibiting a molecular weight of 30 kD; and (2) a second band (attributed to the heavy chain to which the PEG is attached specifically at the hinge SH) exhibiting increasing molecular weights of 40, 45, 70, 110, 125, 150 and 300 kD. This result suggested that PEGylation was specifically restricted to the heavy chain of the Fab's whereas the light chain remained unmodified.

The lower panel is non-reduced PAGE showing the size of the anti-IL-8 Fab fragments modified with PEG of molecular weight 5 kD (linear), 20 kD (linear), 30 kD (linear), 40 kD (linear), 40 kD (branched), or 100 kD (linear). The PEGylated fragments exhibited molecular weights of approximately 70 kD, 115 kD, 120 kD, 140 kD, 200 kD and 300 kD.

The SDS PAGE gels confirm that all Fab'-S-PEG molecules were purified to homogeneity and that the molecules differed only with respect to the size of the PEG molecule attached to them.

U. Amine Specific Pegylation of Anti-IL-8 F(ab')₂ Fragments

Pegylated F(ab')₂ species were generated by using large MW or branched PEGs in order to achieve a large effective size with minimal protein modification which might affect activity. Modification involved N-hydroxysuccinamide chemistry which reacts with primary amines (lysines and the N-terminus). To decrease the probability of modifying the N-terminus, which is in close proximity to the CDR region, a reaction pH of 8, rather than the commonly used pH of 7, was employed. At pH 8.0, the amount of the reactive species (charged $NH_3^+$) would be considerably more for the $\epsilon$-NH2 group of lysines ($pK_a$=10.3) than for the $\alpha$-NH2 group ($pK_a$ of approximately 7) of the amino-terminus. For the linear PEGs, a methoxy-succinimidyl derivative of an NHS-PEG was used because of the significantly longer half-life in solution (17 minutes at 25° C. at pH 8.0) compared to the NHS esters of PEGs (which have 5–7 minute half life under the above conditions). By using a PEG that is less prone to hydrolysis, a greater extent of modification is achieved with less PEG. Branched PEGs were used to induce a large increase in effective size of the antibody fragments.

a. Materials

All PEG reagents were purchased from Shearwater Polymers and stored at −70° C. in a desiccator: branched N-hydroxysuccinamide-PEG (PEG2-NHS-40 kDa) has a 20 kDa PEG on each of the two branches, methoxy-succinimidyl-propionic acid-PEG (M-SPA-20000) is a linear PEG molecule with 20 kDa PEG. Protein was recombinantly produced in E. coli and purified as a (Fab)'₂ as described in Sections (K) and (O) above.

b. Methods

IEX method: A J. T. Baker Wide-Pore Carboxy-sulfone (CSX), 5 micron, 7.75×100 mm HPLC column was used for fractionation of the different pegylated products, taking advantage of the difference in charge as the lysines are modified. The column was heated at 40° C. A gradient as shown in Table 7 below was used where Buffer A was 25 mM sodium Borate/25 mM sodium phosphate pH 6.0, and Buffer B was 1 M ammonium sulfate, and Buffer C was 50 mM sodium acetate pH 5.0.

TABLE 7

| Time (min) | % B | % C | flow mL/min |
|---|---|---|---|
| 0 | 10 | 10 | 1.5 |
| 20 | 18 | 7.5 | 1.5 |
| 25 | 25 | 7.5 | 1.5 |
| 27 | 70 | 3.0 | 2.5 |
| 29 | 70 | 3.0 | 2.5 |
| 30 | 10 | 10 | 2.5 |
| 33 | 10 | 10 | 2.5 |

SEC-HPLC: The hydrodynamic or effective size of each molecule was determined using a Pharmacia Superose-6 HR 10/30 column (10×300 mm). The mobile phase was 200 mM NaCl, 50 mM sodium phosphate pH 6.0. Flow rate was at 0.5 ml/min and the column was kept at ambient temperature. Absorbance at 280 nm was monitored where PEG contributed little signal. Biorad MW standards containing cyanocobalamin, myoglobin, ovalbumin, IgG, Thyroglobulin monomer and dimer were used to generate a standard curve from which the effective size of the pegylated species was estimated.

SEC-HPLC-Light Scattering: For determination of the exact molecular weight, this column was connected to an on-line light scattering detector (Wyatt Minidawn) equipped with three detection angles of 50°, 90°, and 135° C. A refractive index detector (Wyatt) was also placed on-line to determine concentration. All buffers were filtered with Millipore $0.1\mu$ filters; in addition al $0.02\mu$ Whatman Anodisc 47 was placed on-line prior to the column.

The intensity of scattered light is directly proportional to the molecular weight (M) of the scattering species, independent of shape, according to:

$$M = R_O/K \cdot c$$

where $R_O$ is the Rayleigh ratio, K is an optical constant relating to the refractive index of the solvent, the wavelength of the incident light, and dn/dc, the differential refractive index between the solvent and the solute with respect to the change in solute concentration, c. The system was calibrated with toluene ($R_0$ of $1.406 \times 10^{-5}$ at 632.8 nm); a dn/dc of 0.18, and an extinction coefficient of 1.2 was used. The system had a mass accuracy of ~5%.

SDS-PAGE: 4–12% Tris-Glycine Novex minigels were used along with the Novex supplied Tris-Glycine running buffers. 10–20 ug of protein was applied in each well and the gels were run in a cold box at 150 mV/gel for 45 minutes. Gels were then stained with colloidal Coomassie Blue (Novex) and then washed with water for a few hours and then preserved and dried in drying buffer (Novex).

Preparation of a linear(1)20 KDa-(N)-(Fab')2: A 4 mg/ml solution of anti-IL8 formulated initially in a pH 5.5 buffer was dialyzed overnight against a pH 8.0 sodium phosphate buffer. 5 mL protein was mixed at a molar ratio of 3:1. The reaction was carried out in a 15 mL polypropylene Falcon tube and the PEG was added while vortexing the sample at low speed for 5 seconds. It was then placed on a nutator for 30 minutes. The extent of modification was evaluated by SDS-PAGE. The whole 5 ml reaction mixture was injected on the IEX for removal of any unreacted PEG and purification of singly or doubly pegylated species. The above reaction generated a mixture of 50% singly-labeled anti-IL8. The other 50% unreacted anti-IL8 was recycled through the pegylation/purification steps. The pooled pegylated product was dialyzed against a pH 5.5 buffer for in vitro assays and animal PK studies. Endotoxin levels were measured before administration to animals or for the cell based assays. Levels were below 0.5 eu/ml. The fractions were also run on SDS-PAGE to confirm homogeneity. Concentration of the final product was assessed by absorbance at 280 nm using an extinction coefficient of 1.34, as well as by amino acid analysis.

Preparation of a branched(1)40 KDa-(N)-(Fab')2: A 4 mg/mL solution of anti-IL8 (Fab')₂ formulated in a pH 5.5 buffer was dialyzed overnight against a pH 8.0 phosphate buffer. Solid PEG powder was added to 5 mL protein in two aliquots to give a final PEG:protein molar ratio of 6:1. Each solid PEG aliquot was added to the protein in a 15 mL polypropylene Falcon tube while vortexing at low speed for 5 sec, and then placing the sample on a nutator for 15 minutes. The extent of modification was evaluated by SDS-PAGE using a 4–12% Tris-Glycine (Novex) gel and stained with colloidal Coomasie blue (Novex). The 5 mL PEG-protein mixture was injected on the ion exchange column for removal of any unreacted PEG. The above reaction generated a mixture of unreacted (37%), singly-labelled (45%), doubly and triply-labeled (18%) species. These were the optimal conditions for obtaining the greatest recovery of the protein with only 1 PEG per antibody rather than the higher molecular weight adducts. The unmodified anti-IL8 was recycled. The pegylated products were separated and fractionated in falcon tubes and then dialyzed against a pH 5.5 buffer for assays and animal PK studies. Endotoxin levels were below 0.5 eu/ml. The fractions were also run on SDS-PAGE to confirm homogeneity. The concentration of the final product was assessed by absorbance at 280 nm using an extinction coefficient of 1.34, as well as by amino acid analysis.

Preparation of branched(2)-40 KDa-(N)(Fab')2: This molecule was most efficiently made by adding three times in 15 minute intervals a 3:1 molar ratio of PEG to the already modified branched(1)-40 KDa-(N)-(Fab')2. The molecule was purified on IEX as 50% branched(2)-40 KDa-(N)-(Fab')2. The unmodified molecule was recycled until ~20 mg protein was isolated for animal PK studies. The product was characterized by SEC-light scattering and SDS-PAGE.

c. Results

Figure 62:
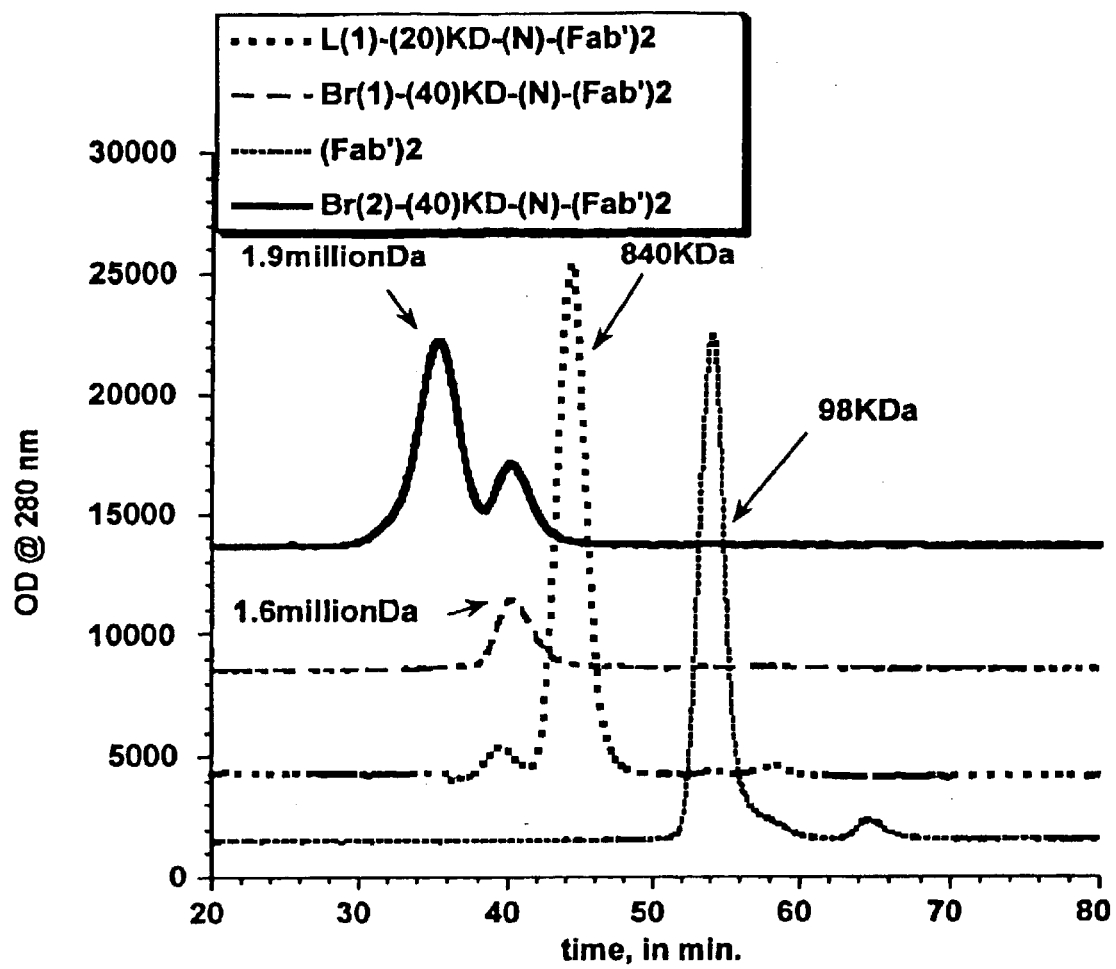
FIG. 62 contains size exclusion chromatograms (SEC-HPLC) depicting the retention times and effective (hydrodynamic) sizes of various PEG-succinimide modified 6G4V11N35A F(ab')$_2$ molecules.

PEGs increased the hydrodynamic or effective size of the product significantly as determined by gel filtration (SEC-HPLC). FIG. 62 shows the SEC profile of the pegylated F(ab')₂ species with UV detection at 280 nm. The hydrodynamic size of each molecule was estimated by reference to the standard MW calibrators. As summarized in FIG. 62, the increase in the effective size of (Fab')₂ was about 7-fold by adding one linear 20 kDa PEG molecule and about 11-fold by adding one branched ("Br(1)") 40 kDa PEG molecule, and somewhat more with addition of two branched ("Br(2)") PEG molecules.

Figure 63:
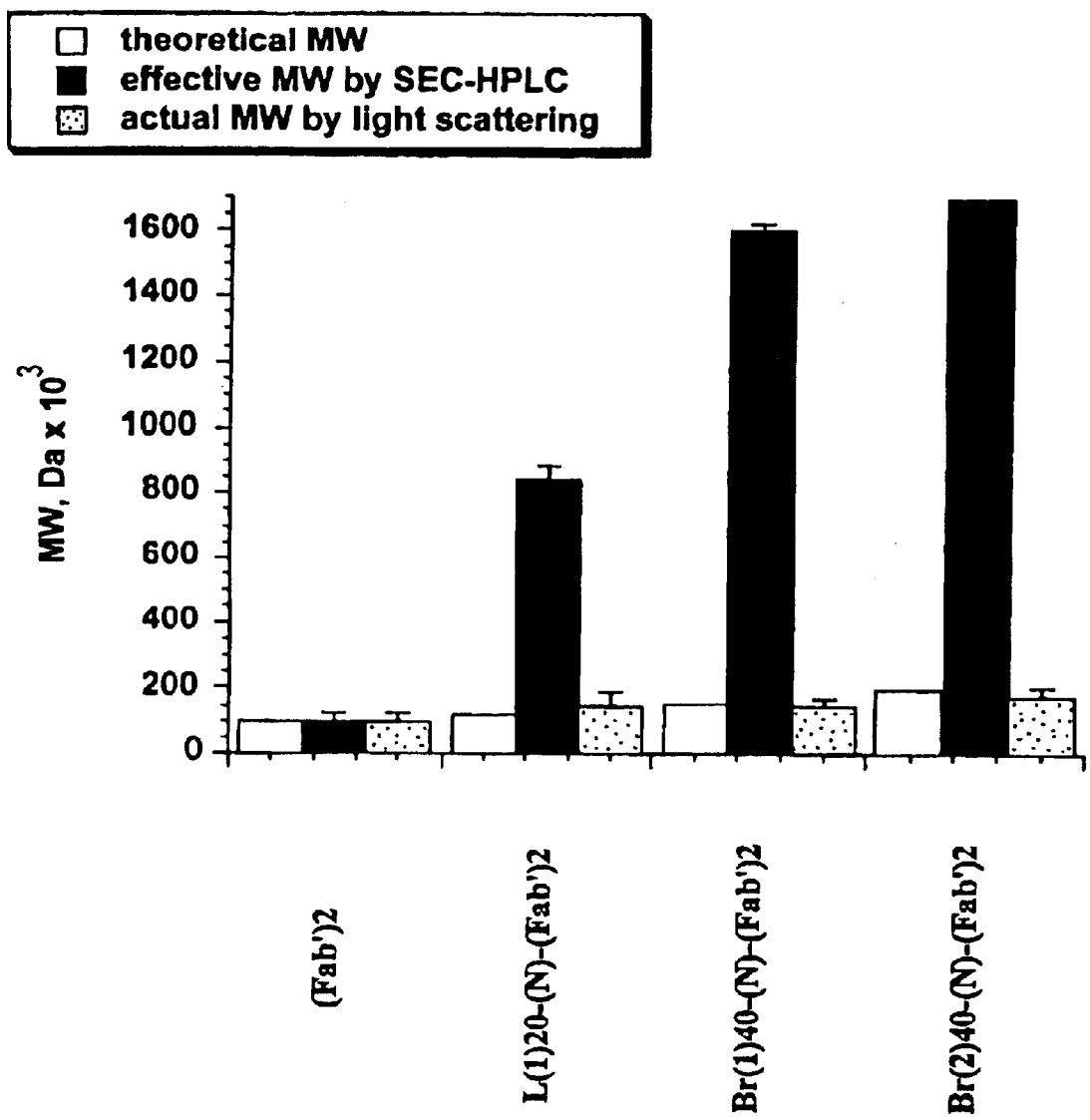
FIG. 63 is a graph depicting the theoretical molecular weight (open columns), effective size determined by SEC-HPLC (solid columns), and the actual molecular weight determined by SEC-light scattering (shaded columns) for various PEG-succinimide modified 6G4V11N35A F(ab')$_2$ molecules.
Figure 64:
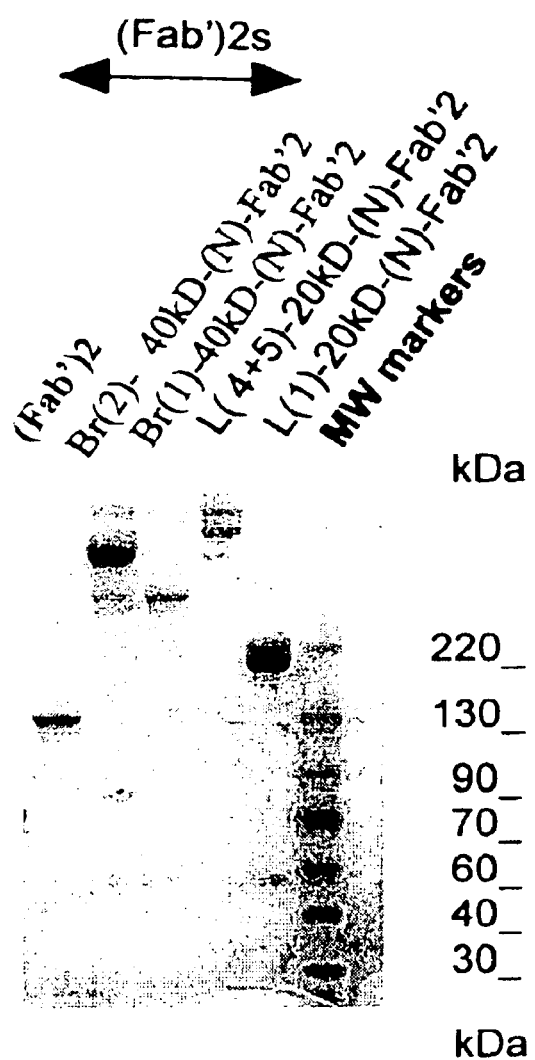
FIG. 64 is an SDS-PAGE gel depicting the electrophoretic mobility of various PEG-succinimide modified 6G4V11N35A F(ab')$_2$ molecules. From left to right, lane 1 contains unmodified F(ab'), lane 2 contains F(ab')$_2$ coupled to two 40 kD branched PEG-succinimide molecules (denoted "Br(2)-40 kD(N)-F(ab')2"), lane 3 contains F(ab')$_2$ coupled to one 40 kD branched PEG-succinimide molecule (denoted "Br(1)-40 kD-(N)-Fab'2"), lane 4 contains a mixture of F(ab')$_2$ coupled to four 20 kD linear PEG-succinimide molecules and F(ab')$_2$ coupled to five 20 kD linear PEG-succinimide molecules (denoted "L(4+5)-20 kD-(N)-Fab'2"), lane 5 contains F(ab')$_2$ coupled to one 20 kD linear PEG-succinimide molecule (denoted "L(1)-20 kD-(N)-Fab'2"), and lane 6 contains molecular weight standards.

Light scattering detection gave the exact molecular weight of the products and confirmed the extent of modification (FIG. 63). The homogeneity of the purified material was shown by SDS-PAGE (FIG. 64). Underivatized F(ab')₂ migrated as a 120 kDa species, the linear(1)20 KD-(N)-F(ab')₂ migrated as a band at 220 kDa, the Br(1)40 KD(N)-F(ab')₂ migrated as one major band at 400 kDa, and the Br(2)40 KD-(N)-F(ab')₂ migrated as a major band at around 500 kDa The proteins appeared somewhat larger than their absolute MW due to the steric effect of PEG.

V. In Vitro Activity Characterization of PEG Modified Fab' Fragments of 6G4V11N35A (Maleimide Coupling Method)

Figure 54A:
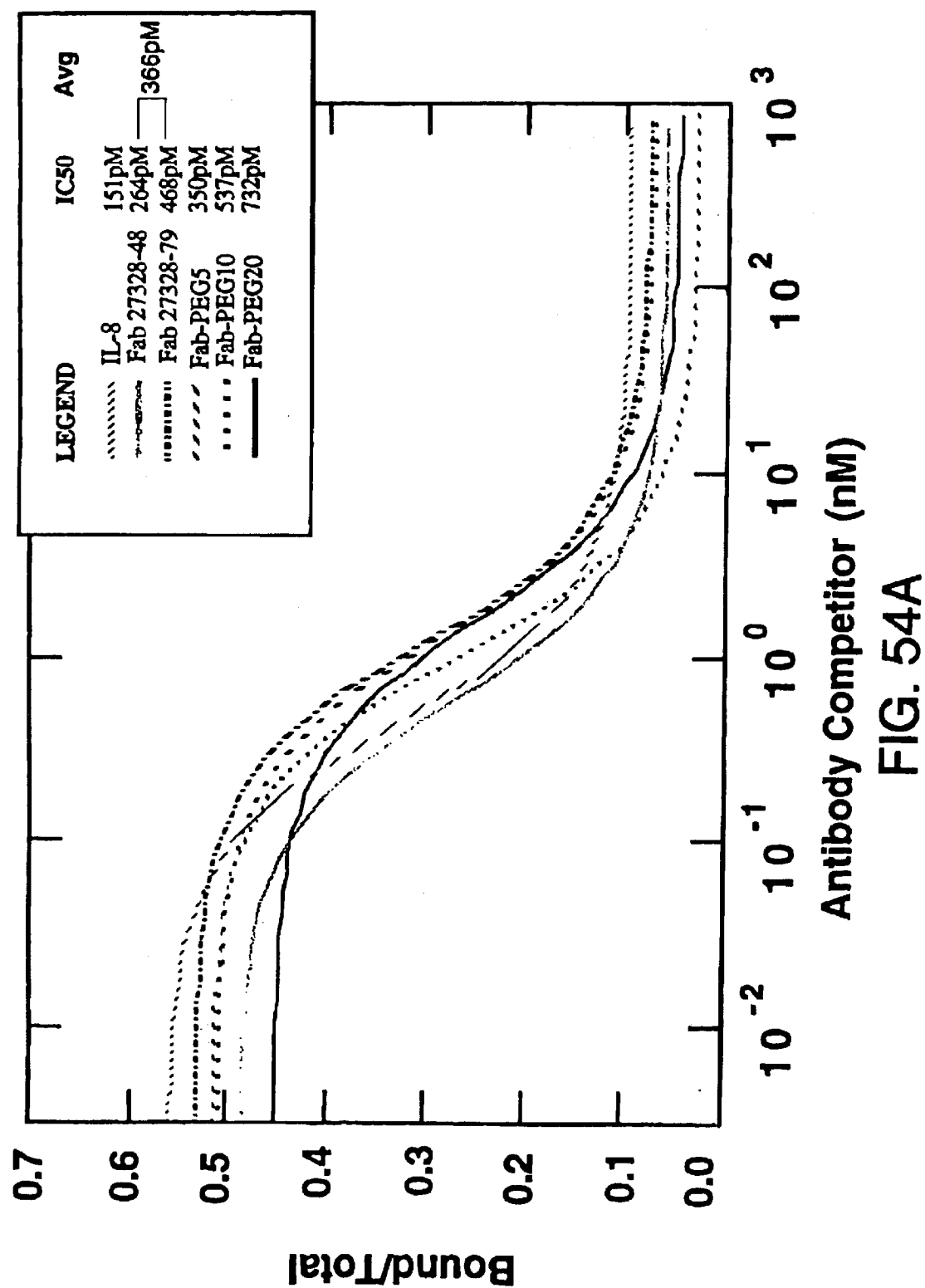
FIGS. 54A–54C contain graphs of displacement curves depicting the IL-8 binding and $IC_{50}$'s for PEG-maleimide modified 6G4V11N35A Fab' molecules.
Figure 54B:
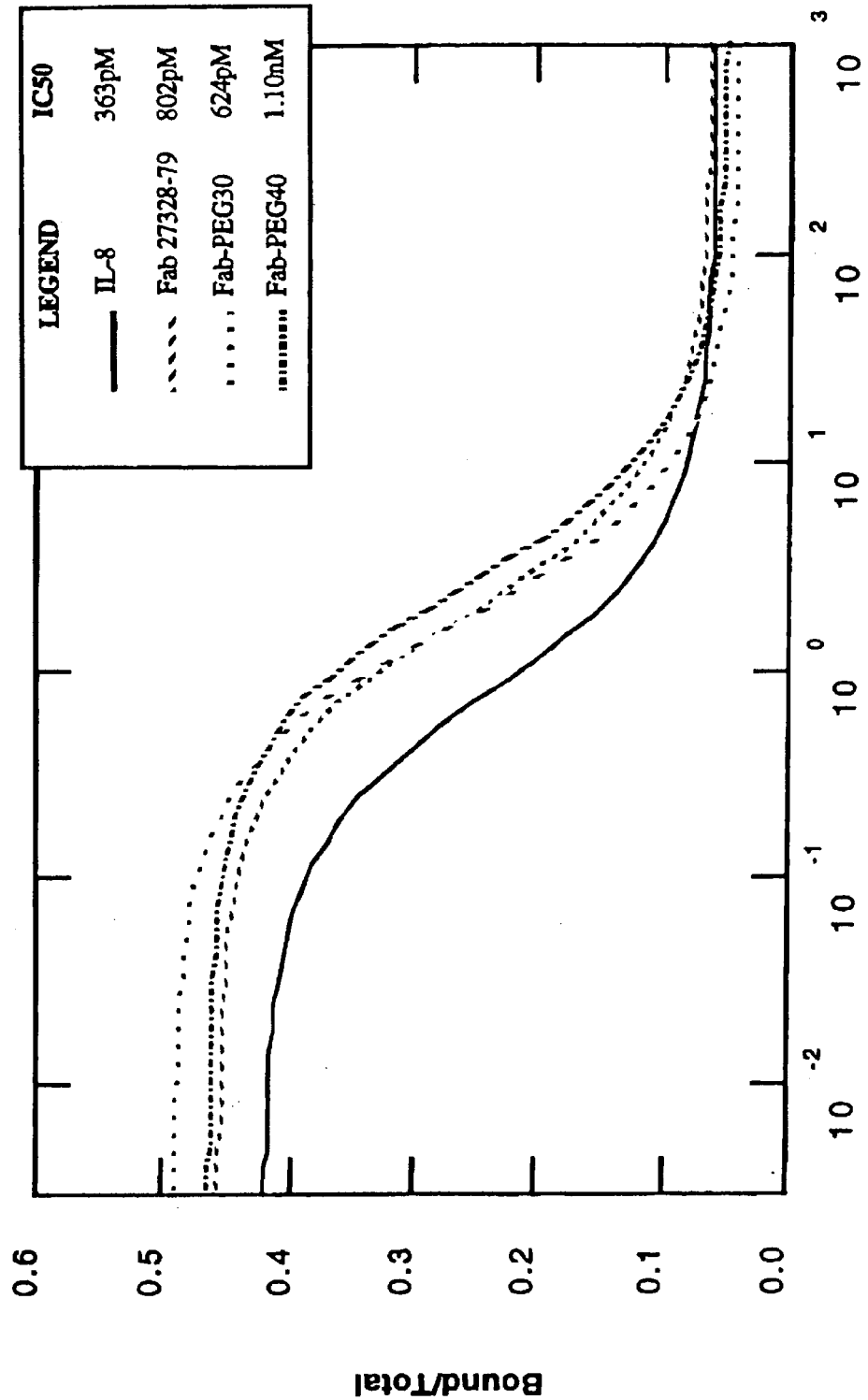
Figure 54C:
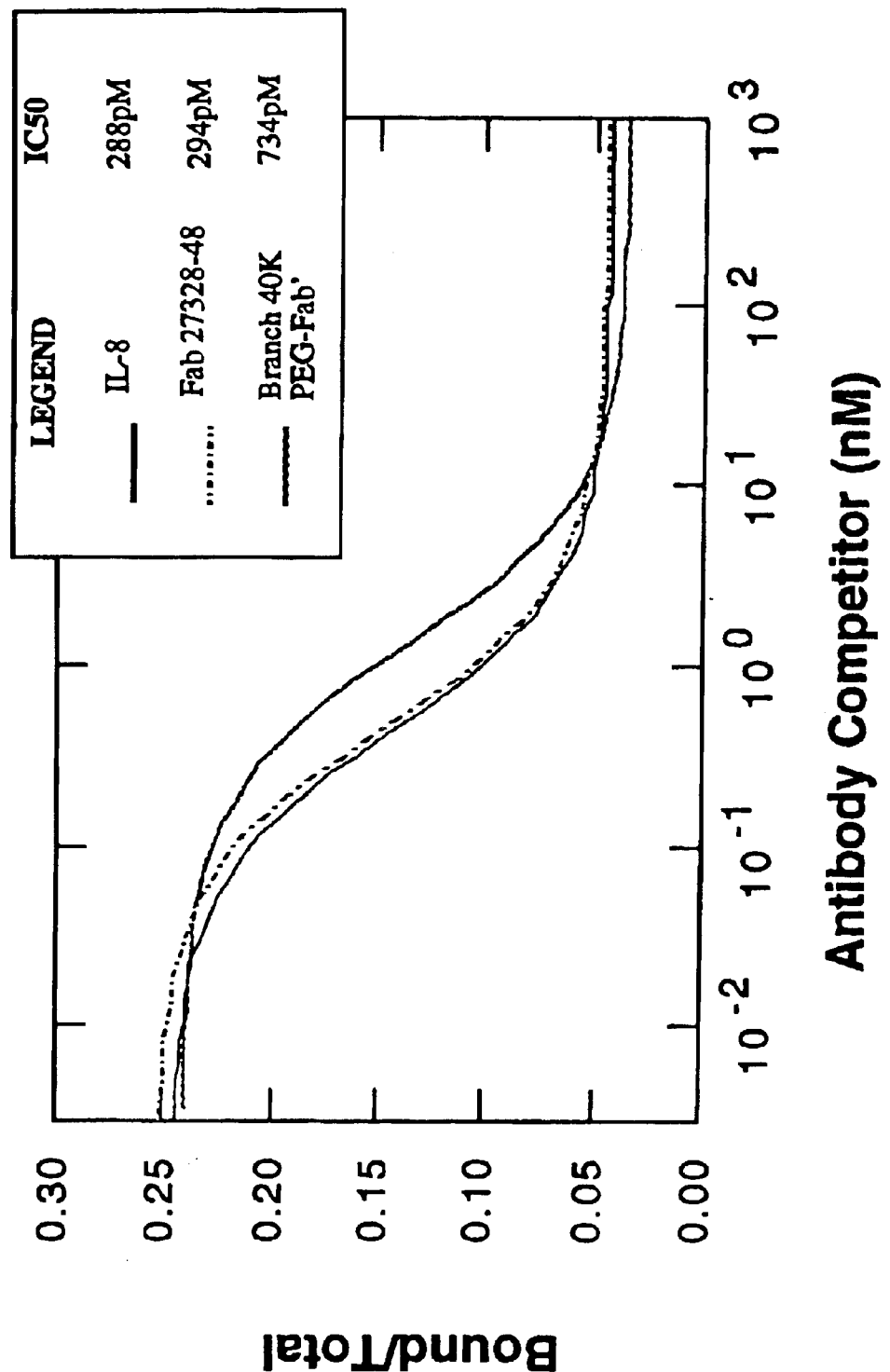

Anti-IL-8 6G4V11N35A Fab' variants modified with 5–40 kD linear PEG molecules and a 40 kD branched PEG molecule were tested for their ability to inhibit both IL-8 binding and activation of human neutrophils; the procedures were described in Sections (B)(1), (B)(2) and (B)(3) above. The binding curves and $IC_{50}$'s for PEG-maleimide modified 6G4V11N35A Fab' molecules are presented in FIGS. 54A–54C. The $IC_{50}$ of the 5 kD pegylated Fab' (350 pM) and the average $IC_{50}$ of the Fab control (366 pM) were not significantly different, suggesting that the addition of a 5 kD MW PEG did not affect the binding of IL-8 to the modified Fab' (FIG. 54A). However, a decrease in the binding of IL-8 to the 10 kD and 20 kD pegylated Fab' molecules was observed as depicted by the progressively higher $IC_{50}$'s (537 pM and 732 pM, respectively) compared to the average $IC_{50}$ of the native Fab. These values represent only a minimal loss of binding activity (between 1.5- and 2.0-fold). A less pronounced difference in IL-8 binding was observed for the 30 kD and 40 kD linear PEG antibodies (FIG. 54B). The $IC_{50}$'s were 624 pM and 1.1 nM, respectively, compared to the 802 pM value of the Fab control. The 40 kD branched PEG Fab' showed the largest decrease in IL-8 binding (2.5 fold) relative to the native Fab (FIG. 54C). Nevertheless, the reduction in binding of IL-8 by these pegylated Fab's is minimal.

Figure 55A:
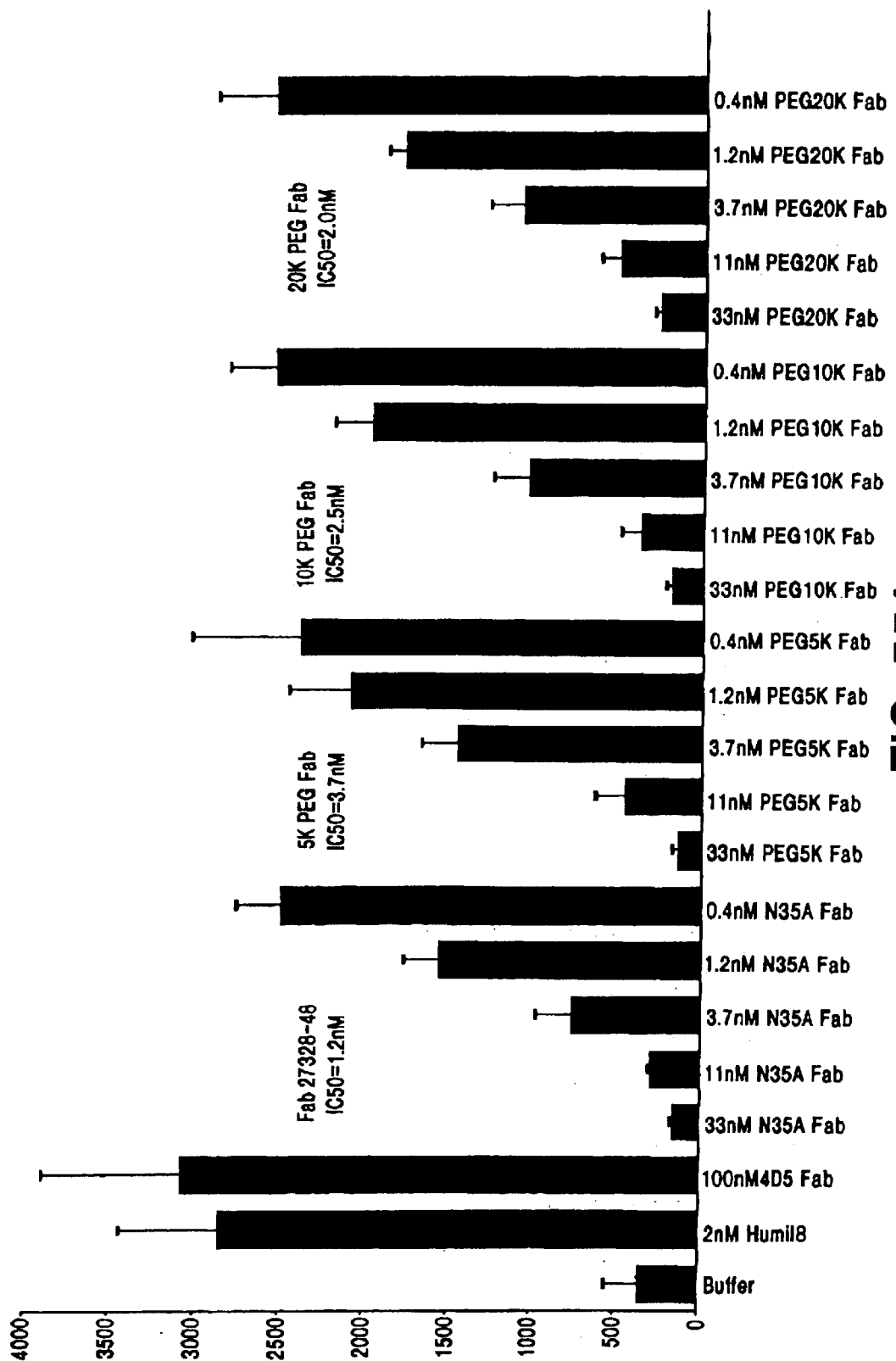
Figure 56A:
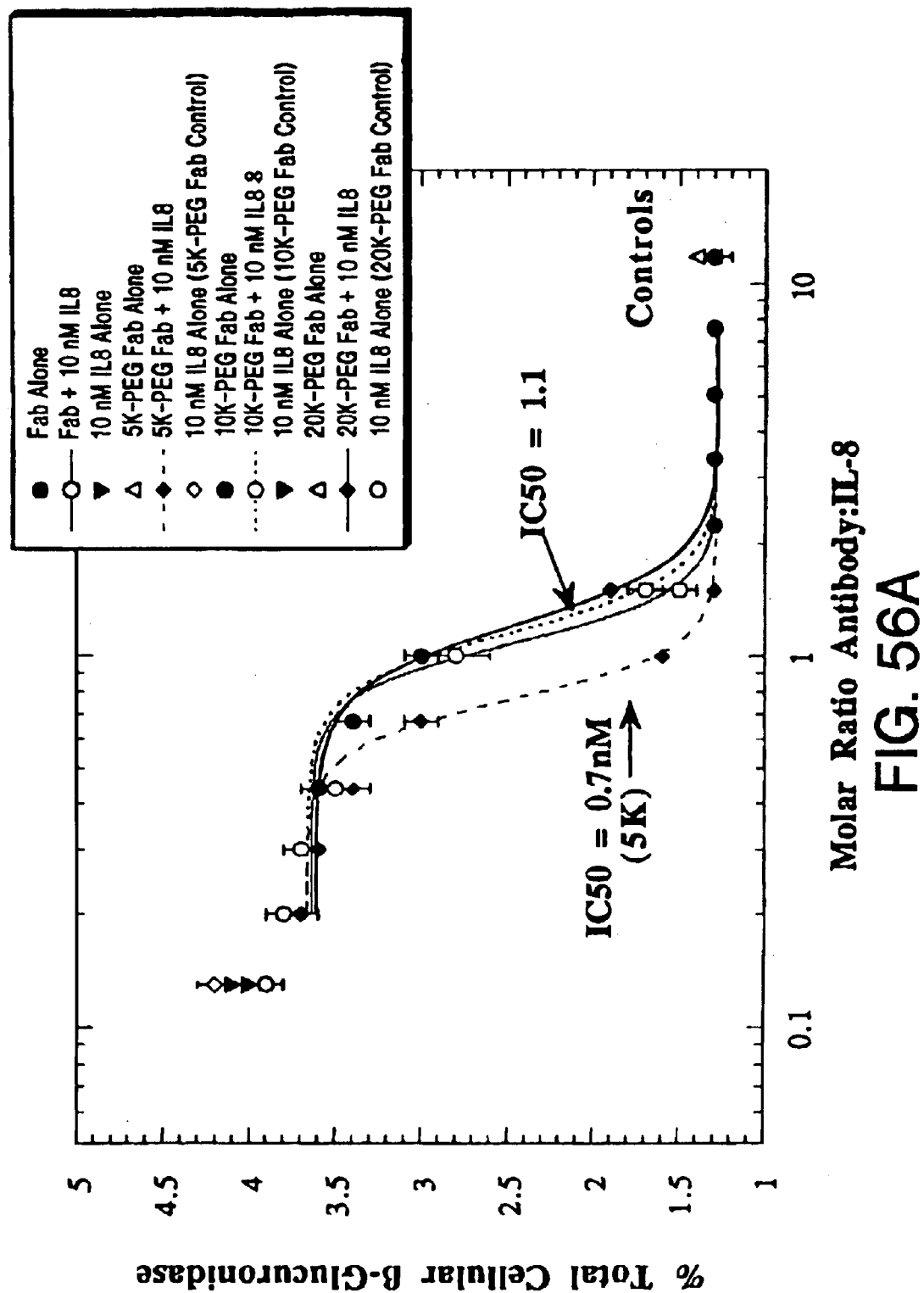
FIGS. 56A–56C are graphs depicting the ability of PEG-maleimide modified 6G4V11N35A Fab' molecules to inhibit IL-8 mediated release of β-glucuronidase from neutrophils.
Figure 56B:
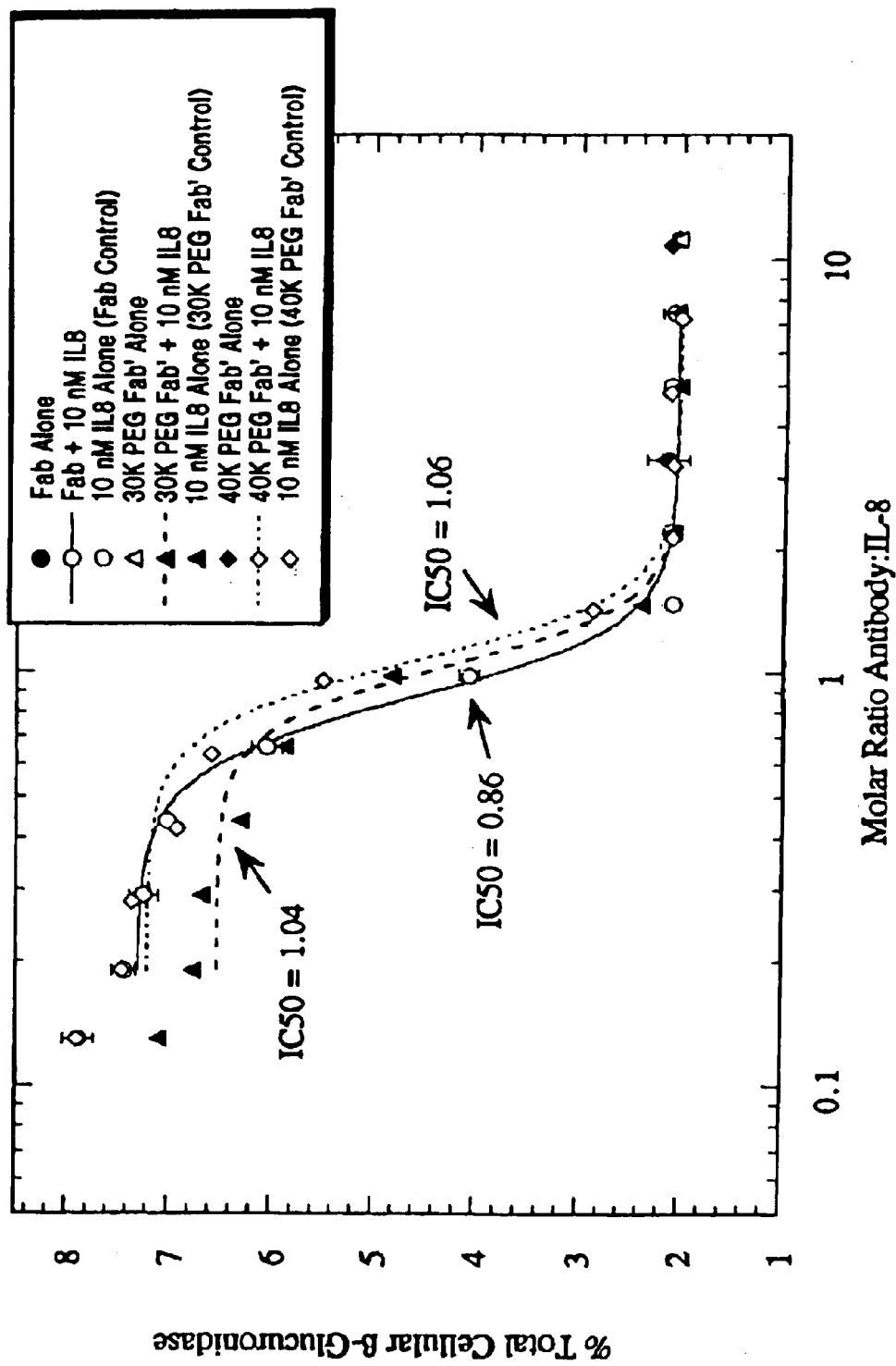
Figure 56C:
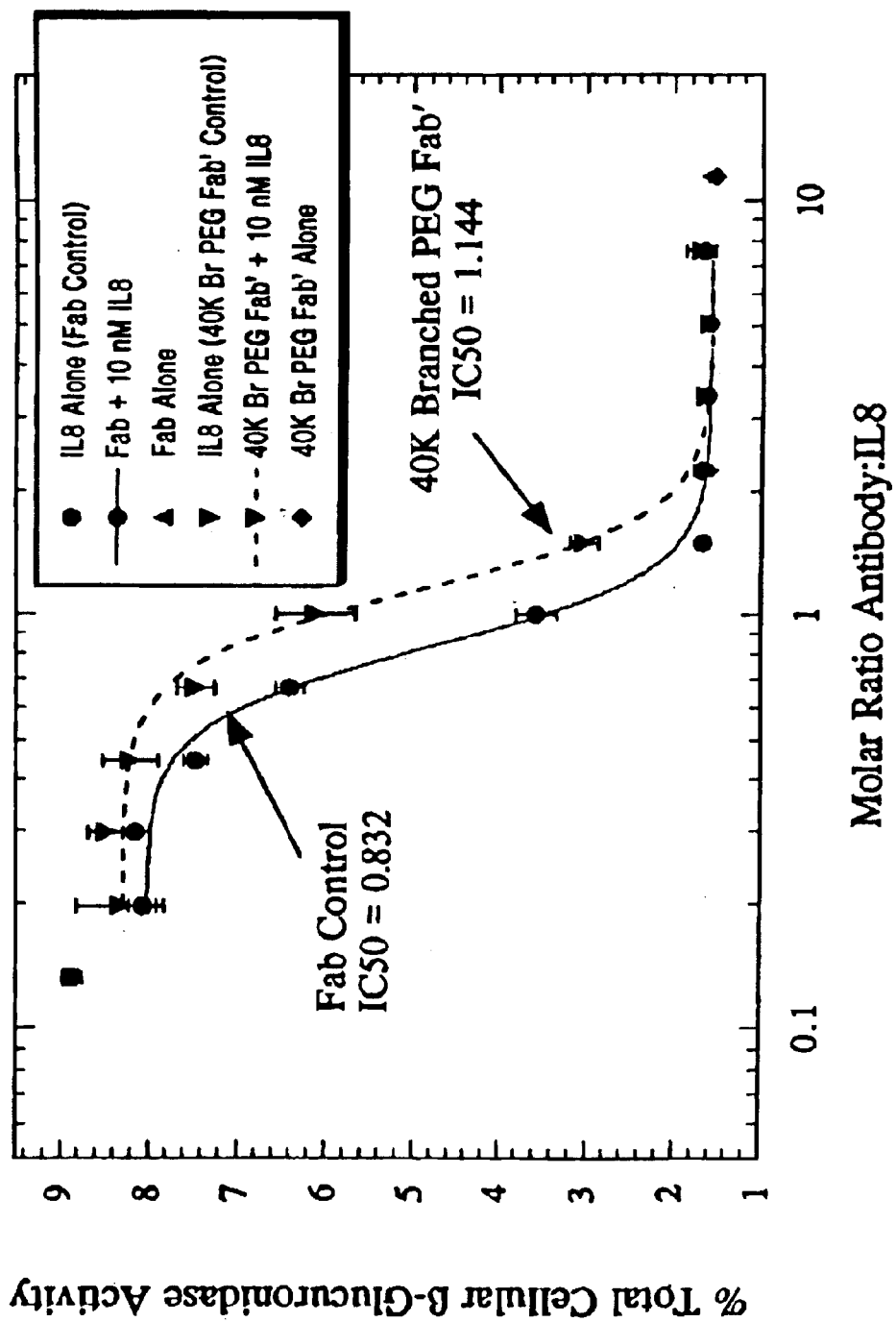

The ability of the pegylated antibodies to block IL-8 mediated activation of human neutrophils was demonstrated using the PMN chemotaxis (according to the method described in Section B(2) above) and β-glucuronidase release (according to the method described in Lowman et al., J. Biol. Chem., 271: 14344 (1996)) assays. The $IC_{50}$'s for blocking IL-8 mediated chemotaxis are shown in FIGS. 55A–55C. The 5–20 kD linear pegylated Fab' antibodies were able to block IL-8 mediated chemotaxis within 2–3 fold of the unpegylated Fab control (FIG. 55A). This difference is not significant because the inherent variation can be up to 2 fold for this type of assay. However, a significant difference was detected for the 30 kD and 40 kD linear pegylated Fab' antibodies as illustrated by the higher $IC_{50}$'s of the 30 kD linear PEG-Fab' (2.5 nM) and 40 kD linear PEG-Fab' (3.7 nM) compared to the Fab control (0.8 nM) (FIG. 55B). The ability of the 40 kD branched PEG Fab' molecule to block IL-8 mediated chemotaxis was similar to that of the 40 kD linear PEG Fab' (FIG. 55C). At most, the ability of the pegylated Fab' antibodies to block IL-8 mediated chemotaxis was only reduced 2–3 fold. Furthermore, release of β-glucuronidase from the granules of neutrophils was used as another criteria for assessing IL-8 mediated activation of human PMNs. FIG. 56A (depicting results obtained with 5 kD, 10 kD and 20 kD linear PEGs), FIG. 56B (depicting results obtained with 30 kD and 40 kD linear PEGs), and FIG. 56C (depicting results obtained with 40 kD branched PEG) show that all the pegylated Fab' antibodies were able to inhibit IL-8 mediated release of β-glucuronidase as well as or better than the unpegylated Fab control. The data collectively shows that the pegylated Fab' variants are biological active and are capable of inhibiting high amounts of exogenous IL-8 in in-vitro assays using human neutrophils.

W. In Vitro Activity Characterization of PEG Modified F(ab')$_2$ Fragments of 6G4V11N35A (Succinimidyl Chemical Coupling Method)

Figure 57A:
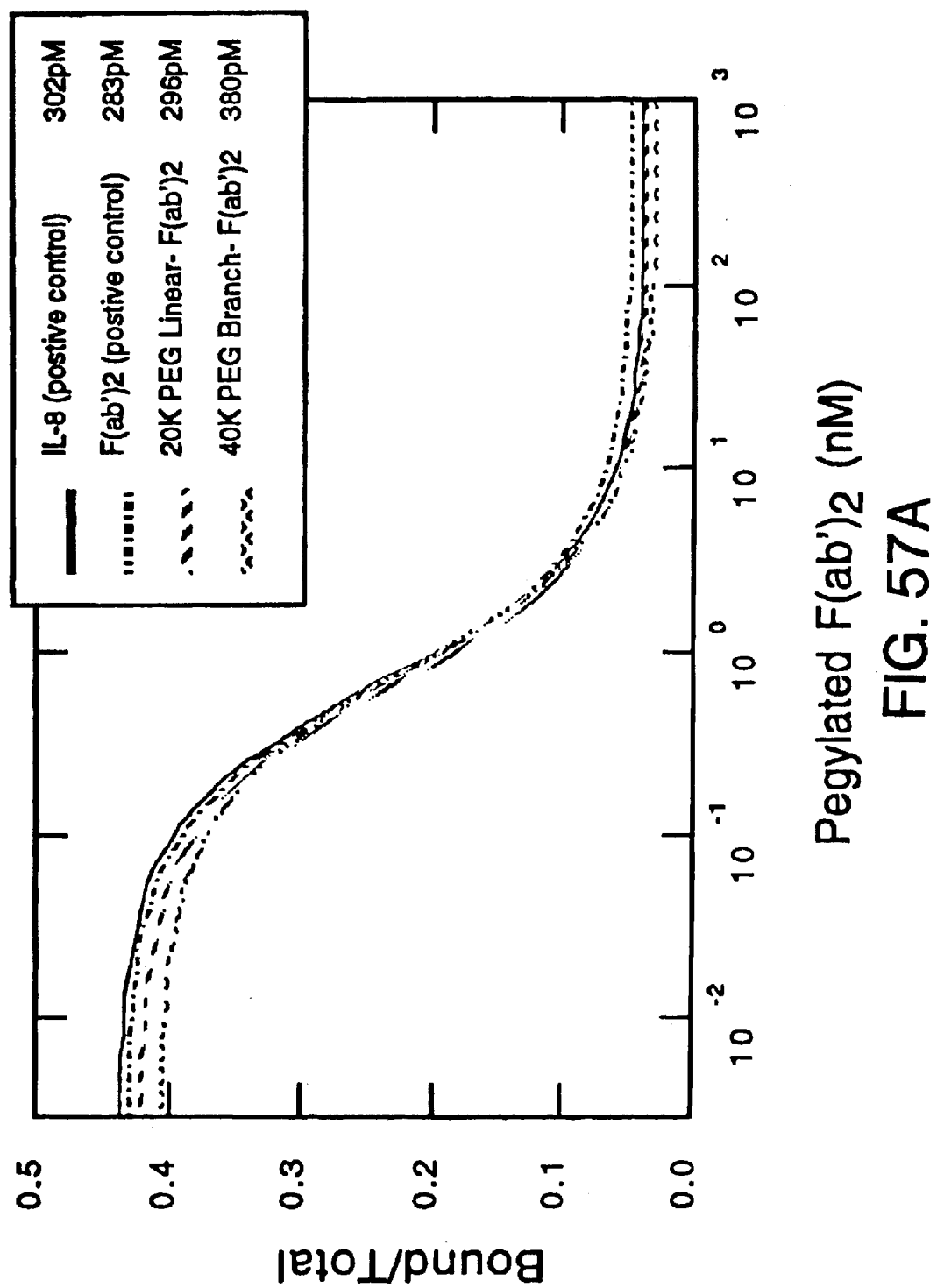

The anti-IL-8 variant 6G4V11N35A F(ab')$_2$ modified with (a) a single 20 kD linear PEG molecule per F(ab')$_2$, (b) a single 40 kD branched PEG molecule per F(ab')$_2$, (c) with three, four, or five 20 kD linear PEG molecules per F(ab')$_2$ (a mixture of: (1) species having three 20 kD linear PEG molecules per F(ab')$_2$; (2) species having four 20 kD linear PEG molecules per F(ab')$_2$; and (3) species having five 20 kD linear PEG molecules per F(ab')$_2$; denoted as "20 kD linear PEG (3,4,5) F(ab')$_2$"), or (d) with two 40 kD branched PEG molecules per F(ab')$_2$ (denoted as "40 kD branch PEG (2) F(ab')$_2$"), were tested for heir ability to inhibit $^{125}$I-IL-8 binding and to neutralize activation of human neutrophils. The procedures used are described in Sections (B)(1), (B)(2) and (B)(3) above. The binding curves for pegylated F(ab')$_2$ variants are shown in FIGS. 57A–57B. No significant differences were observed amongst the F(ab')$_2$ control, the single 20 kD linear PEG-modified F(ab')$_2$, and the single 40 kD branched PEG-modified F(ab')$_2$ (FIG. 57A). However, the F(ab')$_2$ variants containing multiple PEG molecules showed a slight reduction (less than 2-fold) in their ability to bind IL-8. The IC$_{50}$'s of the 20 kD linear PEG (3,4,5) F(ab')$_2$ and 40 kD branch PEG (2) F(ab')$_2$ variants were 437 pM and 510 pM, respectively, compared to 349 pM of the F(ab')$_2$ control (FIG. 57B).

The ability of these pegylated F(ab')$_2$ variants to block IL-8 mediated neutrophil chemotaxis is presented in FIGS. 58A–58B. Consistent with the PMN binding data, the single linear and branched PEG F(ab')$_2$ variants were able to block IL-8 mediated chemotaxis similar to the unpegylated F(ab')$_2$ control (FIG. 58A). The ability of the 40 kD branch PEG (2) F(ab')$_2$ variant to inhibit PMN chemotaxis was identical to the control F(ab')$_2$ while the 20 kD linear PEG (3,4,5) F(ab')$_2$ mixture was able to inhibit within 3-fold of the control antibody (FIG. 58B).

Figure 59A:
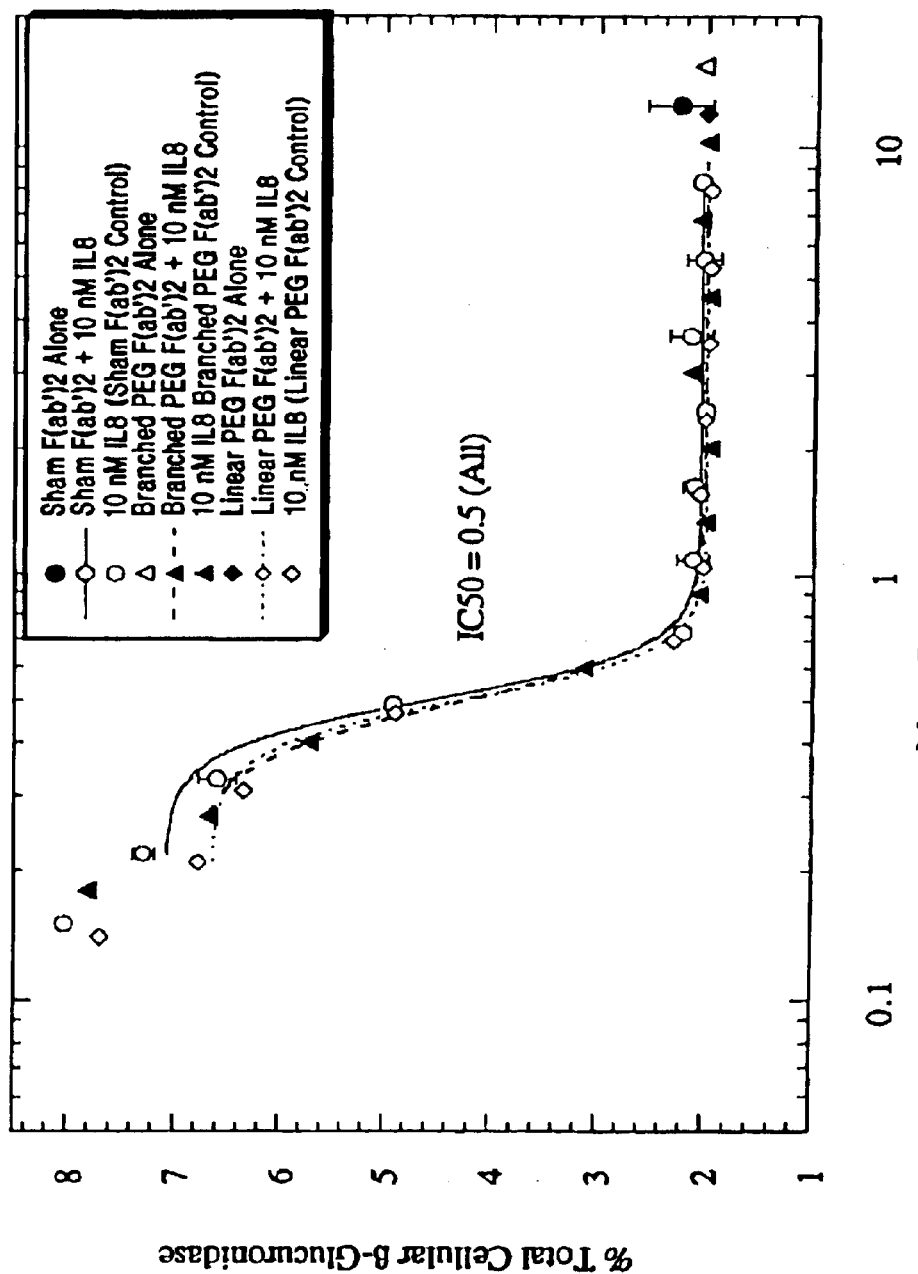
FIGS. 59A–59B are graphs depicting the ability of PEG-succinimide modified 6G4V11N35A F(ab')$_2$ molecules to inhibit human IL-8 mediated release of β-glucuronidase from neutrophils.
Figure 59B:
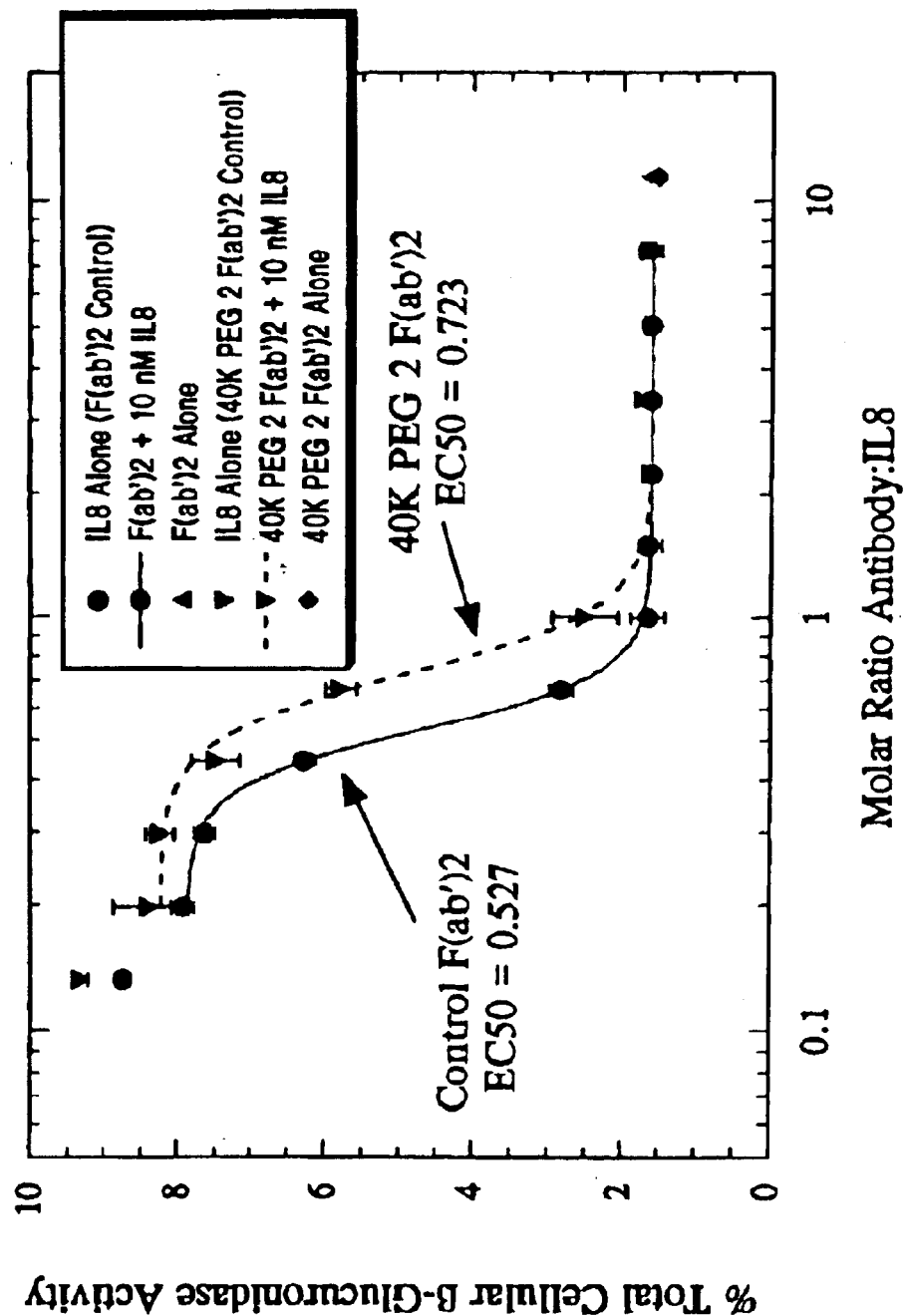

Shown in FIGS. 59A and 59B are the results of the β-glucuronidase release assay which is a measure of degranulation by IL-8 stimulated human neutrophils. The single 20 kD linear PEG-modified F(ab')$_2$ and the single 40 kD branched PEG-modified F(ab')$_2$ variants were able to inhibit release of β-glucuronidase as well as the F(ab')$_2$ control (FIG. 59A). The 40 kD branch PEG (2) F(ab')$_2$ inhibited this response within 2-fold of the F(ab')$_2$ control (FIG. 59B). The 20 kD linear PEG (3,4,5) molecule was not tested. Overall, the F(ab')$_2$ pegylated anti-IL-8 antibodies were biologically active and effectively prevented IL-8 binding to human neutrophils and the signaling events leading to cellular activation.

X. Pharmacokinetic and Safety Study of Eight Constructs of Pegylated Anti-IL-8 (Humanized) F (ab')2 and Fab' Fragments in Normal Rabbits Following Intravenous Administration The objective of this study was to evaluate the effect of pegylation on the pharmacokinetics and safety of six pegylated humanized anti-IL-8 constructs (pegylated 6G4V11N35A.Fab' and pegylated 6G4V11N35A.F(ab')$_2$ obtained as described in Sections (T) and (U) above) relative to the non-pegylated fragments in normal rabbits. Eight groups of two/three male rabbits received equivalent protein amounts of pegylated 6G4V11N35A.Fab' or pegylated 6G4V11N35A.F(ab')$_2$ constructs (2 mg/kg) via a single intravenous (IV) bolus dose of one anti-IL8 construct. Serum samples were collected according to the schedule shown in Table 8 below and analyzed for anti-IL8 protein concentrations and antibody formation against anti-IL8 constructs by ELISA.

TABLE 8

| Group No. | Dose level/ Route | Material | Blood Collection |
|---|---|---|---|
| 1 | 2 mg/kg (protein conc.) IV bolus | Fab' control | 0,5,30 min; 1,2,3,4,6,8,10, 14,20,24,360 hr |
| 2 | | linear(1)20K(s) Fab' | 0,5,30 min; 1,2,4,6,8,10,12, 24,28,32,48,72,96,168,216, 264,336,360 hr |
| 3 | | linear(1)40K(s) Fab' | |
| 4 | | branched(1)40K (N)F(ab')$_2$ | |
| 5 | | F(ab')$_2$ control | 0,5,30 min; 1,2,4,6,8,10,12, 24,28,32,48,52,56,336 hr |
| 6 | | branched(2) 40K(s)Fab' | 0,5,30 min; 1,2,4,6,8,10,12, 24,28,32,48,72,96,168,216,264,3 36 hr; Day 17,21,25 |
| 7 | | branched(2) 40K(N)F(ab')$_2$ | 0,5,30 min; 1,2,4,6,8,10,12, 24,28,32,48,72,144,192,240 hr; Day 13,16,20,23 |
| 8 | | linear(1)30K(s) Fab' | 0,5,30 min; 1,2,4,6,8,10,12, 24,28,32,48,72,96,168,216,264,3 36 hr; Day 17,21,25 | a. Methods

Three male New Zealand White (NZW) rabbits per group (with exception to Group 7, n=2) received an equivalent amount of 6G4V11N35A protein (Fab' or F(ab')$_2$) construct at 2 mg/kg via an IV bolus dose in a marginal ear vein. Amino acid composition analysis and absorbance at 280 nm using extinction coefficients of 1.26 for 6G4V11N35A Fab' constructs and 1.34 for 6G4V11N35A F(ab')$_2$ constructs were performed to determine the protein concentration. Whole blood samples were collected via an ear artery cannulation (ear opposing dosing ear) at the above time points. Samples were harvested for serum and assayed for free 6G4V11N35A Fab' or F(ab')$_2$ constructs using an IL-8 Binding ELISA. Assays were conducted throughout the study as samples became available. All animals were sacrificed following the last blood draw, and necropsies were performed on all animals in Groups 1, 4–8. Due to the development of antibodies against the 6G4V11N35A constructs, non-compartmental pharmacokinetic analysis was conducted on concentration versus time data only up to 168 hours.

b. Results

In four animals (Animals B, P, Q, V), interference to rabbit serum in the ELISA assay was detected (i.e. measurable concentrations of anti-IL8 antibodies at pre-dose). However, because these values were at insignificant levels and did not effect the pharmacokinetic analysis, the data were not corrected for this interference.

One animal (Animal G; Group 3) was exsanguinated before the termination of the study and was excluded from the pharmacokinetic analysis. At 4 hours, the animal showed signs of a stroke that was not believed to be drug related, as this can occur in rabbits following blood draws via ear artery cannulation.

Figure 65A:
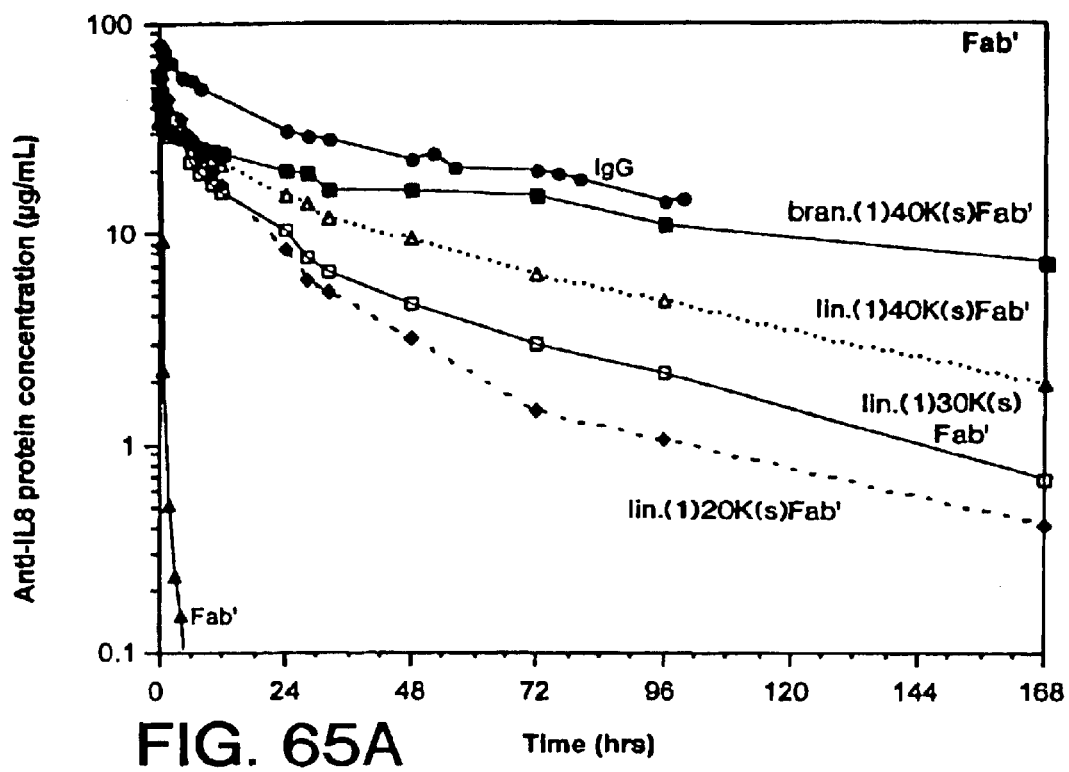
FIG. 65 contains graphs comparing the serum concentration vs. time profiles of various PEG-maleimide modified 6G4V11N35A Fab' molecules (upper graph) and various PEG-succinimide modified 6G4V11N35A F(ab')$_2$ molecules (lower graph) in rabbits. In the upper graph, "bran.(1)40K (s)Fab'" denotes 6G4V11N35A Fab' coupled to one 40 kD branched PEG-maleimide molecule, "lin.(1))40K(s)Fab'" denotes 6G4V11N35A Fab' coupled to one 40 kD linear PEG-maleimide molecule, "lin.(1)30K(s)Fab'" denotes 6G4V11N35A Fab' coupled to one 30 kD linear PEG-maleimide molecule, "lin.(1)20K(s)Fab'" denotes 6G4V11N35A Fab' coupled to one 20 kD linear PEG-maleimide molecule. In the lower graph, "bran.(2)40K(N) Fab'2" denotes 6G4V11N35A F(ab')$_2$ coupled to two 40 kD branched PEG-succinimide molecules, "bran.(1)40K(N) Fab'2" denotes 6G4V11N35A F(ab')$_2$ coupled to one 40 kD branched PEG-succinimide molecule, and "Fab'2" denotes unmodified 6G4V11N35A F(ab')$_2$. In both graphs, "IgG" denotes a full length IgG1 equivalent of the human-murine chimeric anti-rabbit IL-8 Fab described in Example F below.
Figure 65B:
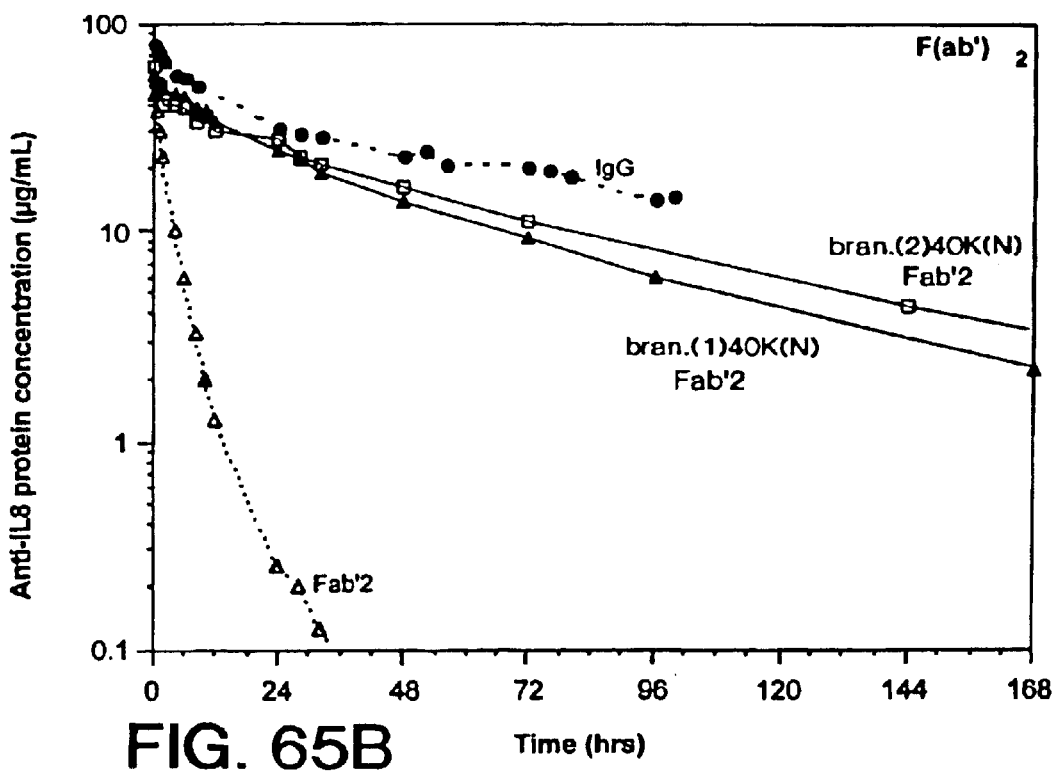

The mean concentration-time profiles of the eight anti-IL8 constructs in normal rabbits are depicted in FIG. 65, and the pharmacokinetic parameters for the eight constructs are summarized in Table 9 below. Significant antibodies to the anti-IL-8 constructs were present at Day 13/14 in all dose groups except Group 1 (Fab' control).

these parameters increased for both pegylated Fab' and F(ab')$_2$ molecules with increasing PEG molecular weight and approached the values of the full-length anti-IL8 (terminal half-life of 74 hours, MRT of 99 hours and CL of

TABLE 9

Pharmacokinetic parameters.

| Molecule | Fab' | | | | | F(ab')$_2$ | | |
|---|---|---|---|---|---|---|---|---|
| Group No. | 1 | 2 | 8 | 3 | 6 | 5 | 4 | 7 |
| PEG structure | — | linear | linear | linear | branched | — | branched | branched |
| Number of PEGs | — | 1 | 1 | 1 | 1 | — | 1 | 2 |
| PEG MW | — | 20 K | 30 K | 40 K | 40 K | — | 40 K | 40 K |
| Dose (mg/kg) | 2 | 2 | 2 | 2 | 2 | 2 | 2 | 2 |
| $V_c$ (mL/kg)$^a$ | 58 ± 3 | 36 ± 3 | 35 ± 1 | 34 | 44 ± 1 | 45 ± 5 | 36 ± 1 | 32 |
| $V_{ss}$ (mL/kg)$^b$ | 68 ± 8 | 80 ± 8 | 110 ± 15 | 79 | 88 ± 21 | 59 ± 4 | 50 ± 3 | 52 |
| Cmax ($\mu$g/mL)$^c$ | 35 ± 1 | 58 ± 3 | 57 ± 1 | 60 | 45 ± 1 | 45 ± 6 | 56 ± 2 | 62 |
| Tmax (min)$^d$ | 5 | 5 | 5 | 5 | 5 | 5 | 5 | 5 |
| $t_{1/2}$ term (hr)$^e$ | 3.0 ± 0.9 | 44 ± 2 | 43 ± 7 | 50 | 105 ± 11 | 8.5 ± 2.1 | 45 ± 3 | 48 |
| AUC$_0$- (hr · $\mu$g/mL)$^f$ | 18 ± 3 | 80 ± 74 | 910 ± 140 | 1600 | 3400 ± 1300 | 140 ± 3 | 2200 ± 77 | 2500 |
| CL (mL/hr/kg)$^g$ | 110 ± 17 | 2.5 ± 0.2 | 2.2 ± 0.4 | 1.3 | 0.63 ± 0.20 | 14 ± 0 | 0.92 ± 0.03 | 0.83 |
| MRT(hr)$^h$ | 0.61 ± 0.15 | 32 ± 2 | 45 ± 9 | 63 | 140 ± 18 | 4.2 ± 0.3 | 55 ± 3 | 64 |
| No. of Animals | 3 | 3 | 3 | 2 | 3 | 3 | 3 | 2 |

$^a$Initial volume of distribution.
$^b$Volume of distribution at steady state.
$^c$Observed maximum concentration.
$^d$Observed time to Cmax.
$^e$$t_{1/2}$ term = half-life associated with the terminal phase of the concentration vs. time profile.
$^f$Area under the concentration versus time curve (extrapolated to infinity).
$^g$CL = serum clearance.
$^h$MRT = Mean residence time.

Pegylation decreased serum CL of anti-IL8 fragments and extended both the terminal half-life and MRT as shown in Table 10 below.

0.47 mL/hr/kg). In comparing the branched(1)40K Fab' (Group 6) and branched(1)40K F(ab')$_2$ (Group 4), unexpected pharmacokinetics were observed. The pegylated Fab'

TABLE 10

Fold decrease/increase in clearance, terminal half-life & MRT of pegylated anti-IL8 fragments.

| anti-IL8 fragment | Fab' | | | | | F(ab')$_2$ | | |
|---|---|---|---|---|---|---|---|---|
| Group No. | 1 | 2 | 8 | 3 | 6 | 5 | 4 | 7 |
| PEG structure | — | linear | linear | linear | bran. | — | bran. | bran. |
| No. of PEG | — | 1 | 1 | 1 | 1 | — | 1 | 2 |
| PEG MW | — | 20 K | 30 K | 40 K | 40 K | — | 40 K | 40 K |
| CL: mean(mL/hr/kg) | 110 | 2.5 | 2.2 | 1.3 | 0.63 | 14 | 0.92 | 0.83 |
| fold decrease | 1 | 46 | 51 | 90 | 180 | 1 | 15 | 17 |
| t1/2 term: mean (hr) | 3.0 | 44 | 43 | 50 | 110 | 8.5 | 45 | 48 |
| fold increase | 1 | 14 | 14 | 17 | 35 | 1 | 5.3 | 5.7 |
| MRT: mean(hr) | 0.61 | 32 | 45 | 63 | 140 | 4.2 | 55 | 64 |
| fold increase | 1 | 53 | 73 | 100 | 240 | 1 | 13 | 15 |

Figure 66:
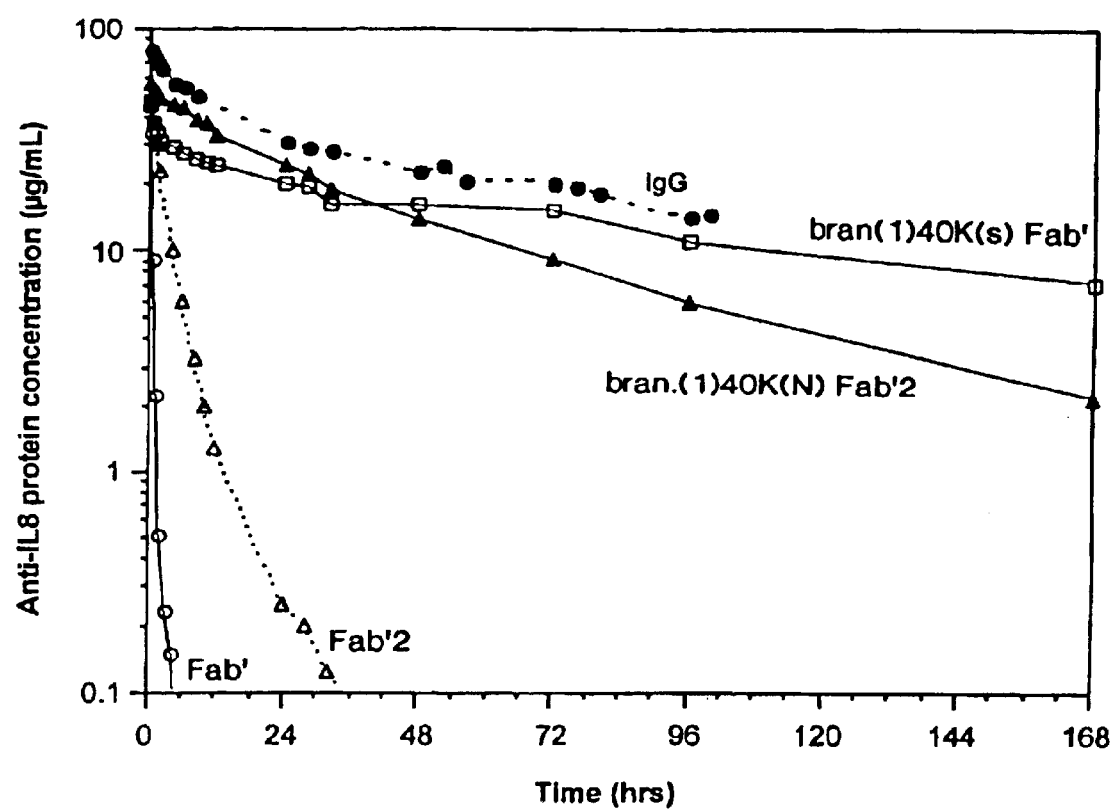
FIG. 66 contains graphs comparing the serum concentration vs. time profiles of 6G4V11N35A Fab' coupled to one 40 kD branched PEG-maleimide molecule (denoted as "bran.(1)40K(s)Fab'"), 6G4V11N35A F(ab')$_2$ coupled to one 40 kD branched PEG-succinimide molecule (denoted as "bran.(1)40K(N)Fab'2"), unmodified 6G4V11N35A F(ab') (denoted as "Fab'2"), unmodified 6G4V11N35A Fab' (denoted as "Fab'"), and a full length IgG1 (denoted as "IgG") equivalent of the human-murine chimeric anti-rabbit IL-8 Fab described in Example F below.

For the pegylated anti-IL8 Fab' fragments, CL decreased by 46 to 180-fold. Terminal half-life and MRT increased 14 to 35-fold and 53 to 240-fold, respectively. For pegylated anti-IL8 F(ab')$_2$ molecules, CL decreased 15 to 17-fold with pegylation, and terminal half-life and MRT increased by greater than 5-fold and 13-fold, respectively. The changes in molecule appeared to remain in the serum longer than the pegylated F(ab')$_2$ (see FIG. 66). The mean CL of branched (1)40K Fab' was 0.63 mL/hr/kg, but a higher CL was observed for branched(1)40 kD F(ab')$_2$ (CL 0.92 mL/hr/kg). The terminal half-life, likewise, was longer for the Fab' than the F(ab')$_2$ pegylated molecule (110 vs 45 hours).

The pharmacokinetic data demonstrated that pegylation decreased CL and increased terminal t1/2 and MRT of anti-IL8 fragments (Fab' and F(ab')$_2$) to approach that of the full-length anti-IL8. Clearance was decreased with pegylation 46 to 180-fold for the Fab' and approximately 16-fold for the F(ab')$_2$. The terminal half-life of the Fab' anti-IL8 fragment was increased by 14 to 35-fold and approximately 5-fold for the F(ab')$_2$ anti-IL8. MRT, likewise, were extended by 53 to 240-fold for the Fab' and approximately 14-fold for the F(ab')$_2$. The branched(1) 40 kD Fab' had a longer terminal half-life and lower clearance compared to the branched(1) 40 kD F(ab')$_2$.

Y. In Vivo Efficacy Testing of Anti-IL-8 Antibody Reagents in Rabbit Model of Ischemia/Reperfusion and Acid Aspiration-induced Acute Respiratory Distress Syndrome (ARDS)

Full length murine anti-rabbit IL-8 monoclonal antibody 6G4.2.5, 40 kD branched PEG-G4V11N35A Fab', and control antibody (anti-HIV gp120 monoclonal antibody 9E3.1F10) were tested in a rabbit ARDS model, The animals were weighed and anaesthetized by intramuscular injection of ketamine (50 mg/kg body weight), xylazine (5 mg/kg body weight), and acepromazine (0.75 mg/kg body weight). A second dose (20% of the first dosage) was given 1M 15 minutes before removal of vascular clip, and third dose (60% of the first dosage) was given at tracheotomy. Intra-arterial catheter (22G, 1 in. Angiocath) and intra-venous catheter (24G, 1 in. angiocath) were be placed in the car central artery and posterior marginal ear vein for blood samplings (arterial blood gases and CBC) and anti-IL-8 and fluid administration, respectively. The anaesthetized animals were transferred in a supine position to an operating tray; the abdominal area was shaved and prepared for surgery. Via a midline laparotomy, the superior mesenteric artery (SMA) was isolated and a microvascular arterial clip applied at the aortic origin. Before the temporary closure of the abdomen using 9 mm wound clip (Autoclip, Baxter), 15 ml of normal saline was given intraperitoneally as fluid supplement After 110 minutes of intestinal ischemia, the abdominal incision was reopened and the arterial clip was released to allow reperfusion. Before closure, 5 ml of normal saline was given intraperitoneally for fluid replacement The laparotomy incision was closed in two layers and the animals allowed to awaken.

After surgery, the animals were placed on a heating pad (38° C.) and continuously monitored for up to 6 hours post reperfusion and lactated Ringer's 8–12 ml/kg/hr IV was given as fluid supplement.

At 22–24 hr post-reperfusion, a tracheotomy was performed under anesthesia. Normal physiologic saline was diluted 1:3 with water and adjusted to pH 1.5 (adjusted by using 1N HCl); 3 ml/kg body weight was then instilled intra-tracheally. Rectal temperature was maintained at 37+/−1 degree C. using a homeothermic heat therapy pad (K-Mod II, Baxter). Fluid supplements (LRS) at a rate of 5 ml/kg/hour IV were given. Blood gases were monitored every hour. The rabbits were returned to the cage after 6 hr of continuous monitoring.

Just prior to aspiration, animals were treated with saline, the control monoclonal antibody (anti-HIV gp-120 IgG 9E3.1F10), the full length murine anti-rabbit IL8 (6 g 4.2.5 murine IgG2a anti-rabbit IL8) or the pegylated 6G4V11N35A Fab' (6G4V1N35A Fab' modified with 40 kD branched PEG-maleimide as described in Section T above, denoted as "40 kD branched PEG-6G4V11N35A Fab' ").

Data from saline or control antibody treated animals was combined and presented as "Control". Arterial blood gases and A-a PO2 gradient measurements were taken daily, and IV fluid supplementation was performed daily. A-a PO2 gradient was measured at 96 hr of reperfusion. The A-a PO2 gradient was calculated as:

$$\text{A-a PO2} = [\text{FIO2}(\text{PB}-\text{PH20})-(\text{PaCO2/RQ})]-\text{PaO2}.$$

PaO2/FiO2 ratios were measured at 24 hr and 48 hr in room air and 100% oxygen.

After the final A-a PO2 gradient measurement, the animals were anesthetized with Nembutal 100 mg/kg i.v. and the animals were euthanized by transecting the abdominal aorta in order to reduce red blood cell contamination of bronchoalveolar lavage fluid (BAL). The lungs were removed en bloc. The entire lung was weighed and then lavaged with an intratracheal tube (Hi-Lo tracheal tube, 3 mm) using 30 ml of HBSS and lidocain. Total and differential leukocyte counts in the BAL were determined. Lesions/changes were verified by histological examination of each lobe of the right lung of each animal.

Figure 67:
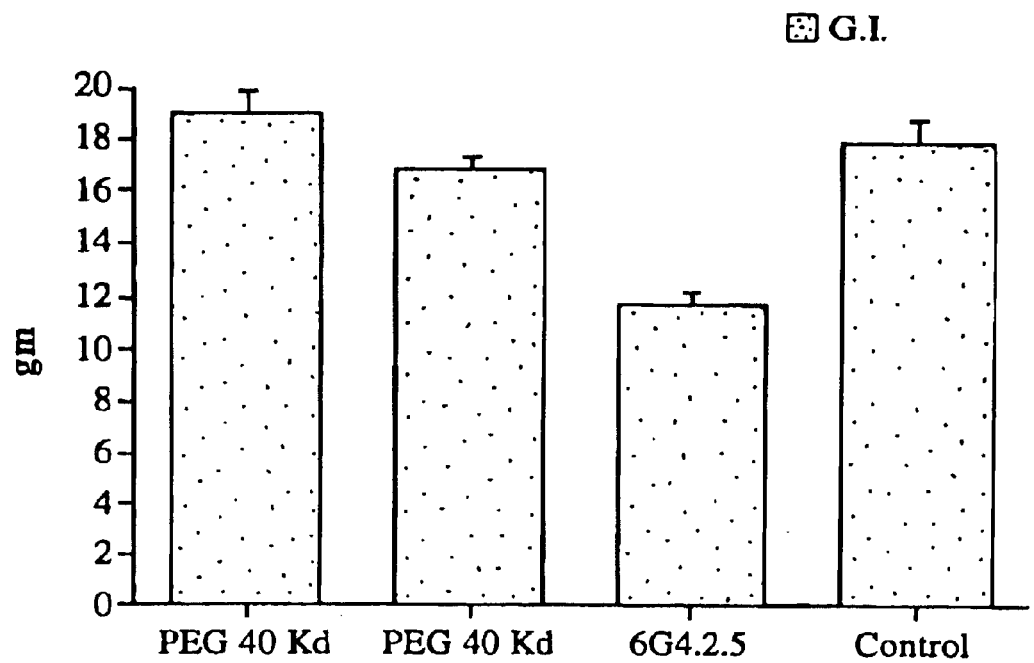
FIG. 67 is a graph depicting the effect of 6G4V11N35A Fab' coupled to one 40 kD branched PEG-maleimide molecule (denoted as "PEG 40 Kd") and murine anti-rabbit IL-8 monoclonal antibody 6G4.2.5 full length IgG2a) (denoted as "6G4.2.5") on gross weight of entire lung in an ARDS rabbit model.
Figure 68:
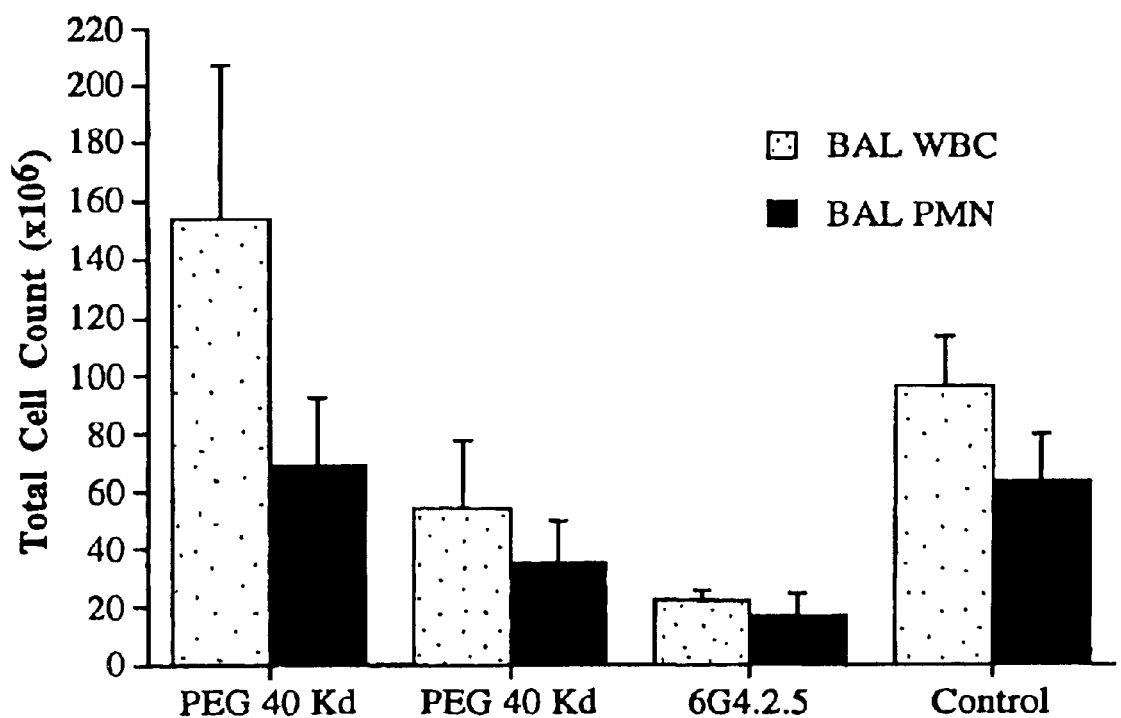
FIG. 68 is a graph depicting the effect of 6G4V11N35A Fab' coupled to one branched 40 kD PEG-maleimide molecule (denoted as "PEG 40 Kd") and murine anti-rabbit IL-8 monoclonal antibody 6G4.2.5 (full length IgG2a) (denoted as "6G4.2.5") on BAL total leukocyte (light columns) and polymorphonuclear cell (dark columns) counts in an ARDS rabbit model. Untreated (no therapeutics) control animal data is denoted as "Control".
Figure 69:
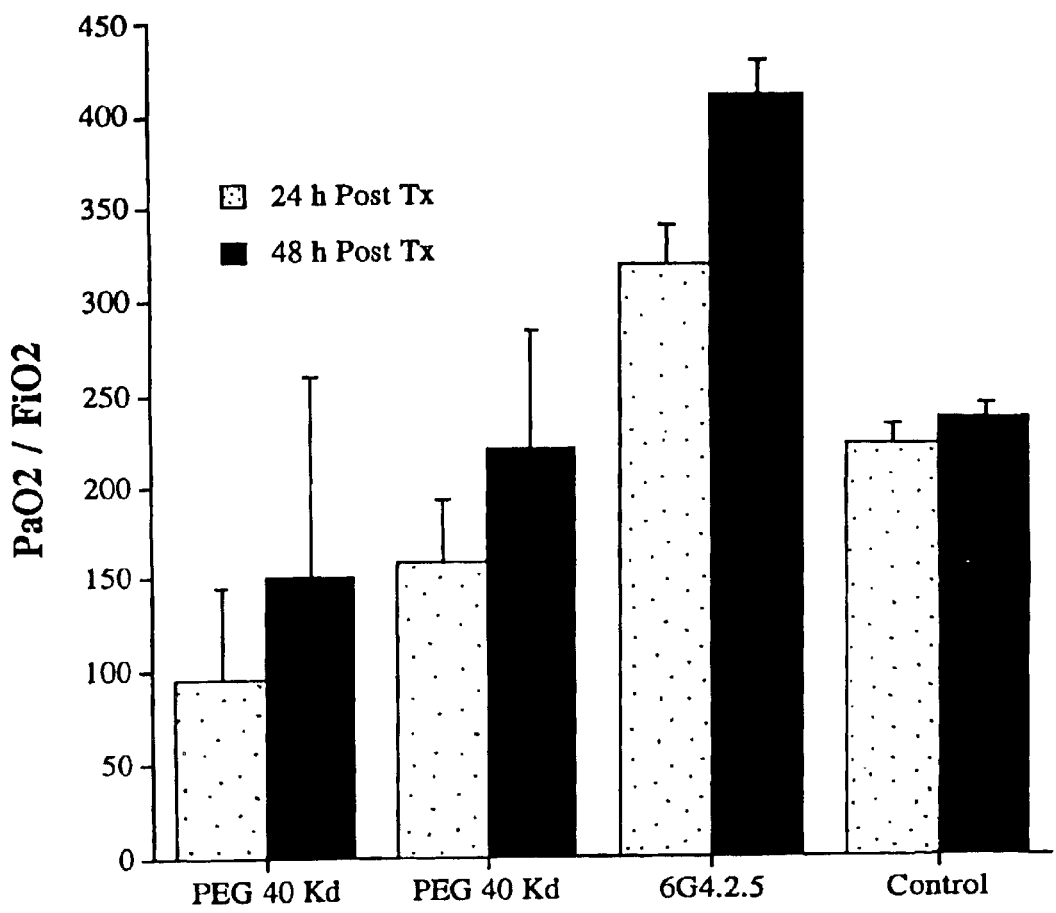
FIG. 69 is a graph depicting the effect of 6G4V11N35A Fab' coupled to one branched 40 kD PEG-maleimide molecule (denoted as "PEG 40 Kd") and murine anti-rabbit IL-8 monoclonal antibody 6G4.2.5 (full length IgG2a) (denoted as "6G4.2.5") on PaO2/FiO2 ratio at 24 hours-post treatment (light columns) and 48 hours post-treatment (dark columns) in an ARDS rabbit model. Untreated (no therapeutics) control animal data is denoted as "Control".

The gross lung weight, total leukocyte and polymorphonuclear cell counts in BAL, and PaO2/FiO2 data obtained are depicted in FIGS. 67, 68 and 69, respectively. Treatment with 40 kD branched PEG-6G4V11N35A Fab' exhibited no effect on the biological parameters measured in the model as compared to the "Control" group. However, the data do not contradict the pharmacokinetic analysis or the in vitro activity analysis for the 40 kD branched PEG-6G4V11N35A Fab' presented in Sections (V) and (X) above. In addition, these data do not contradict the ability of the 40 kD branched PEG-6G4V11N35A Fab' to reach and act on disease effector targets in circulation or other tissues.

The following biological materials have been deposited with the American Type Culture Collection, 10801 University Boulevard, Manassas, Va. 20110-2209, USA (ATCC):

| Material | ATCC Accession No. | Deposit Date |
|---|---|---|
| hybridoma cell line 5.12.14 | HB 11553 | Feb. 15, 1993 |
| hybridoma cell line 6G4.2.5 | HB 11722 | Sep. 28, 1994 |
| pantiIL-8.2, E. coli strain 294 mm | 97056 | Feb. 10, 1995 |
| p6G425chim2, E. coli strain 294 mm | 97055 | Feb. 10, 1995 |
| p6G4V11N35A.F(ab')$_2$ | 97890 | Feb. 20, 1997 |
| E. coli strain 49D6(p6G4V11N35A.F(ab')$_2$) | 98332 | Feb. 20, 1997 |
| p6G425V11N35A.choSD | 209552 | Dec. 16, 1997 |
| clone#1933 aIL8.92 NB 28605/12 | CRL-12444 | Dec. 11, 1997 |
| clone#1934 aIL8.42 NB 28605/14 | CRL-12445 | Dec. 11, 1997 |

These deposits were made under the provisions of the Budapest Treaty on the International Recognition of the Deposit of Microorganisms for the Purpose of Patent Procedure and the Regulations thereunder (Budapest Treaty). This assures maintenance of a viable deposit for 30 years from the date of deposit. These cell lines will be made available by ATCC under the terms of the Budapest Treaty, and subject to an agreement between Genentech, Inc. and ATCC, which assures permanent and unrestricted availability of the cell lines to the public upon issuance of the pertinent U.S. patent or upon laying open to the public of any U.S. or foreign patent application, whichever comes first, and assures availability of the cell lines to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if the deposited cell lines should be lost or destroyed when cultivated under suitable conditions, they will be promptly replaced on notification with a specimen of the same cell line. Availability of the deposited cell lines is not to be construed as a license to practice the invention in contravention of the rights granted under the authority of any government in accordance with its patent laws.

We claim:

1. A conjugate consisting essentially of an antibody fragment covalently modified by one or two nonproteinaceous polymer molecules at a free sulfhydryl group of a cysteine residue within the hinge region of the antibody fragment, wherein (a) the apparent molecular weight of the conjugate, as determined by size exclusion chromatography, is at least about 500 kD, (b) the average actual molecular weight of each nonproteinaceous molecule is at least 20 kD, and (c) the antibody fragment has an antigen binding site that binds human interleukin-8 (IL-8) comprising an anti-IL-8 monoclonal antibody light chain sequence comprising amino acids 1–219 of the humanized antibody light chain 6G4.2.5v11 (SEQ ID NO: 51).

2. The conjugate of claim 1, wherein the antibody fragment is selected from the group consisting of Fab, Fab', and Fab'-SH modified by one PEG molecule having an average actual molecular weight of about 30 kD.

3. The conjugate of claim 1, wherein the antibody fragment comprises an anti-IL-8 monoclonal antibody light chain sequence comprising the amino acid sequence of humanized antibody light chain 6G4.2.5v11 (SEQ ID NO: 51).

4. The conjugate of claim 3, wherein the antibody fragment is selected from the group consisting of Fab, Fab', and Fab'-SH modified by one PEG molecule having an average actual molecular weight of about 30 kD.

5. A conjugate consisting essentially of an antibody fragment covalently modified by one or two nonproteinaceous polymer molecules at a free sulfhydryl group of a cysteine residue within the hinge region of the antibody fragment, wherein (a) the apparent molecular weight of the conjugate, as determined by size exclusion chromatography, is at least about 500 kD, (b) the average actual molecular weight of each nonproteinaceous molecule is at least 20 kD, and (c) the antibody fragment has an antigen binding site that binds human interleukin-8 (IL-8) comprising an anti-IL-8 monoclonal antibody heavy chain sequence comprising amino acids 1–230 of the humanized antibody 6G4.2.5v11 heavy chain (SEQ ID NO: 60).

6. The conjugate of claim 5, wherein the antibody fragment is selected from the group consisting of Fab, Fab', and Fab'-SH modified by one PEG molecule having an average actual molecular weight of about 30 kD.

7. The conjugate of claim 5, further comprising a leucine zipper sequence.

8. The conjugate of claim 5, wherein the antibody fragment comprises an anti-IL-8 monoclonal antibody heavy chain sequence comprising the amino acid sequence of the humanized antibody 6G4.2.5v11 heavy chain (SEQ ID NO: 60).

9. The conjugate of claim 8, wherein the antibody fragment is selected from the group consisting of Fab, Fab', and Fab'-SH modified by one PEG molecule having an average actual molecular weight of about 30 kD.

10. The conjugate of claim 8, further comprising a leucine zipper sequence.

\* \* \* \* \*

UNITED STATES PATENT AND TRADEMARK OFFICE
CERTIFICATE OF CORRECTION

PATENT NO. : 6,870,033 B1
DATED : March 22, 2005
INVENTOR(S) : Hsei et al.

It is certified that error appears in the above-identified patent and that said Letters Patent is hereby corrected as shown below:

Column 2,
Line 47, after "that" and before "isotype", please replace "a" with -- an --.

Column 5,
Line 46, after "B", please replace "an" with -- and --.

Column 17,
Line 2, after "D," and before "or", please delete ".".

Column 33,
Line 13, after "30,000" and before "in", please insert -- D --.

Column 44,
Line 2, please replace "difference" with -- different --.
Line 34, please replace "fluroescent" with -- fluorescent --.

Column 45,
Lines 1-2, please replace "raidonuclide" with -- radionuclide --.

Column 51,
Line 57, please replace "correspond" with -- corresponds --.

Column 51, Line 67 through Column 52, Line 1,
Please replace "correspond" with -- corresponds --.

Column 52,
Lines 10-11, 21, 30, 40, 49-50 and 59, please replace "correspond" with -- corresponds --.

Column 53,
Line 2, 12, 21-22, 32, 44, 54 and 66, please replace "correspond" with -- corresponds --.

Column 54,
Lines 9, 21 and 33, please replace "correspond" with -- corresponds --.

Column 56,
Line 61, please replace "correspond" with -- corresponds --.

Column 57,
Lines 6, 17, 29, 40 and 52, please replace "correspond" with -- corresponds --.

UNITED STATES PATENT AND TRADEMARK OFFICE
CERTIFICATE OF CORRECTION

PATENT NO.    : 6,870,033 B1
DATED         : March 22, 2005
INVENTOR(S)   : Hsei et al.

It is certified that error appears in the above-identified patent and that said Letters Patent is hereby corrected as shown below:

Column 58,
Lines 9, 22, 35, 47 and 60, please replace "correspond" with -- corresponds --.

Column 59,
Lines 6 and 20, please replace "correspond" with -- corresponds --.

Column 72,
Line 47, please replace "(arc)" with -- (are) --.
Line 54, please replace "I&E" with -- IgE --.

Column 93,
Line 21, please replace "usefull" with -- useful --.
Line 38, after "integrant" and before "Depending", please insert --. --.

Column 103,
Line 15, please replace "(Ncuro" with -- (Neuro --.

Column 106,
Line 36, please replace "pantiIL-8.2" with -- pantIL-8.2 --.
Line 39, after "it" and before "The", please insert --. --.

Column 116,
Line 37, after "against" and before "The", please insert --. --.

Column 117,
Line 38, please replace "for2" with -- for 2 --.

Column 121,
Line 48, after "6.0" and before "The", please insert -- . --.

UNITED STATES PATENT AND TRADEMARK OFFICE
CERTIFICATE OF CORRECTION

PATENT NO. : 6,870,033 B1
DATED : March 22, 2005
INVENTOR(S) : Hsei et al.

It is certified that error appears in the above-identified patent and that said Letters Patent is hereby corrected as shown below:

Column 122,
Line 64, after "volumes.", please insert -- ) --.

Signed and Sealed this

Eleventh Day of October, 2005

JON W. DUDAS
*Director of the United States Patent and Trademark Office*